US012666862B2

(12) United States Patent
Nie et al.

(10) Patent No.: US 12,666,862 B2
(45) Date of Patent: Jun. 23, 2026

(54) ARYLAMINE COMPOUND, ELECTRONIC COMPONENT USING SAME AND ELECTRONIC DEVICE

(71) Applicant: Shaanxi Lighte Optoelectronics Material Co., Ltd., Xi'an (CN)

(72) Inventors: Qiqi Nie, Xi'an (CN); Jiamei Cao, Xi'an (CN)

(73) Assignee: SHAANXI LGHTE OPTOELECTRONICS MATERIAL CO., LTD., Xi'an (CN)

( * ) Notice: Subject to any disclaimer, the term of this patent is extended or adjusted under 35 U.S.C. 154(b) by 957 days.

(21) Appl. No.: 17/794,291

(22) PCT Filed: Mar. 22, 2021

(86) PCT No.: PCT/CN2021/082177
§ 371 (c)(1),
(2) Date: Jul. 21, 2022

(87) PCT Pub. No.: WO2021/213109
PCT Pub. Date: Oct. 28, 2021

(65) Prior Publication Data

US 2023/0146030 A1 May 11, 2023

(30) Foreign Application Priority Data

Apr. 20, 2020 (CN) ........................ 202010313320.8
Sep. 27, 2020 (CN) ........................ 202011036168.X

(51) Int. Cl.

| | |
|---|---|
| *H01L 51/54* | (2006.01) |
| *C07C 211/61* | (2006.01) |
| *C07D 209/86* | (2006.01) |
| *C07D 307/91* | (2006.01) |
| *C07D 333/76* | (2006.01) |
| *H10K 85/60* | (2023.01) |
| *H10K 50/15* | (2023.01) |

(52) U.S. Cl.
CPC .......... *H10K 85/633* (2023.02); *C07C 211/61* (2013.01); *C07D 209/86* (2013.01); *C07D 307/91* (2013.01); *C07D 333/76* (2013.01); *H10K 85/636* (2023.02); *H10K 85/6574* (2023.02); *H10K 50/156* (2023.02); *H10K 85/626* (2023.02); *H10K 85/6572* (2023.02); *H10K 85/6576* (2023.02)

(58) Field of Classification Search
None
See application file for complete search history.

(56) References Cited

FOREIGN PATENT DOCUMENTS

| | | | |
|---|---|---|---|
| CN | 109535011 | A | 3/2019 |
| CN | 109928885 | A | 6/2019 |
| CN | 110128279 | A | 8/2019 |
| CN | 111518017 | A | 8/2020 |
| CN | 111699191 | A | 9/2020 |
| CN | 112110825 | A | 12/2020 |
| CN | 112266373 | A | 1/2021 |
| CN | 112759582 | A | 5/2021 |
| KR | 20190118515 | A | 10/2019 |
| KR | 20200107854 | A | 9/2020 |
| WO | 2020060271 | A1 | 3/2020 |
| WO | 2020080872 | A1 | 4/2020 |

OTHER PUBLICATIONS

International Search Report from corresponding International Application No. PCT/CN2021/082177, mailed May 17, 2021, 4 pages with translation.

Huang, Bin et al., "Organic Small Molecules Host Materials for Blue Phosphorescent Organic Light-Emitting Diodes," Chinese Journal of Organic Chemistry, dated 2013, 24 pages with machine translation.

*Primary Examiner* — Andrew K Bohaty
(74) *Attorney, Agent, or Firm* — Tucker Ellis LLP

(57) ABSTRACT

The present disclosure belongs to the field of organic materials, and relates to an arylamine compound, and an electronic component using the same and an electronic device. The arylamine compound has a structure as shown in a Formula 1. The arylamine compound of the present disclosure is applied as a hole transport material in an OLED device, such that a good device performance and a lower voltage can be obtained.

Formula 1

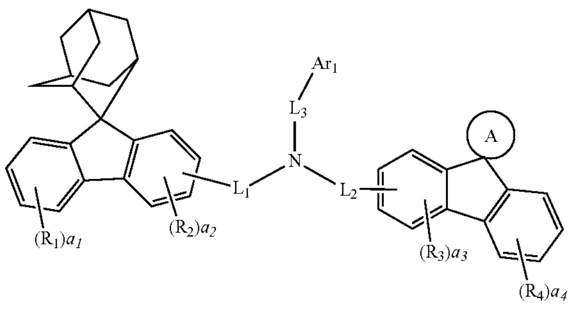

18 Claims, 2 Drawing Sheets

ARYLAMINE COMPOUND, ELECTRONIC COMPONENT USING SAME AND ELECTRONIC DEVICE

CROSS REFERENCE TO RELATED APPLICATIONS

The application claims the priority of the Chinese patent application No.

CN202010313320.8 filed on Apr. 20, 2020 and the priority of the Chinese patent application No. CN202011036168.X filed on Sep. 27, 2020, and the contents of the Chinese patent applications are hereby incorporated by reference in their entirety as a part of the application.

TECHNICAL FIELD

The present disclosure belongs to the technical field of organic materials, and particularly provides an arylamine compound, an electronic component and an electronic device using the same.

BACKGROUND

With the development of electronic technology and the progress of material science, the range of applications of electronic components for realizing electroluminescence or photoelectric conversion becomes more and more extensive. Such electronic component generally includes a cathode and an anode which are disposed oppositely, and a functional layer disposed between the cathode and the anode. The functional layer is composed of multiple organic or inorganic film layers and generally includes an energy conversion layer, a hole transport layer disposed between the energy conversion layer and the anode, and an electron transport layer disposed between the energy conversion layer and the cathode.

For example, when the electronic component is an organic electroluminescent device, the electronic component generally includes an anode, a hole transport layer, an electroluminescent layer serving as an energy conversion layer, an electron transport layer and a cathode which are sequentially stacked. When a voltage is applied to the cathode and the anode, the two electrodes generate an electric field. Under the action of the electric field, the electrons on the cathode side move to the electroluminescent layer, while the holes on the anode side also move to the electroluminescent layer, so the electrons and the holes are combined in the electroluminescent layer to form excitons, the excitons are in an excited state and release energy outwards, which in turn makes the electroluminescent layer emits light outward.

At present, when the organic electroluminescent device is driven at a high temperature, the organic electroluminescent device have problems such as increased operating voltage, reduced luminous efficiency, and shortened service life and so on, which will lead to the decline of the performance of the organic electroluminescent device.

SUMMARY

The aims of the present disclosure are to provide an organic photoelectric material with excellent performance, and the organic photoelectric material can be used as a hole transport layer in an electronic component.

In order to achieve the above purpose, in a first aspect, the present disclosure provides an arylamine compound, having a structure as shown in the following Formula 1:

Formula 1

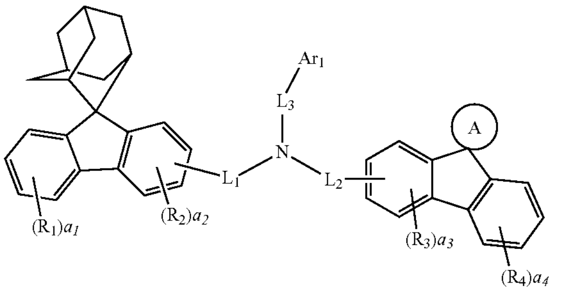

where a ring A is a substituted or unsubstituted 5- to 16-membered aliphatic hydrocarbon ring;

$L_1$, $L_2$ and $L_3$ are each independently a single bond, substituted or unsubstituted arylene with 6 to 30 carbon atoms, or substituted or unsubstituted heteroarylene with 3 to 30 carbon atoms;

$Ar_1$ is selected from the following substituted or unsubstituted groups: alkyl with 1 to 20 carbon atoms, cycloalkyl with 3 to 20 carbon atoms, aryl with 6 to 30 carbon atoms and heteroaryl with 3 to 30 carbon atoms;

$R_1$, $R_2$, $R_3$ and $R_4$ are the same or different from each other, and are each independently selected from deuterium, halogen group, cyano, cycloalkyl with 3 to 20 carbon atoms, heterocycloalkyl with 2 to 20 carbon atoms, alkyl with 1 to 20 carbon atoms, aryl with 6 to 30 carbon atoms and heteroaryl with 3 to 30 carbon atoms; and $a_1$, $a_2$, $a_3$ and as are the numbers of $R_1$, $R_2$, $R_3$ and $R_4$ respectively;

$a_1$ and $a_4$ are each independently selected from 0, 1, 2, 3 or 4, and when $a_1$ is greater than one, any two $R_1$s are the same or different, or any two adjacent $R_1$s are connected with each other to form a saturated or unsaturated ring with 3 to 15 carbon atoms; and when $a_4$ is greater than one, any two $R_4$s are the same or different, or any two adjacent $R_4$s are connected with each other to form a saturated or unsaturated ring with 3 to 15 carbon atoms;

$a_2$ and $a_3$ are each independently selected from 0, 1, 2 or 3, and when $a_2$ is greater than one, any two $R_2$s are the same or different, or any two adjacent $R_4$s are connected with each other to form a saturated or unsaturated ring with 3 to 15 carbon atoms; and when $a_3$ is greater than one, any two $R_3$s are the same or different, or any two adjacent $R_3$s are connected with each other to form a saturated or unsaturated ring with 3 to 15 carbon atoms;

the substituents in the ring A are selected from the group consisting of deuterium, halogen group, cyano, alkyl with 1 to 15 carbon atoms, aryl with 6 to 12 carbon atoms and heteroaryl with 3 to 18 carbon atoms;

the substituents in $Ar_1$, $L_1$, $L_2$ and $L_3$ are the same or different, and are each independently selected from the group consisting of deuterium, halogen group, cyano, heteroaryl with 3 to 30 carbon atoms, aryl with 6 to 30 carbon atoms which can be optionally substituted by 0, 1, 2, 3, 4 or 5 substituents selected from deuterium, fluorine, chlorine, cyano, methyl and tert-butyl, alkyl with 1 to 15 carbon atoms, cycloalkyl with 3 to 20 carbon atoms, heterocycloalkyl with 2 to 20 carbon atoms, aralkyl with 7 to 15 carbon atoms, heteroaralkyl with 4 to 15 carbon atoms, alkoxy with 1 to 30 carbon atoms, alkylthio with 1 to 30 carbon atoms, alkylsilyl with 1 to 30 carbon atoms, trialkylsilyl with 3 to 12 carbon atoms, triarylsilyl with 18 to 24 carbon atoms, aryloxy with 6 to 30 carbon atoms, and arylthio with 6 to 30 carbon atoms.

According to a second aspect of the present disclosure, provided is an electronic component, comprising an anode, a cathode which is disposed oppositely to the anode, and a functional layer disposed between the anode and the cathode; and the functional layer contains the arylamine compound.

According to a third aspect of the present disclosure, provided is an electronic device, comprising the electronic component.

The arylamine compound provided by the present disclosure has relatively large steric hindrance and firm rigidity, so that the arylamine compound has excellent thermal stability. Not only that, the arylamine compound provided by the present disclosure has two fluorene groups, and a large-steric-hindrance cycloalkyl group is spiro-bonded to fluorene, so that planar triarylamine is not easy to stack. And spiro cycloalkyl has an electron-rich effect, so that the hole mobility can be effectively improved, and the driving voltage of an electronic component is reduced. In addition, the compound provided by the present disclosure is small in intermolecular acting force, which can reduce the crystallinity of molecules, improve the film-forming property of the material, and further improve the service life of the electronic component. When the arylamine compound of the present disclosure is used as a hole transport material of the electronic component, the voltage of the device can be reduced, and the efficiency can be improved.

Other features and advantages of the present disclosure will be described in detail in the subsequent specific examples.

BRIEF DESCRIPTION OF THE DRAWINGS

The drawings are used to provide a further understanding of the present disclosure and constitute a part of the description, and are used to explain the present disclosure together with the following specific embodiments, but do not constitute limitations on the present disclosure. In the drawings.

DESCRIPTION OF REFERENCE SIGNS

Figure 1:
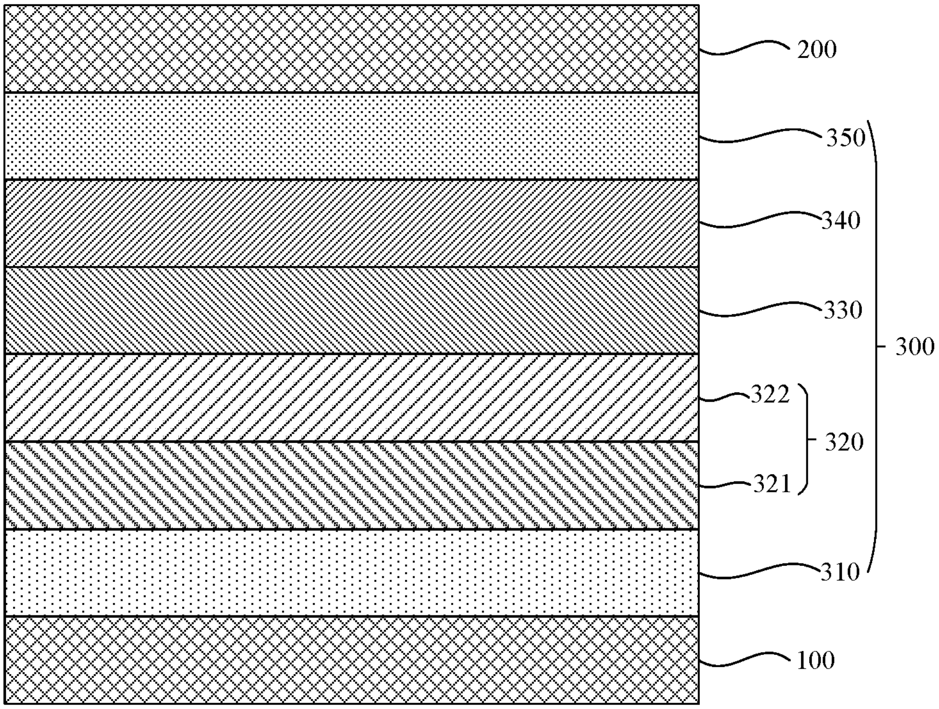
FIG. 1 is a structural schematic diagram of an organic electroluminescent device according to the embodiments of the present disclosure.

100, anode; 200, cathode; 300, functional layer; 310, hole injection layer; 320, hole transport layer; 321, first hole transport layer; 322, second hole transport layer; 330, organic light-emitting layer; 340, electron transport layer; 350, electron injection layer; 360, photoelectric conversion layer; 400, first electronic device; and 500, second electronic device.

DETAILED DESCRIPTION

The specific embodiments of the present disclosure are described in detail below in combination with the drawings.

It should be understood that the specific embodiments described herein are only used to illustrate and interpret the present disclosure, but not to limit the present disclosure.

In a first aspect, the present disclosure provides an arylamine compound, having a structure as shown in the following Formula 1:

Formula 1

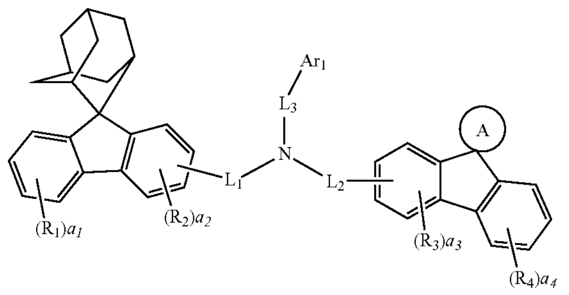

where a ring A is a substituted or unsubstituted 5- to 16-membered aliphatic hydrocarbon ring;

$L_1$, $L_2$ and $L_3$ are each independently a single bond, substituted or unsubstituted arylene with 6 to 30 carbon atoms, and substituted or unsubstituted heteroarylene with 3 to 30 carbon atoms;

$Ar_1$ is selected from the following substituted or unsubstituted groups: alkyl with 1 to 20 carbon atoms, cycloalkyl with 3 to 20 carbon atoms, aryl with 6 to 30 carbon atoms and heteroaryl with 3 to 30 carbon atoms;

$R_1$, $R_2$, $R_3$ and $R_4$ are the same or different from each other, and are each independently selected from deuterium, halogen group, cyano, cycloalkyl with 3 to 20 carbon atoms, heterocycloalkyl with 2 to 20 carbon atoms, alkyl with 1 to 20 carbon atoms, aryl with 6 to 30 carbon atoms and heteroaryl with 3 to 30 carbon atoms; and $a_1$, $a_2$, $a_3$ and a are the numbers of $R_1$, $R_2$, $R_3$ and $R_4$ respectively;

$a_1$ and $a_4$ are each independently selected from 0, 1, 2, 3 or 4, and when $a_1$ is greater than one, any two $R_1$s are the same or different, or any two adjacent $R_1$s are connected with each other to form a saturated or unsaturated ring with 3 to 15 carbon atoms; and when $a_4$ is greater than one, any two $R_4$s are the same or different, or any two adjacent $R_4$s are connected with each other to form a saturated or unsaturated ring with 3 to 15 carbon atoms;

$a_2$ and $a_3$ are each independently selected from 0, 1, 2 or 3, and when $a_2$ is greater than one, any two $R_2$s are the same or different, or any two adjacent $R_2$s are connected with each other to form a saturated or unsaturated ring with 3 to 15 carbon atoms; and when $a_3$ is greater than one, any two $R_3$s are the same or different, or any two adjacent $R_3$s are connected with each other to form a saturated or unsaturated ring with 3 to 15 carbon atoms;

the substituents in the ring A are selected from the group consisting of deuterium, halogen group, cyano, alkyl with 1 to 15 carbon atoms, aryl with 6 to 12 carbon atoms and heteroaryl with 3 to 18 carbon atoms;

the substituents in $Ar_1$, $L_1$, $L_2$ and $L_3$ are the same or different, and are each independently selected from the group consisting of deuterium, halogen group, cyano, heteroaryl with 3 to 30 carbon atoms, aryl with 6 to 30 carbon atoms which can be optionally substituted by 0, 1, 2, 3, 4 or 5 substituents selected from deuterium, fluorine, chlorine, cyano, methyl and tert-butyl, alkyl with 1 to 15 carbon atoms, cycloalkyl with 3 to 20 carbon atoms, heterocycloalkyl with 2 to 20 carbon atoms, aralkyl with 7 to 15 carbon atoms, heteroaralkyl with 4 to 15 carbon atoms, alkoxy with 1 to 30 carbon atoms, alkylthio with 1 to 30 carbon atoms, alkylsilyl with 1 to 30 carbon atoms, trialkylsilyl with 3 to 12 carbon atoms, triarylsilyl with 18 to 24 carbon atoms, aryloxy with 6 to 30 carbon atoms, and arylthio with 6 to 30 carbon atoms.

The "aryl with 6 to 30 carbon atoms which can be optionally substituted by 0, 1, 2, 3, 4 or 5 substituents selected from deuterium, fluorine, chlorine, cyano, methyl and tert-butyl" means that the aryl can be substituted by one or more of deuterium, fluorine, chlorine, cyano, methyl and tert-butyl and also can not be substituted, and when the number of substituents on the aryl is greater than or equal to two, the substituents may be the same or different.

Optionally, the substituents in $Ar_1$, $L_1$, $L_2$ and $L_3$ are the same or different, and are each independently selected from the group consisting of deuterium, halogen group, cyano, alkyl with 1 to 15 carbon atoms, cycloalkyl with 3 to 20 carbon atoms, heterocycloalkyl with 2 to 20 carbon atoms, aralkyl with 7 to 15 carbon atoms, heteroaralkyl with 4 to 15 carbon atoms, aryl with 6 to 30 carbon atoms, heteroaryl with 3 to 30 carbon atoms, alkoxy with 1 to 30 carbon atoms, alkylthio with 1 to 30 carbon atoms, alkylsilyl with 1 to 30 carbon atoms, trialkylsilyl with 3 to 12 carbon atoms, triarylsilyl with 18 to 24 carbon atoms, aryloxy with 6 to 30 carbon atoms and arylthio with 6 to 30 carbon atoms.

The arylamine compound provided by the present disclosure has relatively large steric hindrance and firm rigidity, so that the arylamine compound has excellent thermal stability. Not only that, the arylamine compound provided by the present disclosure has two fluorene groups, and a large-steric-hindrance cycloalkyl group is spiro-bonded to fluorene, so that planar triarylamine is not easy to stack. And spiro cycloalkyl has an electron-rich effect, so that the hole mobility can be effectively improved, and the driving voltage of an electronic component is reduced. In addition, the compound provided by the present disclosure is small in intermolecular acting force, which can reduce the crystallinity of molecules, improve the film-forming property of the material, and further improve the service life of the electronic component. When the arylamine compound of the present disclosure is used as a hole transport material of the electronic component, the voltage of the device can be reduced, and the efficiency can be improved.

In one specific embodiment of the present disclosure, the arylamine compound is not

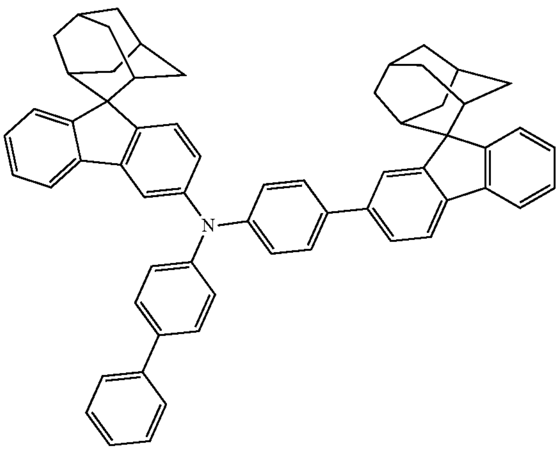

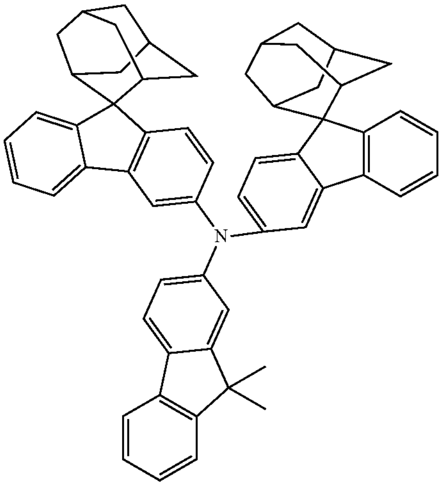

.

In the present disclosure, the ring A in the Formula 1 is a substituted or unsubstituted 5- to 16-membered aliphatic hydrocarbon ring. When the ring A is polycycloalkyl, the ring A presents different shapes due to different drawing modes. For example: when the ring A is adamantyl, the following structures

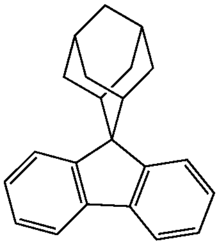

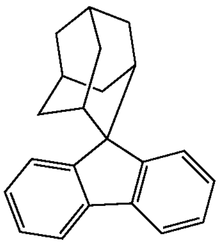

-continued

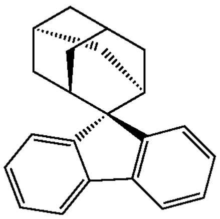

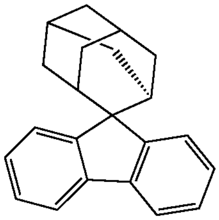

are the same.

When the ring A is norbornyl, the structures shown

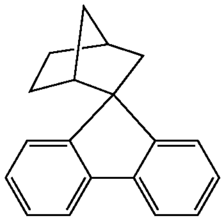

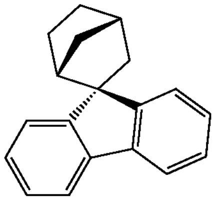

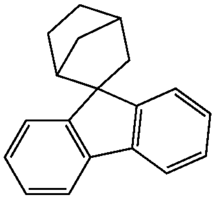

are the same.

In the present disclosure, the adopted description modes "each . . . are independently", " . . . are respectively and independently" and " . . . are independently selected from" can be interchanged, and should be understood in a broad sense, which means that in different groups, specific options expressed between the same symbols do not influence each other, or in a same group, specific options expressed between the same symbols do not influence each other. For example, the meaning of Formula Q-1

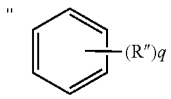

Formula Q-2

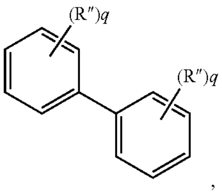

, where each q is independently 0, 1, 2 or 3, and each R" is independently selected from hydrogen, deuterium, fluorine and chlorine" is as follows: a Formula Q-1 represents that q substituents R" exist on a benzene ring, each R" can be the same or different, and options of each R" do not influence each other; and a Formula Q-2 represents that each benzene ring of biphenyl has q substituents R", the number q of the substituents R" on the two benzene rings can be the same or different, each R" can be the same or different, and options of each R" do not influence each other.

In the present disclosure, the number of carbon atoms of $L_1$, $L_2$, $L_3$, $Ar_1$, $R_1$, $R_2$, $R_3$ and $R_4$ refers to the number of all carbon atoms. For example, $L_1$ is substituted arylene with 12 carbon atoms, the number of all carbon atoms of the arylene and substituents on the arylene is 12. For example, $Ar_1$ is

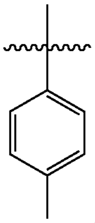

, the number of carbon atoms is 7; and $L_1$ is

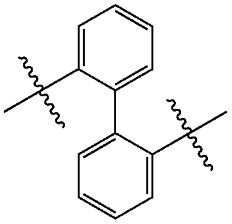

, the number of carbon atoms is 12.

In the present disclosure, the term such as "substituted or unsubstituted" means that a functional group described behind the term may have or do not have a substituent Rc. For example, "substituted or unsubstituted alkyl" refers to alkyl having the substituent Rc or unsubstituted alkyl. The substituent, namely Rc can be one or more of deuterium, cyano, halogen group, alkyl with 1 to 15 carbon atoms, cycloalkyl with 3 to 20 carbon atoms, heterocycloalkyl with 2 to 20 carbon atoms, aralkyl with 7 to 15 carbon atoms, heteroaralkyl with 4 to 15 carbon atoms, heteroaryl with 3 to 30 carbon atoms, alkoxy with 1 to 30 carbon atoms, alkylthio with 1 to 30 carbon atoms, alkylsilyl with 1 to 30 carbon atoms, trialkylsilyl with 3-12 carbon atoms, triarylsilyl with 18 to 24 carbon atoms, aryloxy with 6 to 30 carbon atoms, arylthio with 6 to 30 carbon atoms, and aryl with 6 to 30 carbon atoms which can be optionally substituted by 0, 1, 2, 3, 4 or 5 substituents selected from deuterium, fluorine, chlorine, cyano, methyl and tert-butyl. The heteroaryl and the heteroaralkyl each contain a heteroatom of at least one of B, N, O, S, Se, P and Si. In the present disclosure, the "substituted" functional group may be substituted by one or two or more substituents in the Rc, or substituted by a substituent formed by connecting two or more substituents in the Rc, and the two or more substituents may be the same as or different from each other.

In specific embodiments of the present disclosure, examples of the substituent Rc include deuterium, cyano, halogen group, alkyl with 1 to 15 carbon atoms, cycloalkyl with 3 to 20 carbon atoms, heterocycloalkyl with 2 to 20 carbon atoms, aralkyl with 7 to 15 carbon atoms, heteroaralkyl with 4 to 15 carbon atoms, aryl with 6 to 30 carbon atoms, heteroaryl with 3 to 30 carbon atoms, alkoxy with 1 to 30 carbon atoms, alkylthio with 1 to 30 carbon atoms, alkylsilyl with 1 to 30 carbon atoms, trialkylsilyl with 3 to 12 carbon atoms, triarylsilyl with 18 to 24 carbon atoms, aryloxy with 6 to 30 carbon atoms and arylthio with 6 to 30 carbon atoms.

In specific embodiments of the present disclosure, examples of the substituent Rc include deuterium, methyl, ethyl, isopropyl, tert-butyl, phenyl, naphthyl, biphenyl, terphenyl, carbazolyl, dibenzofuranyl, dibenzothienyl, cyclohexyl, pyridyl, trimethylsilyl, triphenylsilyl, fluorine, anthryl, phenanthryl, silyl, and cyano.

In the present disclosure, "alkyl" with 1 to 20 carbon atoms can be linear alkyl or branched alkyl. Specifically, the alkyl with 1 to 20 carbon atoms can be linear alkyl with 1 to 20 carbon atoms or branched alkyl with 3 to 20 carbon atoms; and can further be linear alkyl with 1 to 10 carbon atoms, or branched alkyl with 3 to 10 carbon atoms. More specifically, the alkyl with 1 to 20 carbon atoms may be methyl, ethyl, n-propyl, isopropyl, n-butyl, isobutyl, tert-butyl, n-amyl, isoamyl, neopentyl, cyclopentyl, hexyl, cyclohexyl, heptyl, octyl, 2-ethylhexyl, nonyl, decyl, 3,7-dimethyloctyl, n-dodecyl, n-tetradecyl, n-hexadecyl, n-octadecyl, and the like, but is not limited thereto. In one embodiment of the present disclosure, the alkyl may have 1 to 10 carbon atoms, in the present disclosure, the range of values such as "1 to 10" refers to each integer in a given range; for example, "1 to 10 carbon atoms" refer to alkyl which may include 1 carbon atom, 2 carbon atoms, 3 carbon atoms, 4 carbon atoms, 5 carbon atoms, 6 carbon atoms, 7 carbon atoms, 8 carbon atoms, 9 carbon atoms, or 10 carbon atoms. The alkyl may also be lower alkyl with 1 to 6 carbon atoms. In addition, the alkyl may be substituted or unsubstituted.

Preferably, alkyl is selected from alkyl with 1 to 6 carbon atoms, and specific embodiments include but are not limited to methyl, ethyl, n-propyl, isopropyl, n-butyl, isobutyl, sec-butyl, tert-butyl, amyl and hexyl.

In the present disclosure, when no specific definition is additionally provided, "hetero" means that at least one heteroatom such as B, N, O, S or P is included in one functional group, and the remaining atoms are carbon and hydrogen. The unsubstituted alkyl may be a "saturated alkyl group" without any double bond or triple bond.

"Cycloalkyl" refers to a saturated hydrocarbon group containing one or more rings in a molecular structure. In the present disclosure, cycloalkyl refers to saturated hydrocarbon containing an alicyclic structure, which includes monocyclic and fused structures. The cycloalkyl group may have 3 to 20 carbon atoms, and a numerical range such as "3 to 20" refers to each integer in the given range. For example, "3 to 20 carbon atoms" refer to cycloalkyl which may include 3 carbon atoms, 4 carbon atoms, 5 carbon atoms, 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, 15 carbon atoms, 16 carbon atoms, 17 carbon atoms, 18 carbon atoms, 19 carbon atoms, or 20 carbon atoms. The cycloalkyl may be a small ring, a ordinary ring, or a large ring with 3 to 20 carbon atoms. Cycloalkyl groups may have a structure selected from monocyclic rings (single ring), bicyclic rings (two rings), polycyclic rings (three or more rings). Cycloalkyl may also have a structure of spiro ring (two rings sharing one carbon atom-spiro ring), fused ring (two rings sharing two carbon atoms), and bridge ring (two rings sharing more than two carbon atoms). In addition, the cycloalkyl group may be substituted or unsubstituted.

Preferably, the cycloalkyl is selected from cycloalkyl with 3 to 15 carbon atoms, and specific embodiments include, but are not limited to, cyclopropyl, cyclobutyl, cyclopentyl, cyclohexyl and adamantyl.

"Heterocycloalkyl" refers to a group in which at least one carbon atom in cycloalkyl is replaced by a heteroatom N, O, P, S or Si. The number of carbon atoms in the heterocycloalkyl can be 1 to 10, and can be 3, 4, 5 or 10. Certainly, the number can be other numbers, which is not specially limited here.

In the present disclosure, "aryl" refers to an optional functional group or substituent derived from an aromatic hydrocarbon ring. The aryl may be monocyclic aryl or polycyclic aryl, in other words, the aryl can be monocyclic aryl, fused aryl, two or more monocyclic aryl conjugatedly connected through carbon-carbon bonds, monocyclic aryl and fused aryl which are conjugatedly connected through a carbon-carbon bond, and two or more fused aryl conjugatedly connected through carbon-carbon bonds. That is, two or more aromatic groups conjugatedly connected by carbon-carbon bonds may also be regarded as the aryl of the present disclosure. The aryl does not contain heteroatoms such as B, N, O, S or P. For example, in the present disclosure, phenyl, biphenyl, terphenyl, etc. are aryl. Examples of the aryl may include phenyl, naphthyl, fluorenyl, anthryl, phenanthryl, biphenyl, terphenyl, quaterphenyl, quinquephenyl, sexiphenyl, benzo[9,10]phenanthryl, pyrenyl, benzofluoranthenyl, chrysenyl, fluorenyl, phenyl-substituted naphthyl, naphthyl-substituted phenyl, phenanthryl-substituted phenyl, phenyl-substituted phenanthryl, and a combination of the above groups, and the like, but are not limited thereto. The "aryl" of the present disclosure may contain 6 to 30 carbon atoms, in some embodiments, the number of carbon atoms in the aryl may be 6 to 25, in other embodiments, the number of carbon atoms in the aryl may be 6 to 18, and in other embodiments, the number of carbon atoms in the aryl may be 6 to 13. For example, the number of carbon atoms of the aryl can be 6, 12, 13, 14, 15, 18, 20, 25 or 30, and certainly, the number of carbon atoms can also be other numbers, which will not be listed here.

In the present disclosure, the substituted aryl refers to that one or more hydrogen atoms in the aryl are substituted by other groups. For example, at least one hydrogen atom is substituted by a deuterium atom, F, Cl, Br, I, CN, hydroxyl, branched alkyl, linear alkyl, cycloalkyl, alkoxy, aryl, heteroaryl or other groups. It should be understood that the substituted aryl with 18 carbon atoms means that the total number of carbon atoms of the aryl and substituents on the aryl is 18. For example, the number of carbon atoms of 9,9-dimethylfluorenyl is 15. The substituted aryl includes but is not limited to the following groups: dibenzofuranyl-substituted phenyl, dibenzothienyl-substituted phenyl and carbazolyl-substituted phenyl.

For example, a group

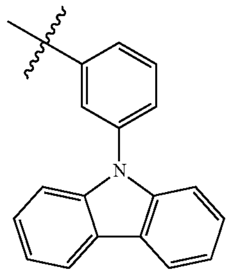 [SMILES: *c1cccc(-n2c3ccccc3c3ccccc32)c1]

is carbazolyl-substituted phenyl, and the number of carbon atoms of the group is 18; and a group

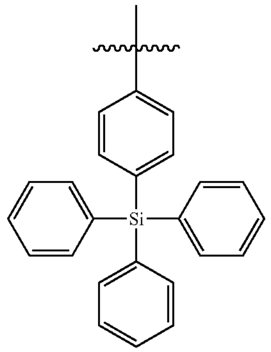 [SMILES: *c1ccc([Si](c2ccccc2)(c2ccccc2)c2ccccc2)cc1]

is triphenylsilyl-substituted phenyl, and the number of carbon atoms of the group is 24.

In specific embodiments of the present disclosure, the aryl with 6 to 30 carbon atoms can be selected from one or more of phenyl, naphthyl, pyrenyl, fluorenyl, dimethylfluorenyl, benzofluorenyl, spirobifluorenyl, anthryl, benzanthryl, fluoranthenyl, phenanthryl, chrysenyl, azulenyl, acenaphthenyl, biphenyl, terphenyl, quaterphenyl, 1,3,5-triphenylphenyl, perylenyl, triphenylene, pyrenyl, indenyl, indenofluorenyl, phenanthrylphenyl, phenylphenanthryl, phenylnaphthyl, naphthylphenyl, phenylanthryl, anthrylphenyl, phenylfluorenyl, phenylpyrenyl and pyrenylphenyl.

In the present disclosure, specific embodiments of aryl as a substituent include but are not limited to phenyl, naphthyl, phenanthryl, anthryl, biphenyl, terphenyl, triphenylene, dimethylfluorenyl and the like.

In the present disclosure, "heteroaryl" may be heteroaryl including at least one of B, O, N, P, Si, and S as a hetero atom. The heteroaryl may be monocyclic heteroaryl or polycyclic heteroaryl. In other words, the heteroaryl may be a single aromatic ring system or a multi-aromatic ring systems conjugatedly connected through carbon-carbon bonds, and any one aromatic ring system is one aromatic monocyclic ring or one aromatic fused ring. For example, the heteroaryl may include thienyl, furyl, pyrrolyl, imidazolyl, thiazolyl, oxazolyl, oxadiazolyl, triazolyl, pyridyl, bipyridyl, pyrimidinyl, triazinyl, acridinyl, pyridazinyl, pyrazinyl, quinolyl, quinazolinyl, quinoxalinyl, phenoxazinyl, phthalazinyl, pyridinopyrimidyl, pyridinopyrazinyl, pyrazinopyrazinyl, isoquinolyl, indolyl, carbazolyl, N-arylcarbazolyl (e.g., N-phenylcarbazolyl, and N-naphthylcarbazolyl), N-heteroarylcarbazolyl, N-alkylcarbazolyl, benzoxazolyl, benzimidazolyl, benzothiazolyl, benzocarbazolyl, benzothienyl, dibenzothienyl, thienothienyl, benzofuryl, phenanthrolinyl, isoxazolyl, thiadiazolyl, benzothiazolyl, phenothiazinyl, dibenzosilyl, dibenzofuranyl, phenyl-substituted dibenzofuranyl, phenyl-substituted dibenzothienyl, phenyl-substituted carbazolyl, and a combination of the above groups, and the like, but is not limited thereto. The thienyl, furyl, phenanthrolinyl and the like are heteroaryl of the single aromatic ring system, and the N-arylcarbazolyl (such as N-phenylcarbazolyl and N-naphthylcarbazolyl), N-heteroarylcarbazolyl, phenyl-substituted dibenzofuranyl and the like are heteroaryl of the multiple of aromatic ring systems conjugatedly connected through carbon-carbon bonds. The "heteroaryl" of the present disclosure may contain 3 to 30 carbon atoms, in some examples, the number of carbon atoms in the heteroaryl may be 3 to 25, in other examples, the number of carbon atoms in the heteroaryl may be 3 to 20, and in other examples, the number of carbon atoms in the heteroaryl may be 12 to 20. For example, the number of carbon atoms in the heteroaryl can be 3, 4, 5, 7, 12, 13, 18, 20, 24, 25 or 30, and certainly, the number of carbon atoms can also be other numbers, which will not be listed here.

In the present disclosure, the substituted heteroaryl means that one or more hydrogen atoms in the heteroaryl are substituted by other groups; for example, at least one hydrogen atom is substituted by a deuterium atom, a halogen group, cyano, alkyl, haloalkyl, cycloalkyl, heterocycloalkyl, aryl, alkoxy, alkylthio, aryloxy, arylthio, silyl, arylsilyl, phosphinyloxy or other groups.

In the present disclosure, specific embodiments of the heteroaryl as a substituent include, but are not limited to, dibenzofuranyl, dibenzothienyl, carbazolyl, N-phenylcarbazolyl, phenanthrolinyl, acridinyl and the like.

For example, a group

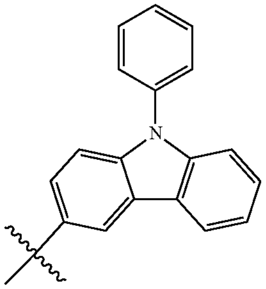 [SMILES: *c1ccc2c(c1)c1ccccc1n2-c1ccccc1]

is phenyl-substituted carbazolyl, and the number of carbon atoms of the group is 18.

In the present disclosure, the interpretation of aryl can be applied to arylene, and the interpretation of heteroaryl is also applied to heteroarylene.

In the present disclosure, the halogen group can be fluorine, chlorine, bromine or iodine.

In specific embodiments of the present disclosure, the heteroaryl with 3 to 30 carbon atoms can be selected from one or more of dibenzofuranyl, dibenzothienyl, carbazolyl, pyridyl, quinolyl, dibenzofuranylphenyl, dibenzothienylphenyl, N-phenylcarbazolyl, pyridylphenyl, triazinyl and triazinylphenyl.

In one embodiment of the present disclosure, $a_1$, $a_2$, $a_3$ and $a_4$ are each independently selected from 0, 1 or 2, and $R_1$, $R_2$, $R_3$ and $R_4$ are the same or different, and are each independently selected from the group consisting of deuterium, halogen group, cyano, cyclopentyl, cyclohexyl, phenyl, biphenyl, naphthyl, terphenyl, carbazolyl, dibenzofuranyl and dibenzothienyl.

In one embodiment of the present disclosure, $a_1$, $a_2$, $a_3$ and $a_4$ are all 0.

In one embodiment of the present disclosure, the ring A is substituted or unsubstituted cyclopentane, substituted or unsubstituted cyclohexane, substituted or unsubstituted cycloheptane, substituted or unsubstituted cyclooctane, substituted or unsubstituted norbornane, and substituted or unsubstituted adamantane.

In one embodiment of the present disclosure, the ring A is an unsubstituted 5- to 10-membered aliphatic hydrocarbon ring, and the 5- to 10-membered aliphatic hydrocarbon ring refers to an aliphatic hydrocarbon ring with 5 to 10 ring-forming carbon atoms.

In one embodiment of the present disclosure, the ring A is selected from the group consisting of groups represented by the following Formulae 2-1 to 2-4:

Formula 2-1

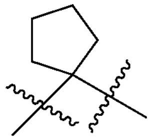

Formula 2-2

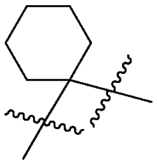

Formula 2-3

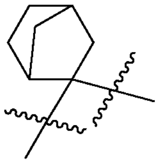

Formula 2-4

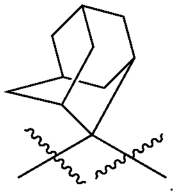

In one embodiment of the present disclosure, $L_1$, $L_2$, and $L_3$ are each independently a single bond, substituted or unsubstituted arylene with 6 to 25 carbon atoms, or substituted, and unsubstituted heteroarylene with 3 to 25 carbon atoms.

the substituents in $L_1$, $L_2$ and $L_3$ are each independently selected from deuterium, fluorine, cyano, aryl with 6 to 20 carbon atoms, heteroaryl with 12 to 20 carbon atoms, trialkylsilyl with 3 to 6 carbon atoms and triarylsilyl with 18 to 24 carbon atoms. Specifically, the substituents in $L_1$, $L_2$ and $L_3$ include but are not limited to deuterium, fluorine, cyano, phenyl, naphthyl, biphenyl, methyl, ethyl, n-propyl, isopropyl and tert-butyl.

Optionally, $L_1$, $L_2$ and $L_3$ are each independently selected from a single bond, substituted or unsubstituted arylene with 6 to 20 carbon atoms, and substituted or unsubstituted heteroarylene with 3 to 20 carbon atoms.

Preferably, $L_1$, $L_2$ and $L_3$ are each independently selected from a single bond, substituted or unsubstituted arylene with 6 to 18 carbon atoms, or substituted or unsubstituted heteroarylene with 3 to 18 carbon atoms.

Preferably, $L_1$, $L_2$ and $L_3$ are each independently selected from a single bond, substituted or unsubstituted arylene with 6 to 15 carbon atoms, or substituted or unsubstituted heteroarylene with 12 to 18 carbon atoms.

Preferably, $L_1$, $L_2$ and $L_3$ are each independently selected from a single bond and substituted or unsubstituted arylene with 6 to 12 carbon atoms.

In one specific embodiment of the present disclosure, $L_1$, $L_2$ and $L_3$ are each independently a single bond, substituted or unsubstituted phenylene, substituted or unsubstituted naphthylene, substituted or unsubstituted biphenylene, substituted or unsubstituted terphenylene, substituted or unsubstituted fluorenylidene, substituted or unsubstituted anthrylene, substituted or unsubstituted phenanthrylene, substituted or unsubstituted carbazolylidene, substituted or unsubstituted dibenzofurylidene, substituted or unsubstituted dibenzothenylidene, substituted or unsubstituted pyridylidene, substituted or unsubstituted pyrimidylidene or substituted or unsubstituted triazinylidene; or $L_1$, $L_2$ and $L_3$ are each independently selected from N-phenylcarbazolylidene.

the substituents in $L_1$, $L_2$ and $L_3$ are the same or different, and are each independently selected from deuterium, fluorine, cyano, alkyl with 1 to 5 carbon atoms and aryl with 6 to 12 carbon atoms; preferably, the substituents in $L_1$, $L_2$ and $L_3$ are each independently selected from deuterium, fluorine, cyano, methyl, ethyl, n-propyl, isopropyl, tert-butyl, phenyl, naphthyl and biphenyl.

In one embodiment of the present disclosure, $L_1$, $L_2$, and $L_3$ are each independently a single bond, or are selected from the group consisting of groups represented by chemical formulae j-1 to j-14:

j-1

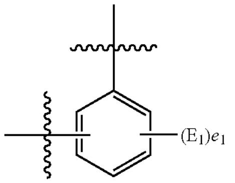

j-2

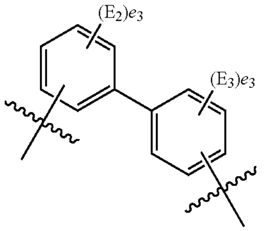

j-3

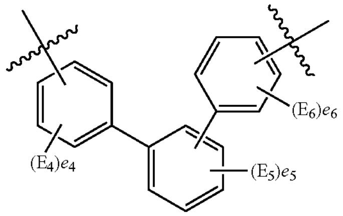

j-4

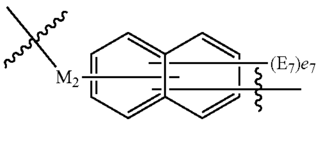

j-5

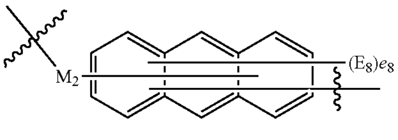

-continued j-6

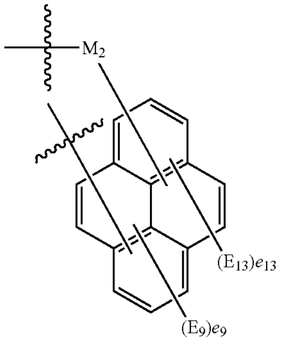

j-7

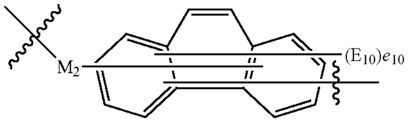

j-8

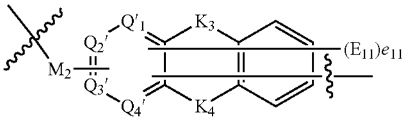

j-9

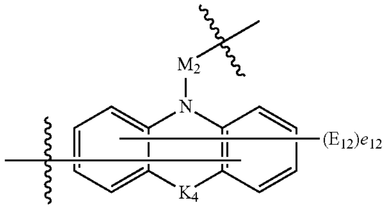

j-10

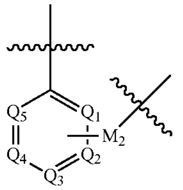

j-11

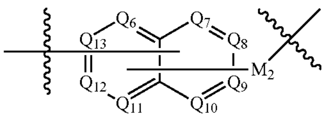

j-12

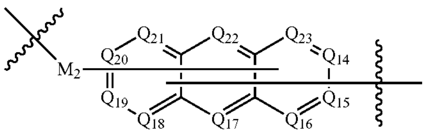

j-13

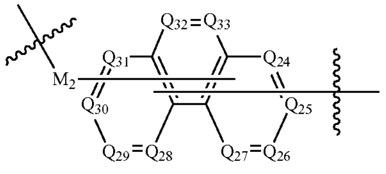

-continued j-14

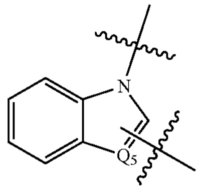

where $M_2$ is selected from a single bond or

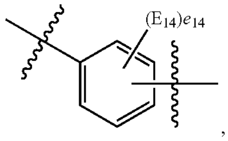

, and

and

represents a chemical bond;

$Q_1$ to $Q_5$ and $Q'_1$ to $Q'_5$ are each independently selected from N or $C(J_5)$, and at least one of $Q_1$ to $Q_5$ is selected from N; and when two or more of $Q_1$ to $Q_5$ are selected from $C(J_5)$, any two $J_5$s are the same or different, and when two or more of $Q'_1$ to $Q'_4$ are selected from $C(J_5)$, any two $J_5$s are the same or different;

$Q_6$ to $Q_{13}$ are each independently selected from N, C or $C(J_6)$, and at least one of $Q_6$ to $Q_{13}$ is selected from N; and when two or more of $Q_6$ to $Q_{13}$ are selected from $C(J_6)$, any two Jos are the same or different;

$Q_{14}$ to $Q_{23}$ are each independently selected from N, C or $C(J_7)$, and at least one of $Q_{14}$ to $Q_{23}$ is selected from N; and when two or more of $Q_{14}$ to $Q_{23}$ are selected from $C(J_7)$, any two $J_7$s are the same or different;

$Q_{24}$ to $Q_{33}$ are each independently selected from N, C or $C(J_8)$, and at least one of $Q_{24}$ to $Q_{33}$ is selected from N; and when two or more of $Q_{24}$ to $Q_{33}$ are selected from $C(J_8)$, any two Jas are the same or different;

$E_1$ to $E_{14}$ and $J_5$ to $J_9$ are each independently selected from hydrogen, deuterium, halogengroup, cyano, heteroaryl with 3 to 20 carbon atoms, aryl with 6 to 20 carbon atoms which can be optionally substituted by 0, 1, 2, 3, 4 or 5 substituents selected from deuterium, fluorine, chlorine, cyano, methyl and tert-butyl, trialkylsilyl with 3 to 12 carbon atoms, alkyl with 1 to 10 carbon atoms, haloalkyl with 1 to 10 carbon atoms, cycloalkyl with 3 to 10 carbon atoms, heterocycloalkyl with 2 to 10 carbon atoms, alkoxy with 1 to 10 carbon atoms, alkylthio with 1 to 10 carbon atoms, aryloxy with 6 to 18 carbon atoms, arylthio with 6 to 18 carbon atoms, phosphinyloxy with 6 to 18 carbon atoms, and triarylsilyl with 18 to 24 carbon atoms; the "aryl with 6 to 20 carbon atoms which can be optionally substituted by 0, 1, 2, 3, 4 or 5 substituents selected from deuterium, fluorine, chlorine, cyano, methyl, ethyl and tert-butyl" means that the aryl can be substituted by one or more of deuterium, fluorine, chlorine, cyano, methyl and tert-butyl and can also be not substituted, and when the number of substituents on the aryl is greater than or equal to two, the substituents can be the same or different.

When any one of $E_1$ to $E_{14}$ is independently selected from aryl with 6 to 20 carbon atoms, $E_1$ to $E_3$ and $E_{14}$ are not aryl;

$e_1$ to $e_{14}$ are represented by $e_r$, $E_1$ to $E_{14}$ are represented by $E_r$, r is a variable and represents any integer of 1 to 14, and $e_r$ represents the number of substituents $E_r$; when r is selected from 1, 2, 3, 4, 5, 6, 9, 13 or 14, $e_r$ is selected from 1, 2, 3 or 4; when r is selected from 7 or 11, $e_r$ is selected from 1, 2, 3, 4, 5 or 6; when r is 12, $e_r$ is selected from 1, 2, 3, 4, 5, 6 or 7; when r is selected from 8 or 10, $e_r$ is selected from 1, 2, 3, 4, 5, 6, 7 or 8; and when $e_r$ is greater than 1, any two $E_r$ are the same or different;

$K_3$ is selected from O, S, Se, $N(E_{15})$, $C(E_{16}E_{17})$ and $Si(E_{18}E_{19})$; wherein $E_{15}$, $E_{16}$, $E_{17}$, $E_{18}$ and $E_{19}$ are each independently selected from aryl with 6 to 20 carbon atoms, heteroaryl with 3 to 20 carbon atoms, alkyl with 1 to 10 carbon atoms, cycloalkyl with 3 to 10 carbon atoms, and heterocycloalkyl with 2 to 10 carbon atoms, or $E_{16}$ and $E_{17}$ are connected with each other to form a saturated or unsaturated ring with 3 to 15 carbon atoms together with atoms to which they are jointly connected, or $E_{18}$ and $E_{19}$ are connected with each other to form a saturated or unsaturated ring with 3 to 15 carbon atoms together with atoms to which they are jointly connected;

$K_4$ is selected from a single bond, O, S, Se, $N(E_{20})$, $C(E_{21}E_{22})$, and $Si(E_{23}E_{24})$; wherein $E_{20}$ to $E_{24}$ are each independently selected from aryl with 6 to 20 carbon atoms, heteroaryl with 3 to 20 carbon atoms, alkyl with 1 to 10 carbon atoms, cycloalkyl with 3 to 10 carbon atoms, and heterocycloalkyl with 2 to 10 carbon atoms, or $E_{21}$ and $E_{22}$ are connected with each other to form a saturated or unsaturated ring with 3 to 15 carbon atoms together with atoms to which they are jointly connected, or $E_{23}$ and $E_{24}$ are connected with each other to form a saturated or unsaturated ring with 3 to 15 carbon atoms together with atoms to which they are jointly connected.

In one embodiment of the present disclosure, $L_1$, $L_2$, and $L_3$ are each independently a single bond, or are selected from the group consisting of the following groups:

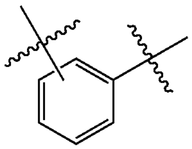

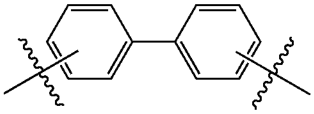

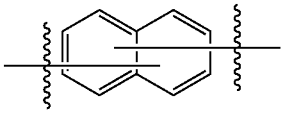

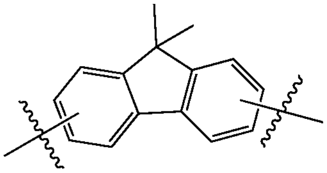

-continued

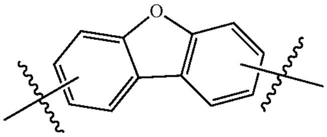

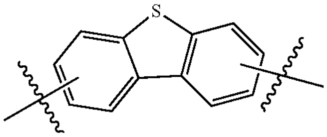

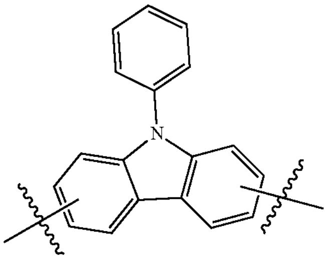

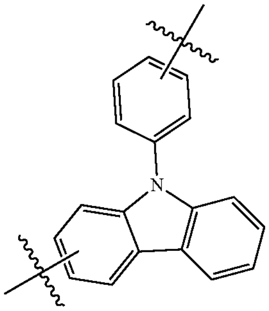

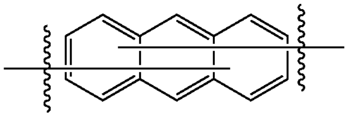

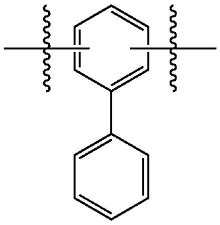

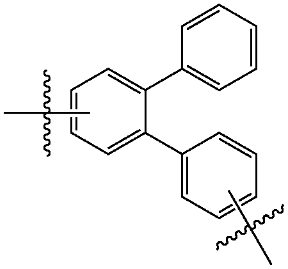

-continued
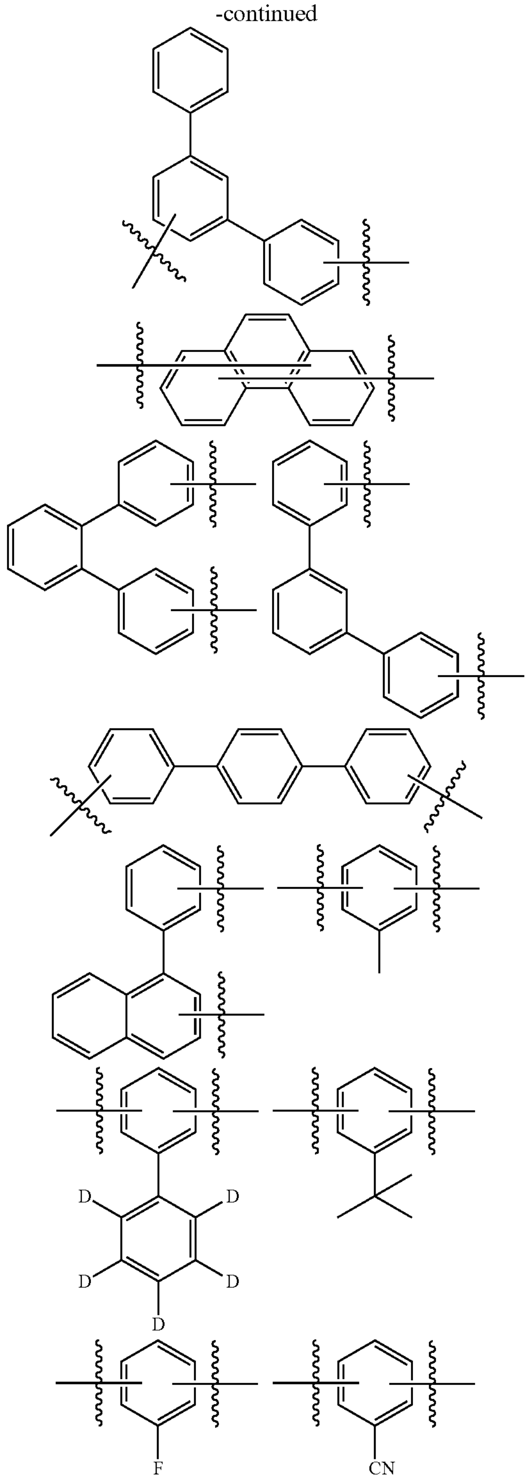
where
represents a chemical bond.
In one embodiment of the present disclosure, $L_1$, $L_2$, and $L_3$ are each independently a single bond, or are selected from the group consisting of the following groups:
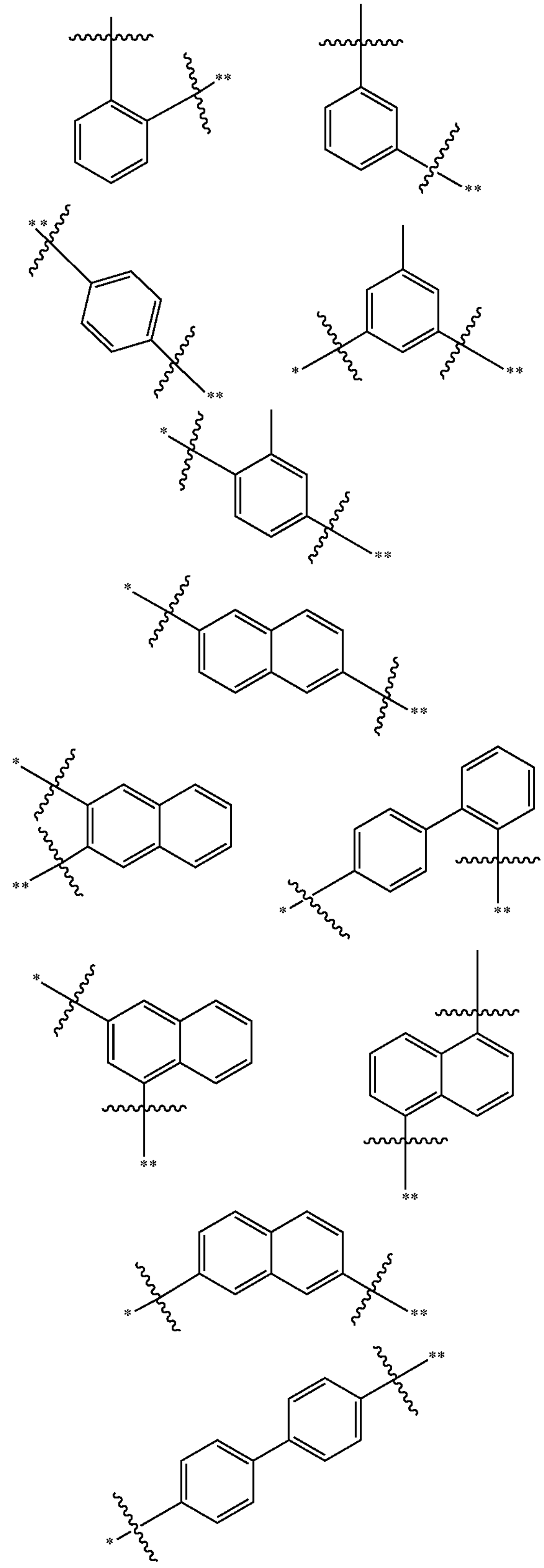

-continued
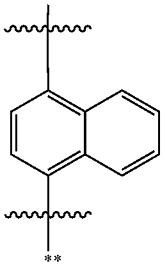
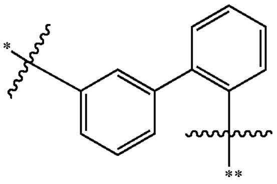
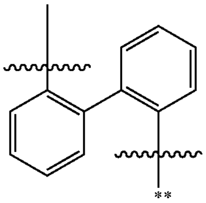
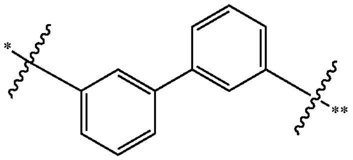
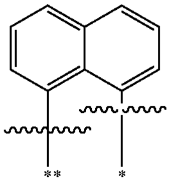
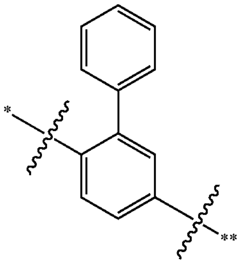
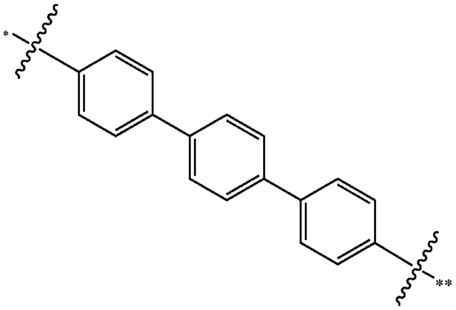
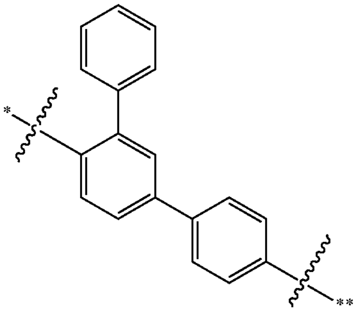
-continued
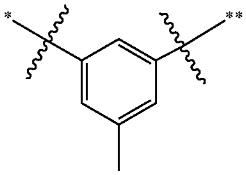
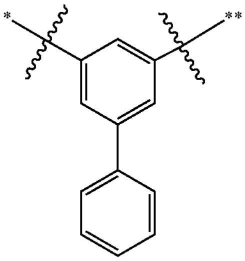
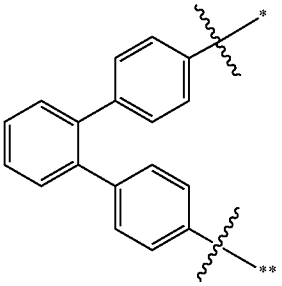
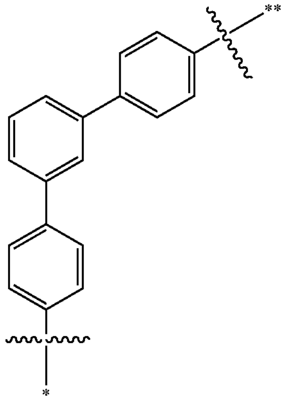
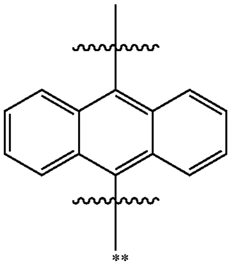
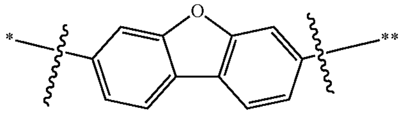
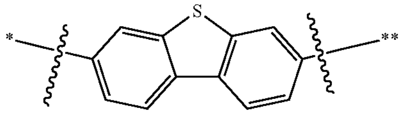
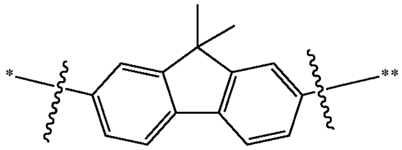
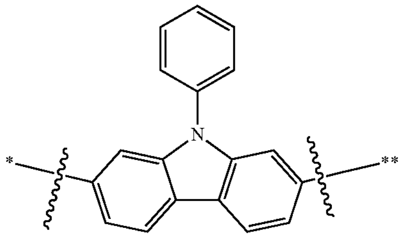
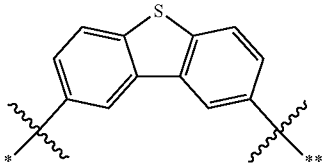

-continued
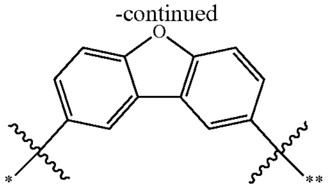
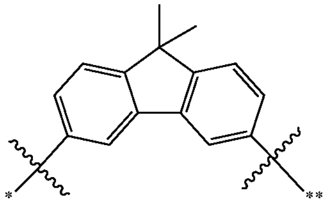
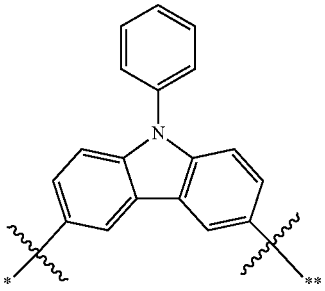
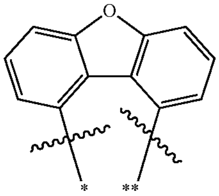
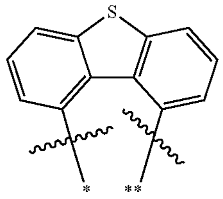
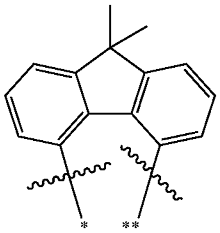
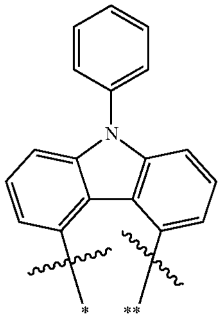
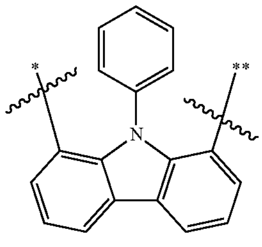
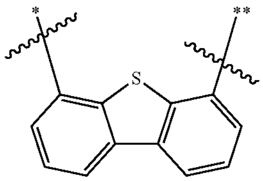
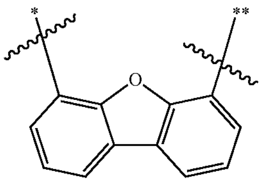
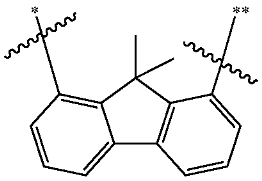
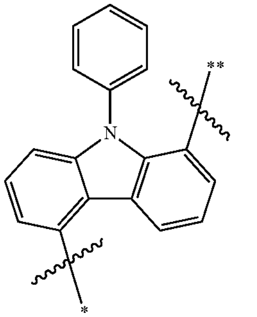
-continued
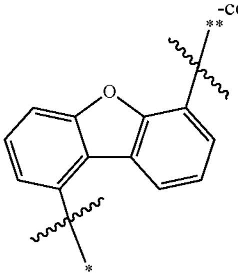
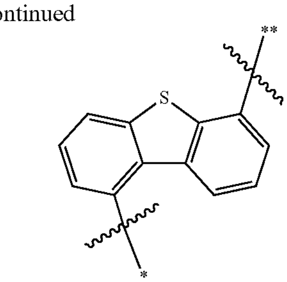
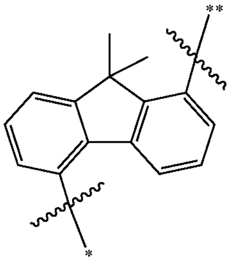
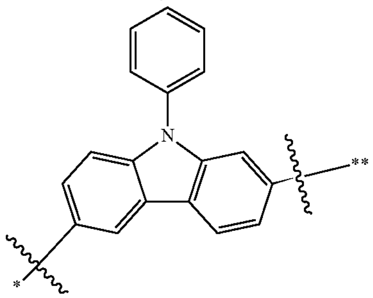
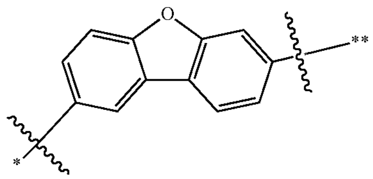
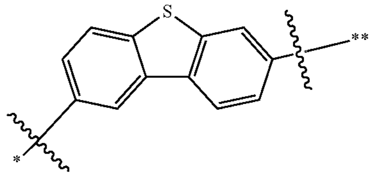
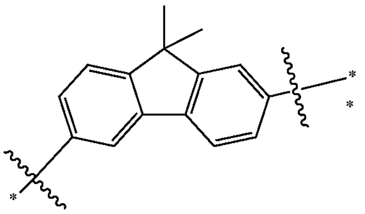
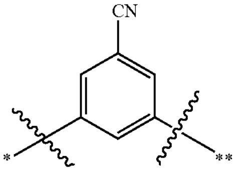
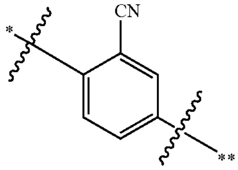
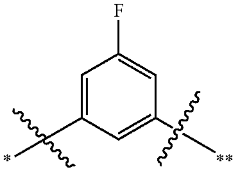
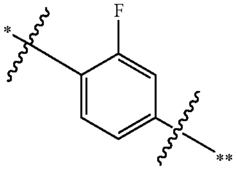

-continued

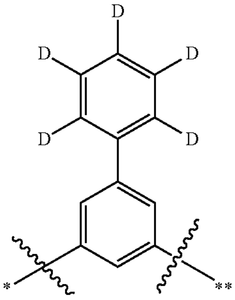

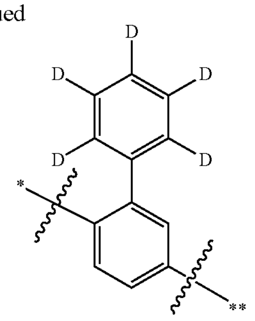

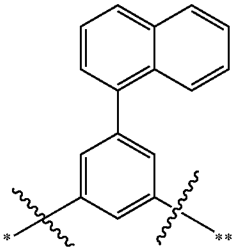

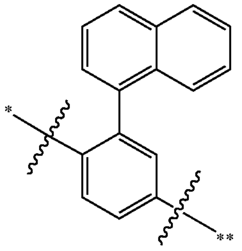

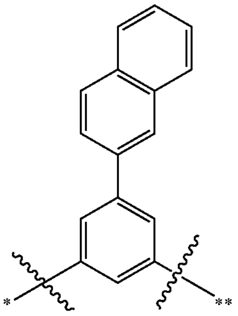

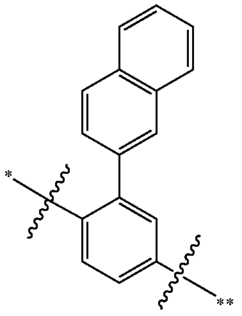

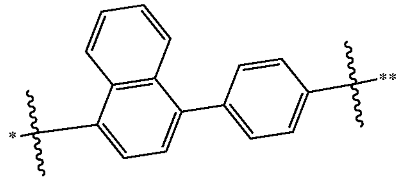

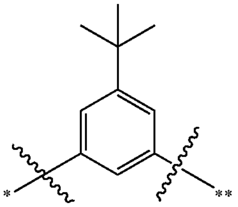

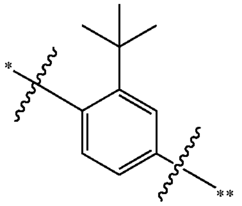

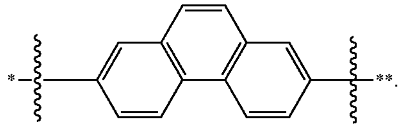

Wherein,

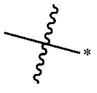 [SMILES: **]

represents a chemical bond used for bonding to a group

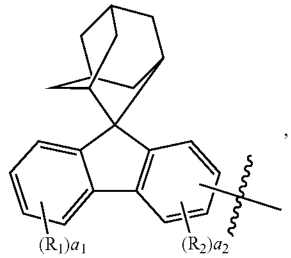

,

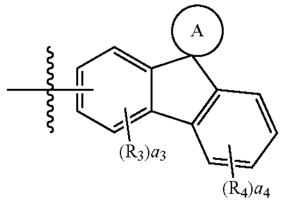

or

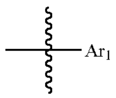

in the formula 1 in the above groups;

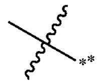

represents a chemical bond for bonding to a group

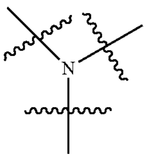 [SMILES: *N(*)*]

in the formula 1 in the above groups.

In one embodiment of the present disclosure, $Ar_1$ is selected from substituted or unsubstituted aryl with 6 to 25 carbon atoms and substituted or unsubstituted heteroaryl with 3 to 25 carbon atoms.

the substituents in $Ar_1$ are selected from deuterium, fluorine, cyano, alkyl with 1 to 5 carbon atoms, cycloalkyl with 3 to 15 carbon atoms, aryl with 6 to 20 carbon atoms, heteroaryl with 12 to 20 carbon atoms, trialkylsilyl with 3 to 6 carbon atoms and triarylsilyl with 18 to 24 carbon atoms. Specifically, the substituent in $Ar_1$ includes but is not limited to deuterium, fluorine, cyano, phenyl, naphthyl, phenanthryl, biphenyl, terphenyl, dimethylfluorenyl, dibenzofuryl, dibenzothienyl, carbazolyl, N-naphthylcarbazolyl, trimethylsilyl, triphenylsilyl, cyclopentyl, cyclohexyl and adamantyl.

Preferably, $Ar_1$ is selected from substituted or unsubstituted aryl with 6 to 20 carbon atoms and substituted or unsubstituted heteroaryl with 5 to 20 carbon atoms.

Preferably, the substituent in $Ar_1$ includes but is not limited to deuterium, fluorine, cyano, phenyl, naphthyl, phenanthryl, biphenyl, terphenyl, dimethylfluorenyl, phenanthrolinyl, dibenzofuryl, dibenzothienyl, carbazolyl, N-phenylcarbazolyl, N-naphthylcarbazolyl, trimethylsilyl and triphenylsilyl.

In one embodiment of the present disclosure, $Ar_1$ is selected from the group consisting of, but is not limited to, the following groups:

-continued
i-1
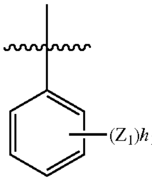
i-2
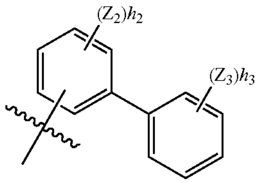
i-3
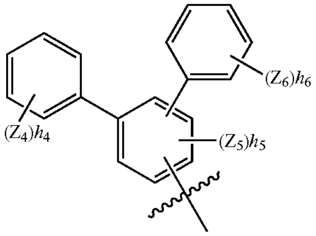
i-4
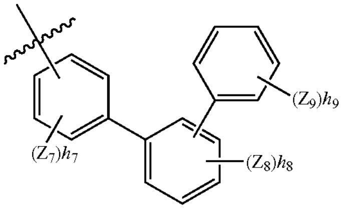
i-5
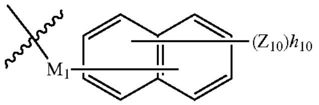
i-6
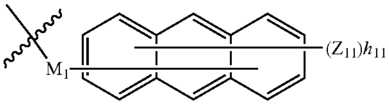
i-7
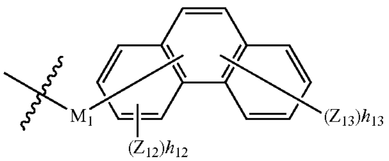
i-8
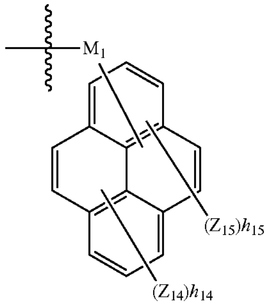
i-9
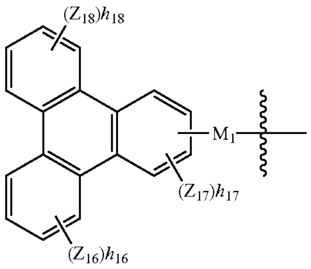
i-10
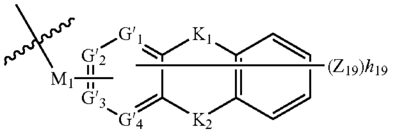
i-11
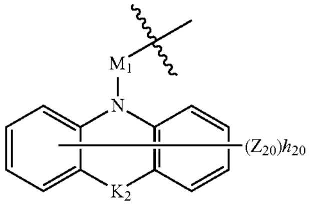
i-12
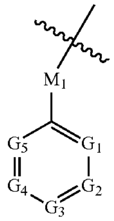
i-13
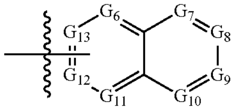
i-14
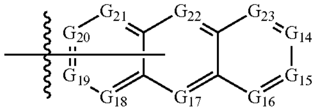
i-15
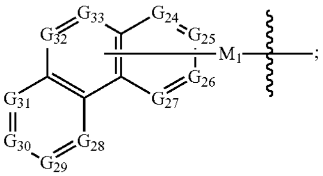
where $M_1$ is selected from a single bond or
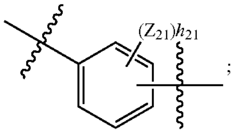
$G_1$ to $G_5$ and $G'_1$ to $G'_4$ are each independently selected from N. C or $C(J_1)$, at least one of $G_1$ to $G_5$ is selected from N, and when two or more of $G_1$ to $G_5$ are selected from $C(J_1)$, any two $J_1$s are the same or different;

$G_6$ to $G_{13}$ are each independently selected from N, C or $C(J_2)$, and at least one of $G_6$ to $G_{13}$ is selected from N; and when two or more of $G_6$ to $G_{13}$ are selected from $C(J_2)$, any two $J_2$s are the same or different;

$G_{14}$ to $G_{23}$ are each independently selected from N, C or $C(J_3)$, and at least one of $G_{14}$ to $G_{23}$ is selected from N; and when two or more of $G_{14}$-$G_{23}$ are selected from $C(J_3)$, any two Jas are the same or different;

$G_{24}$ to $G_{33}$ are each independently selected from N, C or $C(J_4)$, and at least one of $G_{24}$ to $G_{33}$ is selected from N; and when two or more of $G_{24}$ to $G_{33}$ are selected from $C(J_4)$, any two $J_4$s are the same or different;

$Z_1$ is selected from hydrogen, deuterium, halogen group, cyano, trialkylsilyl with 3 to 12 carbon atoms, alkyl with 1 to 10 carbon atoms, haloalkyl with 1 to 10 carbon atoms, cycloalkyl with 3 to 10 carbon atoms, alkoxy with 1 to 10 carbon atoms, alkylthio with 1 to 10 carbon atoms and triarylsilyl with 18 to 24 carbon atoms;

$Z_2$ to $Z_9$ and $Z_{21}$ are each independently selected from hydrogen, deuterium, halogen group, cyano, trialkylsilyl with 3 to 12 carbon atoms, alkyl with 1 to 10 carbon atoms, haloalkyl with 1 to 10 carbon atoms, cycloalkyl with 3 to 10 carbon atoms, alkoxy with 1 to 10 carbon atoms, alkylthio with 1 to 10 carbon atoms, heteroaryl with 3 to 18 carbon atoms and triarylsilyl with 18 to 24 carbon atoms;

$Z_{10}$ to $Z_{20}$ and $J_1$ to $J_4$ are each independently selected from hydrogen, deuterium, halogen group, cyano, trialkylsilyl with 3 to 12 carbon atoms, alkyl with 1 to 10 carbon atoms, haloalkyl with 1 to 10 carbon atoms, cycloalkyl with 3 to 10 carbon atoms, alkoxy with 1 to 10 carbon atoms, alkylthio with 1 to 10 carbon atoms, aryl with 6 to 18 carbon atoms which can be optionally substituted by 0, 1, 2, 3, 4 or 5 substituents selected from deuterium, fluorine, chlorine, cyano, methyl, ethyl and tert-butyl, heteroaryl with 3 to 18 carbon atoms, and triarylsilyl with 18 to 24 carbon atoms; in the present disclosure, "aryl with 6 to 18 carbon atoms which can be optionally substituted by 0, 1, 2, 3, 4 or 5 substituents selected from deuterium, fluorine, chlorine, cyano, methyl, ethyl and tert-butyl" means that the aryl can be substituted by one or more of deuterium, fluorine, chlorine, cyano, methyl and tert-butyl and can also be not substituted, and when the number of substituents on the aryl is greater than or equal to two, the substituents may be the same or different.

$h_1$ to $h_{21}$ are represented by $h_k$, $Z_1$ to $Z_{21}$ are represented by $Z_k$, k is a variable and represents any integer of 1 to 21, and $h_k$ represents the number of substituents $Z_k$; when k is selected from 5 or 17, $h_k$ is selected from 1, 2 or 3; when k is selected from 2, 7, 8, 12, 15, 16, 18 or 21, $h_k$ is selected from 1, 2, 3 or 4; when k is selected from 1, 3, 4, 6, 9 or 14, $h_k$ is selected from 1, 2, 3, 4 or 5; when k is 13, $h_k$ is selected from 1, 2, 3, 4, 5 or 6; when k is selected from 10 or 19, $h_k$ is selected from 1, 2, 3, 4, 5, 6 or 7; when k is 20, $h_k$ is selected from 1, 2, 3, 4, 5, 6, 7 or 8; when k is 11, $h_k$ is selected from 1, 2, 3, 4, 5, 6, 7, 8 or 9; and when $h_k$ is greater than one, any two $Z_k$ are the same or different;

$K_1$ is selected from O, S, $N(Z_{22})$, $C(Z_{23}Z_{24})$ and $Si(Z_{28}Z_{29})$; wherein $Z_{22}$, $Z_{23}$, $Z_{24}$, $Z_{28}$ and $Z_{29}$ are each independently selected from aryl with 6 to 18 carbon atoms, heteroaryl with 3 to 18 carbon atoms, alkyl with 1 to 10 carbon atoms or cycloalkyl with 3 to 10 carbon atoms, or the $Z_{23}$ and the $Z_{24}$ are connected with each other to form a saturated or unsaturated ring with 3 to 15 carbon atoms together with atoms to which they are jointly connected, or the $Z_{28}$ and the $Z_{29}$ are connected with each other to form a saturated or unsaturated ring with 3 to 15 carbon atoms together with atoms to which they are jointly connected;

$K_2$ is selected from a single bond, O, S, $N(Z_{25})$, $C(Z_{26}Z_{27})$, and $Si(Z_{30}Z_{31})$; wherein $Z_{25}$, $Z_{26}$, $Z_{27}$, $Z_{30}$ and $Z_{31}$ are each independently selected from aryl with 6 to 18 carbon atoms, heteroaryl with 3 to 18 carbon atoms, alkyl with 1 to 10 carbon atoms or cycloalkyl with 3 to 10 carbon atoms, or the $Z_{26}$ and the $Z_{27}$ are connected with each other to form a saturated or unsaturated ring with 3 to 15 carbon atoms together with atoms to which they are jointly connected, or the $Z_{30}$ and the $Z_{31}$ are connected with each other to form a saturated or unsaturated ring with 3 to 15 carbon atoms together with atoms to which they are jointly connected. In the present disclosure, the ring refers to a saturated or unsaturated ring, such as

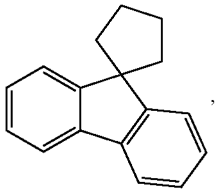
,
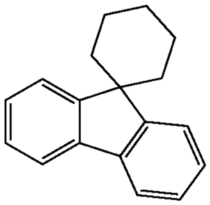
and
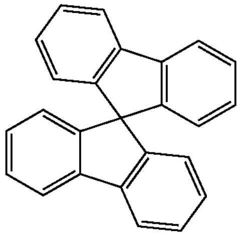
, but is not limited thereto.

Optionally, the above formed ring is a 3- to 10-membered ring.

In one embodiment of the present disclosure, $Ar_1$ is selected from the group consisting of the following groups:

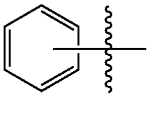
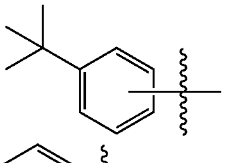
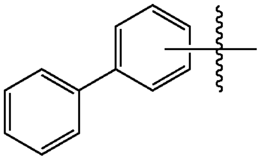
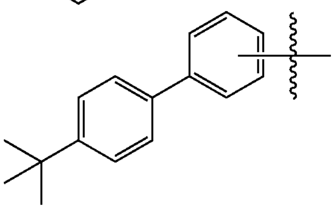

-continued
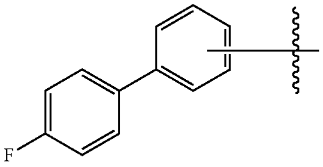
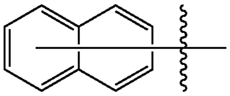
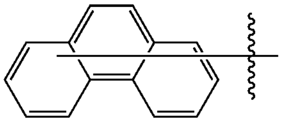
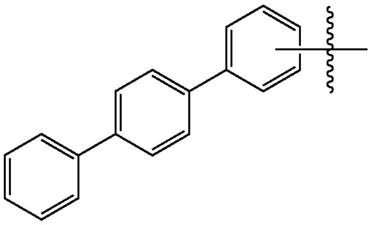
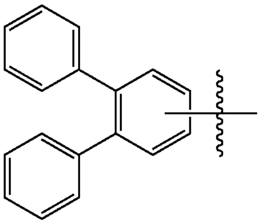
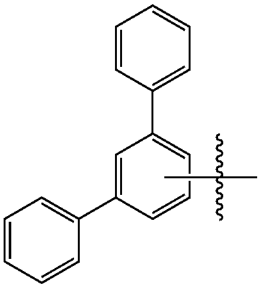
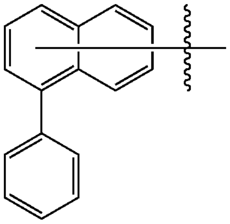
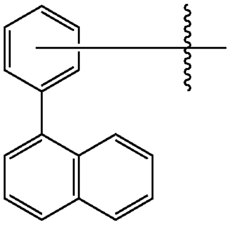
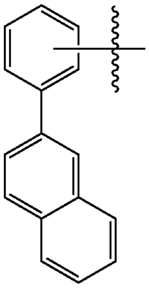
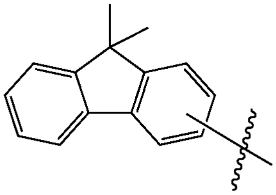
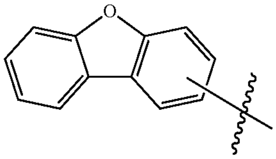
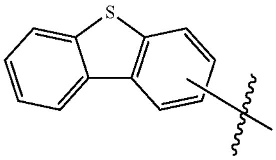
-continued
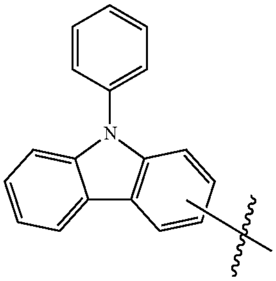
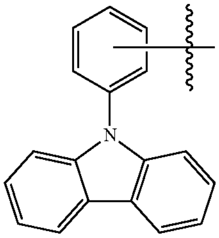
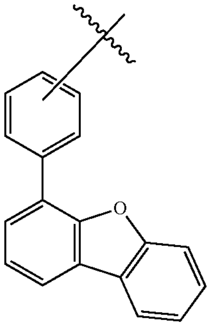
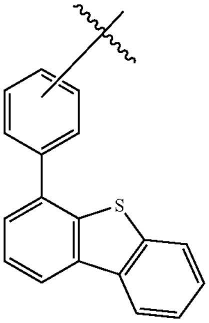
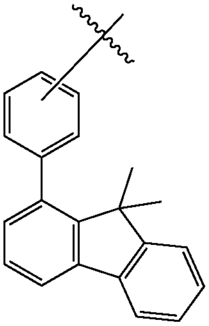
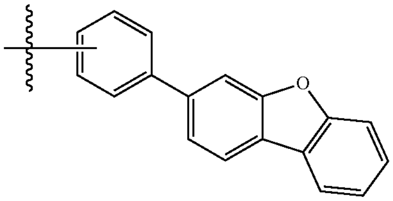
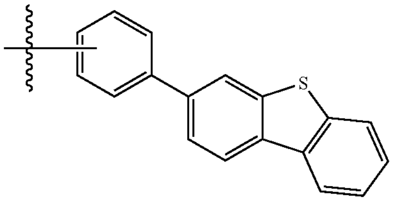
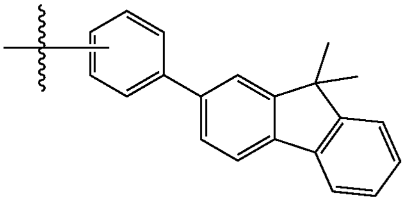

-continued
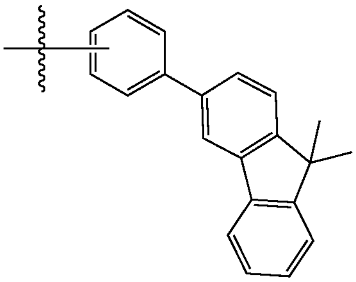
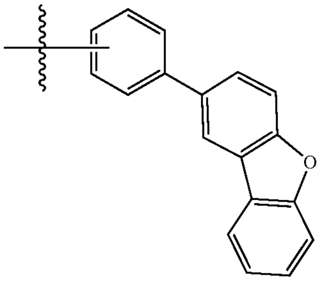
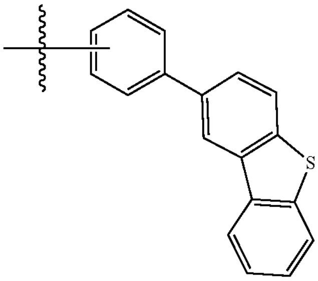
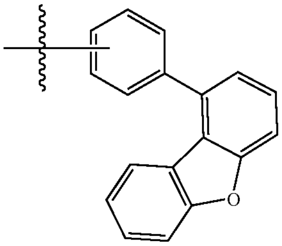
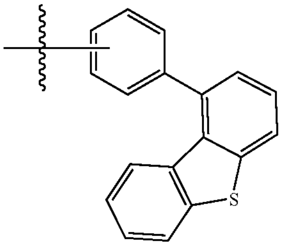
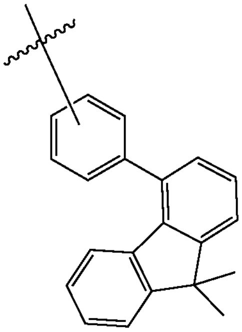
-continued
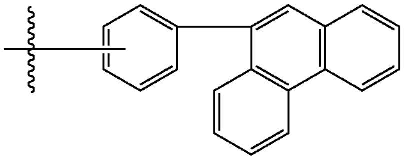
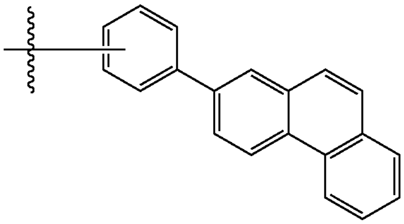
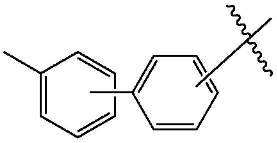
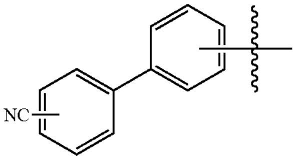
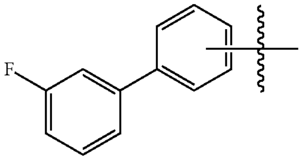
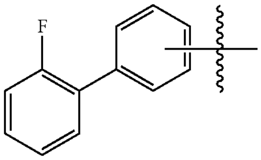
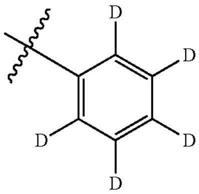
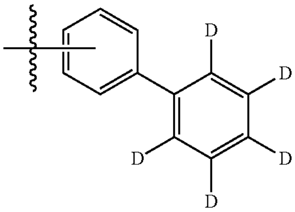
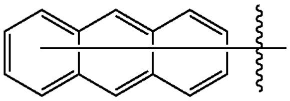
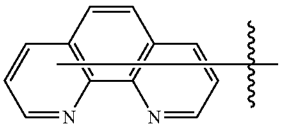
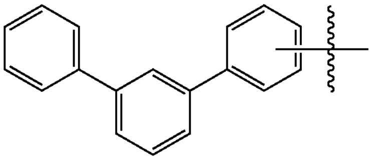

-continued
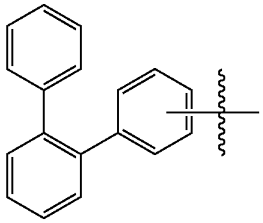
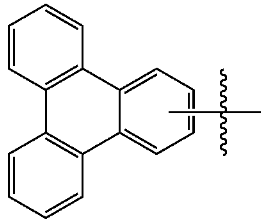
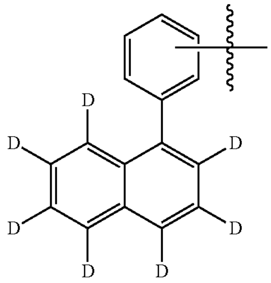
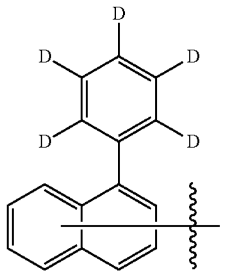
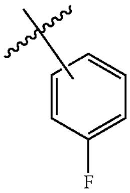
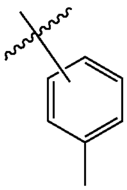
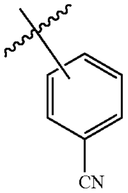
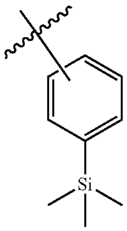
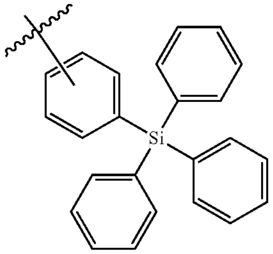
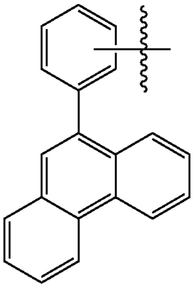
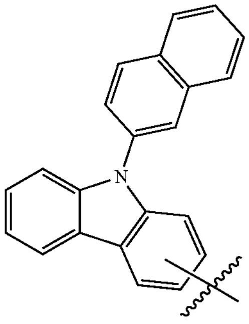
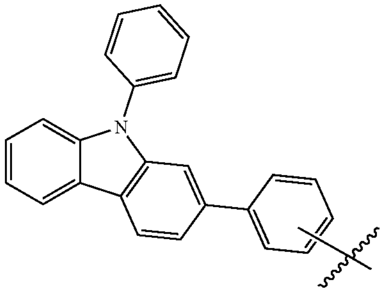
-continued
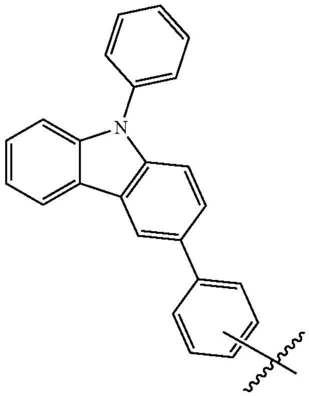
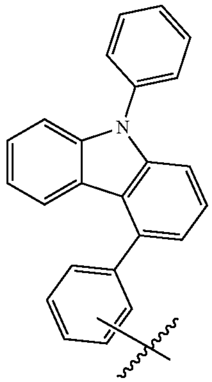
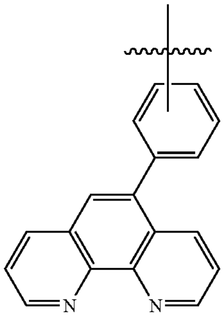
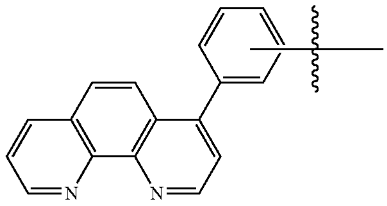
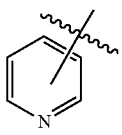
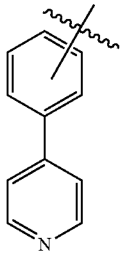
.
In one embodiment of the present disclosure, $Ar_1$ is selected from the group consisting of, but is not limited to, the following groups:

-continued
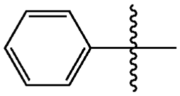
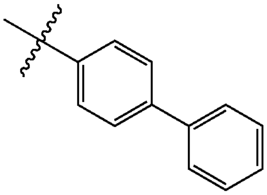
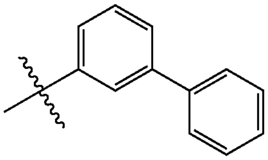
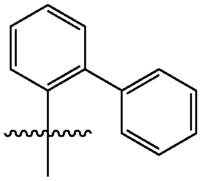
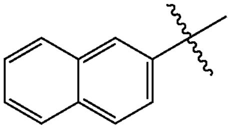
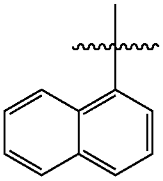
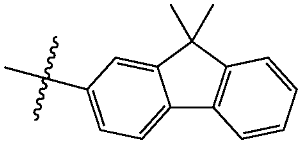
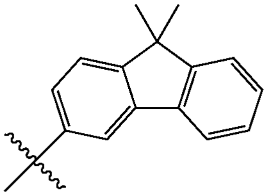
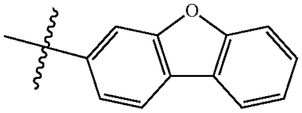
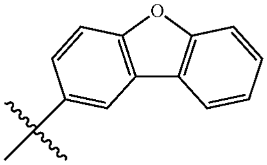
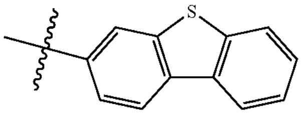
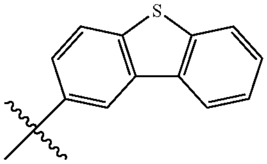
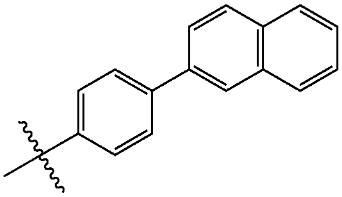
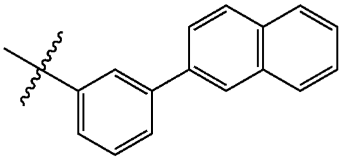
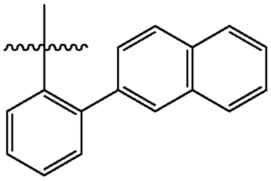
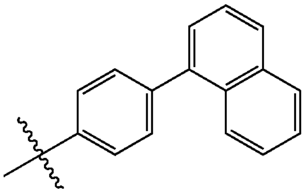
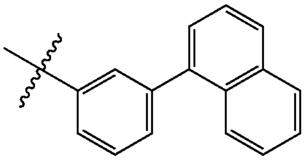
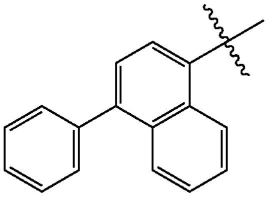
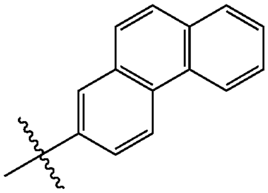
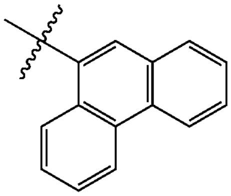
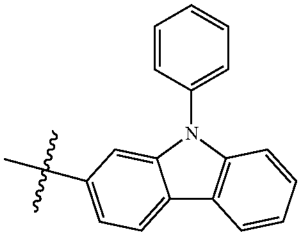
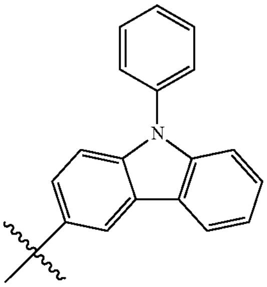
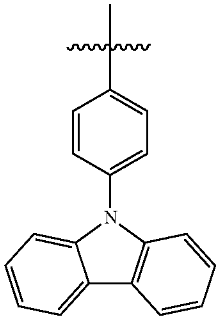
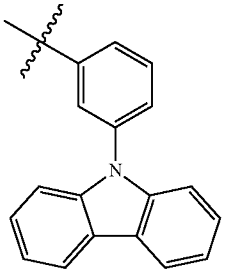
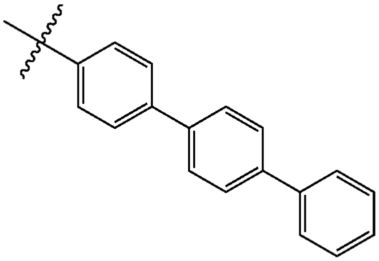

-continued
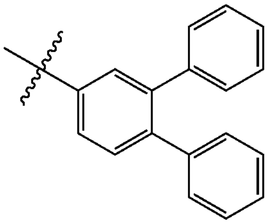
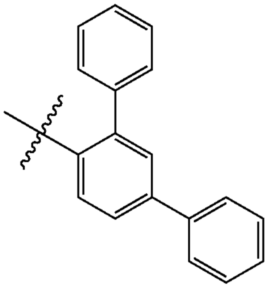
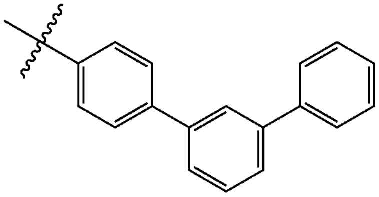
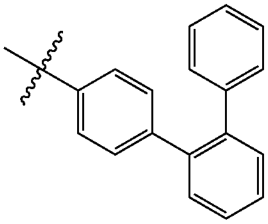
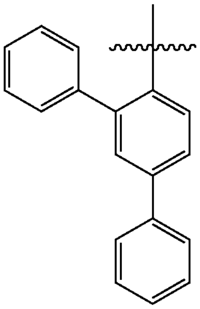
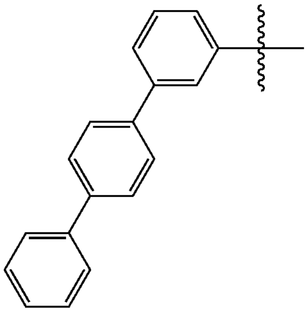
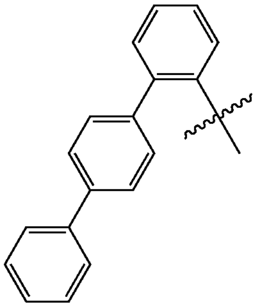
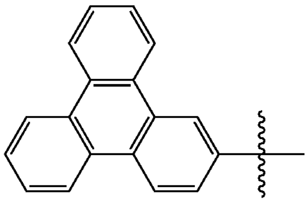
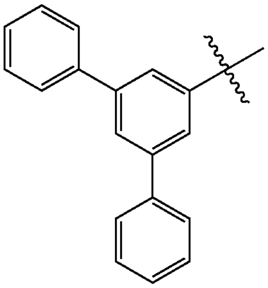
-continued
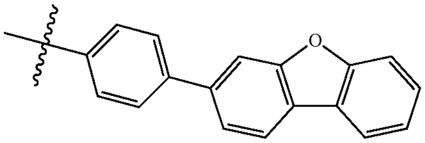
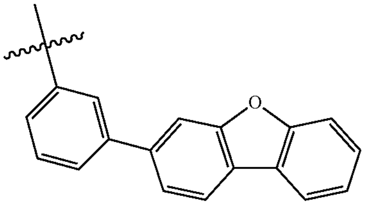
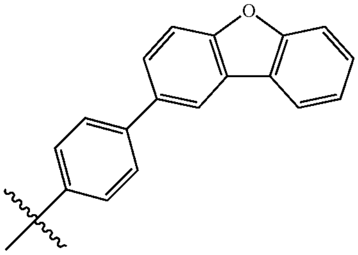
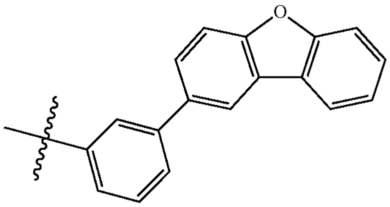
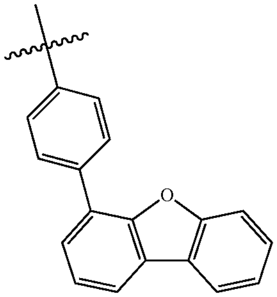
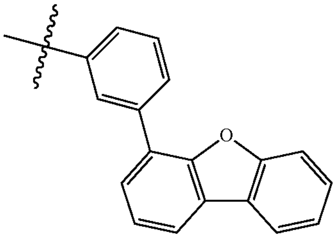
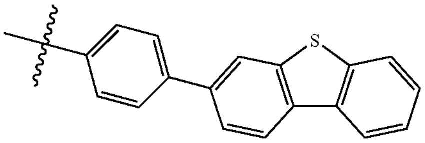
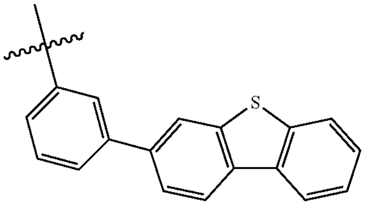

-continued
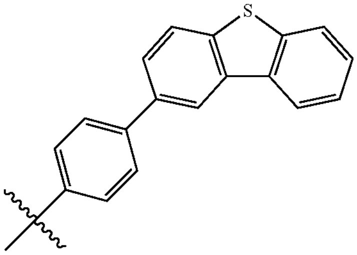
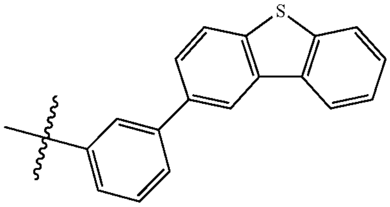
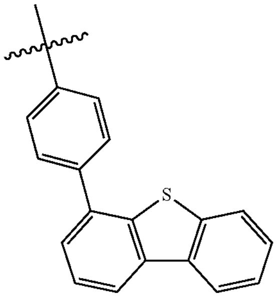
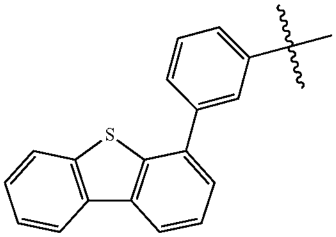
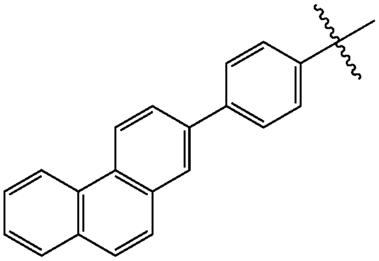
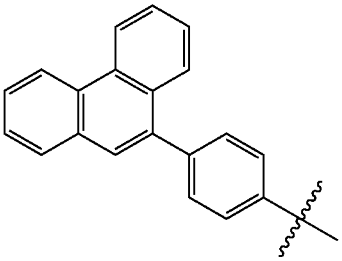
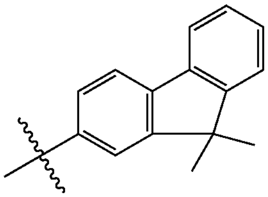
-continued
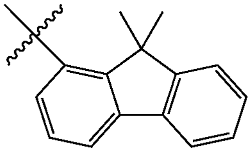
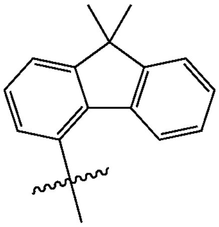
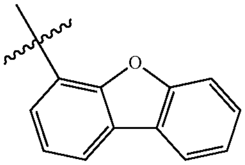
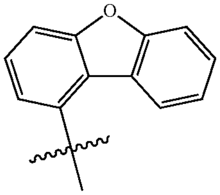
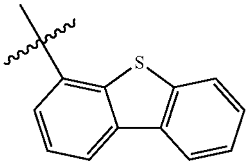
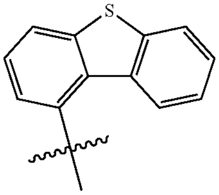
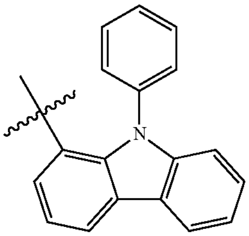
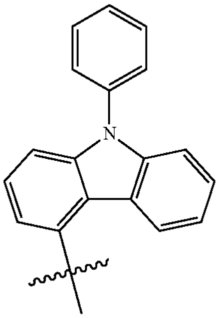
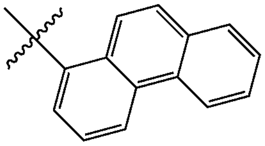
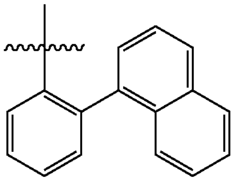
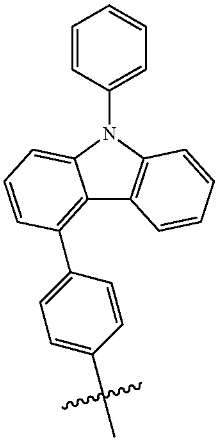
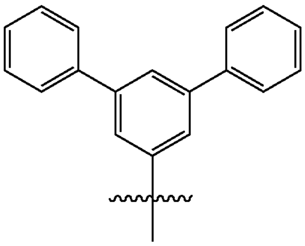

-continued
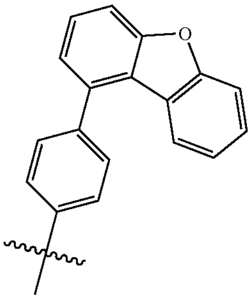
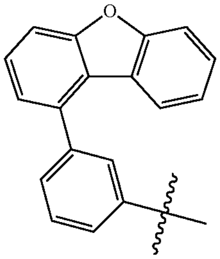
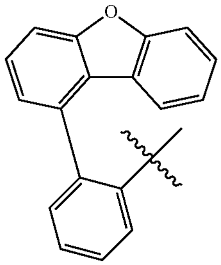
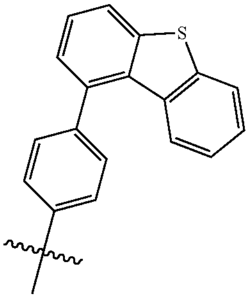
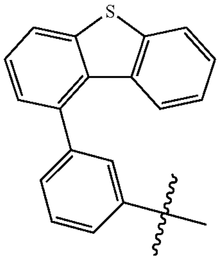
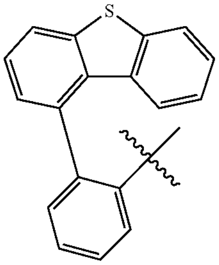
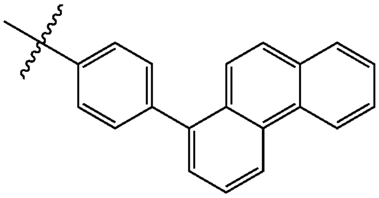
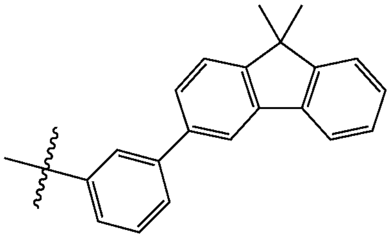
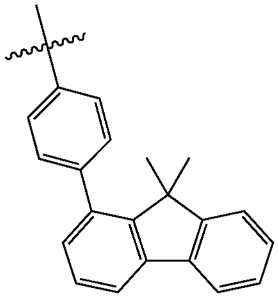
-continued
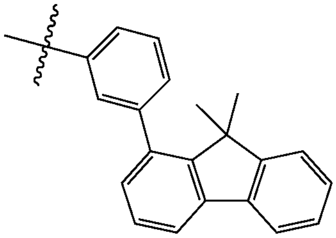
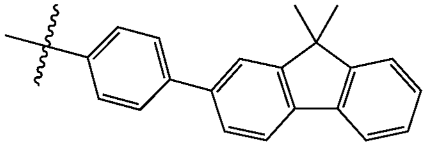
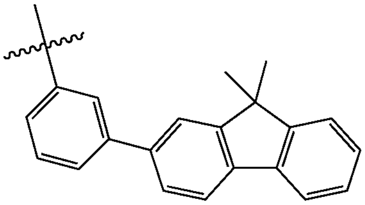
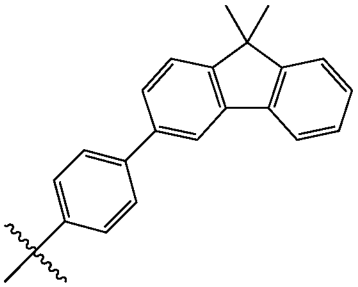
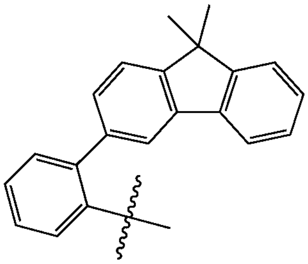
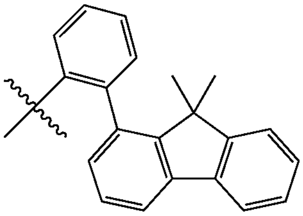
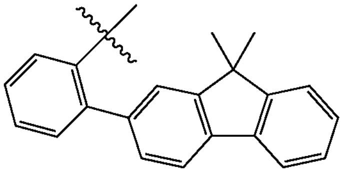

-continued
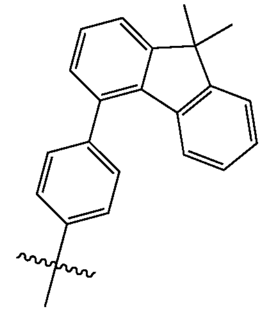
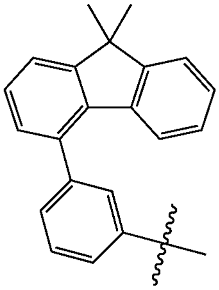
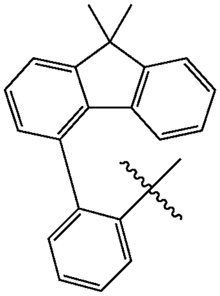
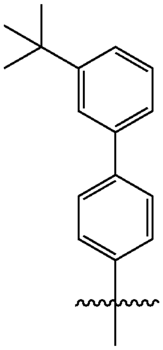
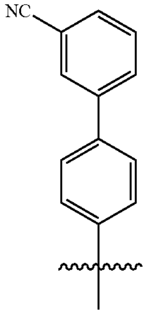
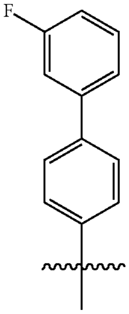
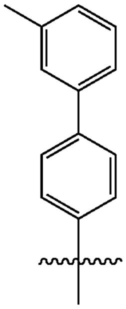
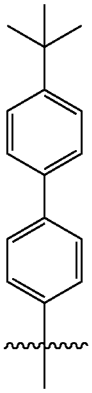
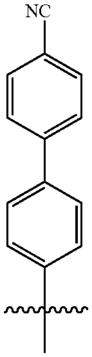
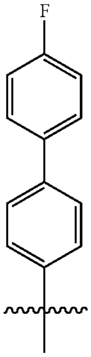
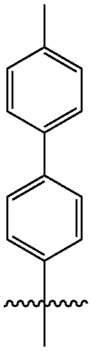
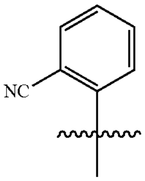
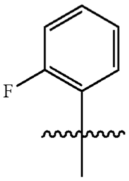
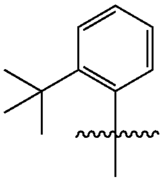
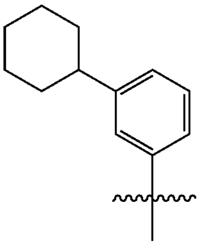
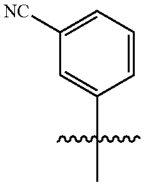
-continued
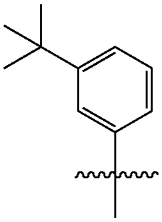
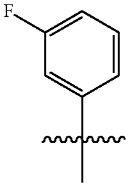
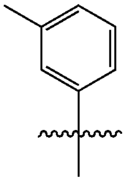
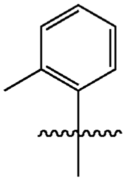
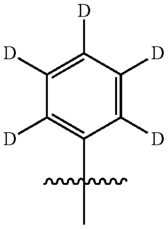
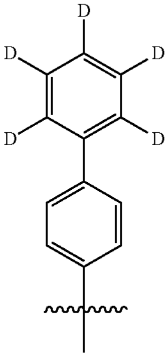
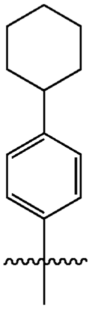
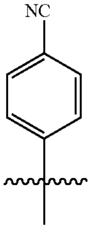
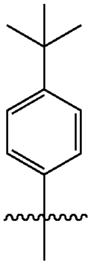
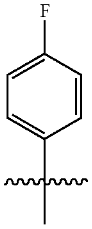
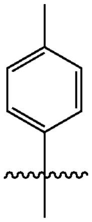
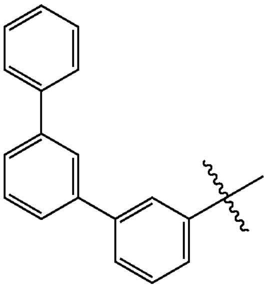
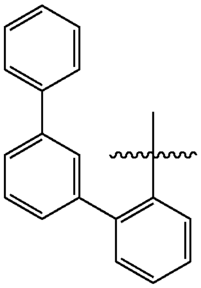
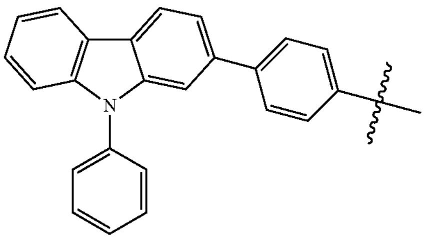

-continued
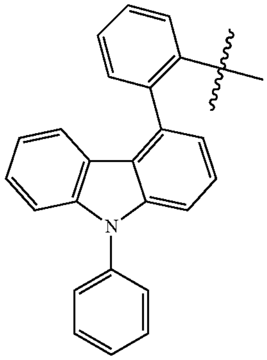
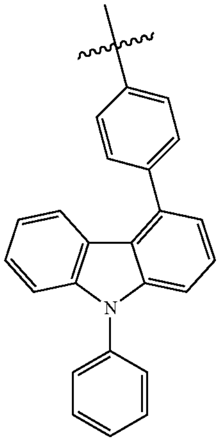
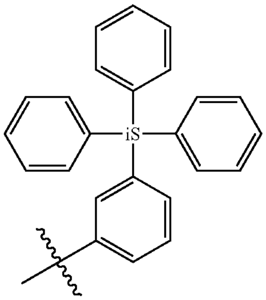
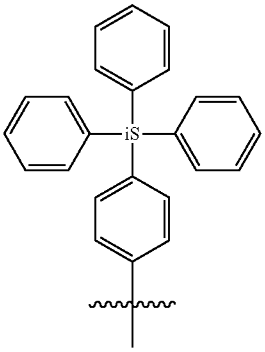
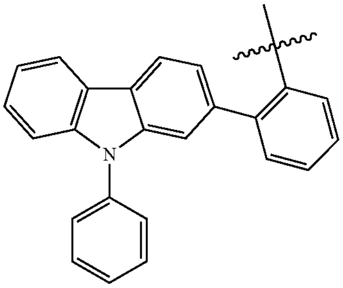
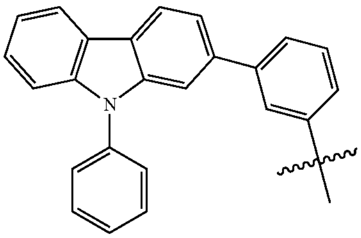
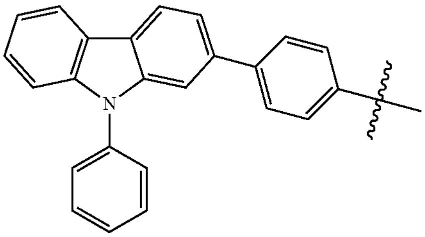
-continued
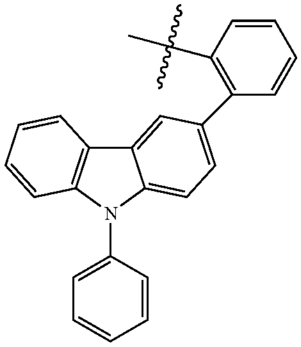
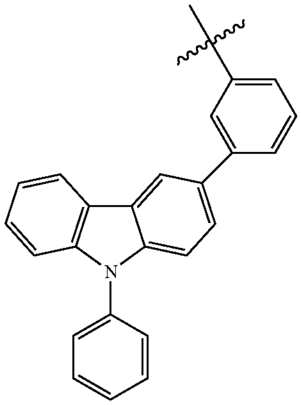
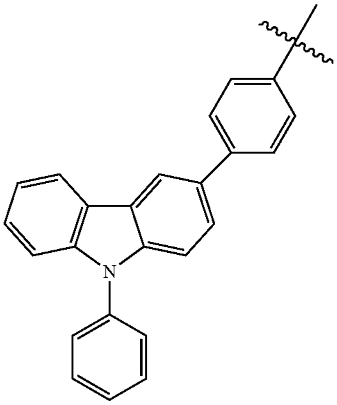
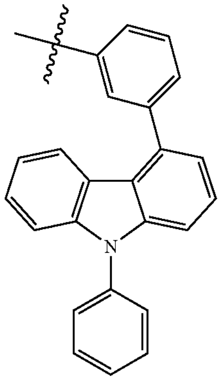
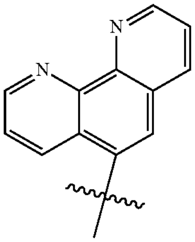
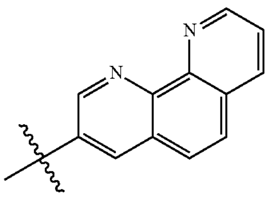
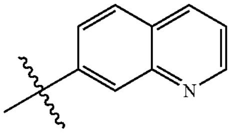
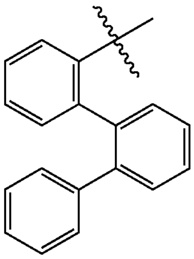

-continued

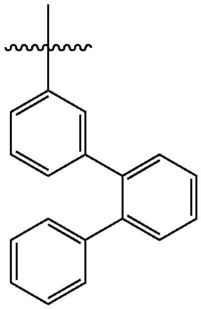
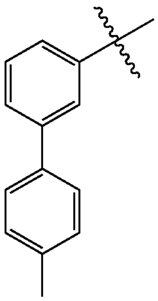
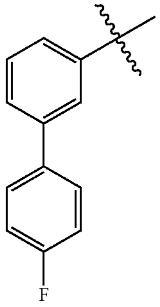
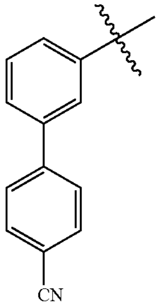
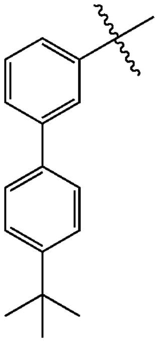
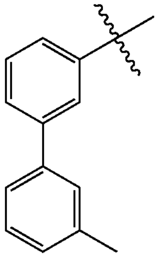
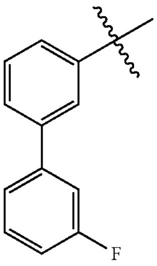
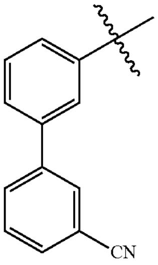
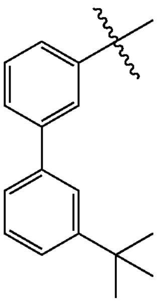

In one embodiment of the present disclosure, the substituents in $Ar_1$, $L_1$, $L_2$ and $L_3$ are the same or different, and are each independently selected from the group consisting of deuterium, fluorine, cyano, trialkylsilyl with 3 to 10 carbon atoms, triarylsilyl with 18 to 24 carbon atoms, alkyl with 1-5 carbon atoms, aryl with 6 to 12 carbon atoms and heteroaryl with 3 to 18 carbon atoms.

Preferably, the substituents in $Ar_1$, $L_1$, $L_2$ and $L_3$ are the same or different, and are each independently selected from deuterium, fluorine, cyano, alkyl with 1 to 4 carbon atoms, cycloalkyl with 3 to 15 carbon atoms, aryl with 6 to 12 carbon atoms, heteroaryl with 12 to 18 carbon atoms, trialkylsilyl with 3 to 12 carbon atoms and triarylsilyl with 18 to 24 carbon atoms.

In one embodiment of the present disclosure, the arylamine compound is selected from the group consisting of, but is not limited to, the following compounds:

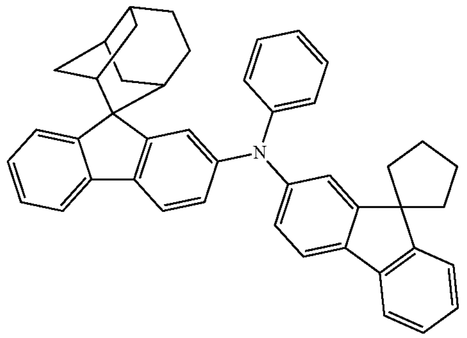
1

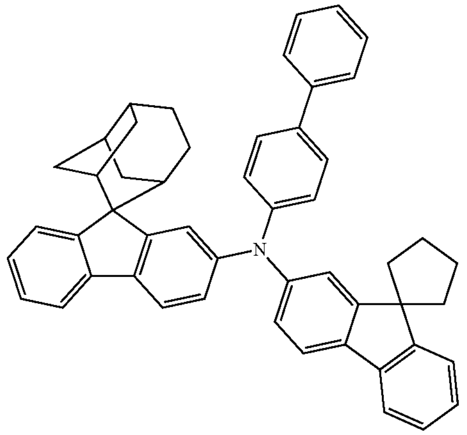
2

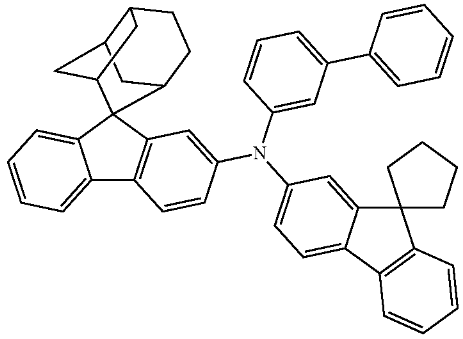
3

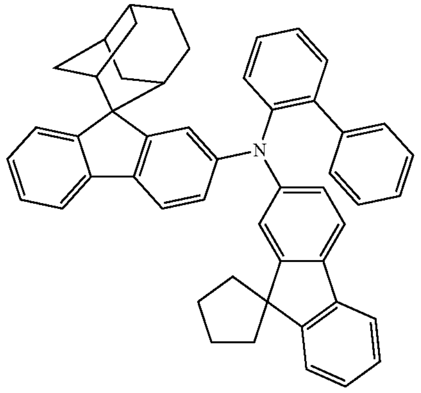
4

5
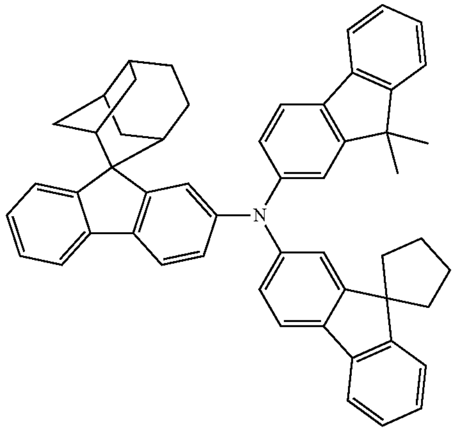
6
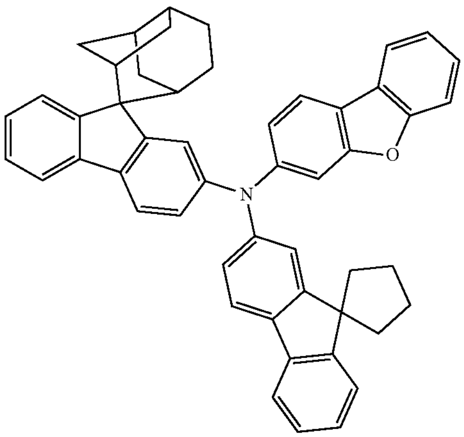
7
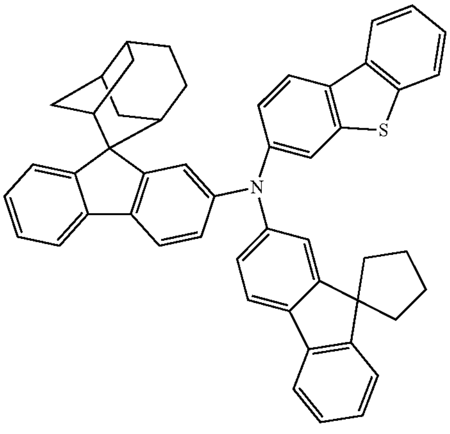
8
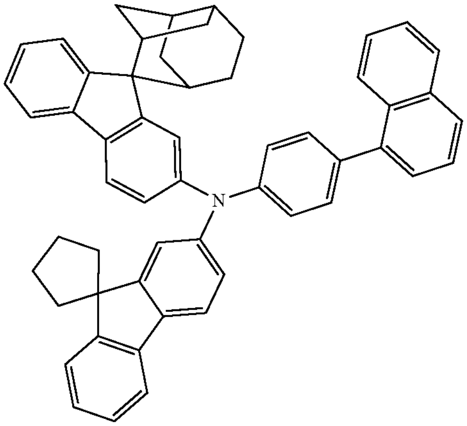
9
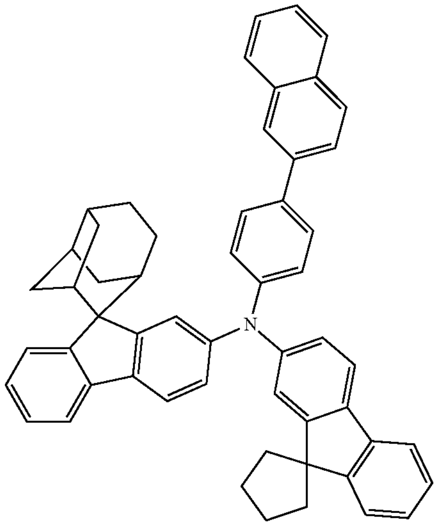
10
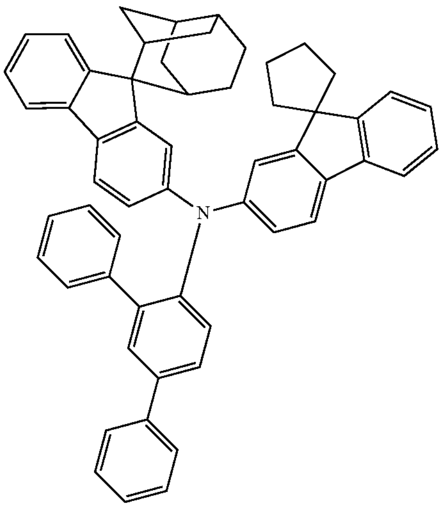

-continued
11
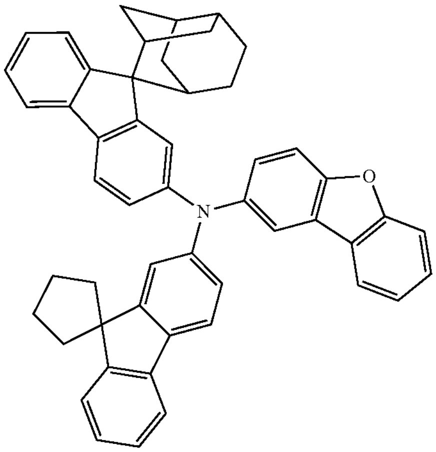
12
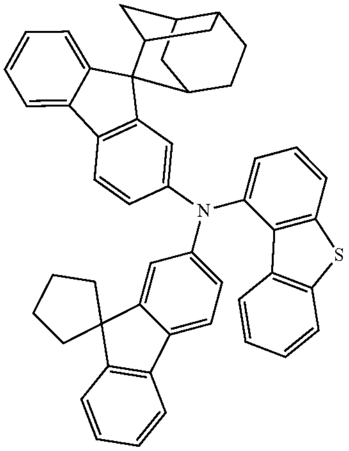
13
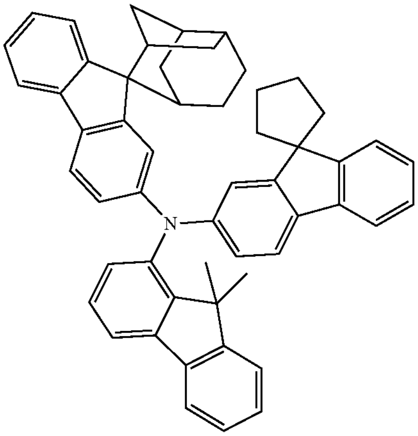
-continued
14
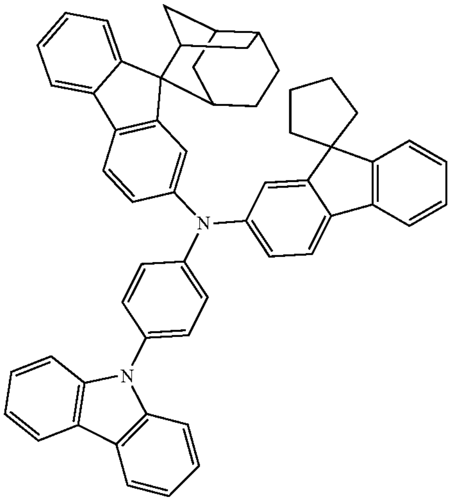
15
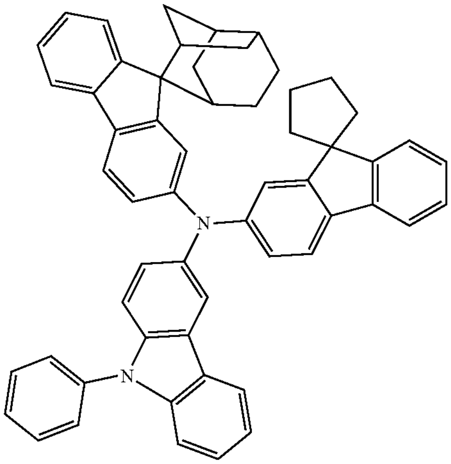
16
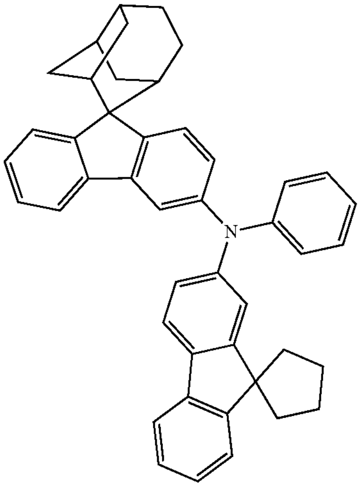

17
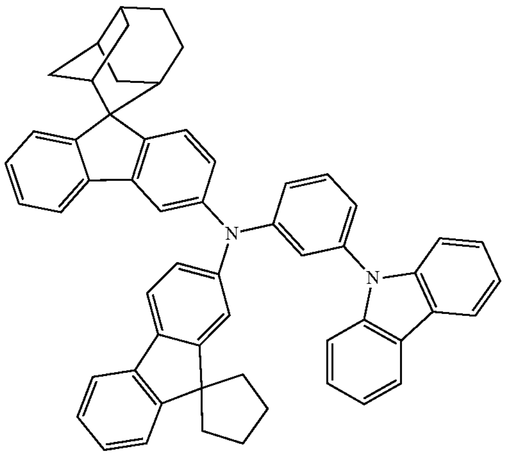
18
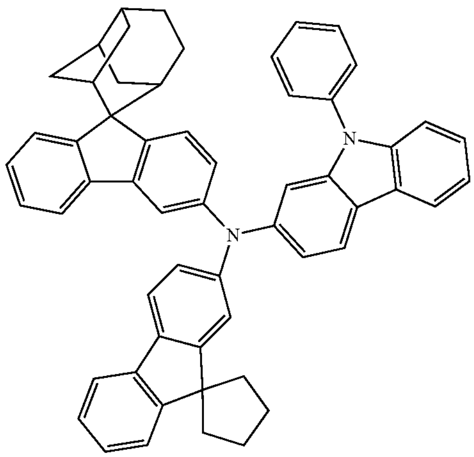
19
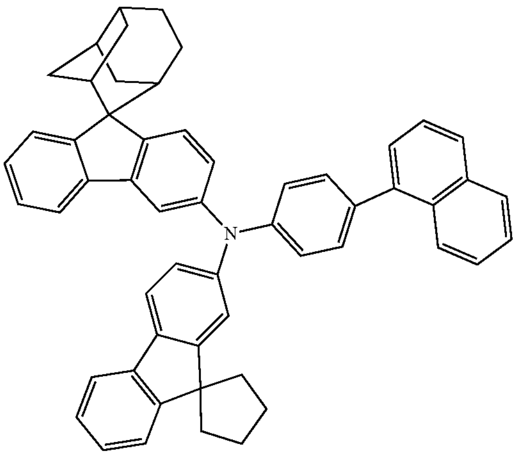
20
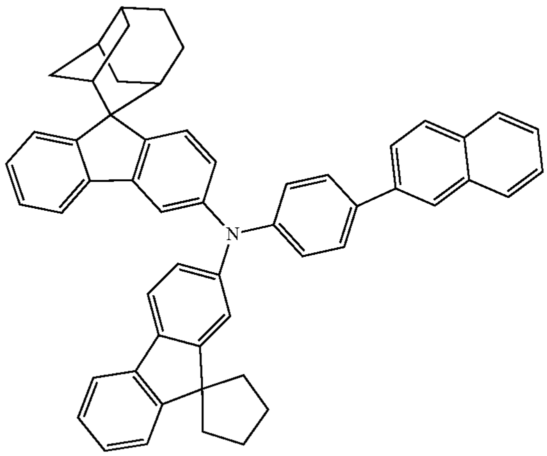
21
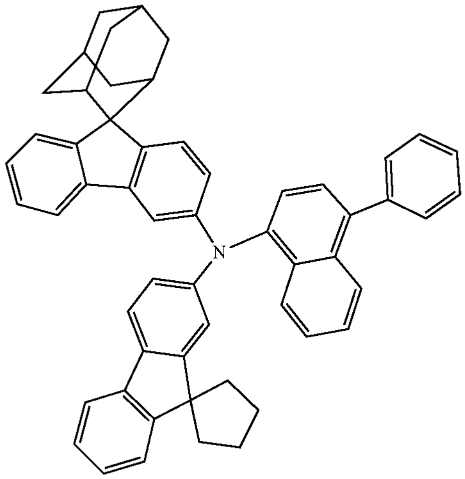
22
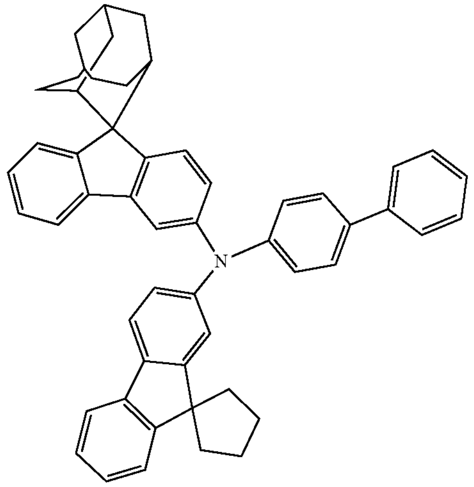

-continued
23
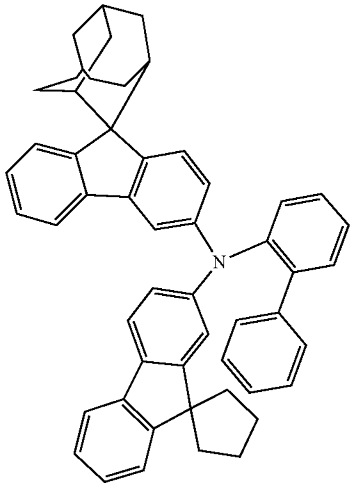
24
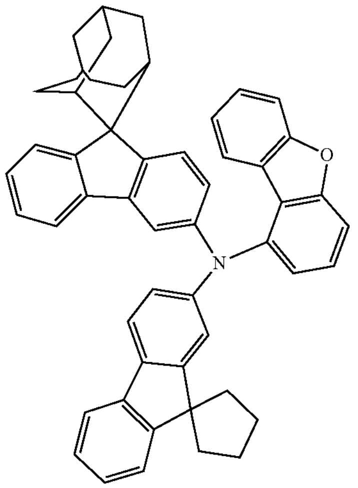
25
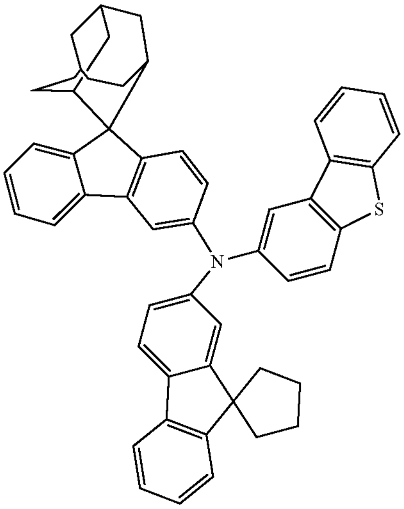
-continued
26
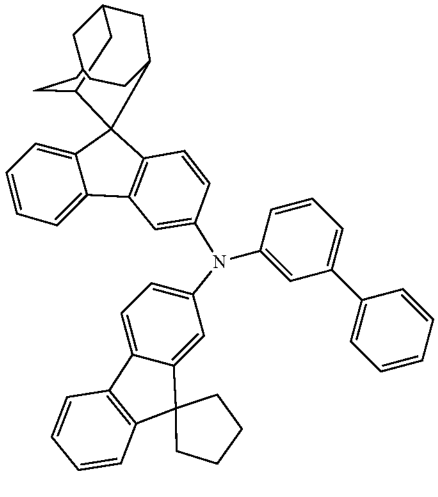
27
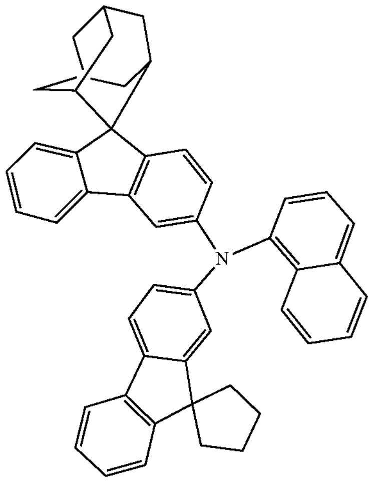
28
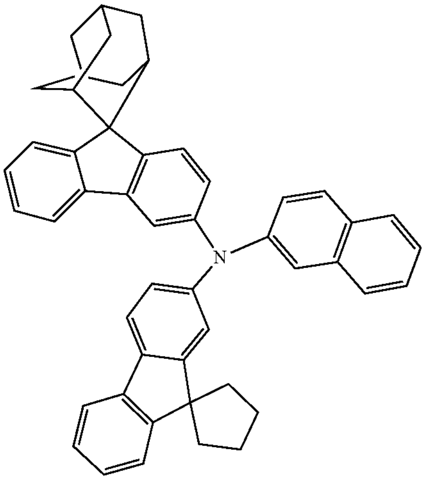

-continued
29
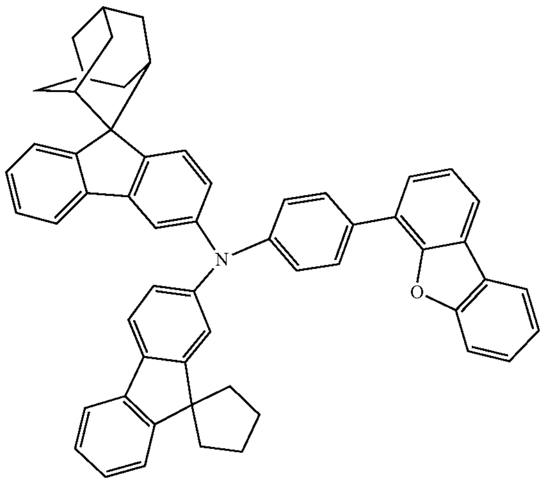
30
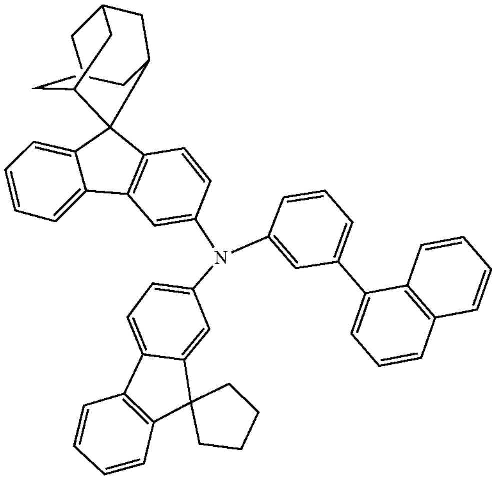
31
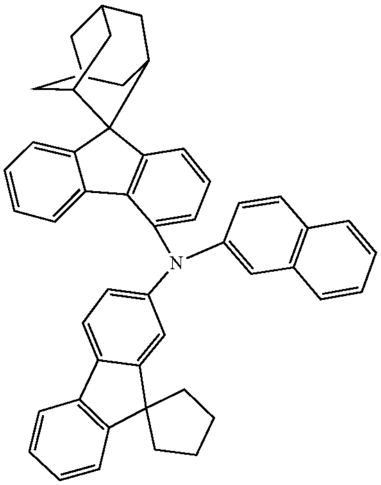
-continued
32
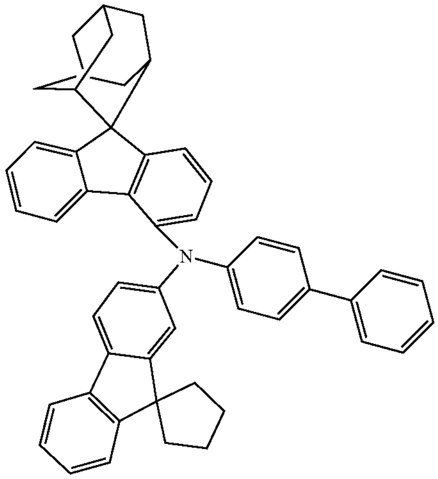
33
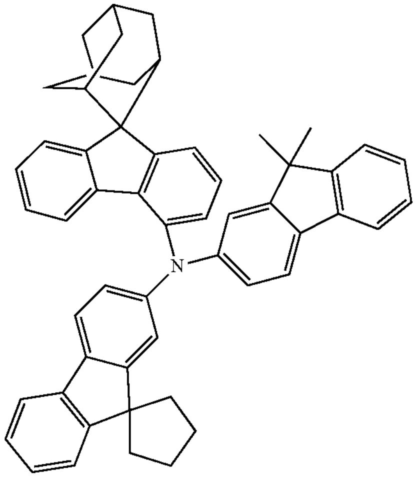
34
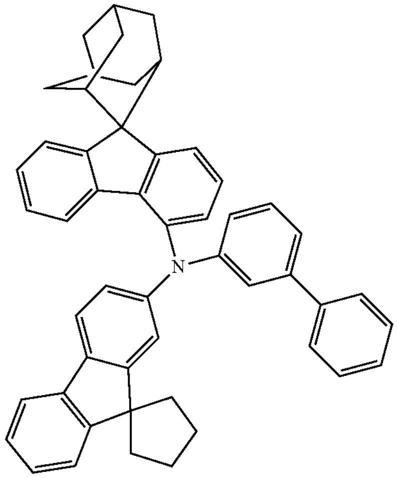

-continued
35
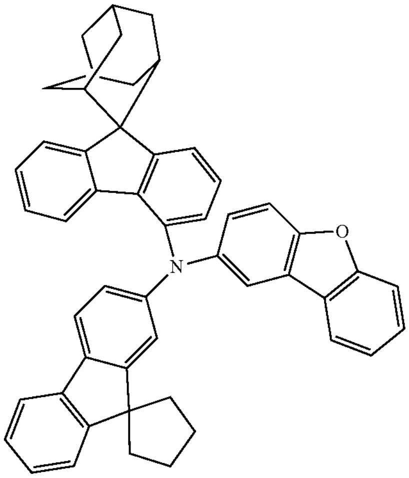
36
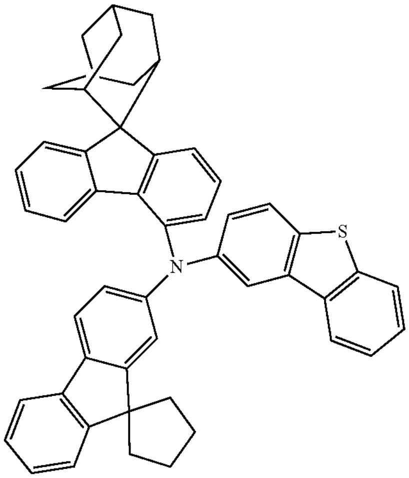
37
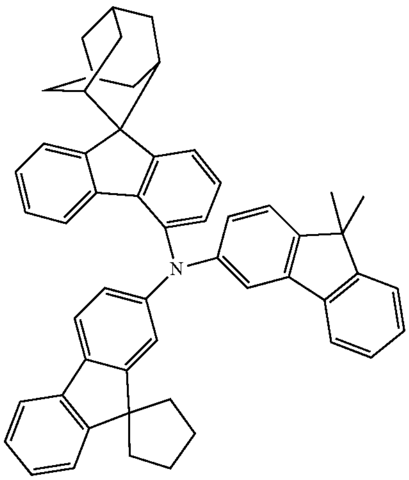
-continued
38
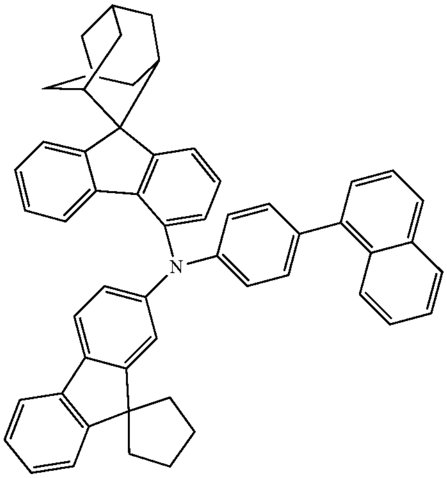
39
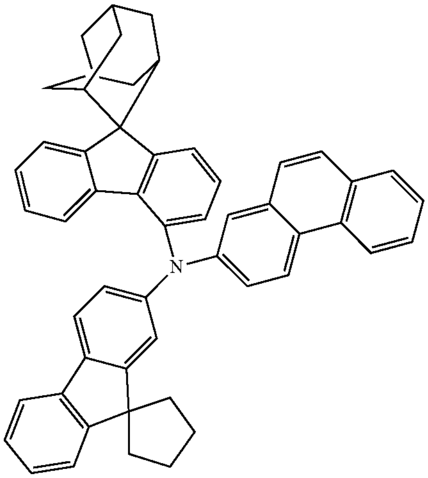
40
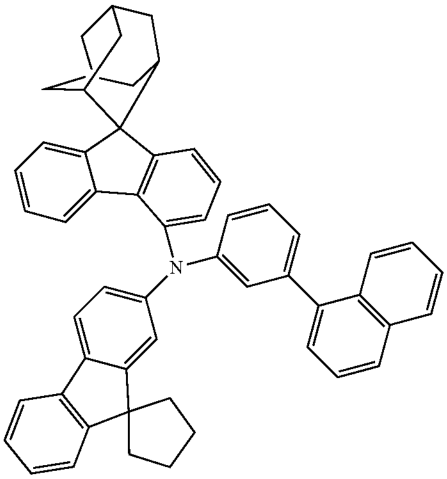

-continued
41
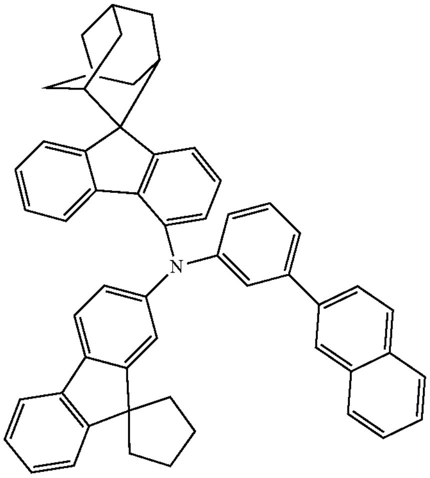
42
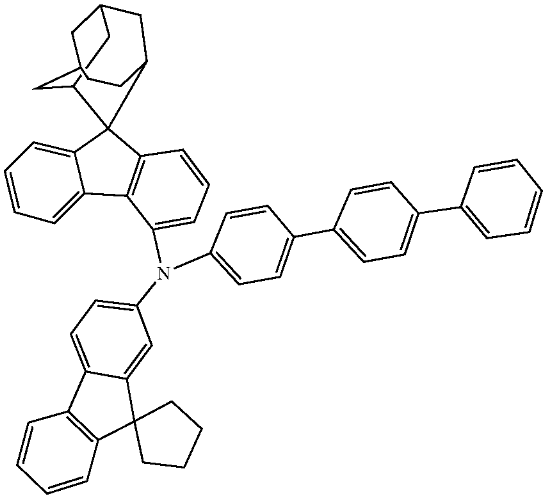
43
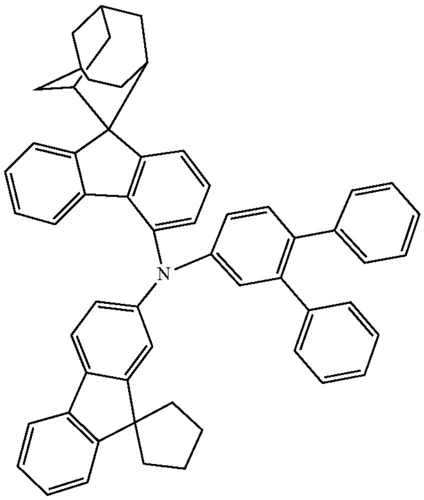
-continued
44
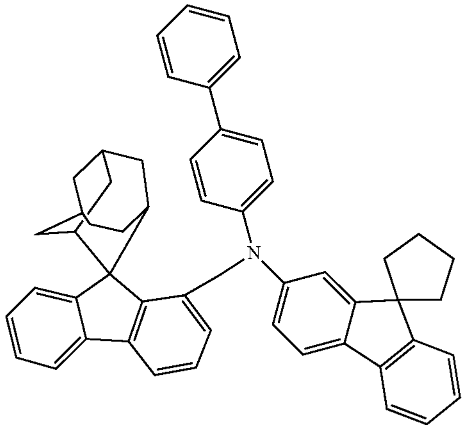
45
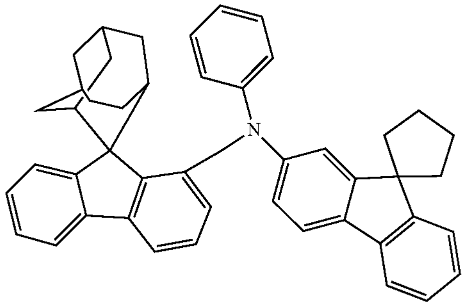
46
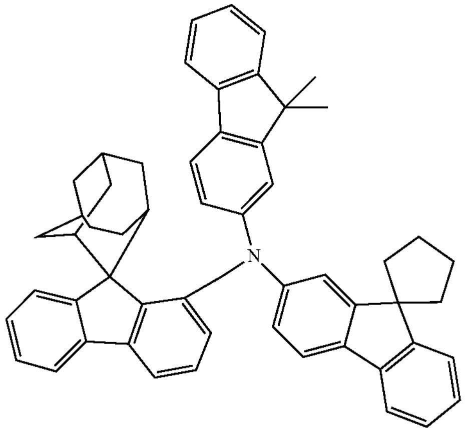
47
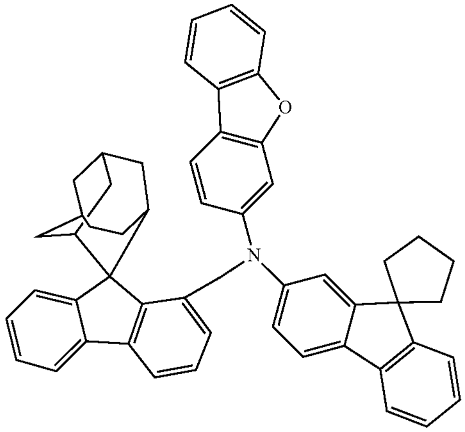

-continued
48
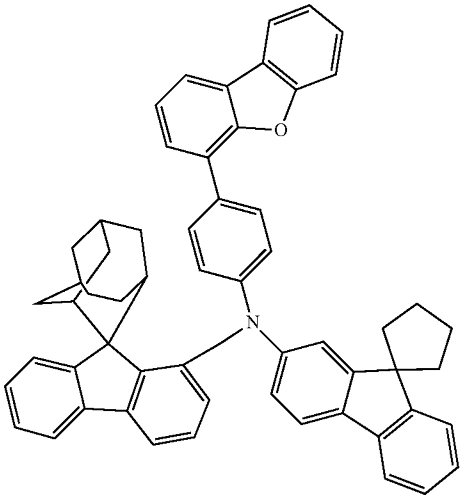
49
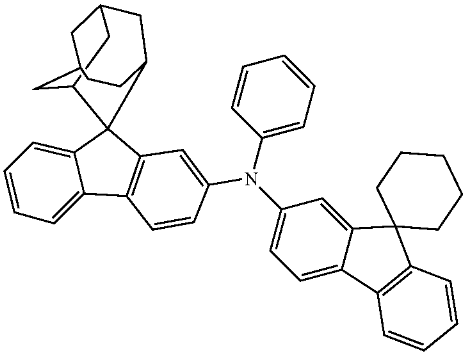
50
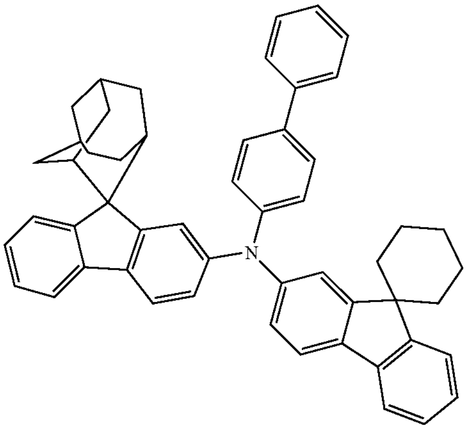
51
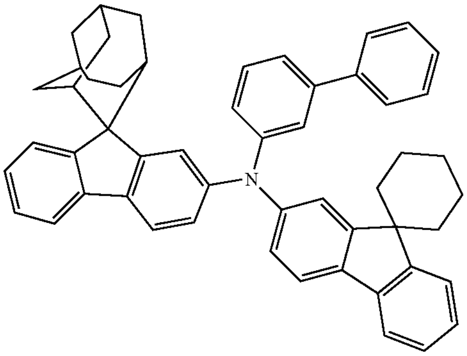
-continued
52
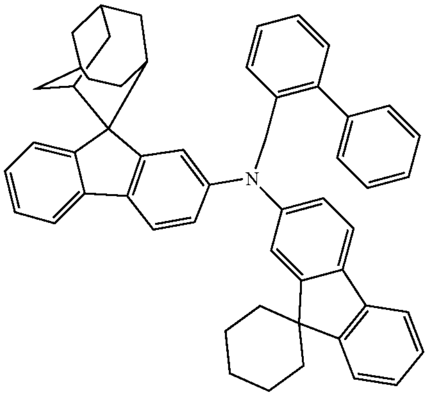
53
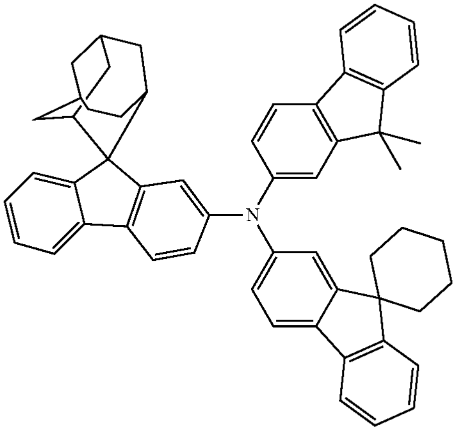
54
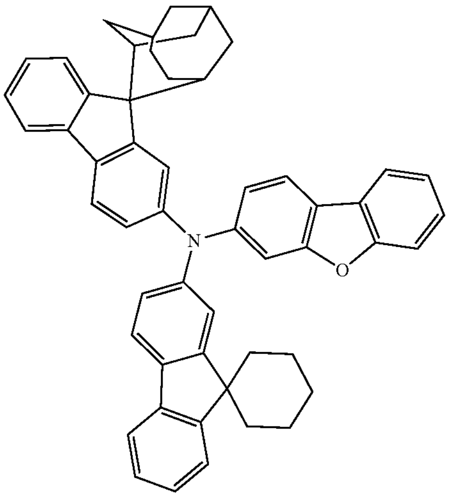

-continued
55
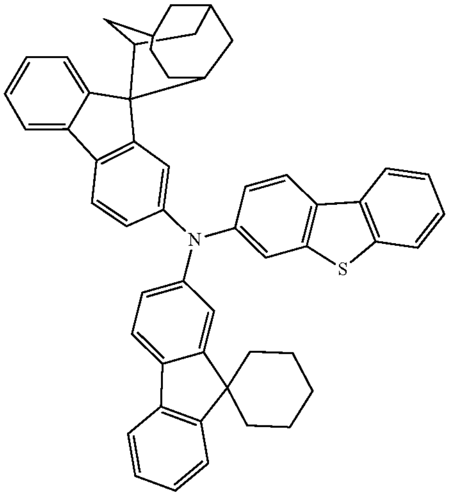
56
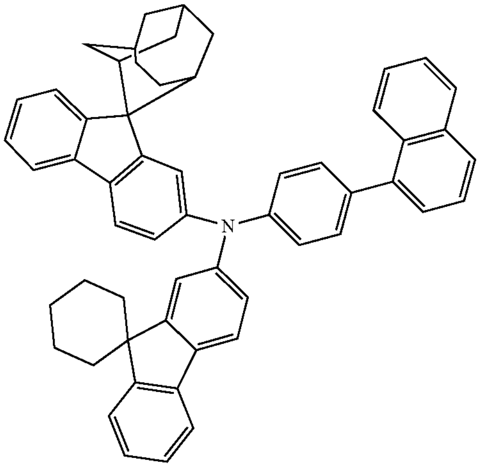
57
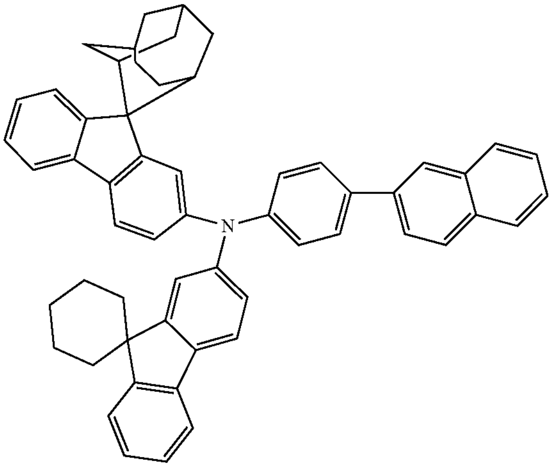
-continued
58
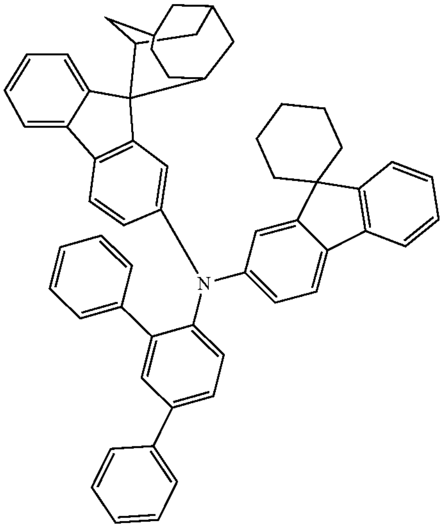
59
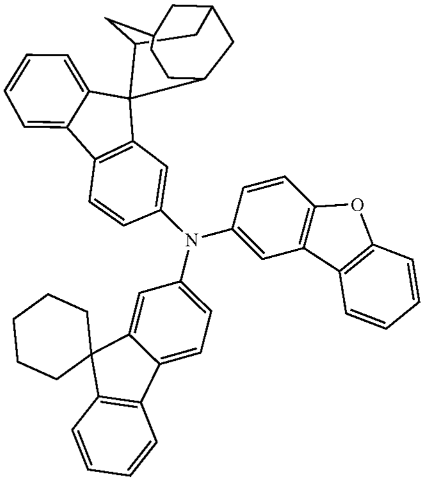
60
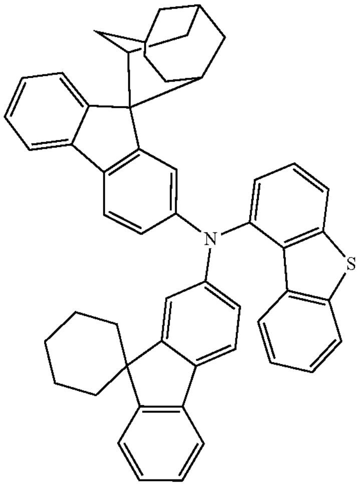

61
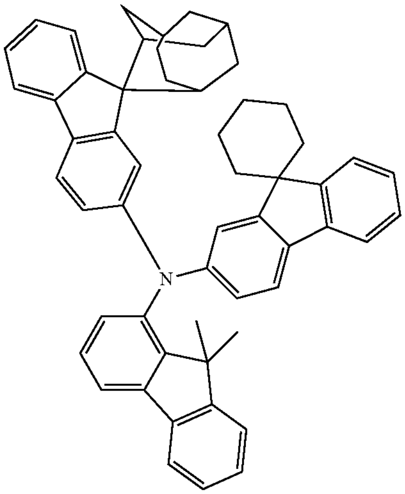
62
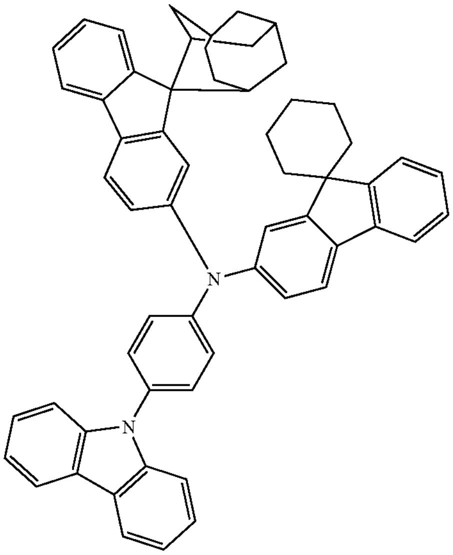
63
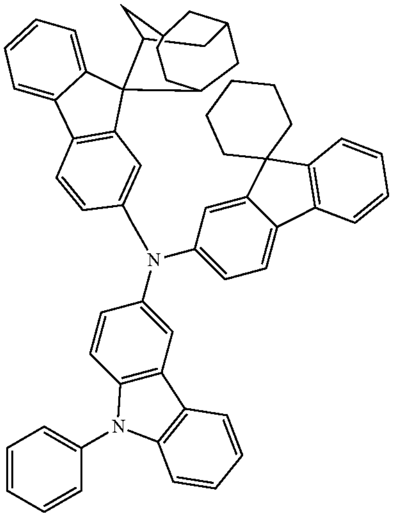
64
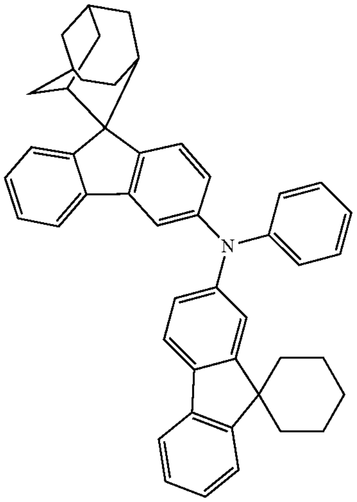
65
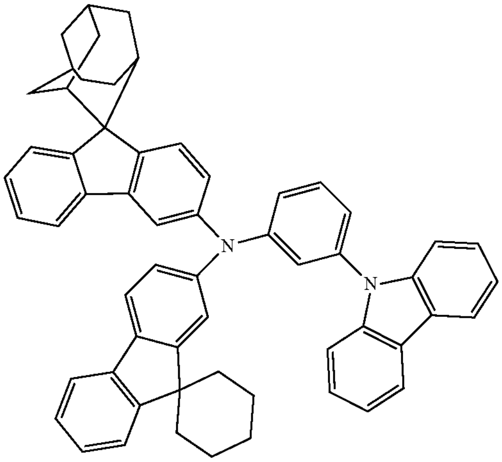
66
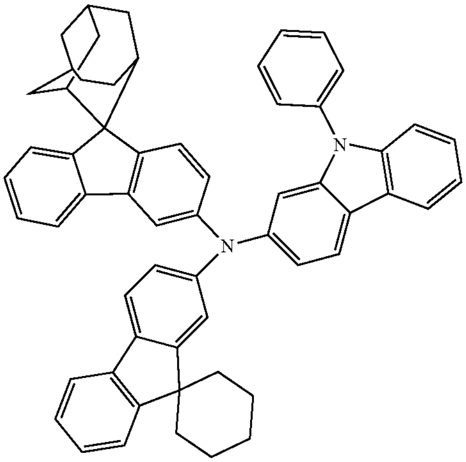

-continued
67
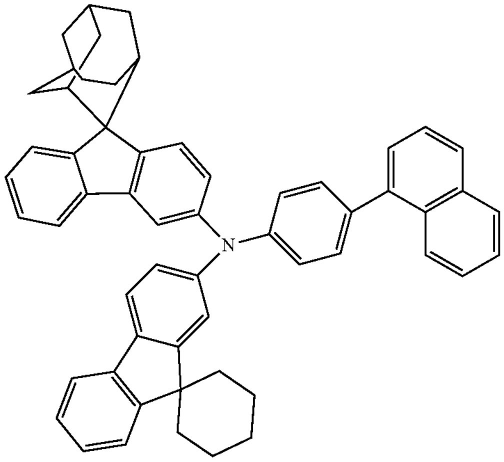
68
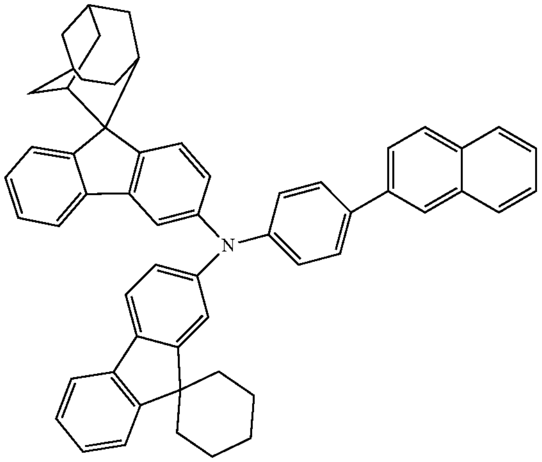
69
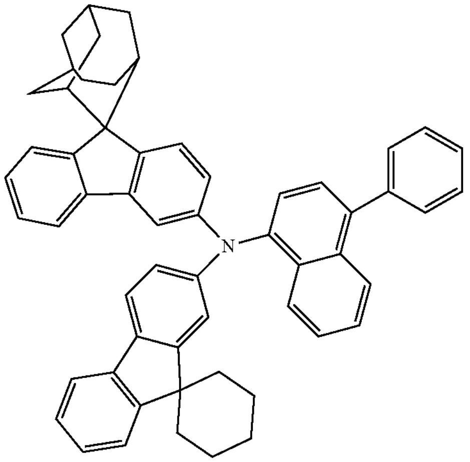
-continued
70
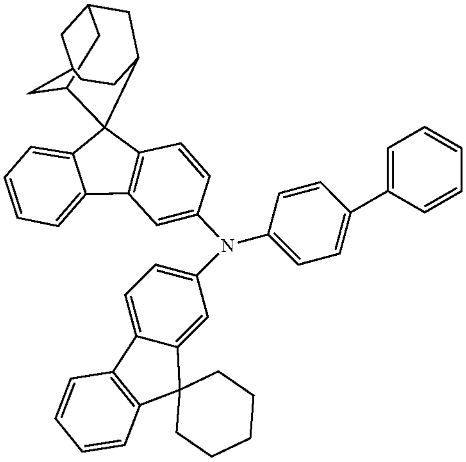
71
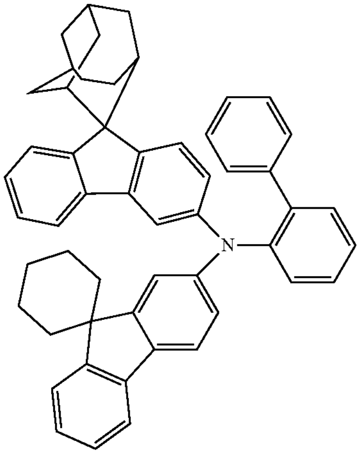
72
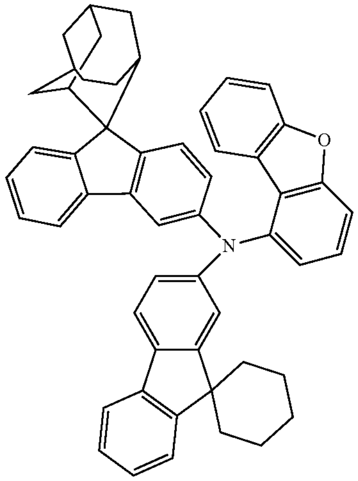

-continued
73
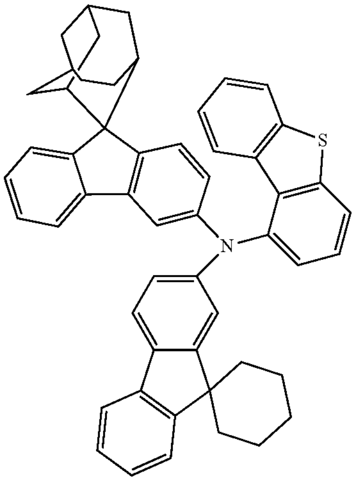
74
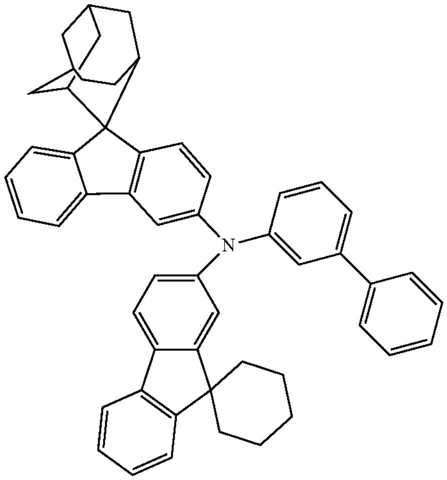
75
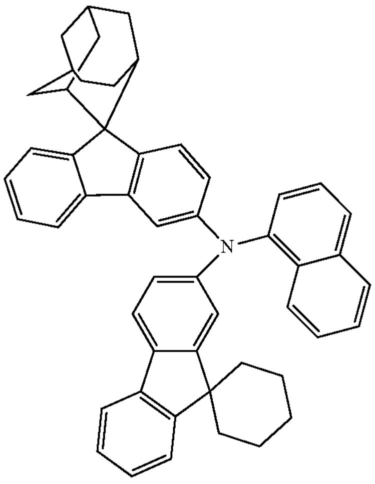
-continued
76
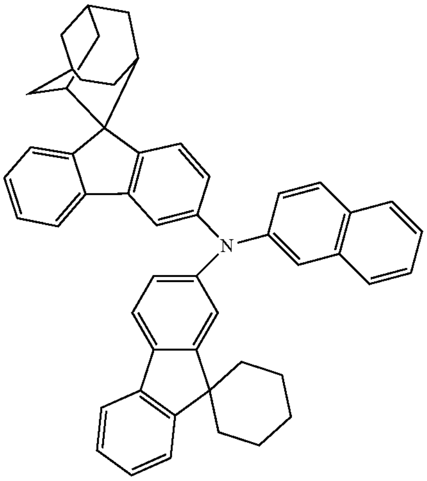
77
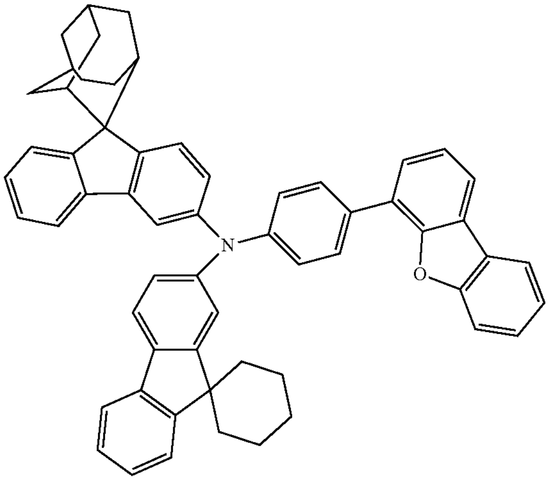
78
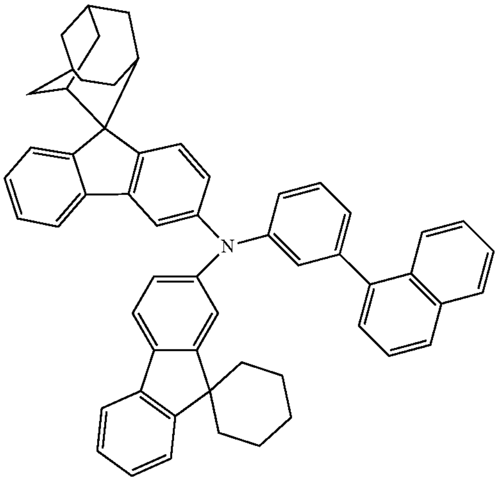

-continued
79
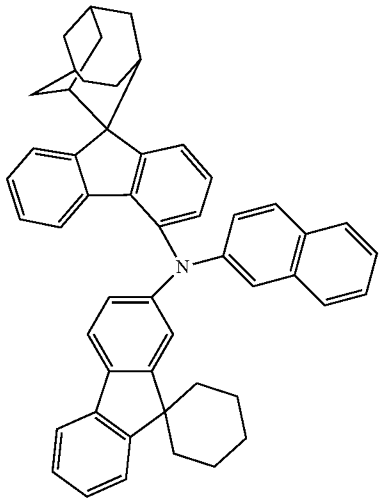
80
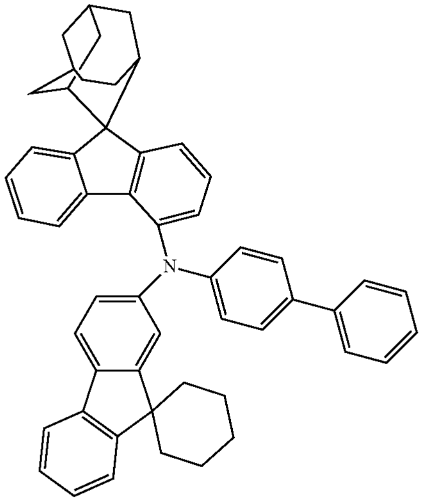
81
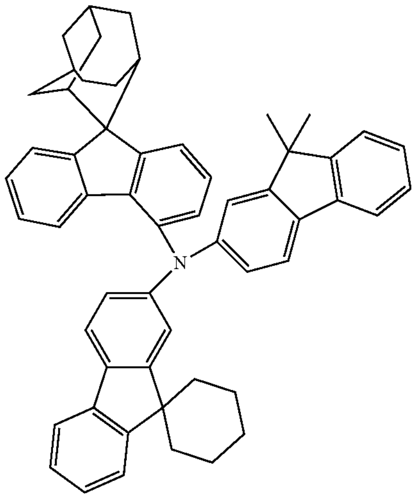
-continued
82
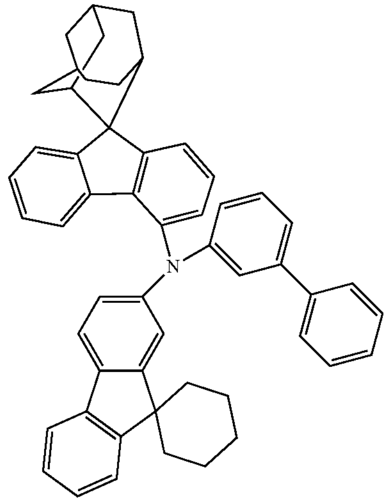
83
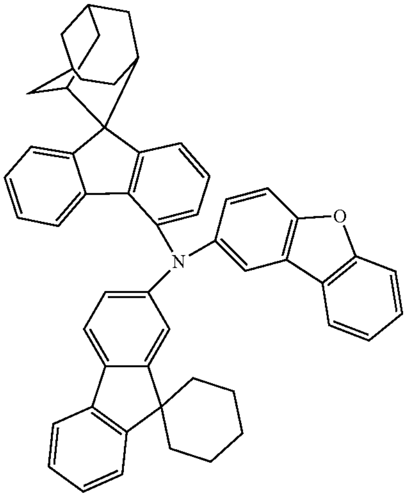
84
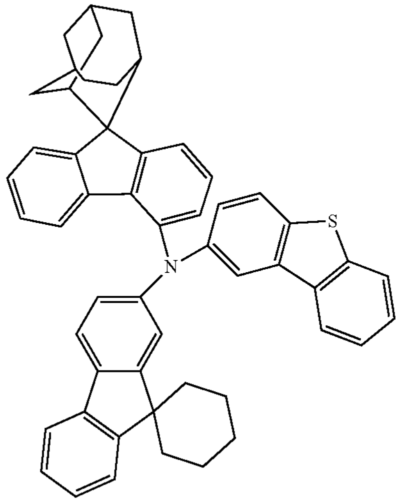

-continued
85
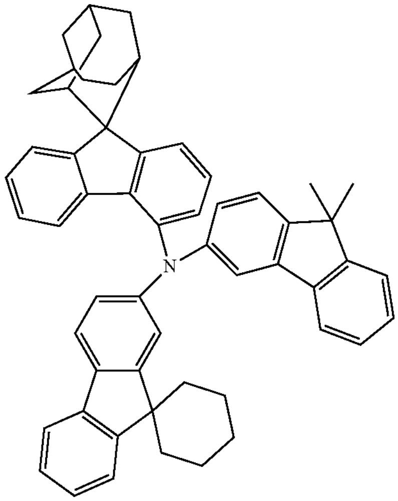
86
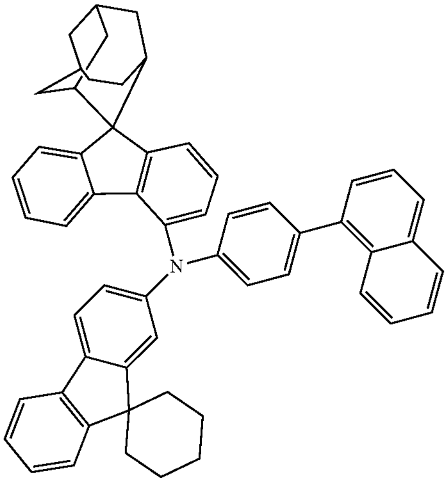
87
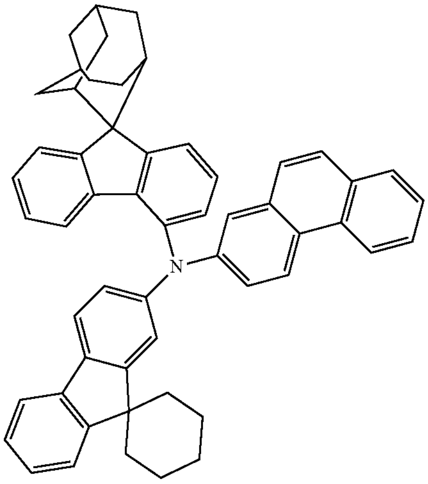
-continued
88
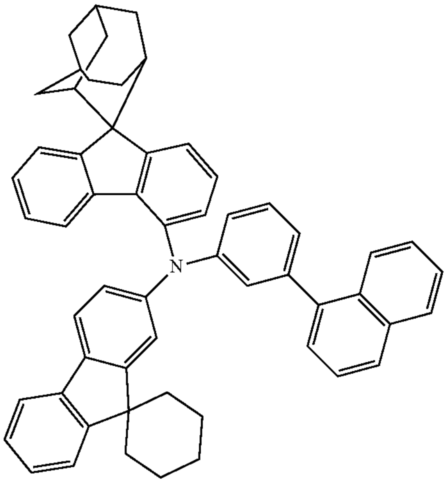
89
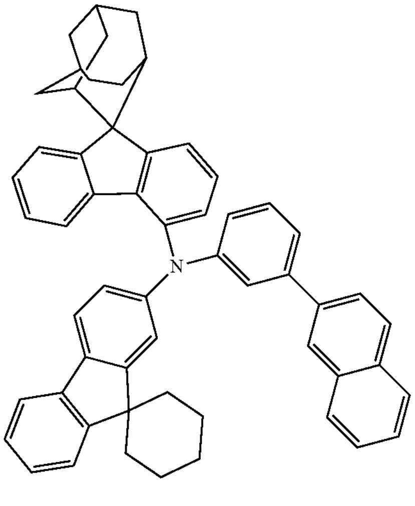
90
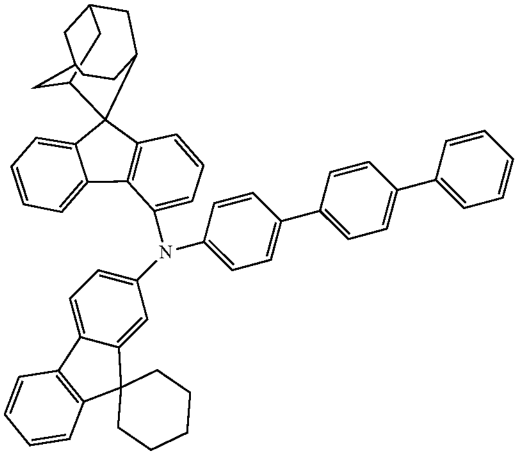

-continued
91
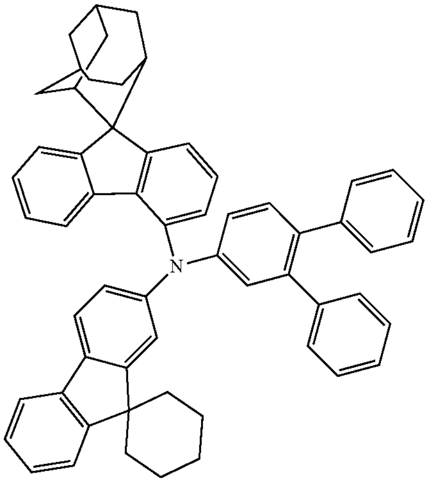
92
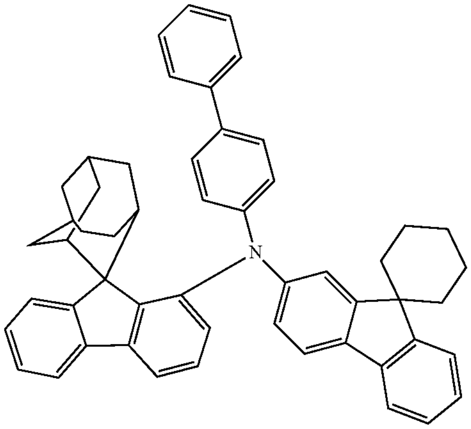
93
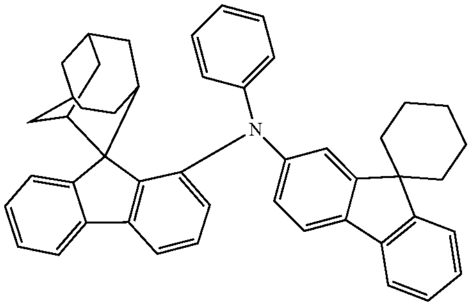
94
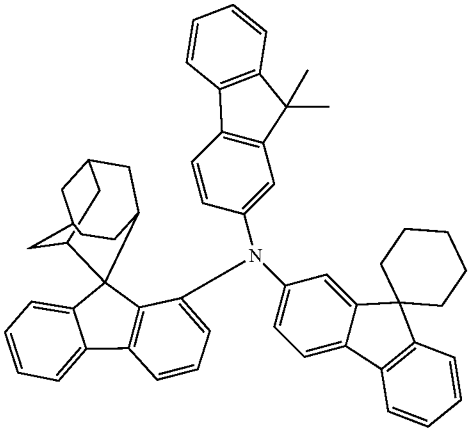
-continued
95
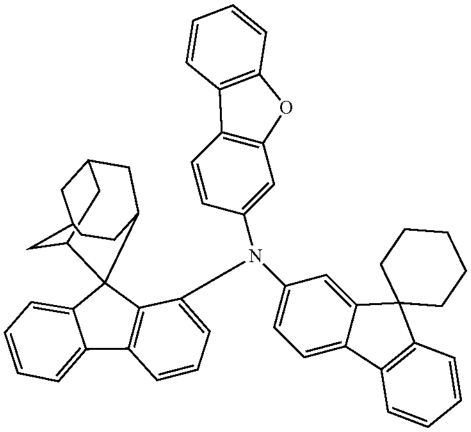
96
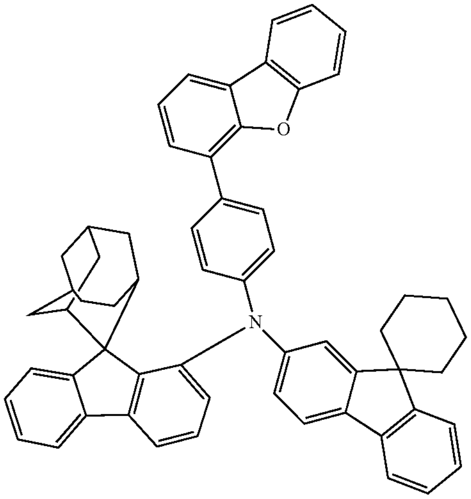
97
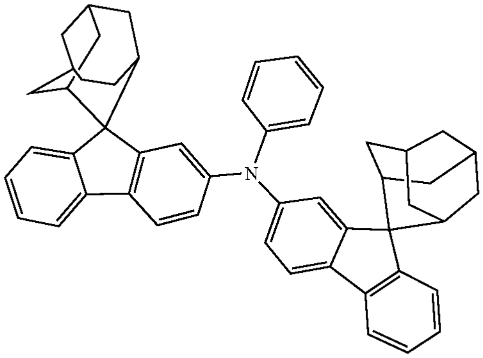

-continued
98
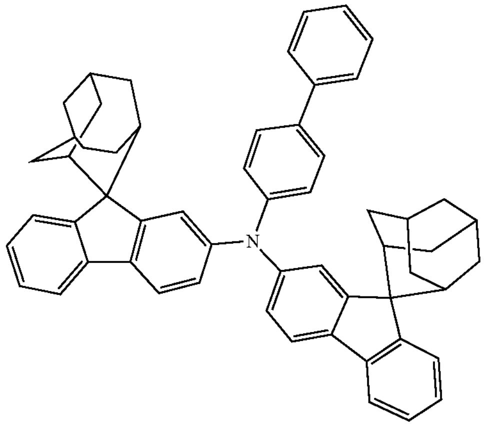
99
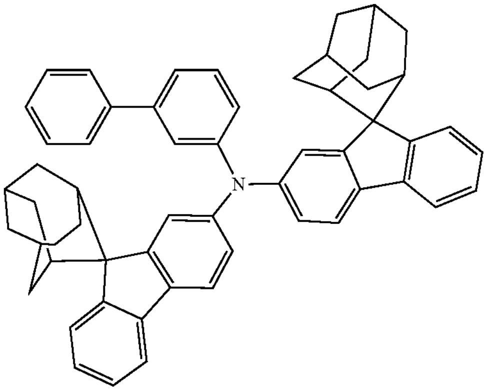
100
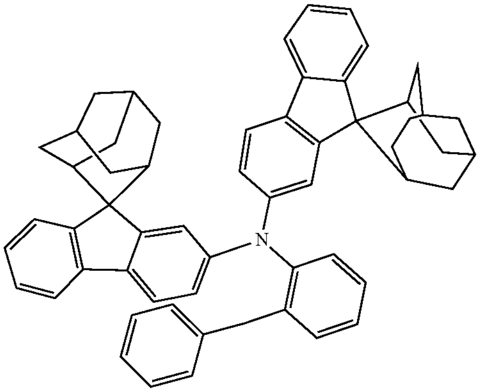
101
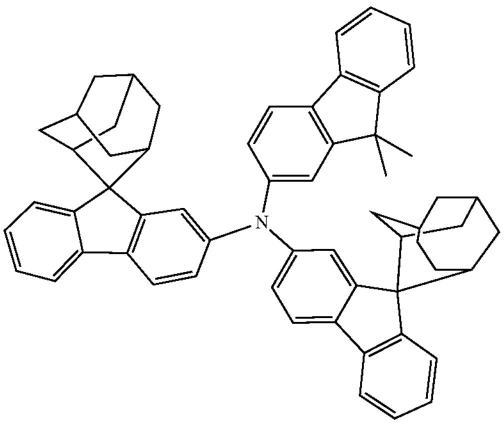
-continued
102
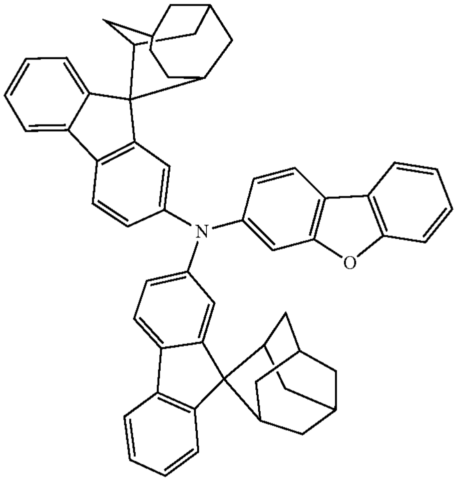
103
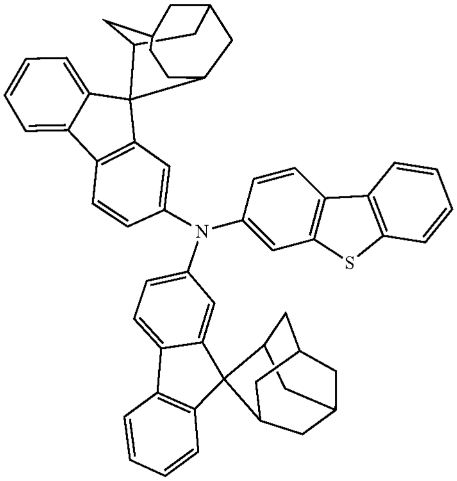
104
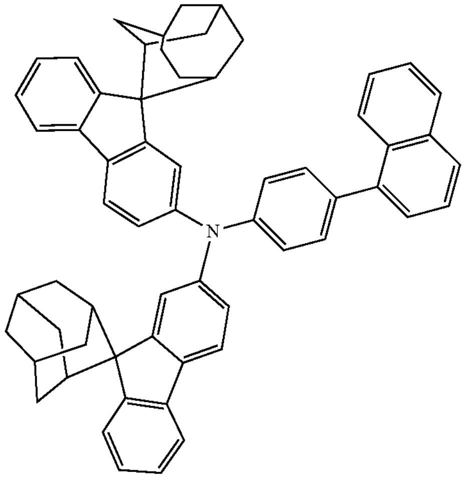

-continued
105
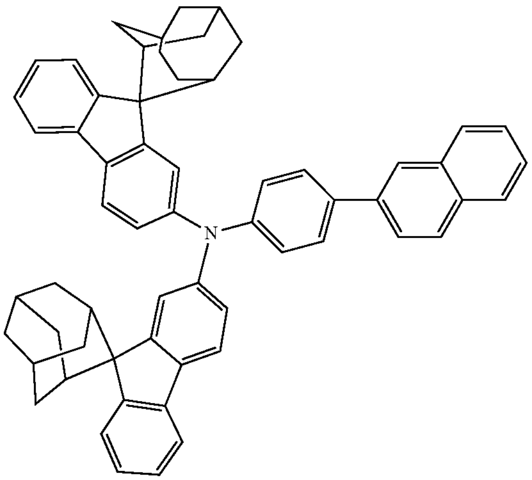
106
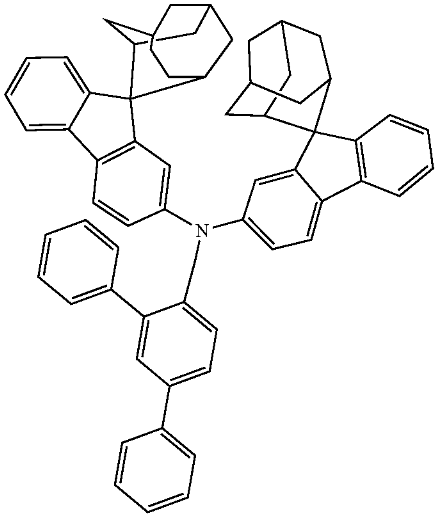
107
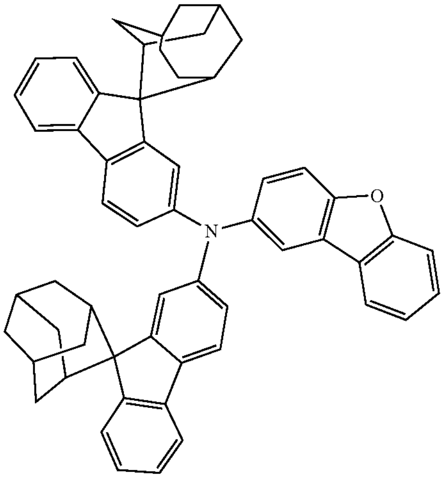
-continued
108
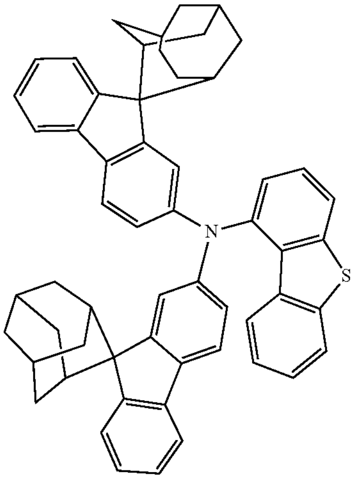
109
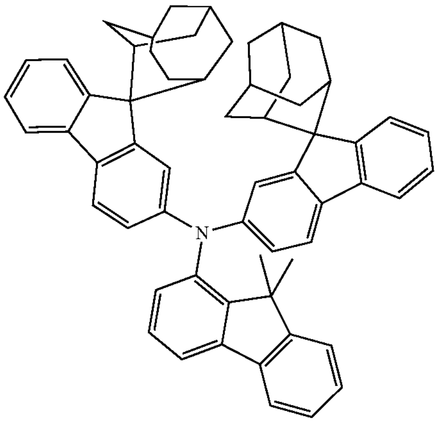
110
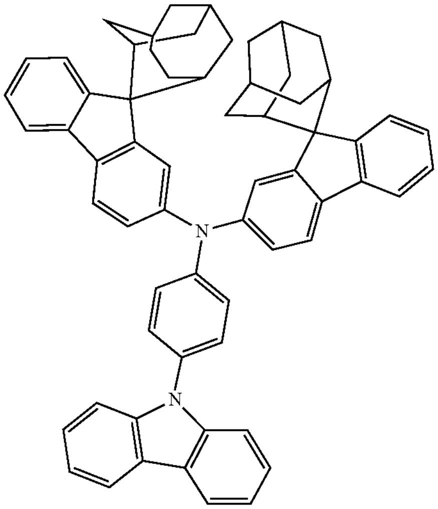

-continued
111
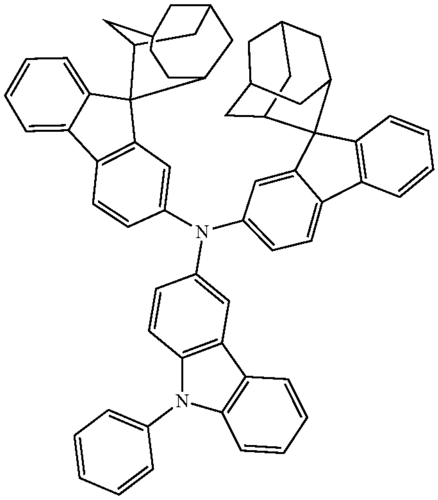
112
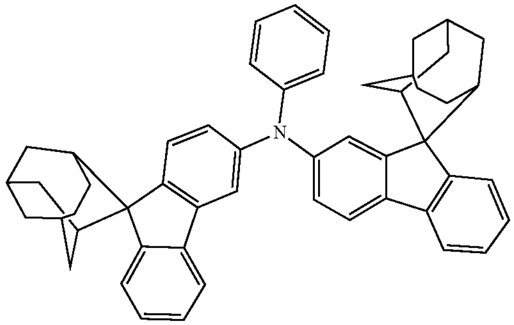
113
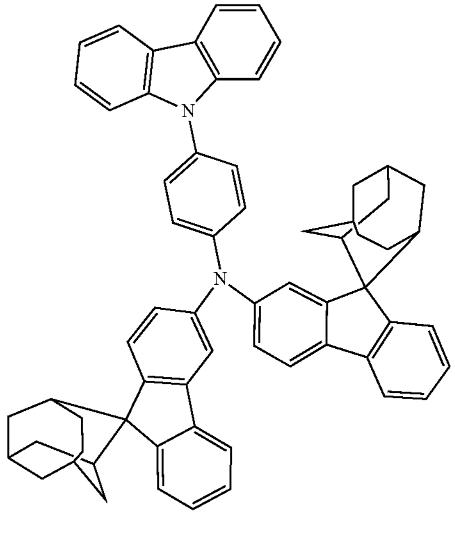
-continued
114
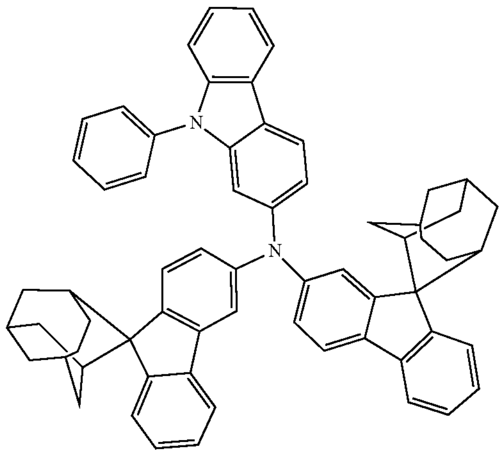
115
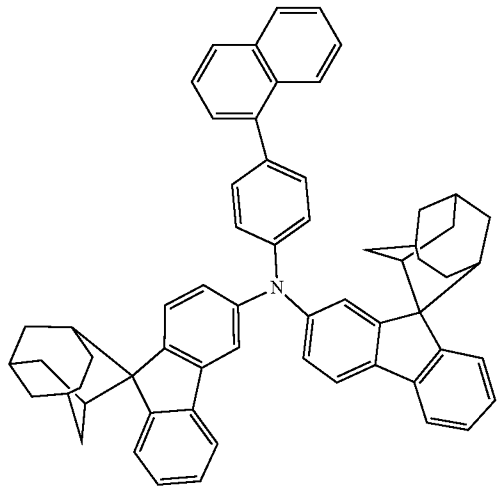
116
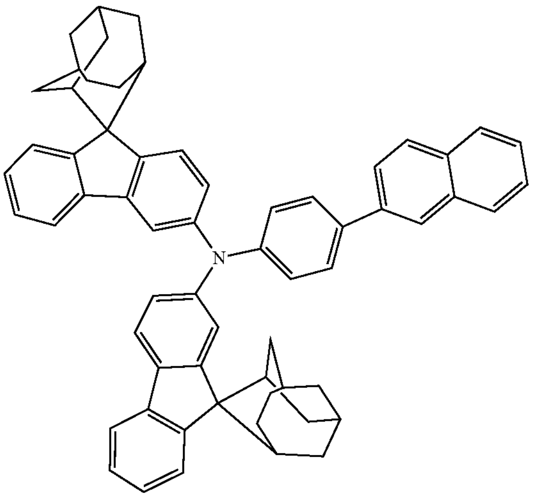

-continued
117
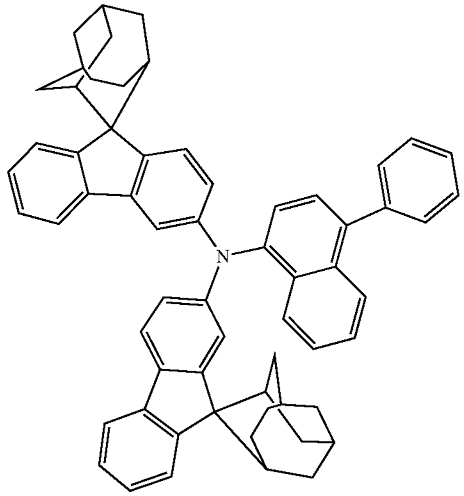
118
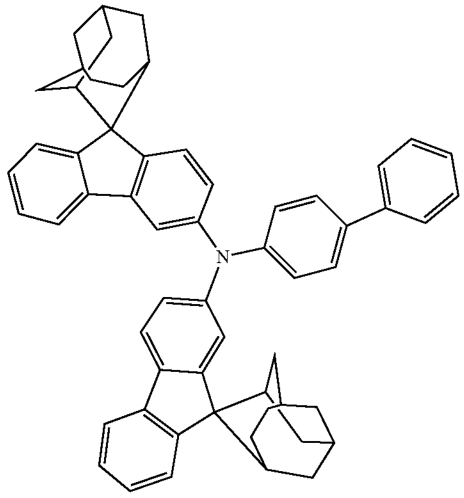
119
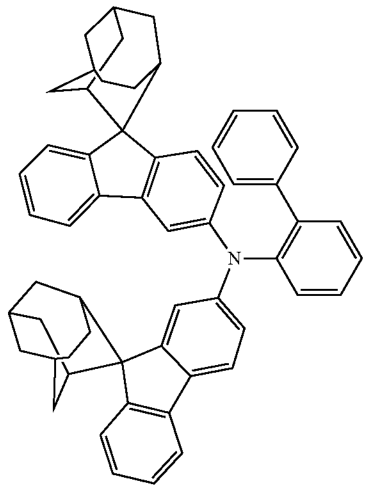
-continued
120
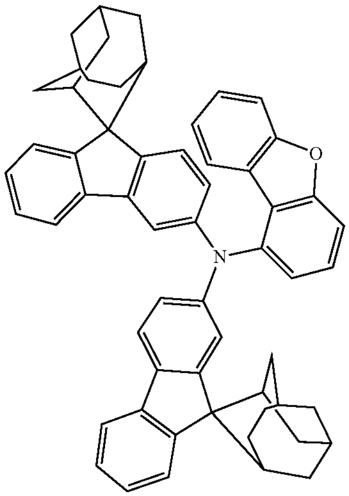
121
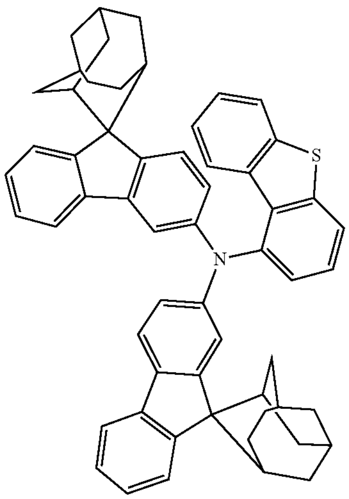
122
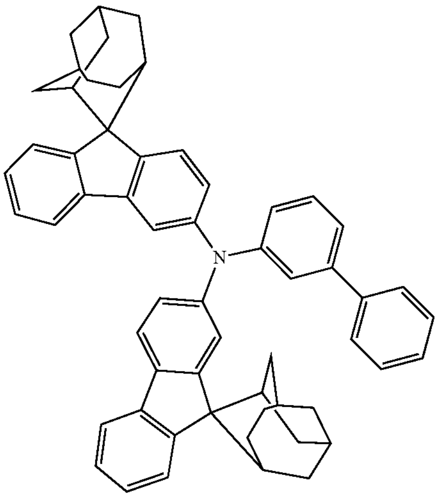

123
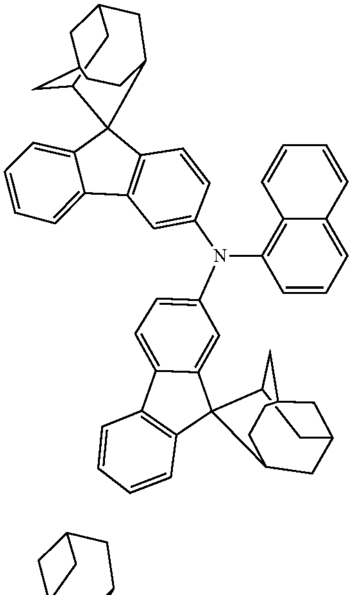
124
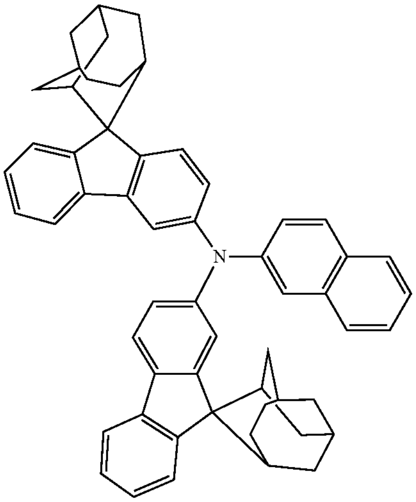
125
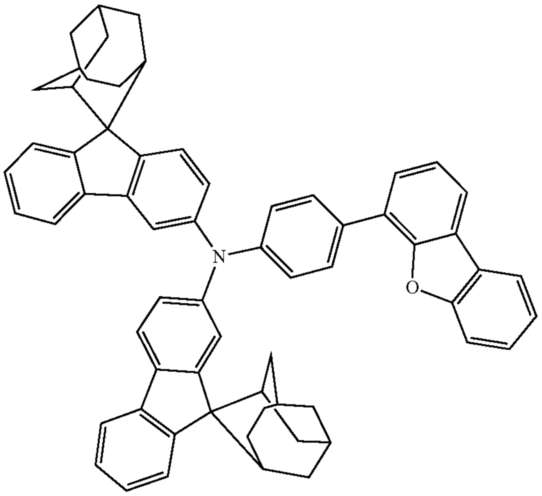
126
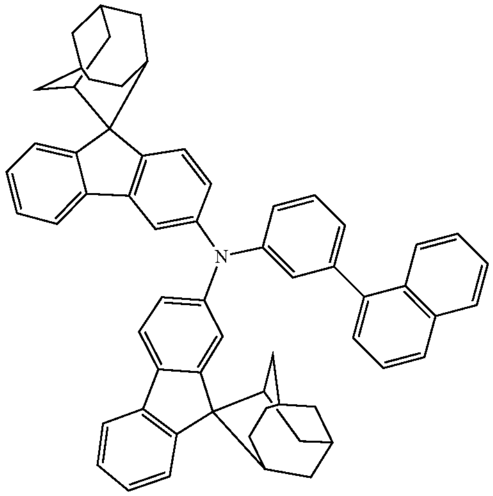
127
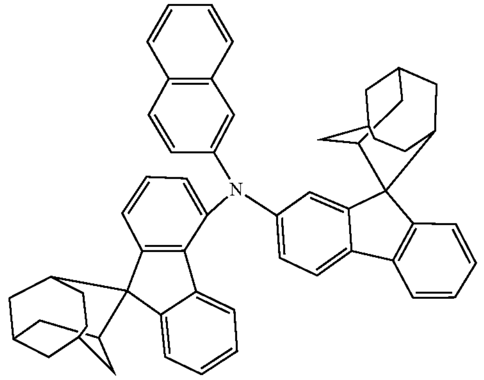
128
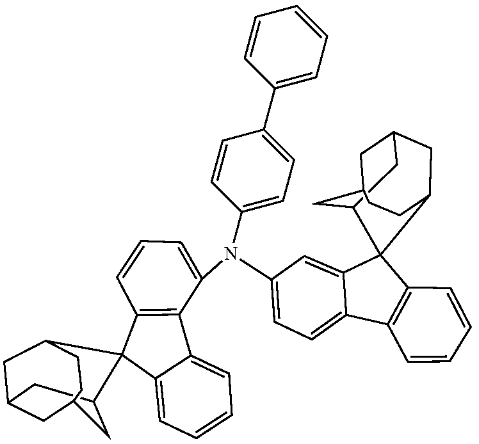

-continued
129
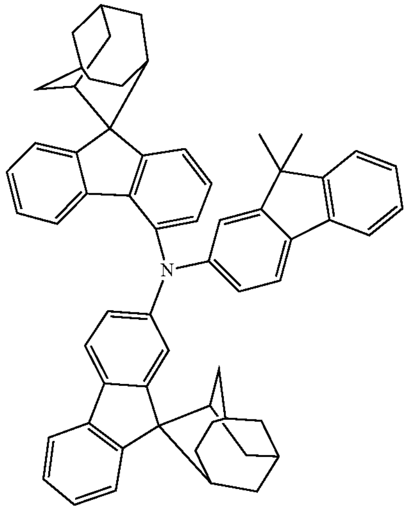
130
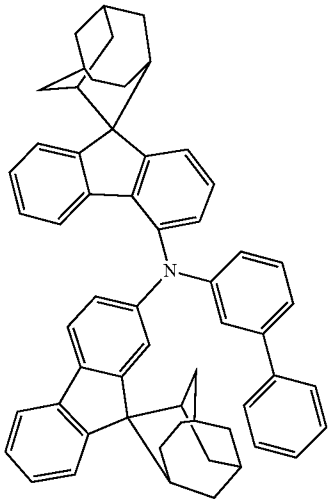
131
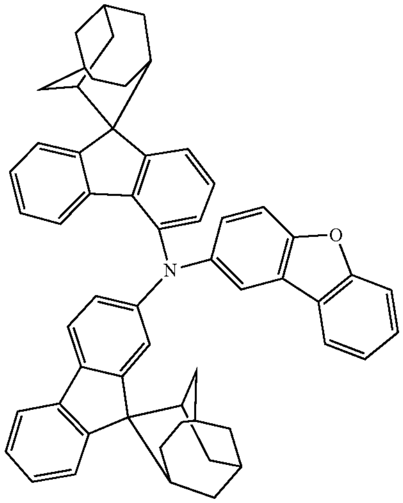
-continued
132
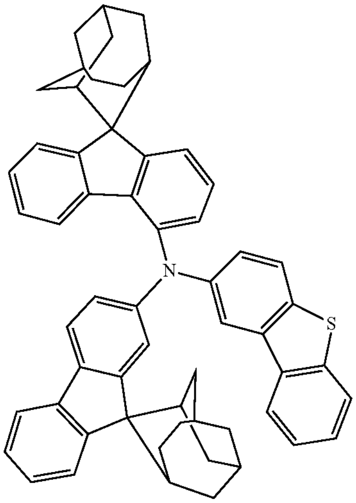
133
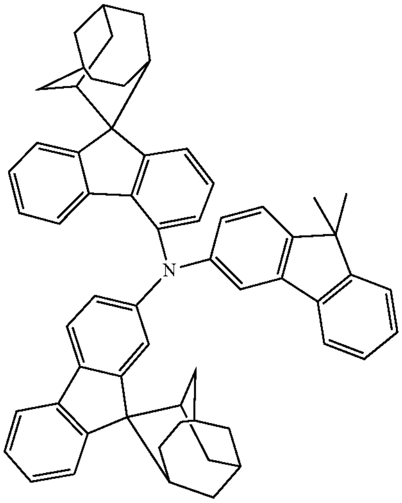
134
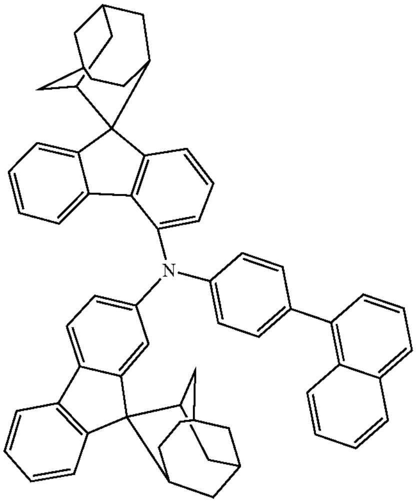

-continued
135
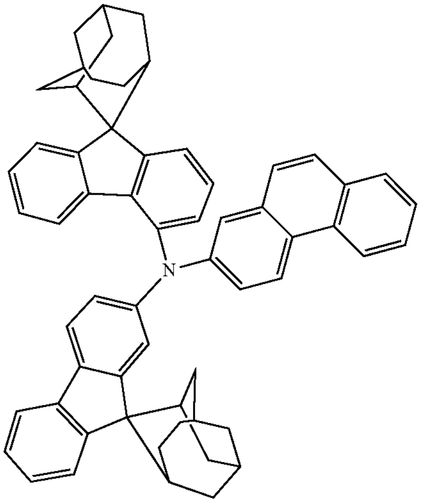
136
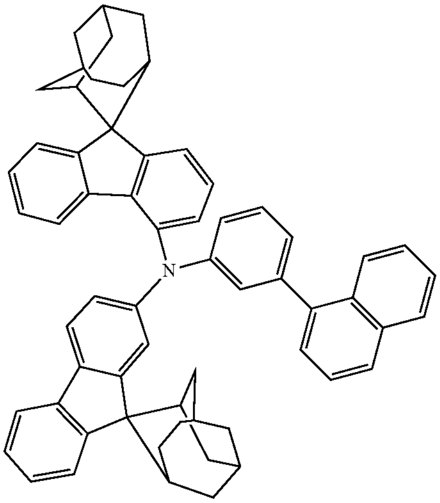
137
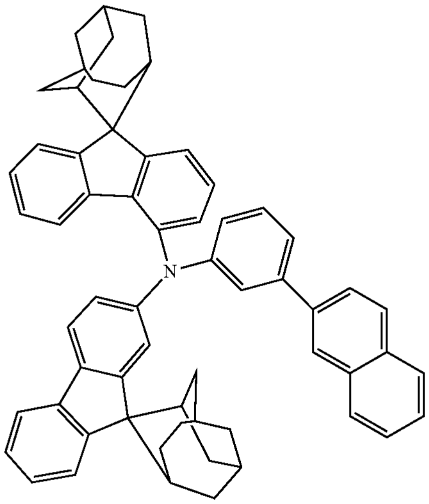
-continued
138
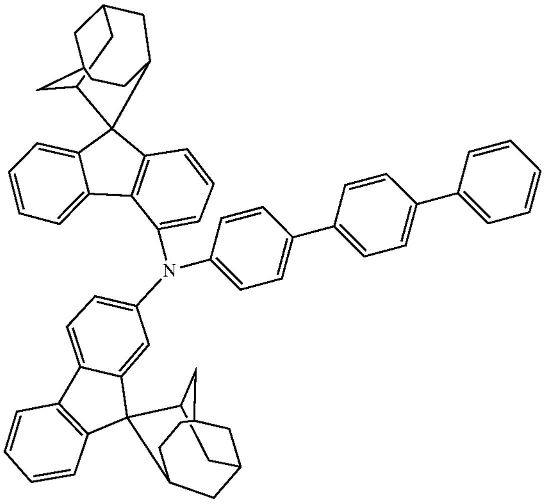
139
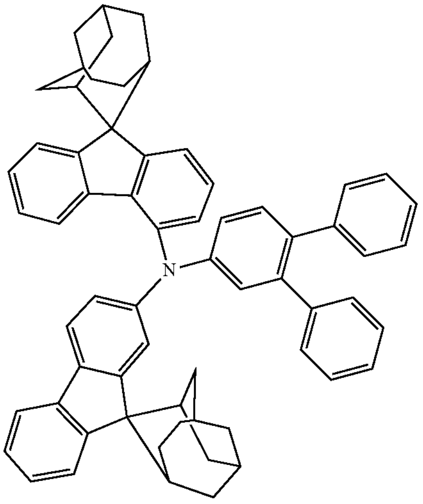
140
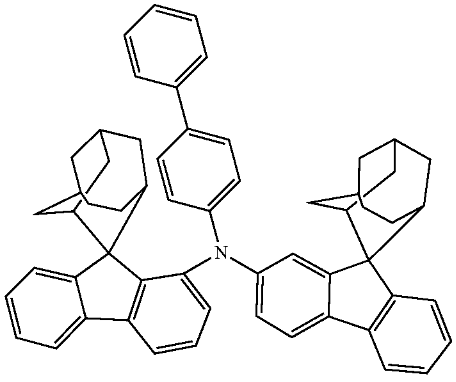

-continued
141
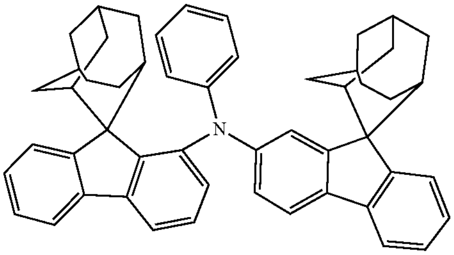
142
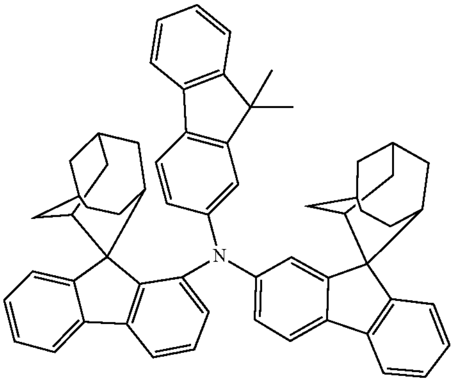
143
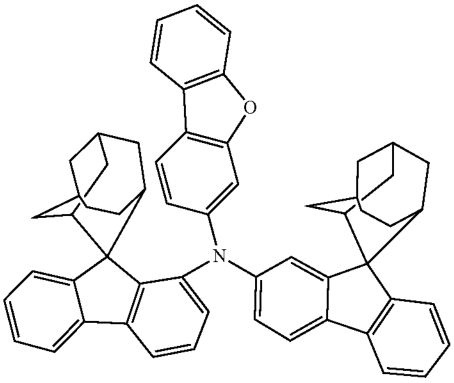
144
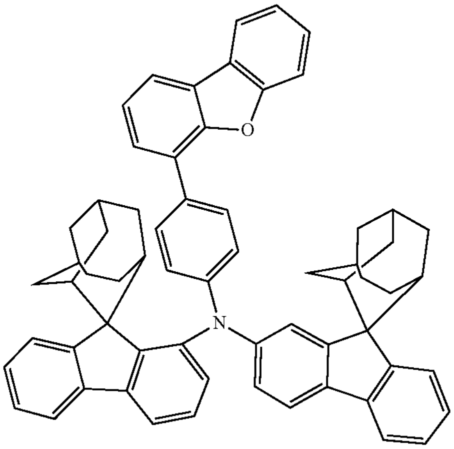
-continued
145
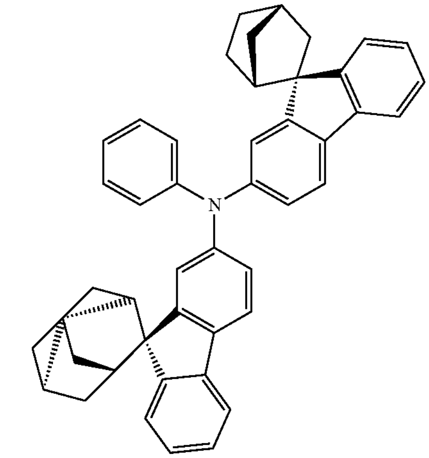
146
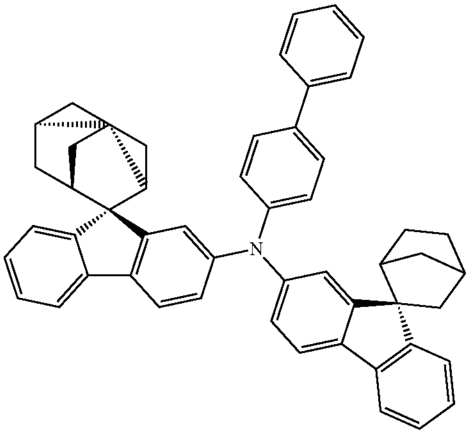
147
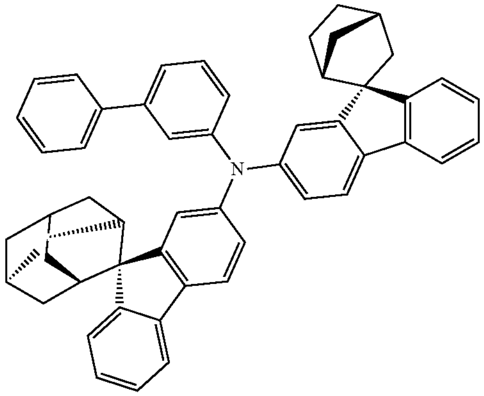

-continued
148
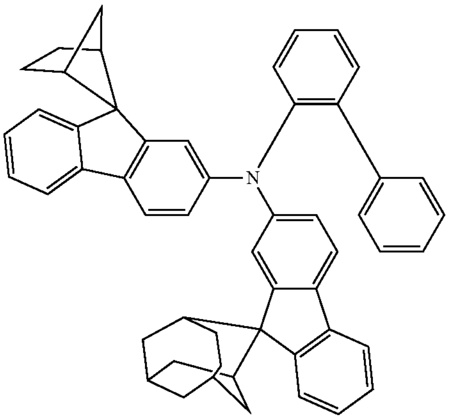
149
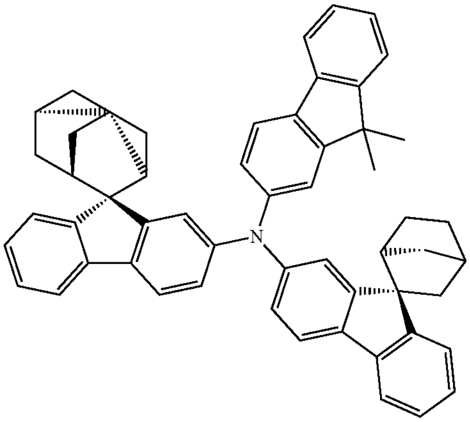
150
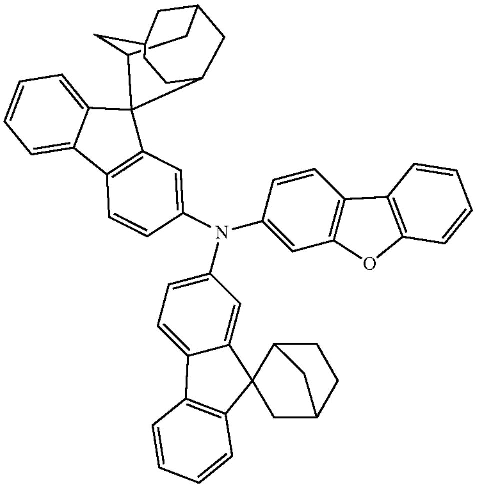
-continued
151
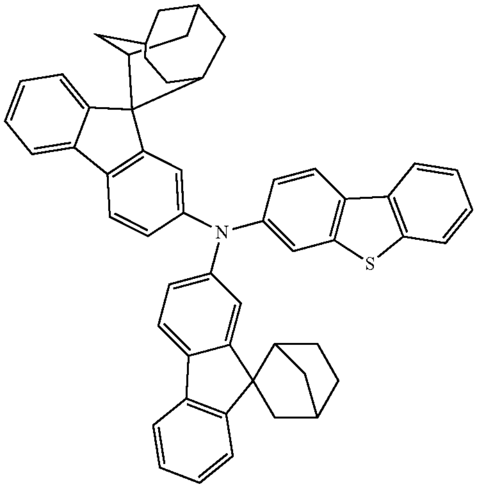
152
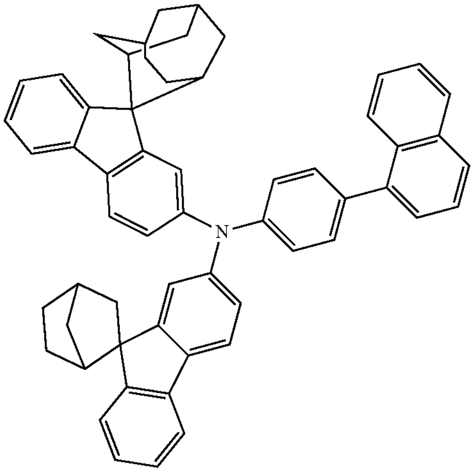
153
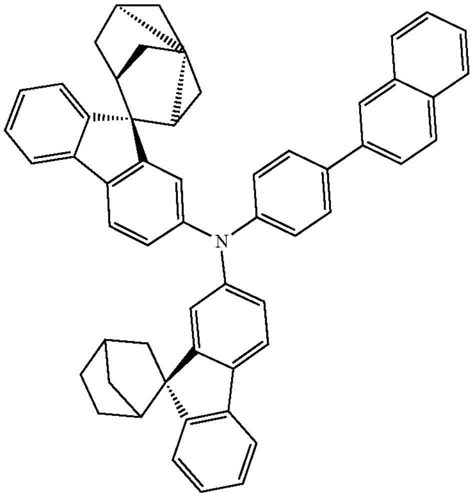

-continued
154
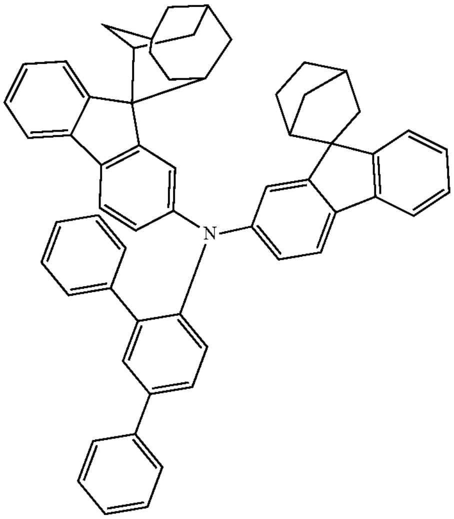
155
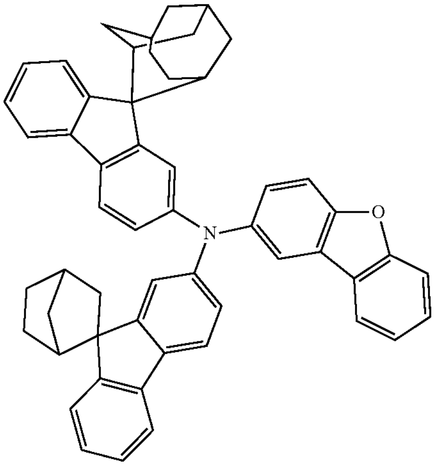
156
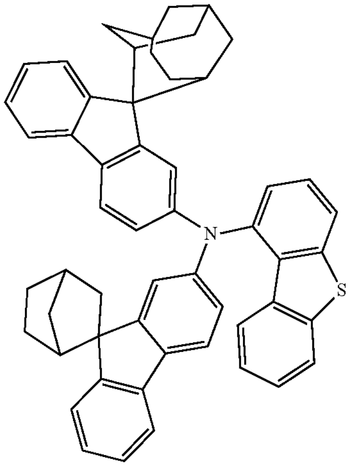
-continued
157
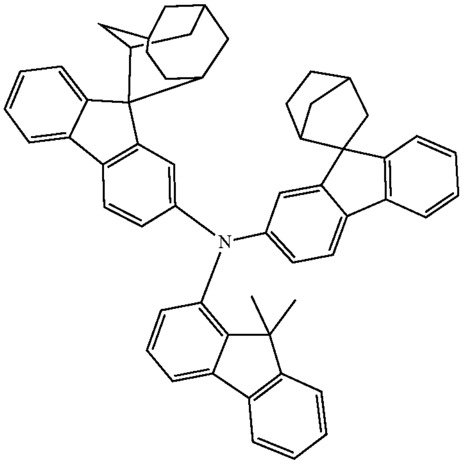
158
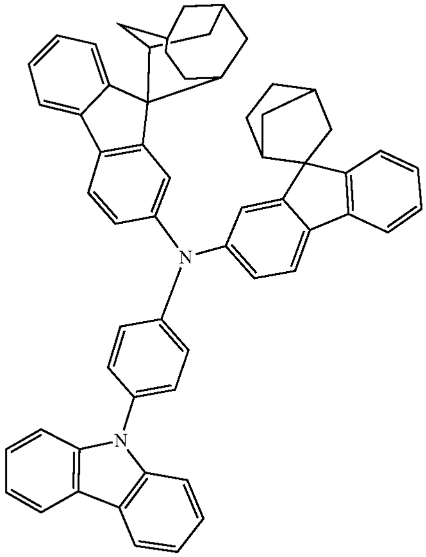
159
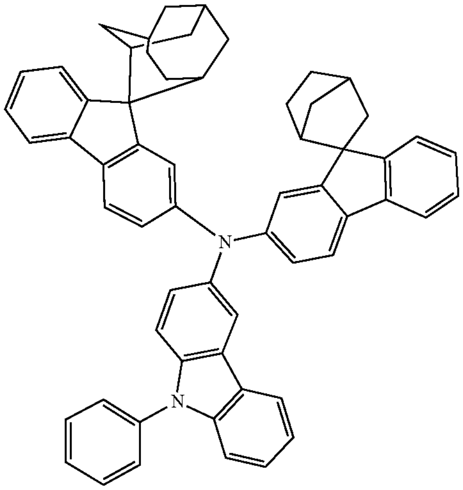

-continued
160
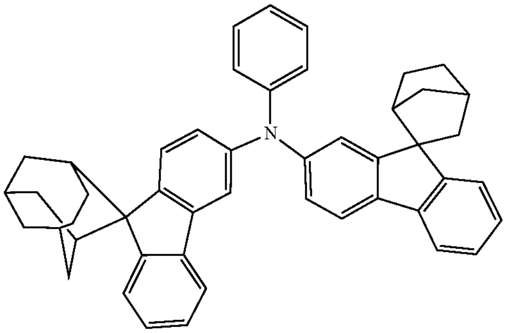
161
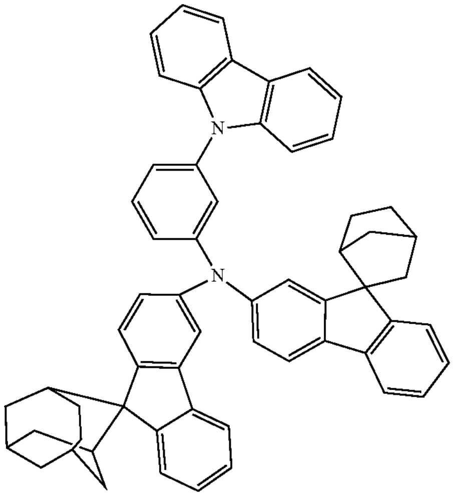
162
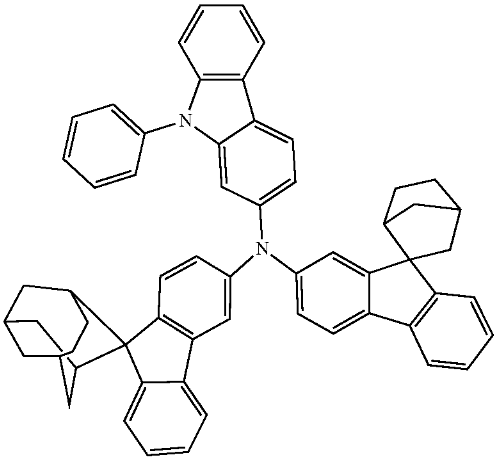
-continued
163
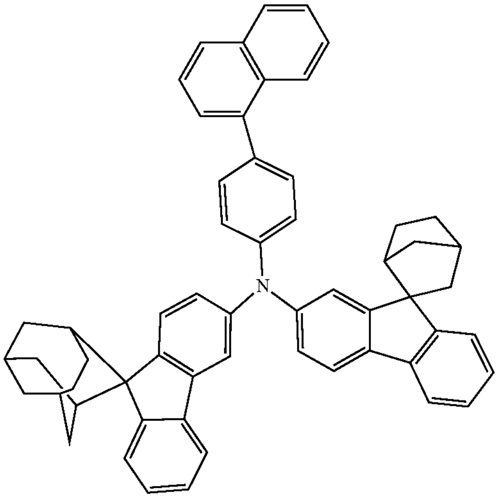
164
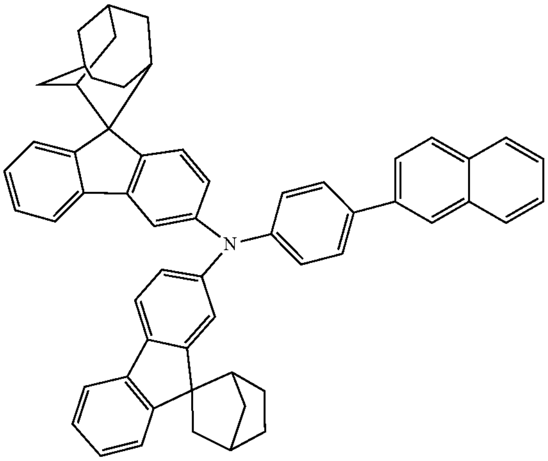
165
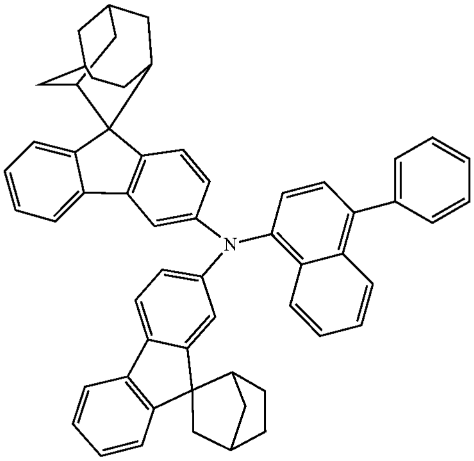

-continued
166
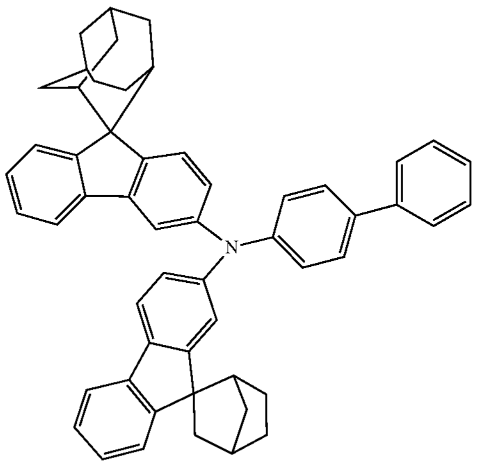
167
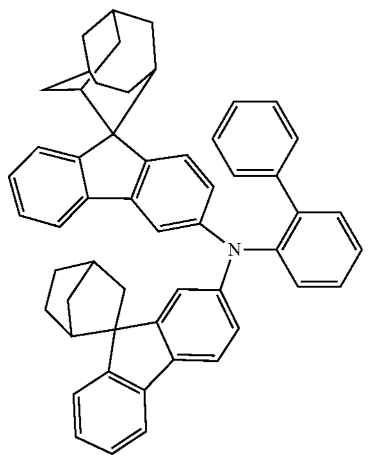
168
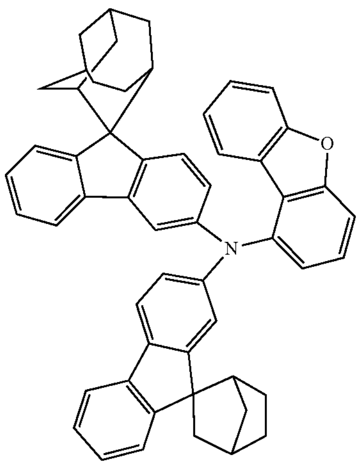
-continued
169
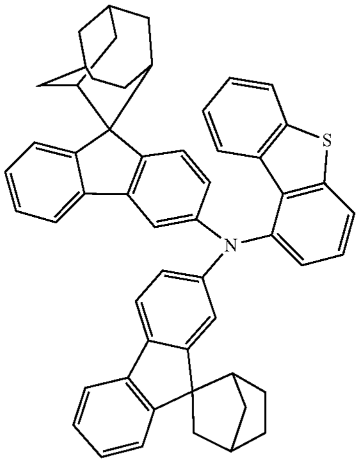
170
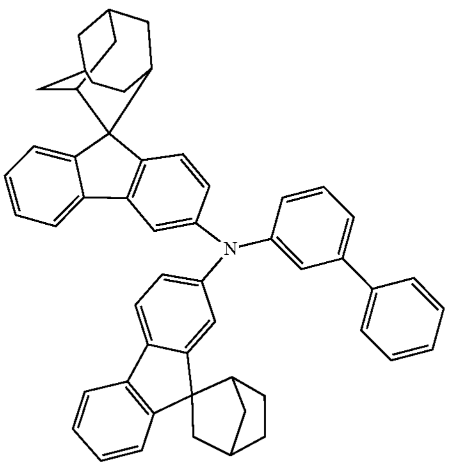
171
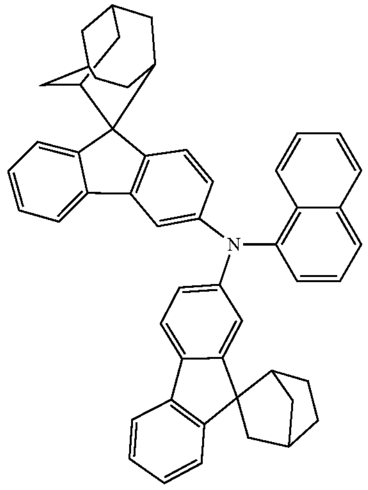

-continued
172
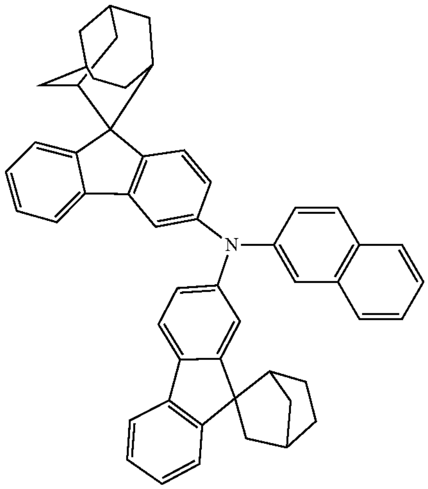
173
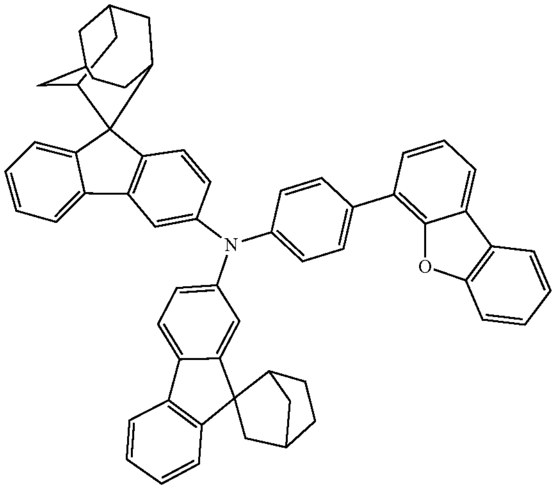
174
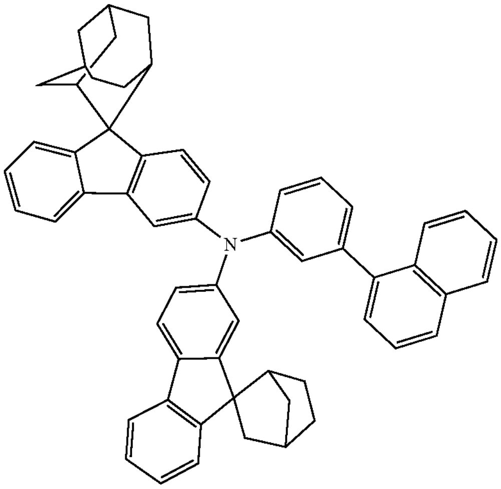
-continued
175
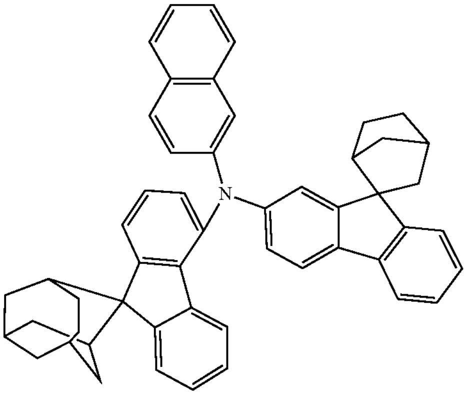
176
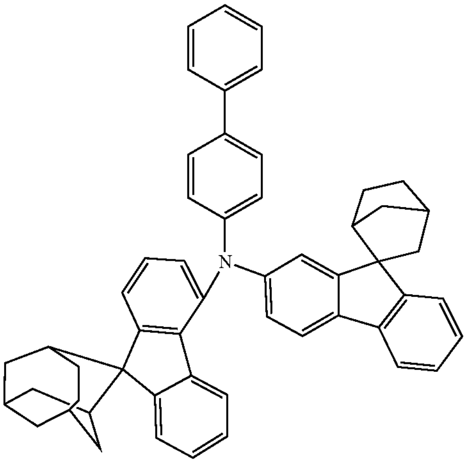
177
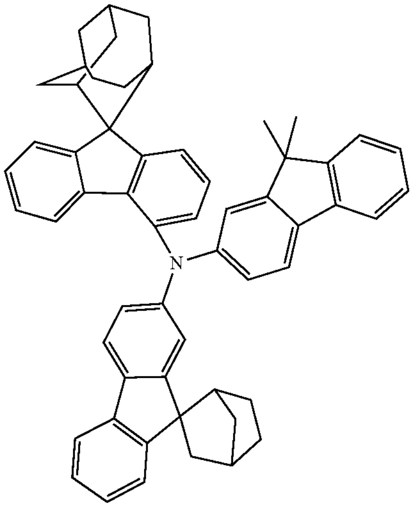

-continued
178
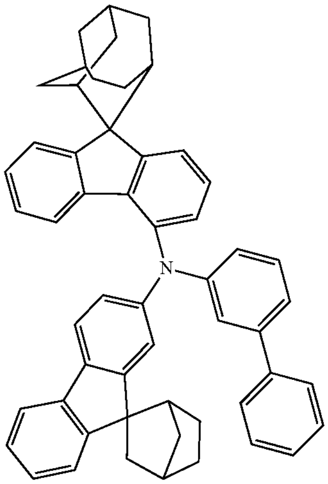
179
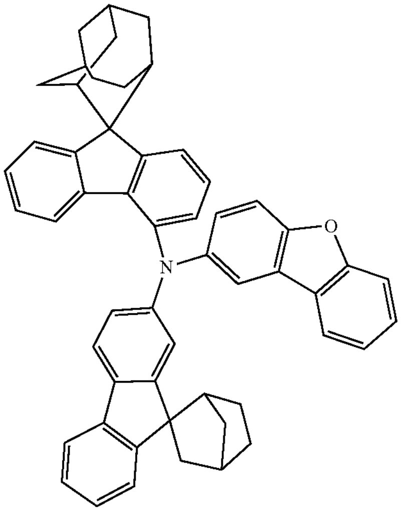
180
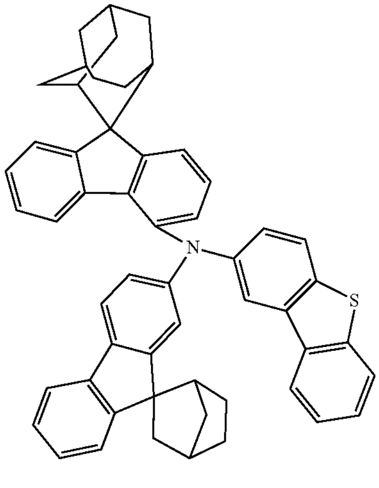
-continued
181
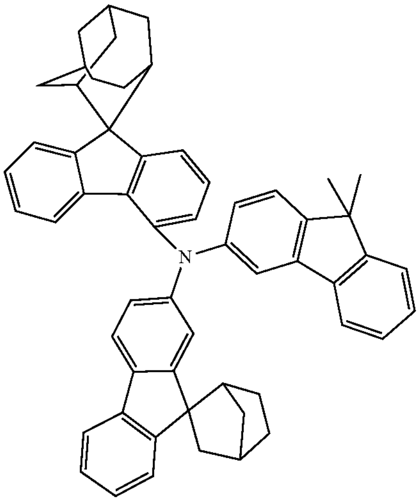
182
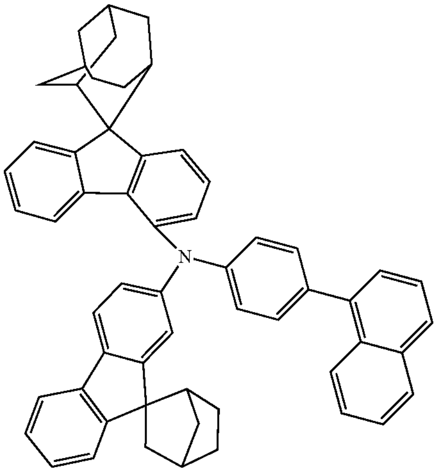
183
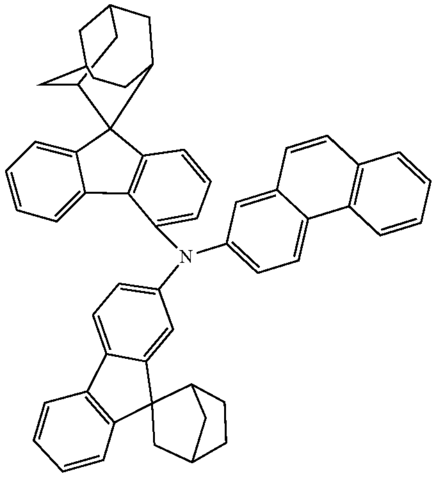

-continued
184
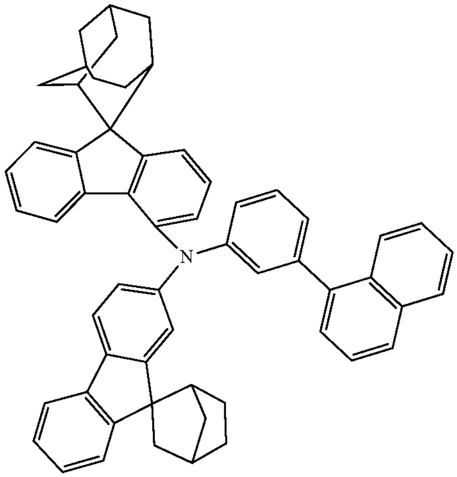
185
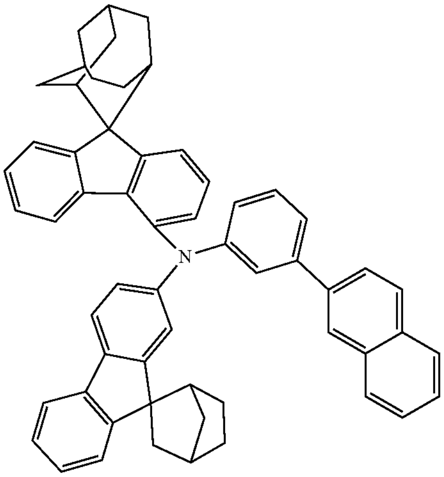
186
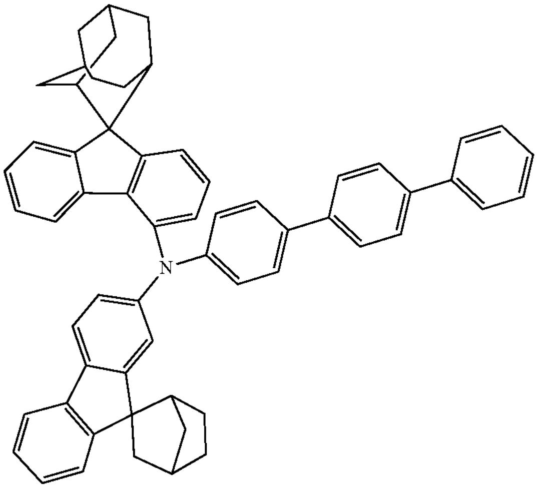
-continued
187
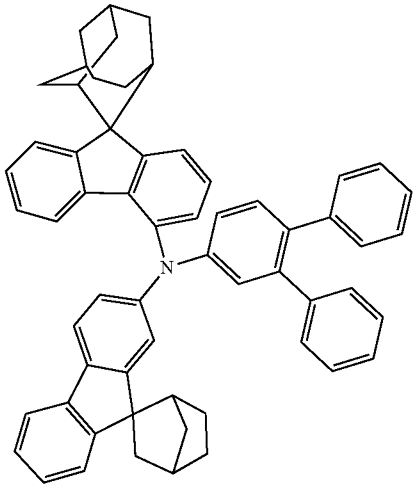
188
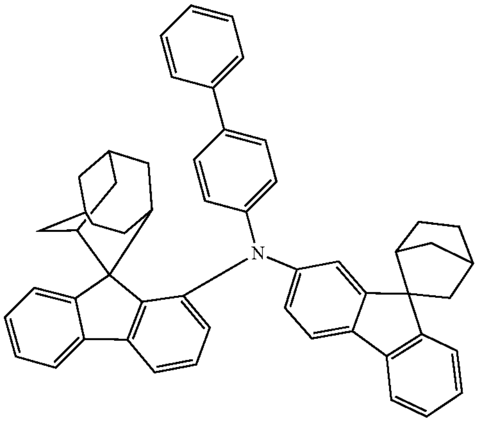
189
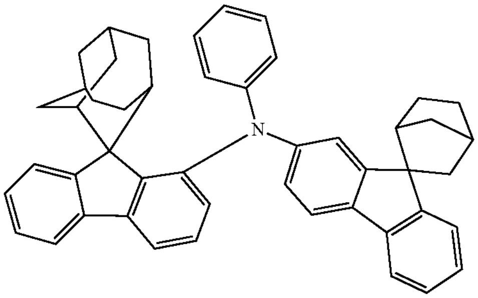
190
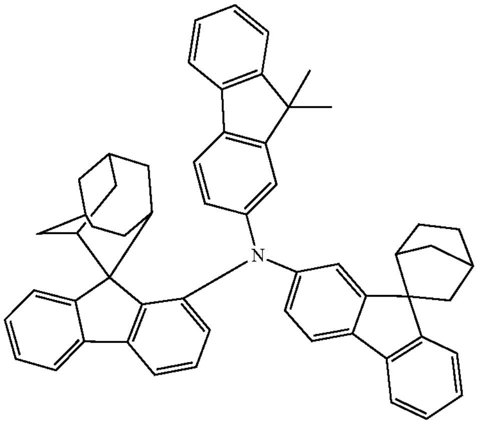

-continued
191
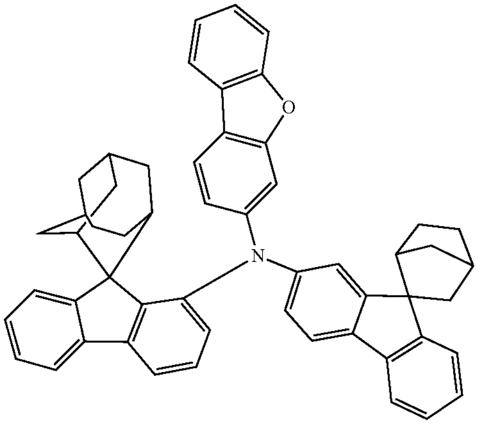
192
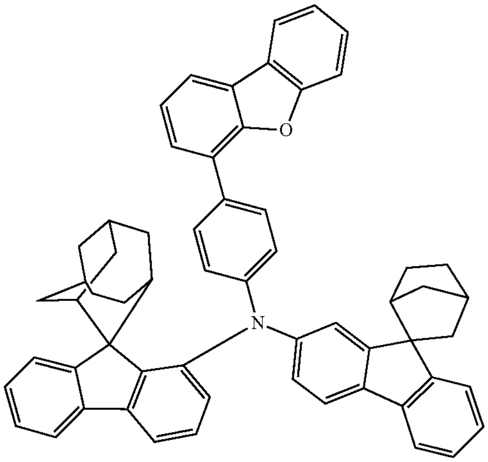
193
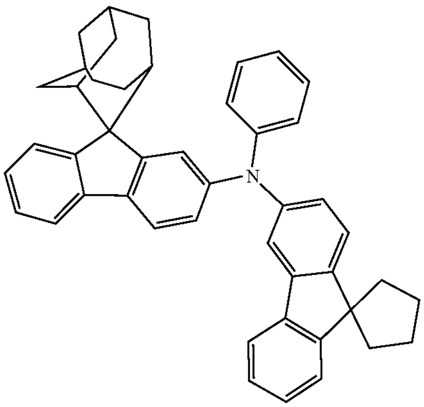
-continued
194
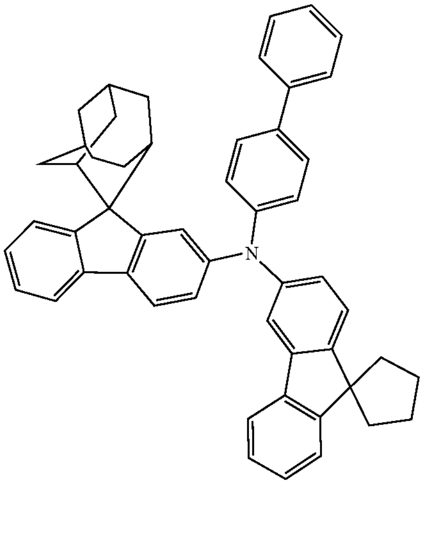
195
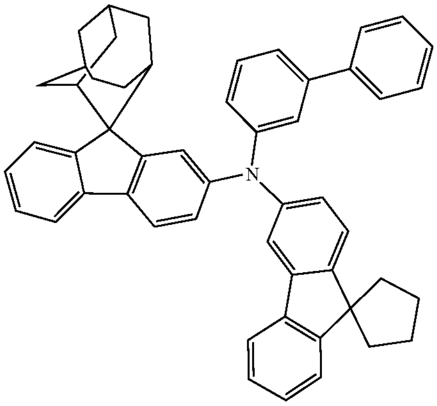
196
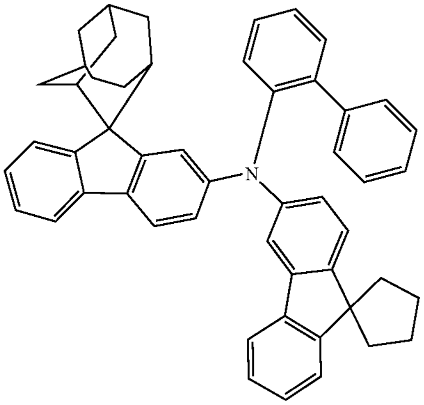

-continued
197
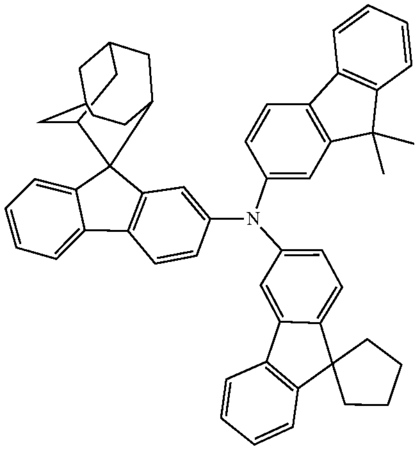
198
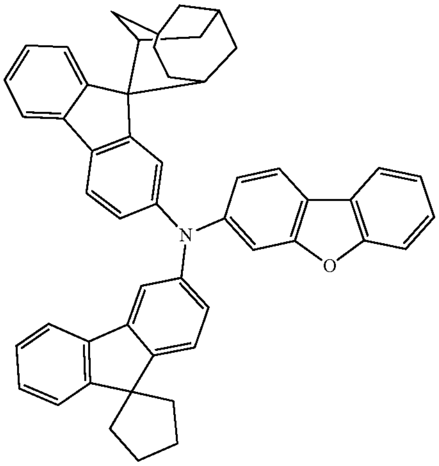
199
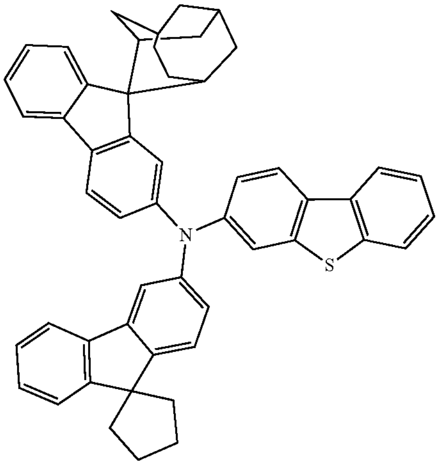
-continued
200
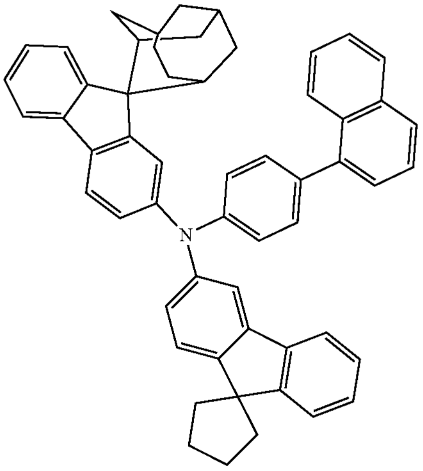
201
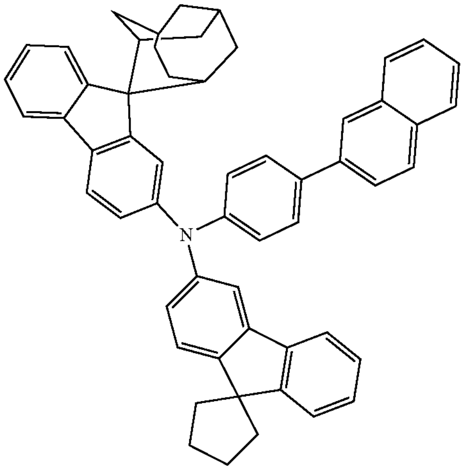
202
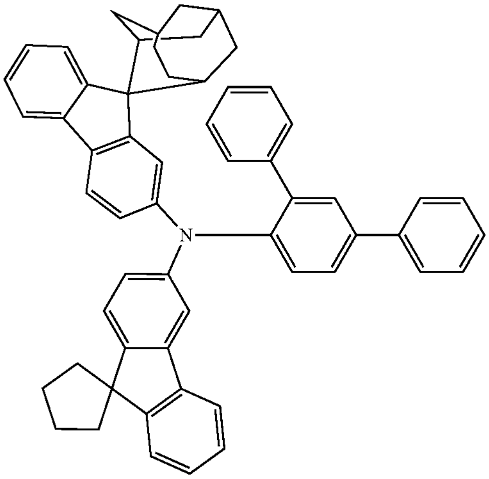

-continued
203
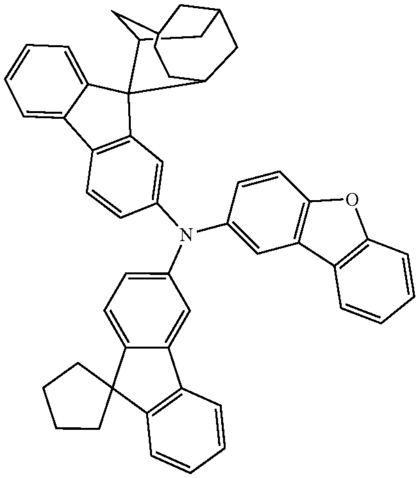
204
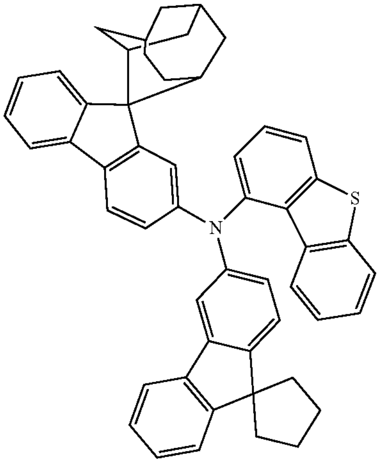
205
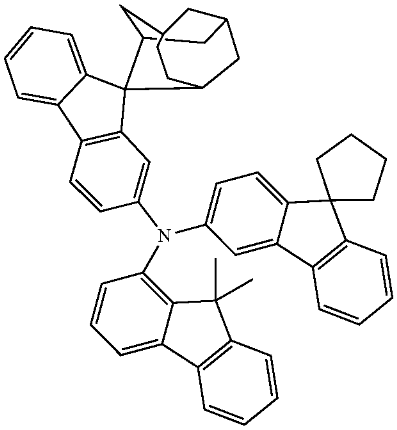
-continued
206
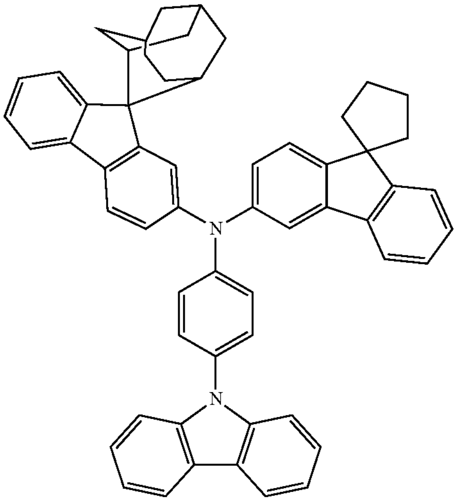
207
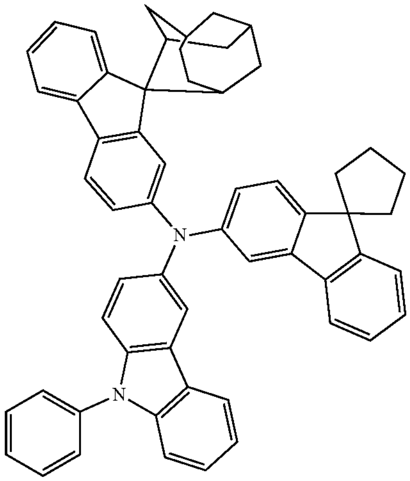
208
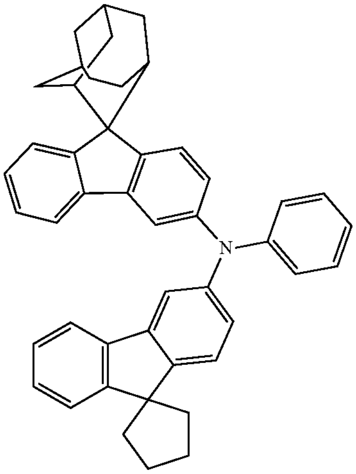

-continued
209
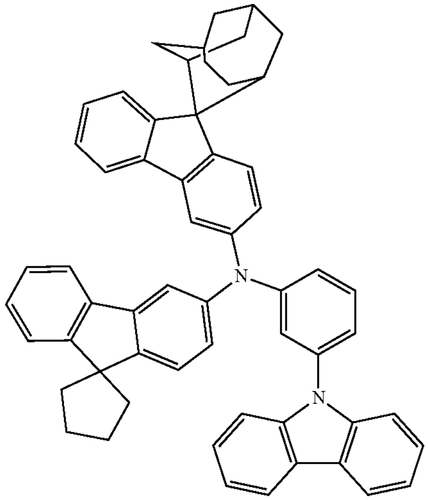
210
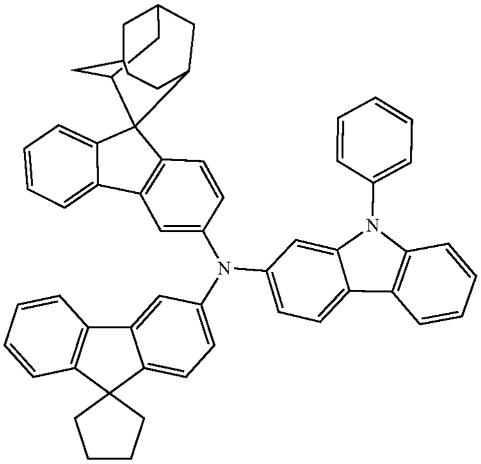
211
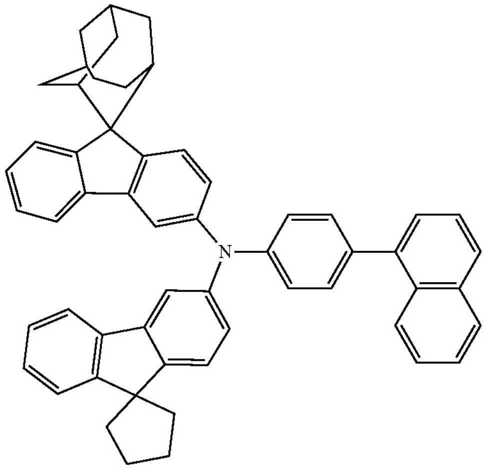
-continued
212
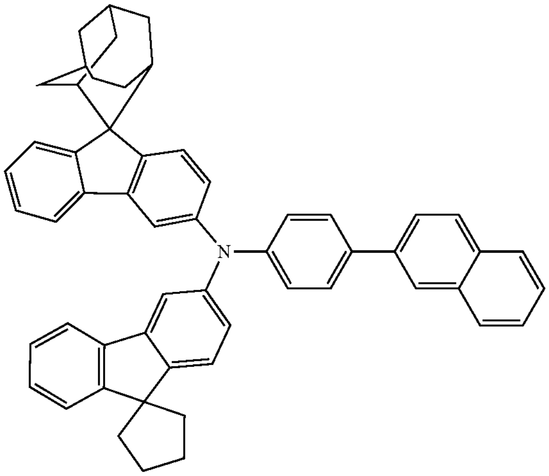
213
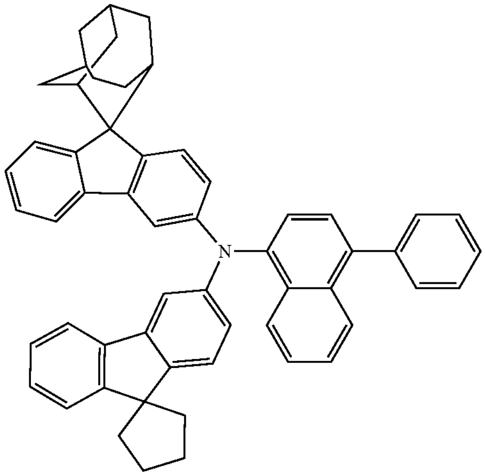
214
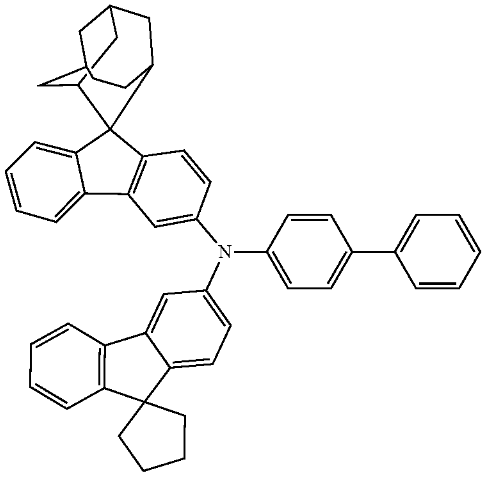

-continued
215
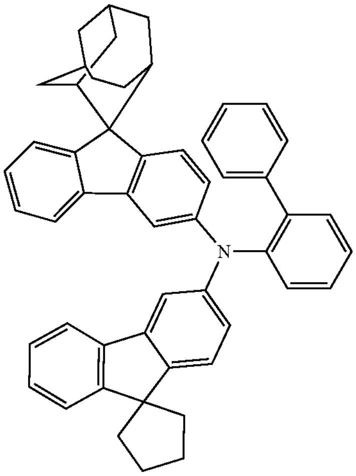
216
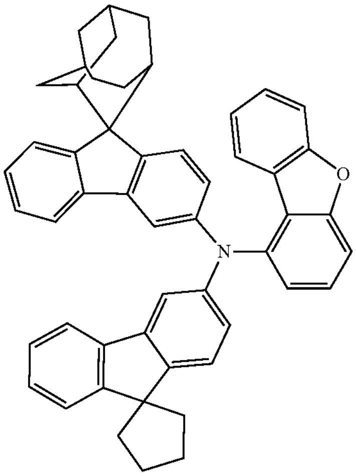
217
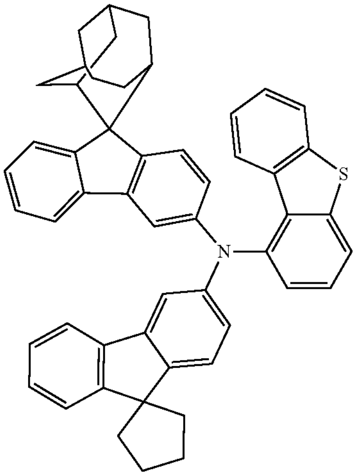
-continued
218
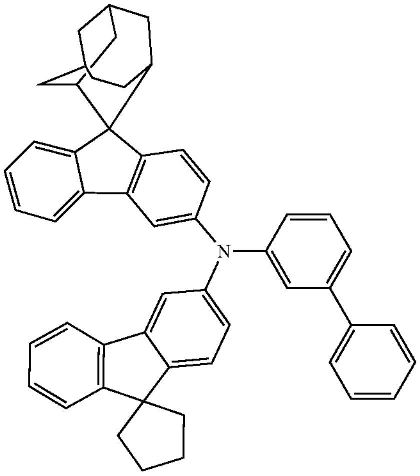
219
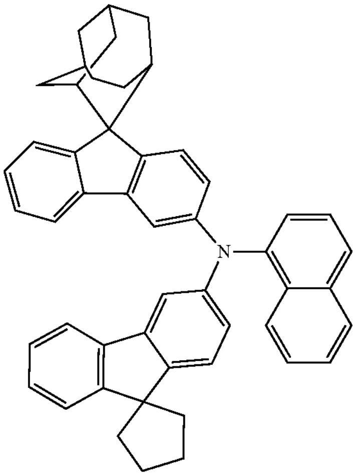
220
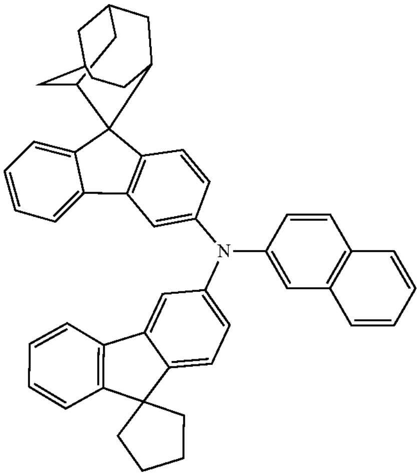

-continued
221
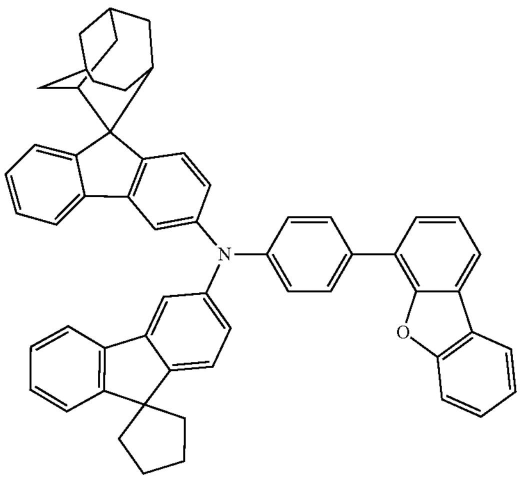
222
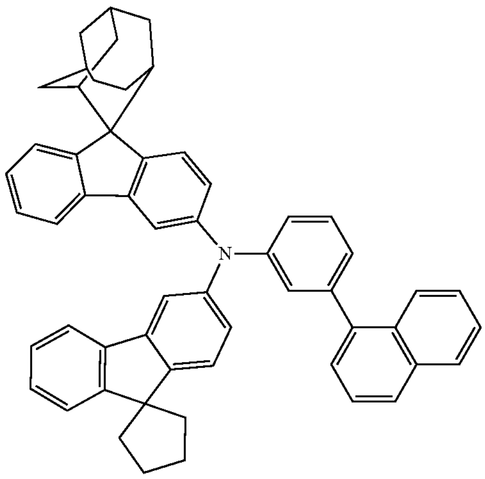
223
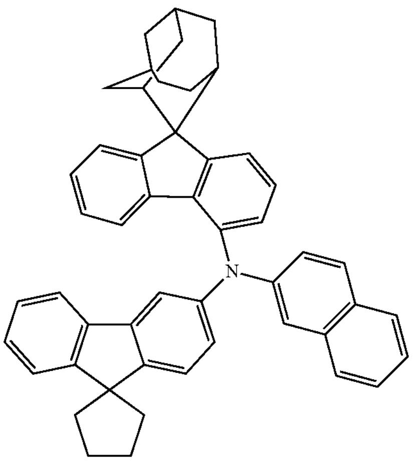
-continued
224
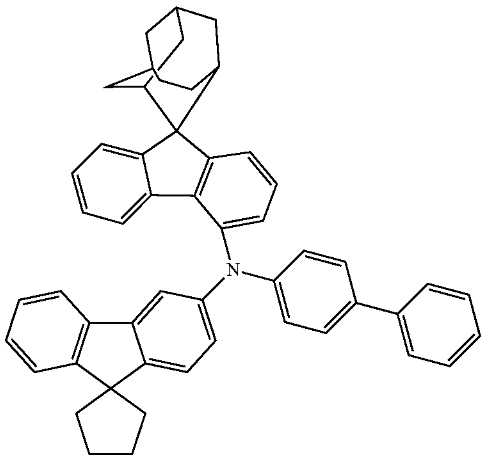
225
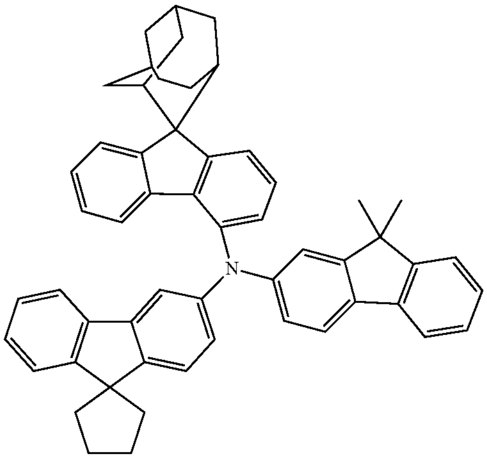
226
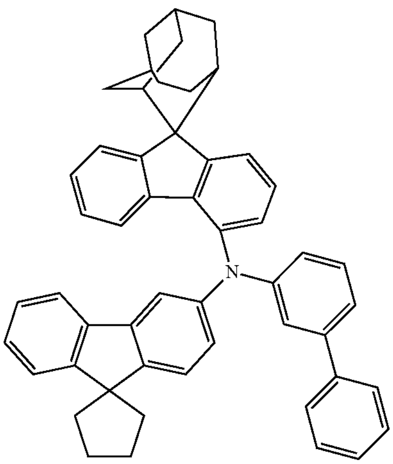

-continued
227
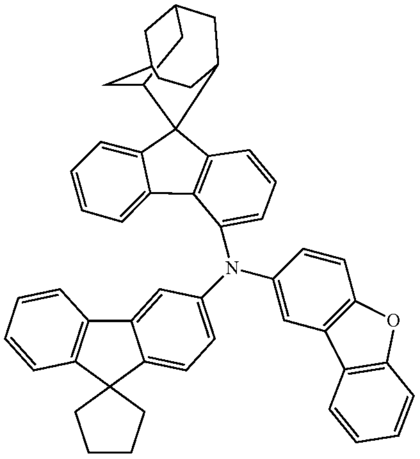
228
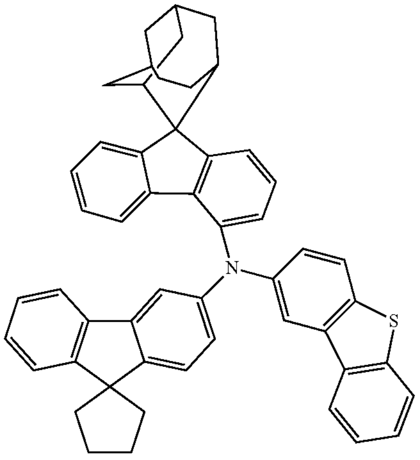
229
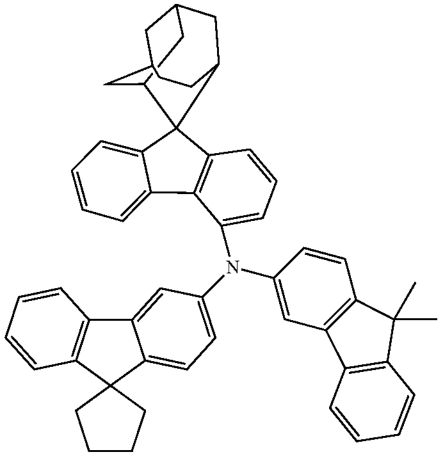
-continued
230
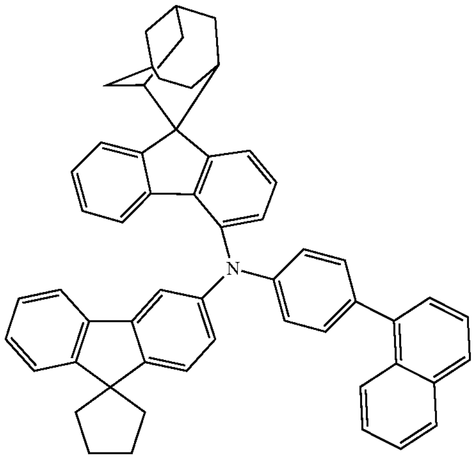
231
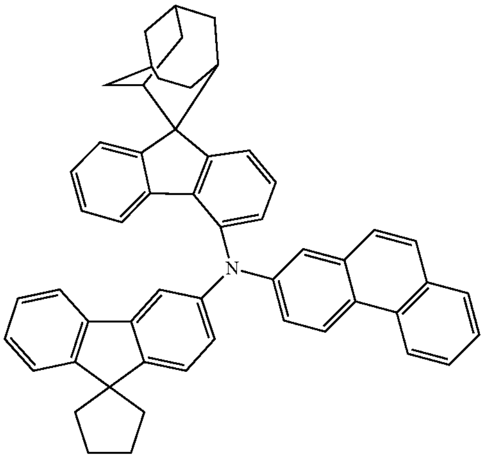
232
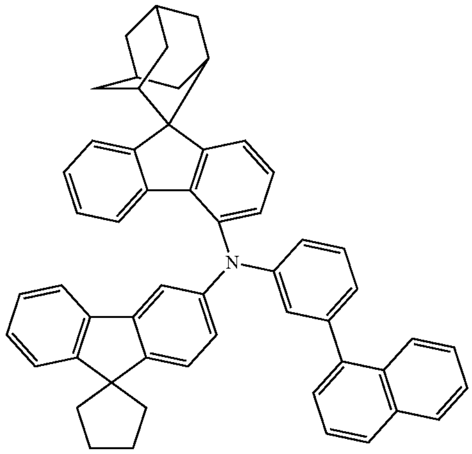

-continued
233
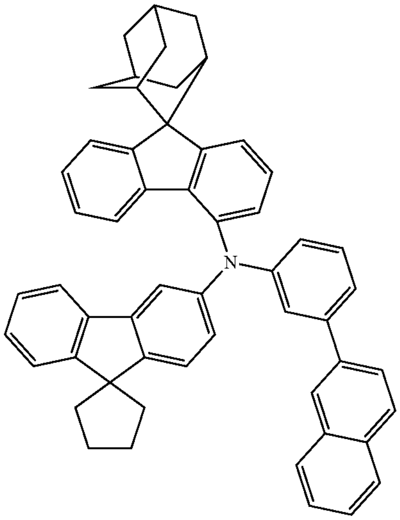
234
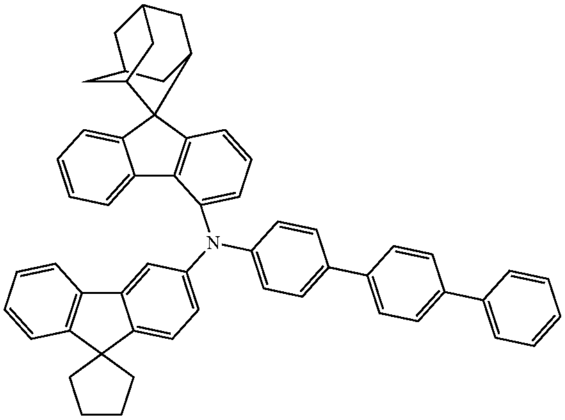
235
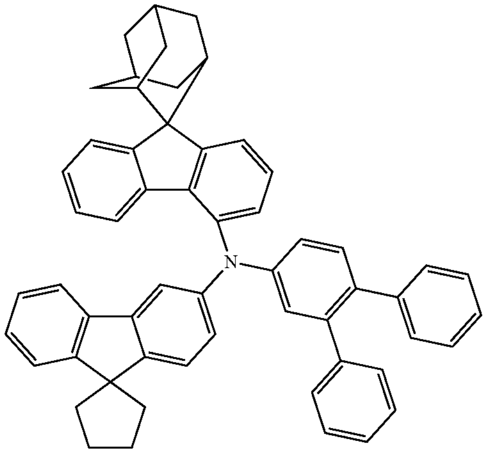
-continued
236
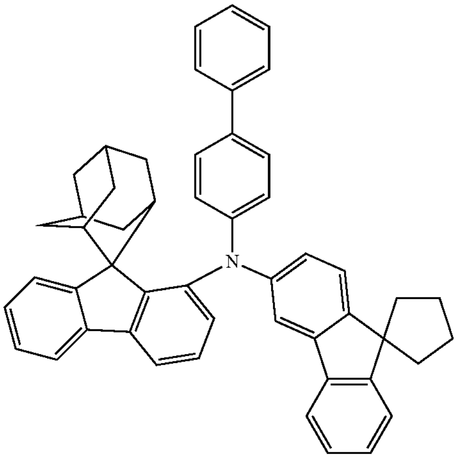
237
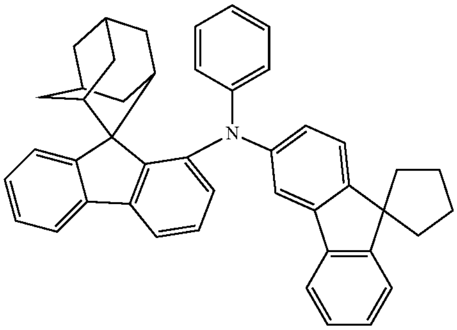
238
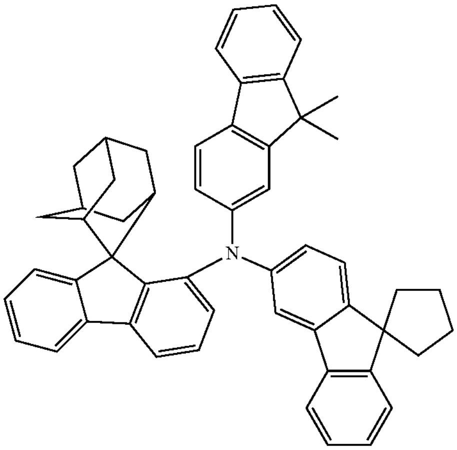

-continued
239
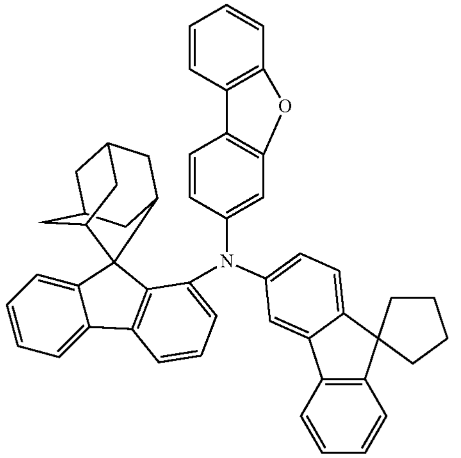
240
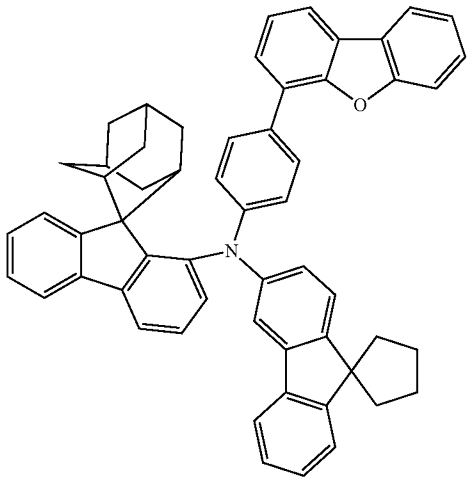
241
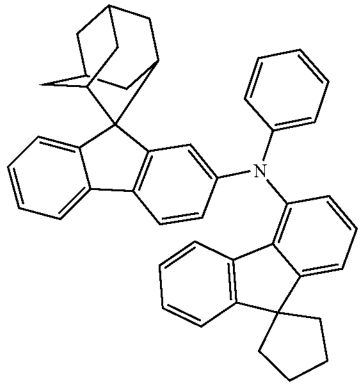
-continued
242
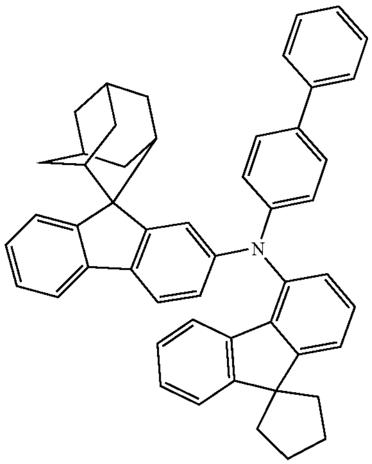
243
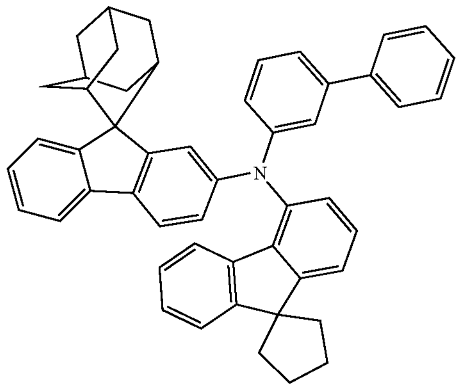
244
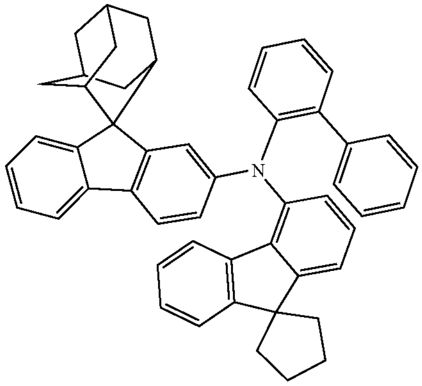

-continued
245
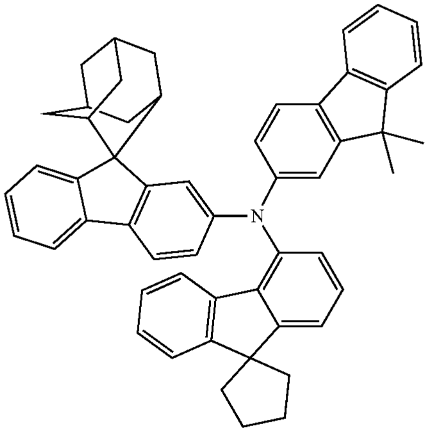
246
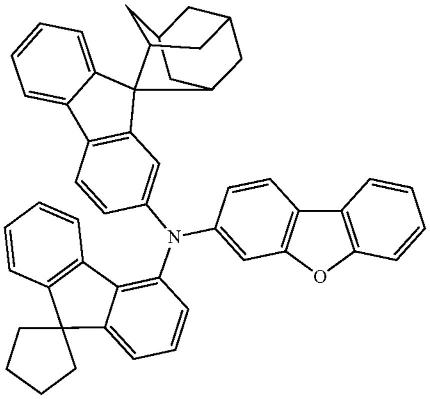
247
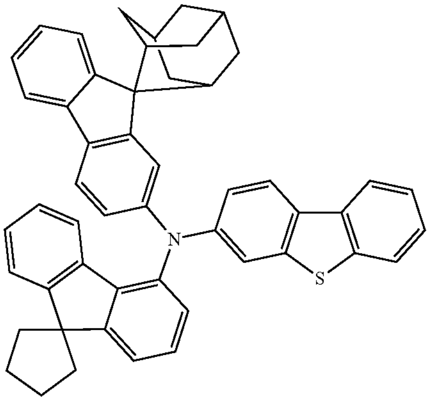
248
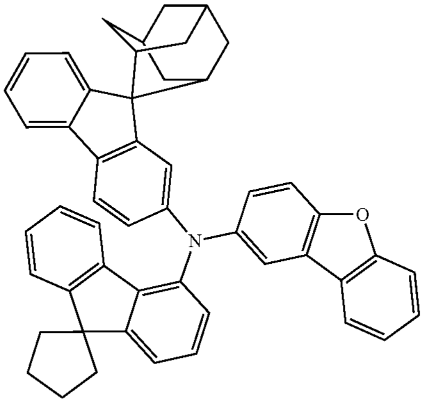
-continued
249
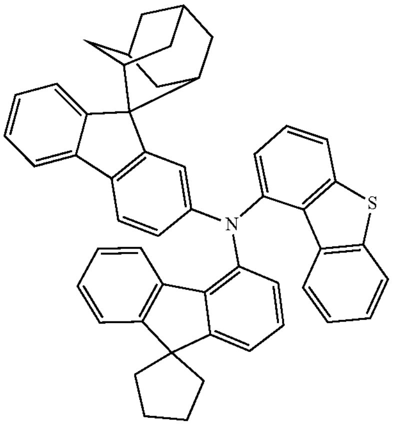
250
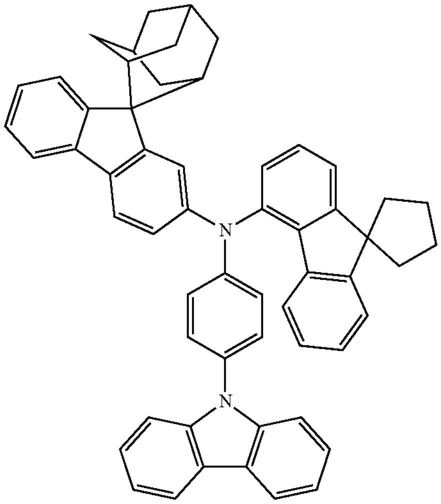
251
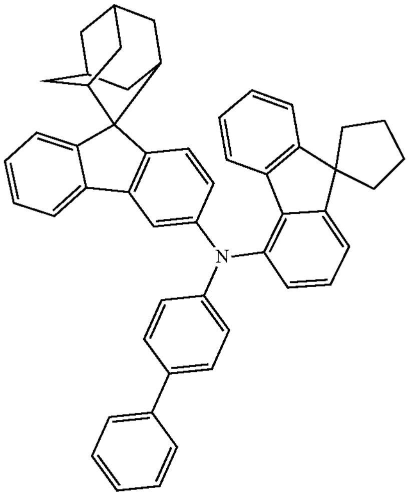

-continued
252
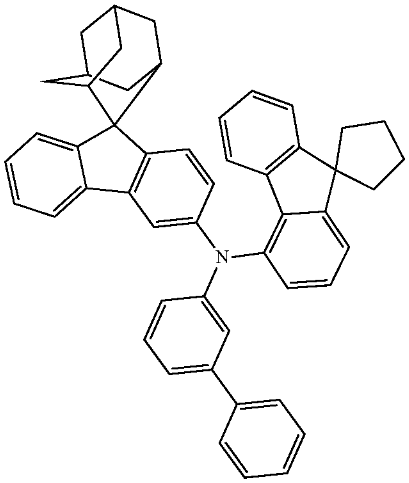
253
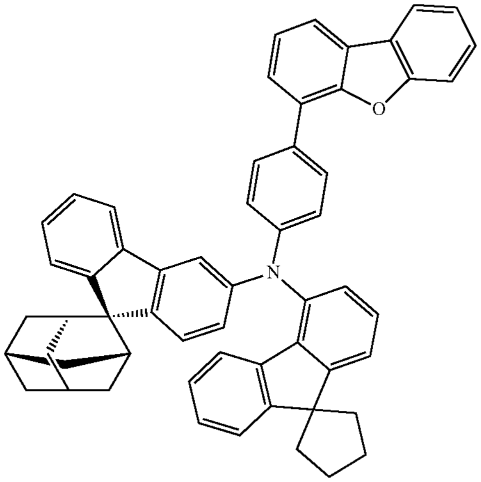
254
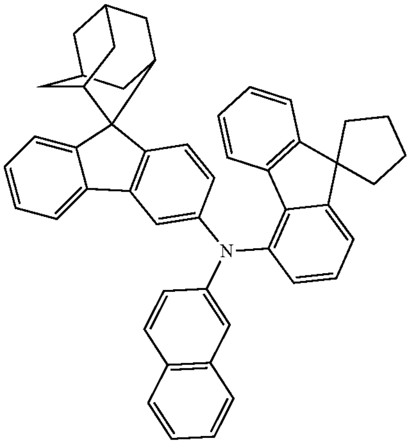
-continued
255
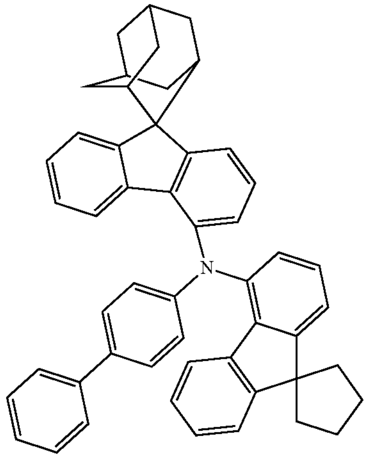
256
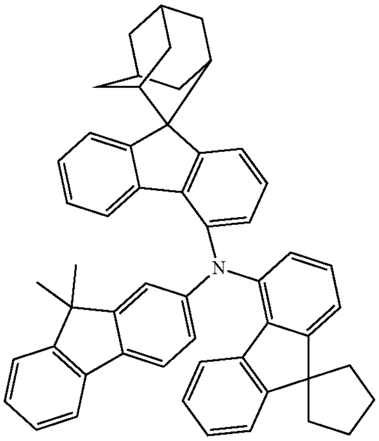
257
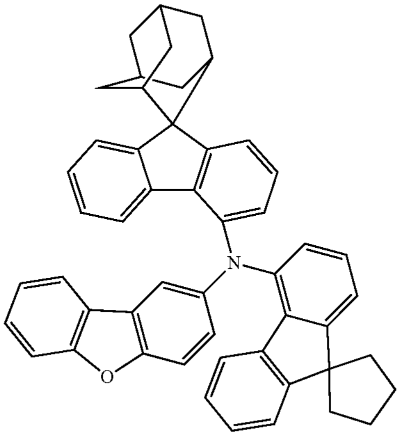

-continued
258
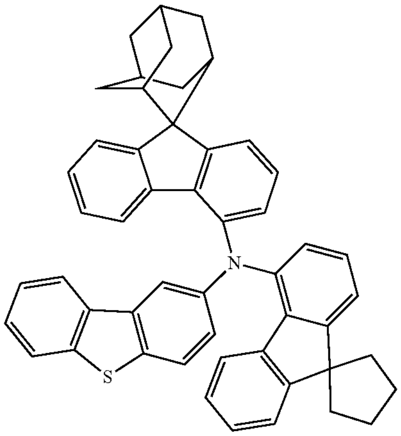
259
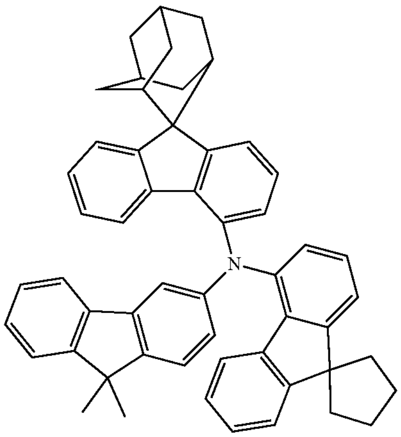
260
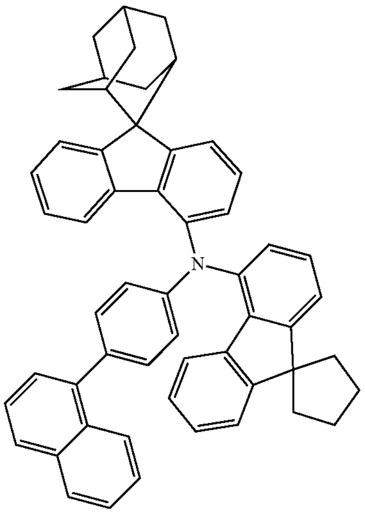
-continued
261
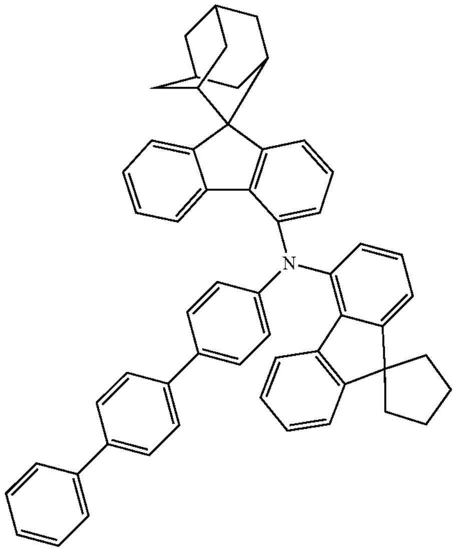
262
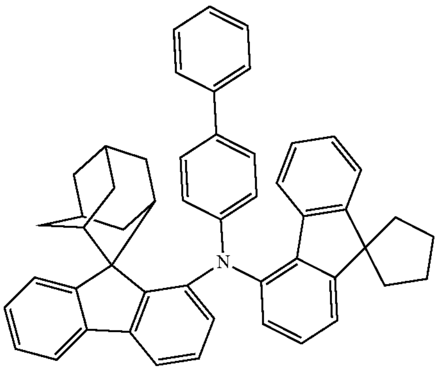
263
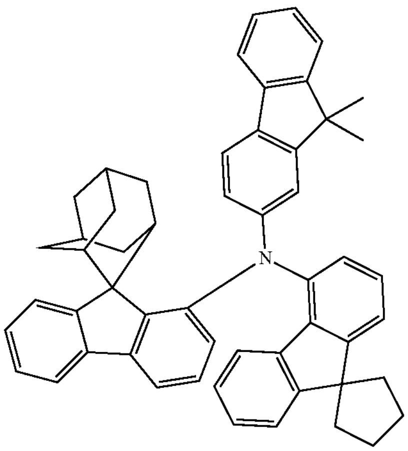

-continued
264
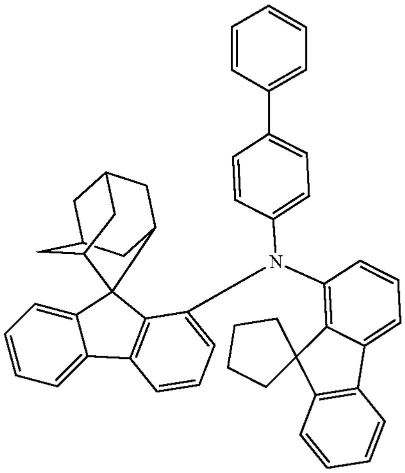
265
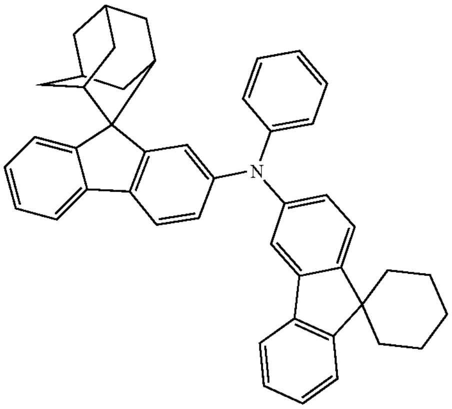
266
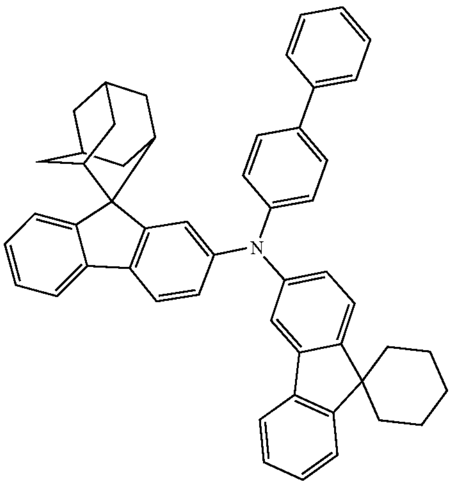
-continued
267
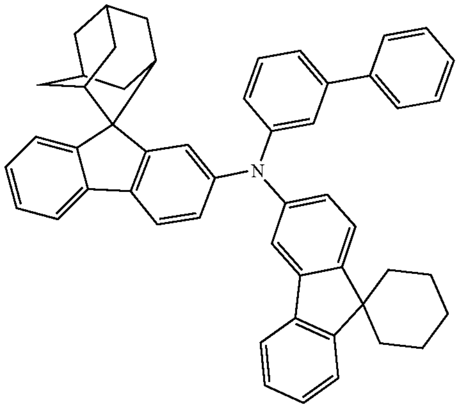
268
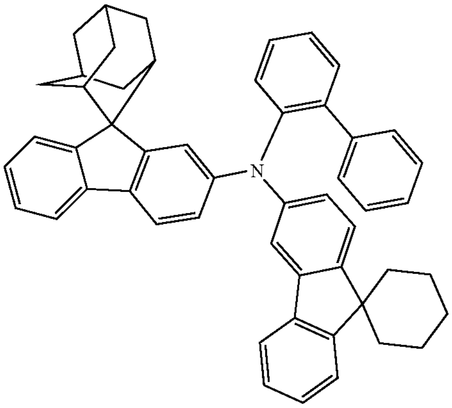
269
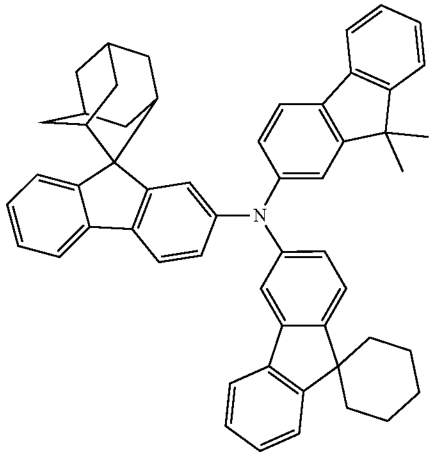

-continued
270
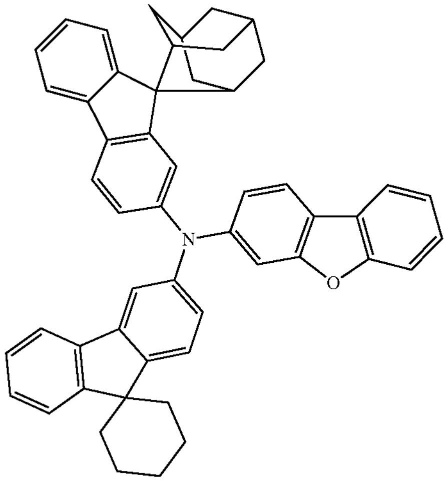
271
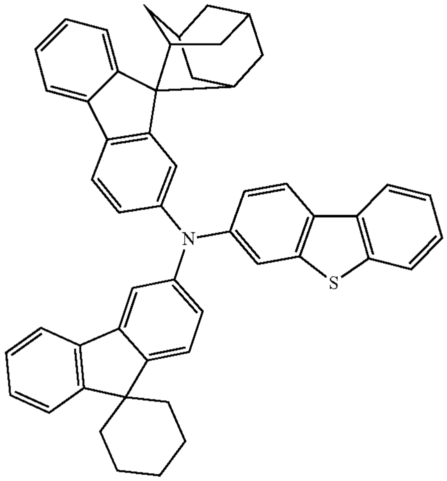
272
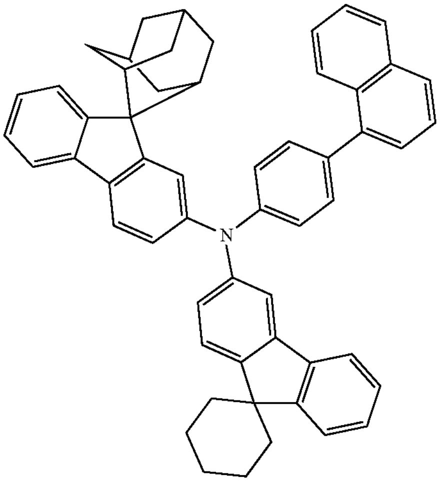
-continued
273
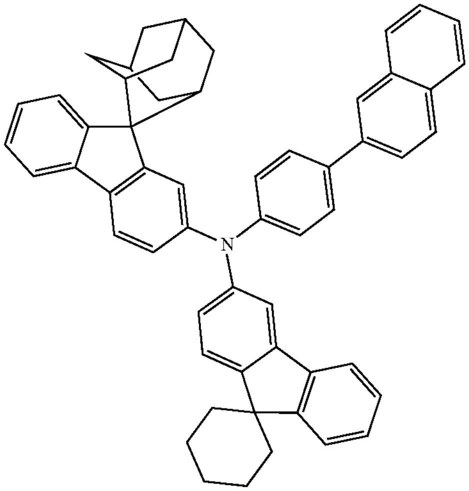
274
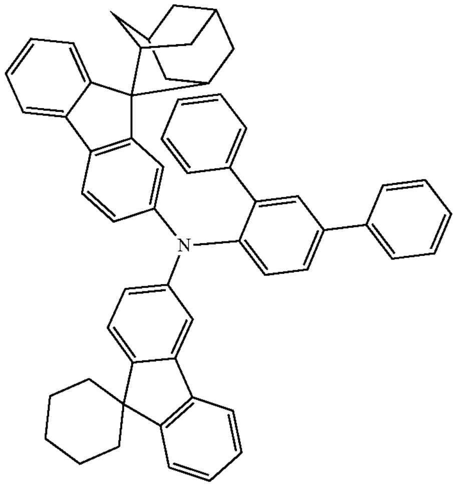
275
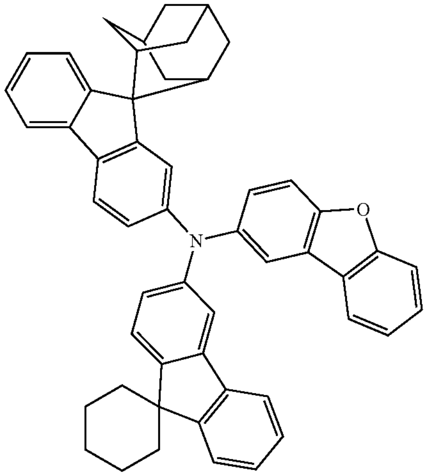

-continued
276
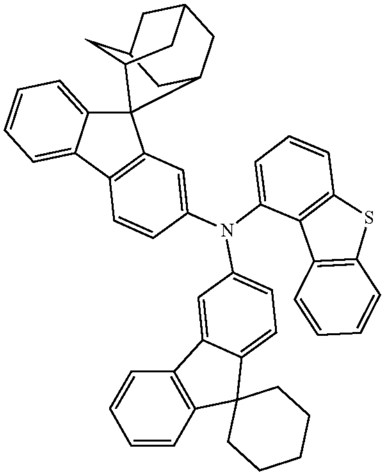
277
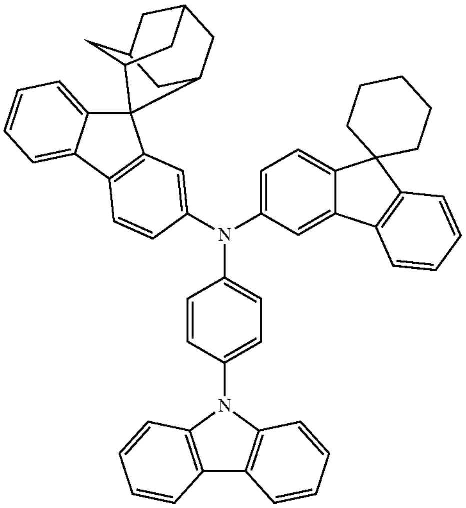
278
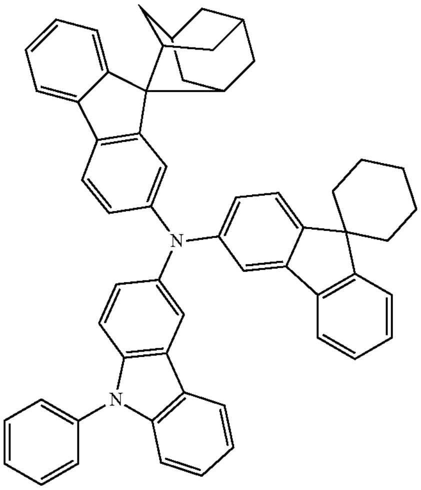
-continued
279
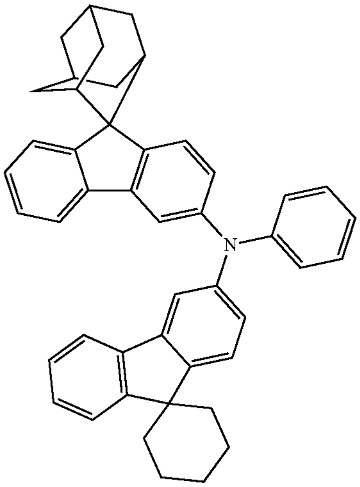
280
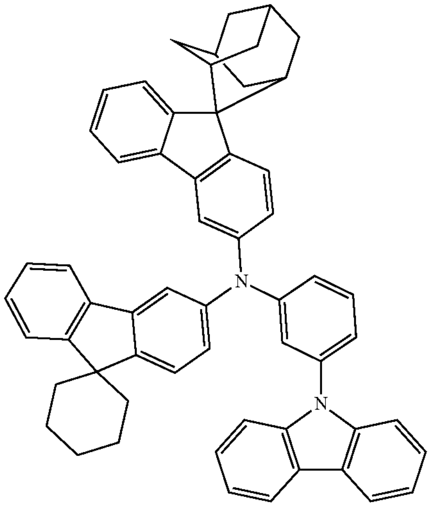
281
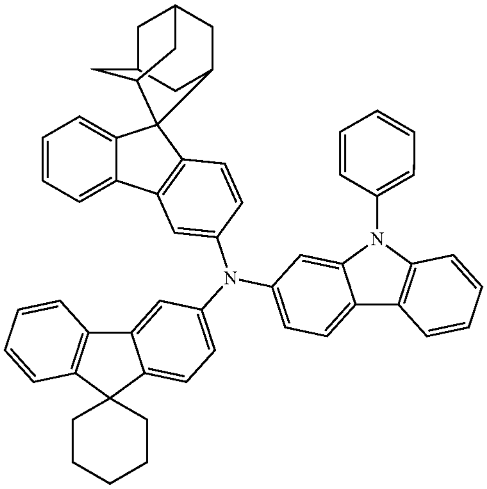

-continued
282
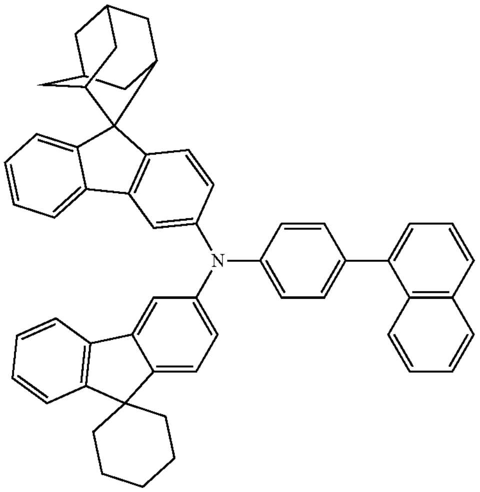
283
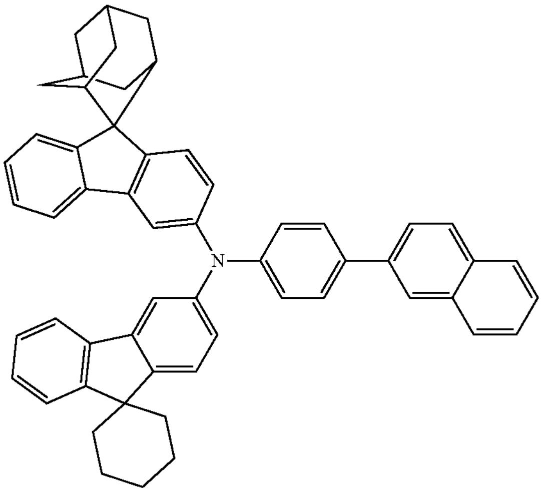
284
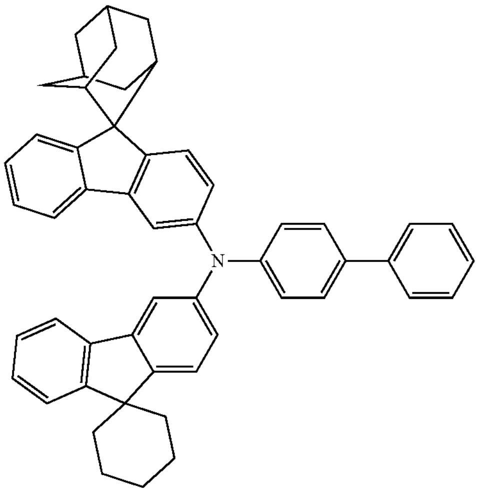
-continued
285
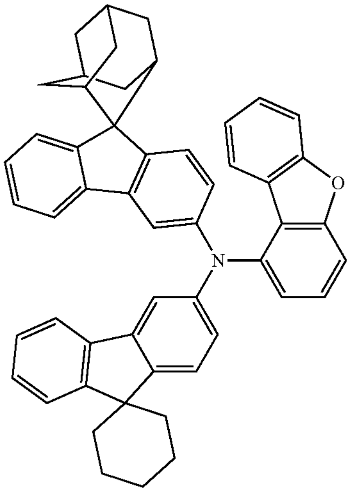
286
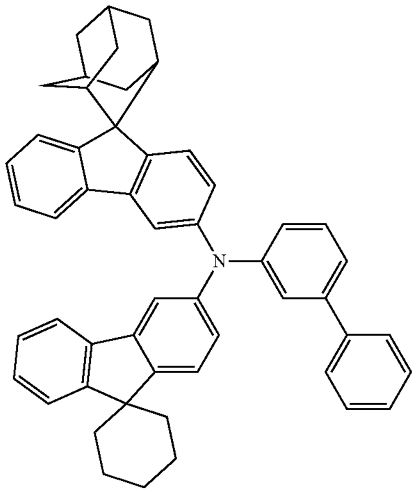
287
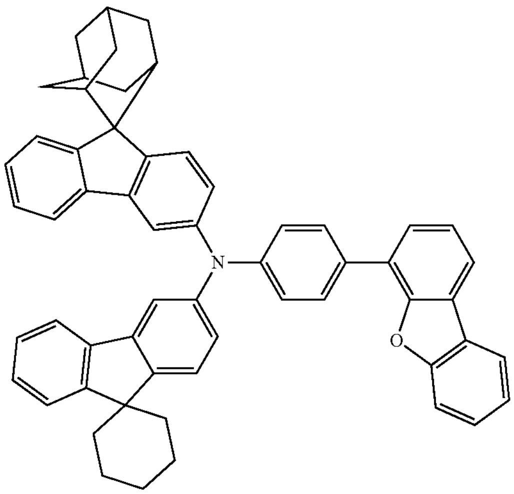

-continued
288
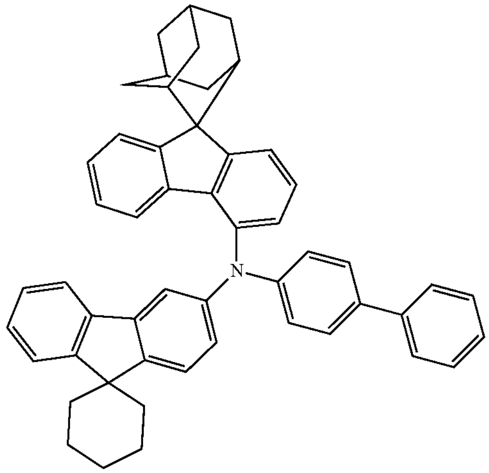
289
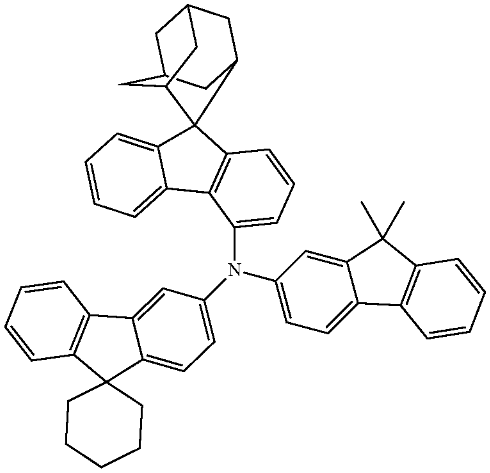
290
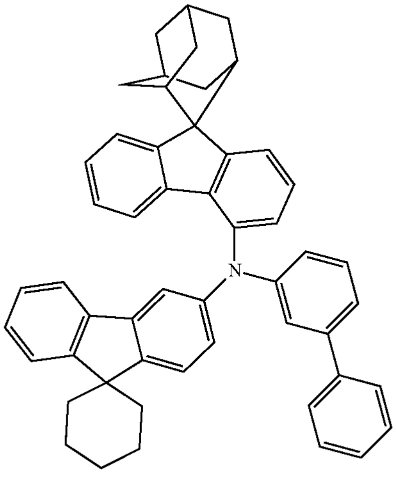
-continued
291
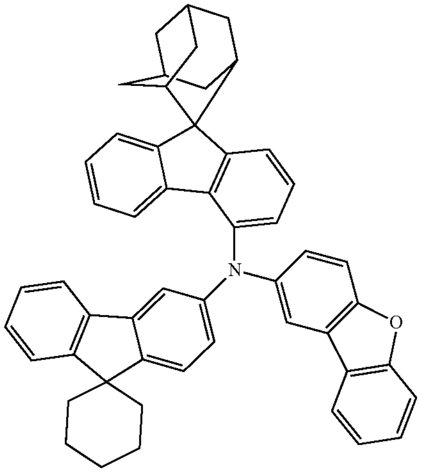
292
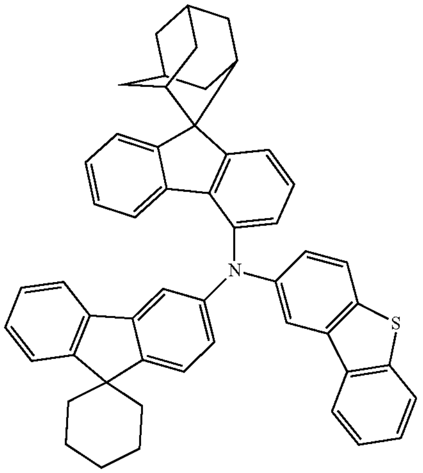
293
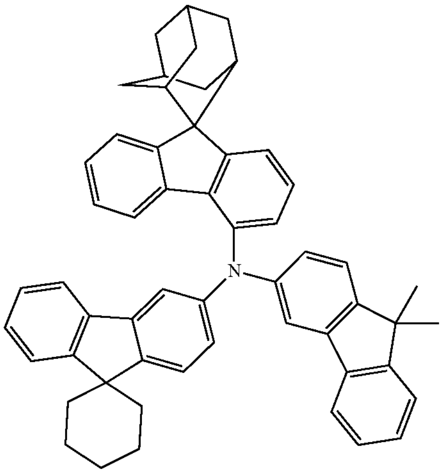

-continued
294
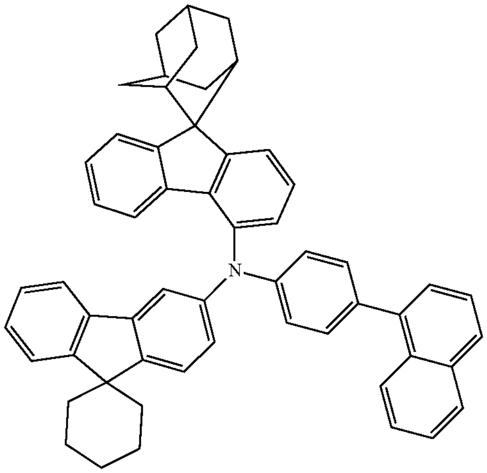
295
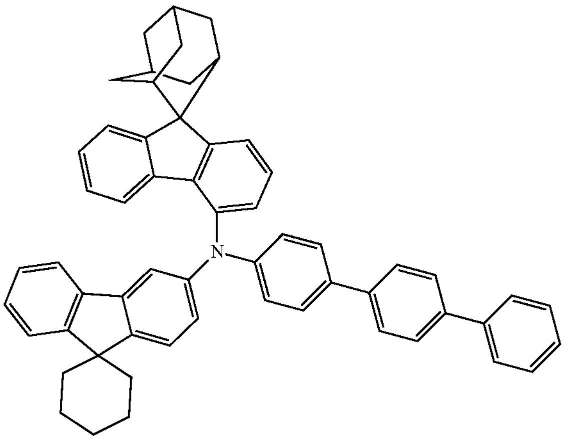
296
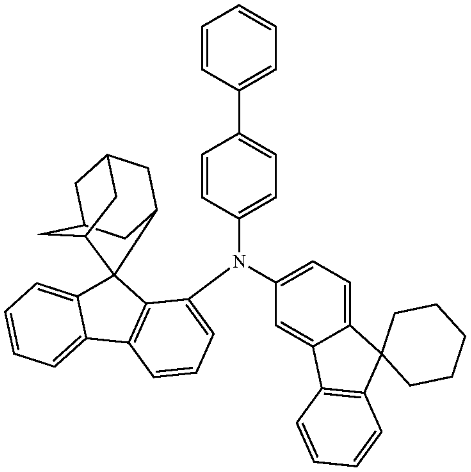
-continued
297
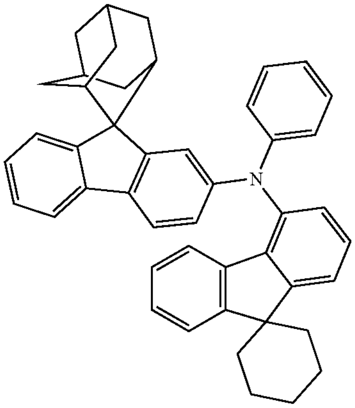
298
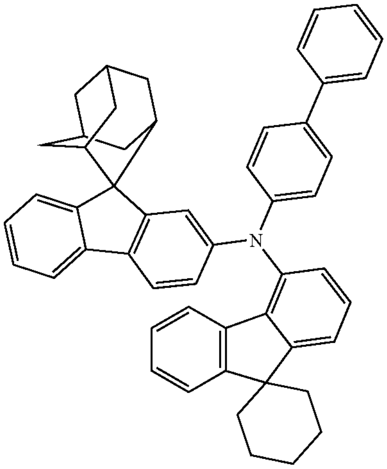
299
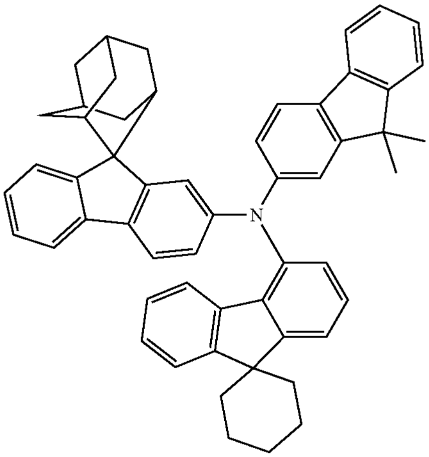

-continued
300
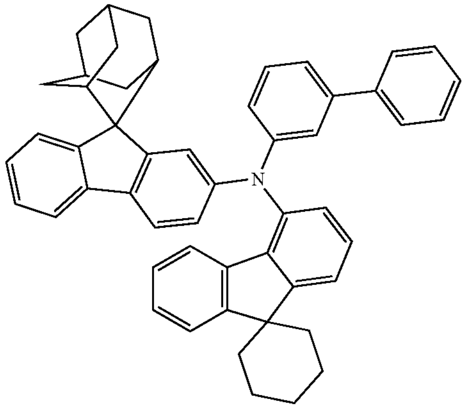
301
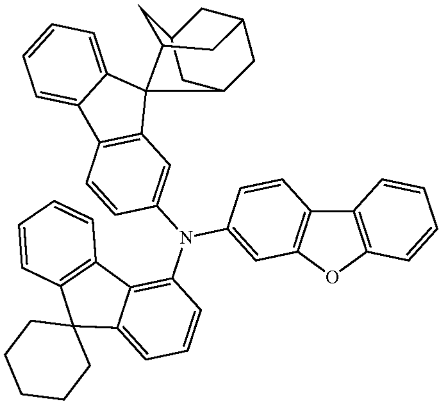
302
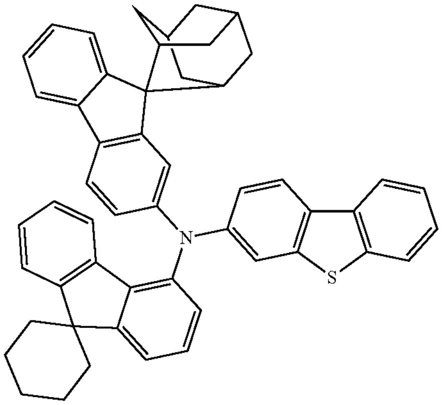
303
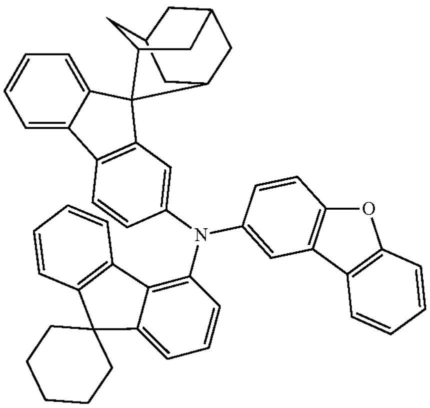
-continued
304
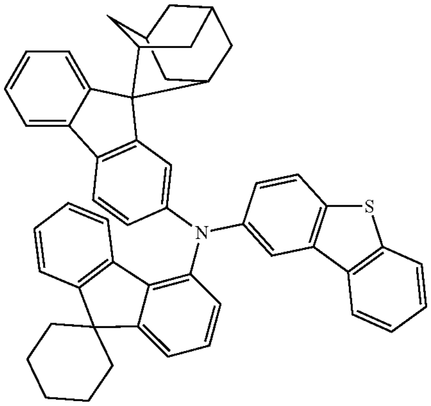
305
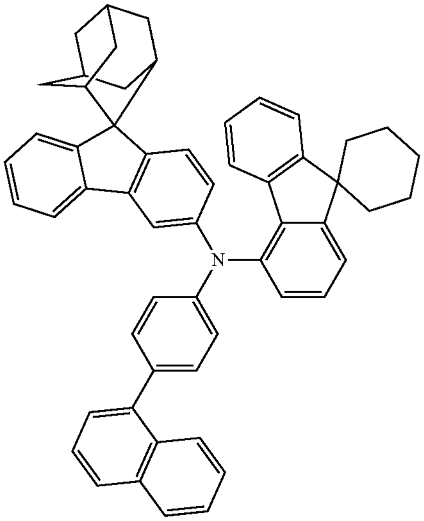
306
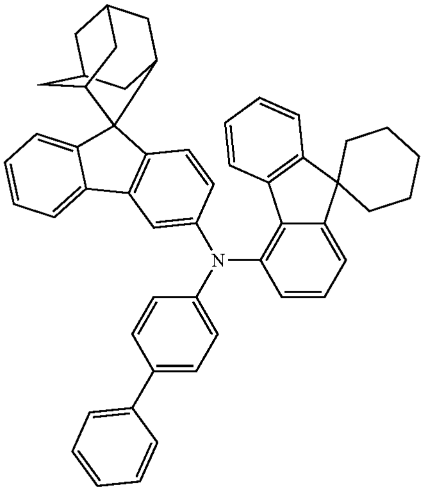

-continued
307
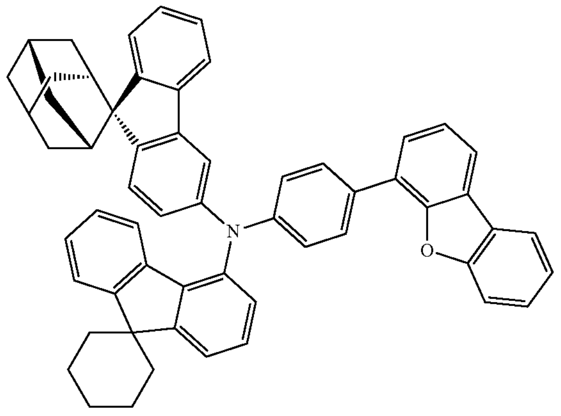
308
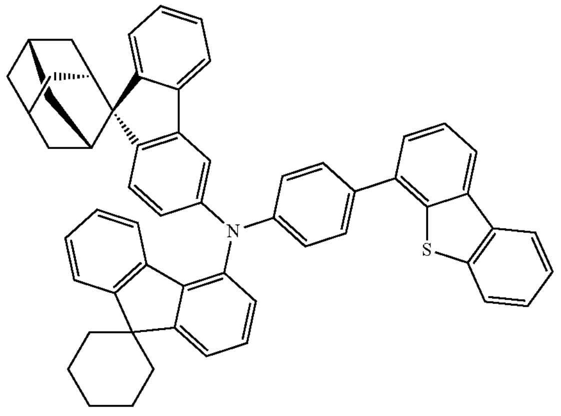
309
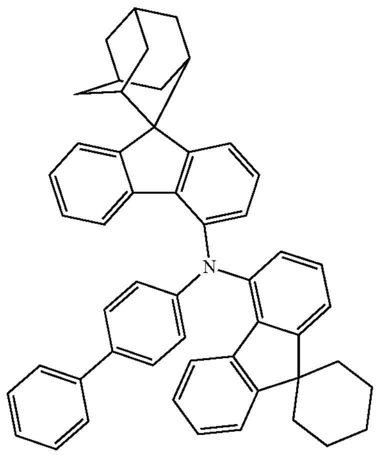
-continued
310
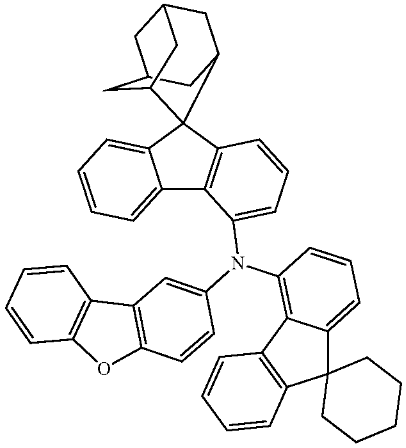
311
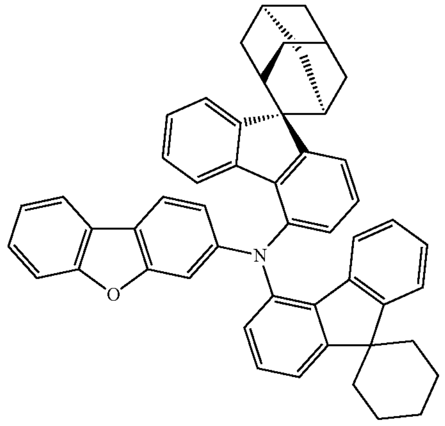
312
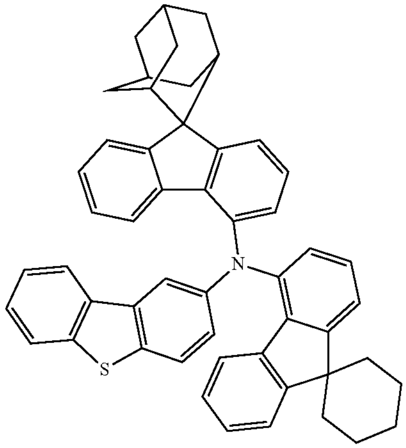

-continued
313
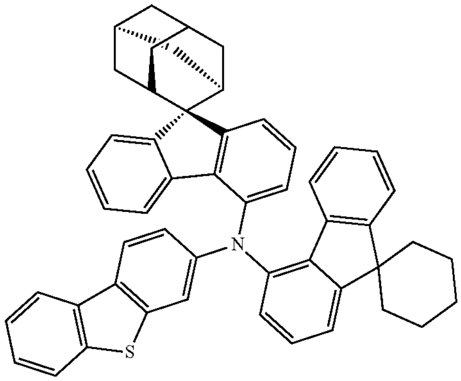
314
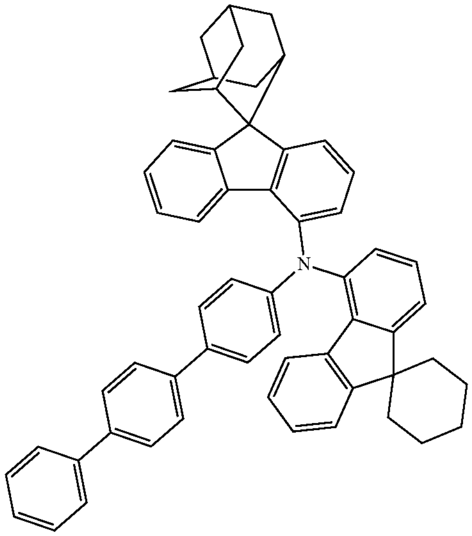
315
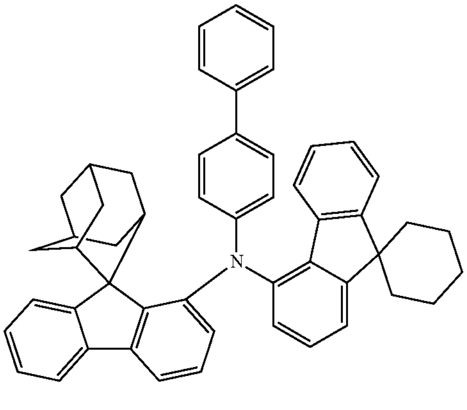
-continued
316
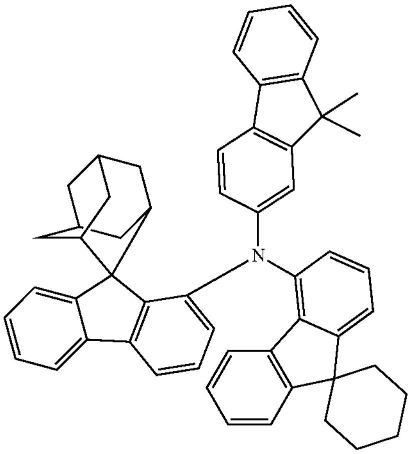
317
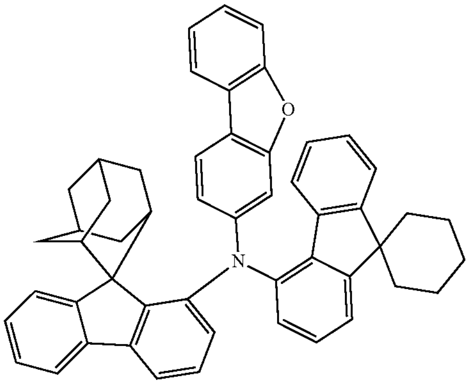
318
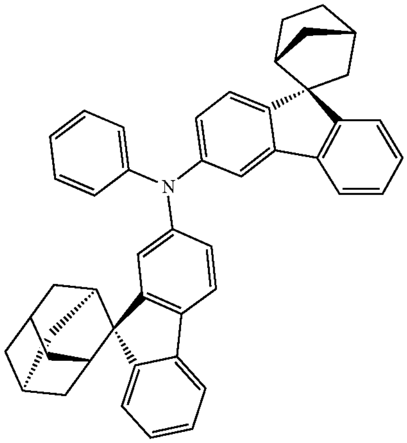

-continued
319
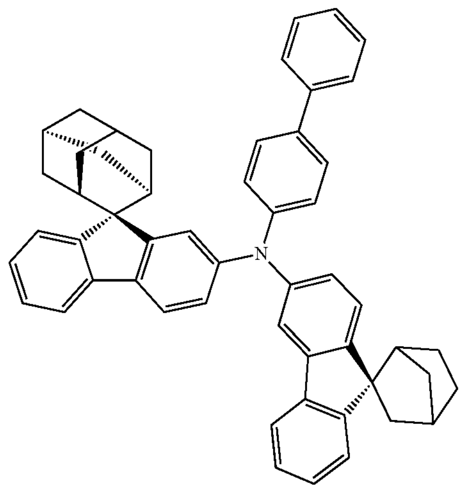
320
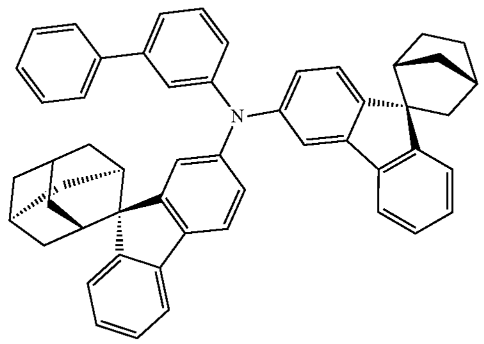
321
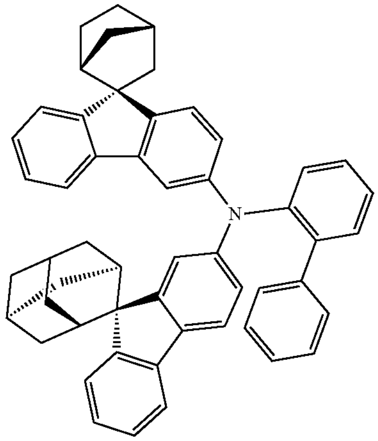
-continued
322
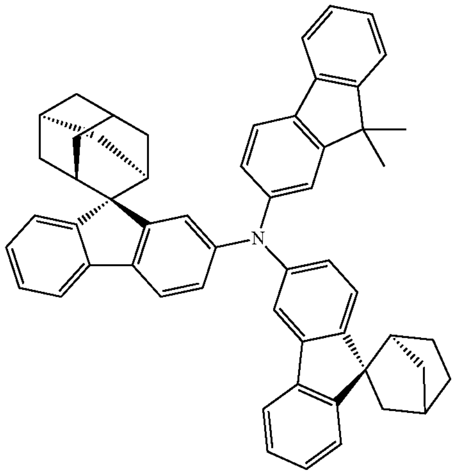
323
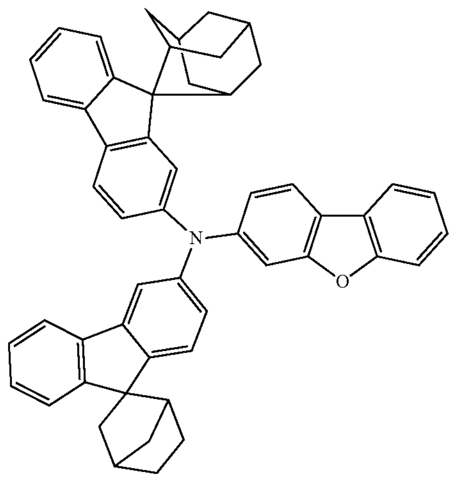
324
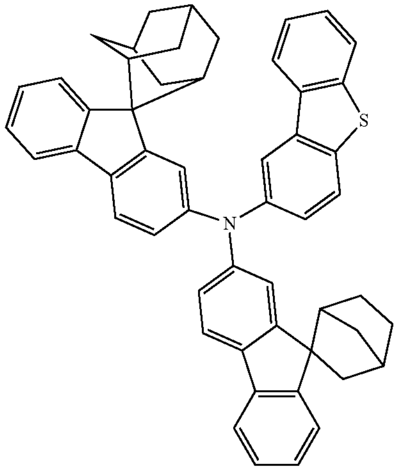

-continued
325
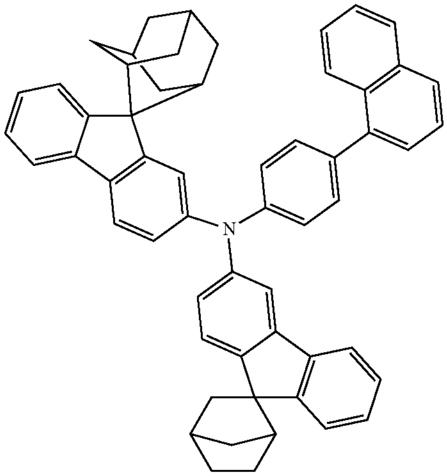
326
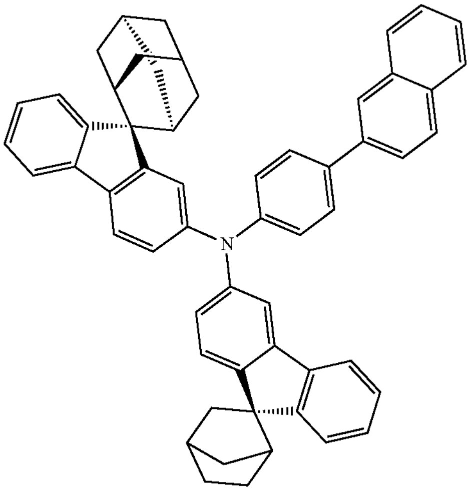
327
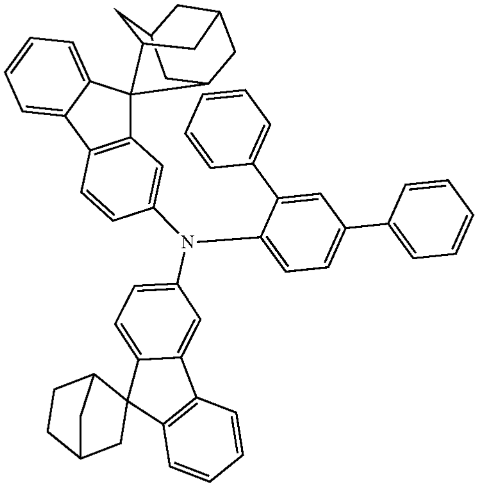
-continued
328
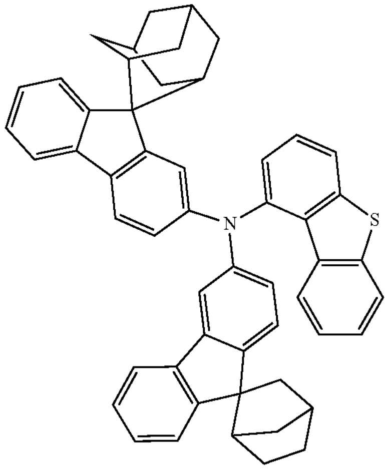
329
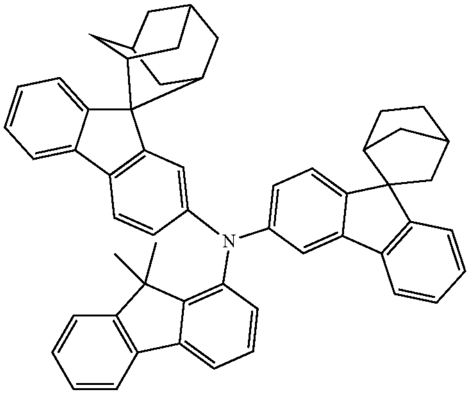
330
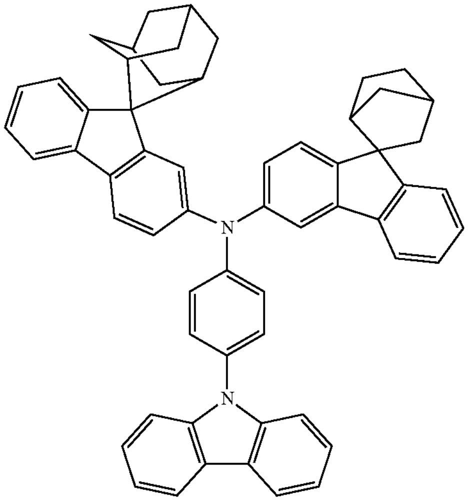

-continued
331
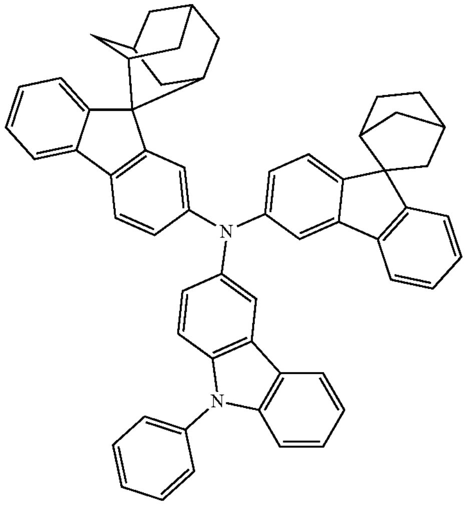
332
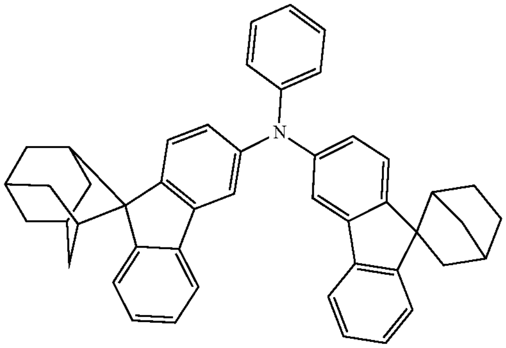
333
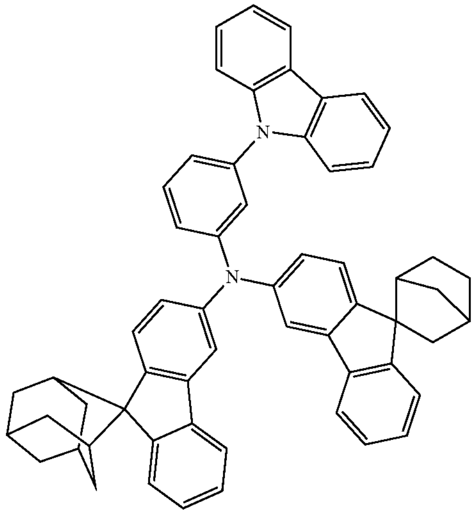
-continued
334
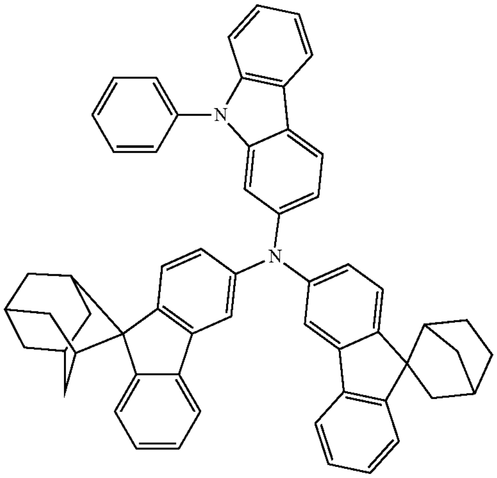
335
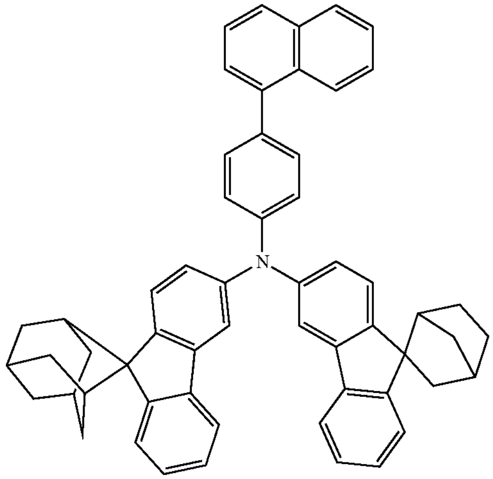
336
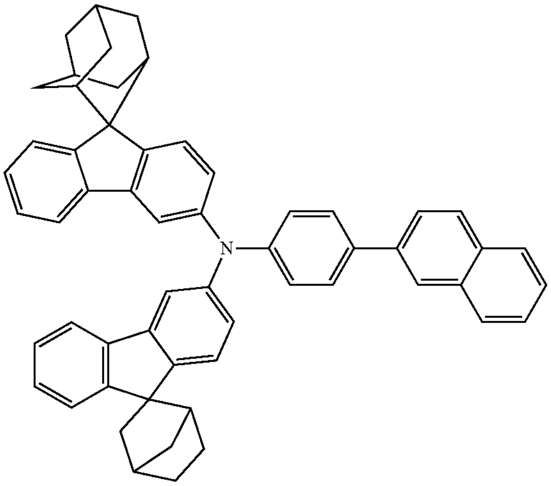

-continued
337
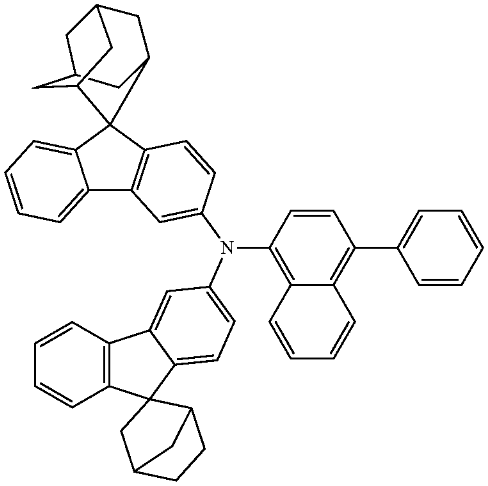
338
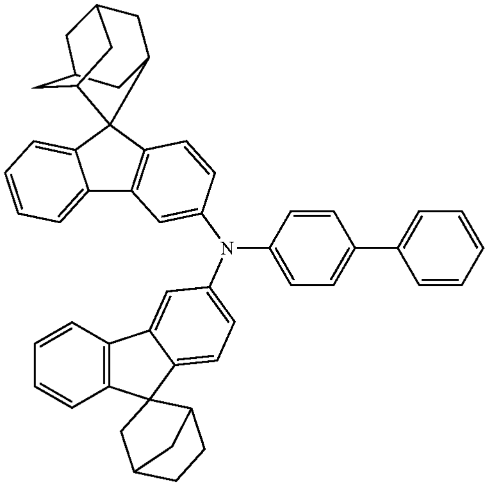
339
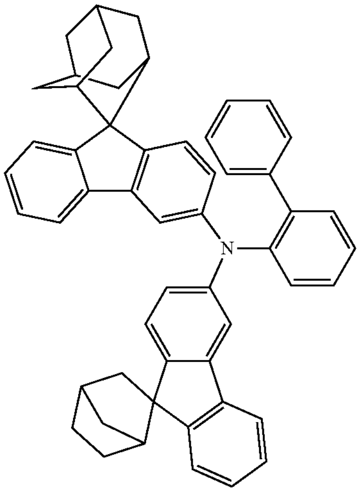
-continued
340
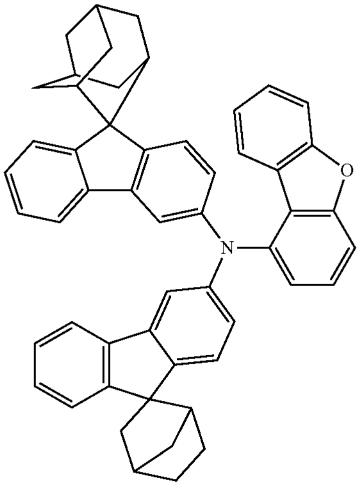
341
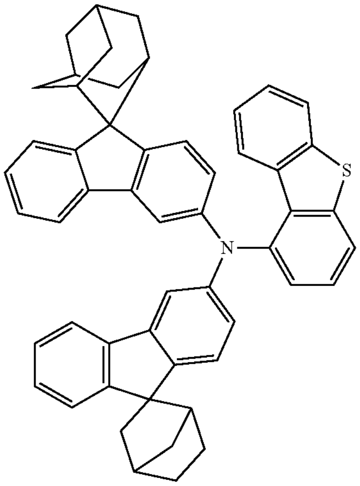
342
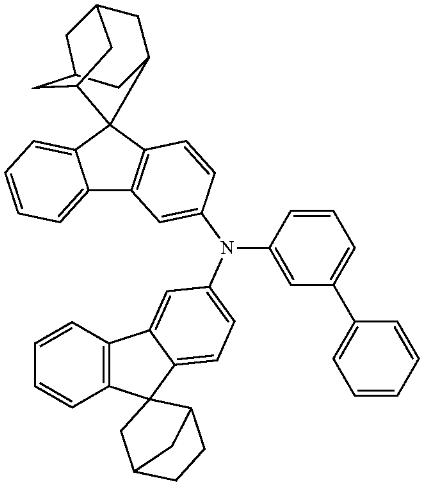

-continued
343
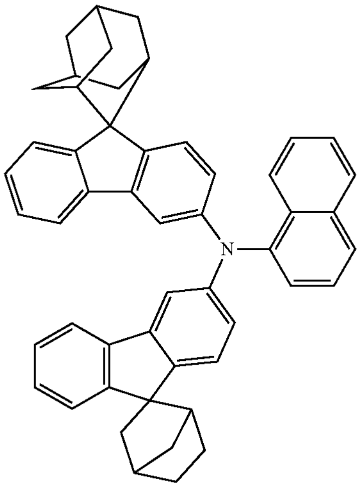
344
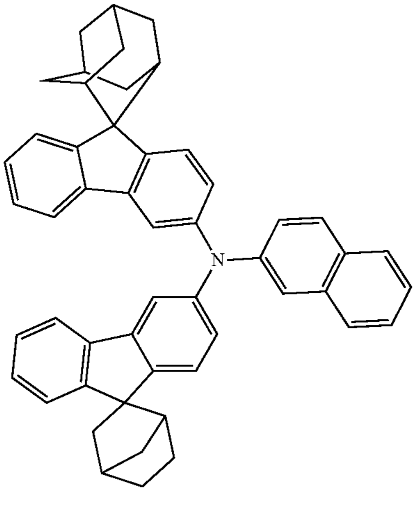
345
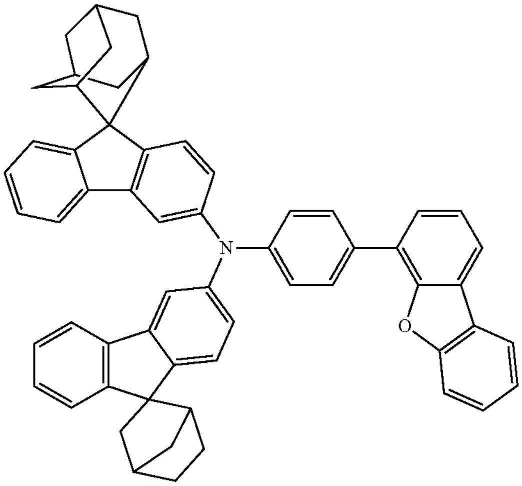
-continued
346
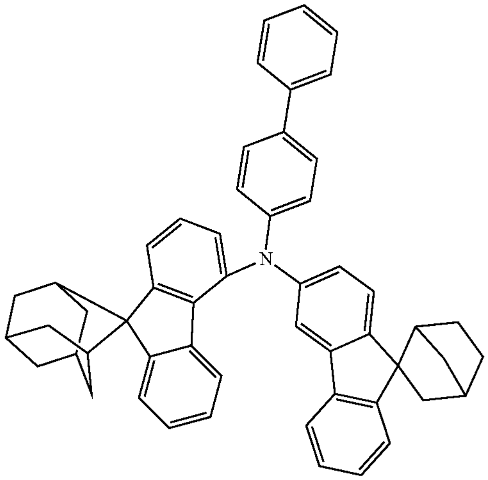
347
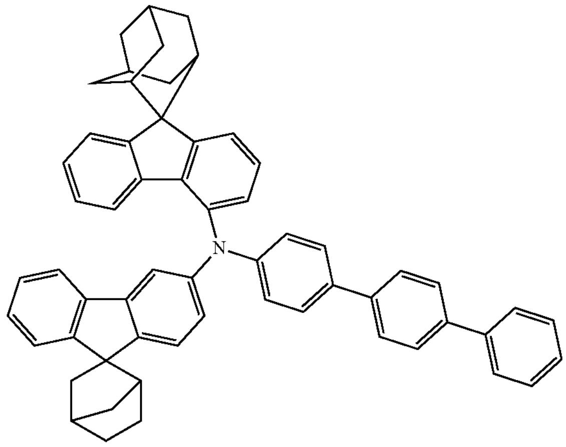
348
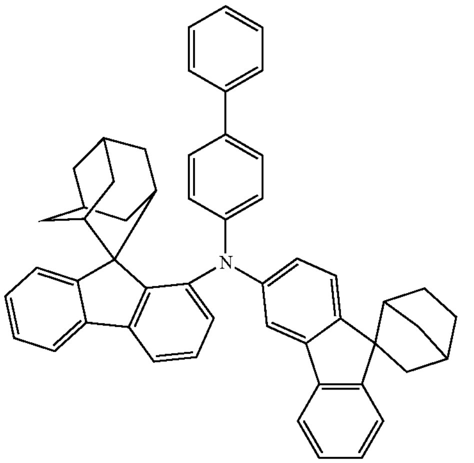

-continued
349
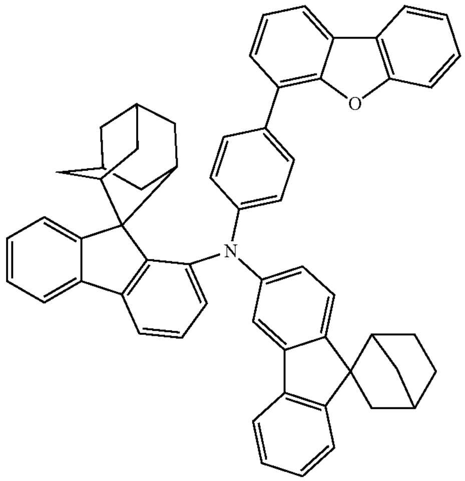
350
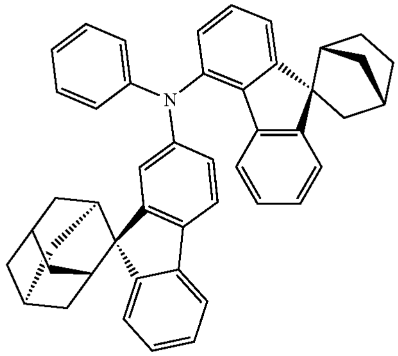
351
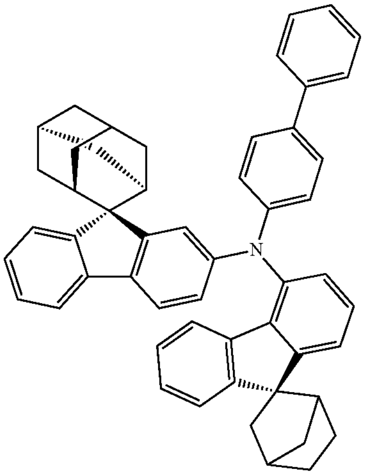
-continued
352
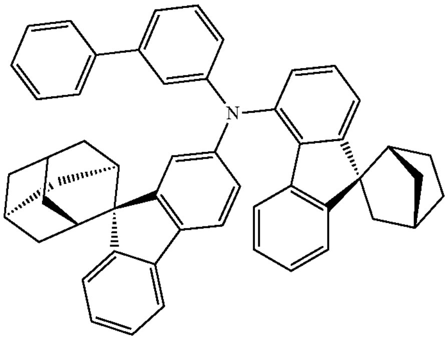
353
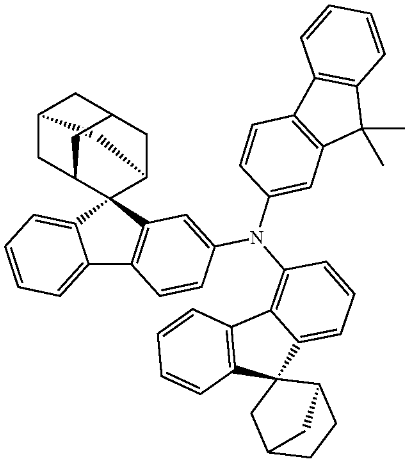
354
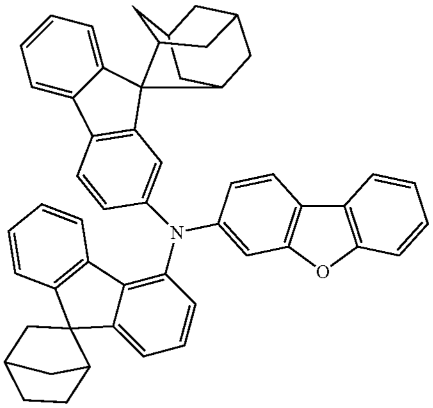
355
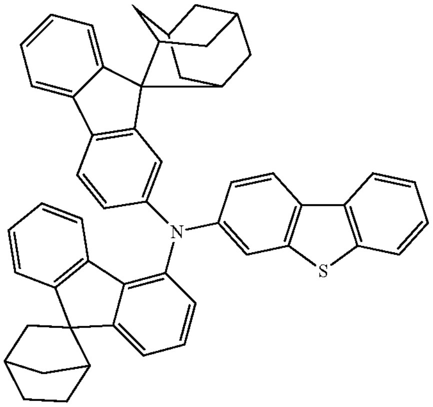

-continued
356
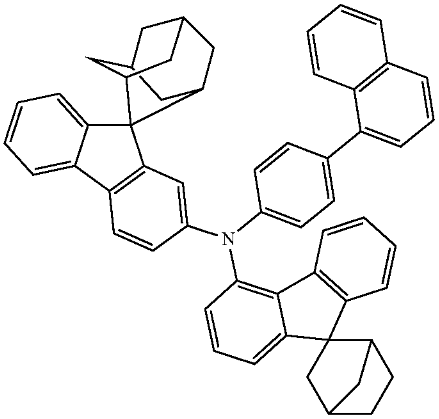
357
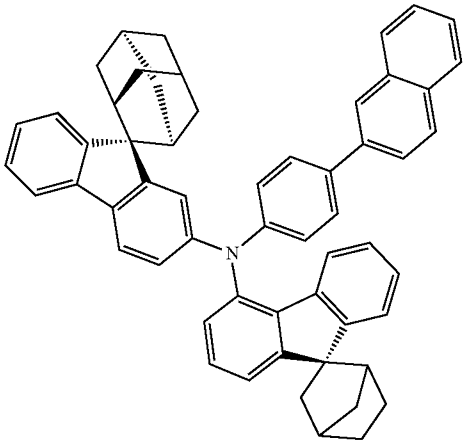
358
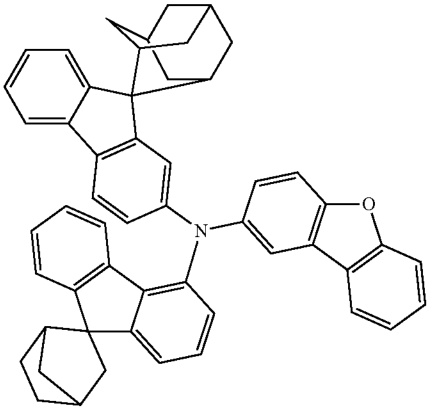
-continued
359
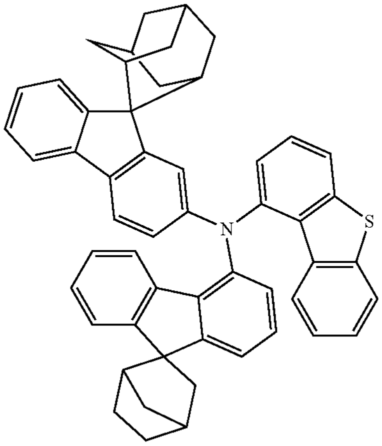
360
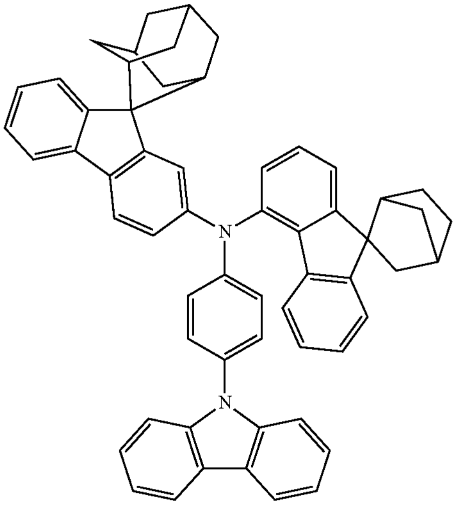
361
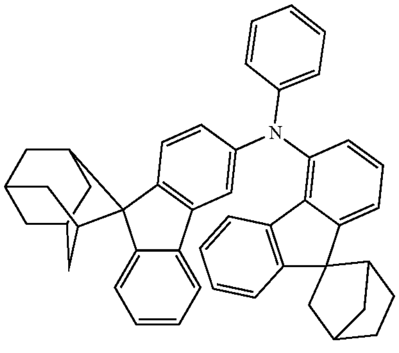

-continued
362
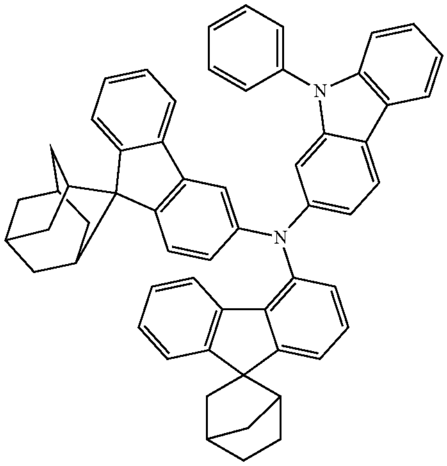
363
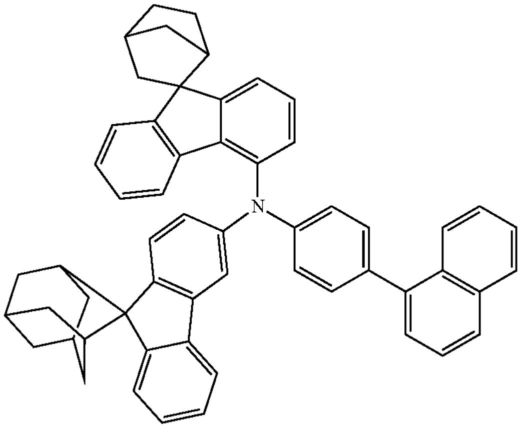
364
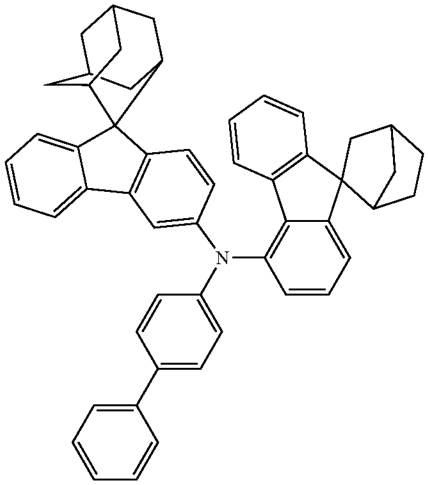
-continued
365
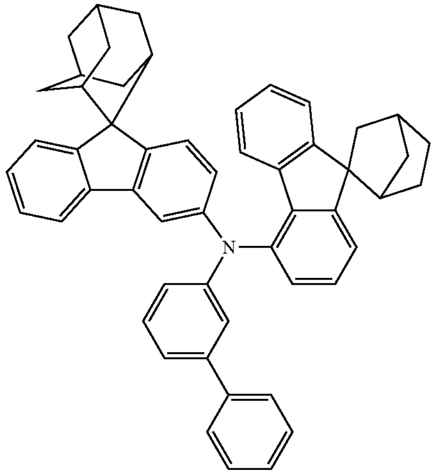
366
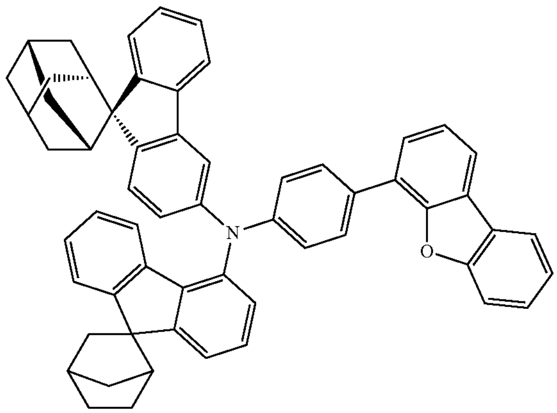
367
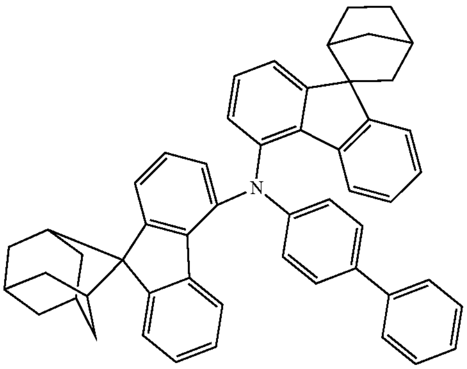

368
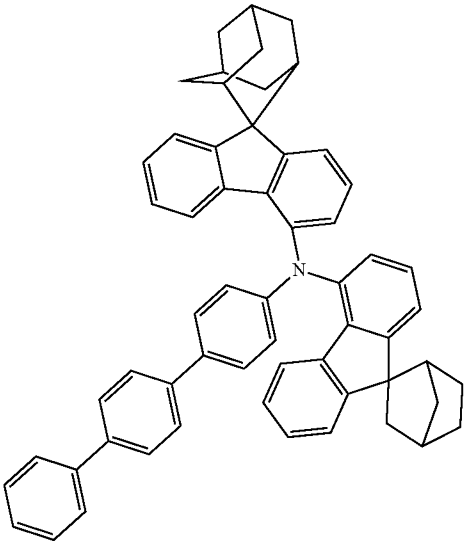
369
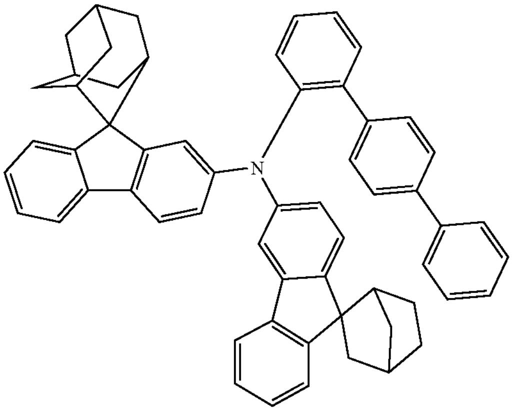
370
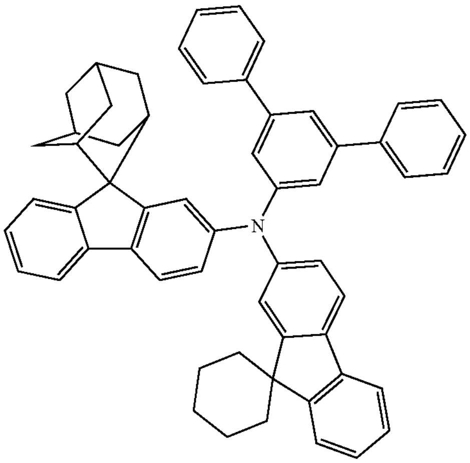
371
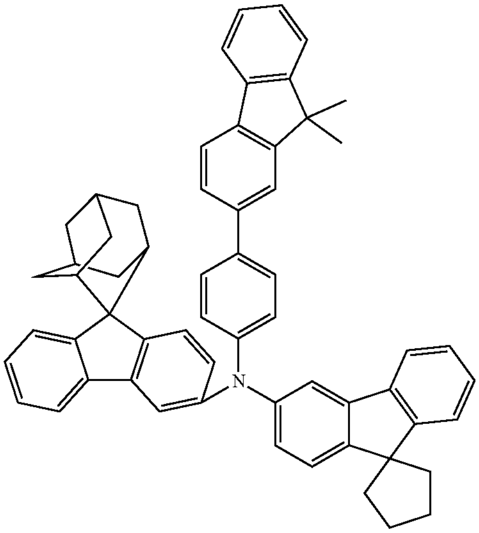
372
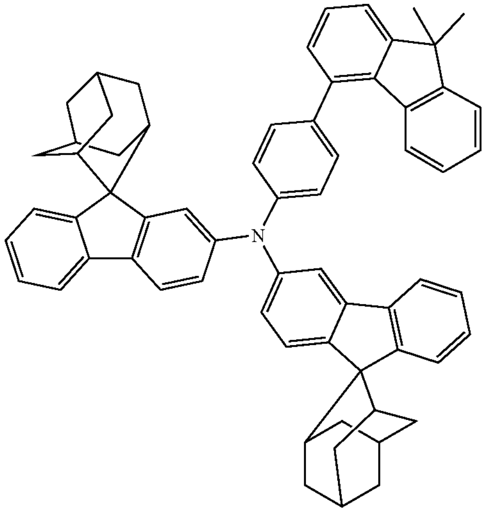
373
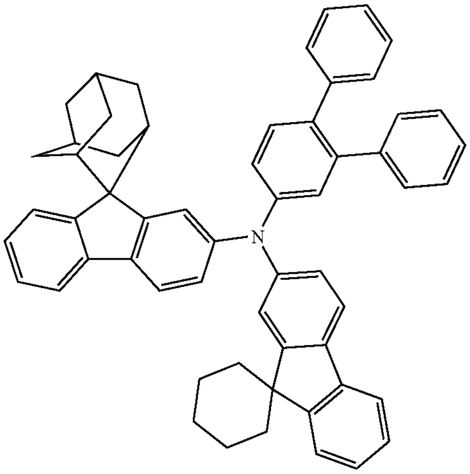

-continued
374
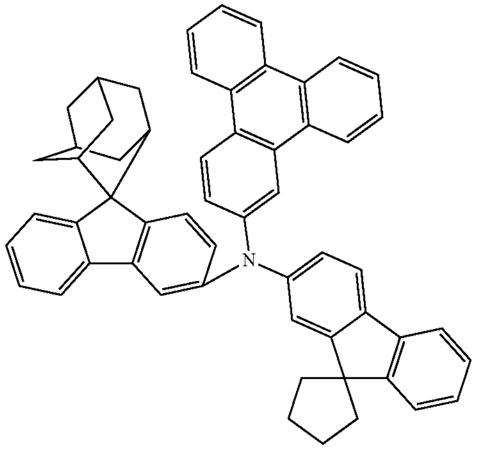
375
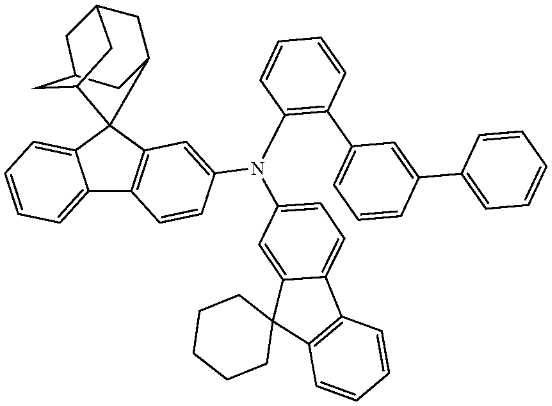
376
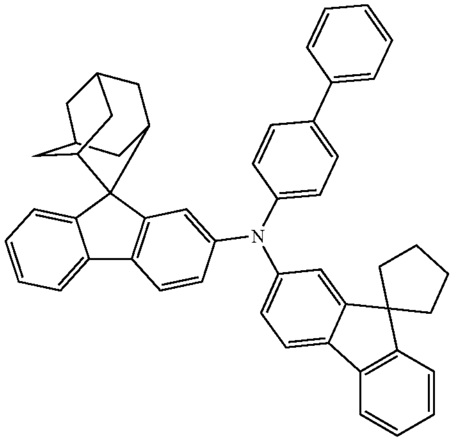
-continued
377
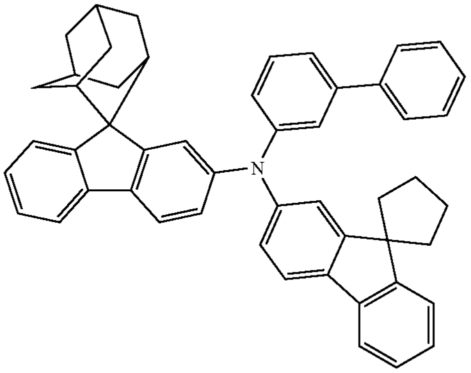
378
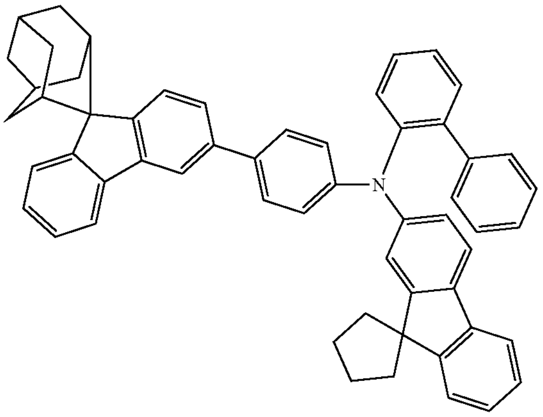
379
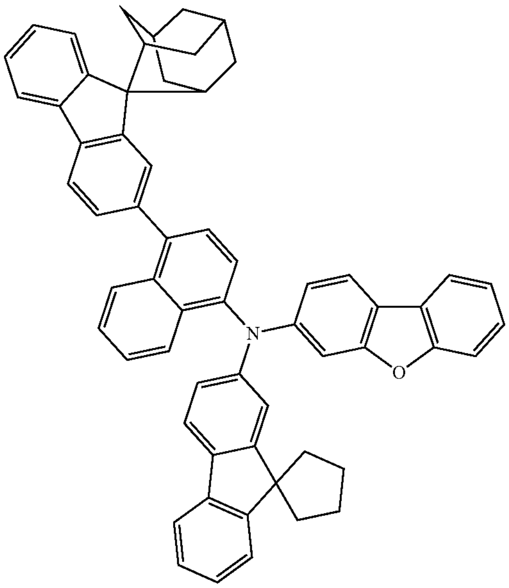

-continued
380
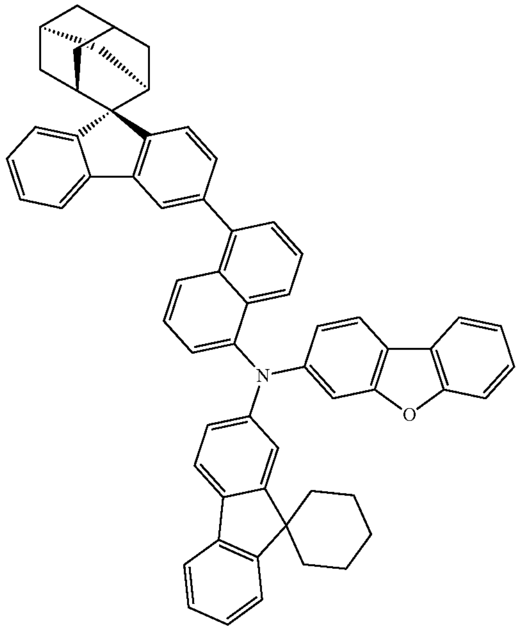
381
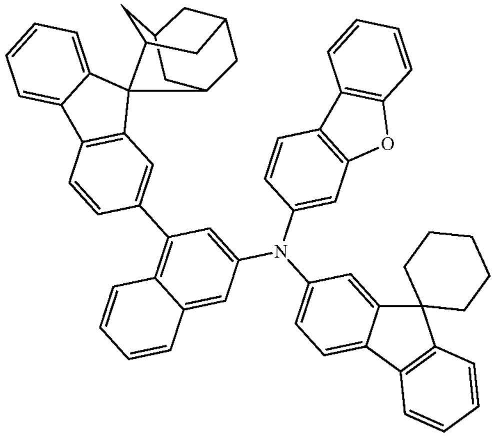
382
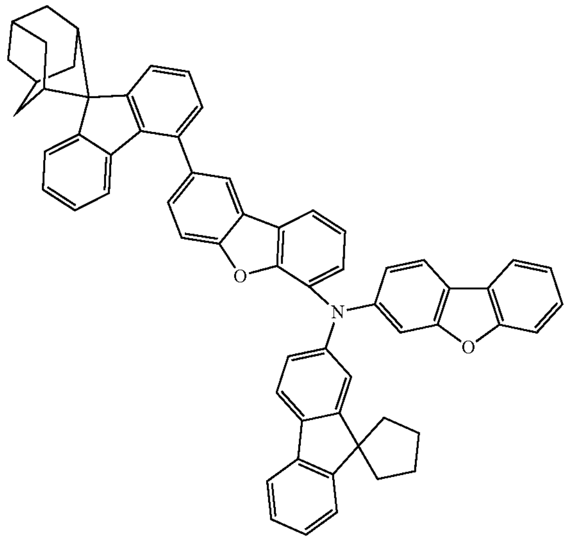
-continued
383
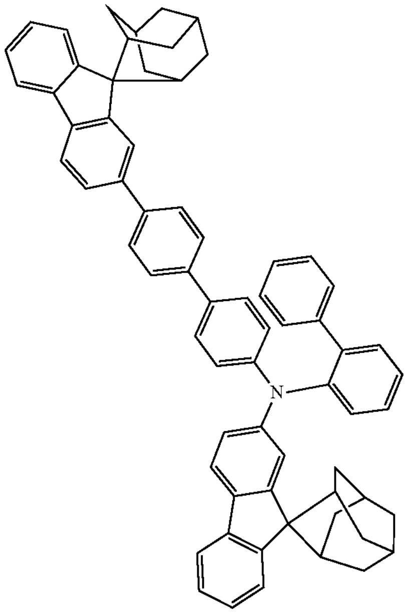
384
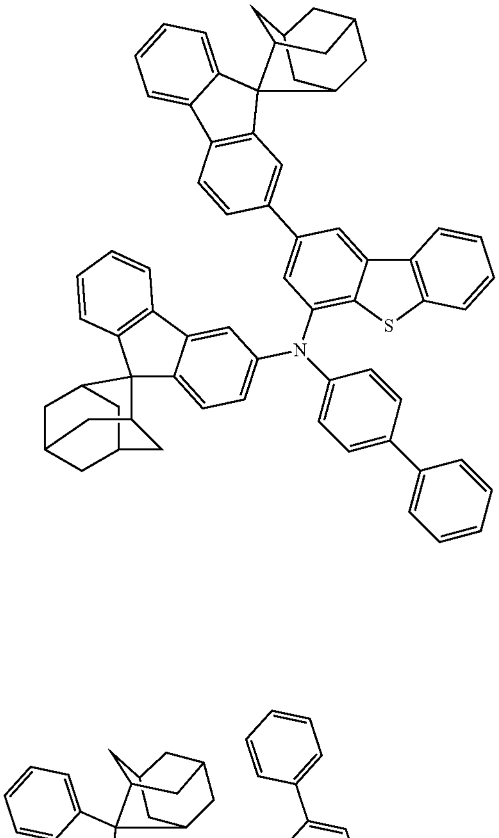
385
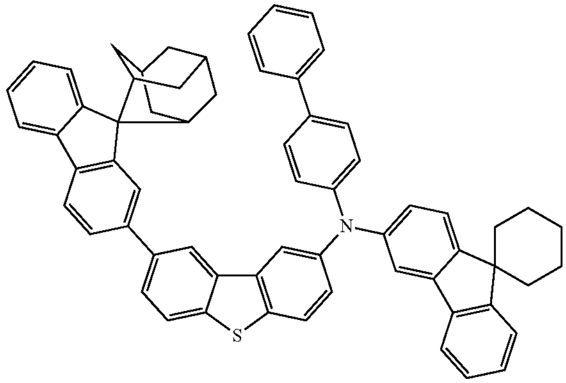

-continued
386
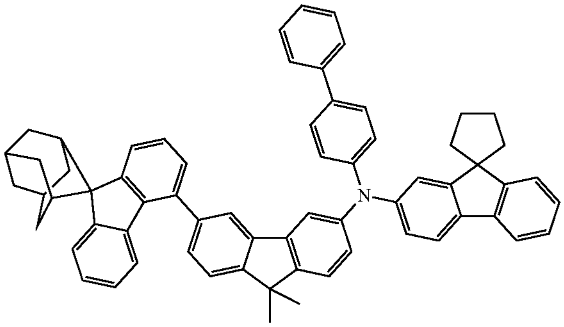
387
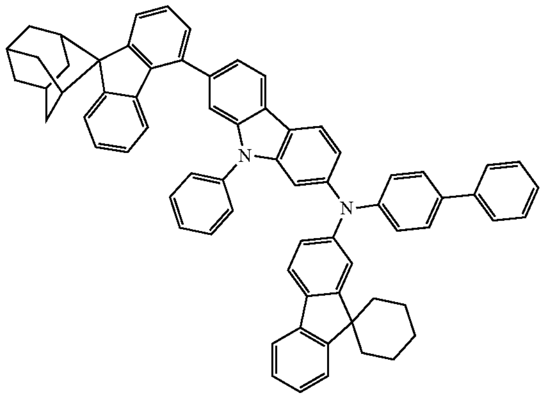
388
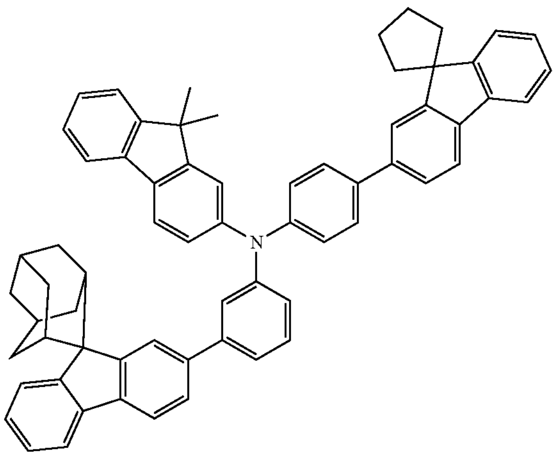
-continued
389
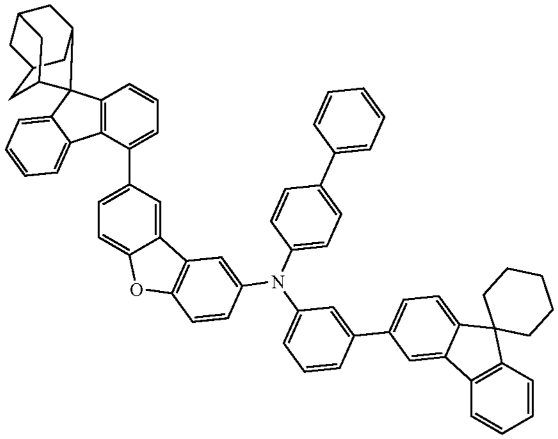
390
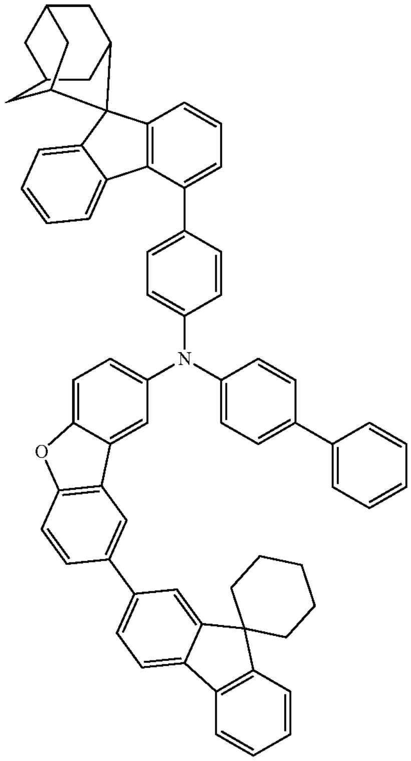
391
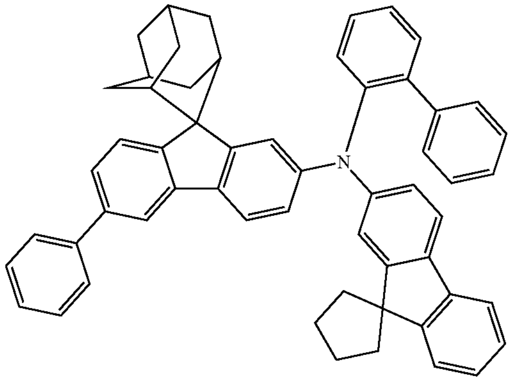

-continued
392
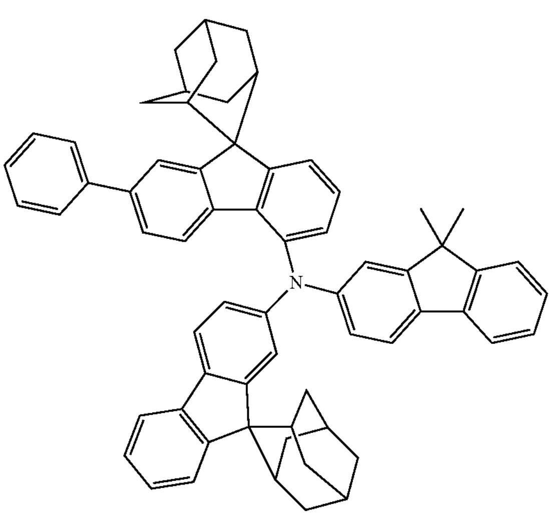
393
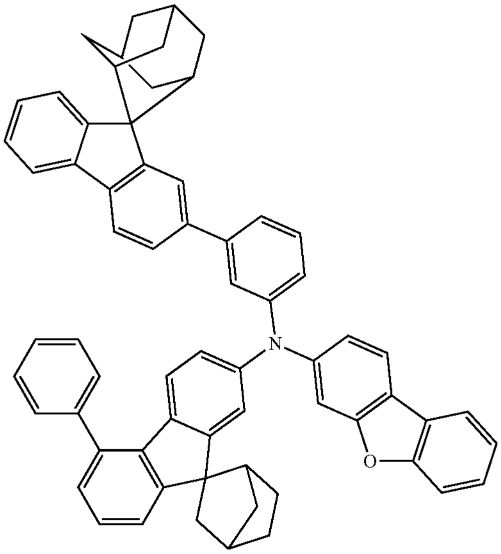
394
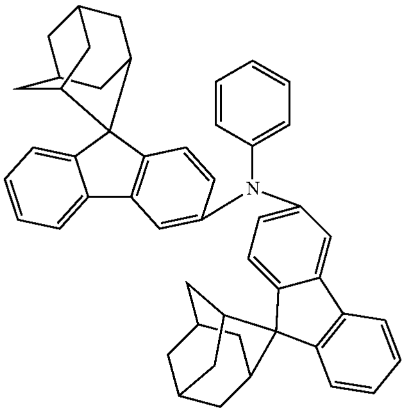
-continued
395
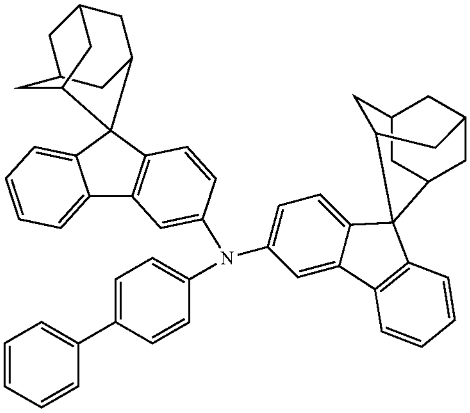
396
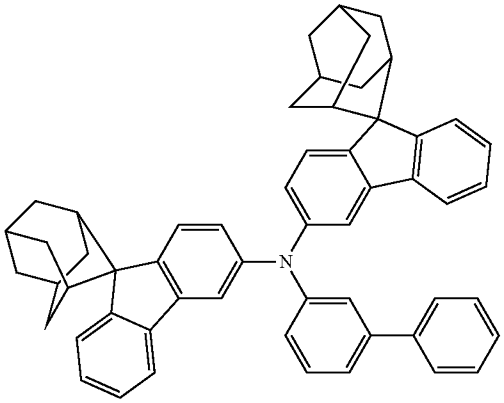
397
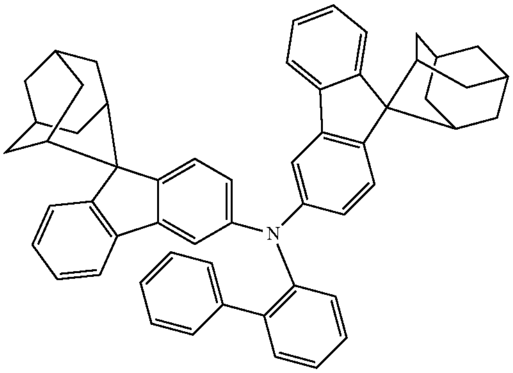

-continued
399
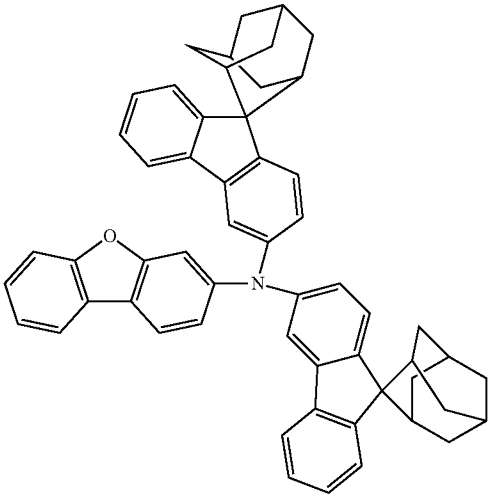
400
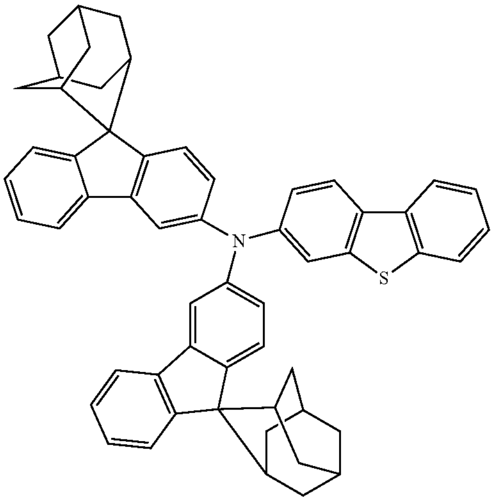
401
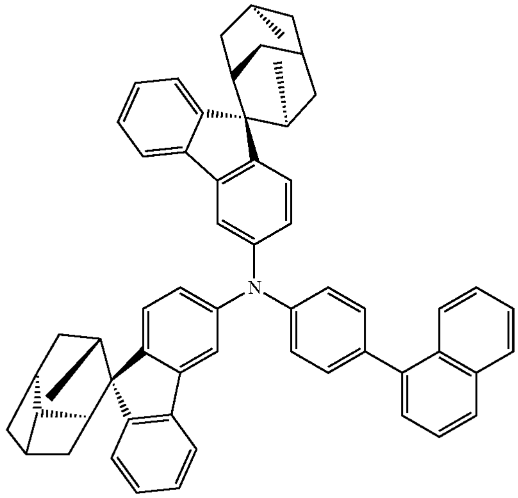
-continued
402
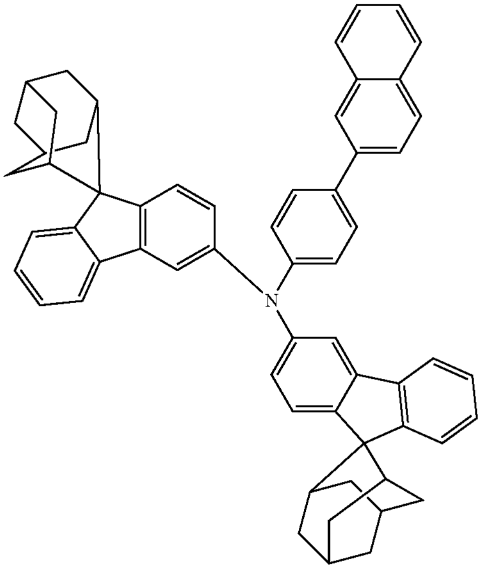
403
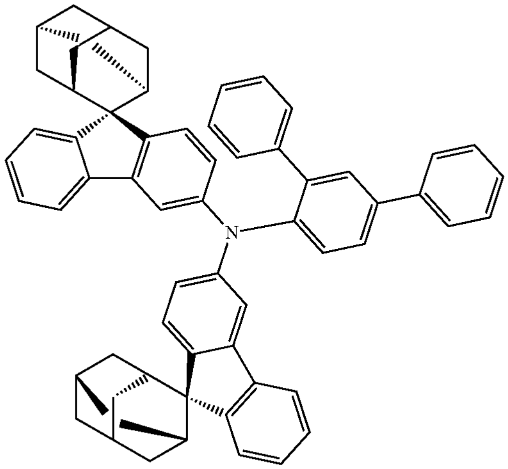
404
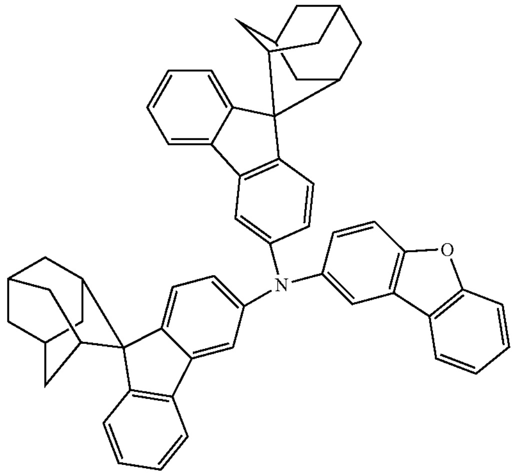

-continued
405
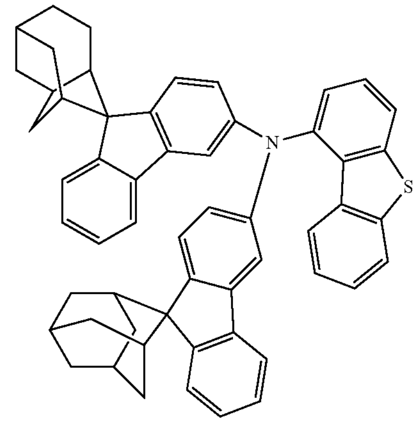
406
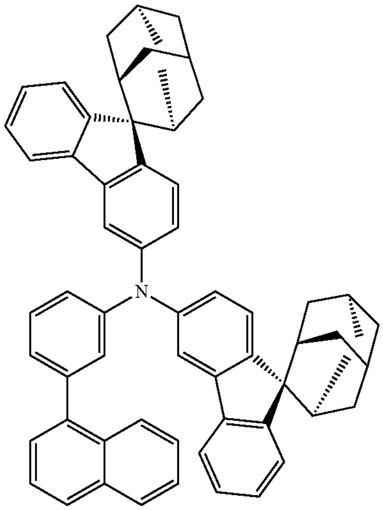
407
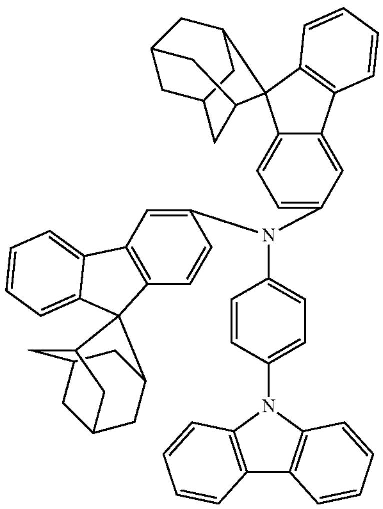
-continued
408
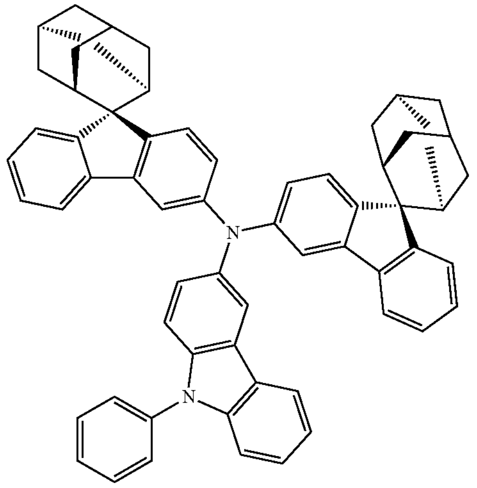
409
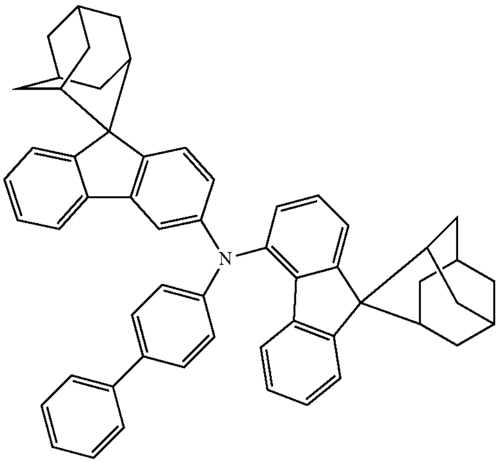
410
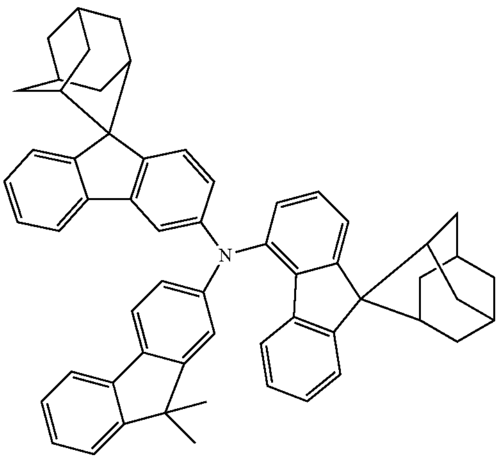

-continued
411
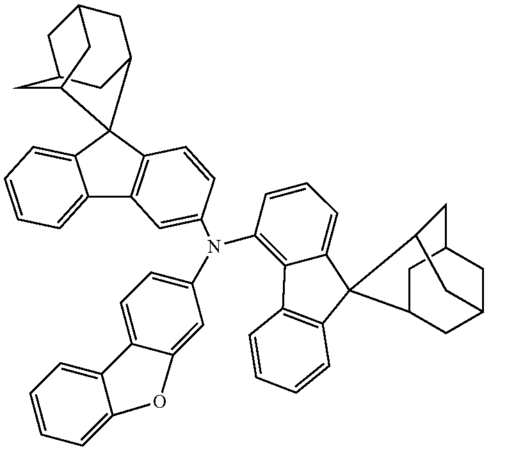
412
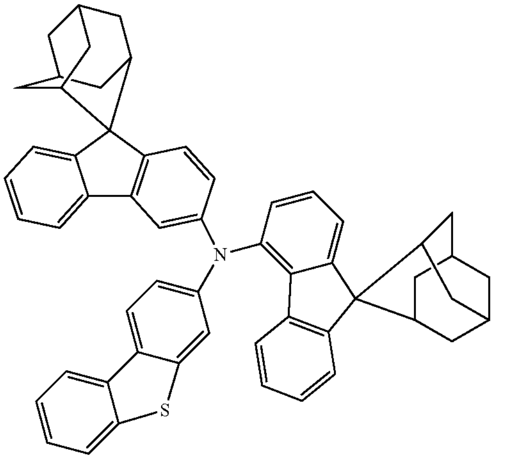
413
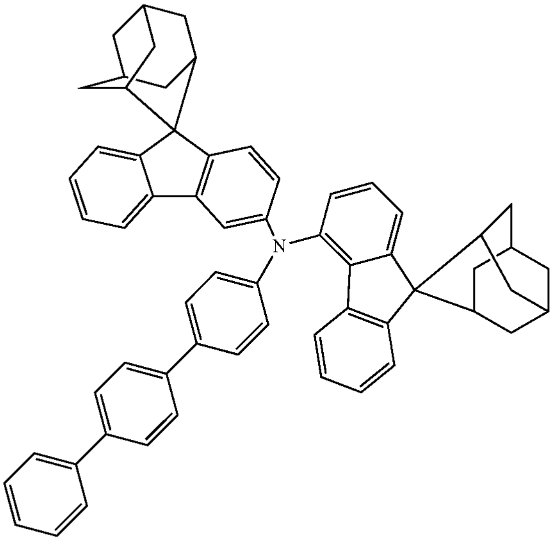
-continued
414
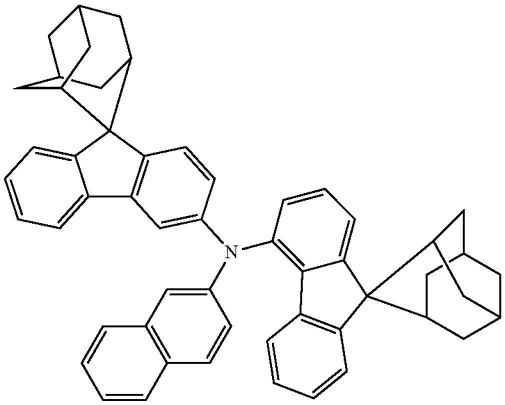
415
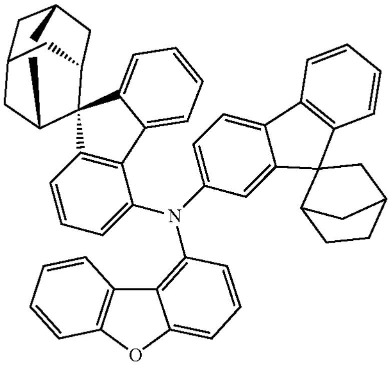
416
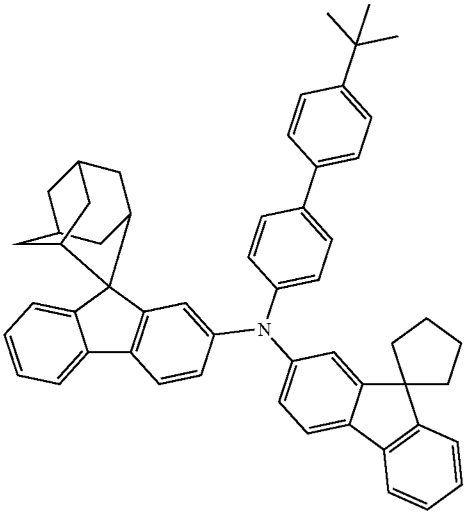

-continued
417
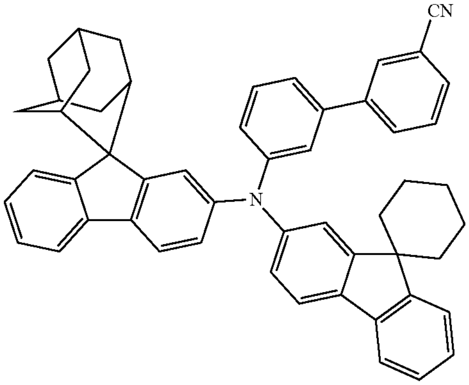
418
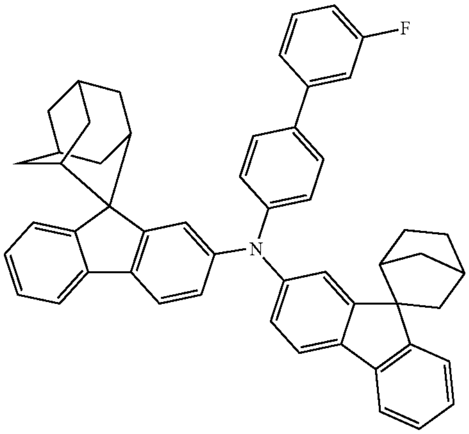
419
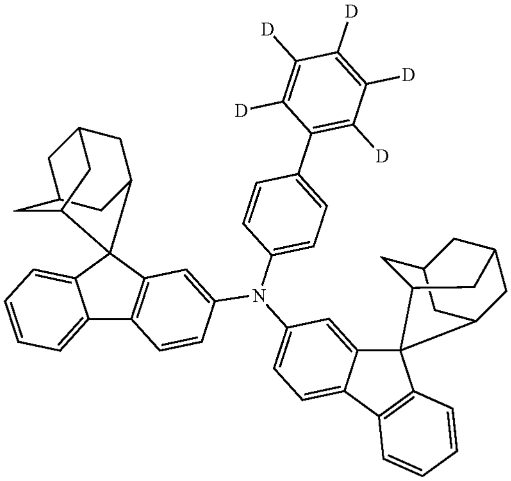
420
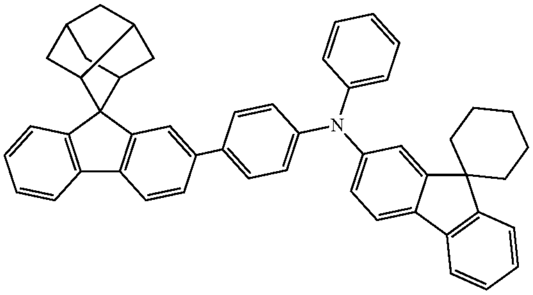
-continued
421
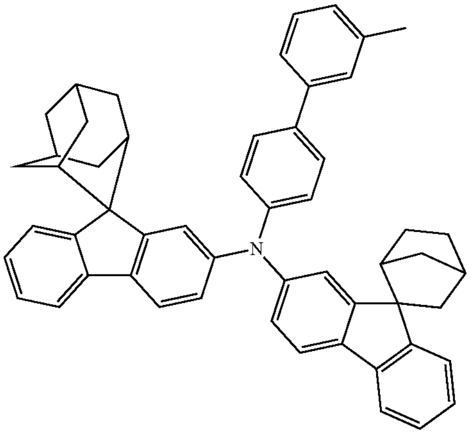
422
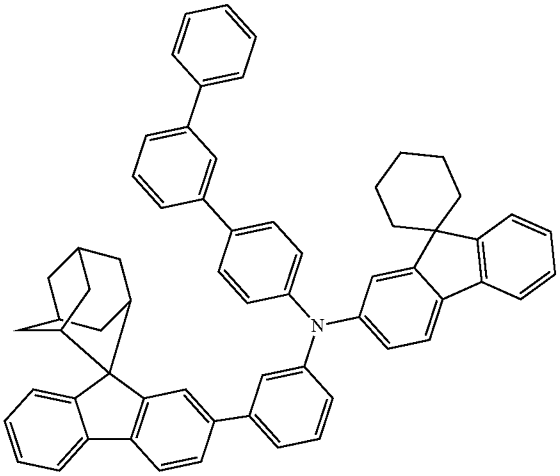
423
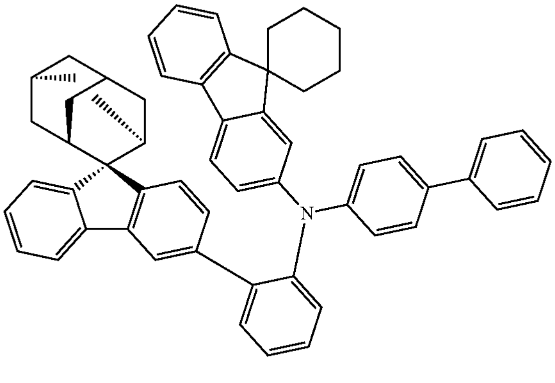

-continued
424
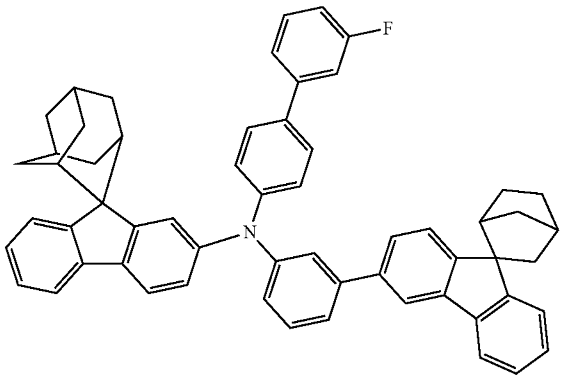
425
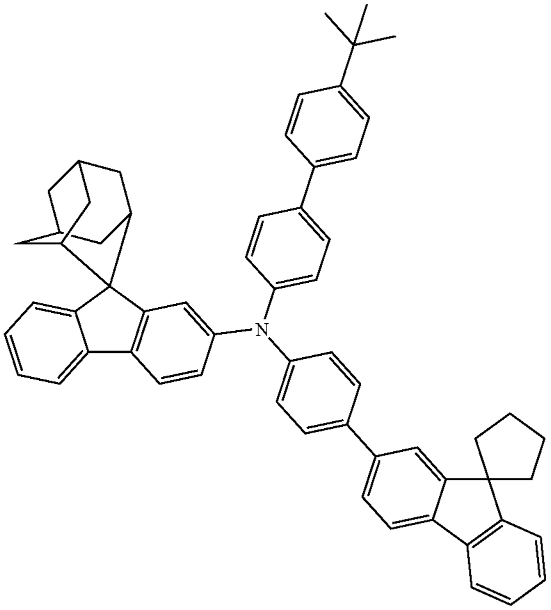
426
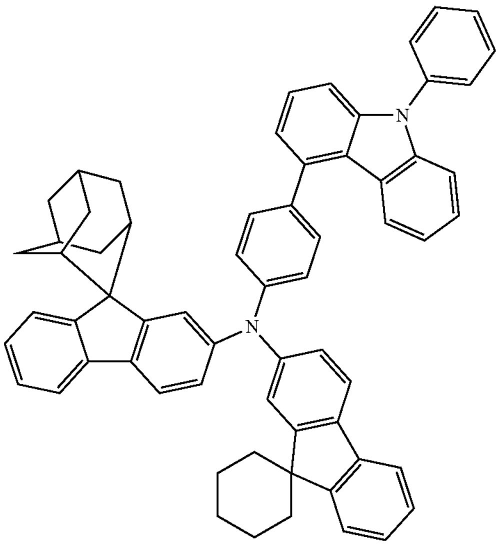
-continued
455
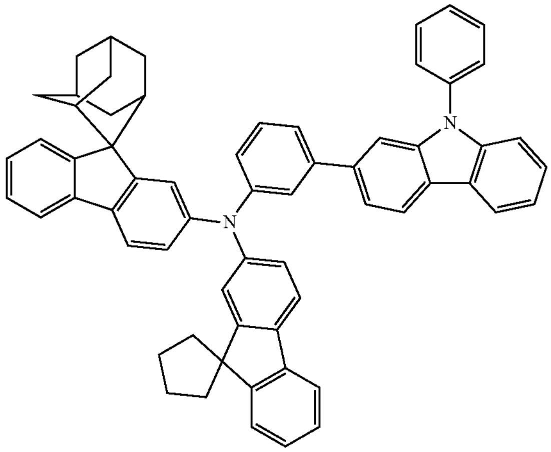
427
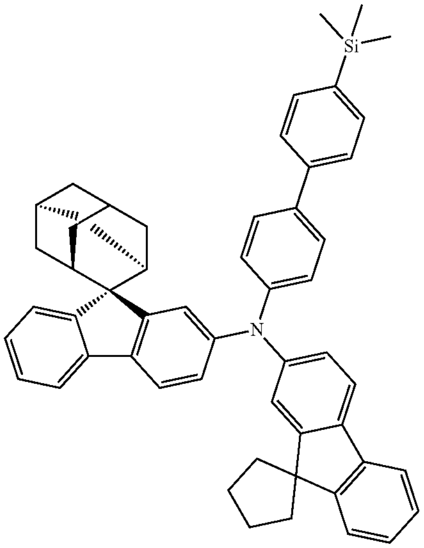
428
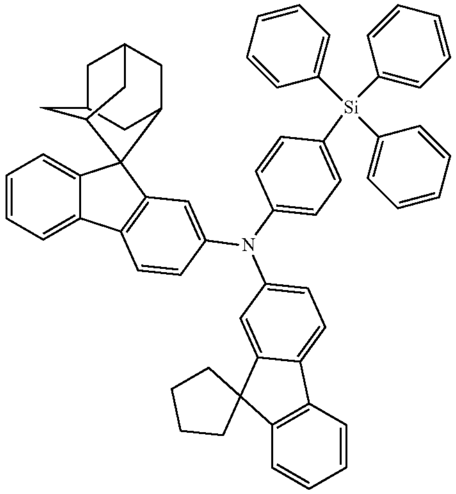

-continued
429
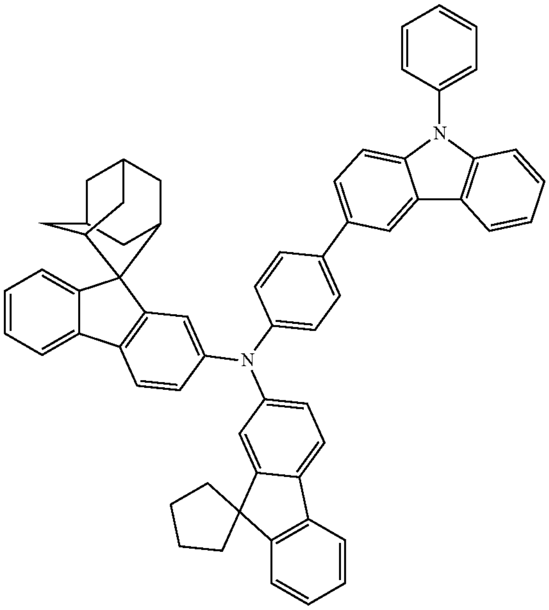
430
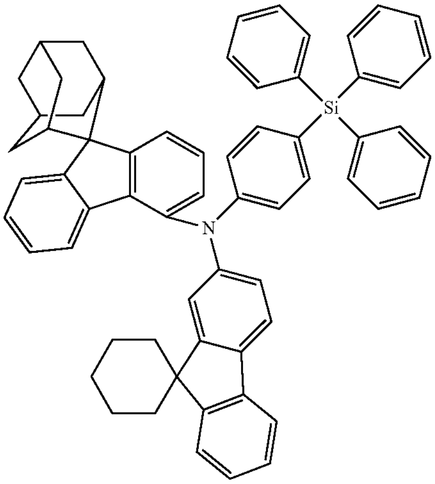
431
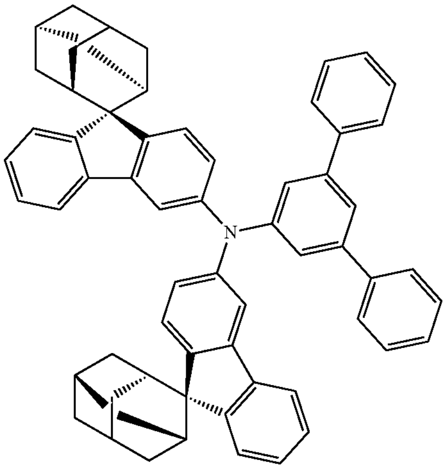
-continued
432
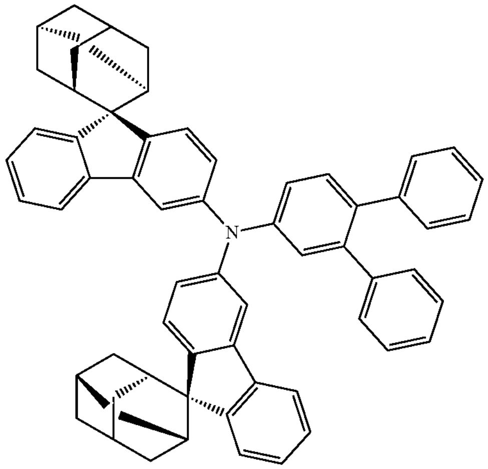
433
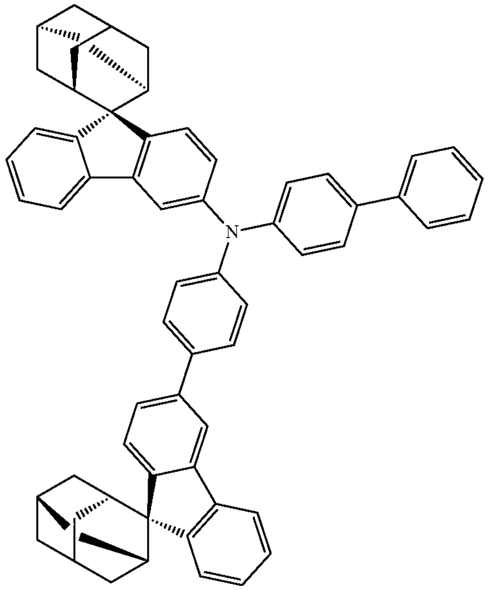
434
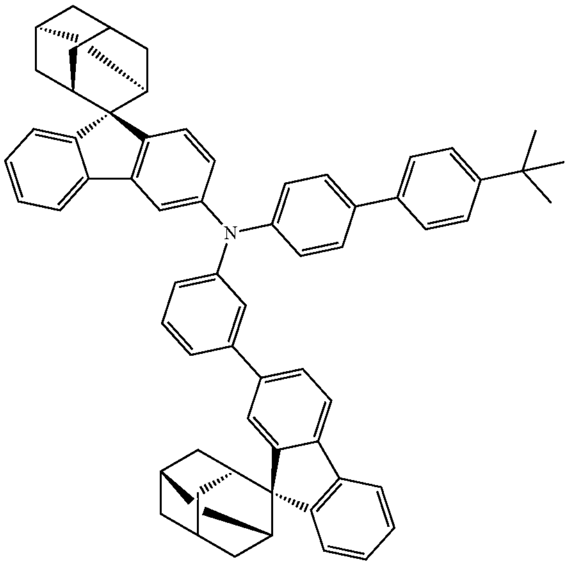

-continued
435
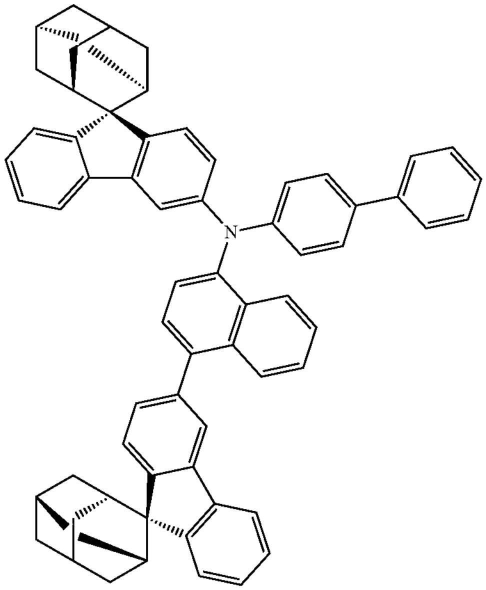
436
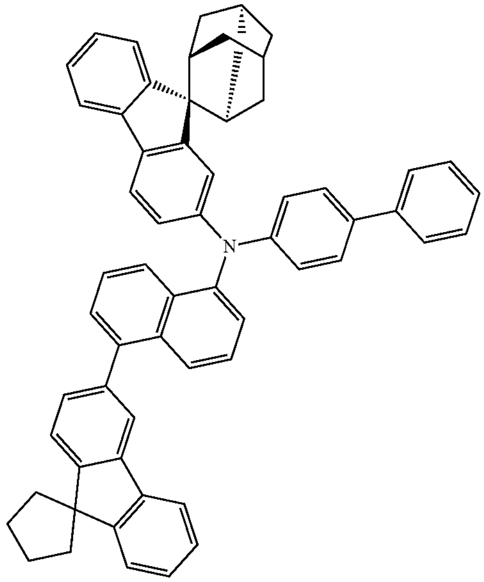
-continued
437
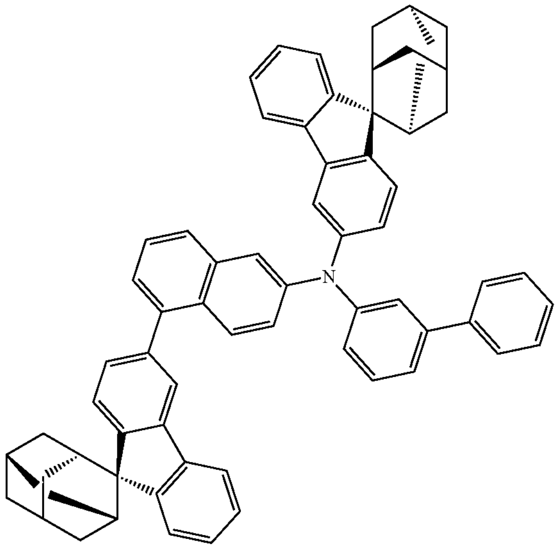
438
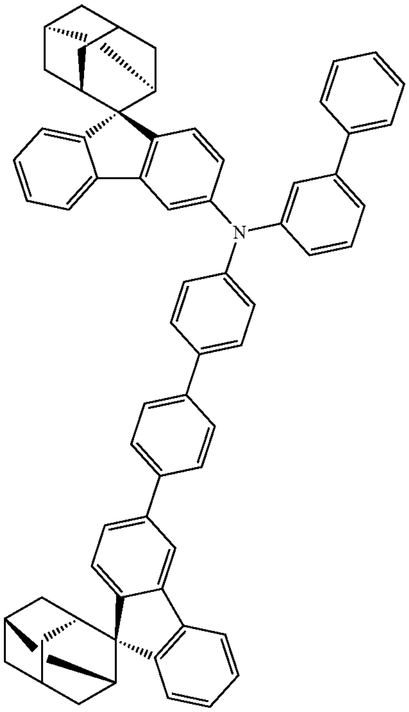

-continued
439
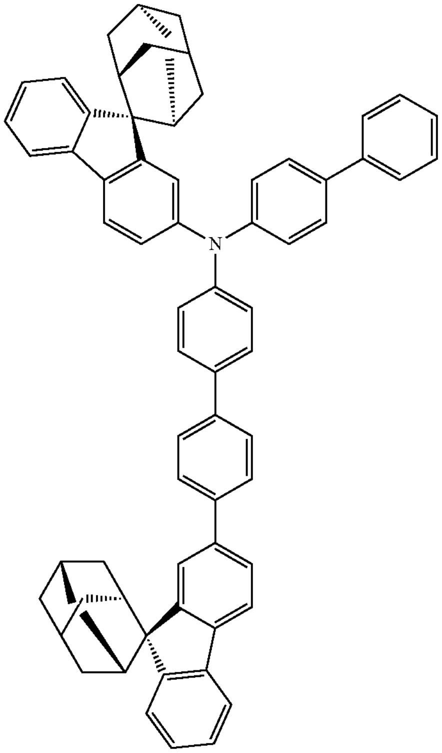
440
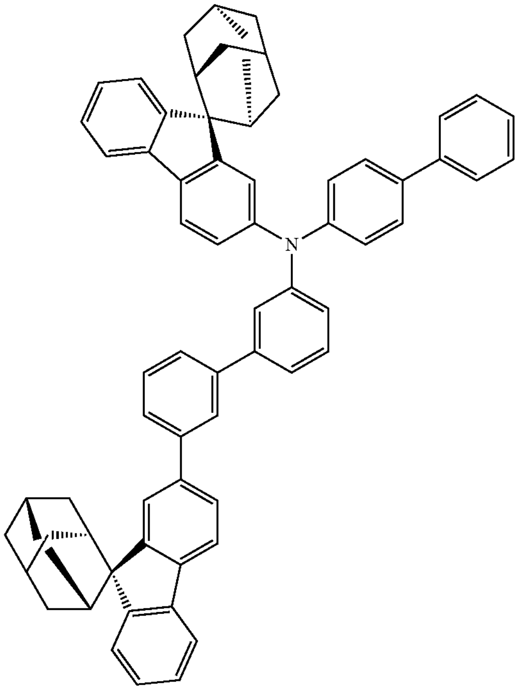
-continued
441
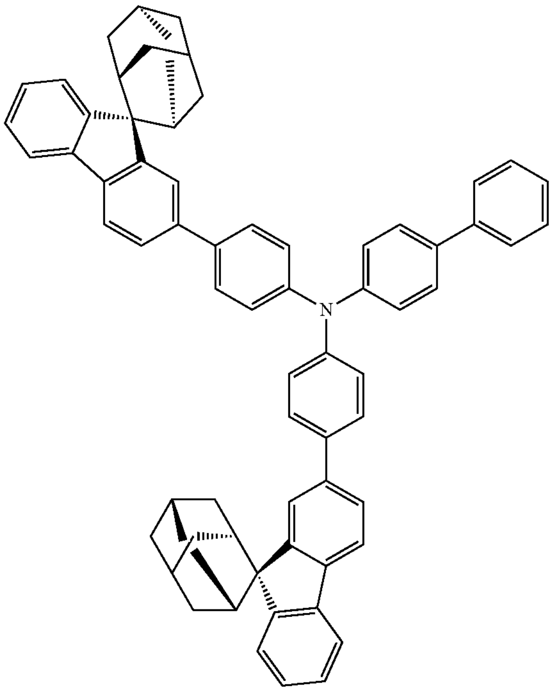
442
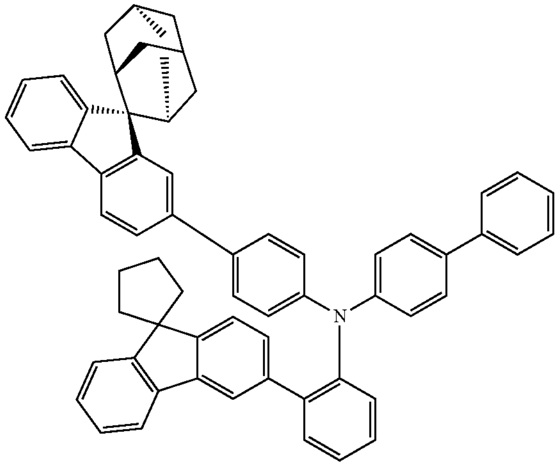

-continued
443
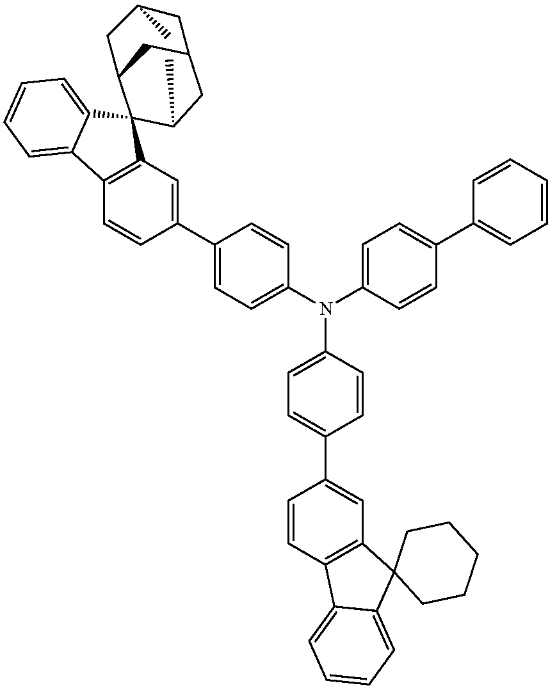
444
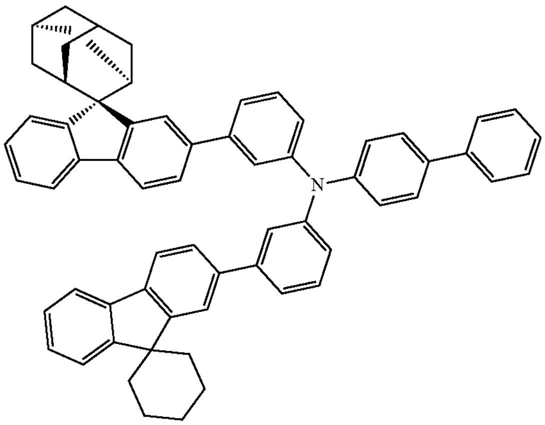
445
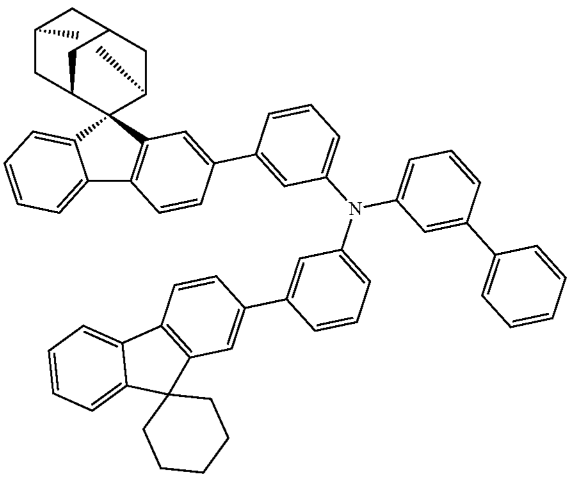
-continued
446
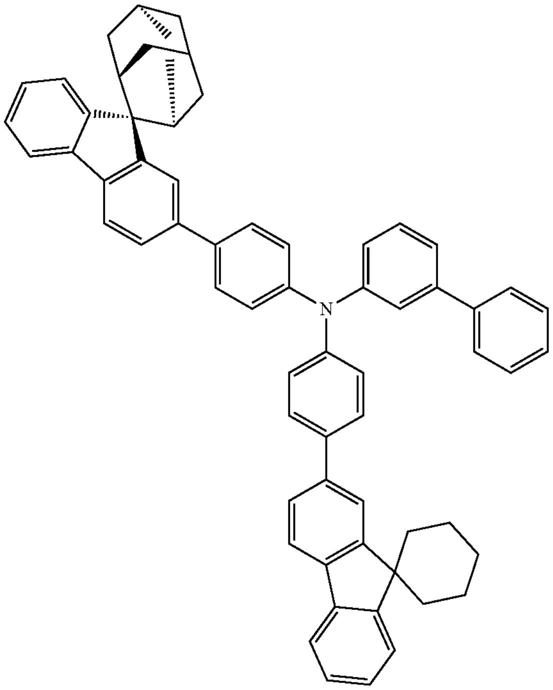
447
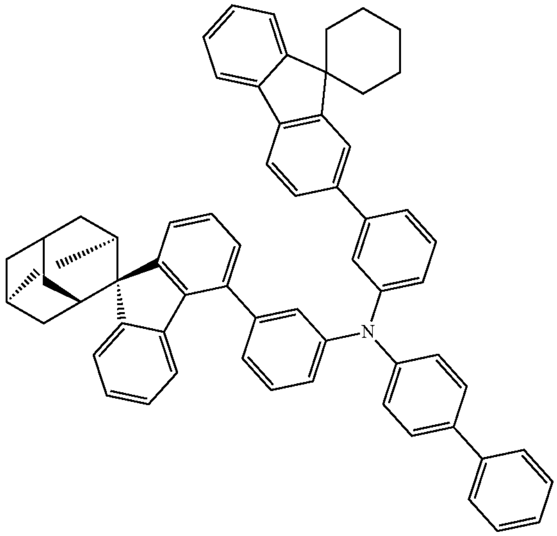

-continued
448
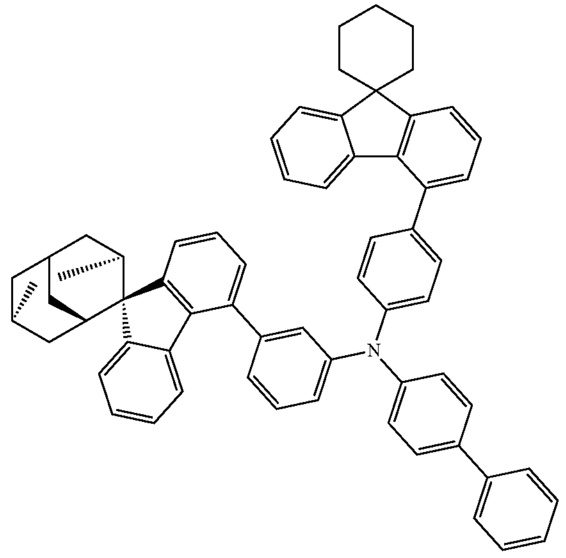
449
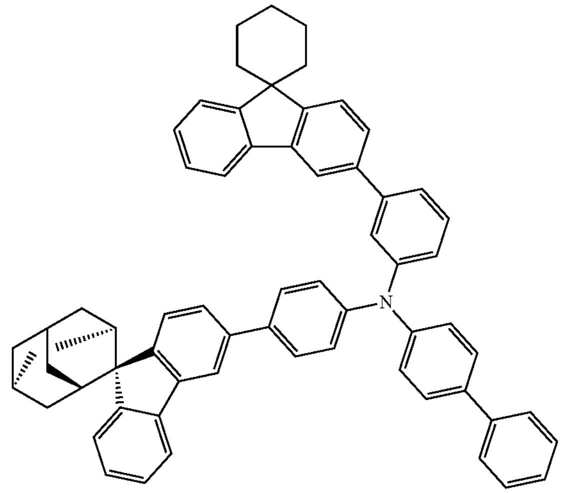
450
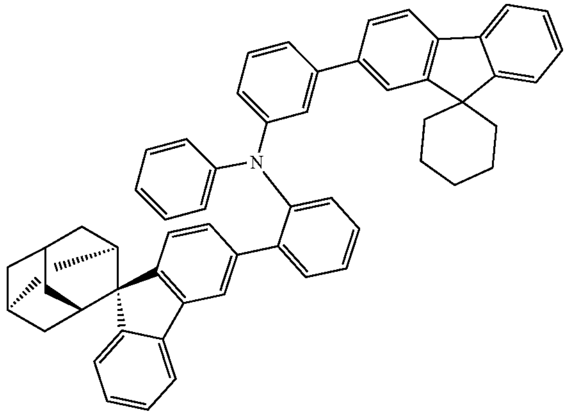
-continued
451
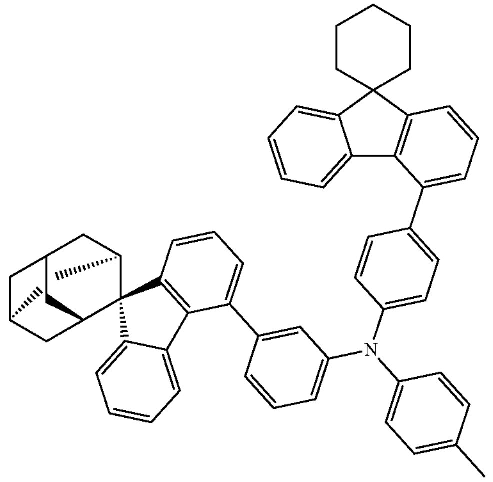
452
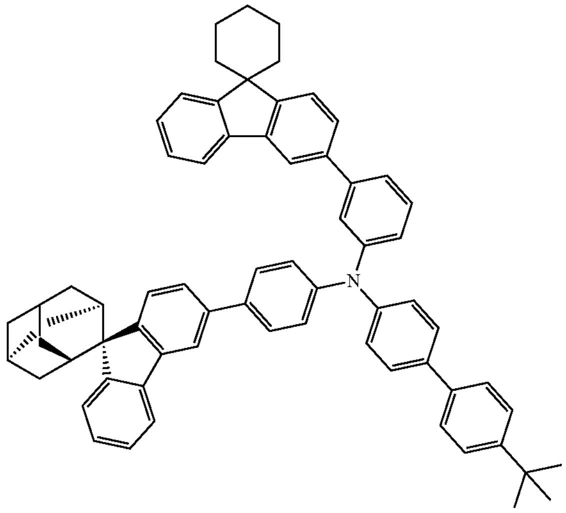
453
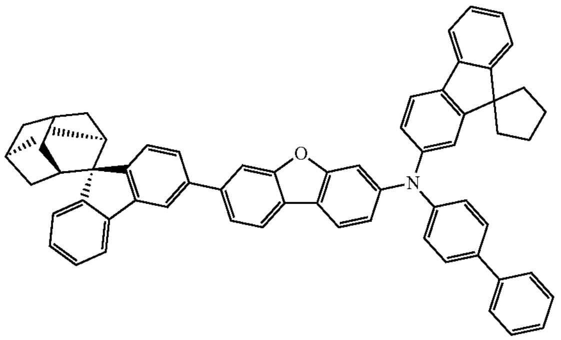

-continued
454
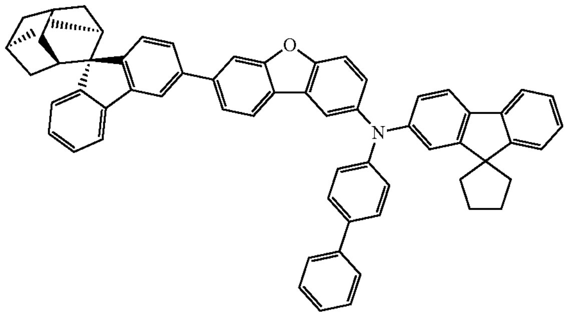
456
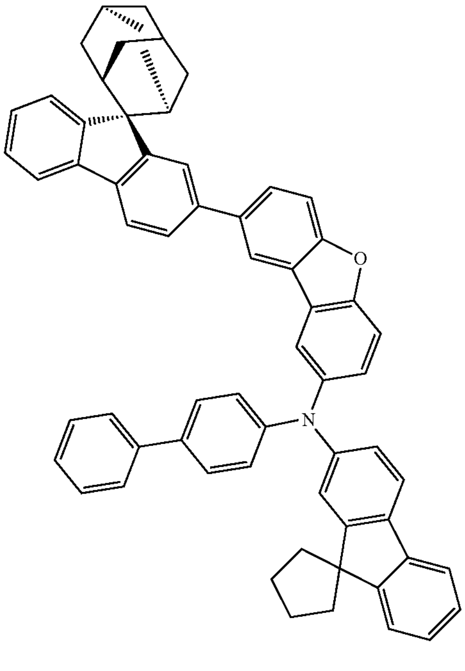
457
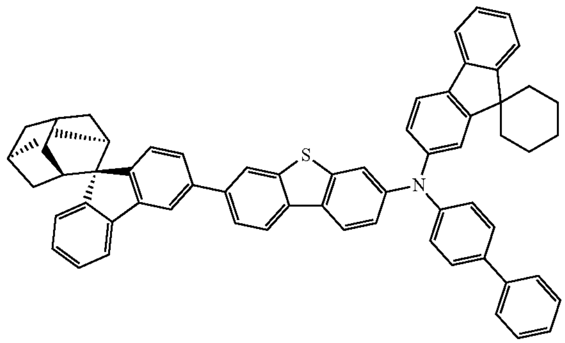
-continued
458
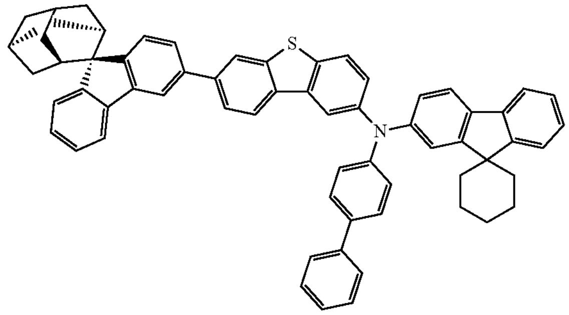
459
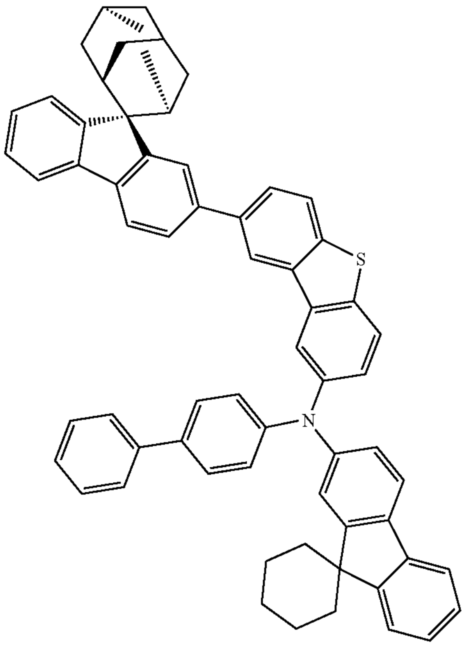
460
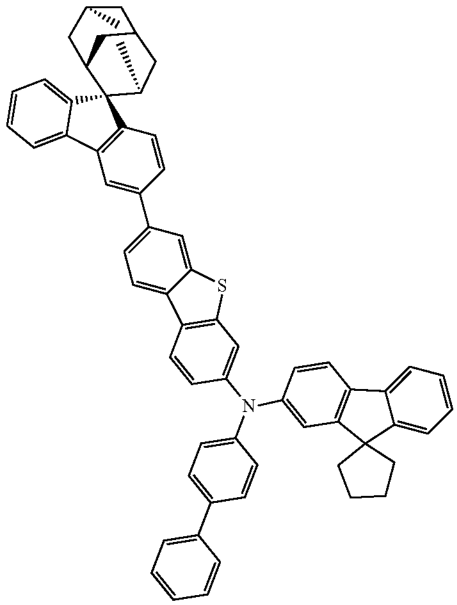

-continued
461
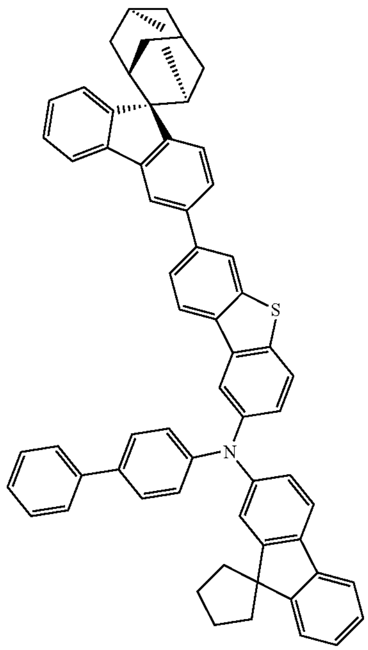
-continued
463
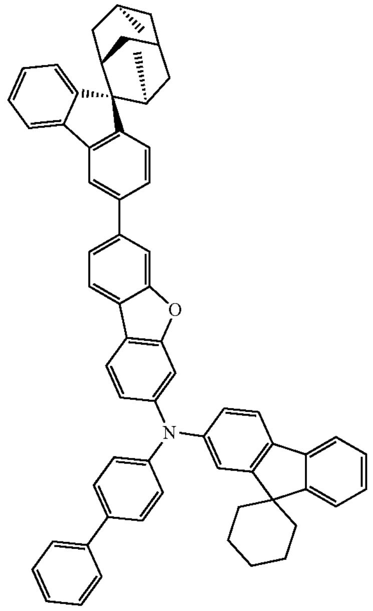
462
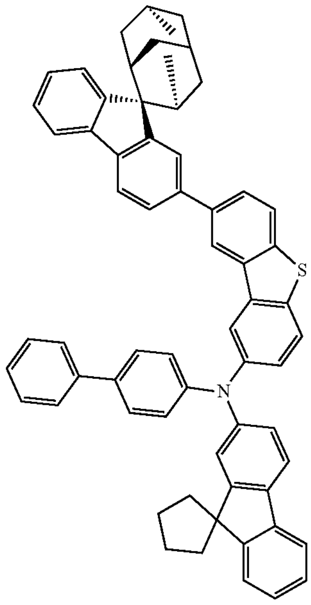
464
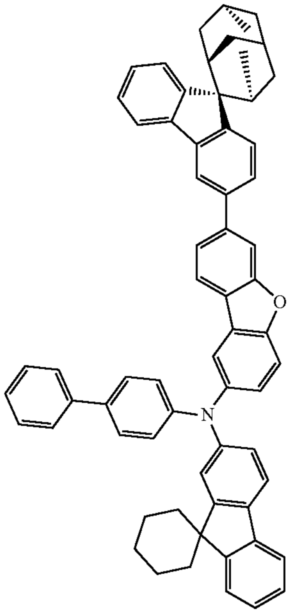

-continued
465
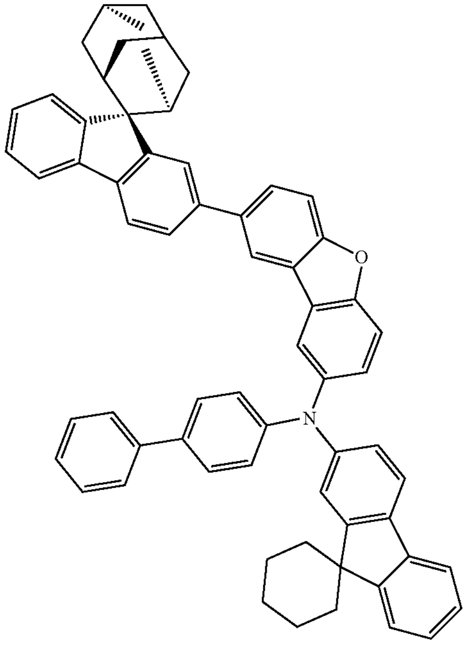
466
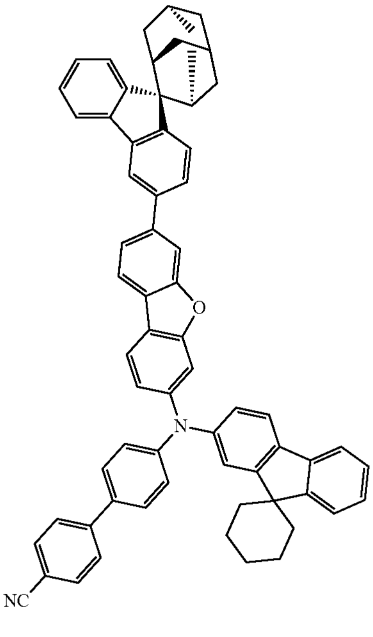
-continued
467
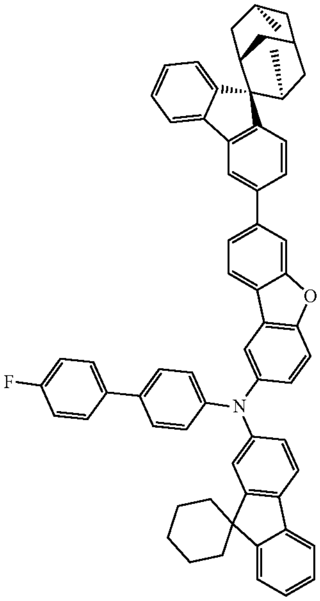
468
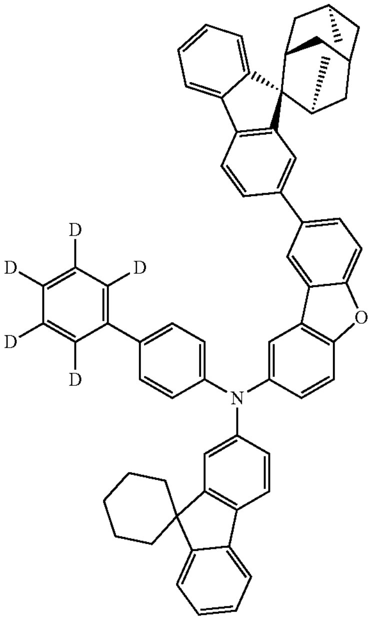

-continued
469
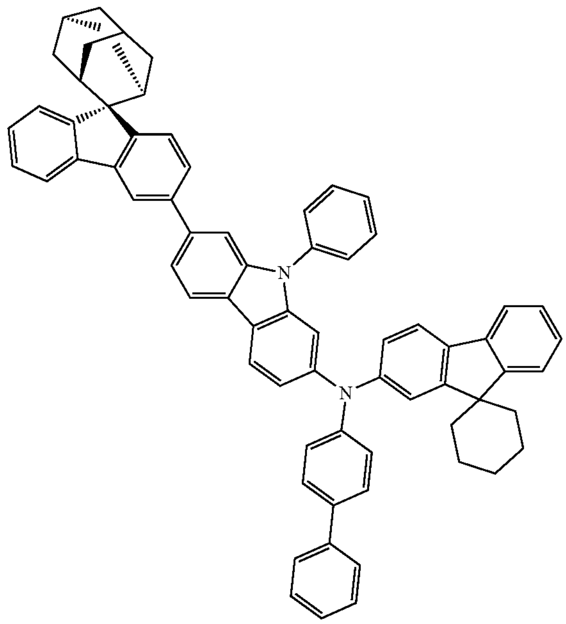
470
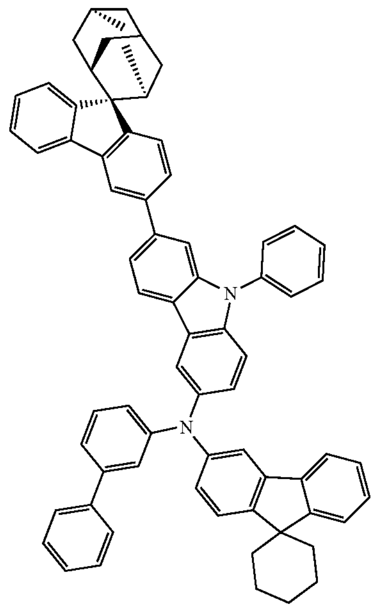
-continued
471
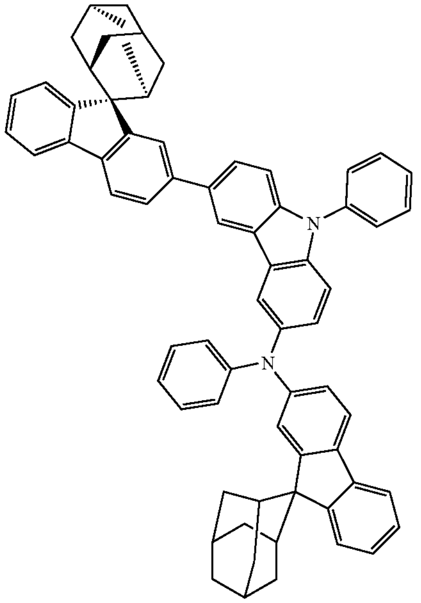
472
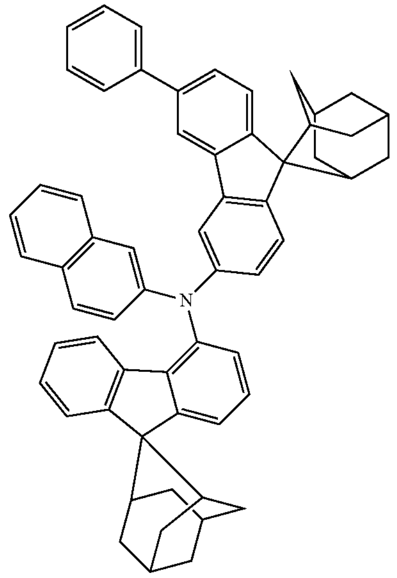
473
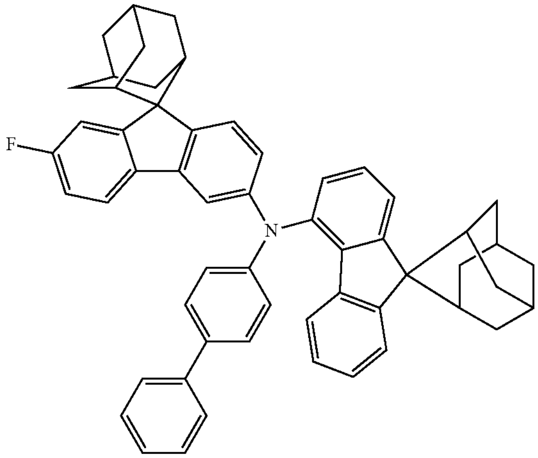

-continued
474
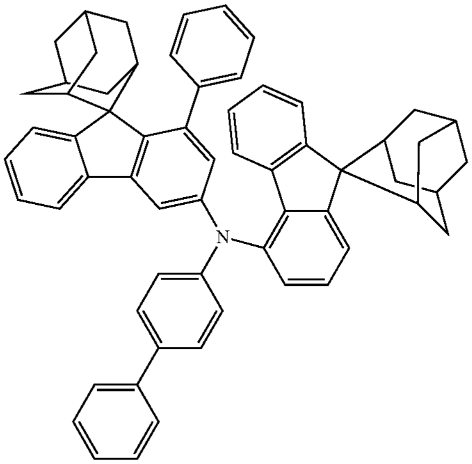
475
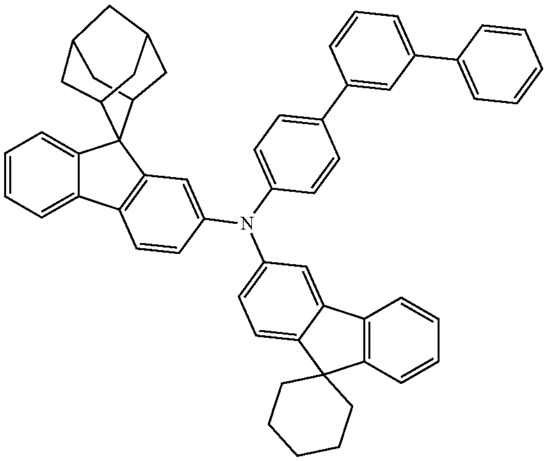
476
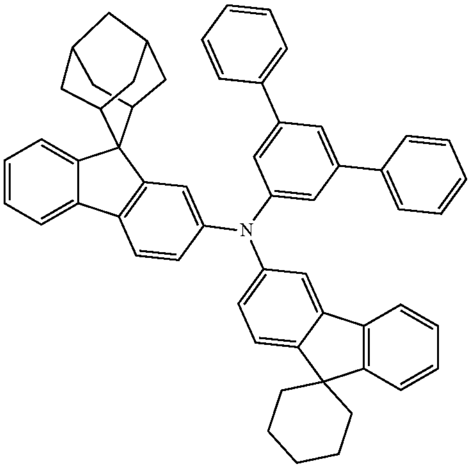
-continued
477
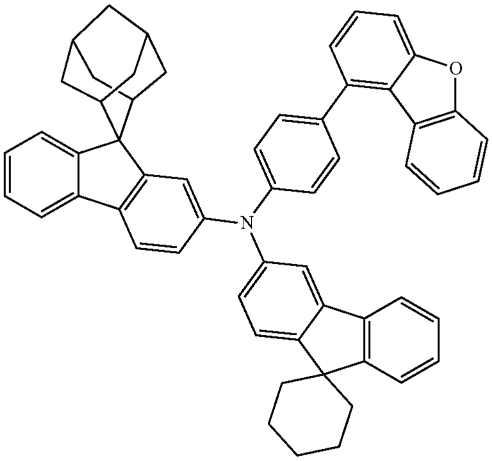
478
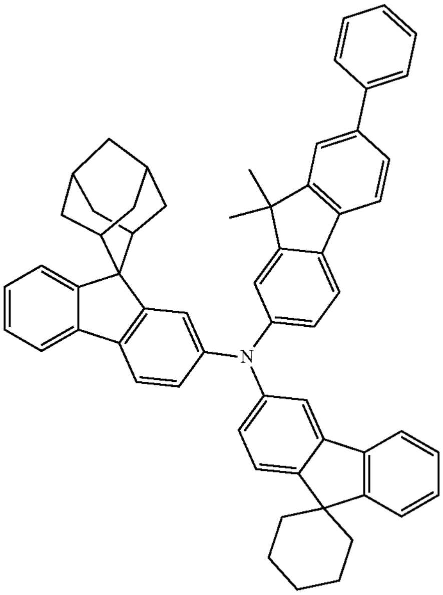
479
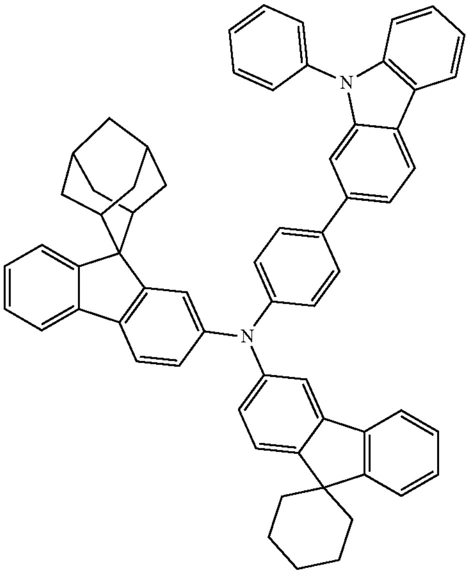

-continued
480
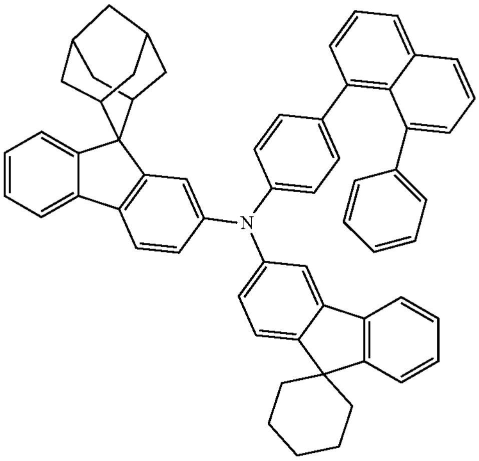
481
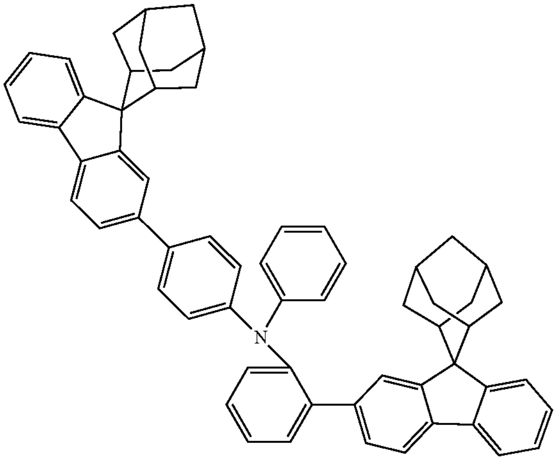
482
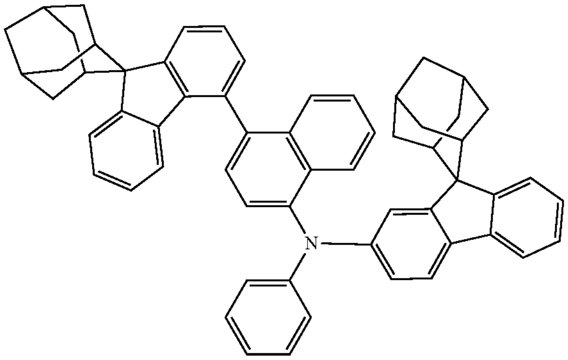
-continued
483
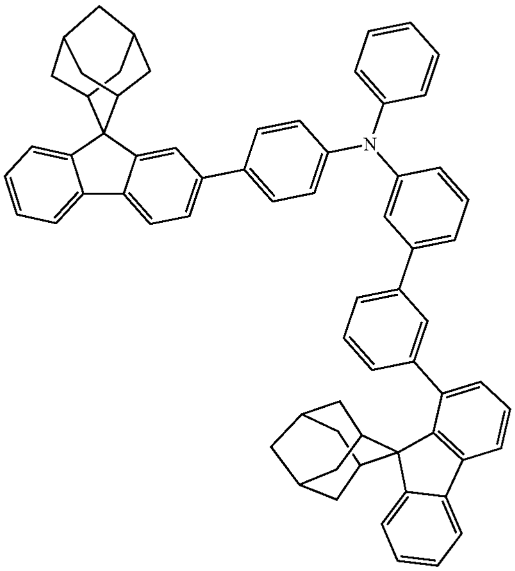
484
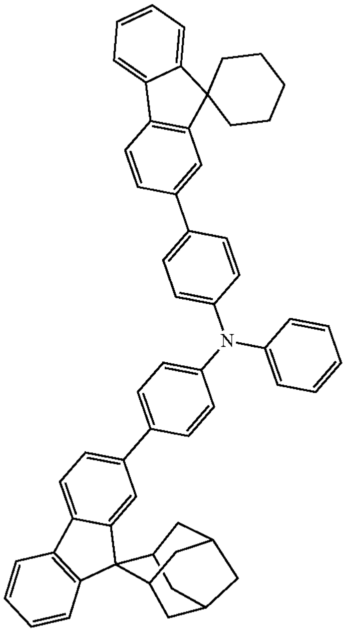
485
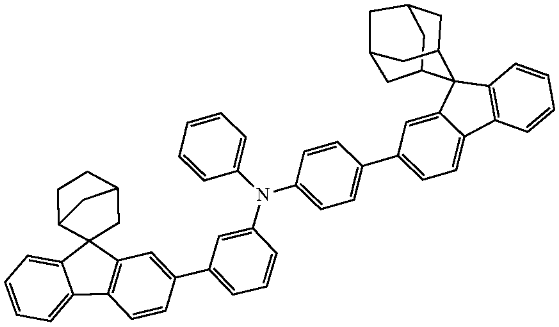

-continued
486
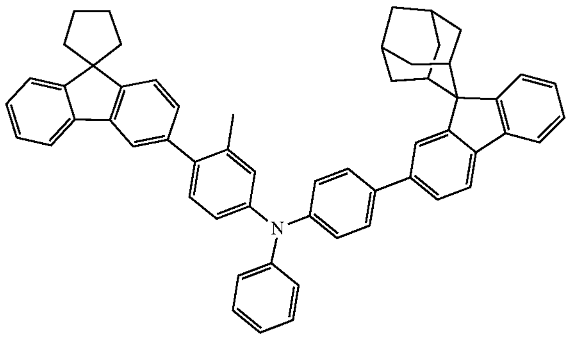
487
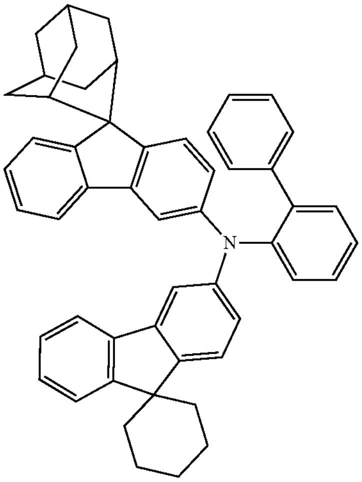
488
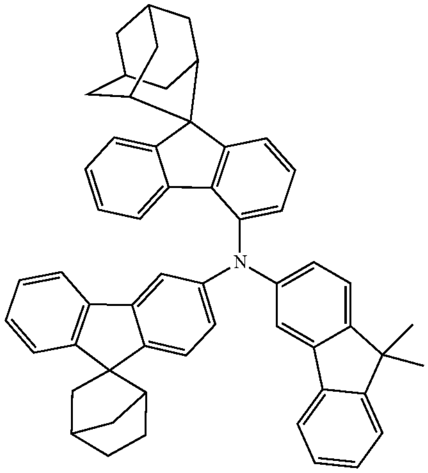
-continued
489
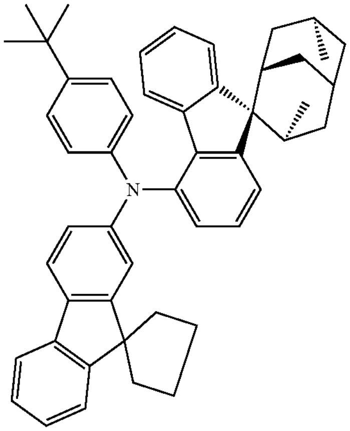
490
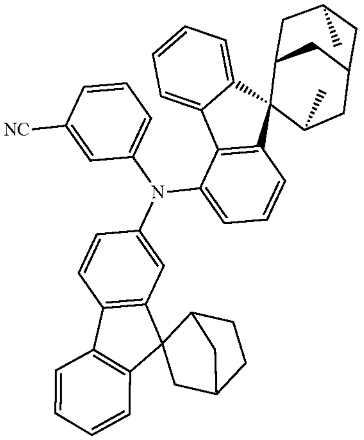
491
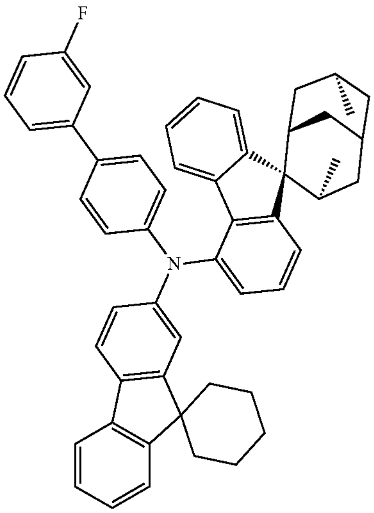

-continued

492

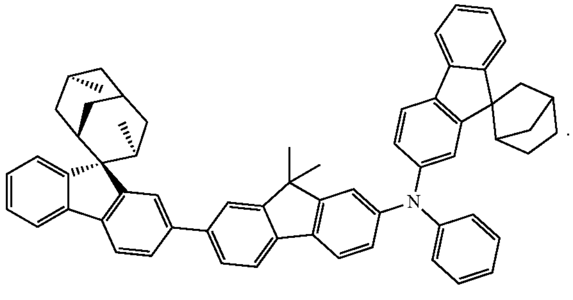

The present disclosure further provides an electronic component, including an anode, a cathode which is disposed oppositely to the anode, and a functional layer disposed between the anode and the cathode. The functional layer contains the arylamine compound.

The arylamine compound provided by the present disclosure can be used for forming at least one organic film layer in the functional layer so as to improve the voltage characteristic, the efficiency characteristic and the service life characteristic of the electronic component. Optionally, an organic film layer containing the arylamine compound of the present disclosure is located between an anode and an energy conversion layer of the electronic component, so that transport of electrons between the anode and the energy conversion layer is improved. Further, the functional layer comprises a hole transport layer, and the hole transport layer contains the arylamine compound.

For example, the electronic component may be an organic electroluminescent device. As shown in FIG. 1, the organic electroluminescent device comprises an anode 100 and a cathode 200 which are oppositely disposed, and a functional layer 300 disposed between the anode 100 and the cathode 200; and the functional layer 300 contains the arylamine compound provided by the present disclosure.

Optionally, the arylamine compound provided by the present disclosure can be used for forming at least one organic thin layer in the functional layer 300, so that the service life characteristic and the efficiency characteristic of the organic electroluminescent device are improved, and the driving voltage is reduced; in some examples, the electrochemical stability and the thermal stability of the organic electroluminescent device can be improved, and the uniformity of the performance of the organic electroluminescent device in mass production is improved.

Optionally, the functional layer 300 comprises a hole transport layer 320, and the hole transport layer 320 contains the arylamine compound provided by the present disclosure. The hole transport layer 320 not only can be composed of the arylamine compound provided by the present disclosure, but also can be composed of the arylamine compound provided by the present disclosure and other materials.

Optionally, the hole transport layer 320 comprises a first hole transport layer 321 and a second hole transport layer 322, and the first hole transport layer 321 is disposed on the surface, close to the anode 100, of the second hole transport layer 322; the first hole transport layer 321 and/or the second hole transport layer 322 contain(s) the arylamine compound provided by the present disclosure. Either the first hole transport layer 321 or the second hole transport layer 322 can contains the arylamine compound provided by the present disclosure, or both the first hole transport layer 321 and the second hole transport layer 322 can contain the arylamine compound provided by the present disclosure. It should be understood that the first hole transport layer 321 and/or the second hole transport layer 322 may also contain other materials, or may not contain other materials. It should be understood that in another embodiment of the present disclosure, the second hole transport layer 322 can be used as an electron blocking layer of the organic electroluminescent device.

Preferably, the first hole transport layer is adjacent to the second hole transport layer and is closer to the anode than the second hole transport layer.

Preferably, the first hole transport layer contains the arylamine compound, and the organic electroluminescent device is a green light or blue light device.

Preferably, the second hole transport layer contains the arylamine compound, and the organic electroluminescent device is a red light device.

In one embodiment of the present disclosure, as shown in FIG. 1, the organic electroluminescent device can comprise an anode 100, a first hole transport layer 321, a second hole transport layer 322, an organic light-emitting layer 330, an electron transport layer 340 and a cathode 200 which are sequentially stacked. The arylamine compound provided by the present disclosure can be applied to the first hole transport layer 321 and/or the second hole transport layer 322 of the organic electroluminescent device, so that the hole characteristics of the organic electroluminescent device can be effectively improved. The hole characteristics mean that holes formed in the anode 100 are easily injected into the organic light-emitting layer 330, and are transported in the organic light-emitting layer 330 according to the HOMO level conduction characteristic.

Optionally, the anode 100 contains the following anode materials, which are preferably materials having a large work function that facilitate hole injection into the functional layer. Specific embodiments of the anode materials contain metals such as nickel, platinum, vanadium, chromium, copper, zinc, and gold, or their alloy; metal oxides such as zinc oxide, indium oxide, indium tin oxide (ITO) and indium zinc oxide (IZO); combined metals and oxides, such as ZnO:Al or $SnO_2$:Sb; or a conductive polymer such as poly(3-methylthiophene), poly[3,4-(ethylene-1,2-dioxy) thiophene] (PEDT), polypyrrole, and polyaniline, but are not limited thereto. It is preferable to include a transparent electrode containing indium tin oxide (ITO) as an anode.

Optionally, the organic light-emitting layer 330 may be composed of a single light-emitting material, and may also contain a host material and a guest material. Optionally, the organic light-emitting layer 330 is composed of a host material and a guest material, holes injected into the organic light-emitting layer 330 and electrons injected into the organic light-emitting layer 330 can be recombined in the organic light-emitting layer 330 to form excitons, the excitons transfer energy to the host material, and the host material transfers energy to the guest material, so that the guest material can emit light.

The host material of the organic light-emitting layer 330 can be a metal chelated compound, a distyryl derivative, an aromatic amine derivative, a dibenzofuran derivative or other types of materials, which is not specially limited in the present disclosure. In one embodiment of the present disclosure, the host material of the organic light-emitting layer 330 may be CBP. In another embodiment of the present disclosure, the host material of the organic light-emitting layer 330 may be α,β-ADN.

The guest material of the organic light-emitting layer 330 may be a compound having a condensed aryl ring or its derivative, a compound having a heteroaryl ring or its derivative, an aromatic amine derivative, or other materials, which is not specially limited in the present disclosure. In one embodiment of the present disclosure, the guest material of the organic light-emitting layer 330 may be $Ir(flq)_2(acac)$. In another embodiment of the present disclosure, the guest material of the organic light-emitting layer 330 may be BD-6MDPA.

The electron transport layer 340 can be of a single-layer structure or a multi-layer structure and can contain one or more electron transport materials, and the electron transport materials can be selected from a benzimidazole derivative, an oxadiazole derivative, a quinoxaline derivative or other electron transport materials, which are not specially limited in the present disclosure. For example, in one embodiment of the present disclosure, the electron transport layer 340 may be composed of BP4mPy and LiQ.

Optionally, the cathode 200 contains the following cathode materials which are materials with a small work function that facilitate electron injection into the functional layer. Specific embodiments of the cathode materials contain metals such as magnesium, calcium, sodium, potassium, titanium, indium, yttrium, lithium, gadolinium, aluminum, silver, tin, and lead, or their alloy; or a plurality of layers of materials such as LiF/Al, Liq/Al, LiO2/Al, LiF/Ca, LiF/Al, and BaF2/Ca, but are not limited thereto. It is preferable to include a metal electrode containing an Mg—Ag alloy as a cathode.

Optionally, as shown in FIG. 1, a hole injection layer 310 can also be disposed between the anode 100 and the first hole transport layer 321, so that the capability of injecting holes into the first hole transport layer 321 is enhanced. The hole injection layer 310 can be made of a benzidine derivative, a starburst arylamine compound, a phthalocyanine derivative or other materials, which is not specially limited in the present disclosure. In one embodiment of the present disclosure, the hole injection layer 310 may be composed of m-MTDATA or HAT-CN.

Optionally, as shown in FIG. 1, an electron injection layer 350 can also be disposed between the cathode 200 and the electron transport layer 340 so as to enhance the capability of injecting electrons into the electron transport layer 340. The electron injection layer 350 may contain an inorganic material such as an alkali metal sulfide, and an alkali metal halide, or may contain a complex of an alkali metal and an organic substance. In one embodiment of the present present disclosure, the electron injection layer 350 may contain Yb.

Figure 3:
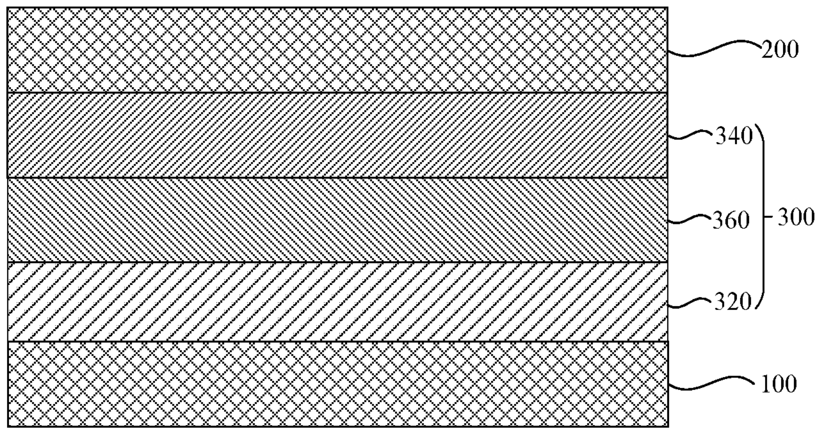
FIG. 3 is a structural schematic diagram of a photoelectric conversion device according to the embodiments of the present disclosure.

For example, the electronic component can be a photoelectric conversion device, as shown in FIG. 3, the photoelectric conversion device can contain an anode 100 and a cathode 200 which are oppositely arranged, and a functional layer 300 arranged between the anode 100 and the cathode 200; and the functional layer 300 contains the arylamine compound provided by the present disclosure.

Optionally, the arylamine compound provided by the present disclosure can be used for forming at least one organic thin layer in the functional layer 300, so that the performance of the photoelectric conversion device is improved, and particularly, the service life of the photoelectric conversion device is prolonged, the open-circuit voltage of the photoelectric conversion device is improved, or the performance uniformity and stability of the photoelectric conversion devices in mass production are improved.

Optionally, the functional layer 300 includes a hole transport layer 320, and the hole transport layer 320 contains the arylamine compound provided by the present disclosure. The hole transport layer 320 not only can be composed of the arylamine compound provided by the present disclosure, but also can be composed of the arylamine compound provided by the present disclosure and other materials.

Optionally, the hole transport layer 320 includes a first hole transport layer 321 and a second hole transport layer 322 (used as an electron blocking layer of the photoelectric conversion device), and the first hole transport layer 321 is arranged on the surface, close to the anode 100, of the second hole transport layer 322; the first hole transport layer 321 and/or the second hole transport layer 322 contain(s) the arylamine compound provided by the present disclosure. Either the first hole transport layer 321 or the second hole transport layer 322 can contain the arylamine compound provided by the present disclosure, or both the first hole transport layer 321 and the second hole transport layer 322 can contain the arylamine compound provided by the present disclosure. It can be understood that the first hole transport layer 321 and/or the second hole transport layer 322 may also contain other materials, or may not contain other materials.

Optionally, the hole transport layer 320 can further include an inorganic doping material, so that the hole transport performance of the hole transport layer 320 is improved.

In one embodiment of the present disclosure, as shown in FIG. 3, the photoelectric conversion device may contain an anode 100, a hole transport layer 320, a photoelectric conversion layer 360, an electron transport layer 340 and a cathode 200 which are sequentially stacked.

Optionally, the photoelectric conversion device can be a solar cell, in particular an organic thin-film solar cell. For example, in one embodiment of the present disclosure, a solar cell contains an anode 100, a first hole transport layer 321, a second hole transport layer 322 (as an electron blocking layer of the photoelectric conversion device), a photoelectric conversion layer 360, an electron transport layer 340 and a cathode 200 which are sequentially stacked, and the second hole transport layer 322 contains the arylamine compound of the present disclosure.

The examples of the present disclosure further provide an electronic device, including any one electronic component described in the embodiments of the electronic component. Since the electronic device is provided with any one electronic component described in the examples of the electronic component, the electronic device has the same beneficial effects, which will not be repeated here.

Figure 2:
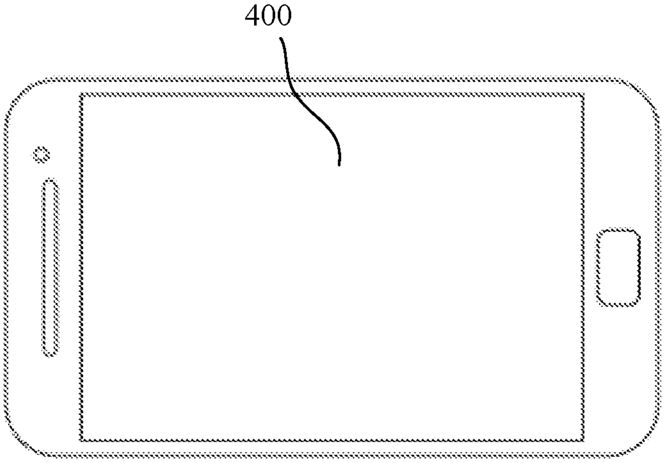
FIG. 2 is a structural schematic diagram of an electronic device according to the embodiments of the present disclosure.

For example, as shown in FIG. 2, the present disclosure provides a first electronic device 400, comprising any one organic electroluminescent device described in the embodiments of the organic electroluminescent device. The electronic device 400 can be a display device, a lighting device, an optical communication device or other types of electronic devices, and may contain, for example, but is not limited to, a computer screen, a mobile phone screen, a television, electronic paper, an emergency lighting lamp, an optical module and the like. Since the first electronic device 400 is provided with any one organic electroluminescent device described in the embodiments of the organic electroluminescent device, the first electronic device 400 has the same beneficial effects, which will not be repeated here.

Figure 4:
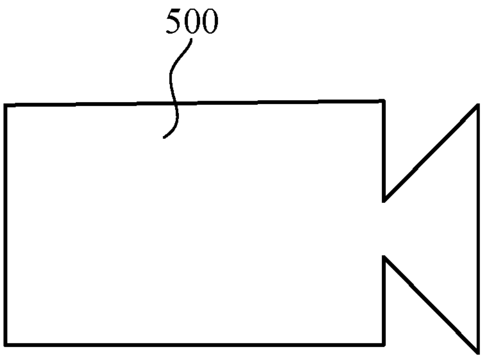
FIG. 4 is a structural schematic diagram of another electronic device according to the embodiments of the present disclosure.

For example, as shown in FIG. 4, the present disclosure provides a second electronic device 500, comprising any one photoelectric conversion device described in the embodiments of the photoelectric conversion device. The electronic device 500 can be a solar power plant, a light detector, a fingerprint identification device, a light module, a CCD camera or other types of electronic devices. Since the second electronic device 500 is provided with any one photoelectric conversion device described in the embodiments of the photoelectric conversion device, the second electronic device 500 has the same beneficial effects, which will not be repeated here.

The present disclosure is further described in detail below by examples. However, the following examples are only examples of the present disclosure, and are not intended to limit the present disclosure.

The compounds in the synthesis method which are not mentioned in the present disclosure are all commercially available raw material products.

An ICP-7700 mass spectrometer and an M5000 elemental analyzer are used for analysis and detection of intermediates and compounds in the present disclosure.

A synthesis method of the arylamine compound of the present disclosure is specifically described below in combination with synthesis examples.

Hereinafter, unless otherwise specified, MC refers to dichloromethane, and rt refers to room temperature.

Synthesis Examples

Synthesis of Compound 22

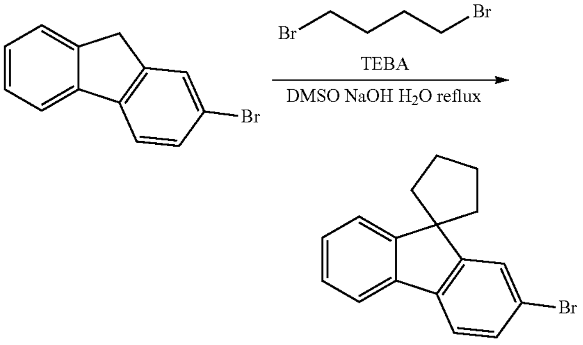

IM-A-1

2-bromo-9H-fluorene (50.0 g, 203.98 mmol), sodium hydroxide (35 g, 446.76 mmol), dimethyl sulfoxide (500 mL), benzyltriethylammonium chloride (1.39 g, 6.12 mmol) and deionized water (100 mL) were added into a round-bottom flask, and heated to 160° C. under the protection of nitrogen, and 1,4-dibromobutane (44 g, 203.98 mmol) was added while stirring; the reaction solution was continued to stir for 3 h, the resulting reaction solution was cooled to room temperature, toluene (200 mL) was added for extraction, organic phases were combined dried over anhydrous magnesium sulfate, and filtered, and a solvent was removed under reduced pressure; and the obtained crude product was purified by silica gel column chromatography using toluene as a mobile phase to obtain a light yellow solid intermediate IM-A-1 (57.0 g, yield: 93.4%).

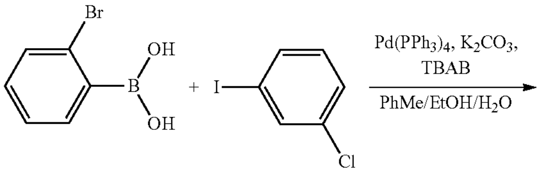

-continued

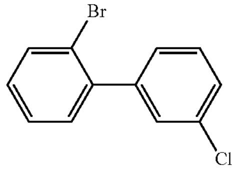

IM-B-1

2-bromophenylboronic acid (100.0 g, 497.86 mmol), 1-chloro-3-iodobenzene (124.6 g, 522.75 mmol), tetrakis (triphenylphosphine) palladium (11.5 g, 9.97 mmol), potassium carbonate (151.15 g, 1095.3 mmol), tetrabutylammonium bromide (32.1 g, 99.6 mmol), toluene (800 mL), ethanol (200 mL) and deionized water (200 mL) were added into a round-bottom flask, heated to 78° C. under the protection of nitrogen, and stirred for 2 h; the resulting reaction solution was cooled to room temperature, toluene (500 mL) was added for extraction, organic phases were combined, dried over anhydrous magnesium sulfate, and filtered, and a solvent was removed under reduced pressure; and the obtained crude product was purified by silica gel column chromatography using n-heptane as a mobile phase, and then purified through recrystallization by using a dichloromethane/ethanol system to obtain a light yellow solid intermediate IM-B-1 (76.0 g, yield: 57%).

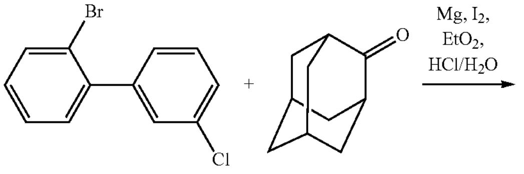

IM-B-1

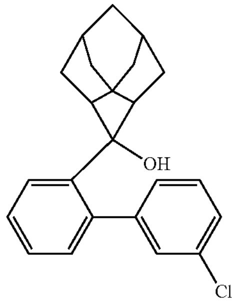

IM-B-2

A magnesium ribbon (16.11 g, 671.16 mmol) and diethyl ether (120 mL) were put into a dry round-bottom flask under the protection of nitrogen, and iodine (120 mg) was added. A diethyl ether (240 mL) solution in which the intermediate IM-B-1 (76.00 g, 284.06 mmol) was dissolved was slowly dropwise dropped into the flask. After the addition was completed, the temperature was raised to 35° C. and the content was stirred for 3 hours. The resulting reaction solution was cooled to 0° C., a diethyl ether (238 mL) solution in which adamantanone (26.71 g, 177.81 mmol) was dissolved was slowly dropwise added into the cooled reaction solution. After the dropwise addition, the temperature was raised to 35° C., and stirred for 6 hours. The resulting reaction solution was cooled to room temperature, 5 wt % hydrochloric acid was added into the cooled reaction solution until a pH value was less than 7. After stirring for 1 hour, diethyl ether (240 mL) was added for extraction, organic phases were combined, dried over anhydrous magnesium sulfate, and filtered, and a solvent was removed under reduced pressure; and the obtained crude product was purified by silica gel column chromatography using n-heptane as a mobile phase to obtain a solid intermediate IM-B-2 (28.56 g, yield: 47%).

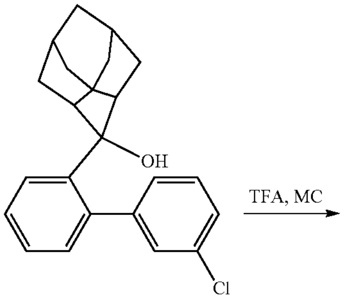

IM-B-2

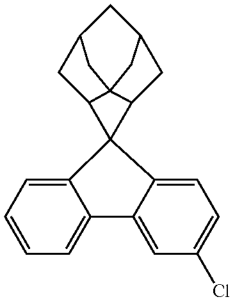

IM-B-3

The intermediate IM-B-2 (28.56 g, 84.3 mmol), trifluoroacetic acid (48.17 g, 422.45 mmol) and dichloromethane (MC, 280 mL) were added into a round-bottom flask, and stirred for 2 h under the protection of nitrogen. Then, sodium hydroxide aqueous solution was added into the resulting reaction solution until a pH value was equal to 8, liquid separation was performed, the organic phase was dried over anhydrous magnesium sulfate, and filtered, and a solvent was removed under reduced pressure; and the obtained crude product was purified through recrystallization by using dichloromethane/n-heptane (in a volume ratio of 1:2) to obtain a white solid intermediate IM-B-3 (25.2 g, yield: 92.5%).

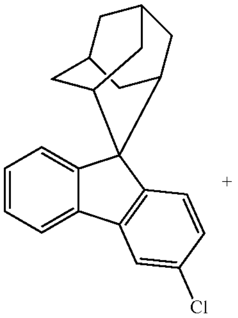

IM-B-3

-continued

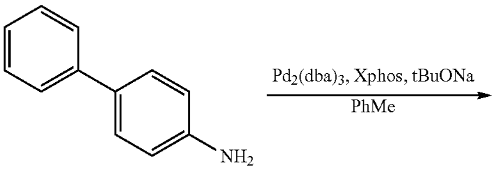

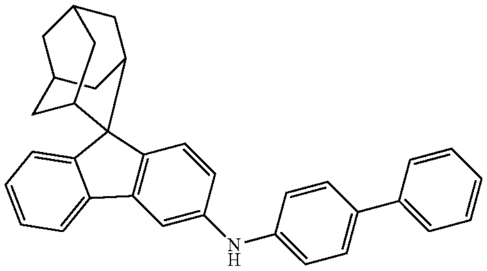

IM-B

The intermediate IM-B-3 (4.0 g, 12.46 mmol), 4-aminobiphenyl (2.11 g, 12.46 mmol), tris(dibenzylideneacetone) dipalladium (0.11 g, 0.12 mmol), 2-dicyclohexylphosphino-2',4',6'-triisopropylbiphenyl (0.12 g, 0.25 mmol) and sodium tert-butoxide (1.8 g, 18.7 mmol) were added into toluene (40 mL), heated to 108° C. under the protection of nitrogen, and stirred for 2 h. Then the reaction solution was cooled to room temperature, and washed with water, dried by adding magnesium sulfate, and filtered, and a solvent was removed from the obtained filtrate under reduced pressure; and the obtained crude product was purified through recrystallization by using a dichloromethane/ethyl acetate system to obtain a light yellow solid intermediate IM-B (4.1 g, yield: 72.6%).

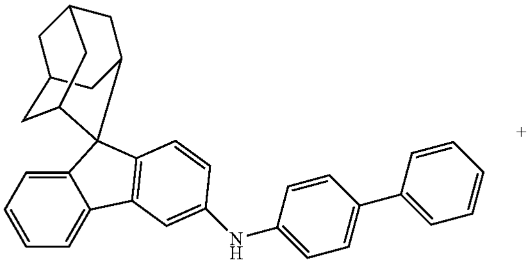

IM-B

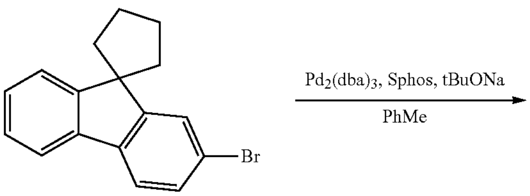

IM-A-1

-continued

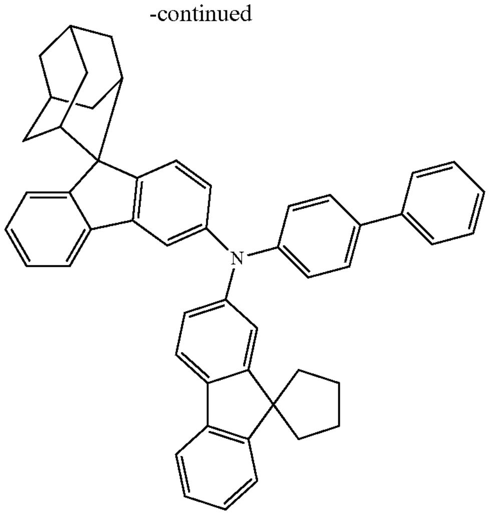

22

The intermediate IM-A-1 (4.1 g, 9.04 mmol), the intermediate IM-B (2.7 g, 9.04 mmol), tris(dibenzylideneacetone)dipalladium (0.08 g, 0.09 mmol), 2-dicyclohexylphosphino-2',6'-dimethoxybiphenyl (0.07 g, 0.18 mmol) and sodium tert-butoxide (1.3 g, 13.55 mmol) were added into toluene (40 mL), heated to 108° C. under the protection of nitrogen, and stirred for 1 h. After cooling to room temperature, the resulting reaction solution was washed with water, dried by adding magnesium sulfate, and filtered, and a solvent was removed from the obtained filtrate under reduced pressure; and the obtained crude product was purified through recrystallization by using a toluene system to obtain a white solid compound 22 (4.35 g, yield: 71.67%). Mass spectrum: m/z=672.4 $[M+H]^+$.

Referring to the synthesis method of the compound 22, a raw material 1 shown in Table 1 was used for replacing the intermediate IM-B-1, a product 1 was prepared by using a synthesis method which was the same as that of the intermediate IM-B-2, and then intermediates IM-C-2 and IM-D-2 were prepared by using a synthesis method which was the same as that of the intermediate IM-B-3.

TABLE 1

| Intermediate No. | Raw material 1 | Product 1 | Intermediate |
|---|---|---|---|
| IM-C-2 | 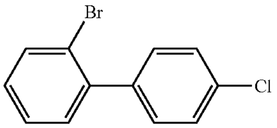 [SMILES: Clc1ccc(-c2ccccc2Br)cc1] | 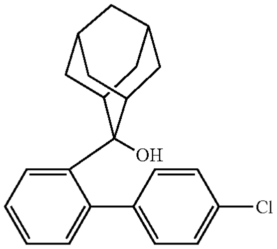 [SMILES: OC1(c2ccccc2-c2ccc(Cl)cc2)C2CC3CC(C2)CC1C3] | 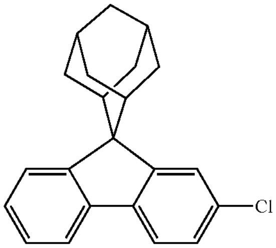 [SMILES: Clc1ccc2c(c1)C1(c3ccccc3-2)C2CC3CC(C2)CC1C3] |
| IM-D-2 | 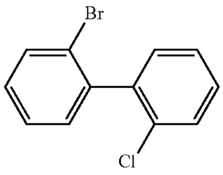 [SMILES: Clc1ccccc1-c1ccccc1Br] | 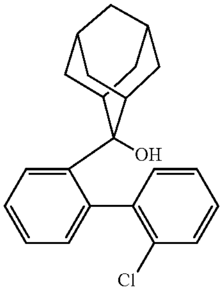 [SMILES: OC1(c2ccccc2-c2ccccc2Cl)C2CC3CC(C2)CC1C3] | 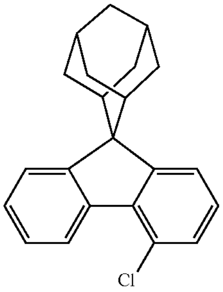 [SMILES: Clc1cccc2c1-c1ccccc1C21C2CC3CC(C2)CC1C3] |

Synthesis of Compound 52

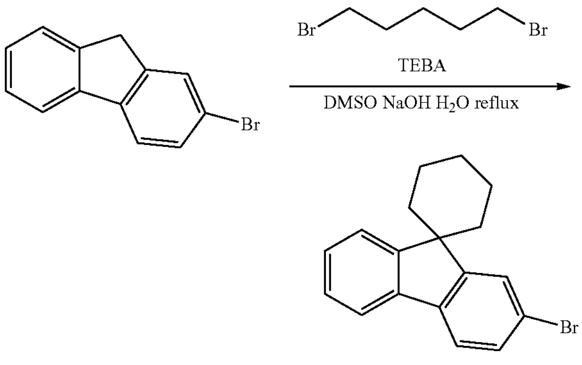

IM-A-2

In addition to using 1,5-dibromopentane instead of 1,4-dibromobutane, an intermediate IM-A-2 was prepared by reference to the same synthesis method as the intermediate IM-A-1.

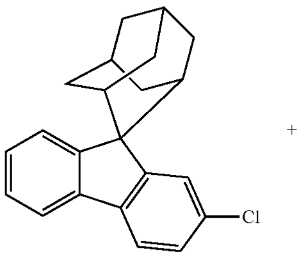

IM-C-2

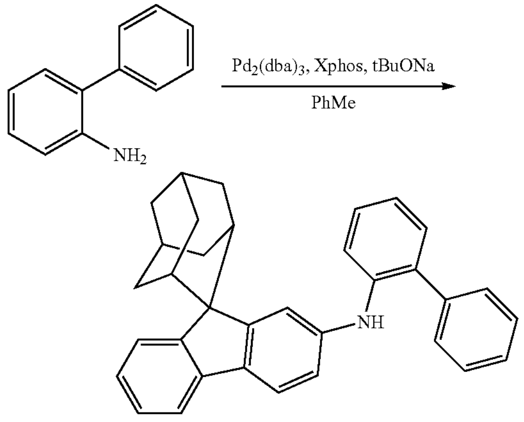

IM-C

The intermediate IM-C-2 (5.0 g, 15.58 mmol), 2-aminobiphenyl (2.77 g, 16.36 mmol), tris(dibenzylideneacetone) dipalladium (0.14 g, 0.16 mmol), 2-dicyclohexylphosphino-2',4',6'-triisopropylbiphenyl (0.15 g, 0.31 mmol) and sodium tert-butoxide (2.25 g, 23.37 mmol) were added into toluene (40 mL), heated to 108° C. under the protection of nitrogen, and stirred for 5 h. After cooling to room temperature, the resulting reaction solution was washed with water, dried by adding magnesium sulfate, and filtered, and a solvent was removed from the obtained filtrate under reduced pressure; and the obtained crude product was purified through recrystallization by using a dichloromethane/ethanol system to obtain a solid intermediate IM-C (5.3 g, yield: 74.96%).

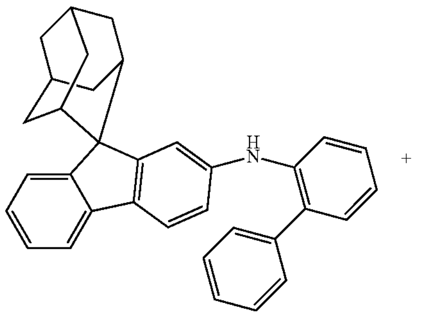

IM-C

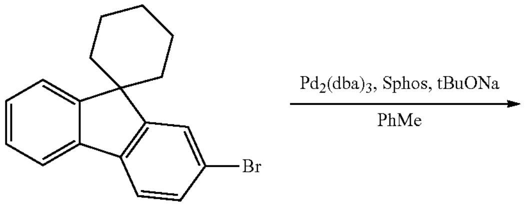

IM-A-2

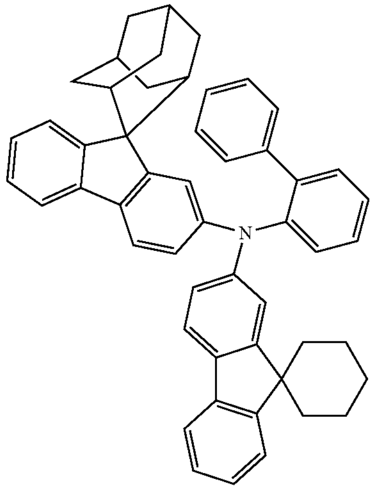

52

The intermediate IM-A-2 (5.3 g, 11.69 mmol), the intermediate IM-C (3.67 g, 11.69 mmol), tris(dibenzylideneacetone) dipalladium (0.11 g, 0.12 mmol), 2-dicyclohexylphosphino-2',6'-dimethoxybiphenyl (0.10 g, 0.24 mmol) and sodium tert-butoxide (1.68 g, 17.53 mmol) were added into toluene (40 mL), heated to 108° C. under the protection of nitrogen, and stirred for 1 h. After cooling to room temperature, the resulting reaction solution was washed with water, dried by adding magnesium sulfate, and filtered, and a solvent was removed from the obtained filtrate under reduced pressure; and the obtained crude product was purified through recrystallization by using a toluene system to obtain a white solid compound 52 (6.91 g, yield: 86.27%). Mass spectrum: m/z=686.4 $[M+H]^+$.

Synthesis of Compound 177

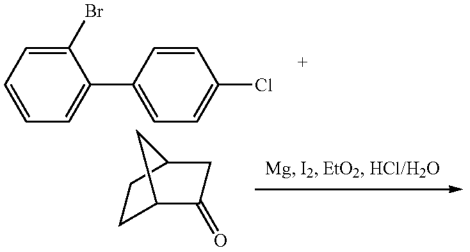

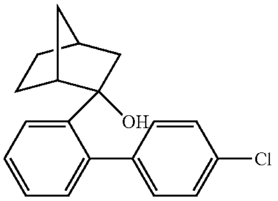

IM-A-3

In addition to replacing adamantanone with norbornanone, an intermediate IM-A-3 was prepared by reference to the same synthesis method as the intermediate IM-B-2.

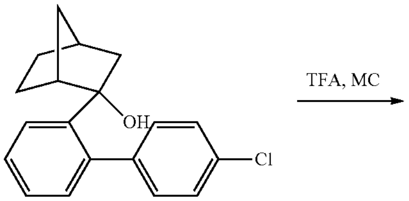

IM-A-3

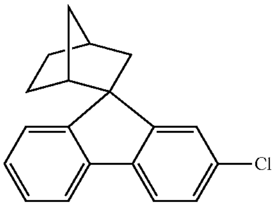

IM-A-4

In addition to replacing the intermediate IM-B-2 with the intermediate IM-A-3, an intermediate IM-A-4 was prepared by reference to the same synthesis method as the intermediate IM-B-3.

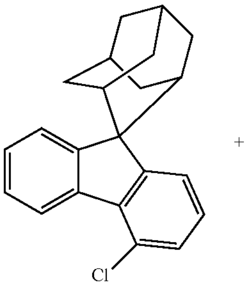

IM-D-2

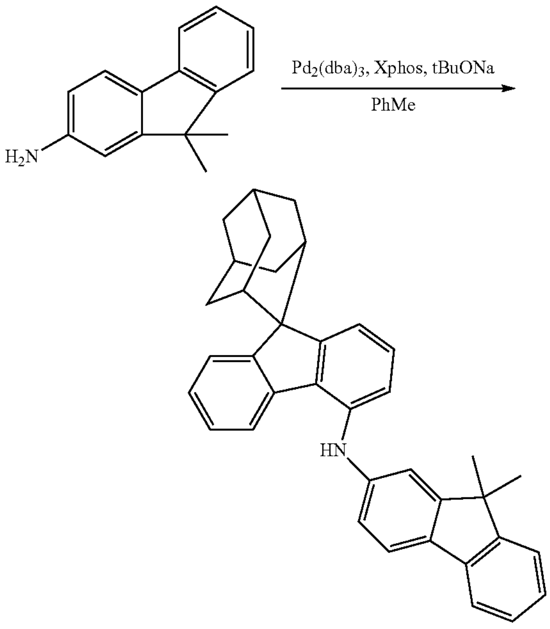

IM-D

According to the synthesis method of the intermediate IM-B, an intermediate IM-D-2 was used for replacing the intermediate IM-B-3, and 2-amino-9,9'-dimethylfluorene was used for replacing the raw material 4-aminobiphenyl, so that an intermediate IM-D was prepared.

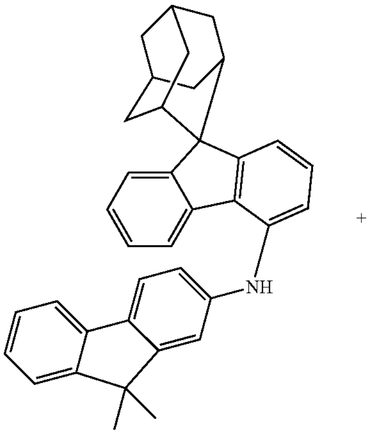

IM-D

-continued

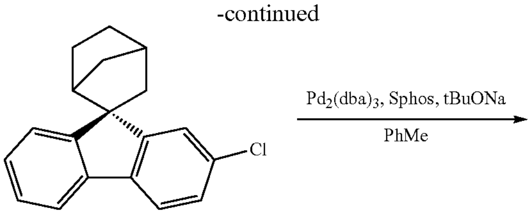

IM-A-4

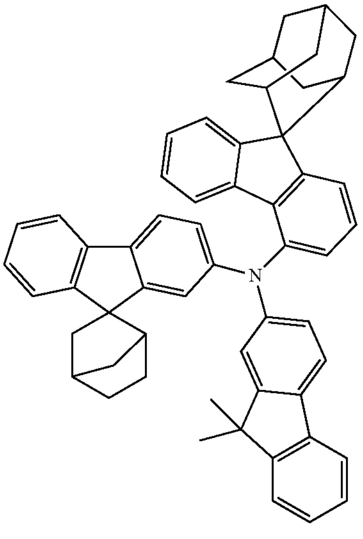

177

The intermediate IM-D (4.1 g, 8.3 mmol), the intermediate IM-A-4 (2.33 g, 8.3 mmol), tris(dibenzylideneacetone) dipalladium (0.08 g, 0.08 mmol), 2-dicyclohexylphosphino-2',6'-dimethoxybiphenyl (0.07 g, 0.17 mmol) and sodium tert-butoxide (1.19 g, 12.46 mmol) were added into toluene (40 mL), heated to 108° C. under the protection of nitrogen, and stirred for 4 h. After cooling to room temperature, the resulting reaction solution was washed with water, dried by adding magnesium sulfate, and filtered, and a solvent was removed from the obtained filtrate under reduced pressure; and the obtained crude product was purified through recrystallization by using a toluene system to obtain a solid compound 177 (5.2 g, yield: 84.83%), and mass spectrum (m/z)=738.4 $[M+H]^+$.

Referring to the synthesis method of the compound 22, an intermediate 2 was synthesized from a raw material 2 instead of 4-aminobiphenyl, and an intermediate 1 instead of the intermediate IM-B-3, and a compound in the fifth column in Table 2 was synthesized from an intermediate 3 instead of the intermediate IM-A-1, and the intermediate 2. Specific compound No., structures, raw materials, characterization data and the like are as shown in Table 2.

TABLE 2
| Compound structure, preparation and characterization data | | | | | |
|---|---|---|---|---|---|
| Raw material 2 | Intermediate 1 | Intermediate 2 | Intermediate 3 | Compound structure and No. | Mass spectrum (m/z) [M + H]+ |
| 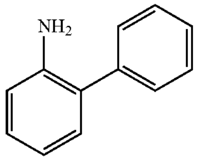 [SMILES: Nc1ccccc1-c1ccccc1] | 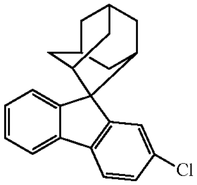 [SMILES: Clc1ccc2c(c1)C1(c3ccccc3-2)C2CC3CC(C2)CC1C3] | 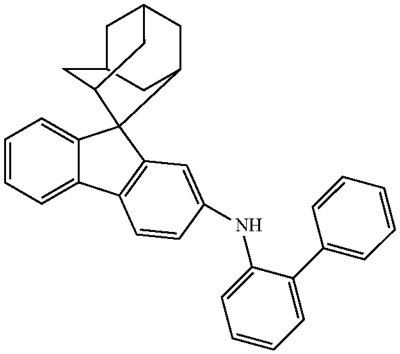 [SMILES: c1ccc(-c2ccccc2Nc2ccc3c(c2)C2(c4ccccc4-3)C3CC4CC(C3)CC2C4)cc1] | 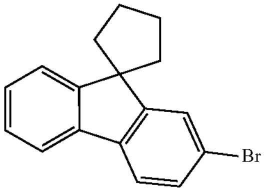 [SMILES: Brc1ccc2c(c1)C1(CCCC1)c1ccccc1-2] | 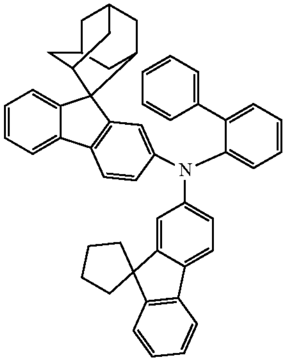 4 | 672.4 |
| 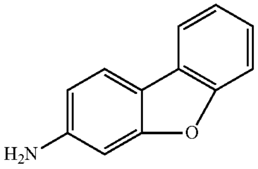 | | 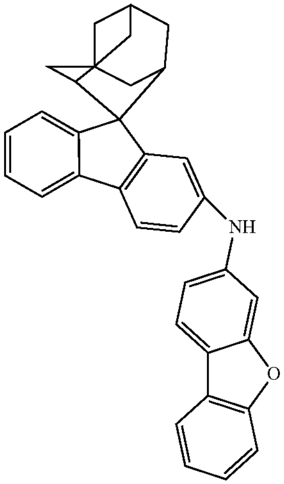 | 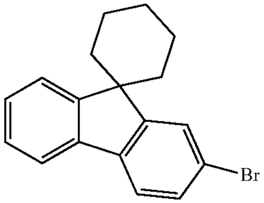 [SMILES: Brc1ccc2c(c1)C1(CCCCC1)c1ccccc1-2] | 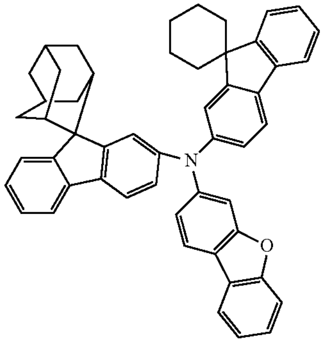 54 | 700.4 |

TABLE 2-continued
| Compound structure, preparation and characterization data | | | | | |
|---|---|---|---|---|---|
| Raw material 2 | Intermediate 1 | Intermediate 2 | Intermediate 3 | Compound structure and No. | Mass spectrum (m/z) $[M + H]^+$ |
| 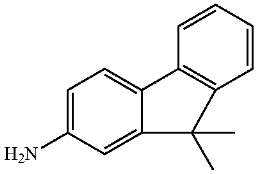 [SMILES: CC1(C)c2ccccc2-c2ccc(N)cc21] | | 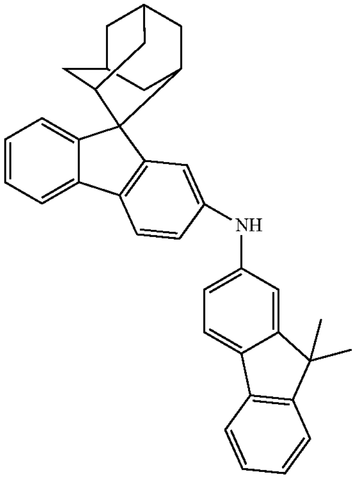 [SMILES: CC1(C)c2ccccc2-c2ccc(Nc3ccc4c(c3)C3(c5ccccc5-4)C4CC5CC(C4)CC3C5)cc21] | 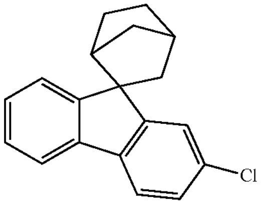 [SMILES: Clc1ccc2c(c1)C1(CC3CCC1C3)c1ccccc1-2] | 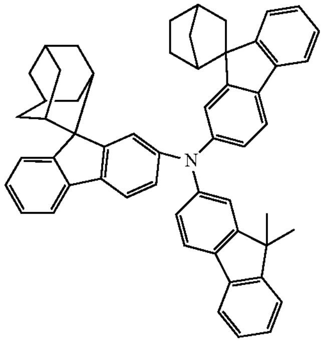 149 | 738.4 |
| 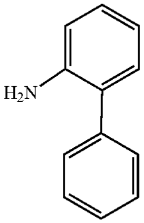 [SMILES: Nc1ccccc1-c1ccccc1] | | 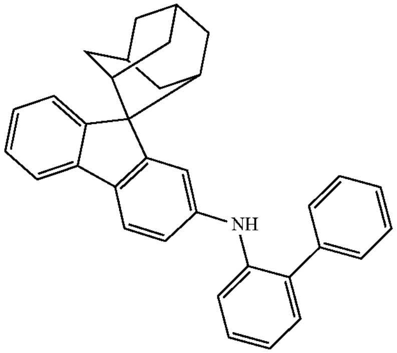 [SMILES: c1ccc(-c2ccccc2Nc2ccc3c(c2)C2(c4ccccc4-3)C3CC4CC(C3)CC2C4)cc1] | 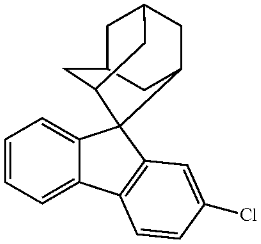 [SMILES: Clc1ccc2c(c1)C1(c3ccccc3-2)C2CC3CC(C2)CC1C3] | 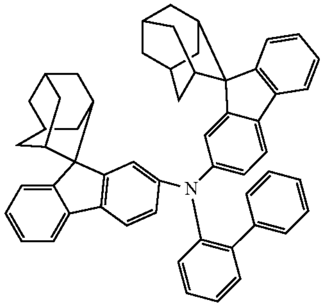 100 | 788.4 |

TABLE 2-continued
| Compound structure, preparation and characterization data | | | | | |
|---|---|---|---|---|---|
| Raw material 2 | Intermediate 1 | Intermediate 2 | Intermediate 3 | Compound structure and No. | Mass spectrum (m/z) [M + H]+ |
| 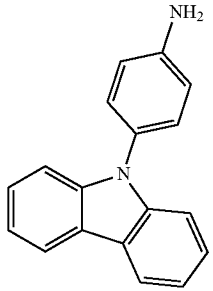 [SMILES: Nc1ccc(-n2c3ccccc3c3ccccc32)cc1] | | 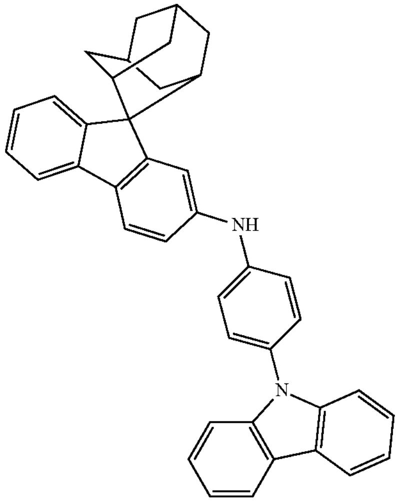 [SMILES: c1ccc2c(c1)-c1ccc(Nc3ccc(-n4c5ccccc5c5ccccc54)cc3)cc1C21C2CC3CC(C2)CC1C3] | 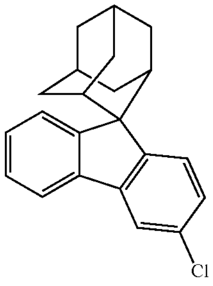 [SMILES: Clc1ccc2c(c1)-c1ccccc1C21C2CC3CC(C2)CC1C3] | 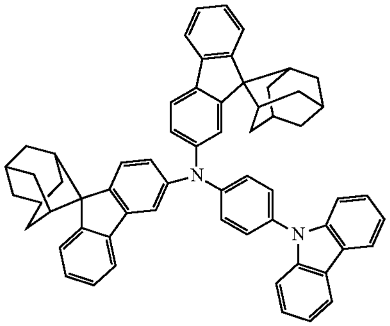 113 | 827.4 |

TABLE 2-continued
| Compound structure, preparation and characterization data | | | | | |
|---|---|---|---|---|---|
| Raw material 2 | Intermediate 1 | Intermediate 2 | Intermediate 3 | Compound structure and No. | Mass spectrum (m/z) [M + H]+ |
| 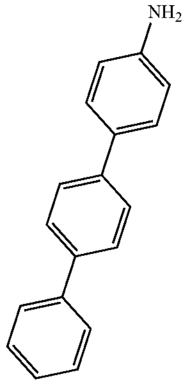 [SMILES: Nc1ccc(-c2ccc(-c3ccccc3)cc2)cc1] | | 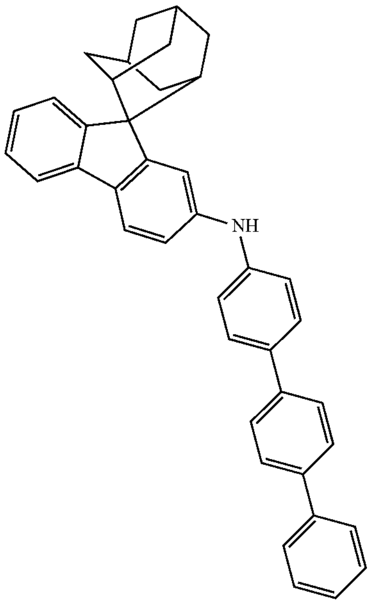 [SMILES: c1ccc(-c2ccc(-c3ccc(Nc4ccc5c(c4)C4(c6ccccc6-5)C5CC6CC(C5)CC4C6)cc3)cc2)cc1] | 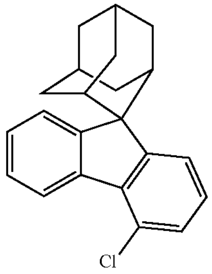 [SMILES: Clc1cccc2c1-c1ccccc1C21C2CC3CC(C2)CC1C3] | 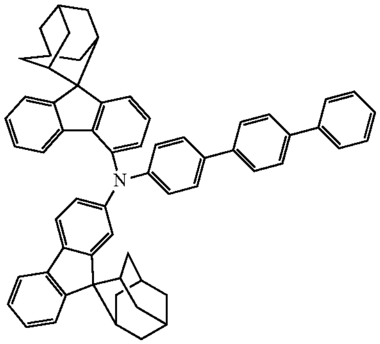 138 | 814.4 |

TABLE 2-continued
| Compound structure, preparation and characterization data | | | | | |
|---|---|---|---|---|---|
| Raw material 2 | Intermediate 1 | Intermediate 2 | Intermediate 3 | Compound structure and No. | Mass spectrum (m/z) $[M + H]^+$ |
| 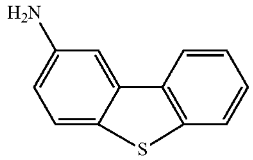 [SMILES: Nc1ccc2sc3ccccc3c2c1] | 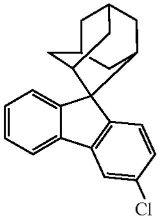 [SMILES: Clc1ccc2c(c1)-c1ccccc1C21C2CC3CC(C2)CC1C3] | 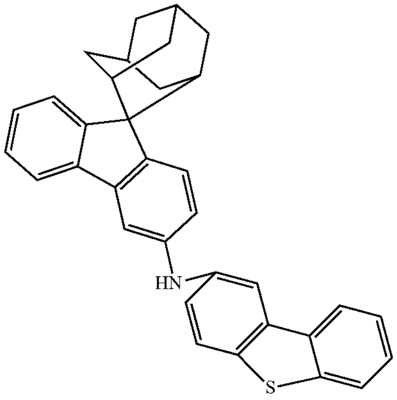 [SMILES: c1ccc2c(c1)-c1cc(Nc3ccc4sc5ccccc5c4c3)ccc1C21C2CC3CC(C2)CC1C3] | 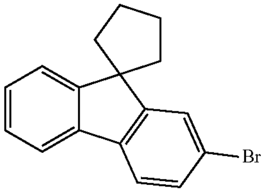 [SMILES: Brc1ccc2c(c1)C1(CCCC1)c1ccccc1-2] | 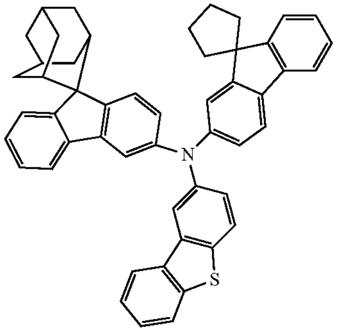 25 | 702.3 |
| 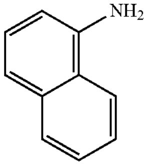 [SMILES: Nc1cccc2ccccc12] | | 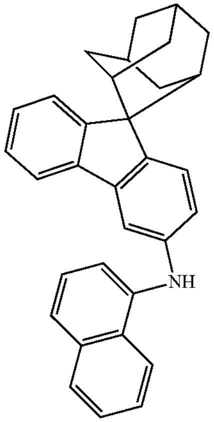 [SMILES: c1ccc2c(c1)-c1cc(Nc3cccc4ccccc34)ccc1C21C2CC3CC(C2)CC1C3] | 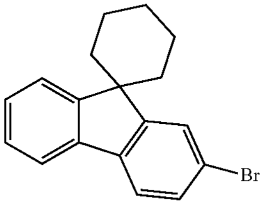 [SMILES: Brc1ccc2c(c1)C1(CCCCC1)c1ccccc1-2] | 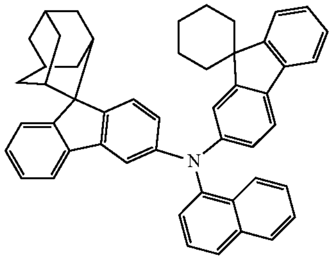 75 | 660.4 |

TABLE 2-continued
| Compound structure, preparation and characterization data | | | | | |
|---|---|---|---|---|---|
| Raw material 2 | Intermediate 1 | Intermediate 2 | Intermediate 3 | Compound structure and No. | Mass spectrum (m/z) $[M + H]^+$ |
| 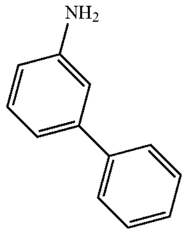 [SMILES: Nc1cccc(-c2ccccc2)c1] | | 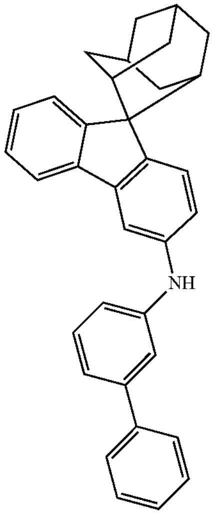 [SMILES: c1ccc(-c2cccc(Nc3ccc4c(c3)-c3ccccc3C43C4CC5CC(C4)CC3C5)c2)cc1] | 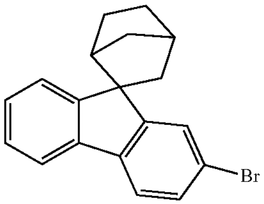 [SMILES: Brc1ccc2c(c1)C1(CC3CCC1C3)c1ccccc1-2] | 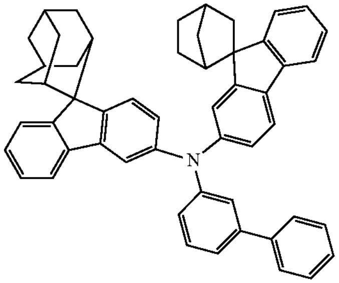 170 | 698.4 |
| 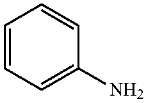 | | 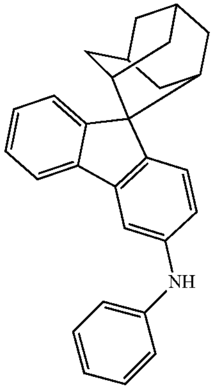 [SMILES: c1ccc(Nc2ccc3c(c2)-c2ccccc2C32C3CC4CC(C3)CC2C4)cc1] | 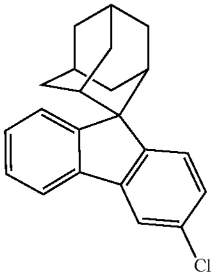 [SMILES: Clc1ccc2c(c1)-c1ccccc1C21C2CC3CC(C2)CC1C3] | 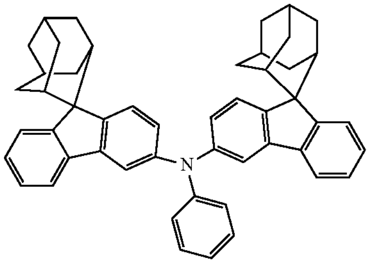 394 | 662.4 |

TABLE 2-continued
| Compound structure, preparation and characterization data | | | | | |
|---|---|---|---|---|---|
| Raw material 2 | Intermediate 1 | Intermediate 2 | Intermediate 3 | Compound structure and No. | Mass spectrum (m/z) $[M + H]^+$ |
| 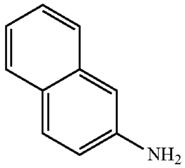 | | 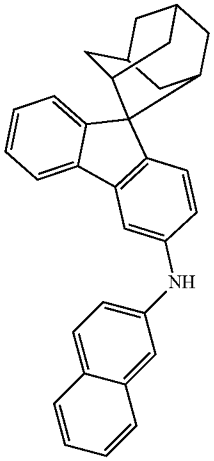 [SMILES: c1ccc2c(c1)-c1cc(Nc3ccc4ccccc4c3)ccc1C21C2CC3CC(C2)CC1C3] | 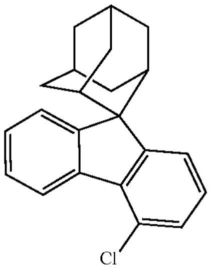 [SMILES: Clc1cccc2c1-c1ccccc1C21C2CC3CC(C2)CC1C3] | 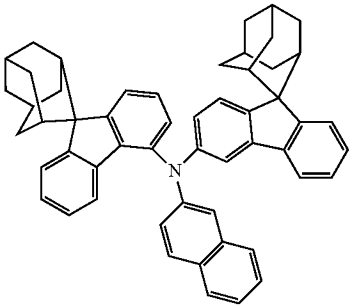 414 | 712.4 |
| 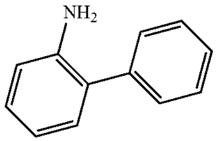 [SMILES: Nc1ccccc1-c1ccccc1] | | 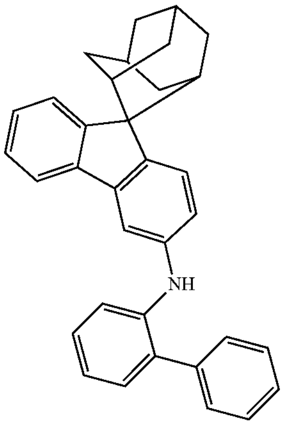 [SMILES: c1ccc(-c2ccccc2Nc2ccc3c(c2)-c2ccccc2C32C3CC4CC(C3)CC2C4)cc1] | 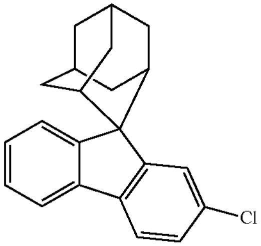 [SMILES: Clc1ccc2c(c1)C1(c3ccccc3-2)C2CC3CC(C2)CC1C3] | 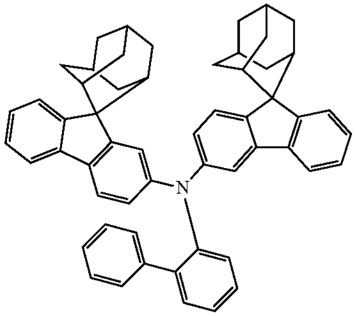 119 | 738.4 |

TABLE 2-continued
| Compound structure, preparation and characterization data | | | | | |
|---|---|---|---|---|---|
| Raw material 2 | Intermediate 1 | Intermediate 2 | Intermediate 3 | Compound structure and No. | Mass spectrum (m/z) [M + H]$^+$ |
| 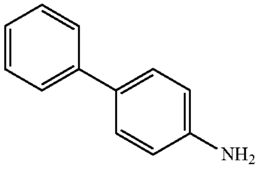 | 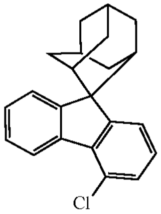 [SMILES: Clc1cccc2c1-c1ccccc1C21C2CC3CC(C2)CC1C3] | 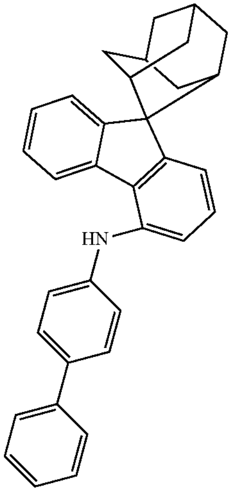 [SMILES: c1ccc(-c2ccc(Nc3cccc4c3-c3ccccc3C43C4CC5CC(C4)CC3C5)cc2)cc1] | 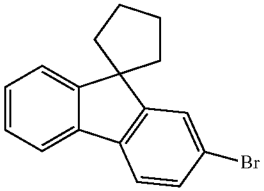 [SMILES: Brc1ccc2c(c1)C1(CCCC1)c1ccccc1-2] | 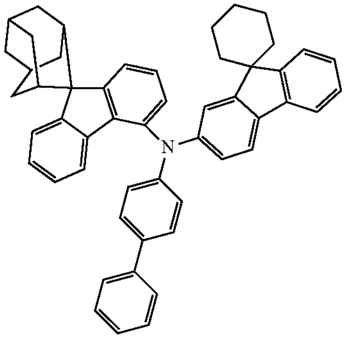 32 | 672.4 |
| 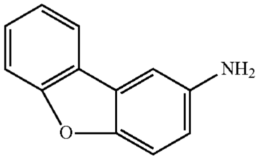 [SMILES: Nc1ccc2oc3ccccc3c2c1] | | 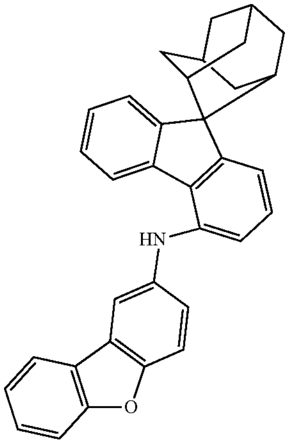 [SMILES: c1ccc2c(c1)-c1c(Nc3ccc4oc5ccccc5c4c3)cccc1C21C2CC3CC(C2)CC1C3] | 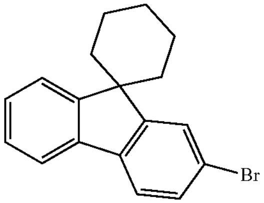 [SMILES: Brc1ccc2c(c1)C1(CCCCC1)c1ccccc1-2] | 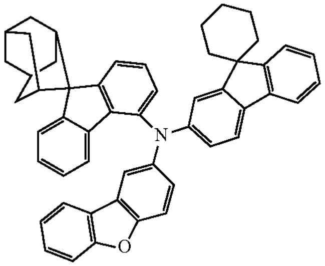 83 | 700.4 |

TABLE 2-continued
| Compound structure, preparation and characterization data | | | | | |
|---|---|---|---|---|---|
| Raw material 2 | Intermediate 1 | Intermediate 2 | Intermediate 3 | Compound structure and No. | Mass spectrum (m/z) [M + H]+ |
| 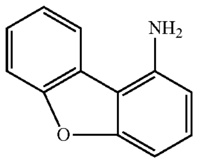 [SMILES: Nc1cccc2oc3ccccc3c12] | | 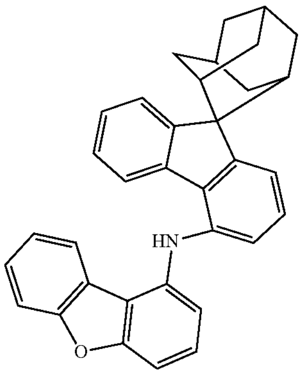 [SMILES: c1ccc2c(c1)-c1c(Nc3cccc4oc5ccccc5c34)cccc1C21C2CC3CC(C2)CC1C3] | 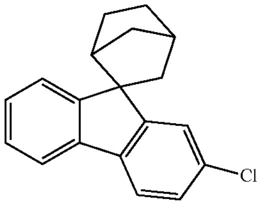 [SMILES: Clc1ccc2c(c1)C1(CC3CCC1C3)c1ccccc1-2] | 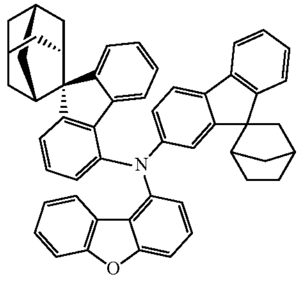 415 | 712.4 |
| 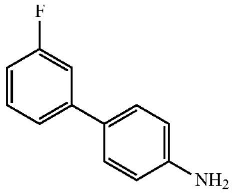 [SMILES: Nc1ccc(-c2cccc(F)c2)cc1] | | 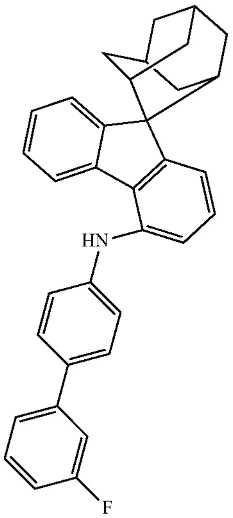 [SMILES: Fc1cccc(-c2ccc(Nc3cccc4c3-c3ccccc3C43C4CC5CC(C4)CC3C5)cc2)c1] | 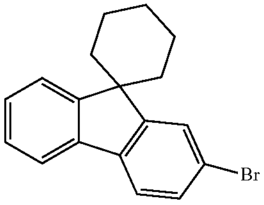 [SMILES: Brc1ccc2c(c1)C1(CCCCC1)c1ccccc1-2] | 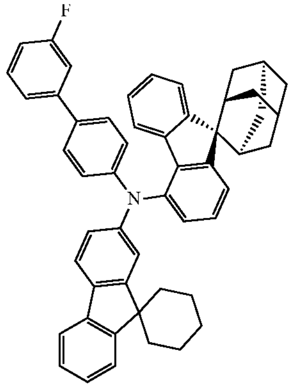 491 | 704.4 |

TABLE 2-continued
| Compound structure, preparation and characterization data | | | | | |
|---|---|---|---|---|---|
| Raw material 2 | Intermediate 1 | Intermediate 2 | Intermediate 3 | Compound structure and No. | Mass spectrum (m/z) [M + H]+ |
| 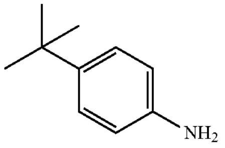 | | 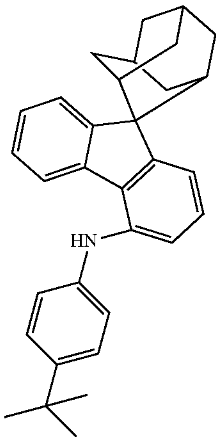 [SMILES: CC(C)(C)c1ccc(Nc2cccc3c2-c2ccccc2C32C3CC4CC(C3)CC2C4)cc1] | 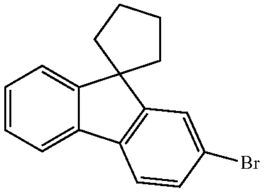 [SMILES: Brc1ccc2c(c1)C1(CCCC1)c1ccccc1-2] | 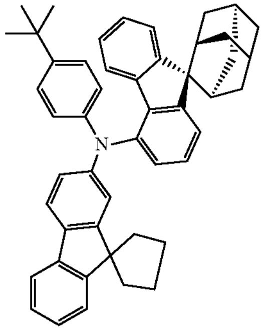 489 | 652.4 |
| 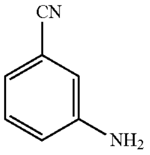 | | 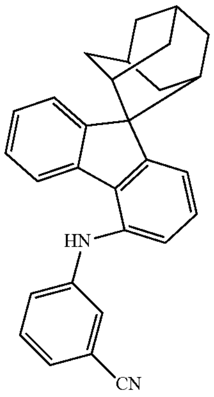 [SMILES: N#Cc1cccc(Nc2cccc3c2-c2ccccc2C32C3CC4CC(C3)CC2C4)c1] | 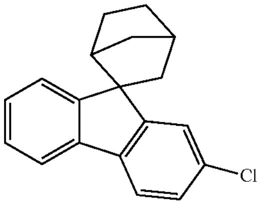 [SMILES: Clc1ccc2c(c1)C1(CC3CCC1C3)c1ccccc1-2] | 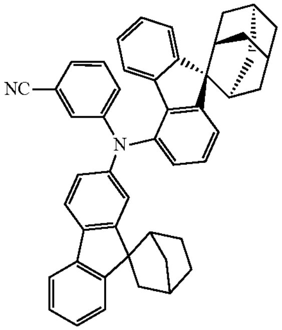 490 | 647.3 |

TABLE 2-continued
| Compound structure, preparation and characterization data | | | | | |
|---|---|---|---|---|---|
| Raw material 2 | Intermediate 1 | Intermediate 2 | Intermediate 3 | Compound structure and No. | Mass spectrum (m/z) $[M + H]^+$ |
| 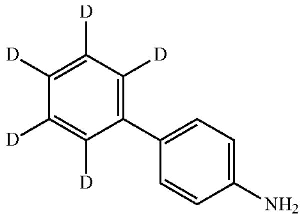 [SMILES: [2H]c1c([2H])c([2H])c(-c2ccc(N)cc2)c([2H])c1[2H]] | 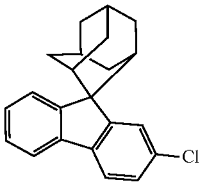 [SMILES: Clc1ccc2c(c1)C1(c3ccccc3-2)C2CC3CC(C2)CC1C3] | 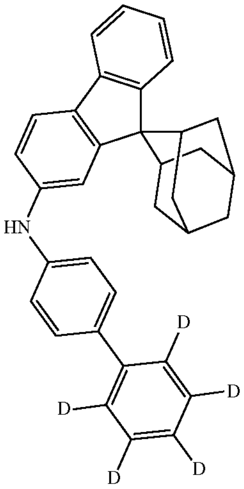 [SMILES: [2H]c1c([2H])c([2H])c(-c2ccc(Nc3ccc4c(c3)C3(c5ccccc5-4)C4CC5CC(C4)CC3C5)cc2)c([2H])c1[2H]] | 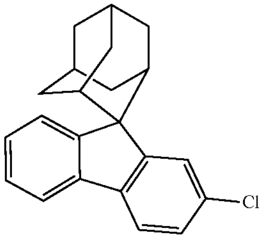 [SMILES: Clc1ccc2c(c1)C1(c3ccccc3-2)C2CC3CC(C2)CC1C3] | 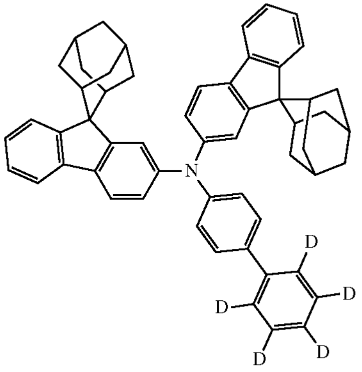 419 | 743.3 |

Synthesis of Compound 420

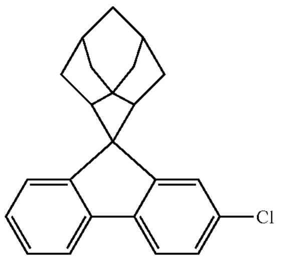

+

IM-C-2

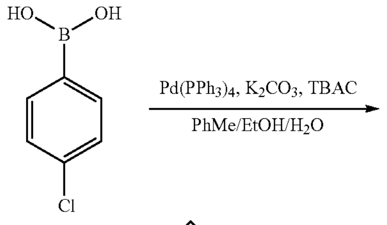

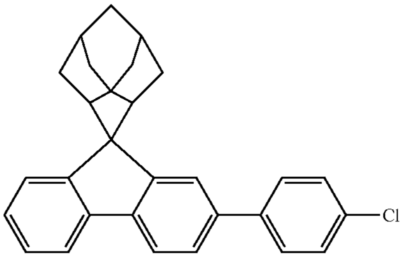

IM-C-3

The intermediate IM-C-2 (10 g, 31.17 mmol), p-chlorophenylboronic acid (3.89 g, 24.93 mmol), tetrakis(triphenylphosphine)palladium (0.72 g, 0.62 mmol), potassium carbonate (6.45 g, 46.75 mmol), tetrabutylammonium chloride (1.73 g, 6.23 mmol), toluene (80 mL), ethanol (20 mL) and deionized water (20 mL) were added into a round-bottom flask, heated to 78° C. under the protection of nitrogen, and stirred for 6 h. The resulting reaction solution was cooled to room temperature, toluene (100 mL) was added for extraction, organic phases were mixed, dried over anhydrous magnesium sulfate, and filtered, and a solvent was removed under reduced pressure; and the obtained crude product was purified by silica gel column chromatography using n-heptane as a mobile phase, and then purified through recrystallization by using a dichloromethane/ethyl acetate system to obtain a white solid intermediate IM-C-3 (7.5 g, yield: 75.8%).

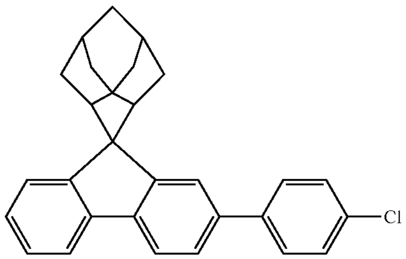

+

IM-C-3

-continued

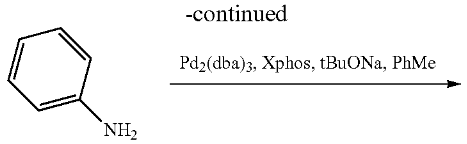

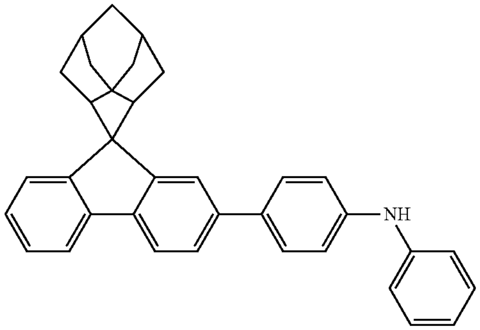

IM-C-4

The intermediate IM-C-3 (1.50 g, 3.78 mmol), aniline (0.36 g, 3.85 mmol), tris(dibenzylideneacetone)dipalladium (0.03 g, 0.04 mmol), 2-dicyclohexylphosphino-2',6'-dimethoxybiphenyl (0.03 g, 0.07 mmol) and sodium tert-butoxide (0.55 g, 5.67 mmol) were added into toluene (20 mL), heated to 108° C. under the protection of nitrogen, and stirred for 5 h. After cooling to room temperature, the resulting reaction solution was washed with water, dried by adding magnesium sulfate, and filtered, and a solvent was removed from the obtained filtrate under reduced pressure; and the obtained crude product was purified through recrystallization by using a toluene system to obtain an intermediate IM-C-4 (1.26 g, 74%).

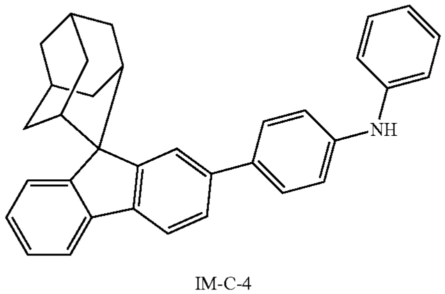

+

IM-C-4

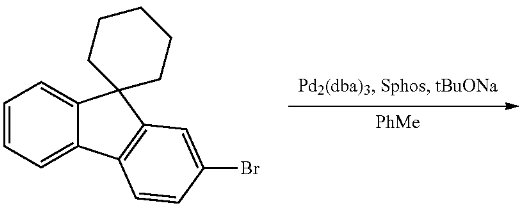

IM-A-2

-continued

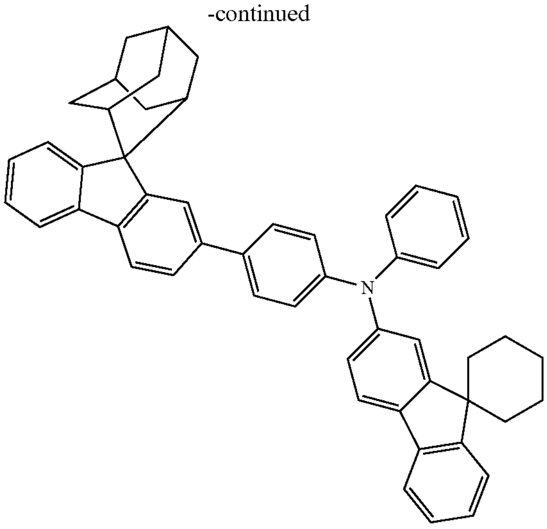

420

The intermediate IM-C-4 (1.7 g, 3.75 mmol), the intermediate IM-A-2 (1.17 g, 3.75 mmol), tris(dibenzylideneacetone) dipalladium (0.03 g, 0.04 mmol), 2-dicyclohexylphosphino-2',6'-dimethoxybiphenyl (0.03 g, 0.08 mmol) and sodium tert-butoxide (0.54 g, 5.26 mmol) were added into toluene (20 mL), heated to 108° C. under the protection of nitrogen, and stirred for 1 h. After cooling to room temperature, the resulting reaction solution was washed with water, dried by adding magnesium sulfate, and filtered, and a solvent was removed from the obtained filtrate under reduced pressure; and the obtained crude product was purified through recrystallization by using a toluene system to obtain a compound 420 (1.87 g, yield: 72.76%). Mass spectrum: m/z=686.4 $[M+H]^+$.

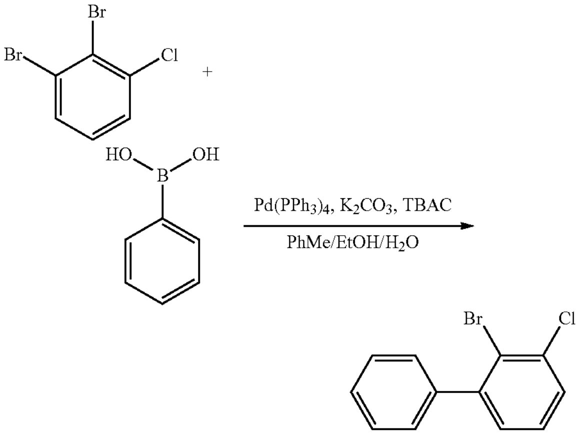

IM-G-1

1,2-dibromo-3-chlorobenzene (80.0 g, 298.7 mmol), phenylboronic acid (36.5 g, 298.7 mmol), tetrakis(triphenylphosphine) palladium (6.9 g, 6.0 mmol), potassium carbonate (103.2 g, 746.7 mmol) and tetrabutylammonium bromide (19.2 g, 59.7 mmol) were added into a flask, a mixed solvent of toluene (600 mL), ethanol (150 mL) and water (150 mL) was added, and the mixture was heated to 80° C. under the protection of nitrogen, and stirred for 18 h while keeping the temperature. After cooling to room temperature, stirring was stopped, the resulting reaction solution was washed with water, an organic phase was separated, and dried over anhydrous magnesium sulfate, and the solvent was removed under reduced pressure to obtain a crude product; and the obtained crude product was purified by silica gel column chromatography using dichloromethane/n-heptane as a mobile phase to obtain a white solid product intermediate IM-G-1 (42.0 g, yield: 53%).

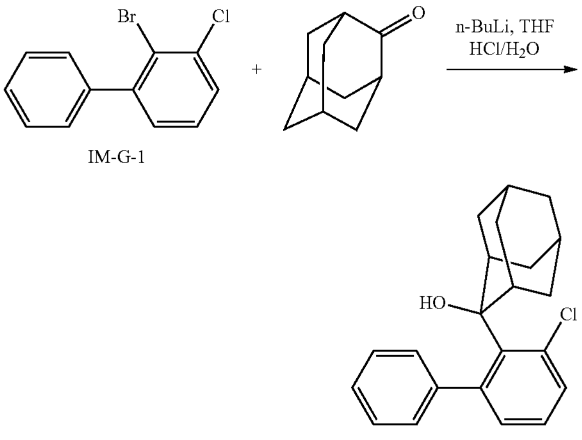

IM-G-1

IM-G-2

The intermediate IM-G-1 (42.0 g, 157.9 mmol) and tetrahydrofuran (300 mL) were added into a flask, and cooled to −78° C. under the protection of nitrogen, a tetrahydrofuran (2.5 M) solution (95 mL, 236.9 mmol) of n-butyllithium was added dropwise under a stirring condition. After the completion of the dropwise addition, the temperature was kept and stirred for 1 hour, and the solution of adamantanone (19.0 g, 126.3 mmol) in tetrahydrofuran (100 mL) was added dropwise at −78° C. After the dropwise addition, the temperature was kept for 1 hour and then raised to room temperature, and stirred for 24 hours. A water (100 mL) solution (26.3 mL, 315.8 mmol) of hydrochloric acid (12M) was added into the resulting reaction solution, and stirring was performed for 1 h; liquid separation was performed, an organic phase was washed to be neutral by using water, and dried by adding anhydrous magnesium sulfate, and a solvent was removed under reduced pressure to obtain a crude product; and the obtained crude product was purified by silica gel column chromatography using an ethyl acetate/n-heptane system to obtain a white solid product intermediate IM-G-2 (25.8 g, yield: 60%).

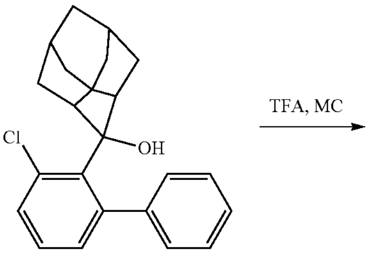

IM-G-2

-continued

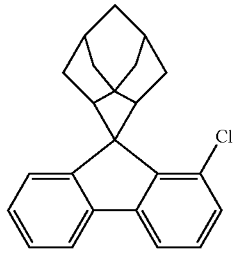

IM-G-3

According to the synthesis method of the intermediate IM-B-3, the intermediate IM-G-2 was used for replacing the intermediate IM-B-2 to synthesize an intermediate IM-G-3 by using the same method.

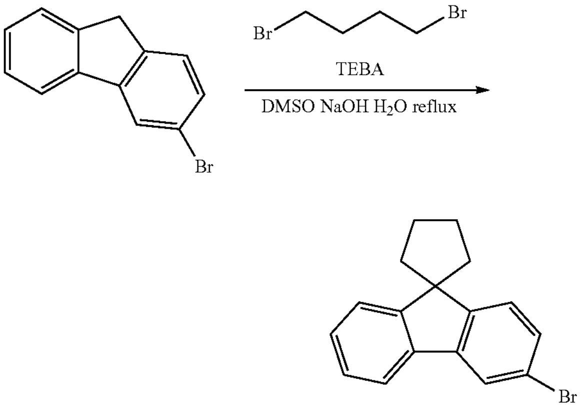

IM-A-5

In addition to replacing 2-bromo-9H-fluorene with 3-bromo-9H-fluorene, an intermediate IM-A-5 was prepared by using the same synthesis method as the intermediate IM-A-1.

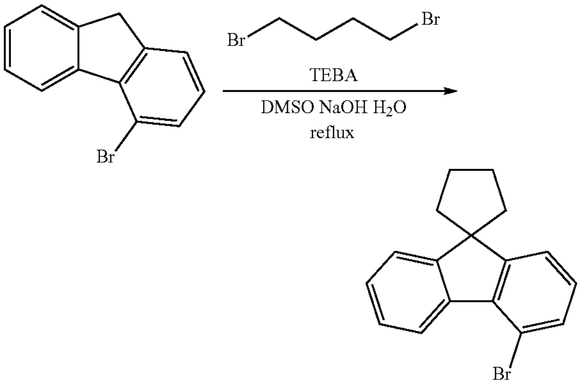

IM-A-6

In addition to replacing 2-bromo-9H-fluorene with 4-bromo-9H-fluorene, an intermediate IM-A-6 was prepared by using the same synthesis method as the intermediate IM-A-1.

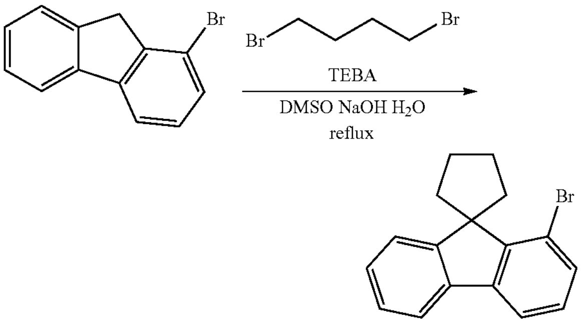

IM-A-7

In addition to replacing 2-bromo-9H-fluorene with 1-bromo-9H-fluorene, an intermediate IM-A-7 was prepared by using the same synthesis method as the intermediate IM-A-1.

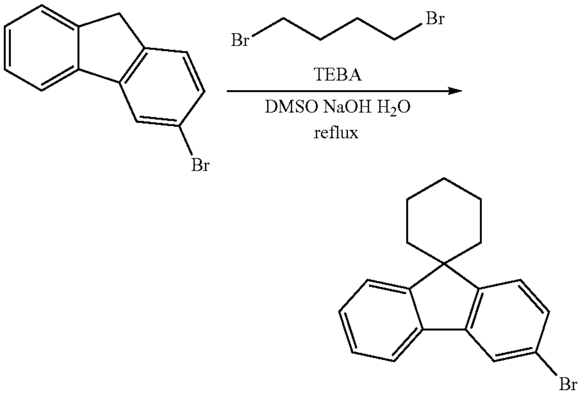

IM-A-8

In addition to replacing 2-bromo-9H-fluorene with 3-bromo-9H-fluorene and replacing 1,4-dibromobutane with 1,5-dibromopentane, an intermediate IM-A-8 was prepared by reference to the same synthesis method as the intermediate IM-A-1.

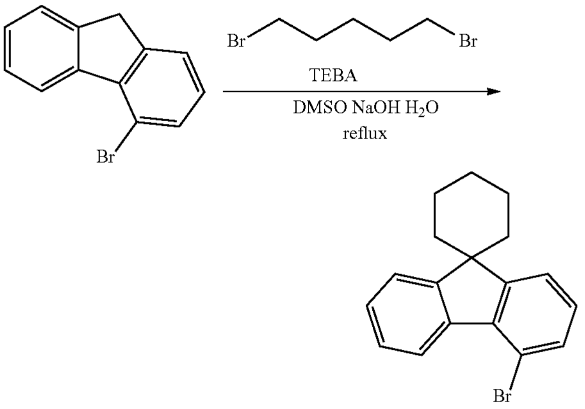

IM-A-9

In addition to replacing 2-bromo-9H-fluorene with 4-bromo-9H-fluorene and replacing 1,4-dibromobutane with 1,5-dibromopentane, an intermediate IM-A-9 was prepared by reference to the same synthesis method as the intermediate IM-A-1.

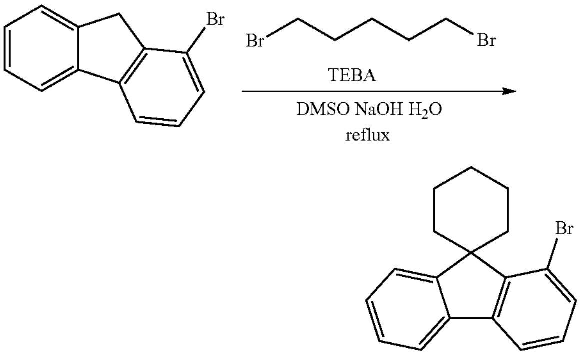

IM-A-10

In addition to replacing 2-bromo-9H-fluorene with 1-bromo-9H-fluorene and replacing 1,4-dibromobutane with 1,5-dibromopentane, an intermediate IM-A-10 was prepared by reference to the synthesis method of the intermediate IM-A-1.

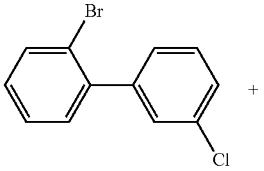

IM-B-1

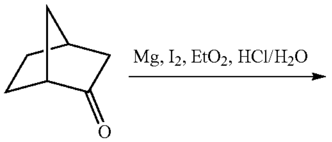

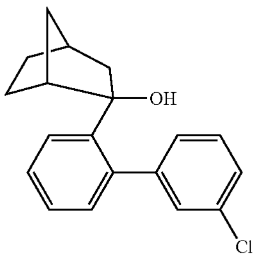

IM-A-11

In addition to replacing adamantanone with norbornanone, an intermediate IM-A-11 was prepared by reference to the synthesis method of the intermediate IM-B-2.

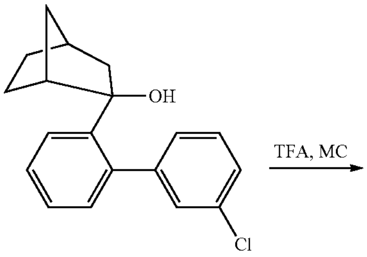

IM-A-11

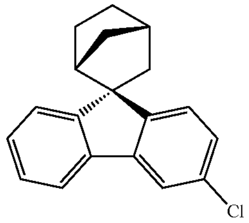

IM-A-12

In addition to replacing the intermediate IM-B-2 with an intermediate A-11, an intermediate IM-A-12 was prepared by referring to the synthesis method of the intermediate IM-B-3.

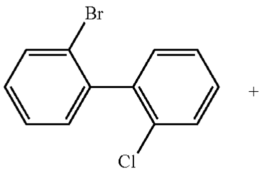

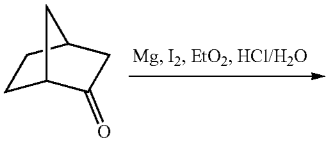

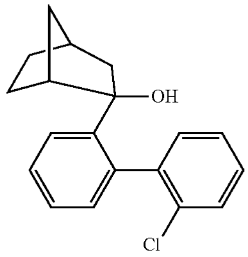

IM-A-13

An intermediate IM-A-13 was prepared from 2-bromo-2'-chloro-1,1'-biphenyl and norbornanone as raw materials by referring to the synthesis method of the intermediate IM-B-2.

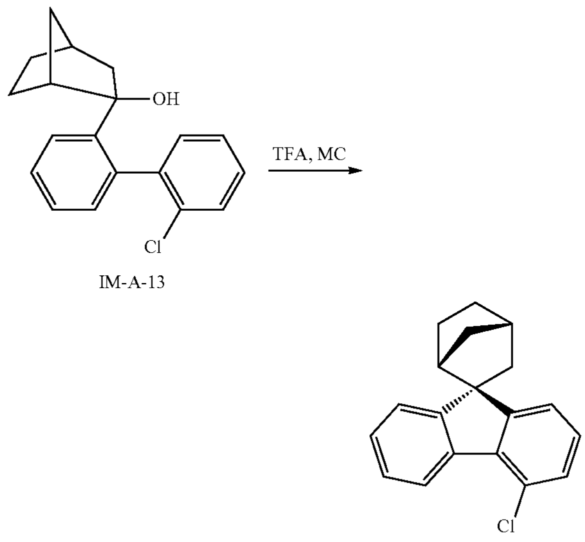

IM-A-13

IM-A-14

In addition to replacing the intermediate IM-B-2 with the intermediate IM-A-13, an intermediate IM-A-14 was prepared by referring to the synthesis method of the intermediate IM-B-3.

Referring to the synthesis method of the compound 22, an intermediate 2 was synthesized from a raw material 1 instead of 4-aminobiphenyl, and an intermediate 1 instead of the intermediate IM-B-3, and a compound in the fifth column in Table 3 was synthesized from an intermediate 3 instead of the intermediate IM-A-1, and the intermediate 2. Specific compound No., structures, raw materials, characterization data and the like are as shown in Table 3.

TABLE 3
| Compound structure, No., and characterization data | | | | | |
|---|---|---|---|---|---|
| Raw material 1 | Intermediate 1 | Intermediate 2 | Intermediate 3 | Compound structure and No. | Mass spectrum (m/z) [M + H]+ |
| 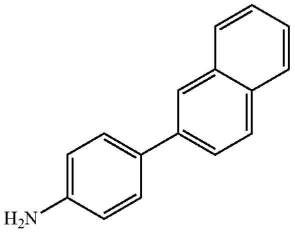 [SMILES: Nc1ccc(-c2ccc3ccccc3c2)cc1] | 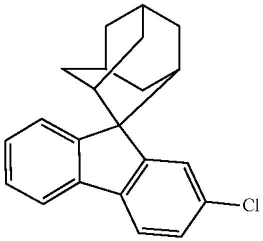 [SMILES: Clc1ccc2c(c1)C1(c3ccccc3-2)C2CC3CC(C2)CC1C3] | 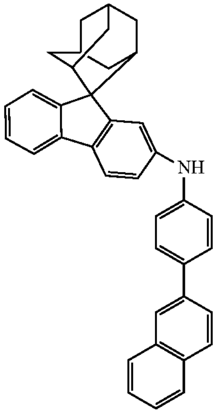 [SMILES: c1ccc2c(c1)-c1ccc(Nc3ccc(-c4ccc5ccccc5c4)cc3)cc1C21C2CC3CC(C2)CC1C3] | 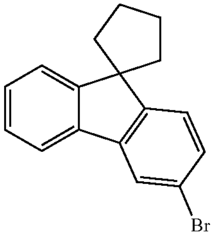 [SMILES: Brc1ccc2c(c1)-c1ccccc1C21CCCC1] | 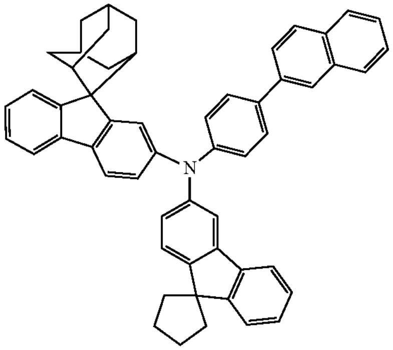 201 | 722.4 |
| 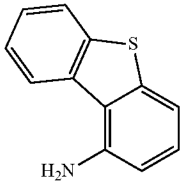 [SMILES: Nc1cccc2sc3ccccc3c12] | 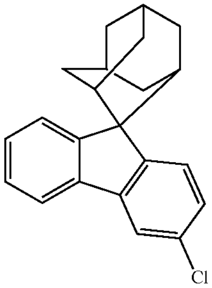 [SMILES: Clc1ccc2c(c1)-c1ccccc1C21C2CC3CC(C2)CC1C3] | 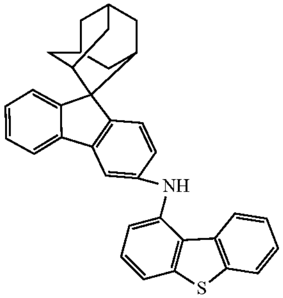 [SMILES: c1ccc2c(c1)-c1cc(Nc3cccc4sc5ccccc5c34)ccc1C21C2CC3CC(C2)CC1C3] | 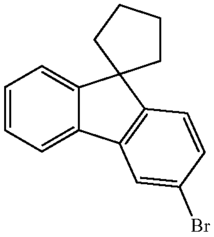 [SMILES: Brc1ccc2c(c1)-c1ccccc1C21CCCC1] | 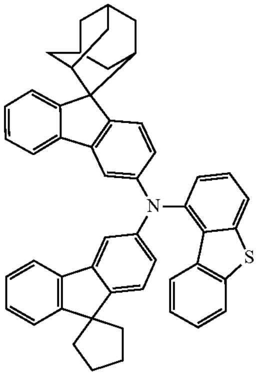 217 | 702.3 |

TABLE 3-continued
| Compound structure, No., and characterization data | | | | | |
|---|---|---|---|---|---|
| Raw material 1 | Intermediate 1 | Intermediate 2 | Intermediate 3 | Compound structure and No. | Mass spectrum (m/z) [M + H]+ |
| 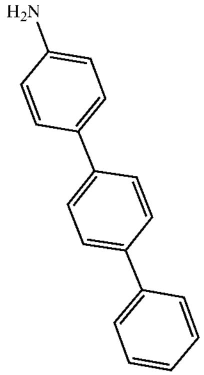 [SMILES: Nc1ccc(-c2ccc(-c3ccccc3)cc2)cc1] | 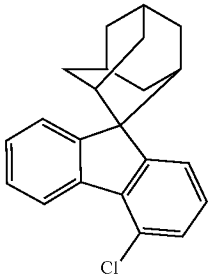 [SMILES: Clc1cccc2c1-c1ccccc1C21C2CC3CC(C2)CC1C3] | 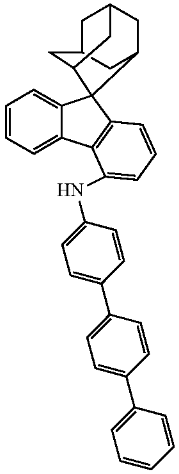 [SMILES: c1ccc(-c2ccc(-c3ccc(Nc4cccc5c4-c4ccccc4C54C5CC6CC(C5)CC4C6)cc3)cc2)cc1] | 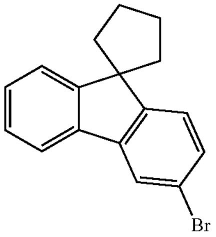 | 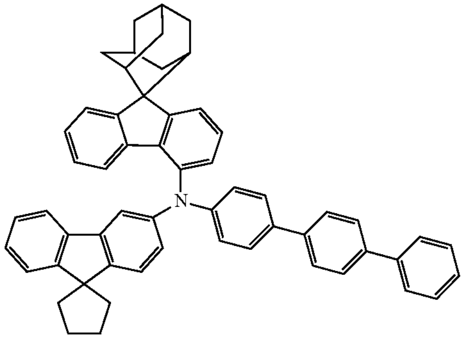 234 | 745.5 |
| 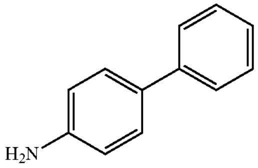 | 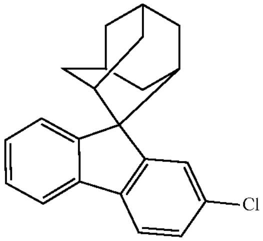 [SMILES: Clc1ccc2c(c1)C1(c3ccccc3-2)C2CC3CC(C2)CC1C3] | 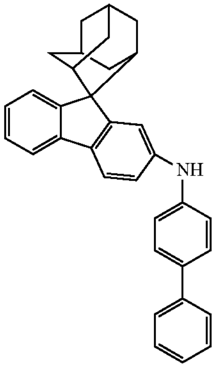 [SMILES: c1ccc(-c2ccc(Nc3ccc4c(c3)C3(c5ccccc5-4)C4CC5CC(C4)CC3C5)cc2)cc1] | 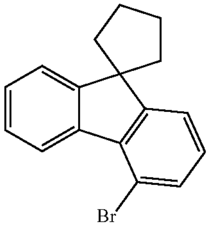 [SMILES: Brc1cccc2c1-c1ccccc1C21CCCC1] | 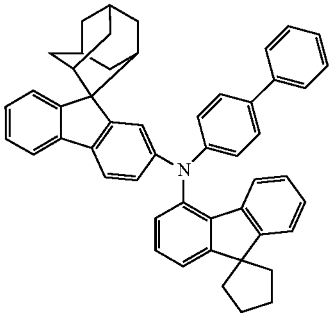 242 | 672.1 |

TABLE 3-continued
| Compound structure, No., and characterization data | | | | | |
|---|---|---|---|---|---|
| Raw material 1 | Intermediate 1 | Intermediate 2 | Intermediate 3 | Compound structure and No. | Mass spectrum (m/z) $[M + H]^+$ |
| 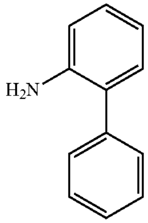 [SMILES: Nc1ccccc1-c1ccccc1] | 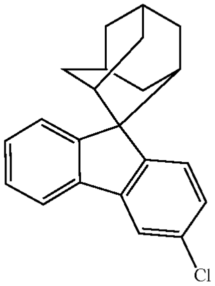 [SMILES: Clc1ccc2c(c1)-c1ccccc1C21C2CC3CC(C2)CC1C3] | 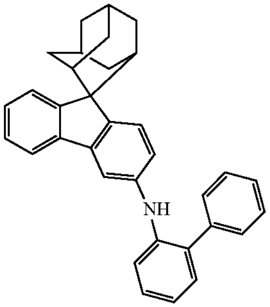 [SMILES: c1ccc(-c2ccccc2Nc2ccc3c(c2)-c2ccccc2C32C3CC4CC(C3)CC2C4)cc1] | 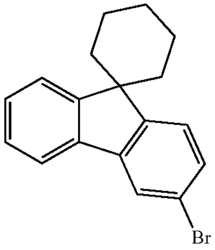 [SMILES: Brc1ccc2c(c1)-c1ccccc1C21CCCCC1] | 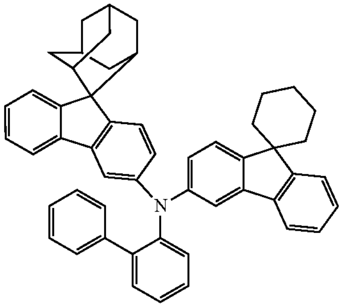 487 | 686.3 |
| 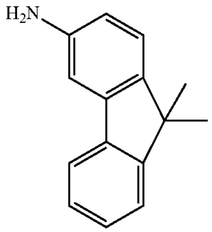 [SMILES: CC1(C)c2ccccc2-c2cc(N)ccc21] | 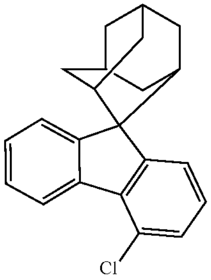 [SMILES: Clc1cccc2c1-c1ccccc1C21C2CC3CC(C2)CC1C3] | 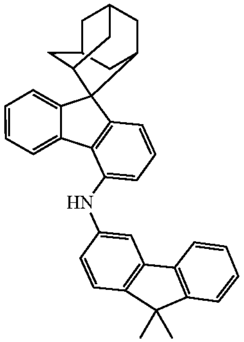 [SMILES: CC1(C)c2ccccc2-c2cc(Nc3cccc4c3-c3ccccc3C43C4CC5CC(C4)CC3C5)ccc21] | 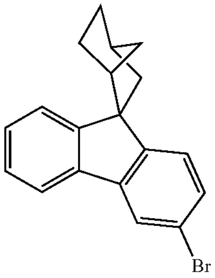 [SMILES: Brc1ccc2c(c1)-c1ccccc1C21CC2CCC1C2] | 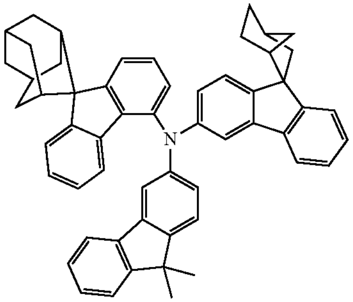 488 | 738.0 |

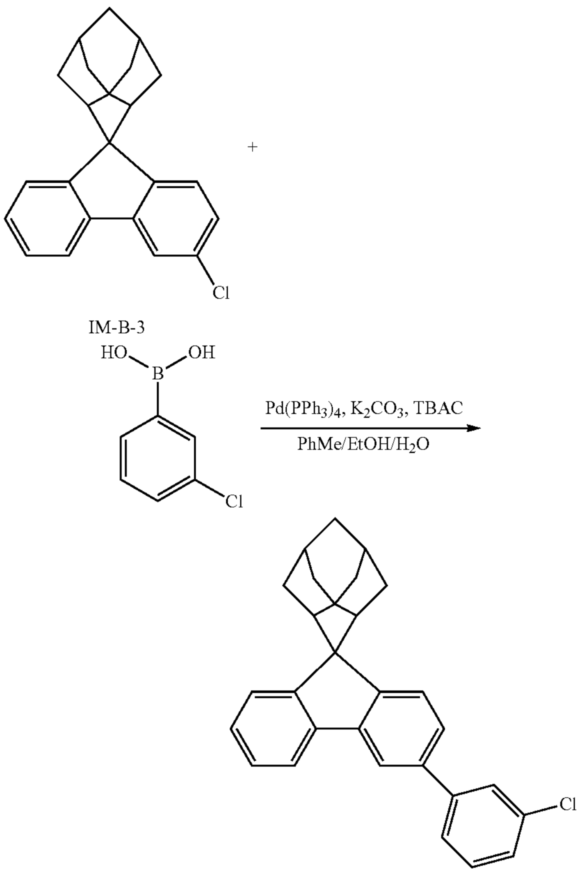

IM-B-3

IM-B-4

The intermediate IM-B-3 (10 g, 31.17 mmol), 3-chlorophenylboronic acid (3.89 g, 24.93 mmol), tetrakis(triphenylphosphine) palladium (0.72 g, 0.62 mmol), potassium carbonate (6.45 g, 46.75 mmol), tetrabutylammonium chloride (1.73 g, 6.23 mmol), toluene (80 mL), ethanol (20 mL) and deionized water (20 mL) were added into a round-bottom flask, heated to 78° C. under the protection of nitrogen, and stirred for 6 h; the resulting reaction solution was cooled to room temperature, toluene (100 mL) was added for extraction, organic phases were mixed, dried over anhydrous magnesium sulfate, and filtered, and a solvent was removed under reduced pressure; and the obtained crude product was purified by silica gel column chromatography using n-heptane as a mobile phase, and then purified through recrystallization by using a dichloromethane/ethyl acetate system to obtain a white solid intermediate IM-B-4 (7.5 g, yield: 75.7%).

Referring to the synthesis method of the intermediate IM-B-4, the difference is that an intermediate 4 in the first column in Table 4 was used for replacing the intermediate IM-B-3, a raw material 3 in the second column in the table was used for replacing 3-chlorophenylboronic acid, so that an intermediate 5 shown in the third column in the following table was synthesized.

TABLE 4

| Structure of intermediate 4 and raw material 3, and structure of intermediate 5 | | |
|---|---|---|
| Intermediate 4 | Raw material 3 | Structure of intermediate 5 |
| 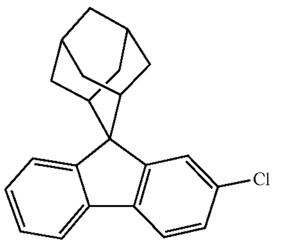 [SMILES: Clc1ccc2c(c1)C1(c3ccccc3-2)C2CC3CC(C2)CC1C3] | 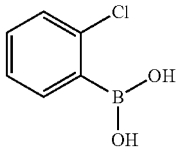 | 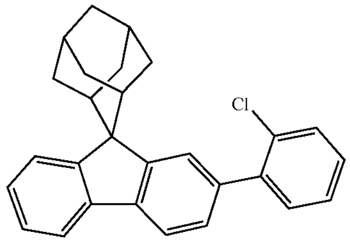 [SMILES: Clc1ccccc1-c1ccc2c(c1)C1(c3ccccc3-2)C2CC3CC(C2)CC1C3] |

TABLE 4-continued
| Structure of intermediate 4 and raw material 3, and structure of intermediate 5 | | |
|---|---|---|
| Intermediate 4 | Raw material 3 | Structure of intermediate 5 |
| 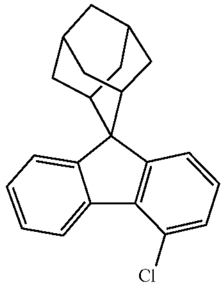 [SMILES: Clc1cccc2c1-c1ccccc1C21C2CC3CC(C2)CC1C3] | 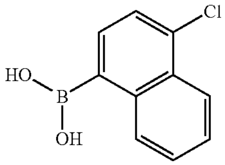 [SMILES: OB(O)c1ccc(Cl)c2ccccc12] | 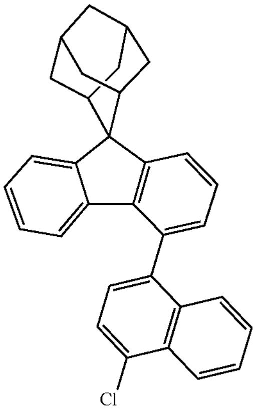 [SMILES: Clc1ccc(-c2cccc3c2-c2ccccc2C32C3CC4CC(C3)CC2C4)c2ccccc12] |
| 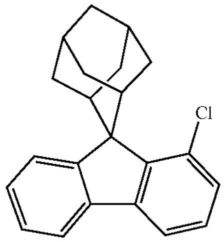 [SMILES: Clc1cccc2c1C1(c3ccccc3-2)C2CC3CC(C2)CC1C3] | 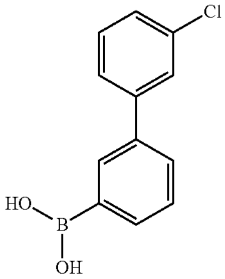 [SMILES: OB(O)c1cccc(-c2cccc(Cl)c2)c1] | 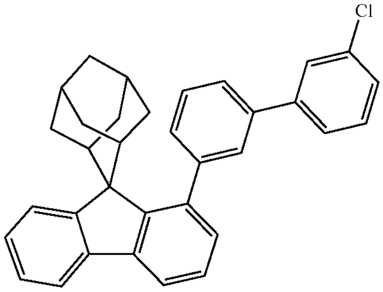 [SMILES: Clc1cccc(-c2cccc(-c3cccc4c3C3(c5ccccc5-4)C4CC5CC(C4)CC3C5)c2)c1] |
| 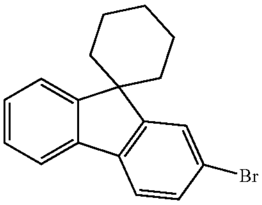 [SMILES: Brc1ccc2c(c1)C1(CCCCC1)c1ccccc1-2] | 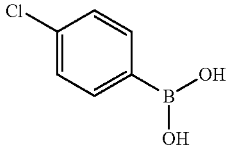 | 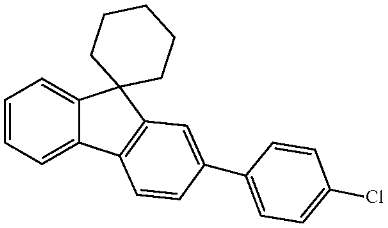 [SMILES: Clc1ccc(-c2ccc3c(c2)C2(CCCCC2)c2ccccc2-3)cc1] |
| 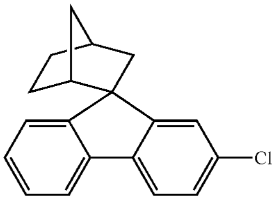 [SMILES: Clc1ccc2c(c1)C1(CC3CCC1C3)c1ccccc1-2] | 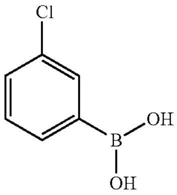 | 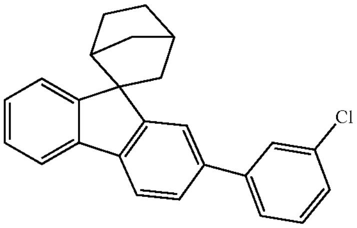 [SMILES: Clc1cccc(-c2ccc3c(c2)C2(CC4CCC2C4)c2ccccc2-3)c1] |
| 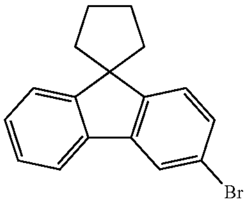 [SMILES: Brc1ccc2c(c1)-c1ccccc1C21CCCC1] | 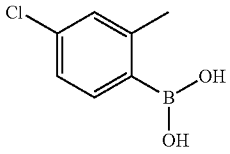 | 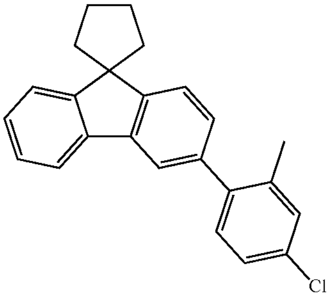 [SMILES: Cc1cc(Cl)ccc1-c1ccc2c(c1)-c1ccccc1C21CCCC1] |
By replacing the intermediate IM-A-2 with the intermediate 5 in the above Table 4, a reaction was carried out by referring to the synthesis method of compound 420 to obtain the following compounds as shown in Table 5

TABLE 5
| Compound No., structure and characterization data | | | | |
|---|---|---|---|---|
| Compound No. | Intermediate 5 | Compound structure | Yield (%) | Mass spectrum (m/z) $[M+H]^+$ |
| 481 | 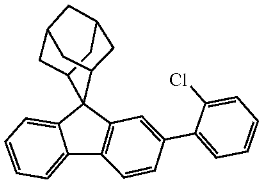 [SMILES: Clc1ccccc1-c1ccc2c(c1)C1(c3ccccc3-2)C2CC3CC(C2)CC1C3] | 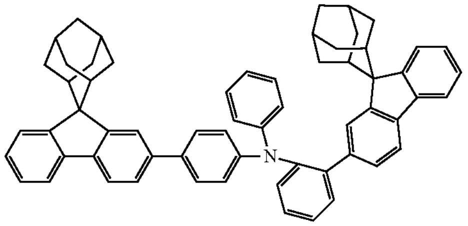 [SMILES: c1ccc(N(c2ccc(-c3ccc4c(c3)C3(c5ccccc5-4)C4CC5CC(C4)CC3C5)cc2)c2ccccc2-c2ccc3c(c2)C2(c4ccccc4-3)C3CC4CC(C3)CC2C4)cc1] | 43 | 814.1 |
| 482 | 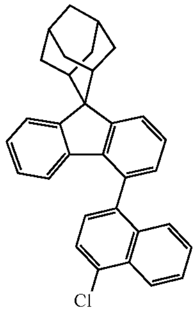 [SMILES: Clc1ccc(-c2cccc3c2-c2ccccc2C32C3CC4CC(C3)CC2C4)c2ccccc12] | 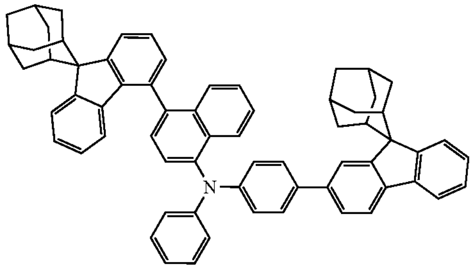 [SMILES: c1ccc(N(c2ccc(-c3ccc4c(c3)C3(c5ccccc5-4)C4CC5CC(C4)CC3C5)cc2)c2ccc(-c3cccc4c3-c3ccccc3C43C4CC5CC(C4)CC3C5)c3ccccc23)cc1] | 41 | 864.4 |
| 483 | 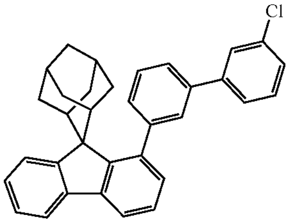 [SMILES: Clc1cccc(-c2cccc(-c3cccc4c3C3(c5ccccc5-4)C4CC5CC(C4)CC3C5)c2)c1] | 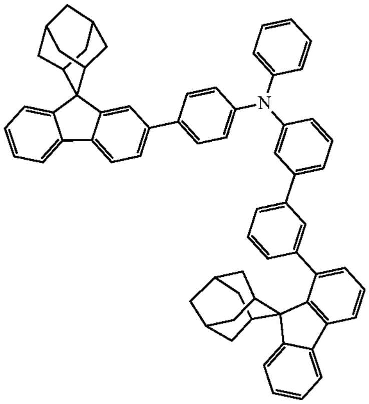 [SMILES: c1ccc(N(c2ccc(-c3ccc4c(c3)C3(c5ccccc5-4)C4CC5CC(C4)CC3C5)cc2)c2cccc(-c3cccc(-c4cccc5c4C4(c6ccccc6-5)C5CC6CC(C5)CC4C6)c3)c2)cc1] | 64 | 890.1 |
| 484 | 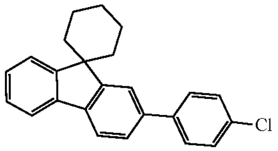 [SMILES: Clc1ccc(-c2ccc3c(c2)C2(CCCCC2)c2ccccc2-3)cc1] | 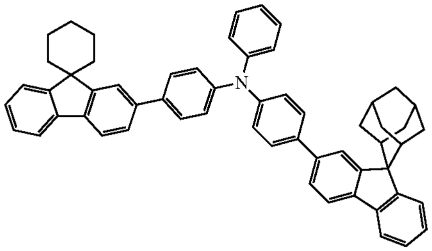 [SMILES: c1ccc(N(c2ccc(-c3ccc4c(c3)C3(CCCCC3)c3ccccc3-4)cc2)c2ccc(-c3ccc4c(c3)C3(c5ccccc5-4)C4CC5CC(C4)CC3C5)cc2)cc1] | 57 | 762.1 |
| 485 | 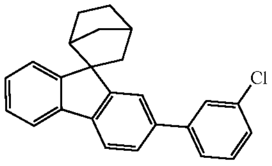 [SMILES: Clc1cccc(-c2ccc3c(c2)C2(CC4CCC2C4)c2ccccc2-3)c1] | 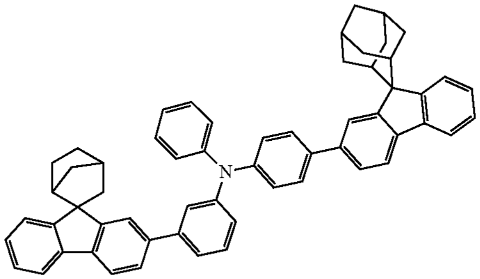 [SMILES: c1ccc(N(c2ccc(-c3ccc4c(c3)C3(c5ccccc5-4)C4CC5CC(C4)CC3C5)cc2)c2cccc(-c3ccc4c(c3)C3(CC5CCC3C5)c3ccccc3-4)c2)cc1] | 66 | 774.4 |

TABLE 5-continued

| Compound No., structure and characterization data | | | | |
|---|---|---|---|---|
| Compound No. | Intermediate 5 | Compound structure | Yield (%) | Mass spectrum (m/z) [M+H]+ |
| 486 | 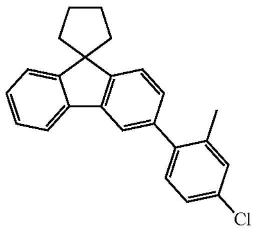 [SMILES: Cc1cc(Cl)ccc1-c1ccc2c(c1)-c1ccccc1C21CCCC1] | 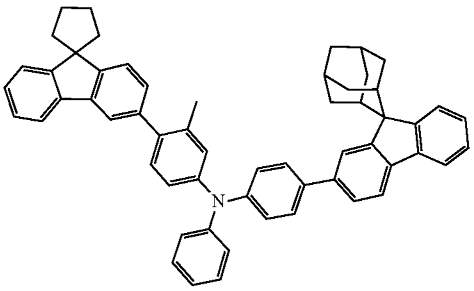 [SMILES: Cc1cc(N(c2ccccc2)c2ccc(-c3ccc4c(c3)C3(c5ccccc5-4)C4CC5CC(C4)CC3C5)cc2)ccc1-c1ccc2c(c1)-c1ccccc1C21CCCC1] | 58 | 762.4 |

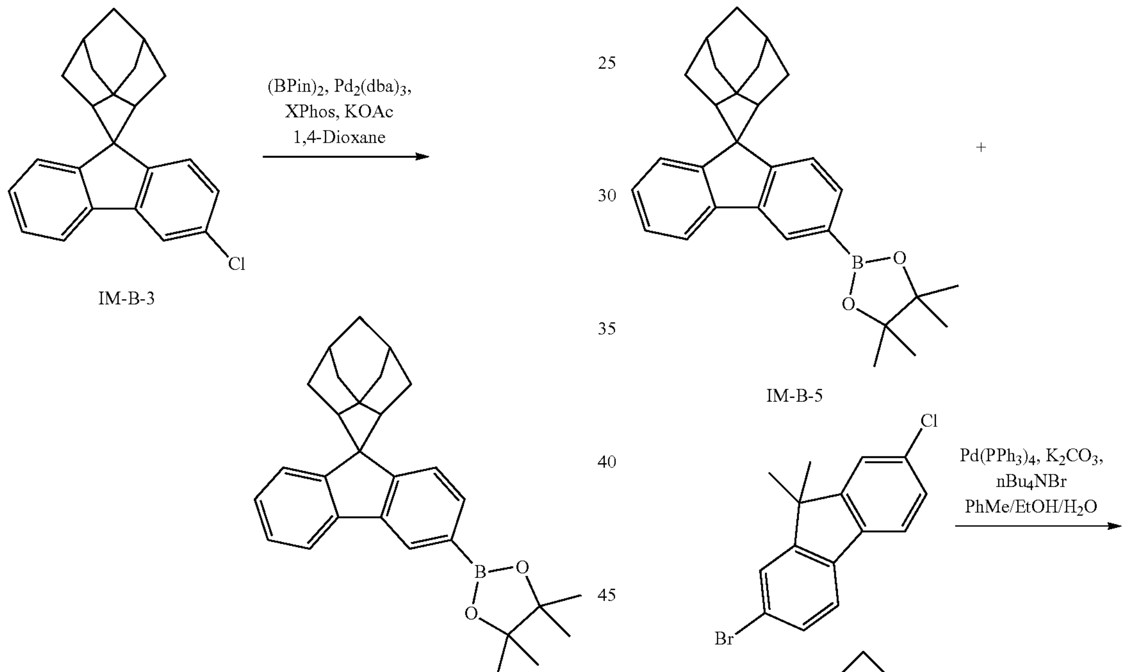

IM-B-3

IM-B-5

IM-B-5

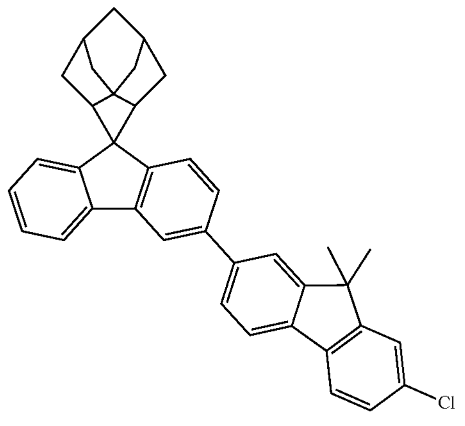

IM-B-6

The intermediate IM-B-3 (20.4 g, 62.3 mmol), bis(pinacolato)diboron (20.6 g, 81.05 mmol), tris(dibenzylideneacetone) dipalladium (0.57 g, 0.62 mmol), 2-dicyclohexylphosphino-2',4',6'-triisopropylbiphenyl (0.59 g, 1.24 mmol), potassium acetate (12.24 g, 124.7 mmol) and 1,4-dioxane (160 mL) were added into a flask, and stirred at 100° C. for 16 h while refluxing under the nitrogen protection condition. After cooling to room temperature, dichloromethane and water were added into the resulting reaction solution, liquid separation was performed, an organic phase was washed with water, and dried over anhydrous magnesium sulfate, and a solvent was removed under a reduced pressure condition to obtain a crude product; and the obtained crude product was purified by silica gel column chromatography using a dichloromethane/n-heptane system to obtain a white solid intermediate IM-B-5 (17.3 g, 67.3%).

The intermediate IM-B-5 (17.3 g, 41.96 mmol), 2-bromo-7-chloro-9,9-dimethylfluorene (14.2 g, 46.16 mmol), tetrakis(triphenylphosphine) palladium (0.48 g, 0.42 mmol), potassium carbonate (12.74 g, 92.31 mmol) and tetrabutylammonium bromide (2.7 g, 8.4 mmol) were added into a flask, a mixed solvent of toluene (136 mL), ethanol (34 mL) and water (34 mL) was added, and the mixture was heated to 80° C. under the protection of nitrogen, and stirred for 24 h while keeping the temperature. After cooling to room temperature, stirring was stopped, the resulting reaction solution was washed with water, an organic phase was separated, and dried over anhydrous magnesium sulfate, and the solvent was removed under reduced pressure to obtain a crude product; and the obtained crude product was purified by silica gel column chromatography using dichloromethane/n-heptane as a mobile phase to obtain a white solid product intermediate IM-B-6 (10.6 g, 49.3%).

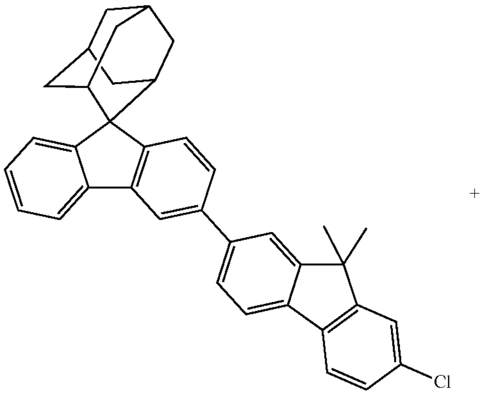

IM-B-6

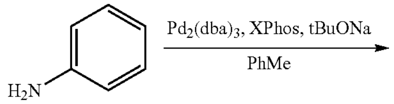

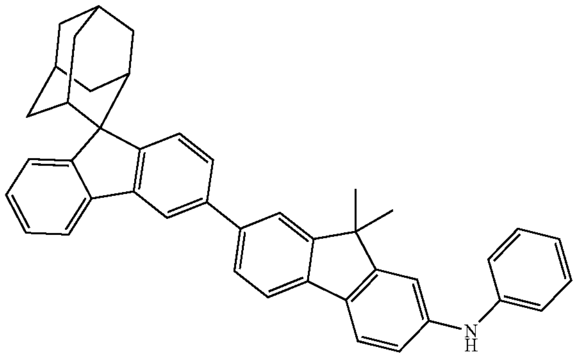

IM-B-8

The intermediate IM-B-6 (5.0 g, 9.75 mmol), aniline (0.91 g, 9.75 mmol), tris(dibenzylideneacetone)dipalladium (0.09 g, 0.10 mmol), 2-dicyclohexylphosphino-2',4',6'-triisopropylbiphenyl (0.09 g, 0.19 mmol) and sodium tert-butoxide (1.4 g, 14.6 mmol) were added into toluene (40 mL), heated to 108° C. under the protection of nitrogen, and stirred for 5 h. After cooling to room temperature, the resulting reaction solution was washed with water, dried by adding magnesium sulfate, and filtered, and a solvent was removed from the obtained filtrate under reduced pressure; and the obtained crude product was purified through recrystallization by using a dichloromethane/n-heptane system to obtain an intermediate IM-B-8 (4.1 g, yield: 74%).

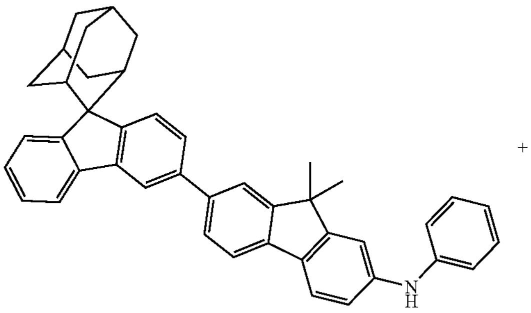

IM-B-8

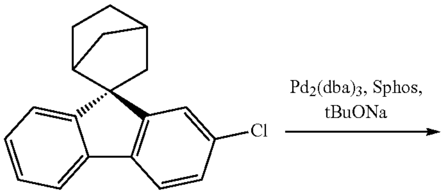

IM-A-4

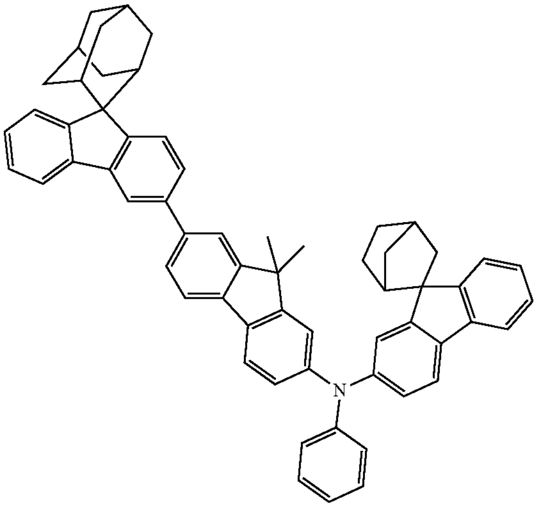

492

The intermediate IM-B-8 (4.1 g, 7.2 mmol), the intermediate IM-A-4 (2.02 g, 7.2 mmol), tris(dibenzylideneacetone) dipalladium (0.07 g, 0.07 mmol), 2-dicyclohexylphosphino-2',6'-dimethoxybiphenyl (0.06 g, 0.14 mmol) and sodium tert-butoxide (1.04 g, 10.8 mmol) were added into toluene (40 mL), heated to 108° C. under the protection of nitrogen, and stirred for 4 h. After cooling to room temperature, the resulting reaction solution was washed with water, dried by adding magnesium sulfate, and filtered, and a solvent was removed from the obtained filtrate under reduced pressure; and the obtained crude product was purified through recrystallization by using a toluene system to obtain a solid compound 492 (5.2 g, yield: 88.7%), and mass spectrum (m/z)=814.3 $[M+H]^+$.

Referring to the compounds prepared in the above synthesis examples, NMR data of some intermediates and compounds are shown in Table 6 below.

TABLE 6

| []NMR data of some intermediates and compounds | |
|---|---|
| Compound | NMR data |
| Intermediate IM-B-3 | $^1$HNMR (400 MHz, $CD_2Cl_2$): 8.11 (d, 1H), 8.03 (d, 1H), 7.41-7.63 (m, 2H), 7.37-7.39 (m, 1H), 7.30-7.33 (m, 1H), 7.23-7.24 (m, 1H), 2.88-2.93 (m, 2H), 2.81-2.85 (m, 2H), 2.19 (s, 2H), 1.99 (s, 2H), 1.77-1.83 (m, 4H), 1.54 (s, 2H). |
| Compound 119 | $^1$H NMR (400 MHz, $CD_2C1_2$): 8.11 (d, 1H), 8.02 (d, 1H), 7.64-7.60 (m, 6H), 7.55 (d, 4H), 7.43 (t, 4H), 7.33-7.24 (m, 8H), 7.06 (dd, 1H), 2.91 (m, 4H), 2.19 (m, 2H), 2.00 (s, 2H), 1.82 (d, 4H), 1.61 (s, 2H). |

An Organic Electroluminescent Device was Manufactured by Adopting the Following Method:

Preparation and Evaluation Examples of Blue Organic Electroluminescent Device

Example 1

An anode is prepared by the following processes: a TOP substrate (manufactured by Corning) with an ITO thickness of 1200 Å was cut into a size of 40 mm (length)×40 mm (width)×0.7 mm (thickness) to be prepared into an experimental substrate with a cathode lap joint area, an anode and an insulating layer pattern by adopting a photoetching process, and surface treatment was performed by utilizing ultraviolet ozone and $O_2$:$N_2$ plasma to increase the work function of the anode (the experiment substrate), and remove scum.

m-MTDATA (4,4',4"-tris(N-3-methylphenyl-N-phenylamino)triphenylamine) was vacuum-evaporated on the experiment substrate (the anode) to form a hole injection layer (HIL) having a thickness of 100 Å, and a compound 22 was vacuum-evaporated on the hole injection layer to form a first hole transport layer (HTL1) having a thickness of 1130 Å.

EB-1 was then evaporated on the first hole transport layer to form a second hole transport layer (HTL2) with a thickness of 150 Å.

Then, α,β-ADN was used as a host, and meanwhile, BD-6MDPA was doped, so that the host and the doping agent form an organic light-emitting layer (EML) with a thickness of 220 Å according to a film thickness ratio of 30:3.

BP4mPy (3,3',5,5'-Tetra[(m-pyridyl)-phen-3-yl]bipheyl) and LiQ ((8-quinolinolato)lithium) were mixed according to a weight ratio of 1:1 and evaporated to form an electron transport layer (ETL) with a thickness of 350 Å, Yb was evaporated on the electron transport layer to form an electron injection layer (EIL) with a thickness of 10 Å, then magnesium (Mg) and silver (Ag) were mixed according to an evaporation rate of 1:10, and vacuum-evaporated on the electron injection layer to form a cathode with a thickness of 120 Å.

CP-1 with a thickness of 700 Å was evaporated on the cathode to form an organic capping layer (CPL), thus completing manufacturing of the organic electroluminescent device. The evaporated device is packaged by ultraviolet curing resin in a nitrogen glove box (the content of water and oxygen needs to be strictly controlled), so that the device is prevented from being corroded by external moisture or other substances.

The structural formulas of m-MTDATA, EB-1, α,β-ADN, BD-6MDPA, BP4mPy and CP-1 are as shown below.

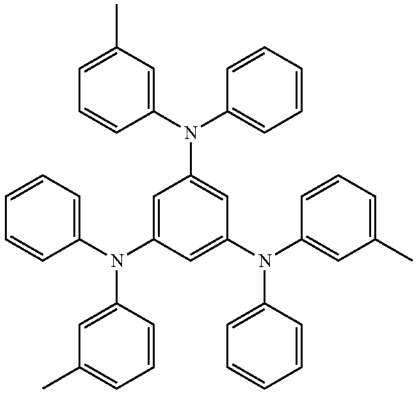

m-MTDATA

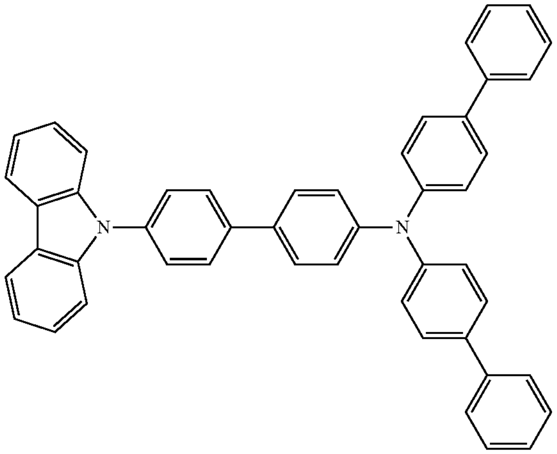

EB-1

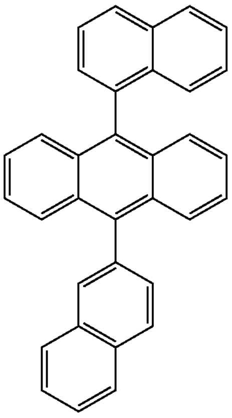

α, β -ADN

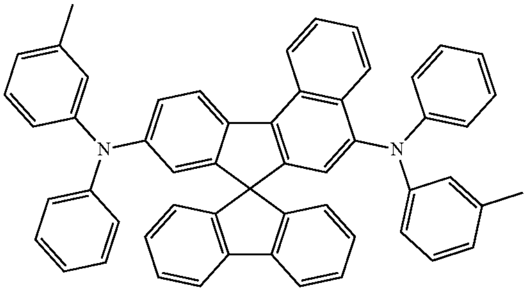

BD-6MDPA

-continued

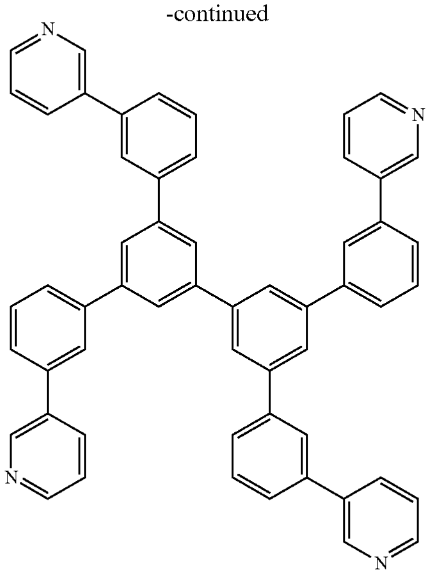

BP4mPy

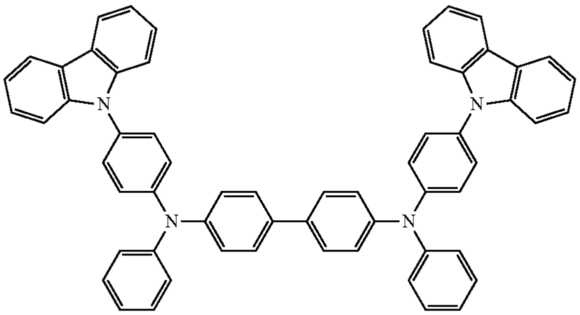

CP-1

Examples 2 to 7

In addition to using compounds shown in Table 7 when forming the first hole transport layer (HTL1), an organic electroluminescent device was manufactured by the same method as in Example 1. The device performance has been listed in Table 7.

Comparative Example 1

In Comparative Example 1, in addition to the use of NPB (N,N'-diphenyl-N,N'-(1-naphthyl)-1,1'-biphenyl-4,4'-diamine) as a first hole transport layer for replacing the compound 22, an organic electroluminescent device was manufactured by using the same method as in Example 1, and the device performance is shown in Table 7.

The structure of NPB is as follows:

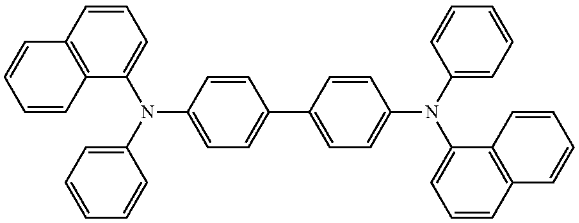

NPB

For the prepared organic electroluminescent device, the IVL performance of the device was analyzed under the condition of 10 mA/cm$^2$, and the T95 service life of the device was tested under a constant current density of 20 mA/cm$^2$.

TABLE 7

Performance of organic electroluminescent device in Examples 1 to 7 and Comparative Example 1

| | HTL1 | Volt (V) | Cd/A | CIEy | EQE % | T95 (h)@20 mA/cm$^2$ |
|---|---|---|---|---|---|---|
| Example 1 | Compound 22 | 3.95 | 6.1 | 0.047 | 12.6 | 151 |
| Example 2 | Compound 4 | 3.97 | 6.0 | 0.047 | 12.4 | 160 |
| Example 3 | Compound 54 | 3.92 | 6.1 | 0.047 | 12.6 | 157 |
| Example 4 | Compound 149 | 3.97 | 6.1 | 0.047 | 12.6 | 164 |
| Example 5 | Compound 100 | 3.91 | 6.3 | 0.048 | 12.9 | 159 |
| Example 6 | Compound 119 | 4.00 | 6.1 | 0.047 | 12.6 | 161 |
| Example 7 | Compound 490 | 3.98 | 6.0 | 0.048 | 12.5 | 158 |
| Comparative Example 1 | NPB | 4.27 | 5.6 | 0.048 | 9.2 | 143 |

According to the Table 7, compared with those in Comparative Example 1, the working voltage of the blue organic electroluminescent device prepared according to the Examples 1 to 7 is at least reduced by 0.27 V, the luminous efficiency (Cd/A) is at least improved by 7.14%, and the service life of the device is at least prolonged by 5.6%.

In conclusion, the blue organic electroluminescent device which is low in voltage, high in luminous efficiency and long in service life can be prepared by using the compounds listed in the examples of the present disclosure in the first hole transport layer (HTL1).

Preparation and Evaluation Examples of Red Organic Electroluminescent Device

Example 8

An anode is prepared by the following processes: an ITO substrate (manufactured by Corning) with an ITO thickness of 1200 Å was cut into a size of 40 mm (length)×40 mm (width)×0.7 mm (thickness) to be prepared into an experimental substrate with a cathode, an anode and an insulating layer pattern by adopting a photoetching process, and surface treatment was performed by utilizing ultraviolet ozone and $O_2$:$N_2$ plasma to increase the work function of the anode (the experiment substrate), and remove scum.

HAT-CN was vacuum-evaporated on the experiment substrate (the anode) to form a hole injection layer (HIL) having a thickness of 100 Å, and a layer of NPB was evaporated on the hole injection layer to form a first hole transport layer (HTL1) having a thickness of 1080 Å.

Then, a compound 113 was vacuum-evaporated on the first hole transport layer to form a second hole transport layer (HTL2) having a thickness of 850 Å.

Then 4,4'-N,N'-dicarbazole-biphenyl (abbreviated as "CBP") was evaporated on the second hole transport layer to serve as a host, and meanwhile, Ir(flq)$_2$(acac) was doped, so that the host and the doping agent form an organic light-emitting layer (EML) with a thickness of 400 Å according to a film thickness ratio of 100:3.

BP4mPy and LiQ were mixed in a weight ratio of 1:1, and evaporated to form an electron transport layer (ETL) having a thickness of 350 Å, Yb was evaporated on the electron transport layer to form an electron injection layer (EIL) having a thickness of 10 Å, and then magnesium (Mg) and silver (Ag) were mixed in an evaporation rate of 1:10, and vacuum-evaporated on the electron injection layer to form a cathode having a thickness of 120 Å.

In addition, CP-1 with a thickness of 700 Å was evaporated on the cathode to form an organic capping layer (CPL), thus completing manufacturing of the organic light-emitting device.

Examples 9 to 33

In addition to using compounds listed in Table 8 when forming the second hole transport layer (HTL2), an organic electroluminescent device was manufactured by the same method as in Example 8. The driving voltage, the luminous efficiency, the external quantum efficiency and the chromaticity coordinate were tested under a constant current density of 10 mA/cm$^2$, and the T95 service life of the device was tested under a constant current density of 20 mA/cm$^2$. And the IVL and device life data of the organic electroluminescent device are listed in Table 8.

The structural formulas of HAT-CN, NPB, CBP, Ir(flq)$_2$(acac), BP4mPy and CP-1 are as follows:

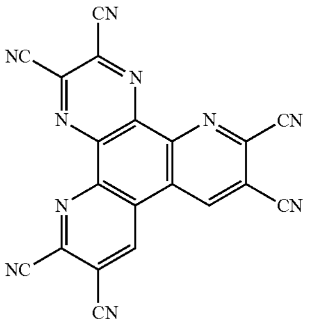

HAT-CN

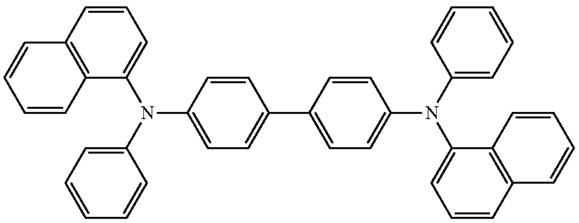

NPB

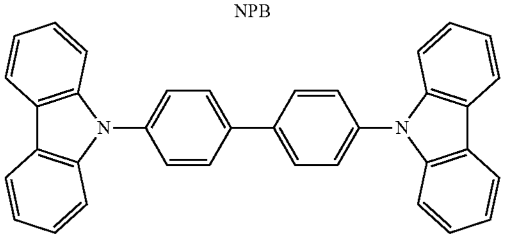

CBP

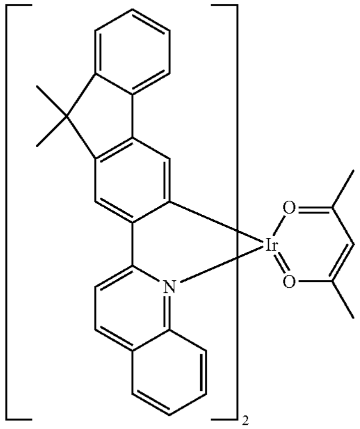

Ir(flq)$_2$(acac)

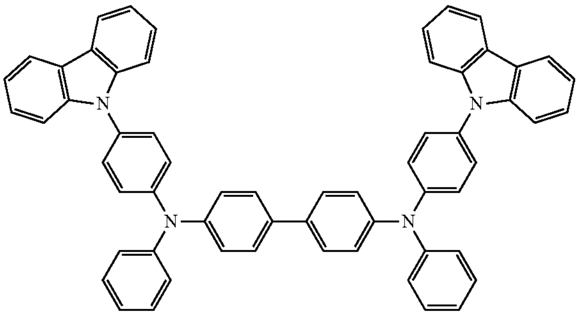

CP-1

-continued

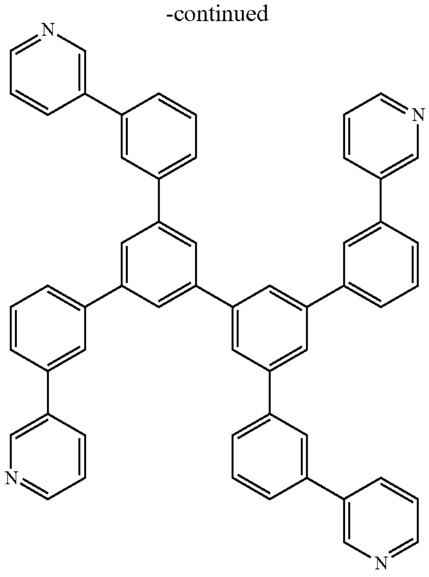

BP4mPy

Comparative Examples 2 to 4

In Comparative Examples 2 to 4, in addition to using a compound A, a compound B, and a compound C as a second hole transport layer instead of the compound in Example 8, an organic electroluminescent device was manufactured by the same method as in Example 8.

In Comparative Example 2, the compound A was adopted to manufacture the organic electroluminescent device, in Comparative Example 3, the compound B was adopted to manufacture the organic electroluminescent device, and in Comparative Example 4, the compound C was adopted to manufacture the organic electroluminescent device. The driving voltage, the luminous efficiency, the external quantum efficiency and the chromaticity coordinate were tested under a constant current density of 10 $mA/cm^2$, and the T95 service life of the device was tested under a constant current density of 20 $mA/cm^2$. And the IVL and device life data of the organic electroluminescent device are listed in Table 8.

The structural formulas of the compound A, the compound B and the compound C are as follows:

Compound A

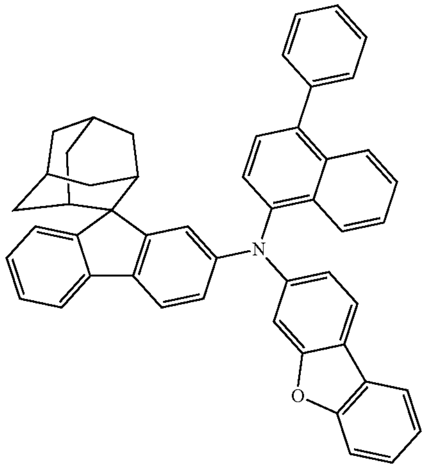

-continued

Compound C

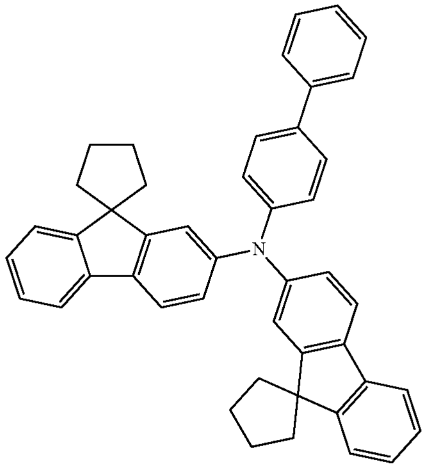

Compound B

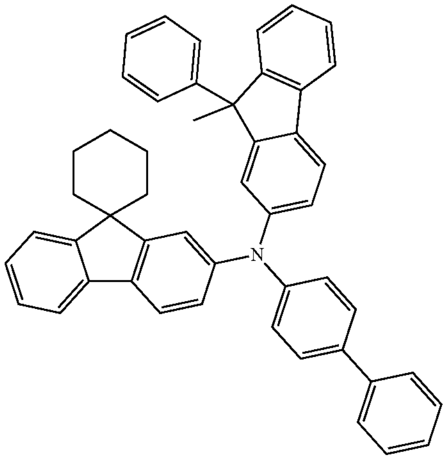

TABLE 8

Performance of organic electroluminescent device in Examples 8 to 33 and Comparative Examples 2 to 4

| Example | Compound | Operating voltage volt (V) | Luminous efficiency (Cd/A) | External quantum efficiency EQE (%) | T95 (h)@20 mA/cm$^2$ | Chromaticity coordinate CIEx |
|---|---|---|---|---|---|---|
| Example 8 | Compound 113 | 3.96 | 34.0 | 23.1 | 550 | 0.678 |
| Example 9 | Compound 138 | 3.99 | 34.9 | 23.7 | 552 | 0.676 |
| Example 10 | Compound 25 | 3.97 | 34.1 | 23.2 | 566 | 0.677 |
| Example 11 | Compound 75 | 3.95 | 34.6 | 23.5 | 558 | 0.676 |
| Example 12 | Compound 70 | 3.95 | 33.9 | 23.0 | 560 | 0.677 |
| Example 13 | Compound 394 | 3.95 | 34.6 | 23.5 | 561 | 0.678 |
| Example 14 | Compound 414 | 4.00 | 34.6 | 23.5 | 552 | 0.676 |
| Example 15 | Compound 32 | 4.04 | 33.7 | 22.9 | 550 | 0.677 |
| Example 16 | Compound 83 | 4.00 | 33.8 | 23.0 | 547 | 0.676 |
| Example 17 | Compound 415 | 4.01 | 33.8 | 23.0 | 549 | 0.676 |
| Example 18 | Compound 491 | 4.00 | 34.3 | 23.3 | 562 | 0.678 |
| Example 19 | Compound 489 | 3.97 | 33.9 | 23.1 | 555 | 0.676 |
| Example 20 | Compound 490 | 3.97 | 34.4 | 23.4 | 557 | 0.677 |
| Example 21 | Compound 419 | 3.98 | 34.3 | 23.3 | 559 | 0.676 |
| Example 22 | Compound 201 | 3.98 | 33.8 | 23.0 | 554 | 0.677 |
| Example 23 | Compound 217 | 3.99 | 34.4 | 23.4 | 558 | 0.678 |
| Example 24 | Compound 234 | 3.98 | 34.3 | 23.3 | 561 | 0.676 |
| Example 25 | Compound 242 | 3.99 | 34.3 | 23.3 | 555 | 0.677 |
| Example 26 | Compound 487 | 3.97 | 34.4 | 23.4 | 554 | 0.676 |
| Example 27 | Compound 488 | 3.99 | 33.9 | 23.1 | 558 | 0.676 |
| Example 28 | Compound 481 | 3.98 | 33.9 | 23.0 | 562 | 0.678 |
| Example 29 | Compound 482 | 3.97 | 34.3 | 23.3 | 556 | 0.676 |
| Example 30 | Compound 483 | 4.00 | 33.9 | 23.0 | 562 | 0.677 |
| Example 31 | Compound 484 | 4.01 | 34.0 | 23.1 | 555 | 0.676 |
| Example 32 | Compound 485 | 3.99 | 34.1 | 23.2 | 562 | 0.677 |
| Example 33 | Compound 486 | 3.98 | 34.1 | 23.2 | 560 | 0.678 |
| Comparative Example 2 | Compound A | 4.32 | 29.9 | 20.8 | 478 | 0.676 |
| Comparative Example 3 | Compound B | 4.34 | 26.8 | 19.8 | 456 | 0.677 |
| Comparative Example 4 | Compound C | 4.45 | 23.5 | 19.2 | 437 | 0.676 |

According to the Table 8, compared with Comparative Examples 2 to 4, the red organic electroluminescent device prepared according to the Examples 8 to 33 has the advantages that the voltage is at least reduced by about 0.3 V, the luminous efficiency is at least improved by 13%, and the service life of the device is at least improved by 69 h.

In conclusion, the red organic electroluminescent device with long service life can be prepared by using the compounds listed in the examples of the present disclosure in the second hole transport layer. The reason is that an adamantyl group is added during the design of molecules, so that the molecules have better film-forming properties. The decomposition temperature Tg of the compound can be increased to a certain extent, and the thermal stability of the material is improved, so that the service life of the device is improved.

Thermal stability data of some materials are shown in the following Table 10, the decomposition temperature Tg is obtained through testing by using a thermal gravimetric analyzer (TGA), and Te is an evaporation temperature of the compound in an evaporator at an evaporation rate of 1 Å/s.

TABLE 9

| Example | Compound | Tg (° C.) | Te (° C.) |
|---|---|---|---|
| Example 34 | Compound 4 | 148 | 239 |
| Example 35 | Compound 100 | 154 | 241 |
| Example 36 | Compound 119 | 162 | 253 |
| Example 37 | Compound 217 | 149 | 239 |
| Example 38 | Compound 487 | 157 | 240 |

TABLE 9-continued

| Example | Compound | Tg (° C.) | Te (° C.) |
|---|---|---|---|
| Example 39 | Compound 488 | 159 | 244 |
| Comparative example 5 | Compound B | 118 | 267 |
| Comparative example 6 | Compound C | 123 | 278 |

It can be seen from Table 9 that the compound provided by the present disclosure has lower decomposition possibility in the film forming process of the device through evaporation at high temperature, and has higher crystallization resistance in an electric Joule thermal environment in the operation of the device.

Compared with the compounds in the comparative examples, the compound provided by the present disclosure has the advantage that under the condition of small molecular weight difference, the evaporation temperature (Te) of the compound provided by the present disclosure is reduced due to relatively high steric hindrance. In this way, the compound provided by the present disclosure has better thermal stability.

The preferable embodiments of the present disclosure are described in detail above n combination with the drawings, however, the present disclosure is not limited to the specific details in the above embodiments, in the technical concept range of the present disclosure, the technical solution of the present disclosure can be subjected to various simple variations, and these simple variations all belong to the protection range of the present disclosure.

In addition, it should be noted that all the specific technical features described in the above specific embodiments can be combined in any appropriate mode without contradiction, and in order to avoid unnecessary repetition, various possible combinations are not described any more in the present disclosure.

In addition, various different embodiments of the present disclosure can also be combined at will, and as long as they do not violate the idea of the present disclosure, they also should be regarded as the contents disclosed by the present disclosure.

What is claimed is:

1. An arylamine compound, having a structure as shown in the following Formula 1:

Formula 1

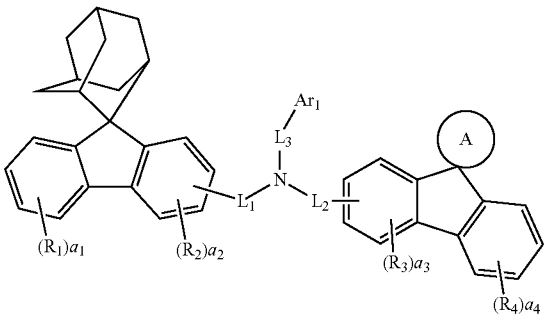

wherein a ring A is a substituted or unsubstituted 5- to 16-membered aliphatic hydrocarbon ring;

$L_1$, $L_2$ and $L_3$ are each independently a single bond, substituted or unsubstituted arylene with 6 to 30 carbon atoms, and substituted or unsubstituted heteroarylene with 3 to 30 carbon atoms;

$Ar_1$ is selected from the following substituted or unsubstituted groups: alkyl with 1 to 20 carbon atoms, cycloalkyl with 3 to 20 carbon atoms, aryl with 6 to 30 carbon atoms and heteroaryl with 3 to 30 carbon atoms;

$R_1$, $R_2$, $R_3$ and $R_4$ are the same or different from each other, and are each independently selected from deuterium, halogen group, cyano, cycloalkyl with 3 to 20 carbon atoms, heterocycloalkyl with 2 to 20 carbon atoms, alkyl with 1 to 20 carbon atoms, aryl with 6 to 30 carbon atoms and heteroaryl with 3 to 30 carbon atoms; and $a_1$, $a_2$, $a_3$ and $a_4$ are the numbers of $R_1$, $R_2$, $R_3$ and $R_4$ respectively;

$a_1$ and $a_4$ are each independently selected from 0, 1, 2, 3 or 4, and when $a_1$ is greater than one, any two $R_1$s are the same or different, or any two adjacent $R_1$s are connected with each other to form a saturated or unsaturated ring with 3 to 15 carbon atoms; and when $a_4$ is greater than one, any two $R_4$s are the same or different, or any two adjacent $R_4$s are connected with each other to form a saturated or unsaturated ring with 3 to 15 carbon atoms;

$a_2$ and $a_3$ are each independently selected from 0, 1, 2 or 3, and when $a_2$ is greater than one, any two $R_2$s are the same or different, or any two adjacent $R_2$s are connected with each other to form a saturated or unsaturated ring with 3 to 15 carbon atoms; and when $a_3$ is greater than one, any two $R_3$s are the same or different, or any two adjacent $R_3$s are connected with each other to form a saturated or unsaturated ring with 3 to 15 carbon atoms;

the substituents in the ring A are selected from the group consisting of deuterium, halogen group, cyano, alkyl with 1 to 15 carbon atoms, aryl with 6 to 12 carbon atoms and heteroaryl with 3 to 18 carbon atoms;

the substituents in $Ar_1$, $L_1$, $L_2$ and $L_3$ are the same or different, and are each independently selected from the group consisting of deuterium, halogen group, cyano, alkyl with 1 to 15 carbon atoms, cycloalkyl with 3 to 20 carbon atoms, heterocycloalkyl with 2 to 20 carbon atoms, aralkyl with 7 to 15 carbon atoms, heteroaralkyl with 4 to 15 carbon atoms, aryl with 6 to 30 carbon atoms, heteroaryl with 3 to 30 carbon atoms, alkoxy with 1 to 30 carbon atoms, alkylthio with 1 to 30 carbon atoms, alkylsilyl with 1 to 30 carbon atoms, trialkylsilyl with 3 to 12 carbon atoms, triarylsilyl with 18 to 24 carbon atoms, aryloxy with 6 to 30 carbon atoms and arylthio with 6 to 30 carbon atoms.

2. The arylamine compound according to claim 1, wherein the ring A is an unsubstituted 5- to 10-membered aliphatic hydrocarbon ring.

3. The arylamine compound according to claim 1, wherein the ring A is selected from the group consisting of groups represented by the following Formulae 2-1 to 2-4:

Formula 2-1

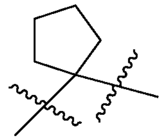

Formula 2-2

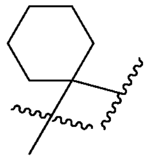

Formula 2-3

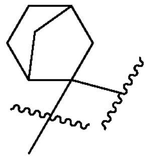

Formula 2-4

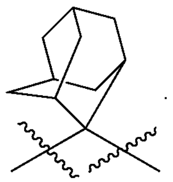

4. The arylamine compound according to claim 1, wherein $Ar_1$ is selected from substituted or unsubstituted aryl with 6 to 25 carbon atoms and substituted or unsubstituted heteroaryl with 3 to 25 carbon atoms.

5. The arylamine compound according to claim 1, wherein $Ar_1$ is selected from the group consisting of the following groups:

i-1
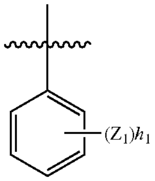
i-2
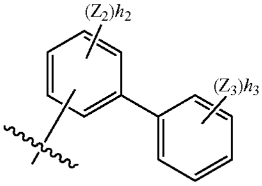
i-3
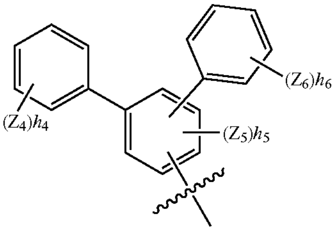
i-4
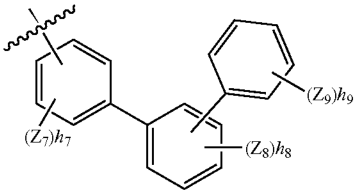
i-5
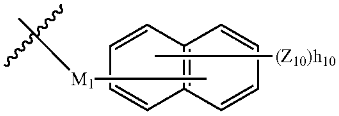
i-6
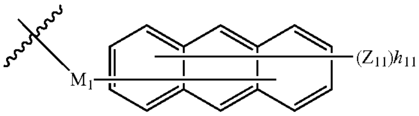
i-7
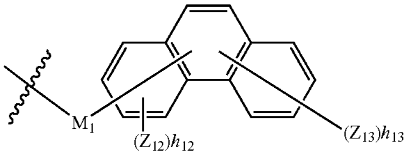
i-8
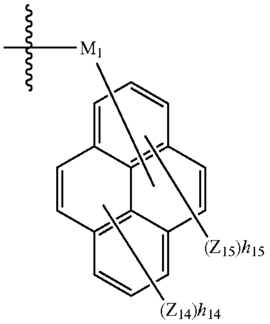
-continued
i-9
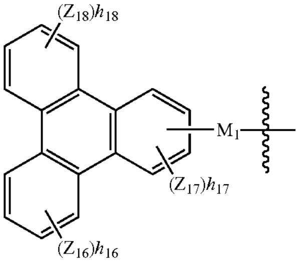
i-10
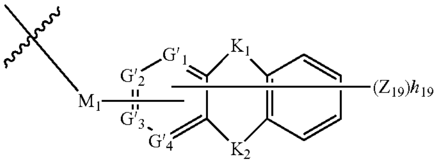
i-11
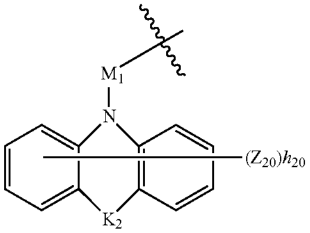
i-12
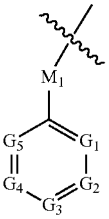
i-13
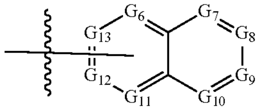
i-14
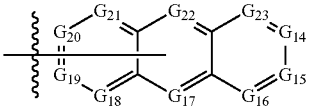
i-15
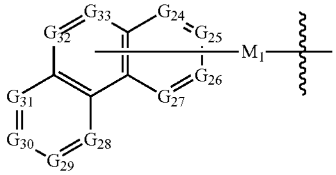
wherein $M_1$ is selected from a single bond or
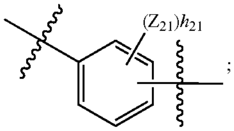
;

$G_1$ to $G_5$ and $G'_1$ to $G'_4$ are each independently selected from N, C or $C(J_1)$, at least one of $G_1$ to $G_5$ is selected from N, and when two or more of $G_1$ to $G_5$ are selected from $C(J_1)$, any two $J_1$s are the same or different;

$G_6$ to $G_{13}$ are each independently selected from N, C or $C(J_2)$, and at least one of $G_6$ to $G_{13}$ is selected from N; and when two or more of $G_6$ to $G_{13}$ are selected from $C(J_2)$, any two $J_2$s are the same or different;

$G_{14}$ to $G_{23}$ are each independently selected from N, C or $C(J_3)$, and at least one of $G_{14}$ to $G_{23}$ is selected from N; and when two or more of $G_{14}$-$G_{23}$ are selected from $C(J_3)$, any two $J_3$s are the same or different;

$G_{24}$ to $G_{33}$ are each independently selected from N, C or $C(J_4)$, and at least one of $G_{24}$ to $G_{33}$ is selected from N; and when two or more of $G_{24}$ to $G_{33}$ are selected from $C(J_4)$, any two $J_4$s are the same or different;

$Z_1$ is selected from hydrogen, deuterium, halogen group, cyano, trialkylsilyl with 3 to 12 carbon atoms, alkyl with 1 to 10 carbon atoms, haloalkyl with 1 to 10 carbon atoms, cycloalkyl with 3 to 10 carbon atoms, alkoxy with 1 to 10 carbon atoms, alkylthio with 1 to 10 carbon atoms and triarylsilyl with 18 to 24 carbon atoms;

$Z_2$ to $Z_9$ and $Z_{21}$ are each independently selected from hydrogen, deuterium, halogen group, cyano, trialkylsilyl with 3 to 12 carbon atoms, alkyl with 1 to 10 carbon atoms, haloalkyl with 1 to 10 carbon atoms, cycloalkyl with 3 to 10 carbon atoms, alkoxy with 1 to 10 carbon atoms, alkylthio with 1 to 10 carbon atoms, heteroaryl with 3 to 18 carbon atoms and triarylsilyl with 18 to 24 carbon atoms;

$Z_{10}$ to $Z_{20}$ and $J_1$ to $J_4$ are each independently selected from hydrogen, deuterium, halogen group, cyano, trialkylsilyl with 3 to 12 carbon atoms, alkyl with 1 to 10 carbon atoms, haloalkyl with 1 to 10 carbon atoms, cycloalkyl with 3 to 10 carbon atoms, alkoxy with 1 to 10 carbon atoms, alkylthio with 1 to 10 carbon atoms, aryl with 6 to 18 carbon atoms, heteroaryl with 3 to 18 carbon atoms, and triarylsilyl with 18 to 24 carbon atoms;

$h_1$ to $h_{21}$ are represented by $h_k$, $Z_1$ to $Z_{21}$ are represented by $Z_k$, k is a variable and represents any integer of 1 to 21, and $h_k$ represents the number of substituents $Z_k$; when k is selected from 5 or 17, $h_k$ is selected from 1, 2 or 3; when k is selected from 2, 7, 8, 12, 15, 16, 18 or 21, $h_k$ is selected from 1, 2, 3 or 4; when k is selected from 1, 3, 4, 6, 9 or 14, $h_k$ is selected from 1, 2, 3, 4 or 5; when k is 13, $h_k$ is selected from 1, 2, 3, 4, 5 or 6; when k is selected from 10 or 19, $h_k$ is selected from 1, 2, 3, 4, 5, 6 or 7; when k is 20, $h_k$ is selected from 1, 2, 3, 4, 5, 6, 7 or 8; when k is 11, $h_k$ is selected from 1, 2, 3, 4, 5, 6, 7, 8 or 9; and when $h_k$ is greater than one, any two $Z_k$ are the same or different;

$K_1$ is selected from O, S, $N(Z_{22})$, $C(Z_{23}Z_{24})$ and $Si(Z_{28}Z_{29})$; wherein $Z_{22}$, $Z_{23}$, $Z_{24}$, $Z_{28}$ and $Z_{29}$ are each independently selected from aryl with 6 to 18 carbon atoms, heteroaryl with 3 to 18 carbon atoms, alkyl with 1 to 10 carbon atoms or cycloalkyl with 3 to 10 carbon atoms, or the $Z_{23}$ and the $Z_{24}$ are connected with each other to form a saturated or unsaturated ring with 3 to 15 carbon atoms together with atoms to which they are jointly connected, or the $Z_{28}$ and the $Z_{29}$ are connected with each other to form a saturated or unsaturated ring with 3 to 15 carbon atoms together with atoms to which they are jointly connected;

$K_2$ is selected from a single bond, O, S, $N(Z_{25})$, $C(Z_{26}Z_{27})$, and $Si(Z_{30}Z_{31})$; wherein $Z_{25}$, $Z_{26}$, $Z_{27}$, $Z_{30}$ and $Z_{31}$ are each independently selected from aryl with 6 to 18 carbon atoms, heteroaryl with 3 to 18 carbon atoms, alkyl with 1 to 10 carbon atoms or cycloalkyl with 3 to 10 carbon atoms, or the $Z_{26}$ and the $Z_{27}$ are connected with each other to form a saturated or unsaturated ring with 3 to 15 carbon atoms together with atoms to which they are jointly connected, or the $Z_{30}$ and the $Z_{31}$ are connected with each other to form a saturated or unsaturated ring with 3 to 15 carbon atoms together with atoms to which they are jointly connected.

6. The arylamine compound according to claim 1, wherein $Ar_1$ is selected from the group consisting of the following groups:

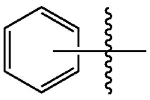
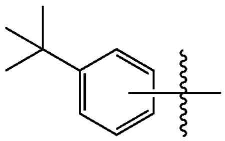
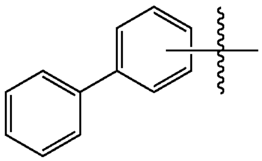
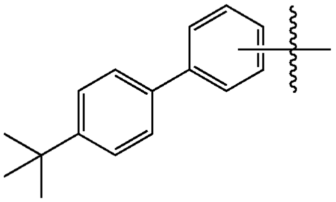
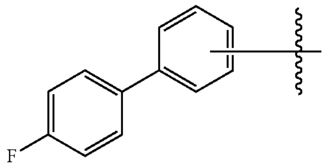
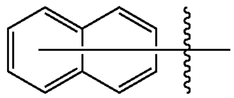
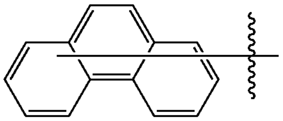
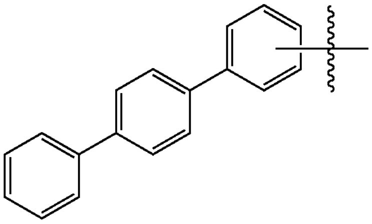
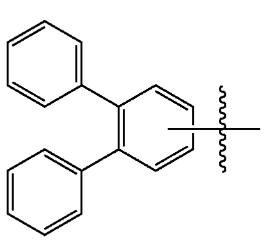
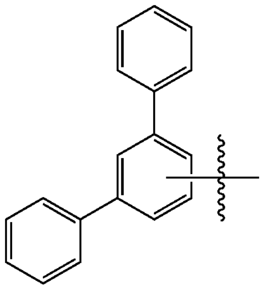

-continued
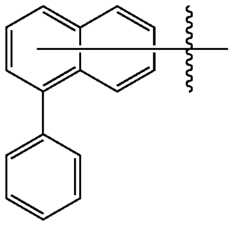
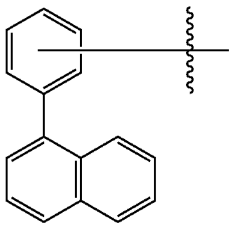
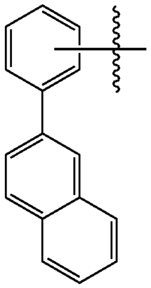
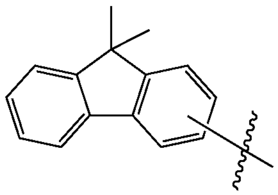
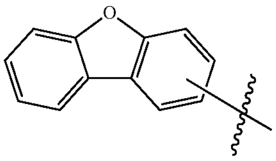
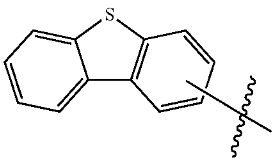
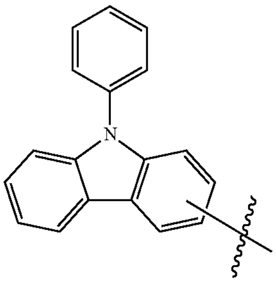
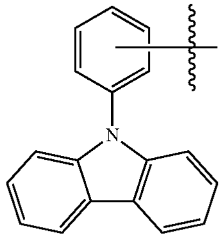
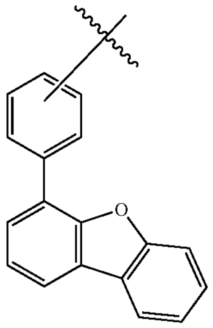
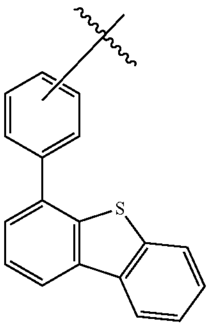
-continued
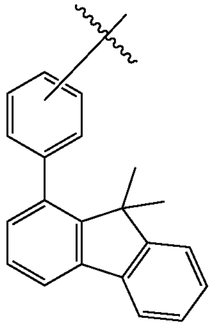
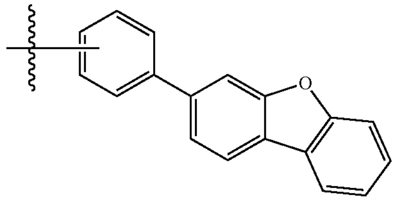
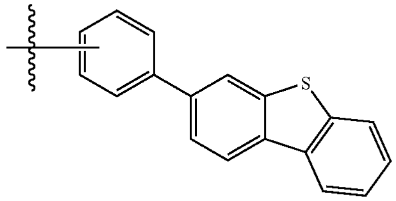
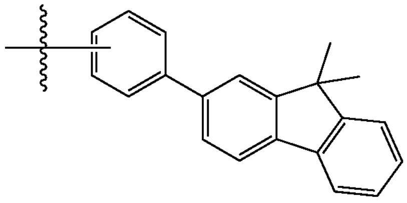
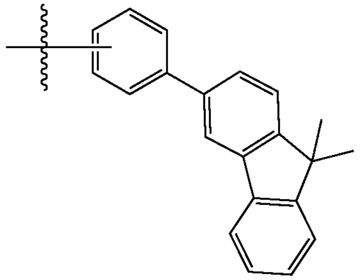
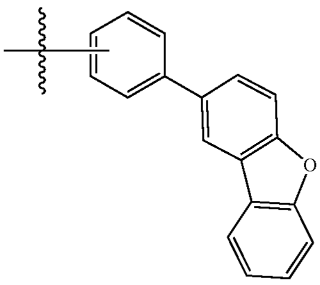

-continued
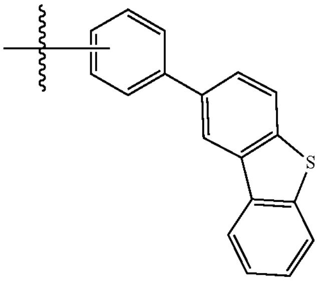
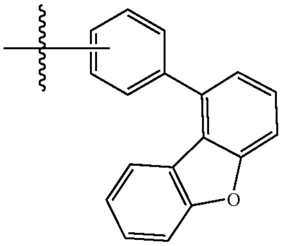
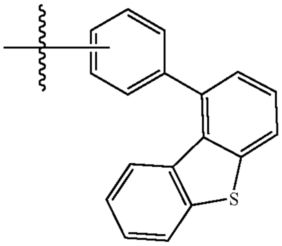
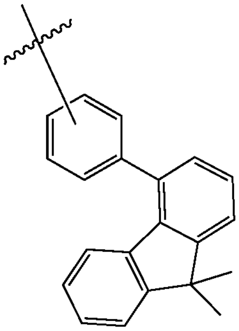
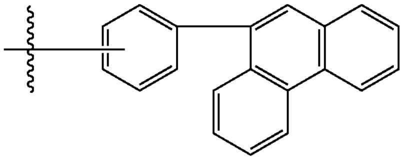
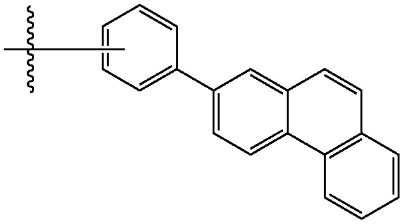
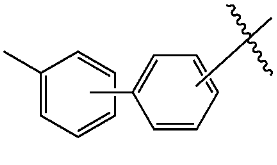
-continued
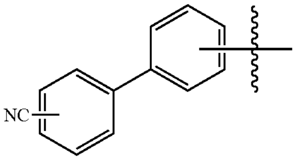
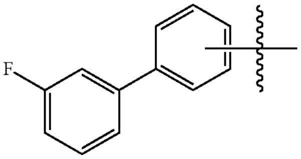
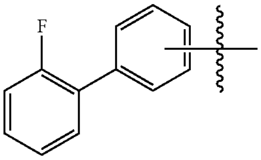
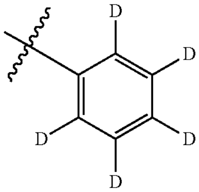
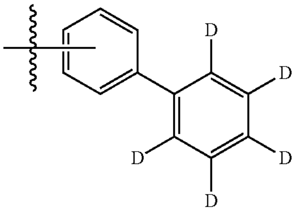
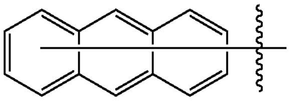
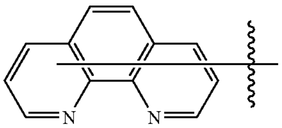
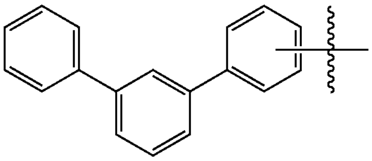
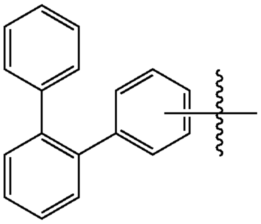
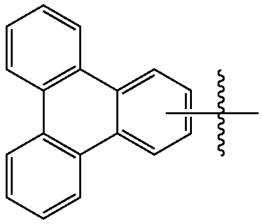
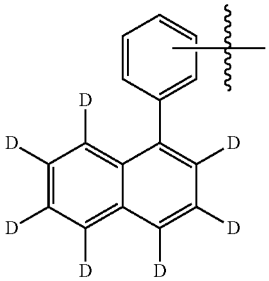
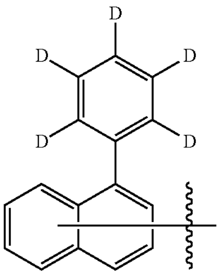

-continued

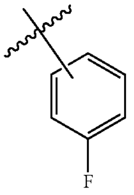

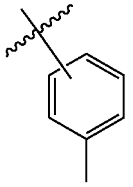

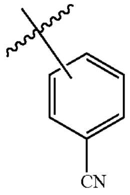

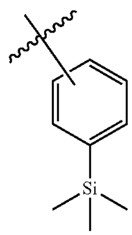

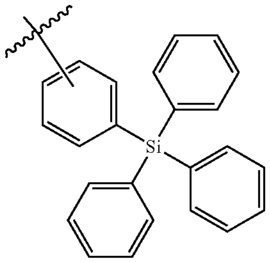

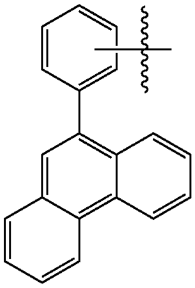

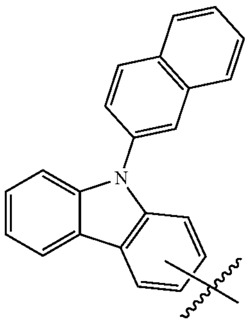

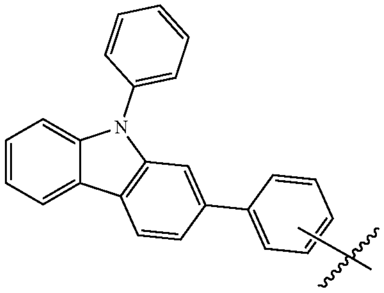

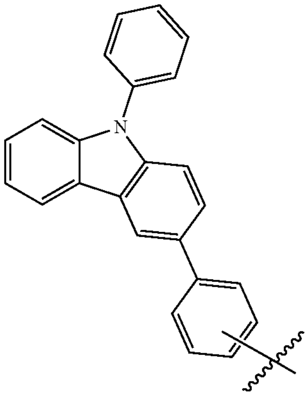

-continued

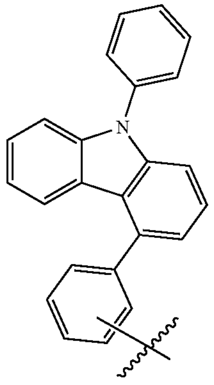

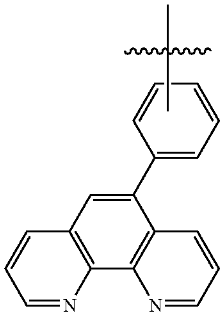

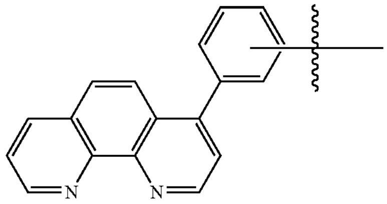

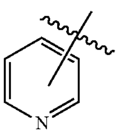

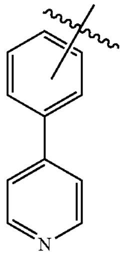

.

7. The arylamine compound according to claim 1, wherein $L_1$, $L_2$ and $L_3$ are each independently a single bond, substituted or unsubstituted arylene with 6 to 20 carbon atoms or substituted or unsubstituted heteroarylene with 3 to 20 carbon atoms.

8. The arylamine compound according to claim 1, wherein $L_1$, $L_2$ and the $L_3$ are each independently a single bond, substituted or unsubstituted phenylene, substituted or unsubstituted naphthylene, substituted or unsubstituted biphenylene, substituted or unsubstituted terphenylene, substituted or unsubstituted fluorenylidene, substituted or unsubstituted anthrylene, substituted or unsubstituted phenanthrylene, substituted or unsubstituted carbazolylidene, substituted or unsubstituted dibenzofurylidene, substituted or unsubstituted dibenzothenylidene, substituted or unsubstituted pyridylidene, substituted or unsubstituted pyrimidylidene or substituted or unsubstituted triazinylidene; or $L_1$, $L_2$ and $L_3$ are each independently selected from

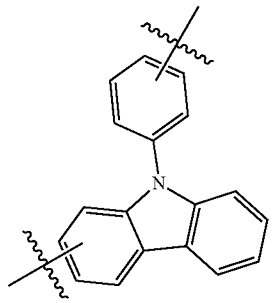

or

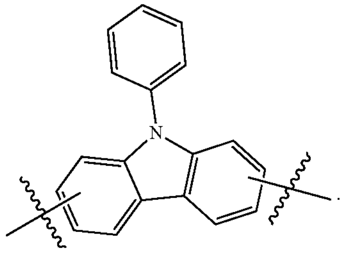

9. The arylamine compound according to claim 1, wherein the substituents in $L_1$, $L_2$ and $L_3$ are the same or different, and are each independently selected from deuterium, fluorine, cyano, alkyl with 1 to 5 carbon atoms and aryl with 6 to 12 carbon atoms.

10. The arylamine compound according to claim 1, wherein $L_1$, $L_2$ and $L_3$ are each independently a single bond, or are selected from the group consisting of groups represented by chemical formulae j-1 to j-14:

j-1

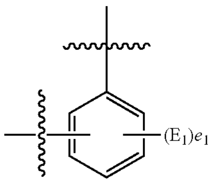

j-2

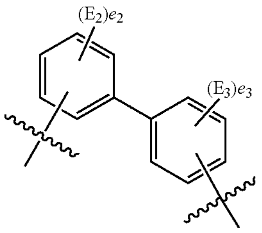

j-3

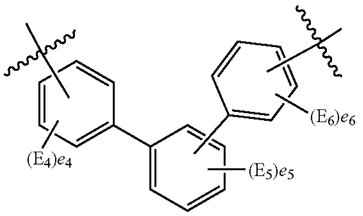

j-4

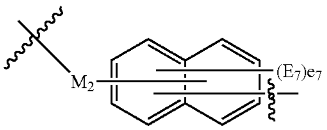

-continued j-5

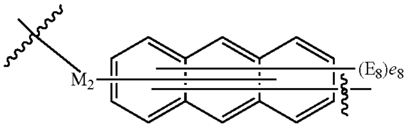

j-6

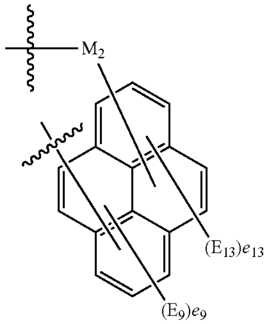

j-7

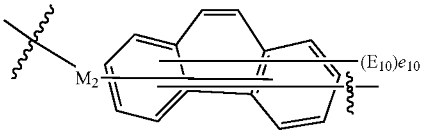

j-8

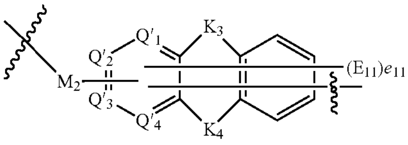

j-9

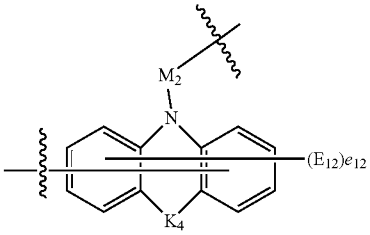

j-10

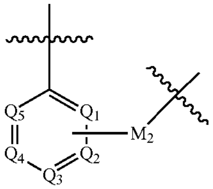

j-11

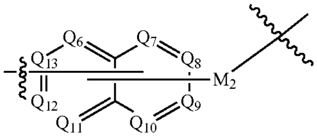

j-12

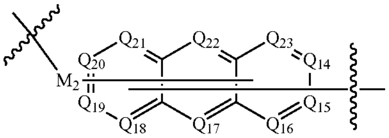

-continued j-13

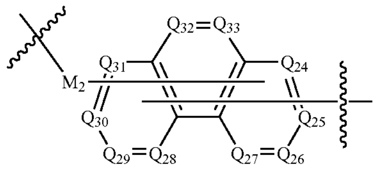

j-14

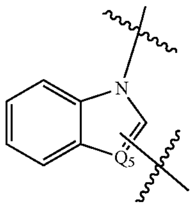

wherein $M_2$ is selected from a single bond or

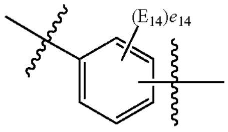

, and

represents a chemical bond;

$Q_1$ to $Q_5$ and $Q'_1$ to $Q'_5$ are each independently selected from N or $C(J_5)$, and at least one of $Q_1$ to $Q_5$ is selected from N; and when two or more of $Q_1$ to $Q_5$ are selected from $C(J_5)$, any two $J_5$s are the same or different, and when two or more of $Q'_1$ to $Q'_4$ are selected from $C(J_5)$, any two $J_5$s are the same or different;

$Q_6$ to $Q_{13}$ are each independently selected from N, C or $C(J_6)$, and at least one of $Q_6$ to $Q_{13}$ is selected from N; and when two or more of $Q_6$ to $Q_{13}$ are selected from $C(J_6)$, any two Jos are the same or different;

$Q_{14}$ to $Q_{23}$ are each independently selected from N, C or $C(J_7)$, and at least one of $Q_{14}$ to $Q_{23}$ is selected from N; and when two or more of $Q_{14}$ to $Q_{23}$ are selected from $C(J_7)$, any two $J_7$s are the same or different;

$Q_{24}$ to $Q_{32}$ are each independently selected from N, C or $C(J_8)$, and at least one of $Q_{24}$ to $Q_{32}$ is selected from N; and when two or more of $Q_{24}$ to $Q_{32}$ are selected from $C(J_8)$, any two Jas are the same or different;

$E_1$ to $E_{14}$ and $J_5$ to $J_9$ are each independently selected from hydrogen, deuterium, halogengroup, cyano, heteroaryl with 3 to 20 carbon atoms, aryl with 6 to 20 carbon atoms, trialkylsilyl with 3 to 12 carbon atoms, alkyl with 1 to 10 carbon atoms, haloalkyl with 1 to 10 carbon atoms, cycloalkyl with 3 to 10 carbon atoms, heterocycloalkyl with 2 to 10 carbon atoms, alkoxy with 1 to 10 carbon atoms, alkylthio with 1 to 10 carbon atoms, aryloxy with 6 to 18 carbon atoms, arylthio with 6 to 18 carbon atoms, phosphinyloxy with 6 to 18 carbon atoms, and triarylsilyl with 18 to 24 carbon atoms;

when any one of $E_1$ to $E_{14}$ is independently selected from aryl with 6 to 20 carbon atoms, $E_1$ to $E_3$ and $E_{14}$ are not aryl;

$e_1$ to $e_{14}$ are represented by $e_r$, $E_1$ to $E_{14}$ are represented by $E_r$, r is a variable and represents any integer of 1 to 14, and $e_r$ represents the number of substituents $E_r$; when r is selected from 1, 2, 3, 4, 5, 6, 9, 13 or 14, $e_r$ is selected from 1, 2, 3 or 4; when r is selected from 7 or 11, $e_r$ is selected from 1, 2, 3, 4, 5 or 6; when r is 12, $e_r$ is selected from 1, 2, 3, 4, 5, 6 or 7; when r is selected from 8 or 10, $e_r$ is selected from 1, 2, 3, 4, 5, 6, 7 or 8; and when $e_r$ is greater than 1, any two $E_r$ are the same or different;

$K_3$ is selected from O, S, Se, $N(E_{15})$, $C(E_{16}E_{17})$ and $Si(E_{18}E_{19})$; wherein $E_{15}$, $E_{16}$, $E_{17}$, $E_{18}$ and $E_{19}$ are each independently selected from aryl with 6 to 20 carbon atoms, heteroaryl with 3 to 20 carbon atoms, alkyl with 1 to 10 carbon atoms, cycloalkyl with 3 to 10 carbon atoms, and heterocycloalkyl with 2 to 10 carbon atoms, or $E_{16}$ and $E_{17}$ are connected with each other to form a saturated or unsaturated ring with 3 to 15 carbon atoms together with atoms to which they are jointly connected, or $E_{18}$ and $E_{19}$ are connected with each other to form a saturated or unsaturated ring with 3 to 15 carbon atoms together with atoms to which they are jointly connected;

$K_4$ is selected from a single bond, O, S, Se, $N(E_{20})$, $C(E_{21}E_{22})$, and $Si(E_{23}E_{24})$; wherein $E_{20}$ to $E_{24}$ are each independently selected from aryl with 6 to 20 carbon atoms, heteroaryl with 3 to 20 carbon atoms, alkyl with 1 to 10 carbon atoms, cycloalkyl with 3 to 10 carbon atoms, and heterocycloalkyl with 2 to 10 carbon atoms, or $E_{21}$ and $E_{22}$ are connected with each other to form a saturated or unsaturated ring with 3 to 15 carbon atoms together with atoms to which they are jointly connected, or $E_{23}$ and $E_{24}$ are connected with each other to form a saturated or unsaturated ring with 3 to 15 carbon atoms together with atoms to which they are jointly connected.

11. The arylamine compound according to claim 1, wherein $L_1$, $L_2$ and $L_3$ are each independently a single bond or are selected from the group consisting of the following groups:

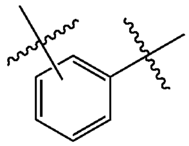

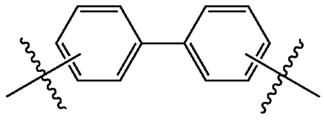

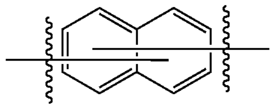

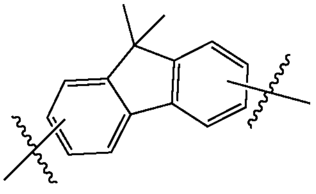

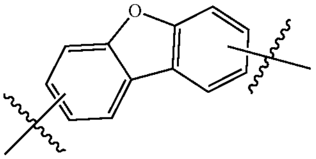

-continued
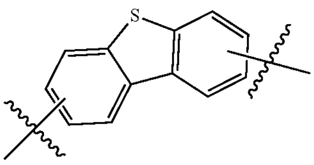
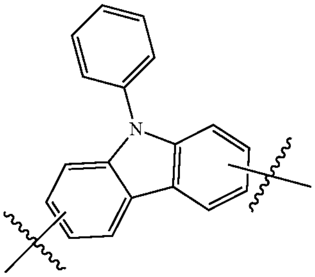
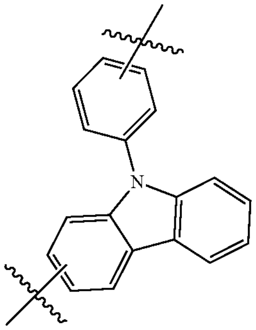
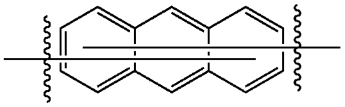
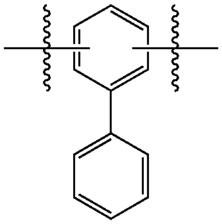
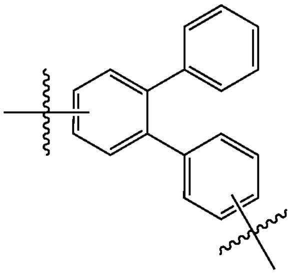
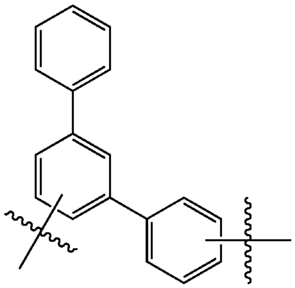
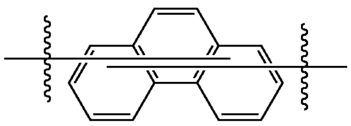
-continued
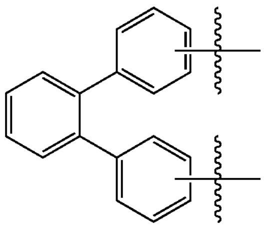
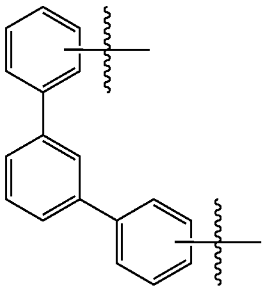
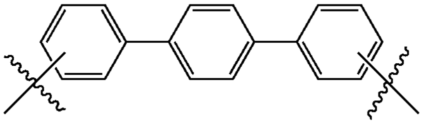
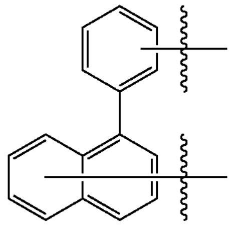
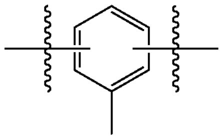
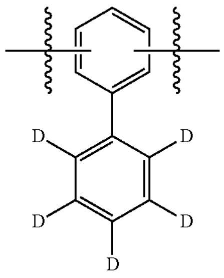
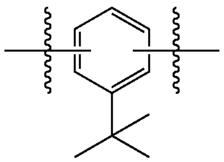
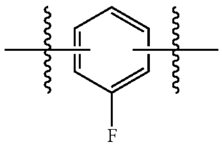
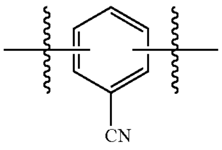;
wherein
represents a chemical bond.
12. The arylamine compound according to claim 1, wherein the arylamine compound is selected from the group consisting of the following compounds:

-continued
1
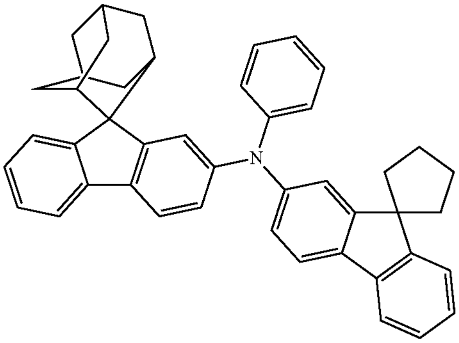
2
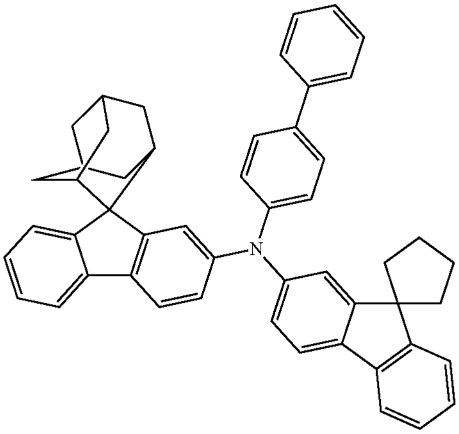
3
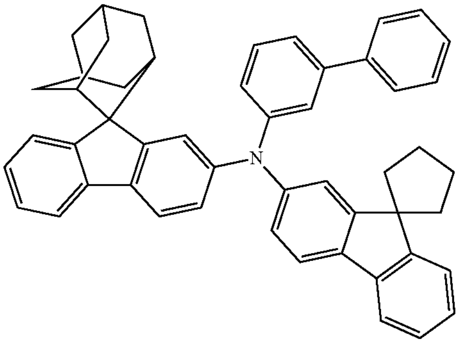
4
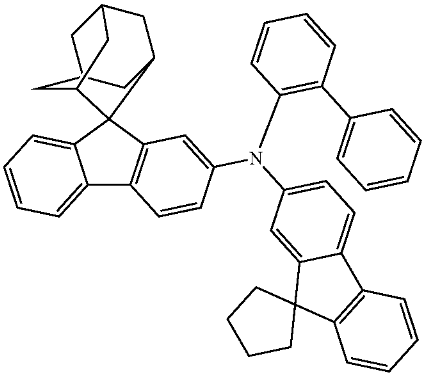
5
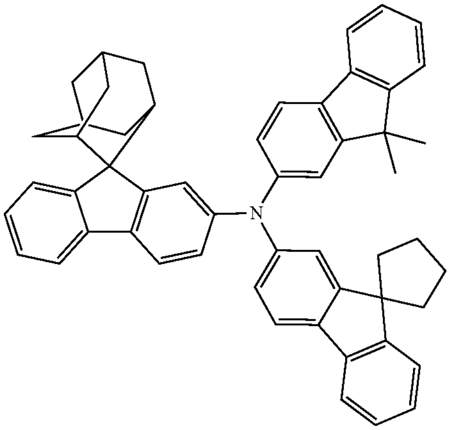
6
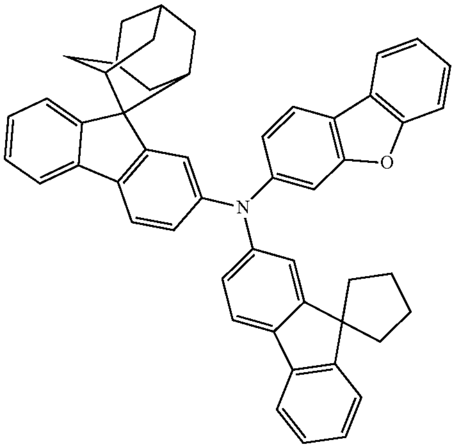
7
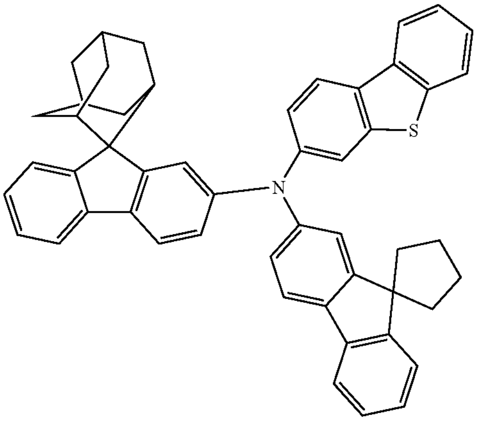

-continued
8
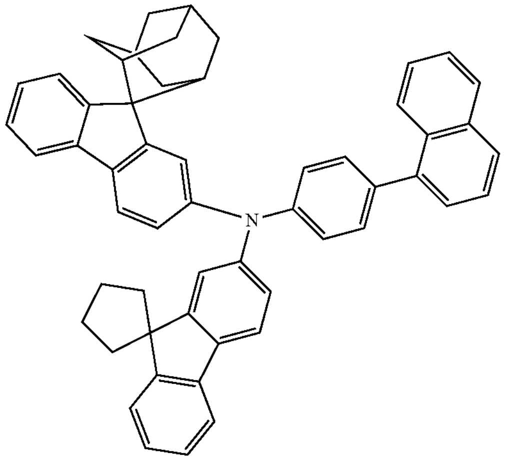
9
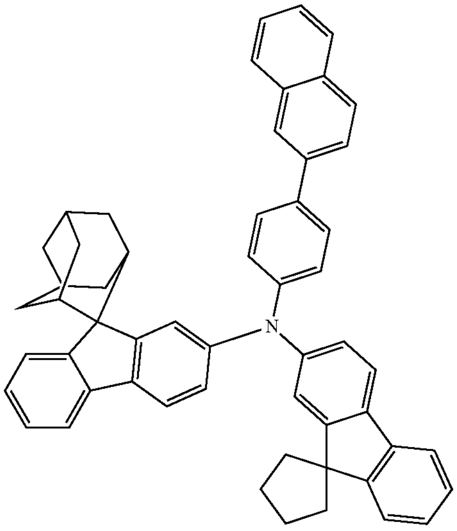
10
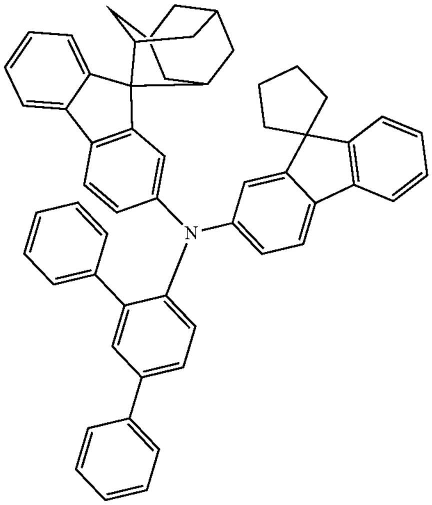
-continued
11
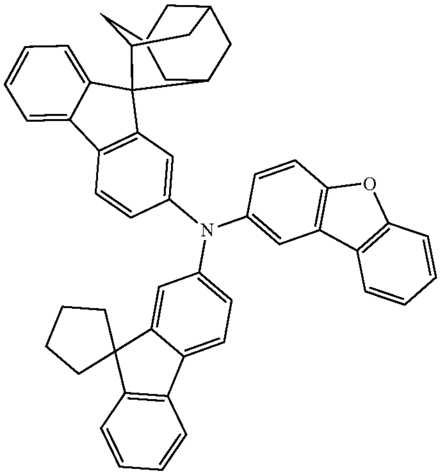
12
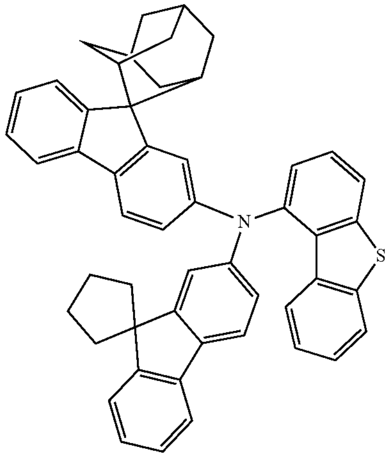
13
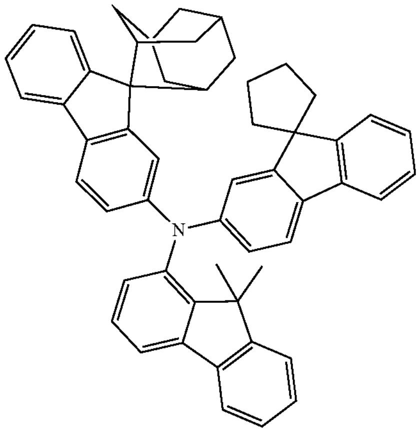

14
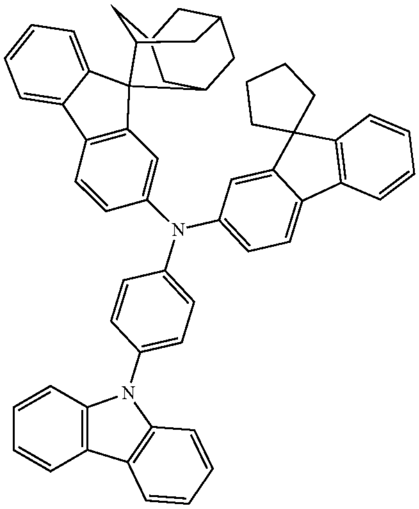
15
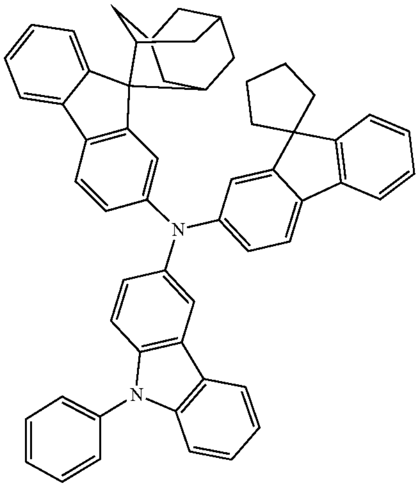
16
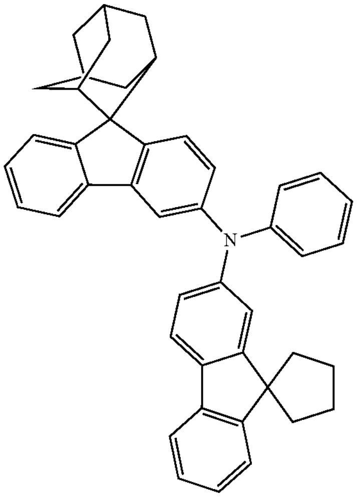
17
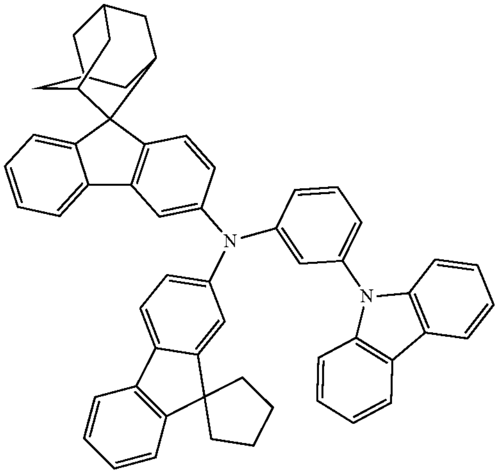
18
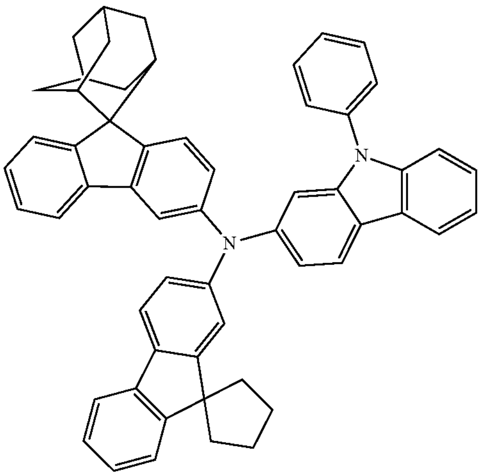
19
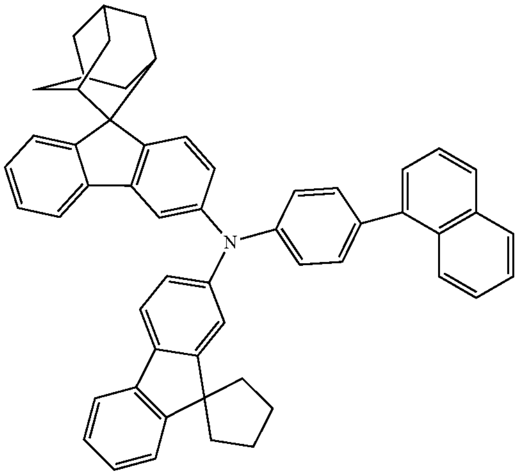

-continued
20
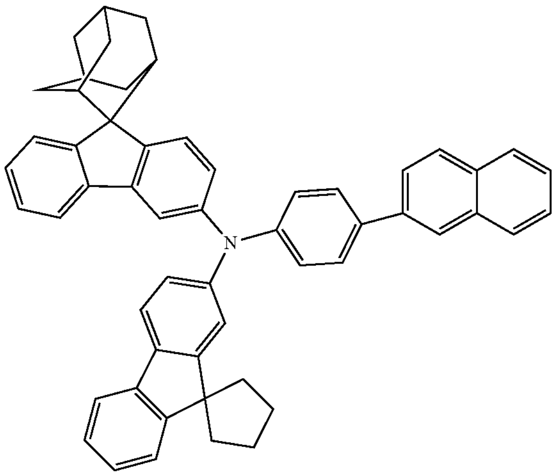
21
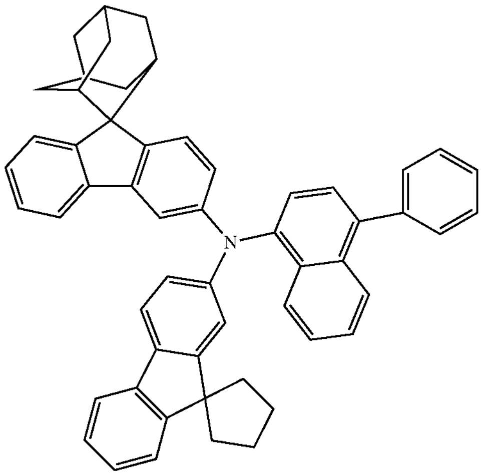
22
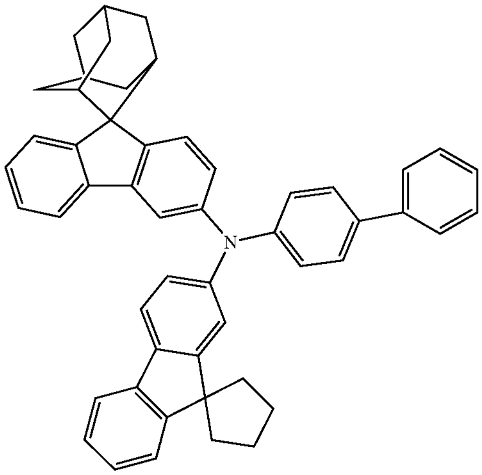
-continued
23
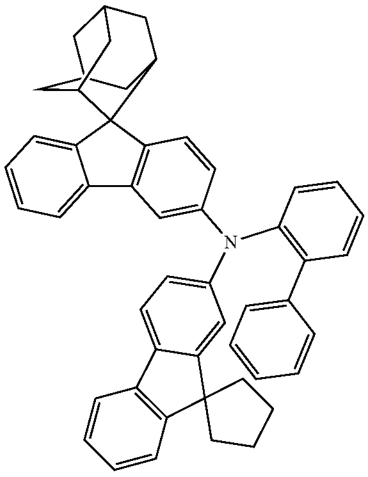
24
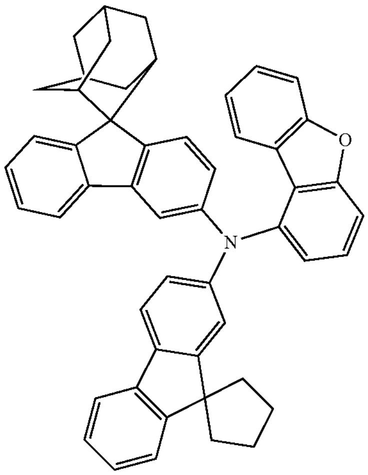
25
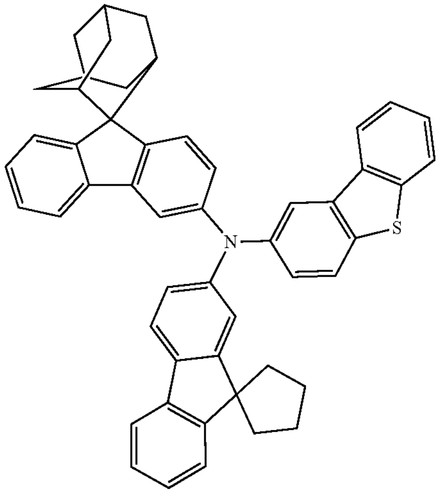

-continued
26
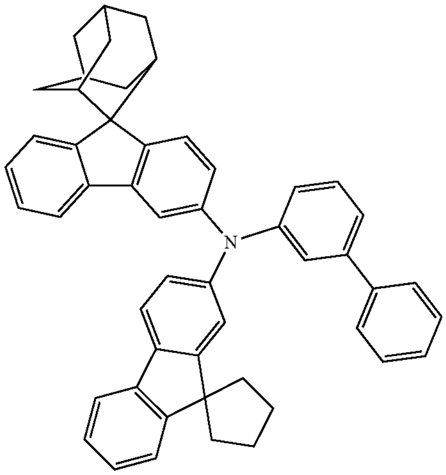
27
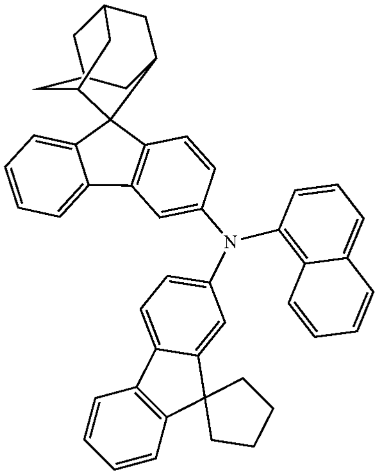
28
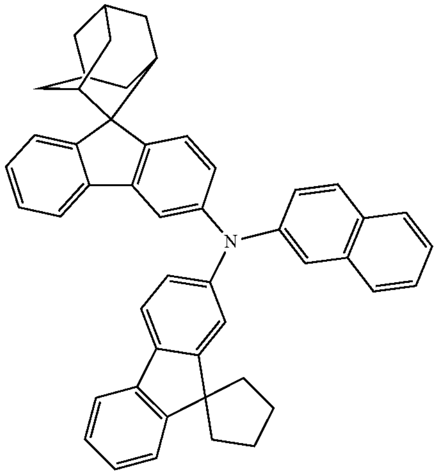
29
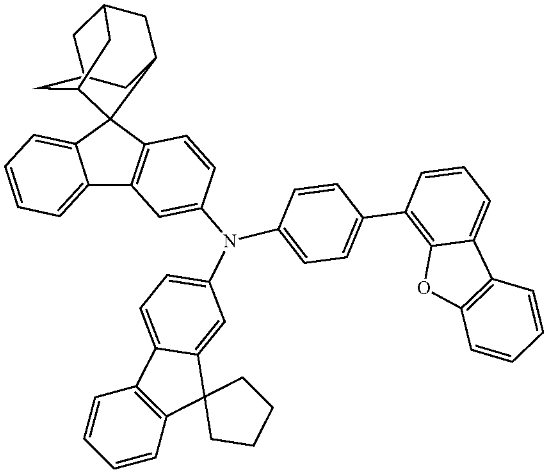
30
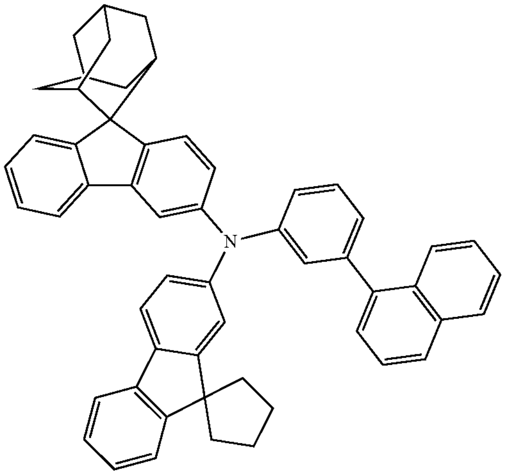
31
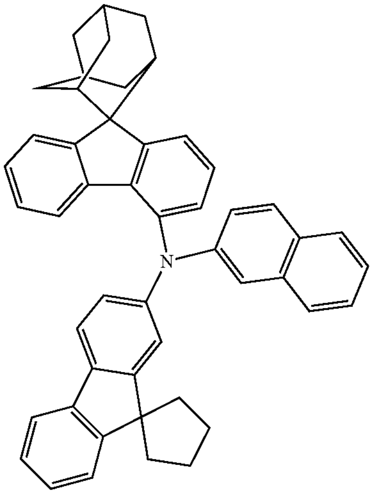

-continued
32
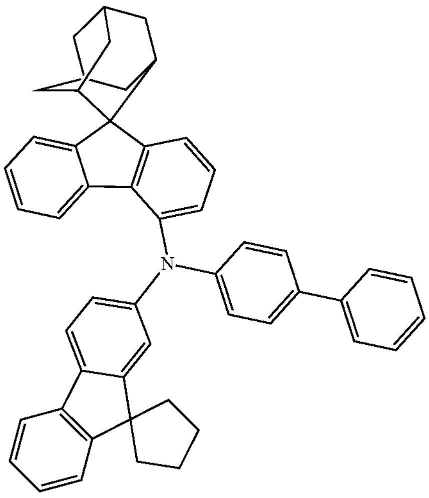
33
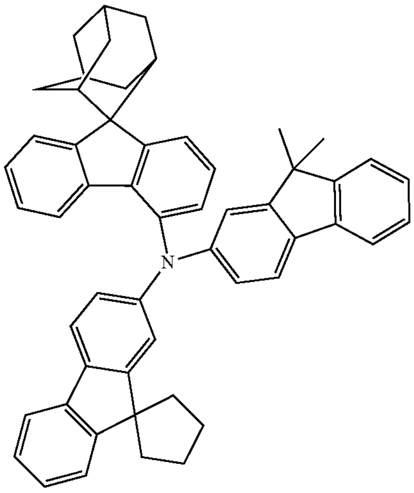
34
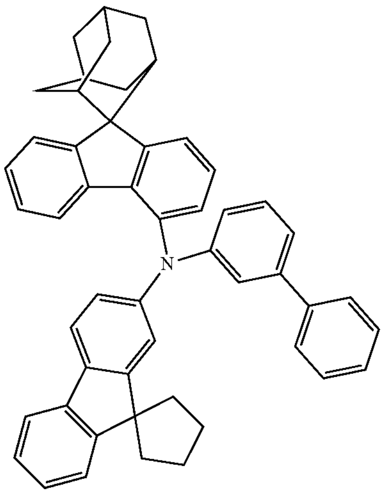
-continued
35
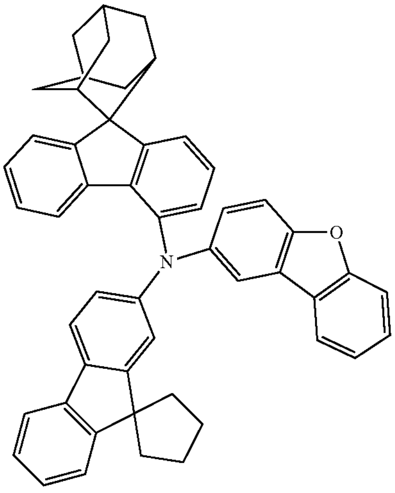
36
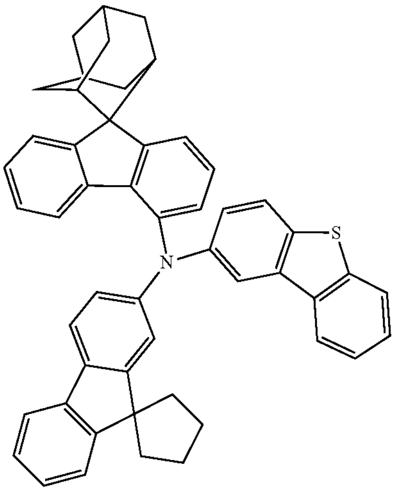
37
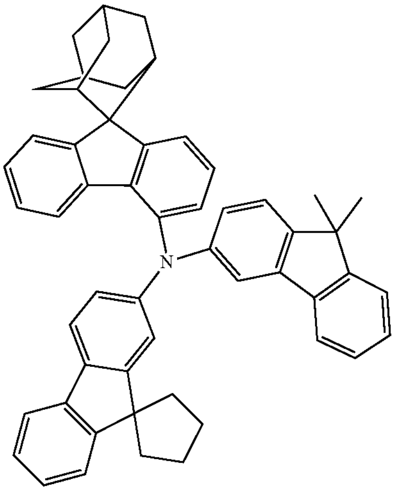

-continued
38
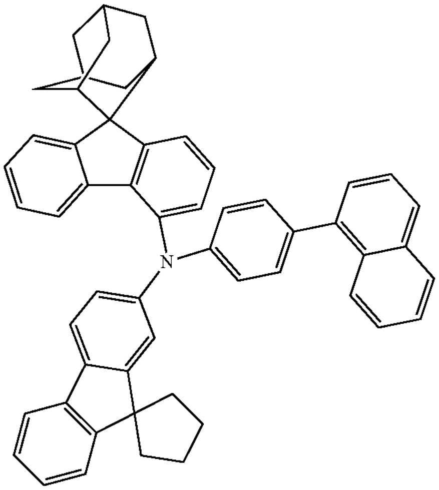
41
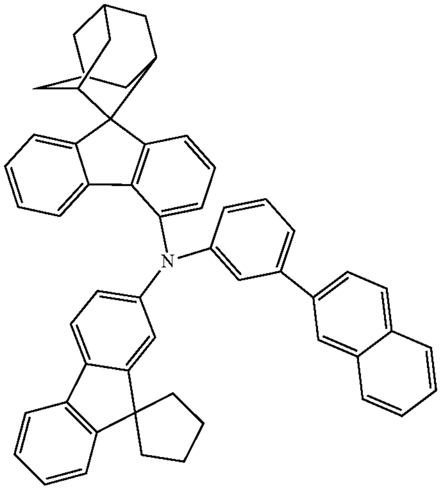
39
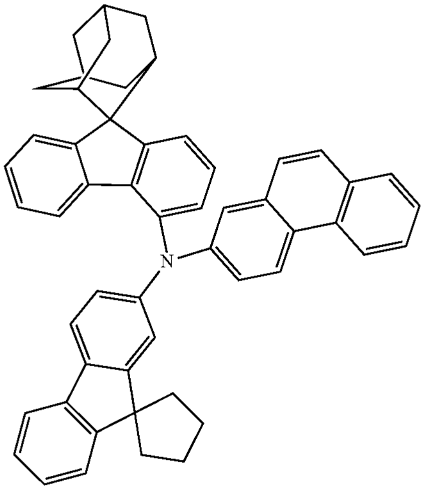
42
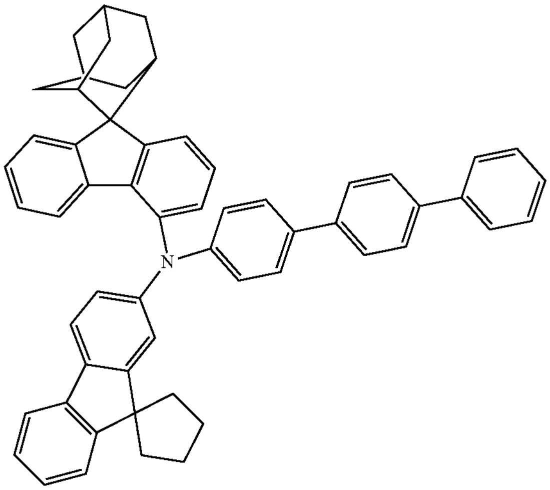
40
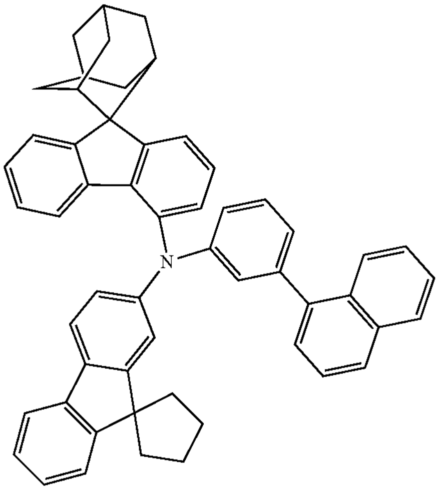
43
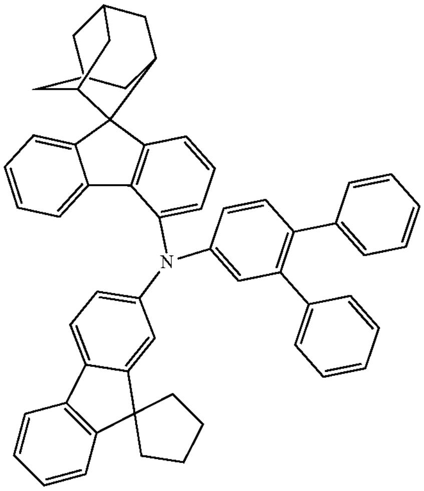

-continued
44
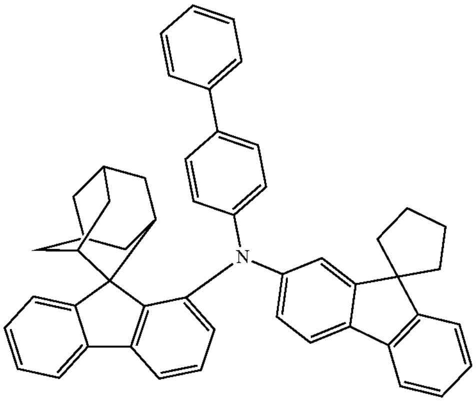
45
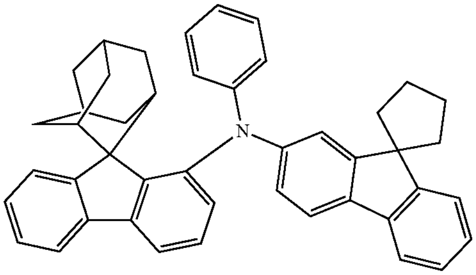
46
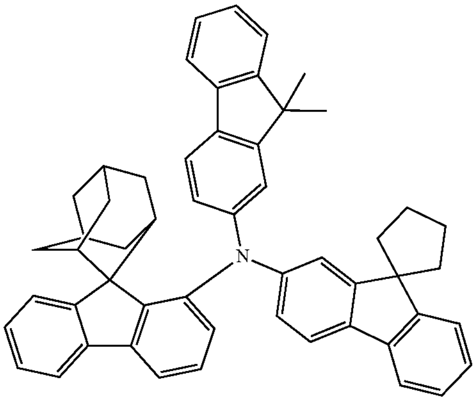
47
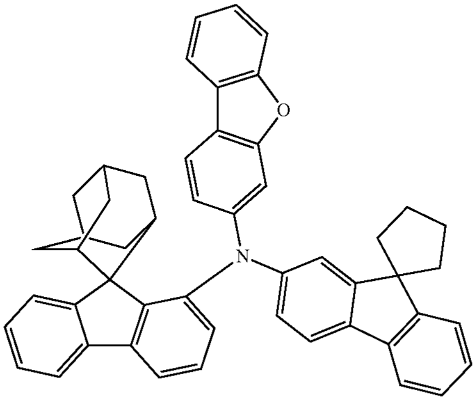
-continued
48
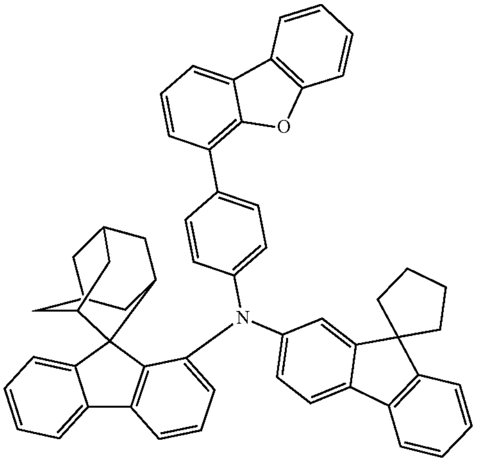
49
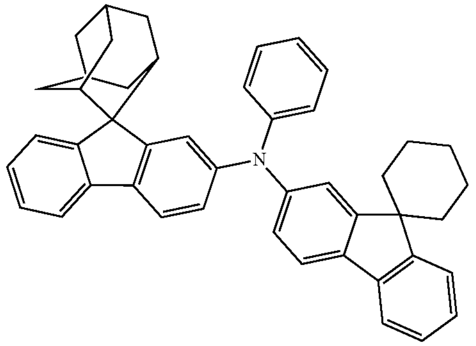
50
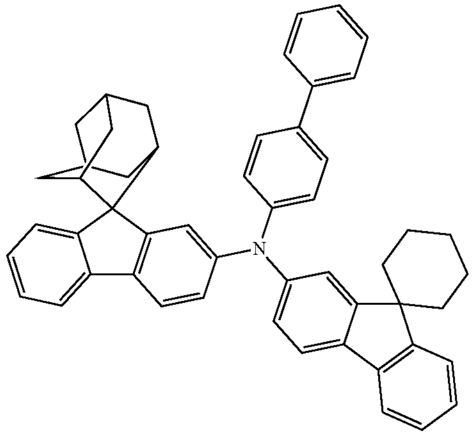
51
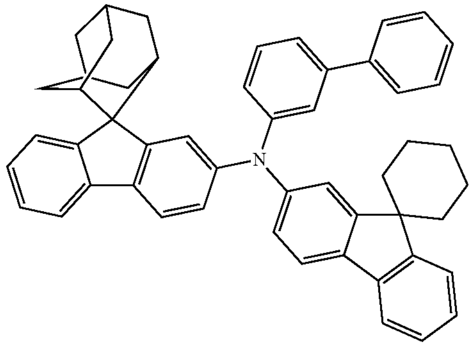

-continued
52
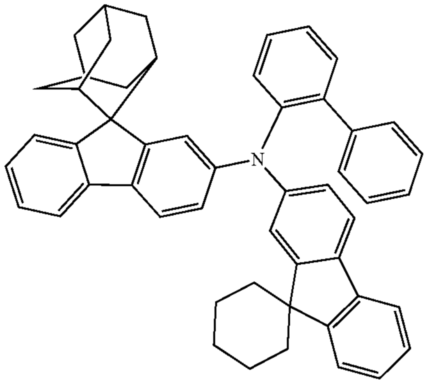
53
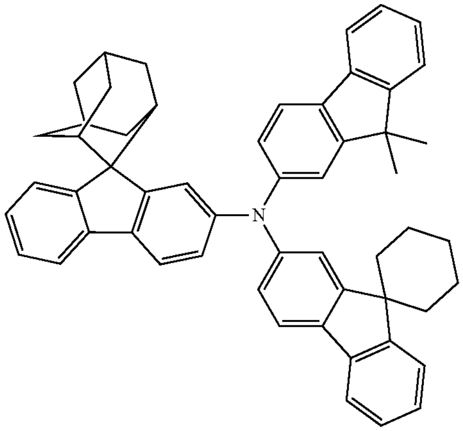
54
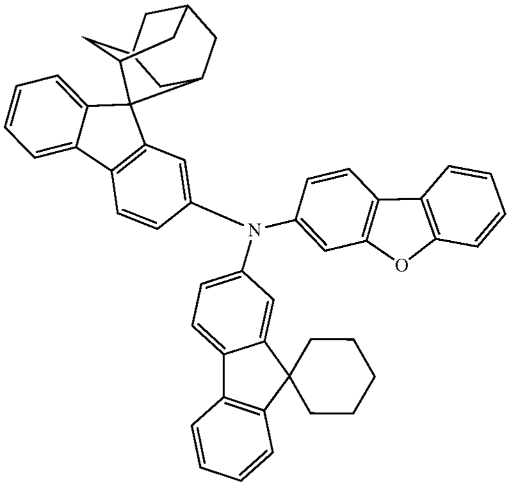
-continued
55
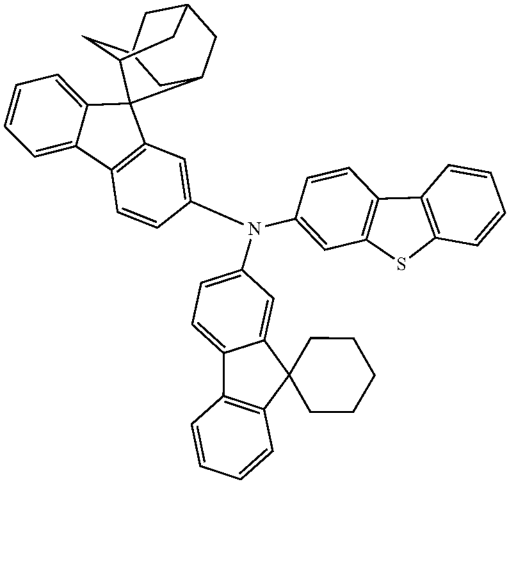
56
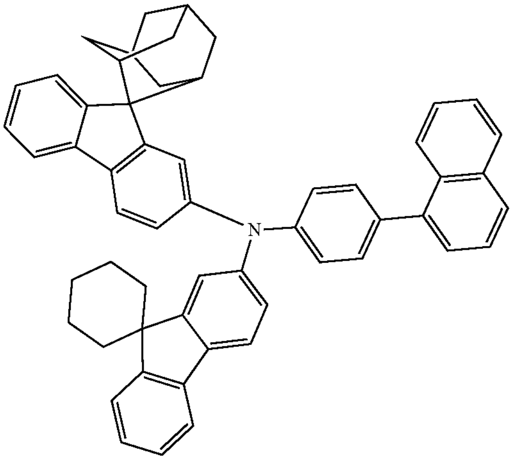
57
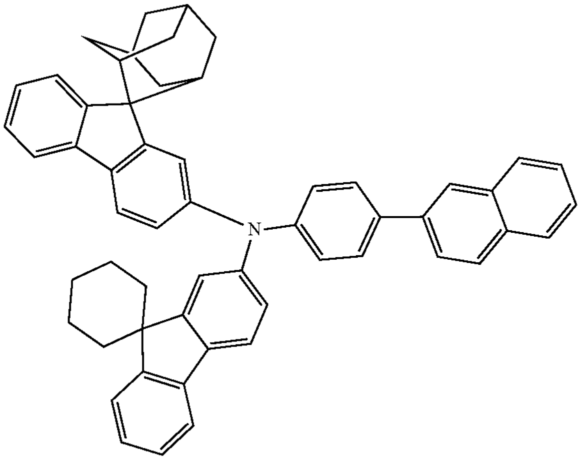

-continued
58
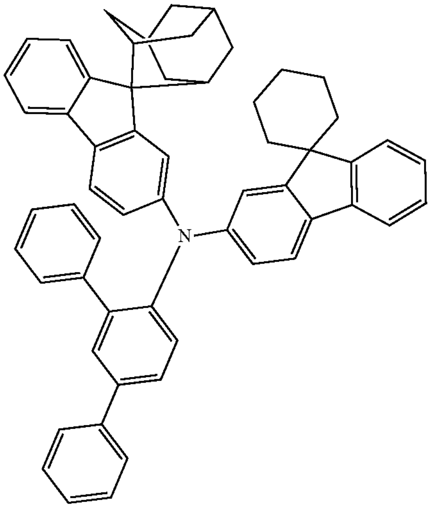
59
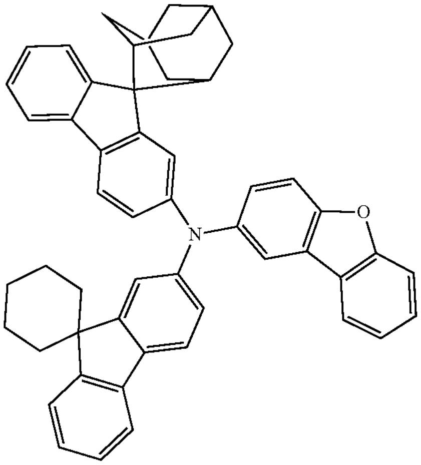
60
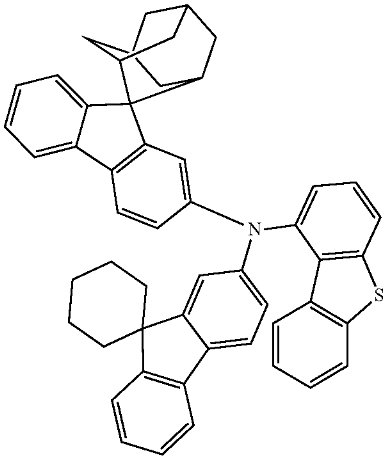
-continued
61
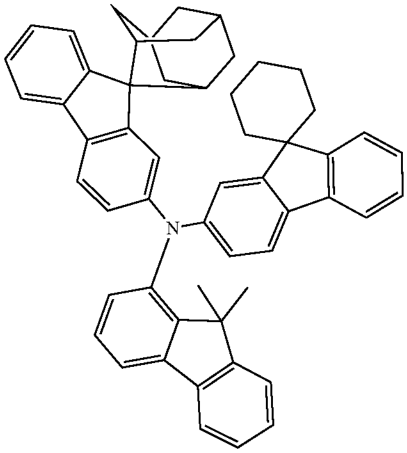
62
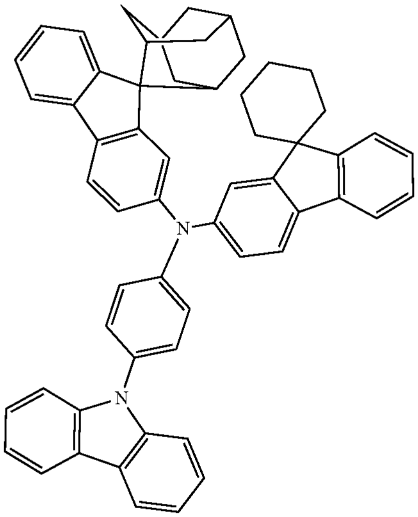
63
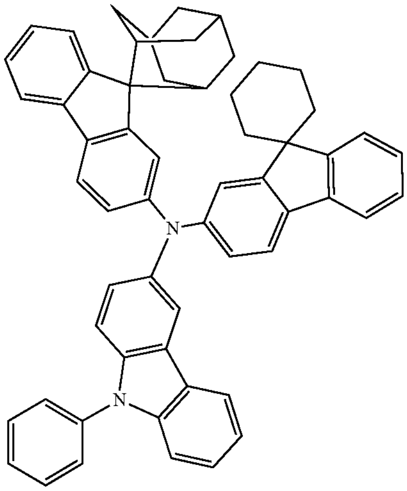

-continued
64
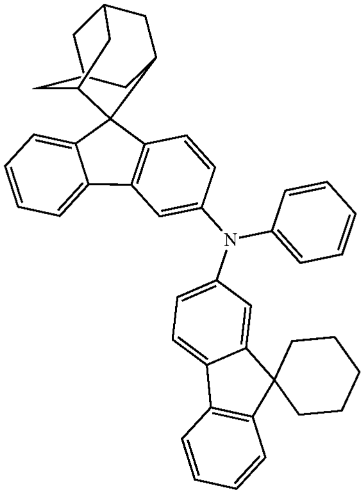
65
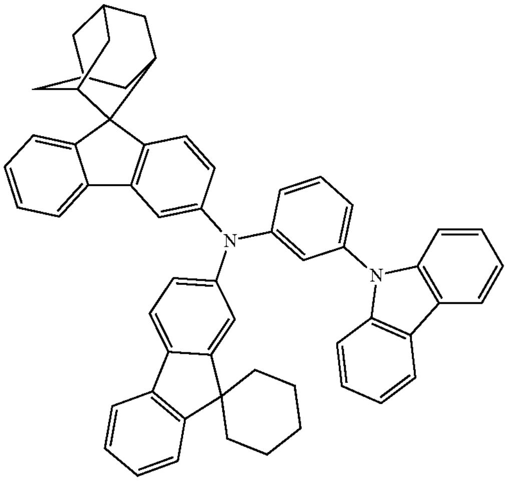
66
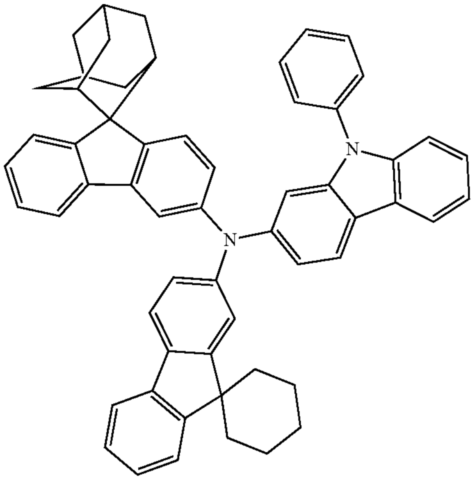
-continued
67
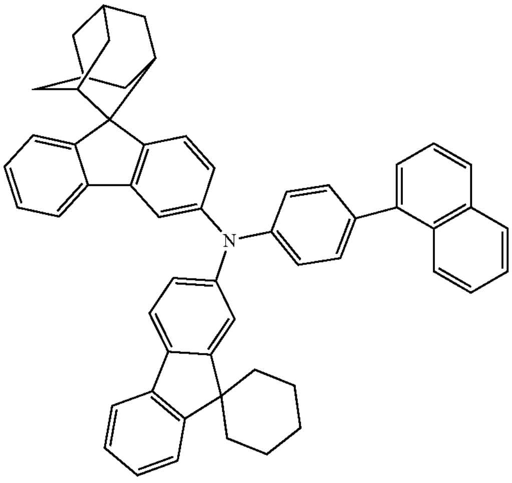
68
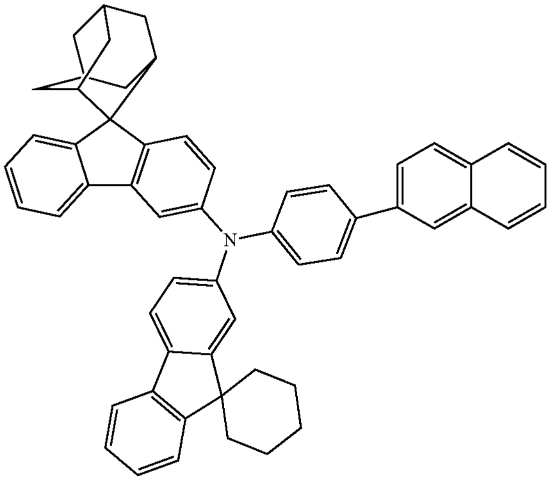
69
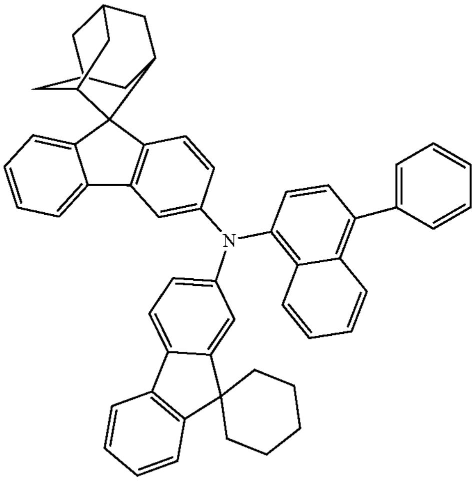

-continued
70
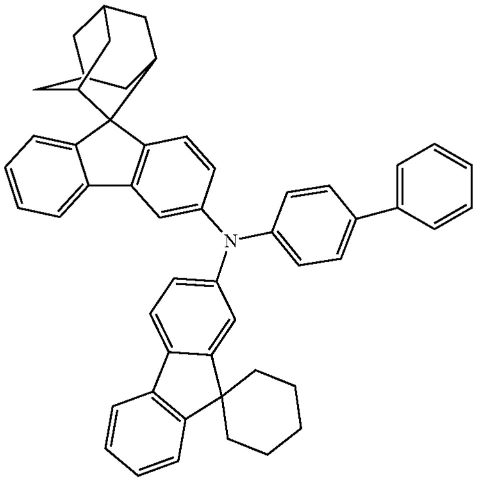
71
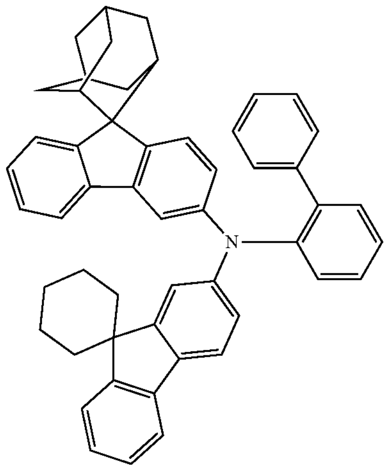
72
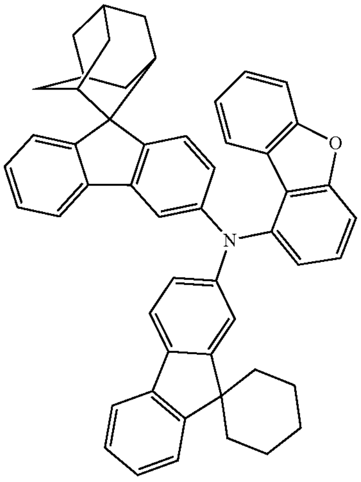
-continued
73
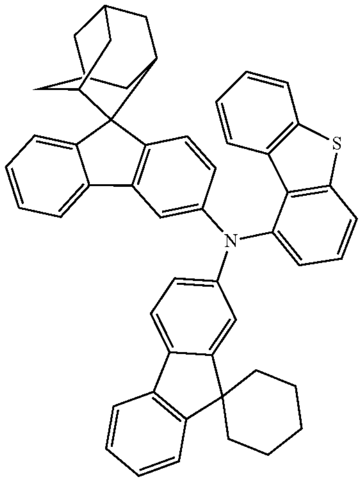
74
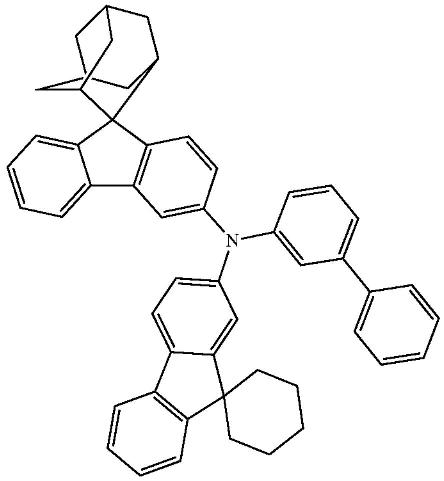
75
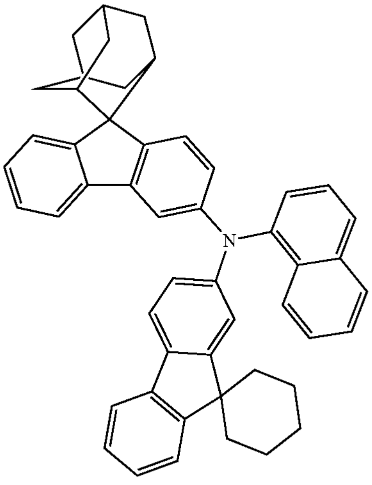

-continued
76
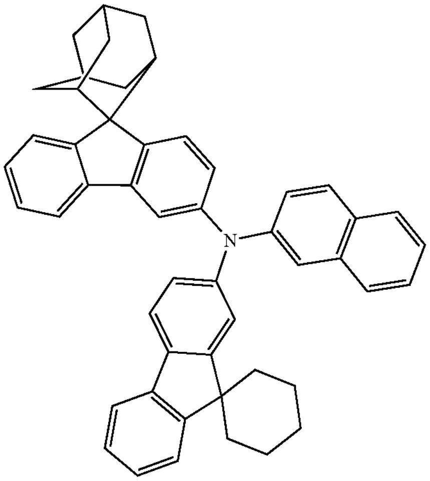
77
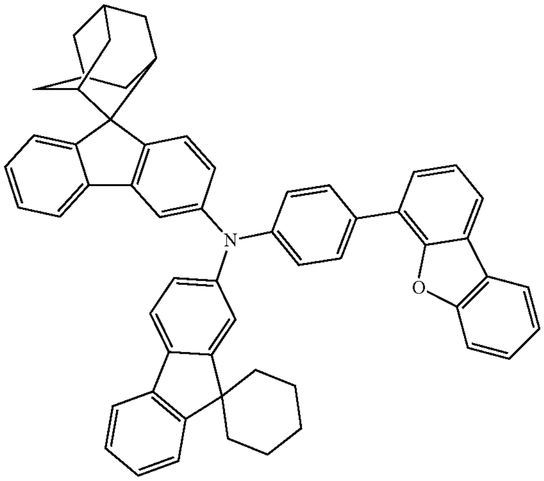
78
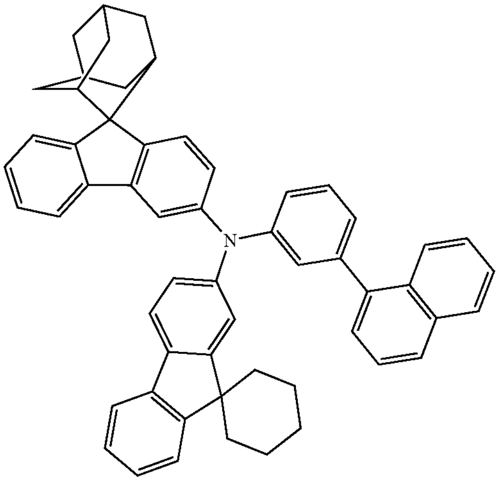
-continued
79
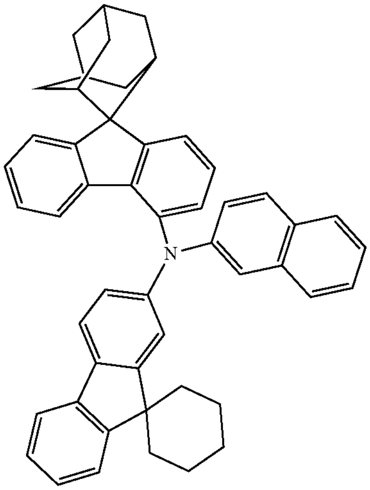
80
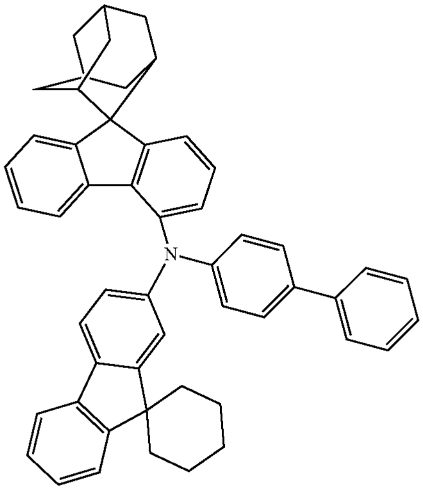
81
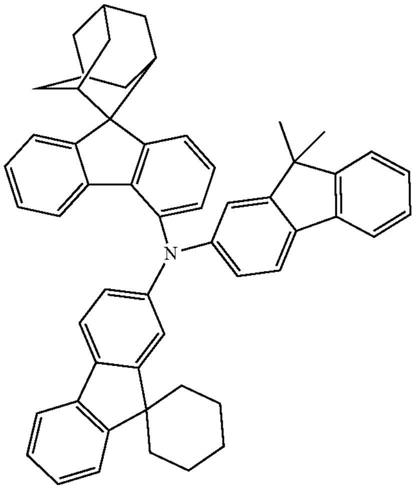

-continued
82
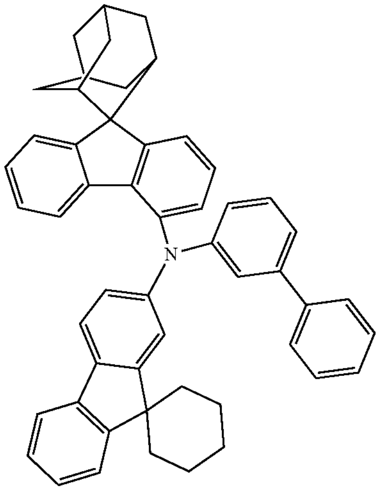
83
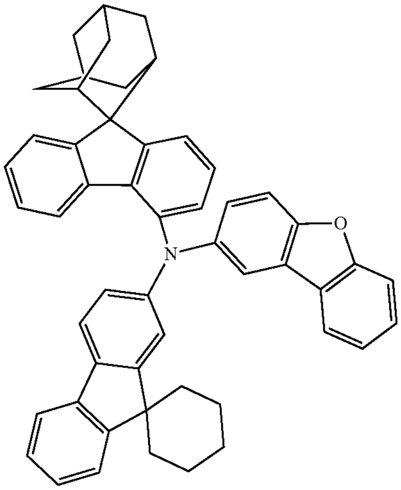
84
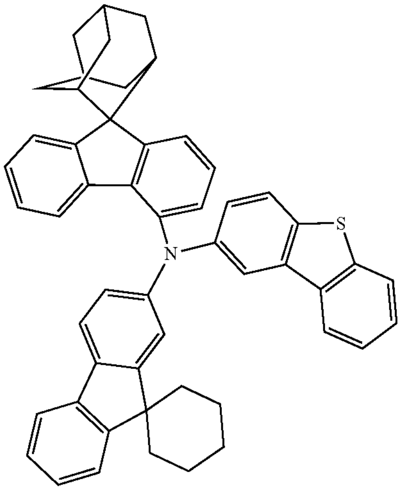
-continued
85
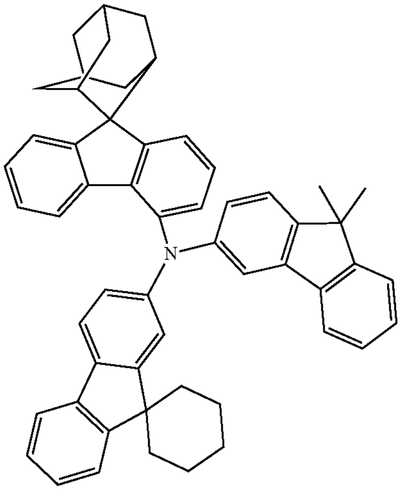
86
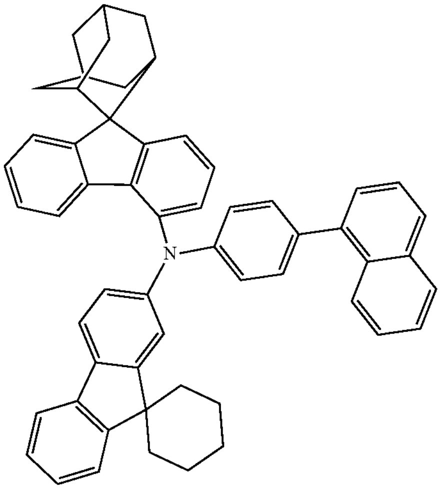
87
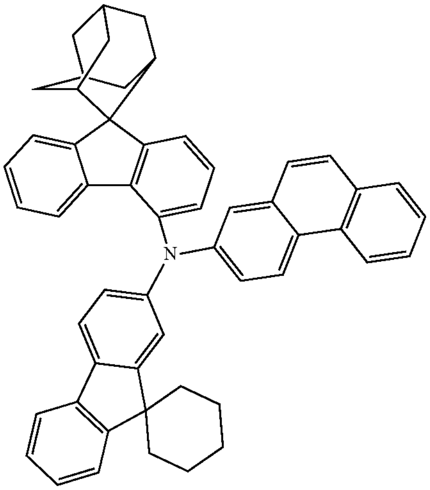

-continued
88
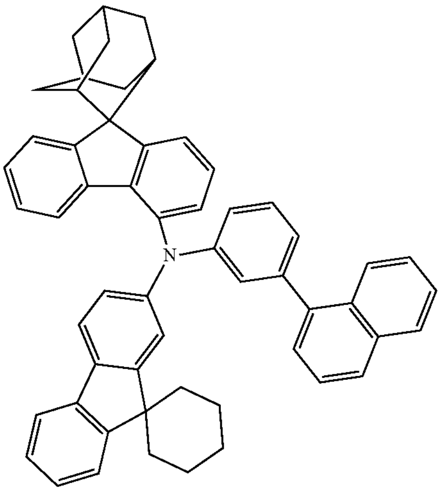
89
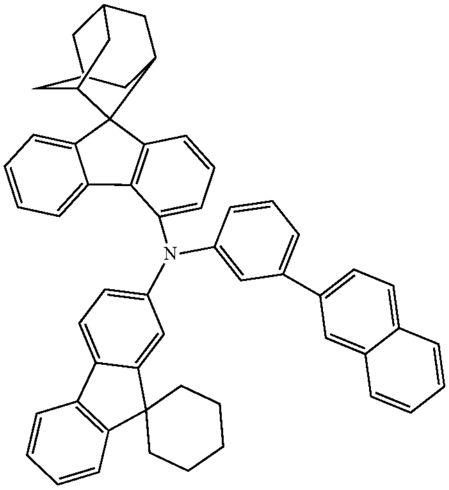
90
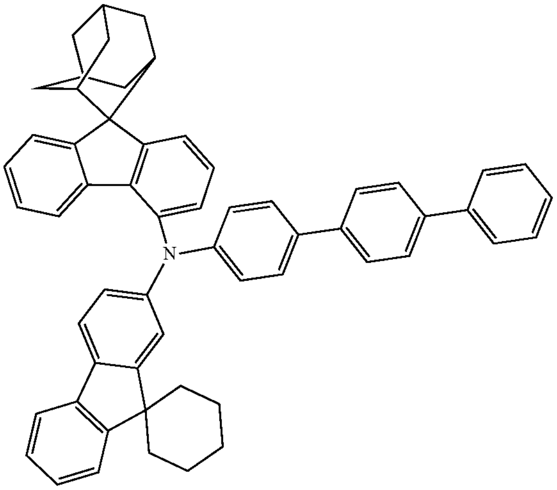
-continued
91
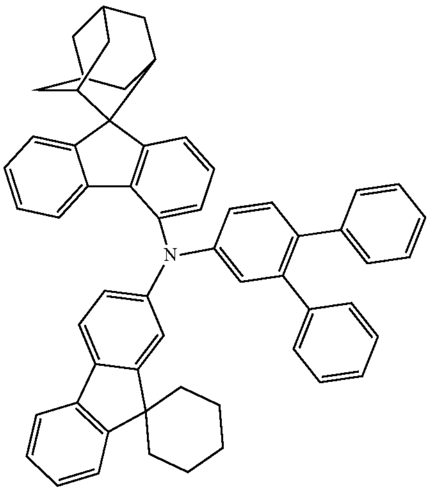
92
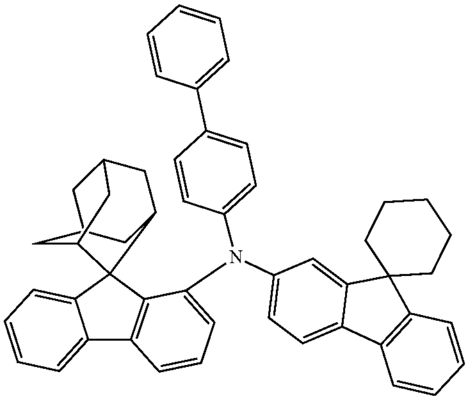
93
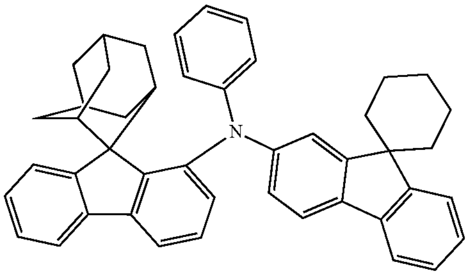
94
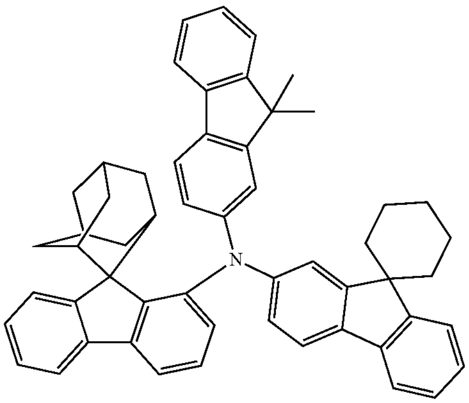

95
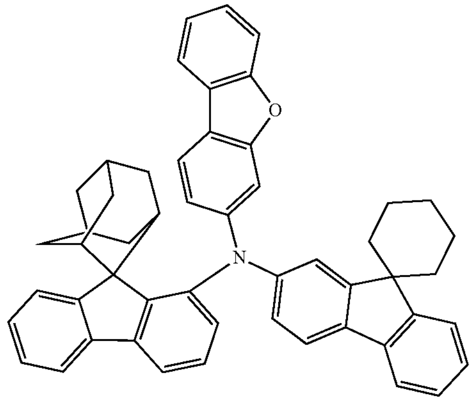
96
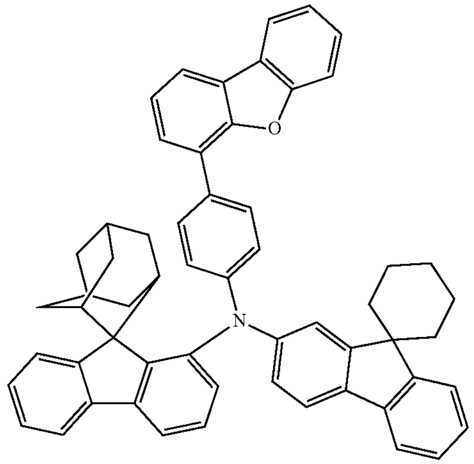
97
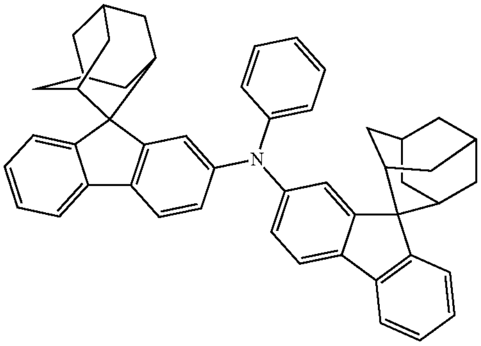
98
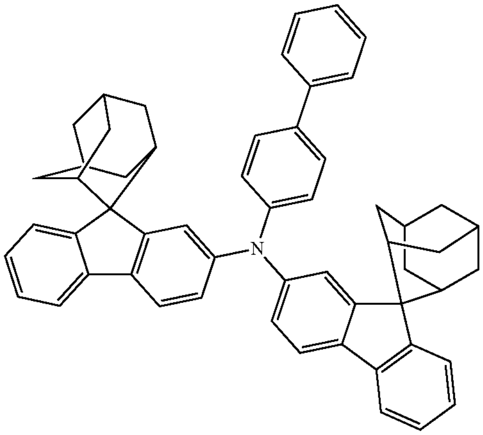
99
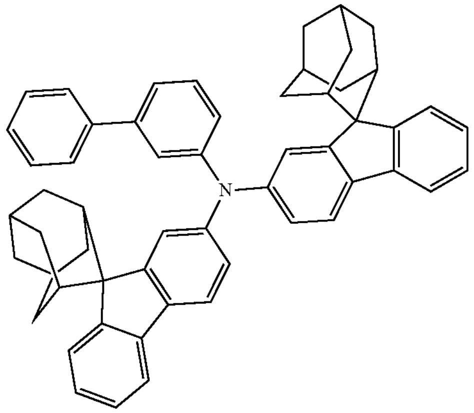
100
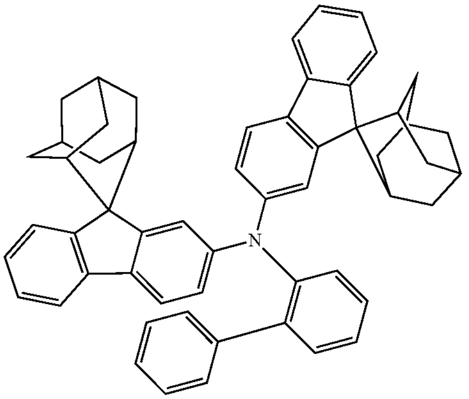
101
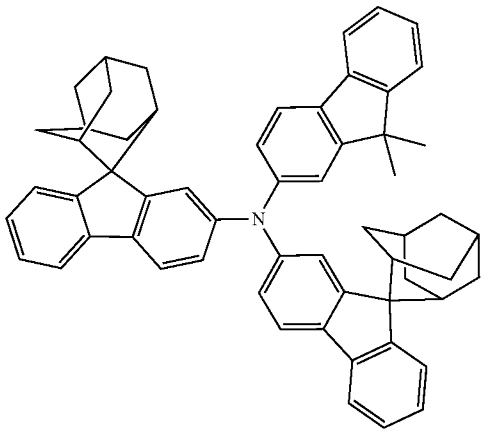

-continued
102
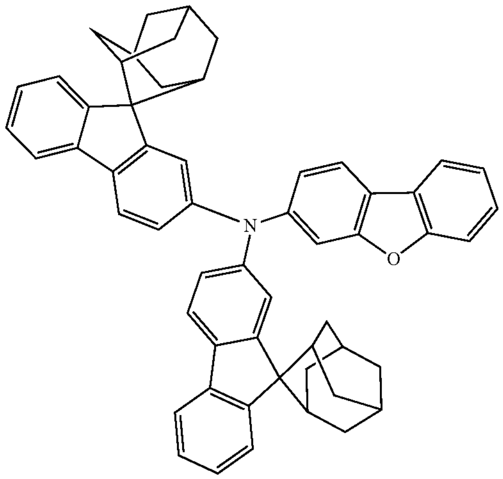
103
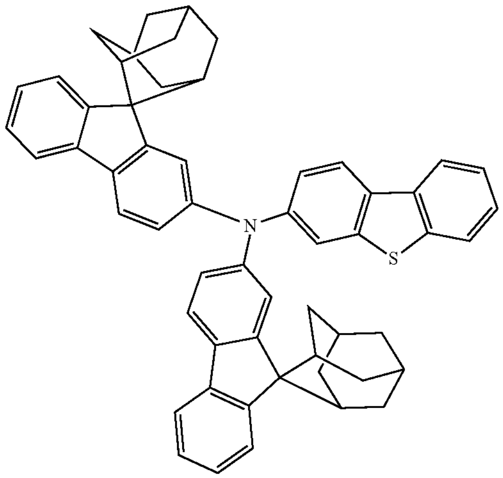
104
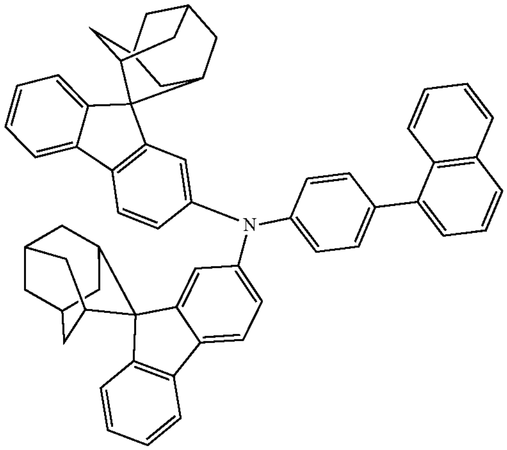
-continued
105
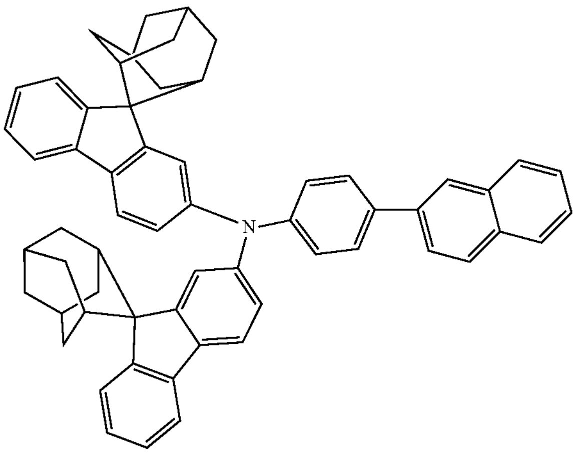
106
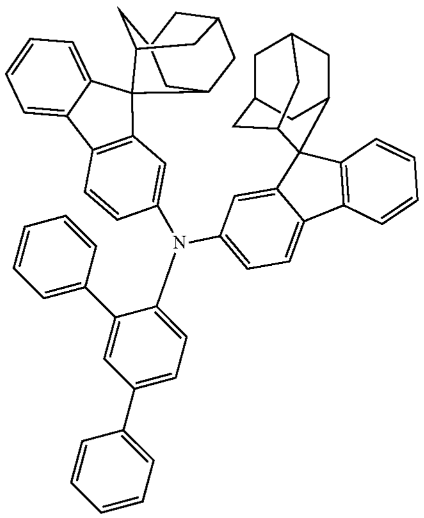
107
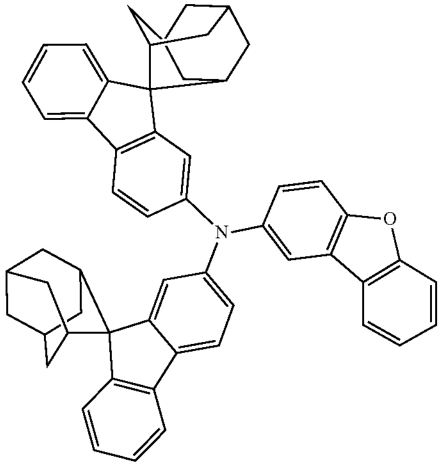

-continued
108
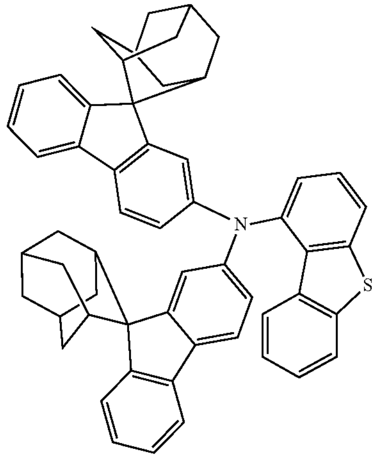
109
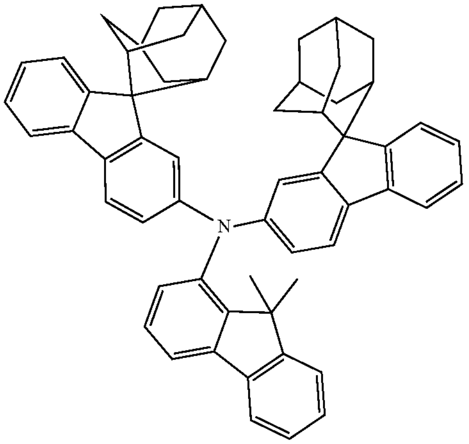
110
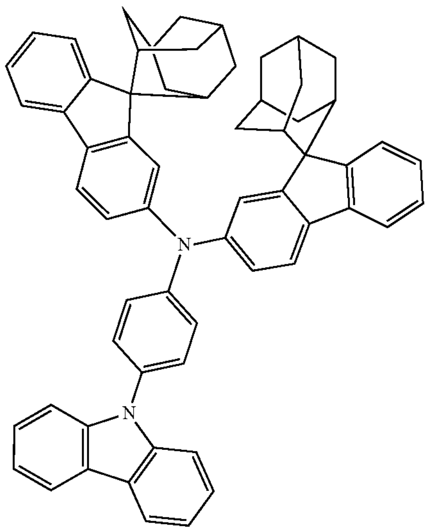
-continued
111
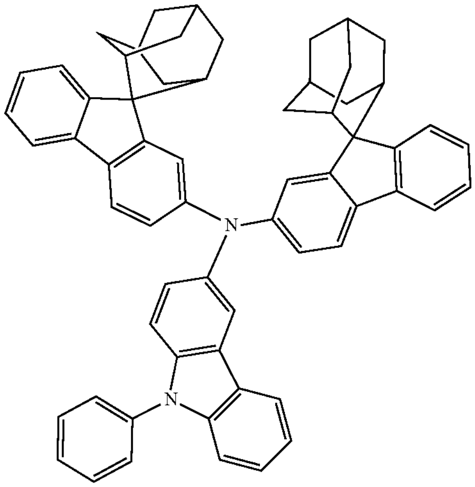
112
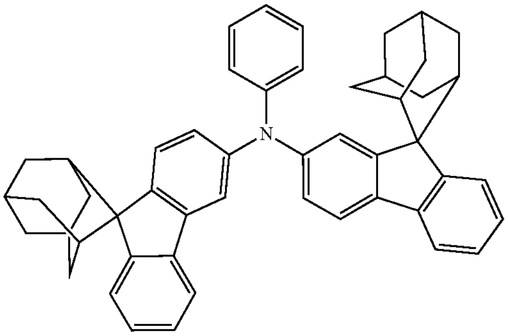
113
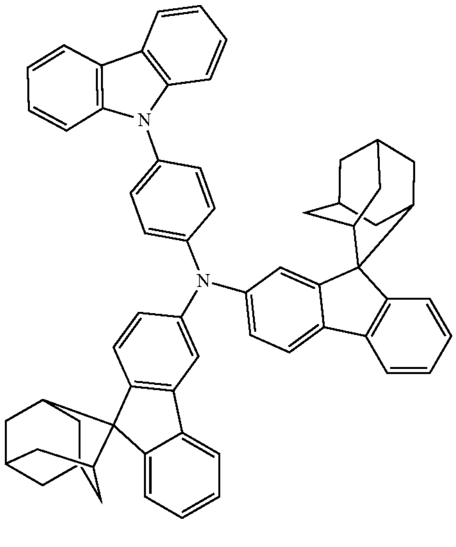

-continued
114
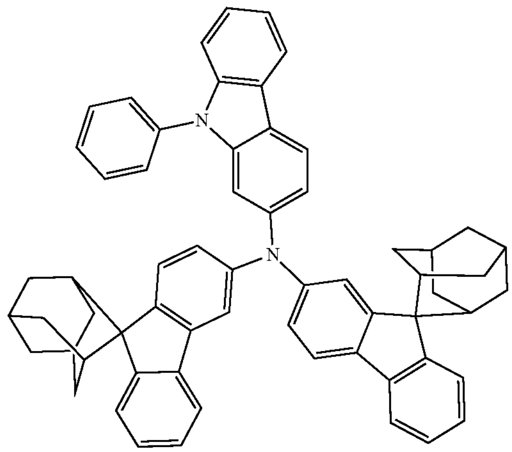
115
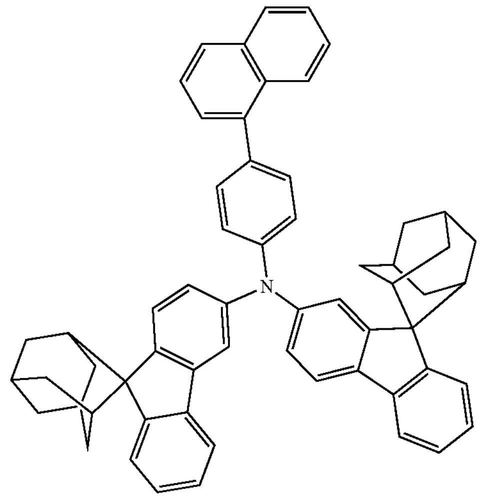
116
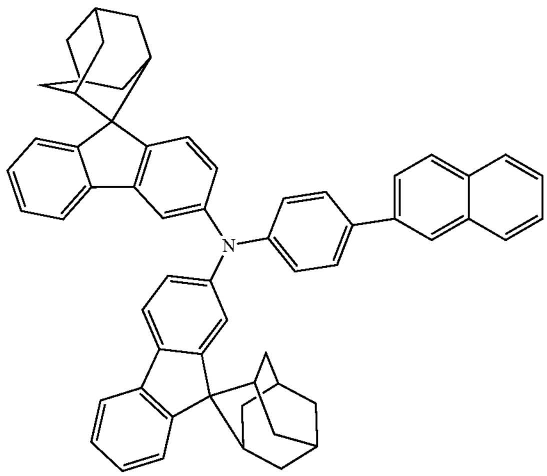
-continued
117
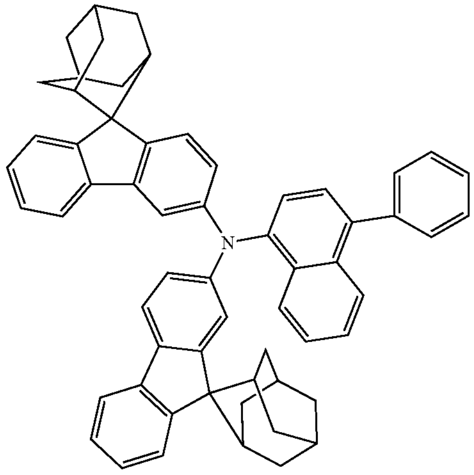
118
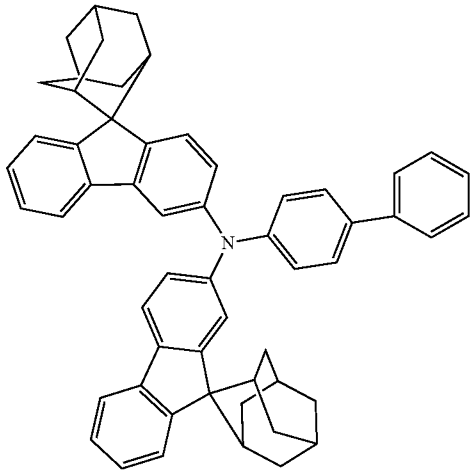
119
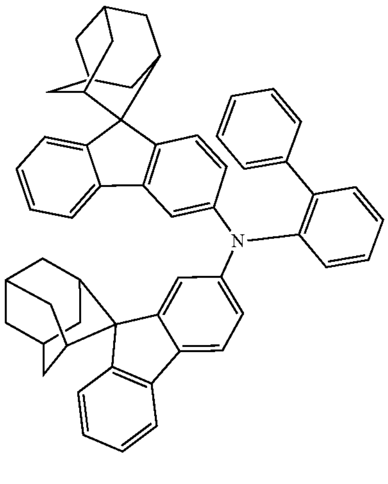

-continued
120
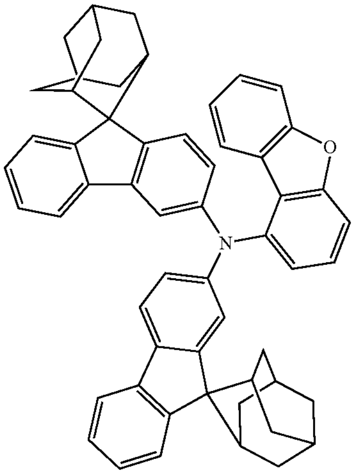
121
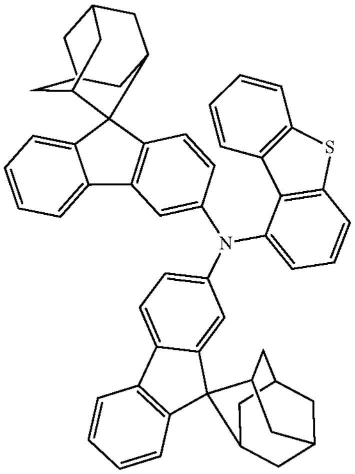
122
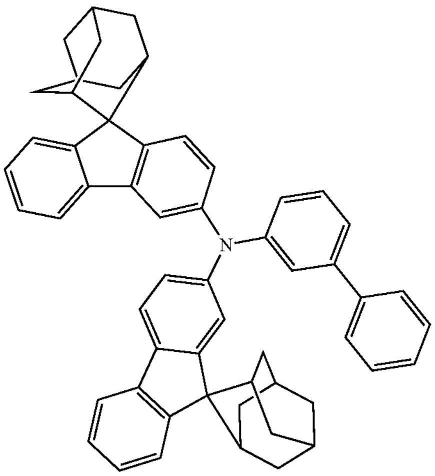
-continued
123
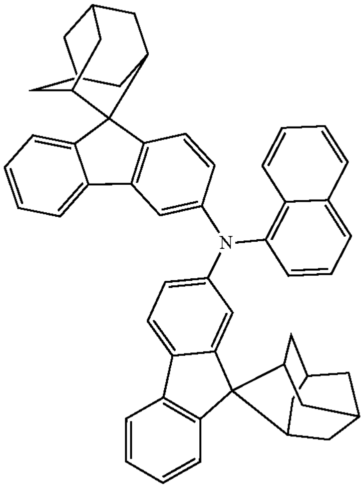
124
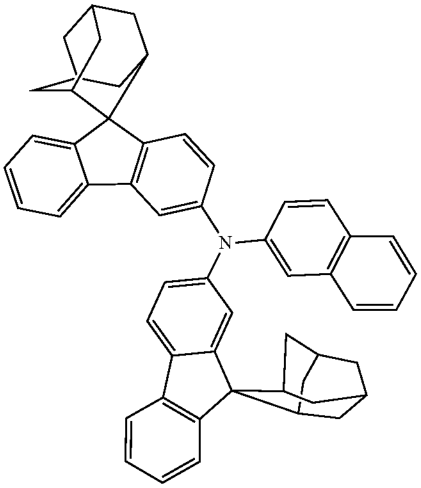
125
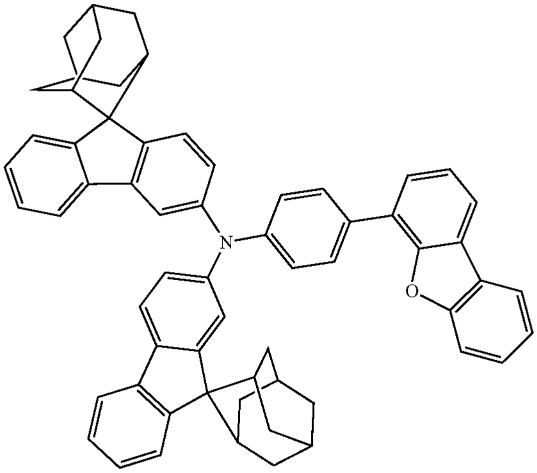

-continued
126
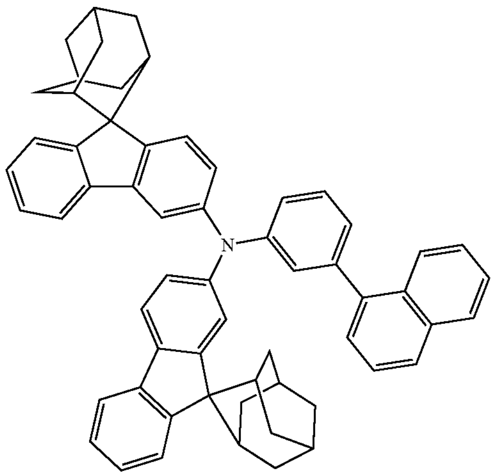
127
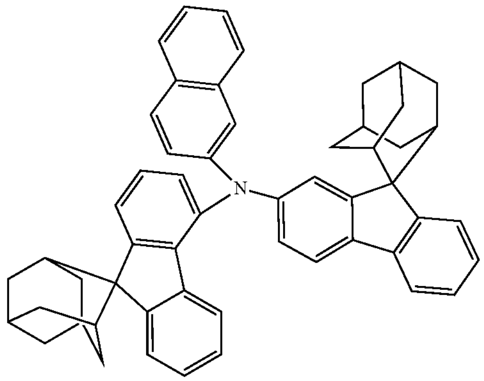
128
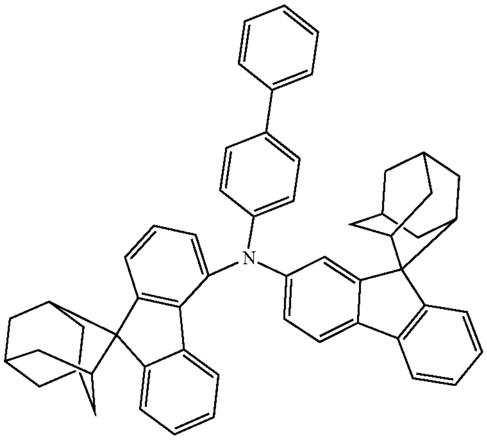
-continued
129
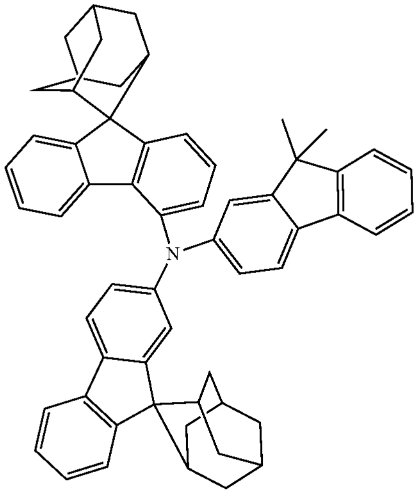
130
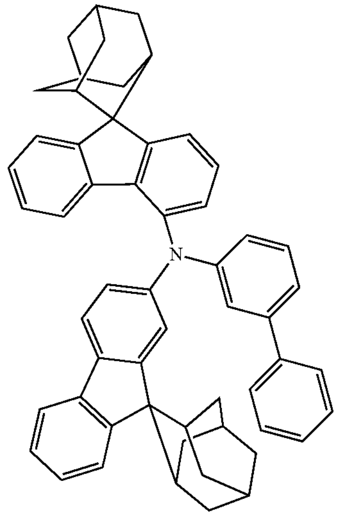
131
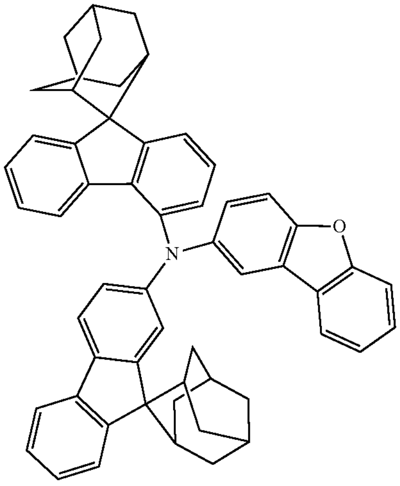

-continued
132
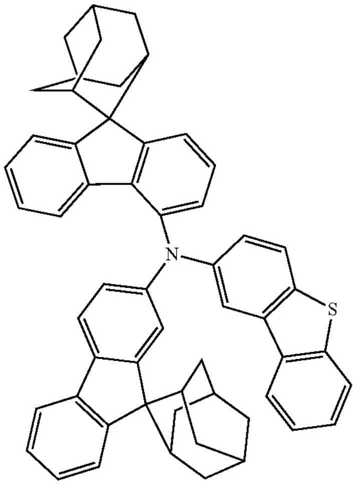
133
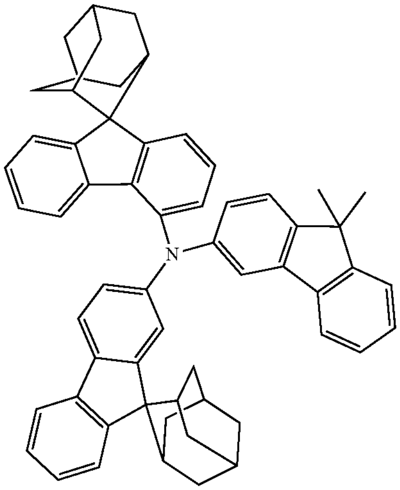
134
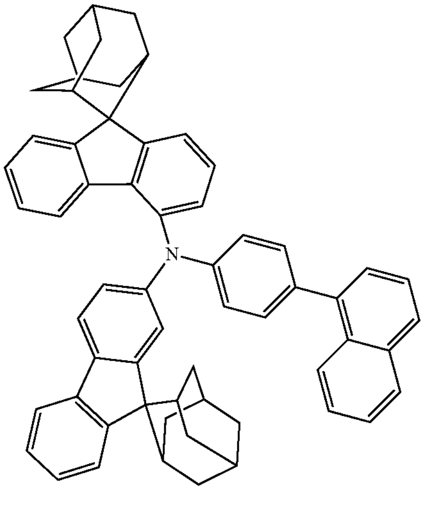
-continued
135
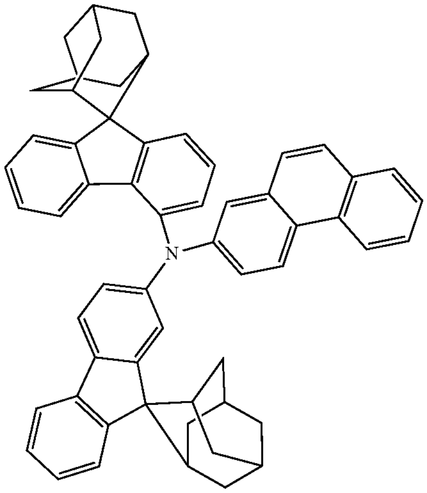
136
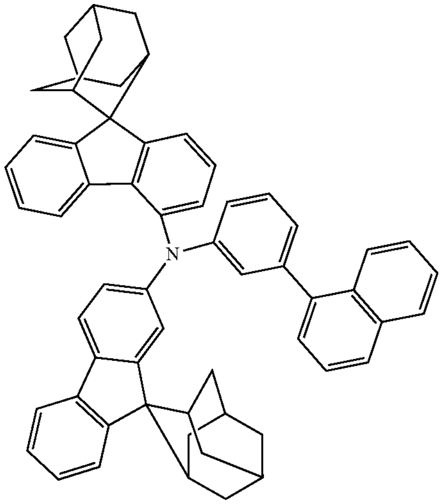
137
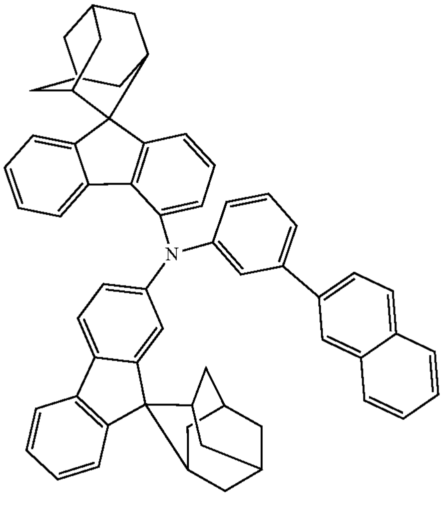

-continued
138
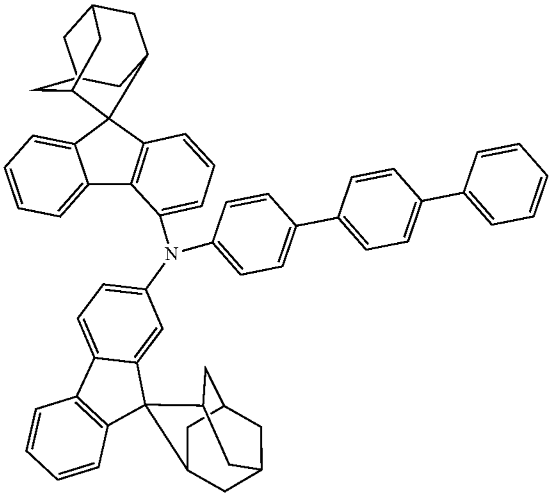
139
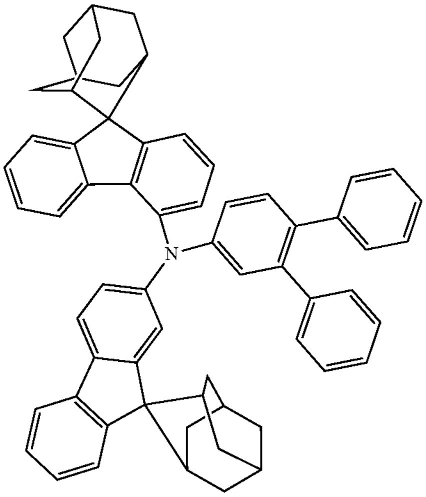
140
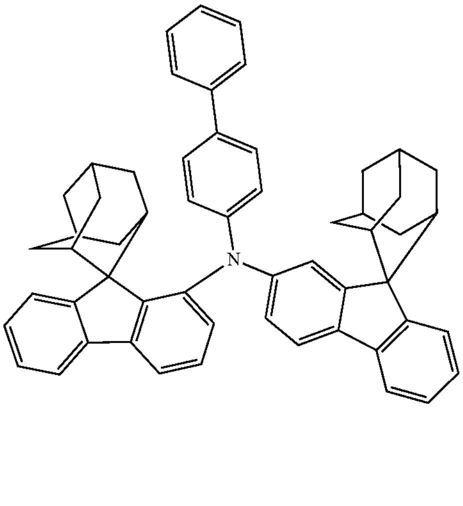
-continued
141
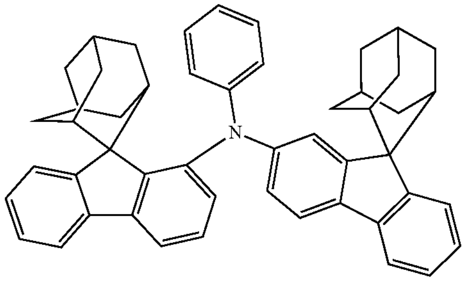
142
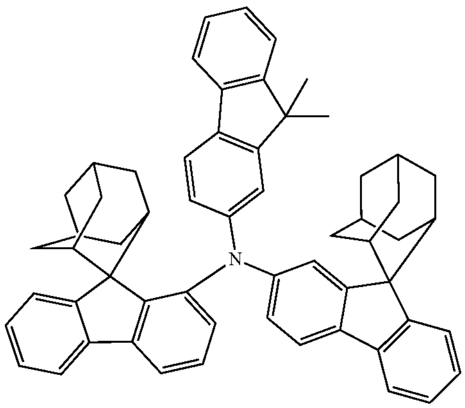
143
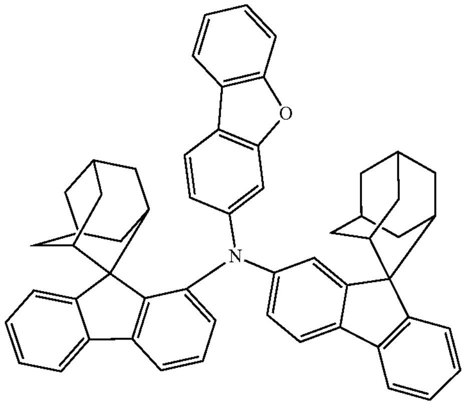
144
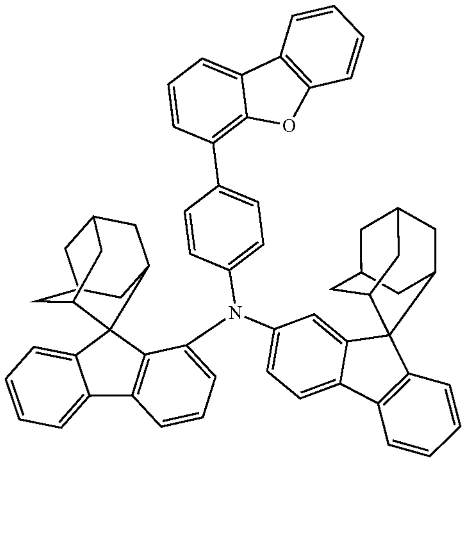

-continued
145
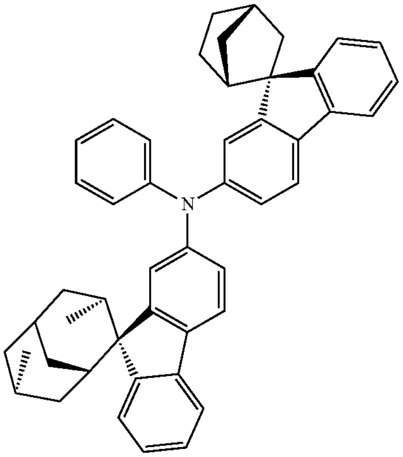
146
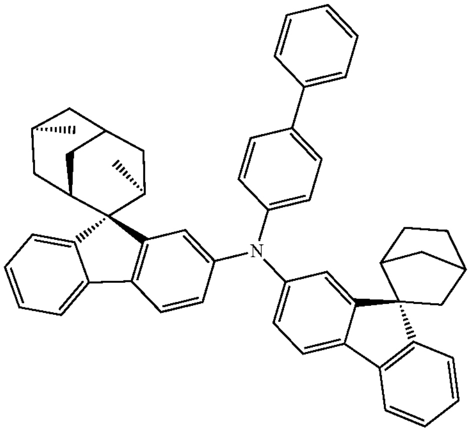
147
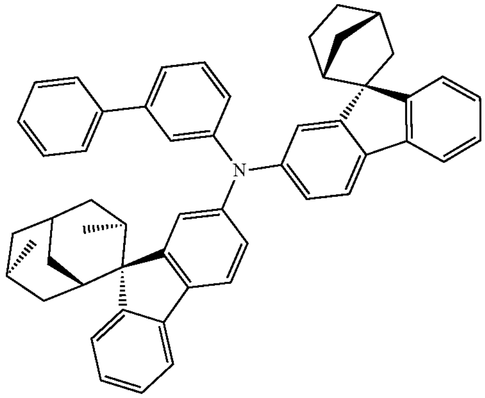
-continued
148
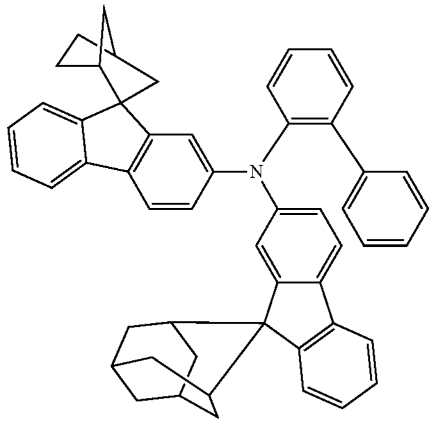
149
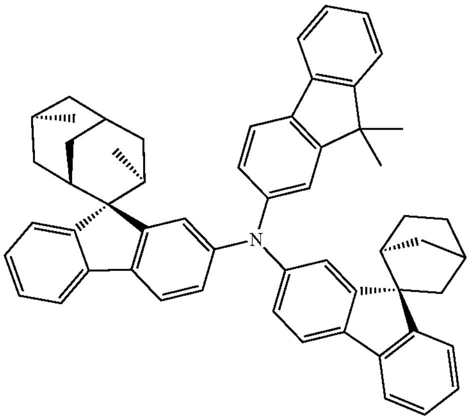
150
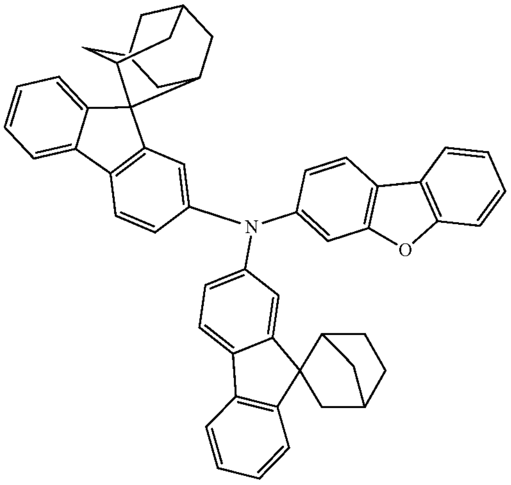

-continued
151
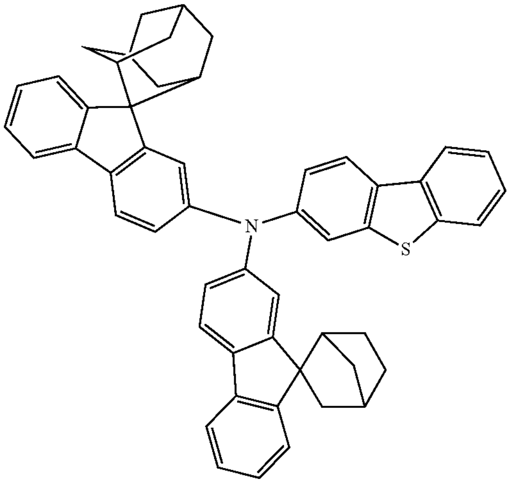
152
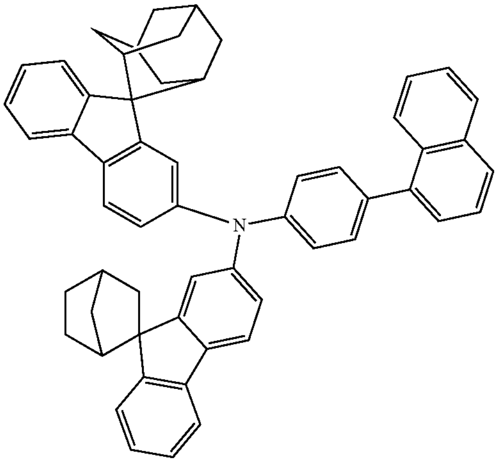
153
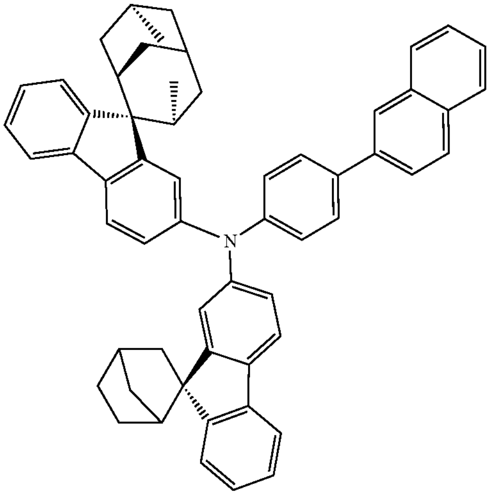
-continued
154
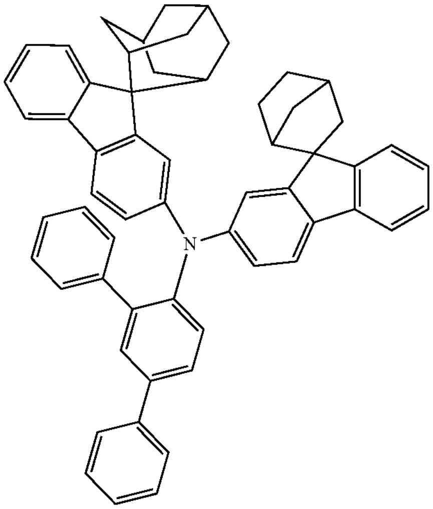
155
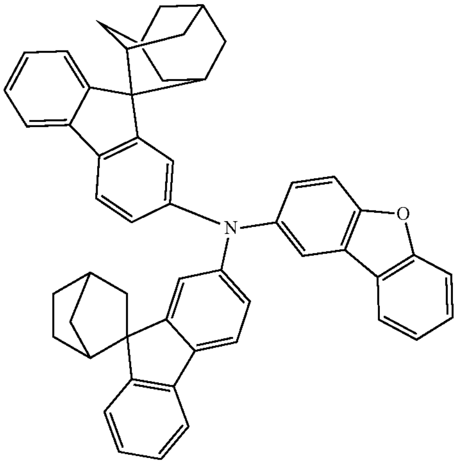
156
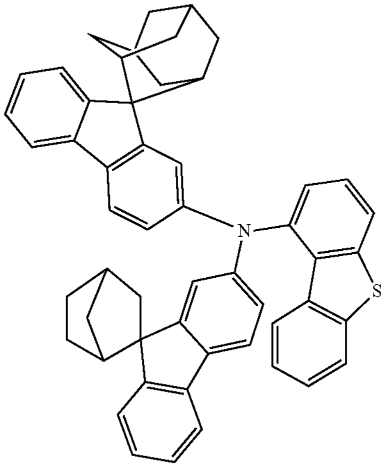

157
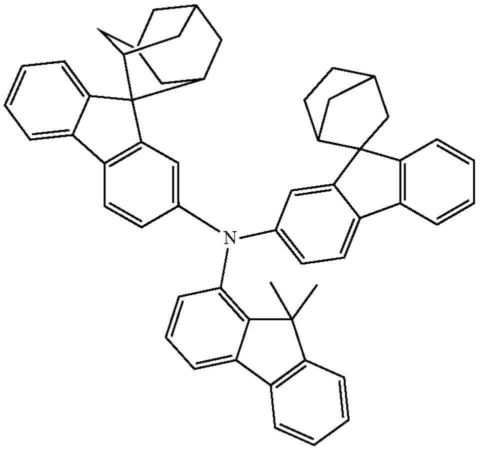
158
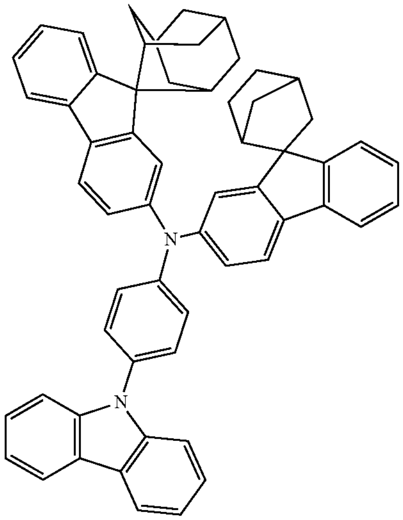
159
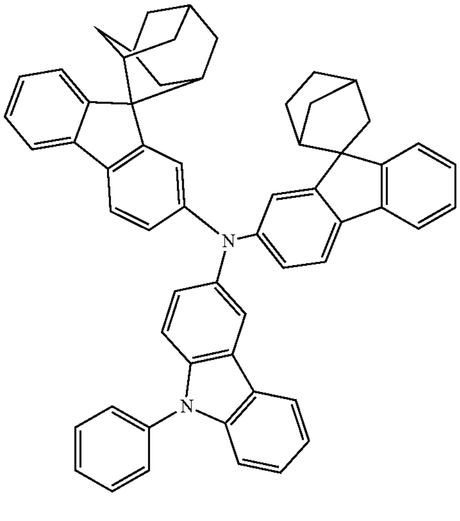
160
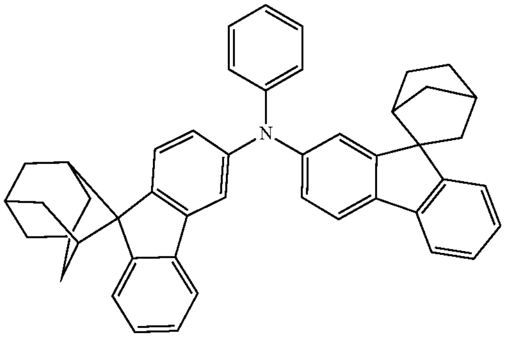
161
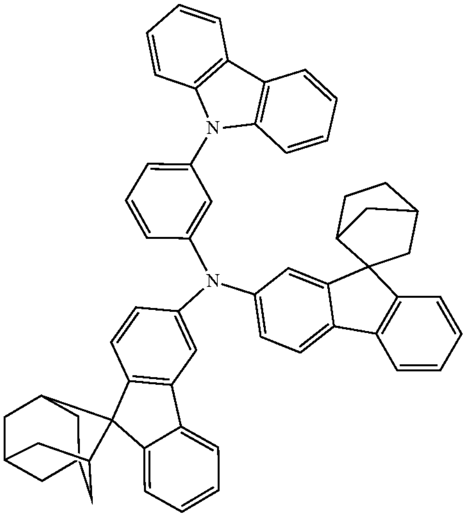
162
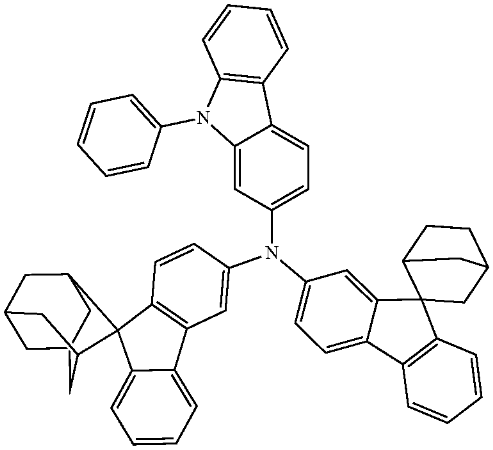

-continued
163
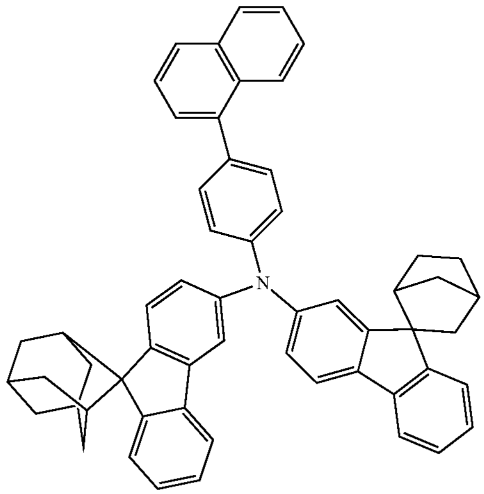
164
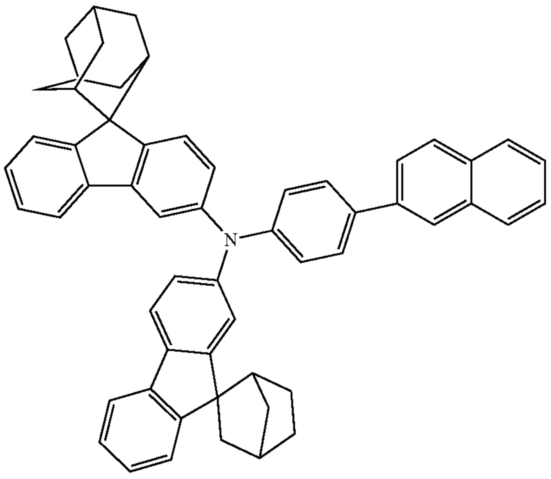
165
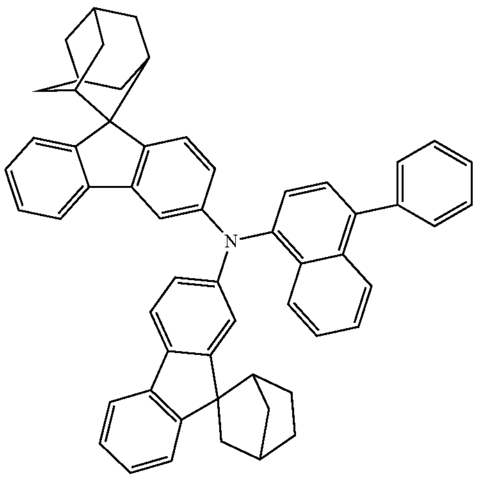
-continued
166
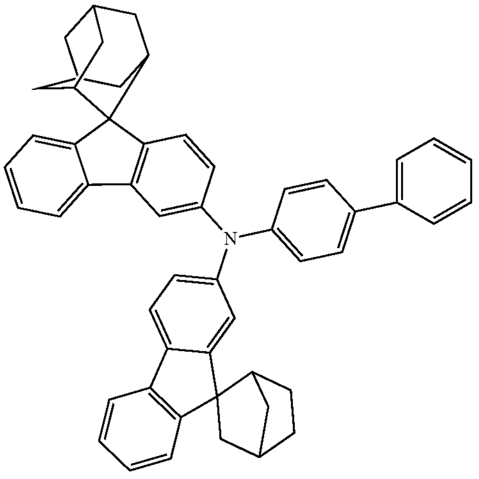
167
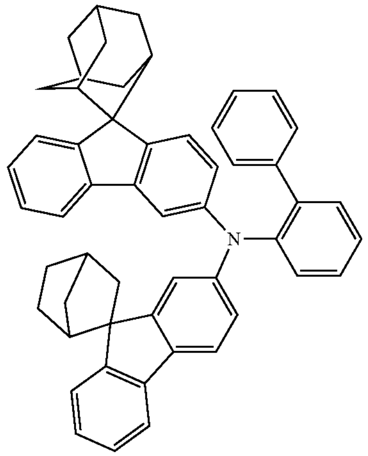
168
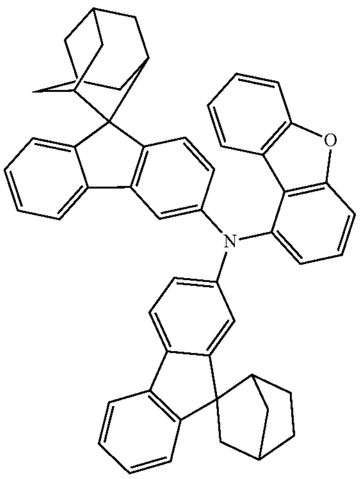

-continued
169
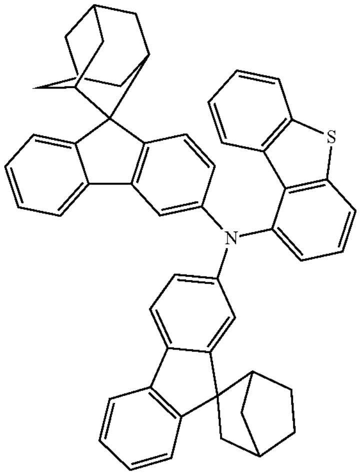
170
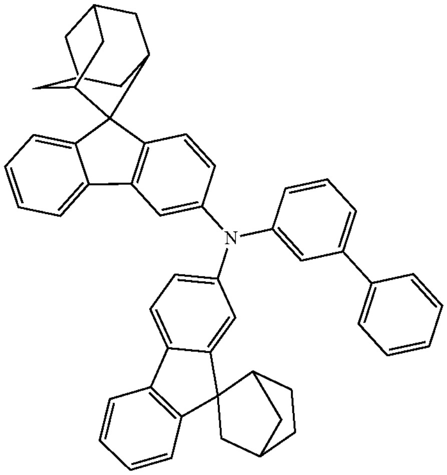
171
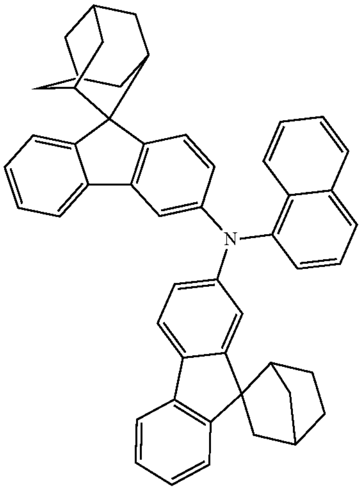
-continued
172
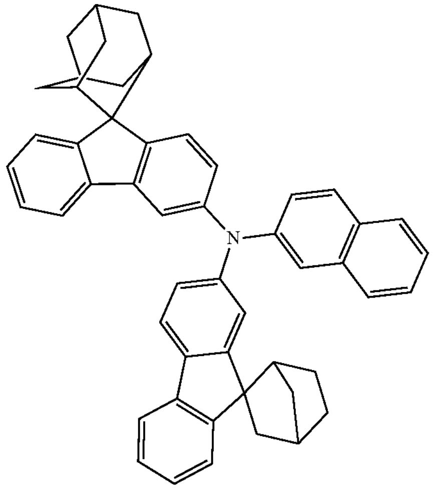
173
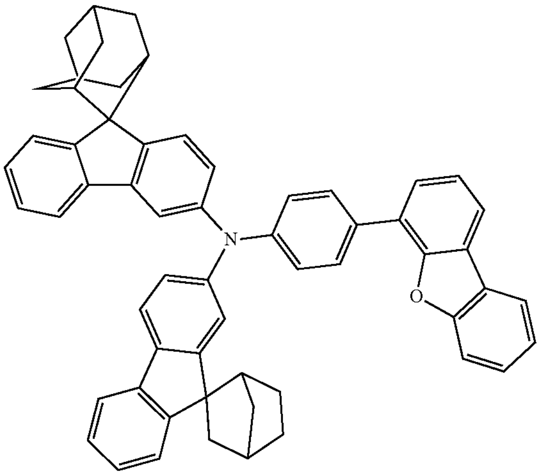
174
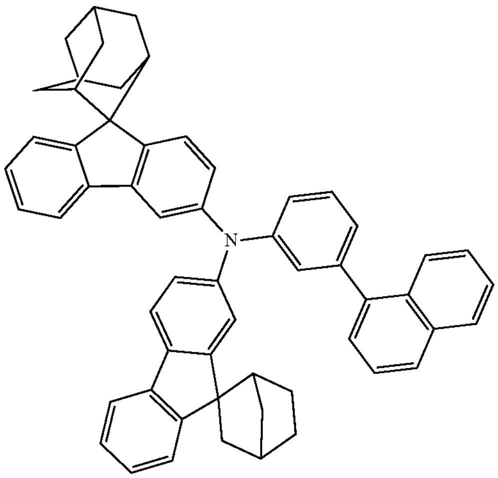

-continued
175
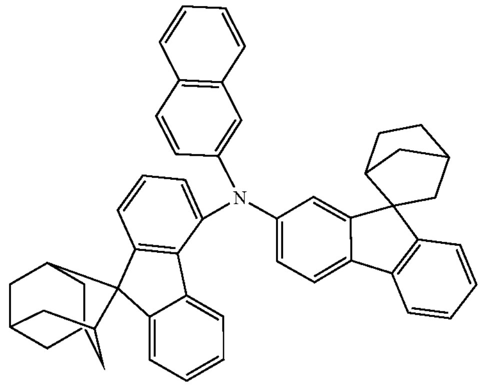
176
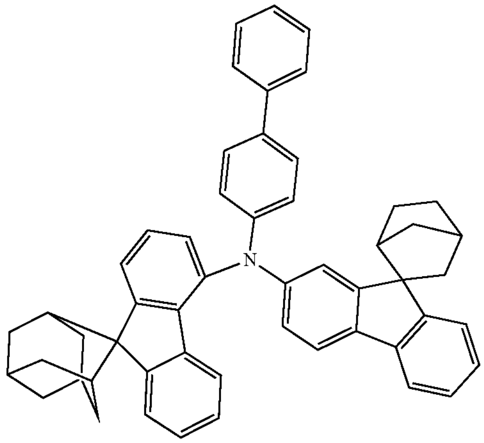
177
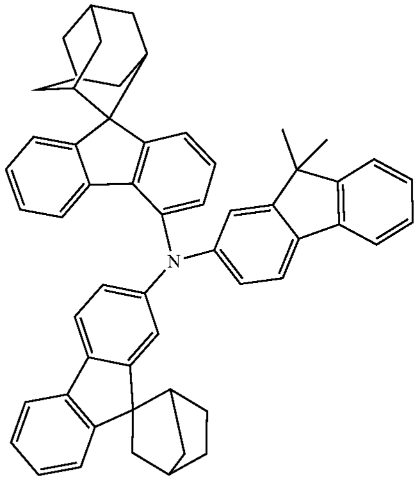
-continued
178
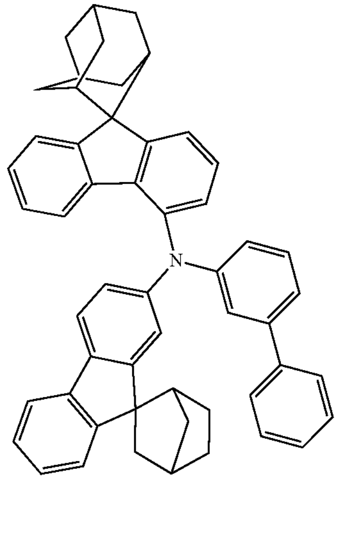
179
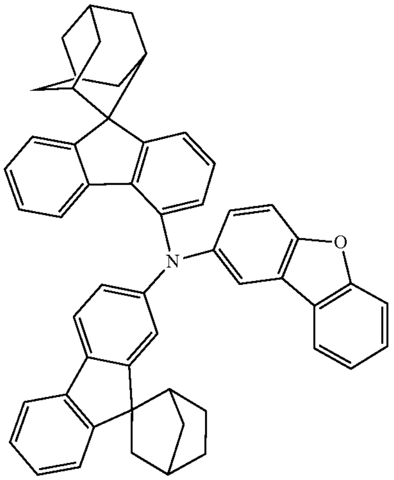
180
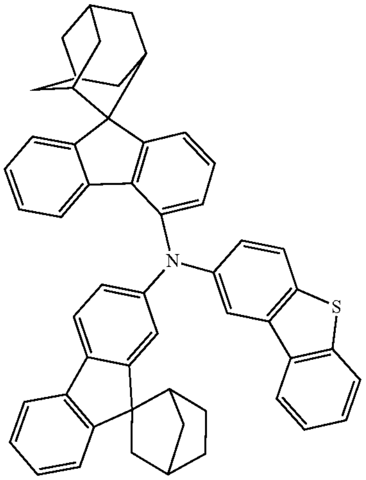

181
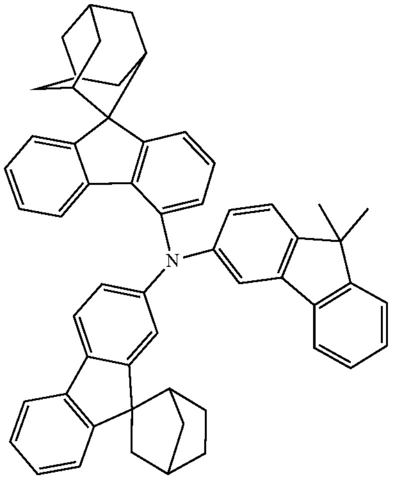
182
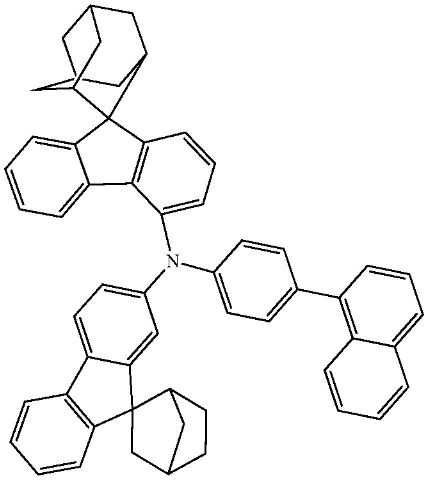
183
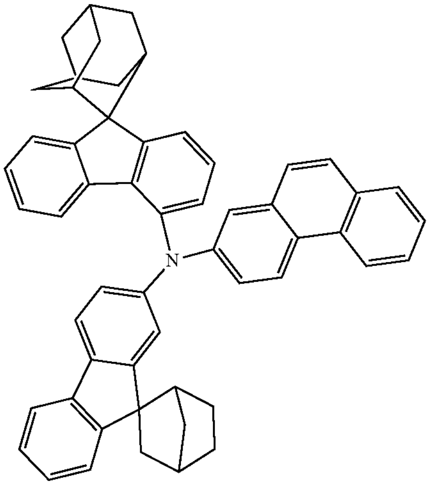
184
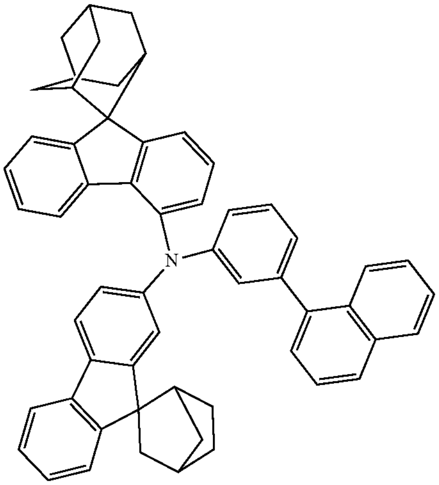
185
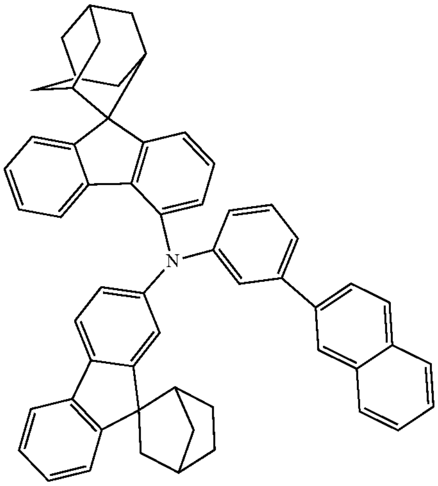
186
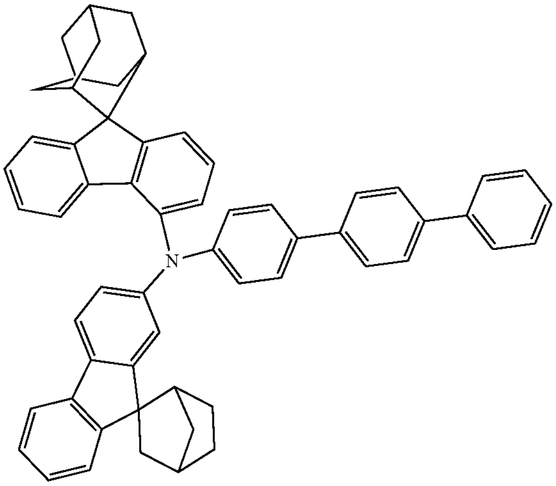

-continued
187
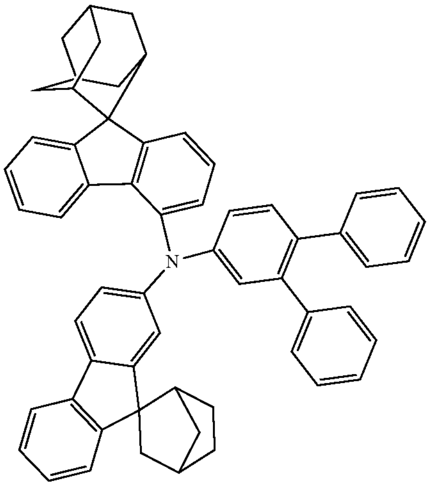
188
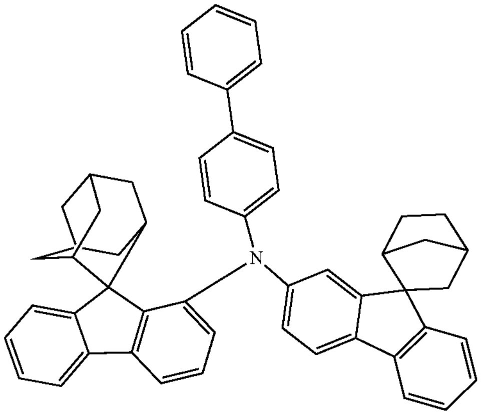
189
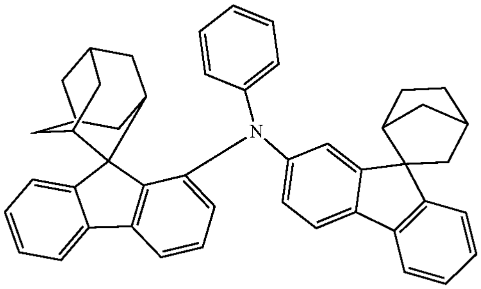
190
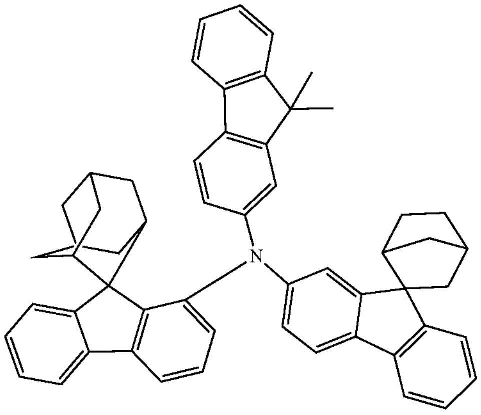
-continued
191
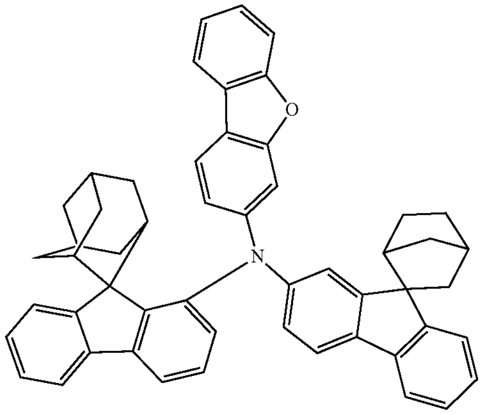
192
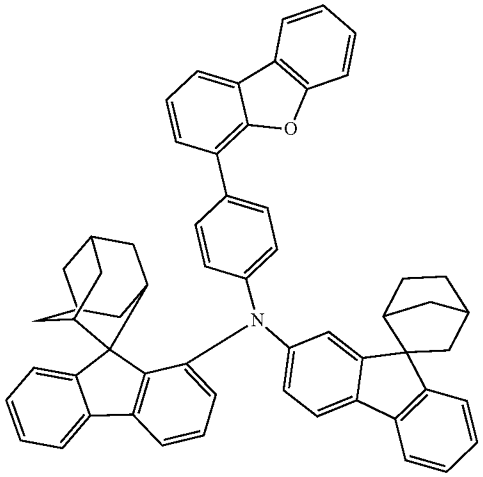
193
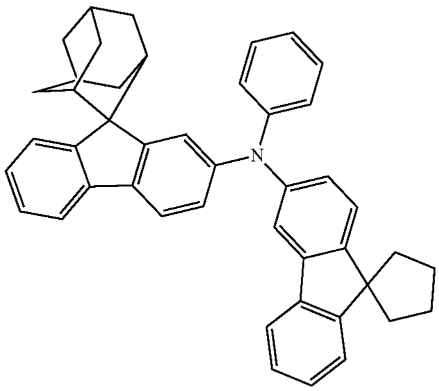

-continued
194
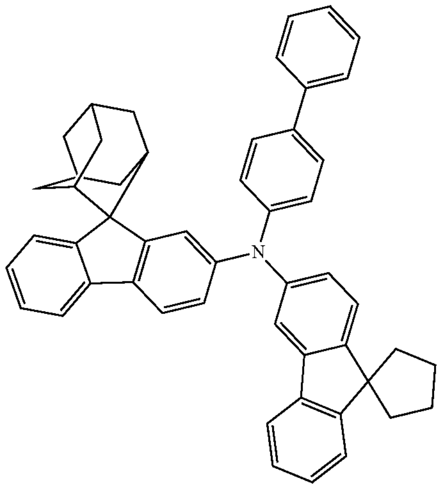
195
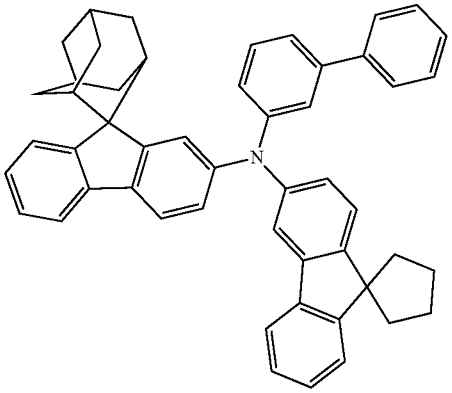
196
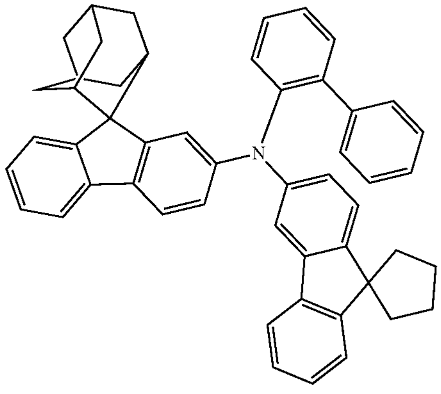
-continued
197
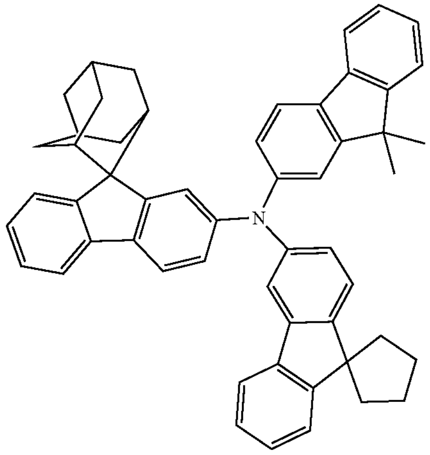
198
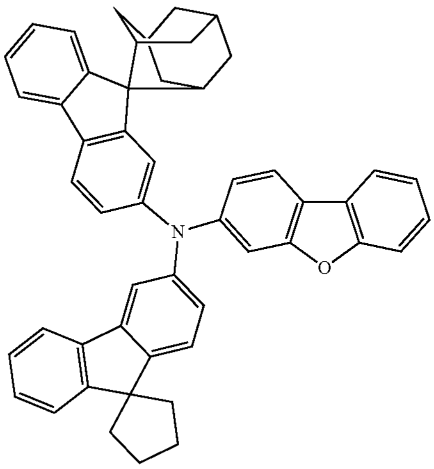
199
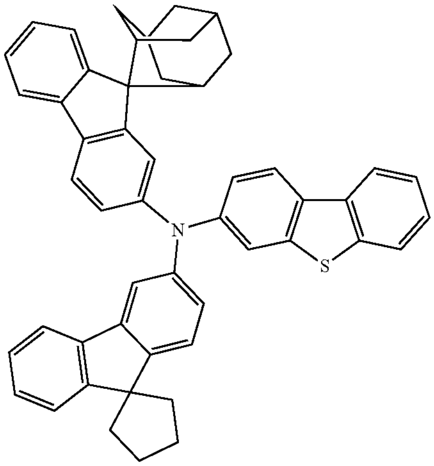

-continued
200
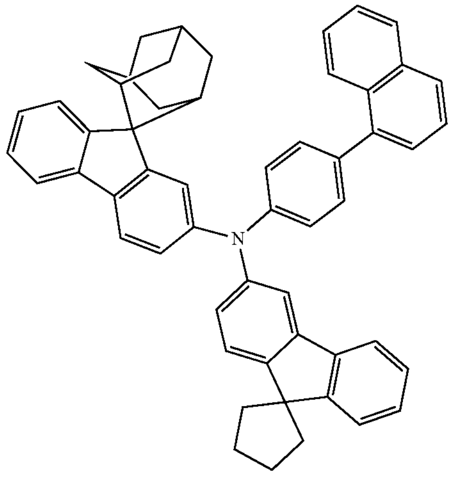
201
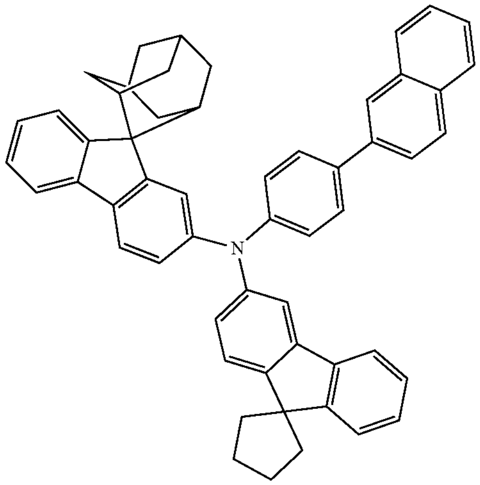
202
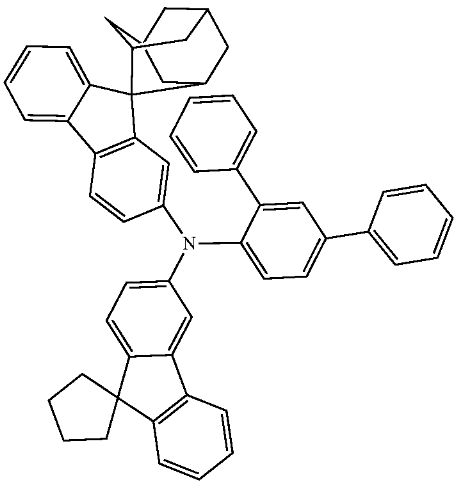
-continued
203
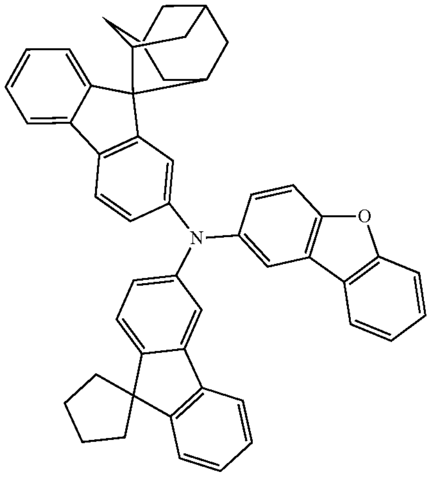
204
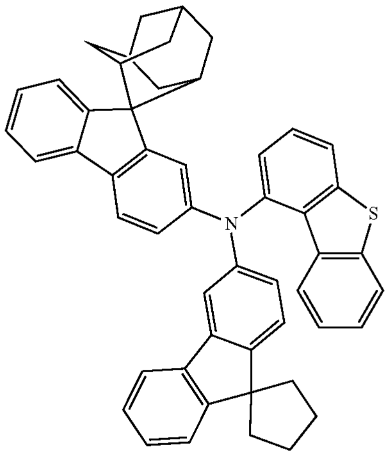
205
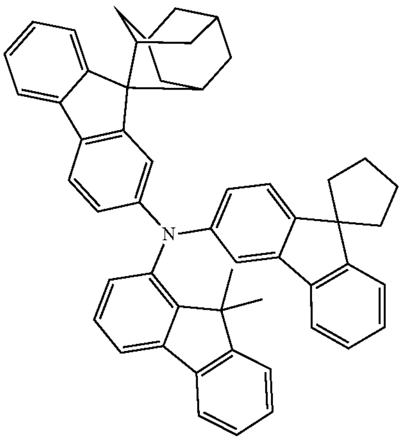

-continued
206
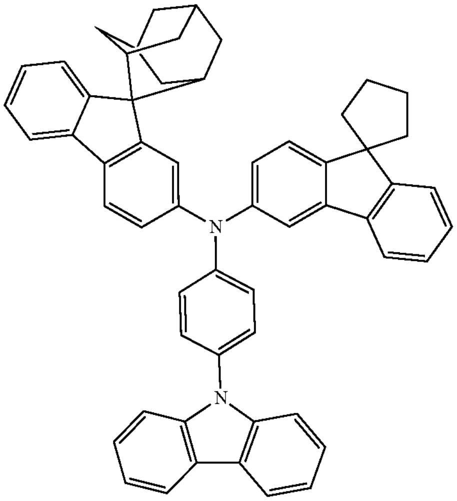
207
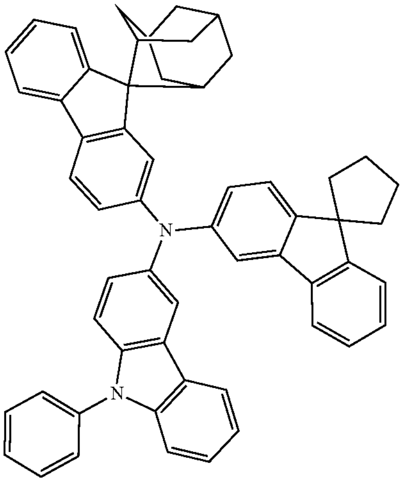
208
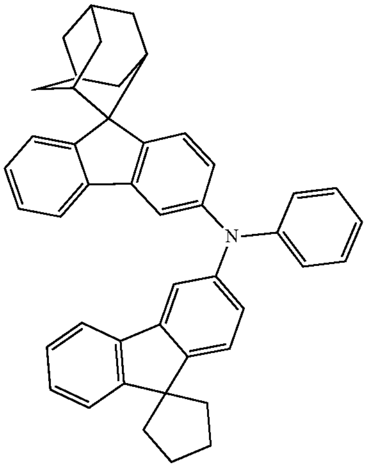
-continued
209
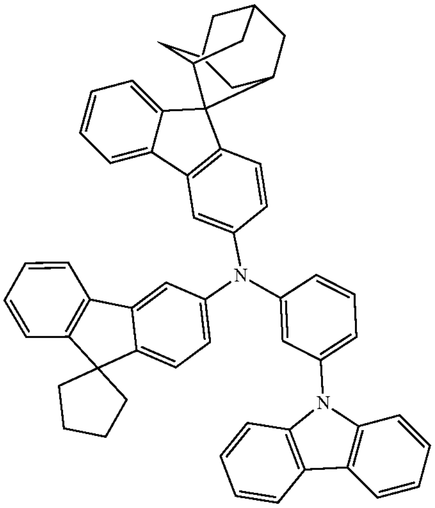
210
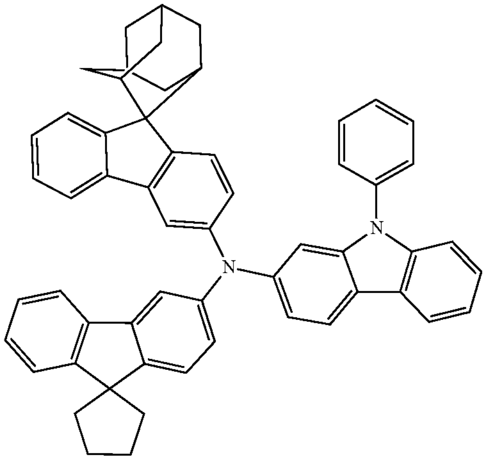
211
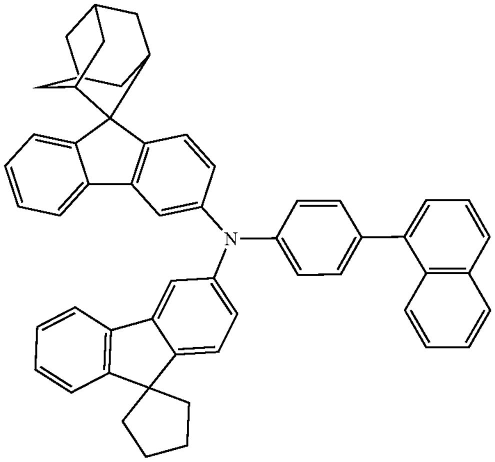

-continued
212
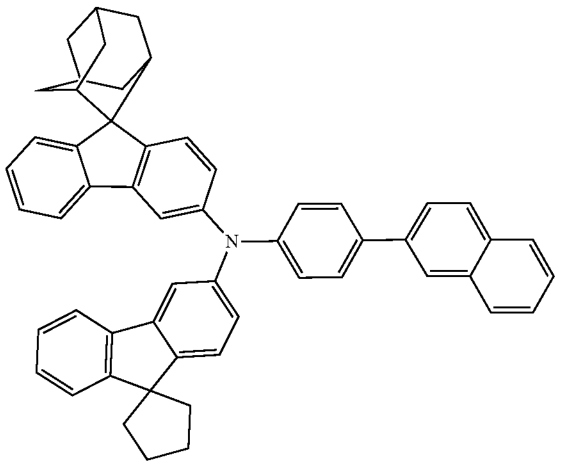
213
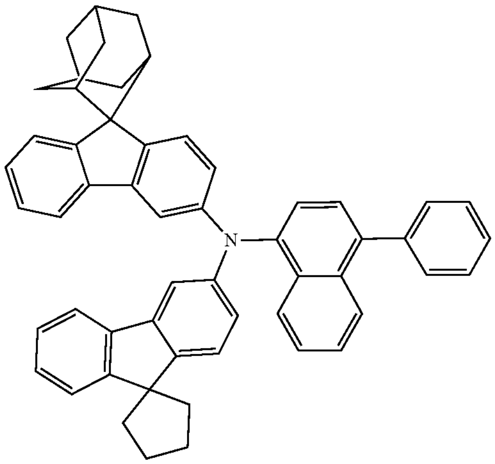
214
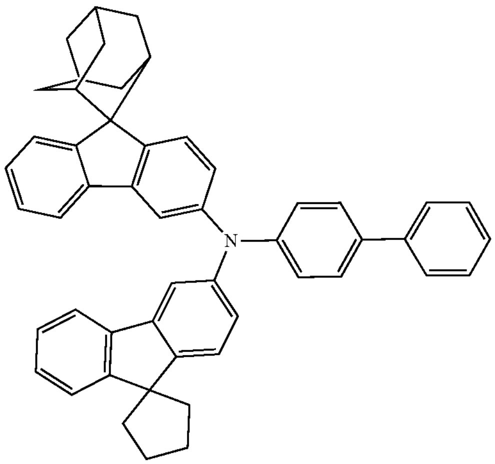
-continued
215
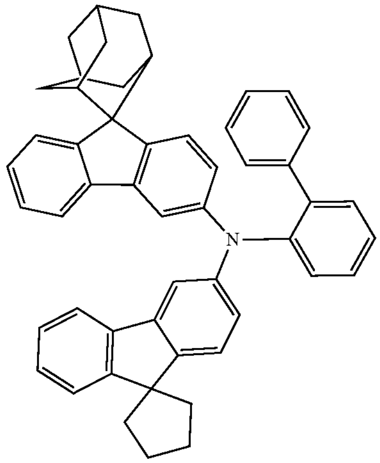
216
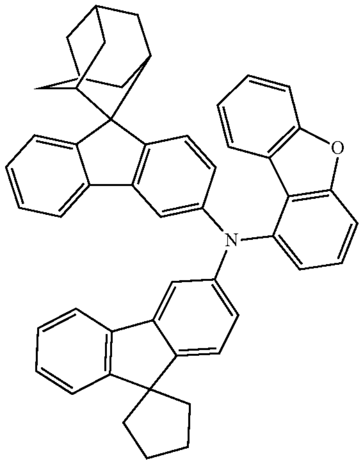
217
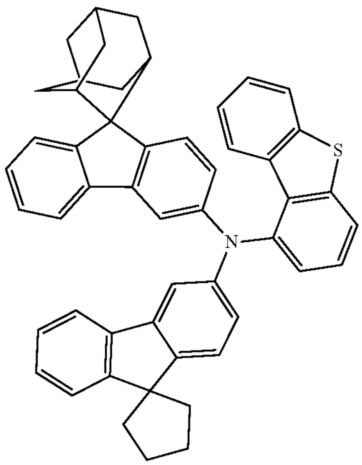

-continued
218
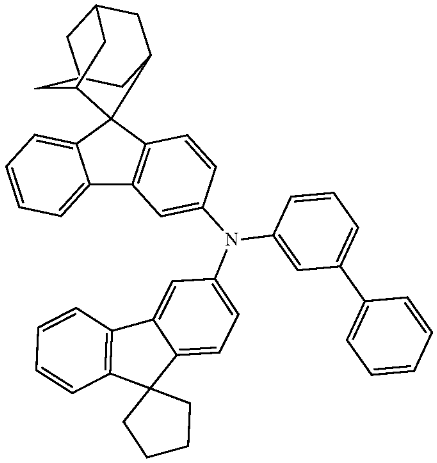
219
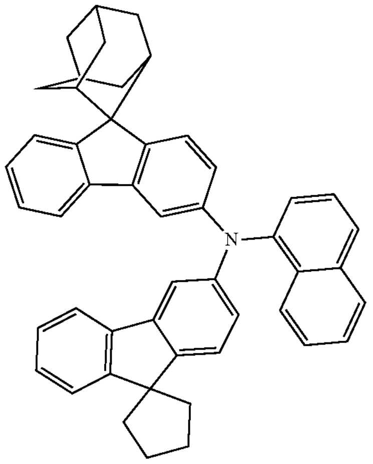
220
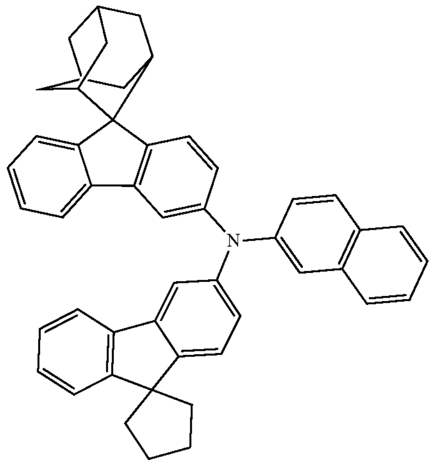
-continued
221
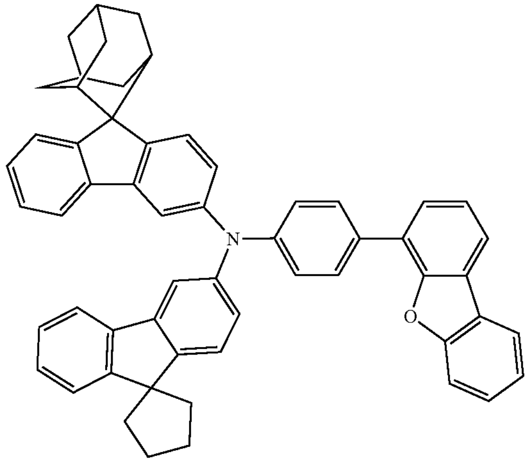
222
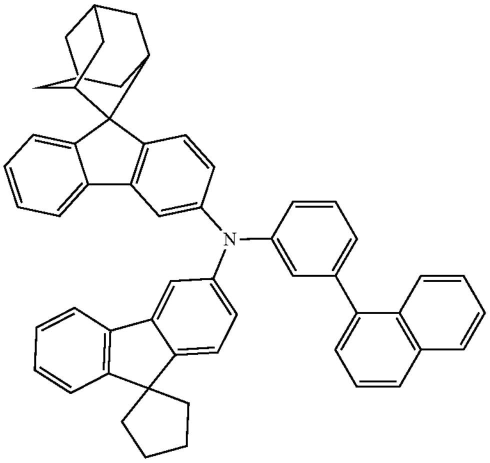
223
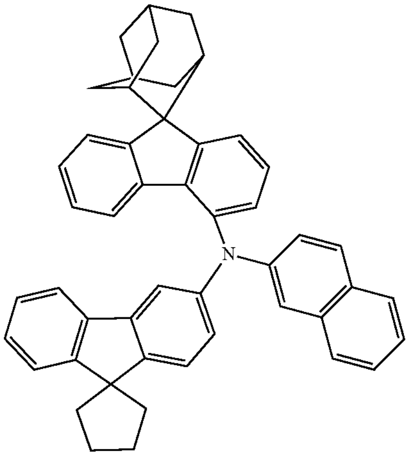

-continued
224
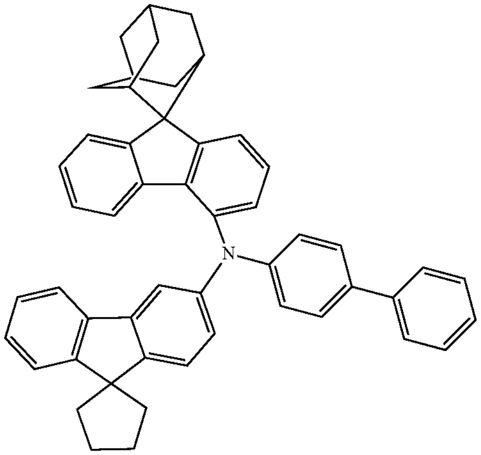
225
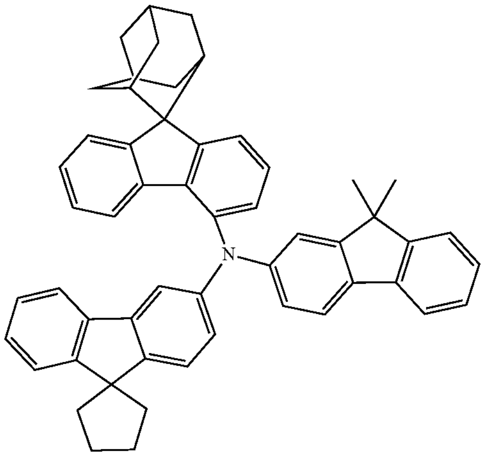
226
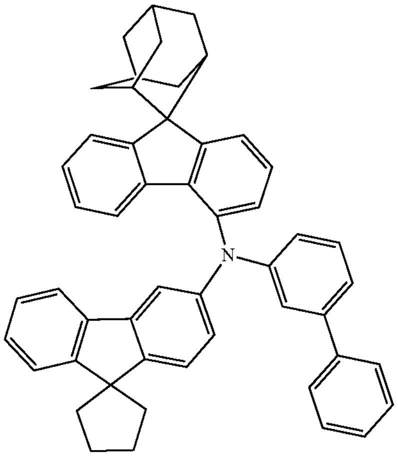
-continued
227
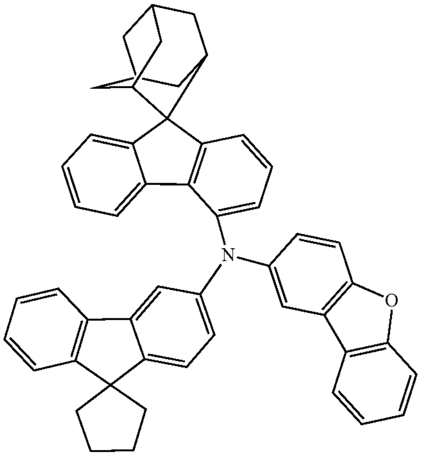
228
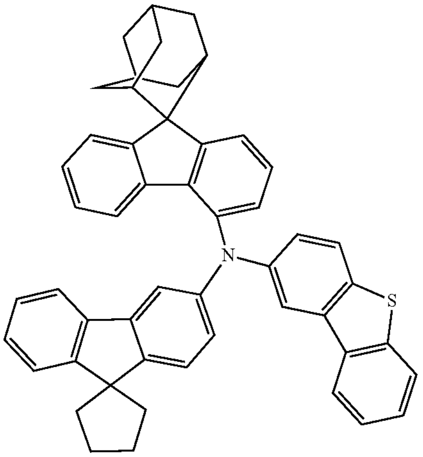
229
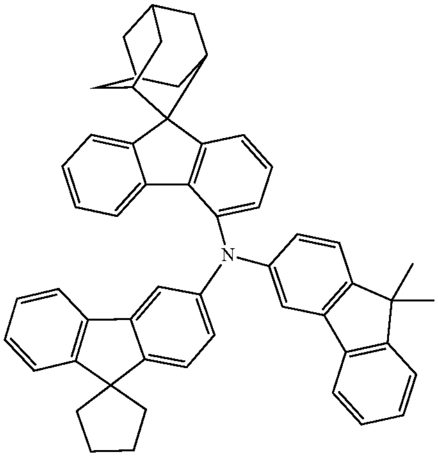

-continued
230
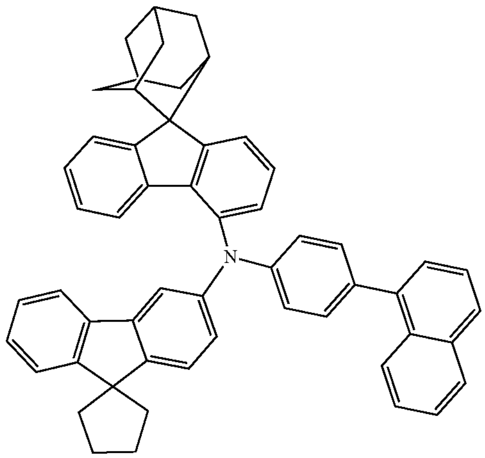
-continued
233
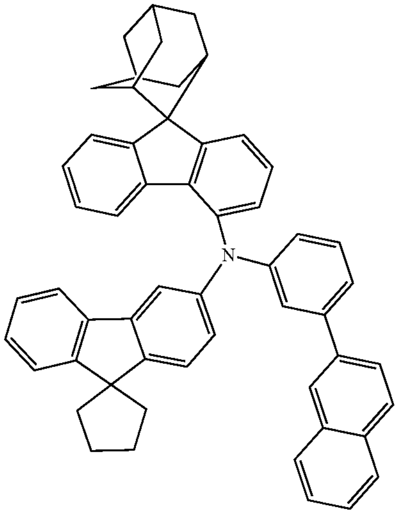
231
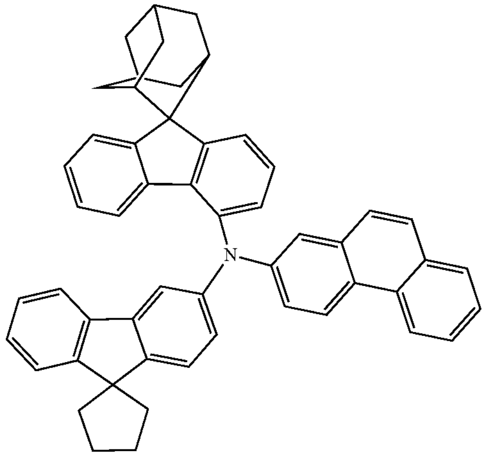
234
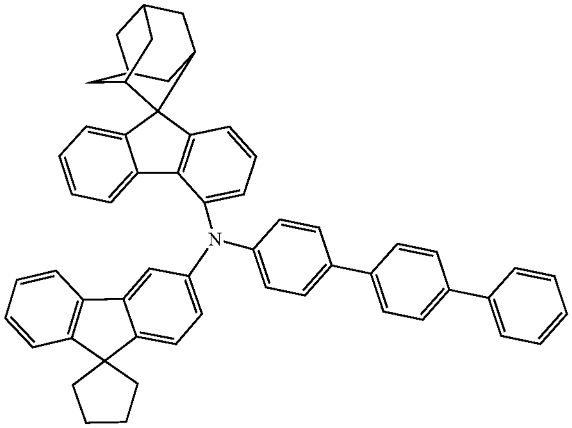
232
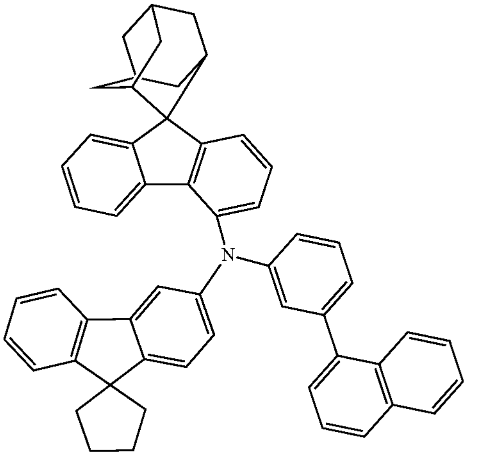
235
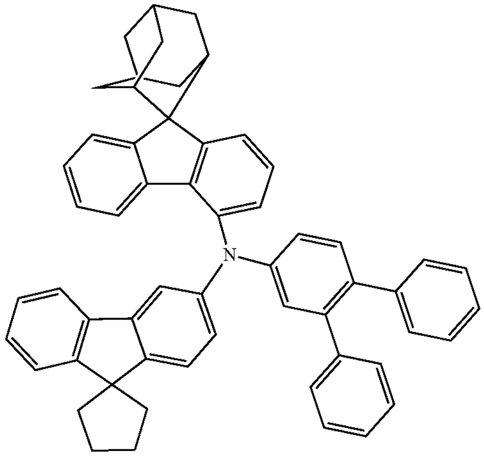

-continued
236
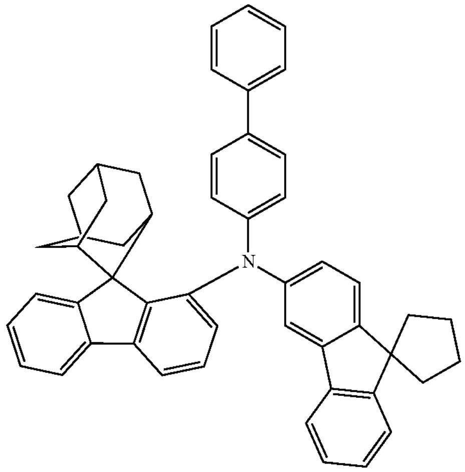
237
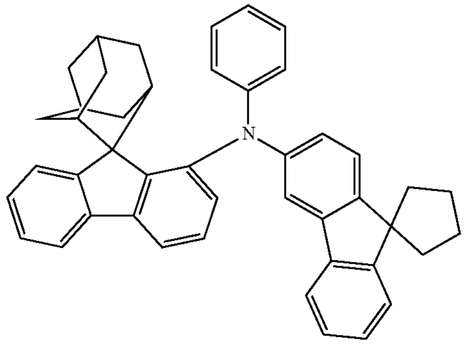
238
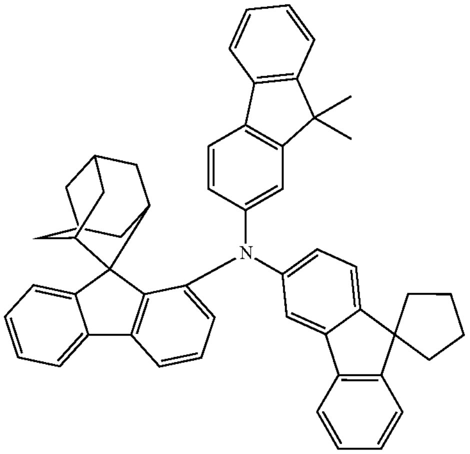
-continued
239
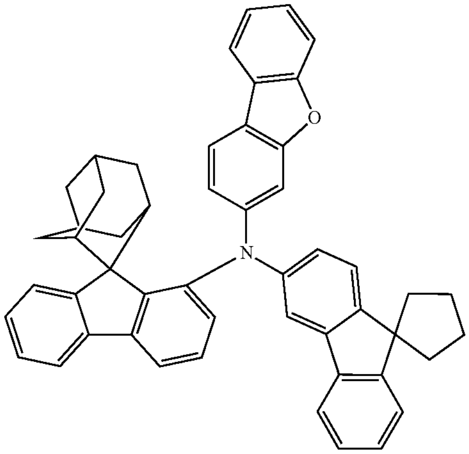
240
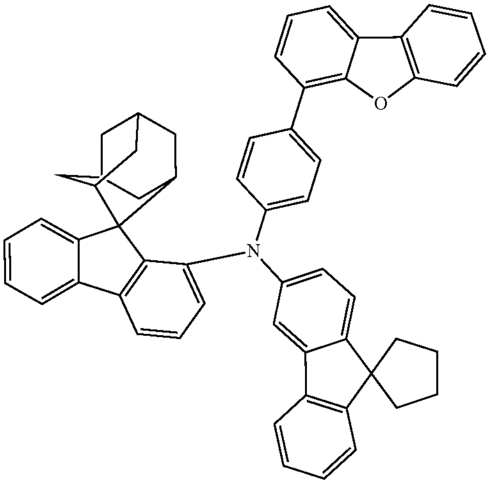
241
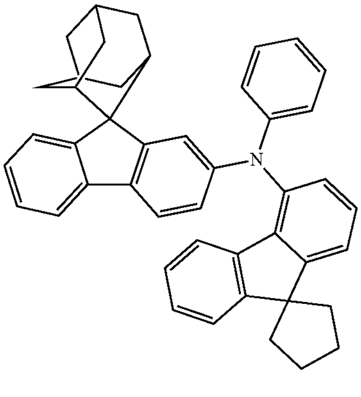

242
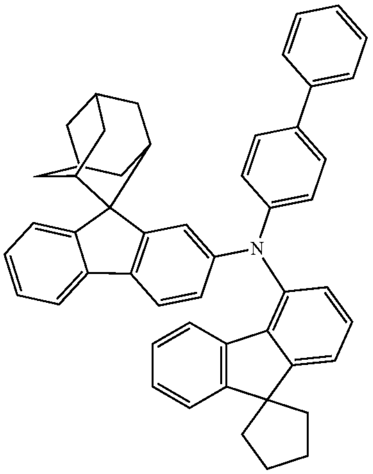
243
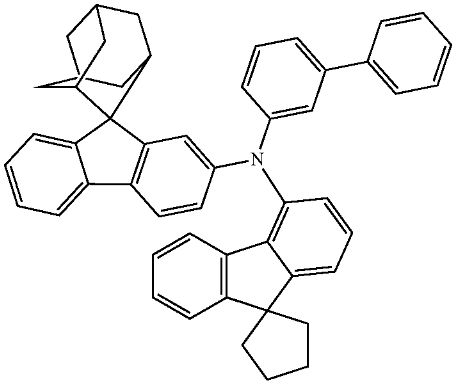
244
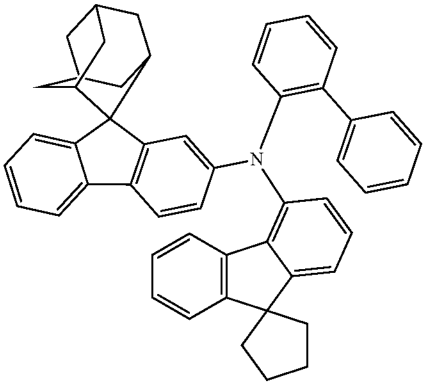
245
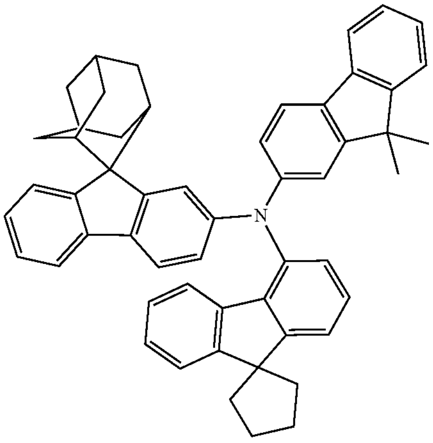
246
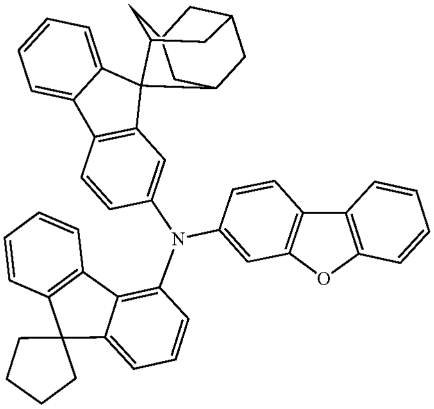
247
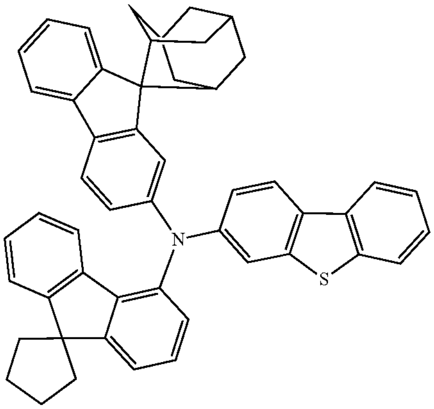

-continued
248
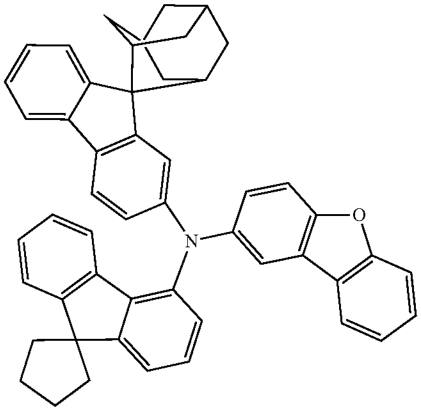
249
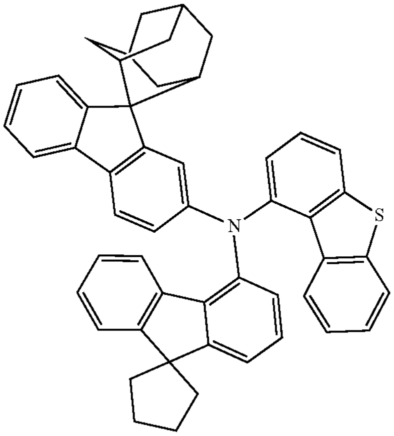
250
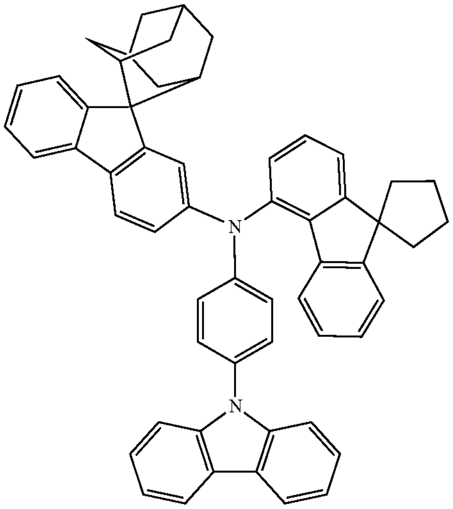
-continued
251
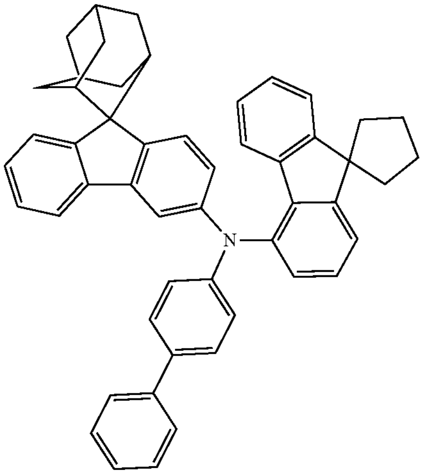
252
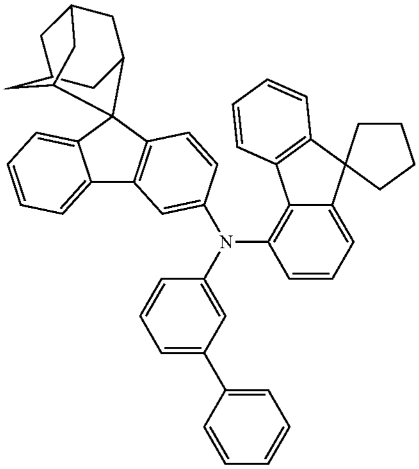
253
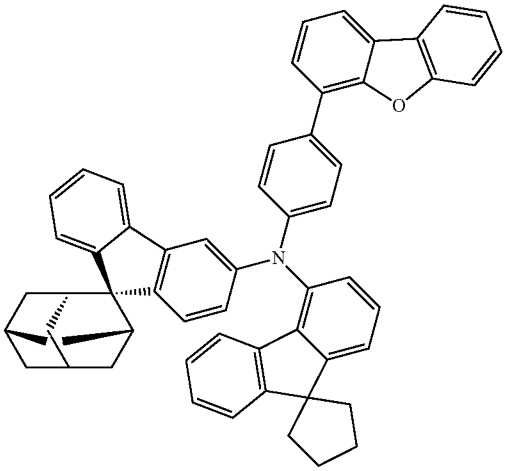

-continued
254
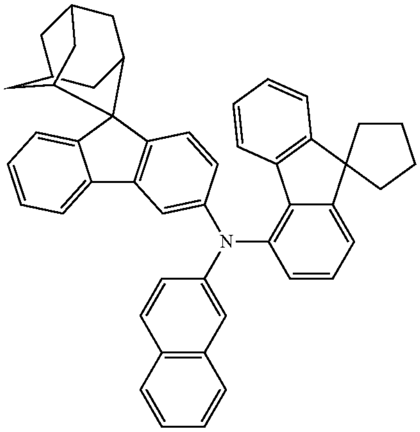
255
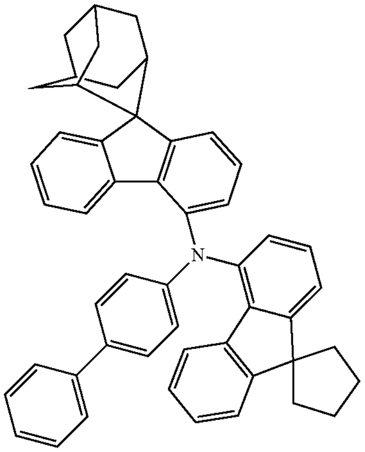
256
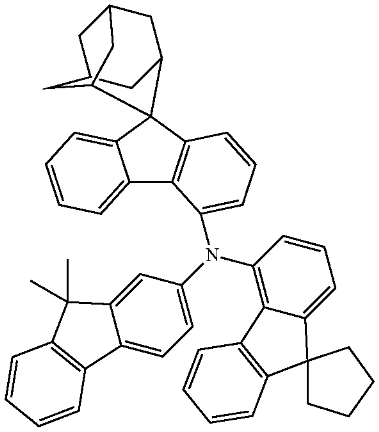
-continued
257
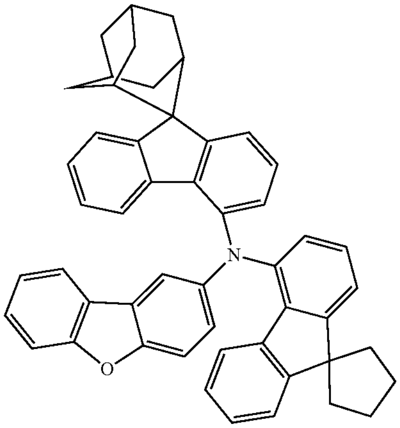
258
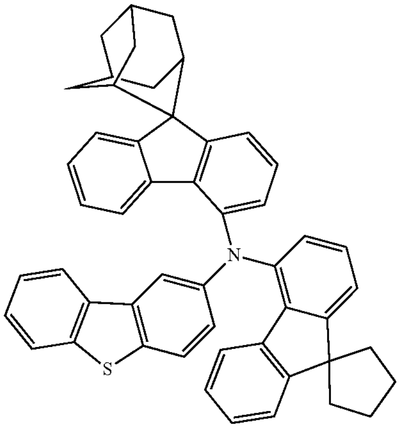
259
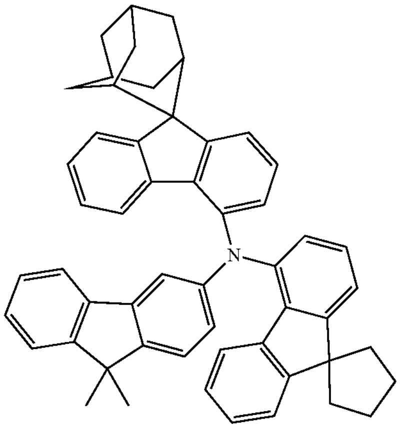

-continued
260
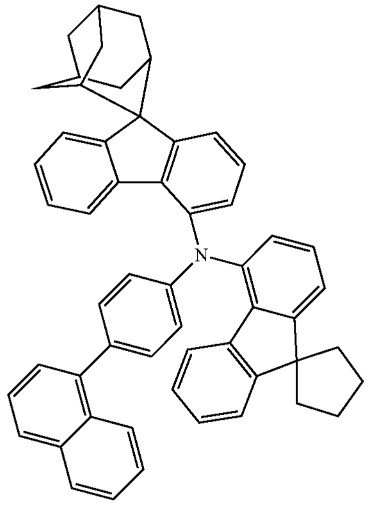
261
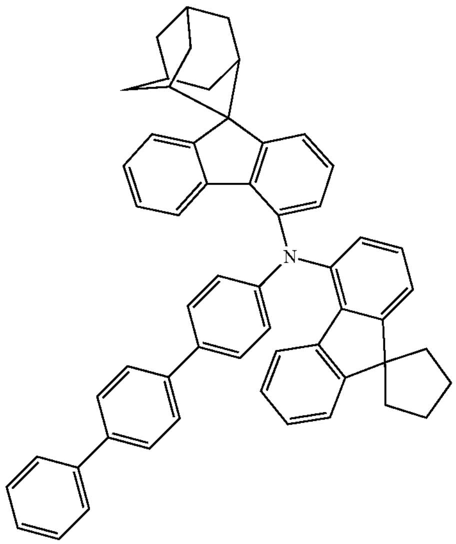
262
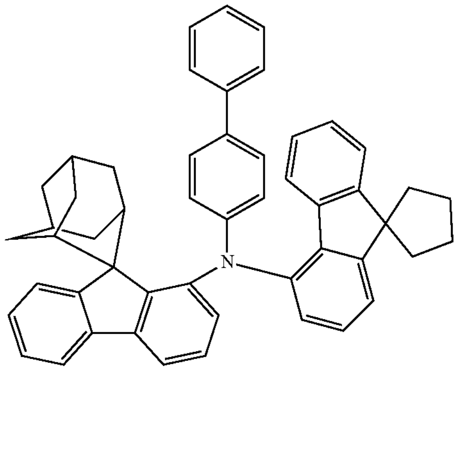
-continued
263
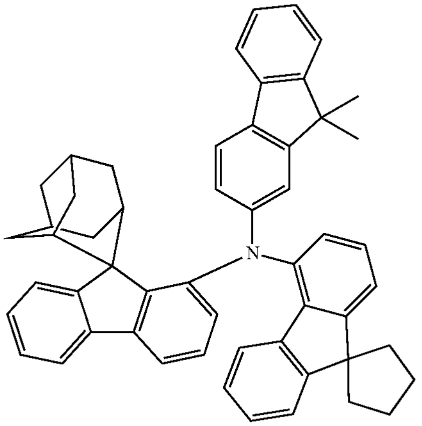
264
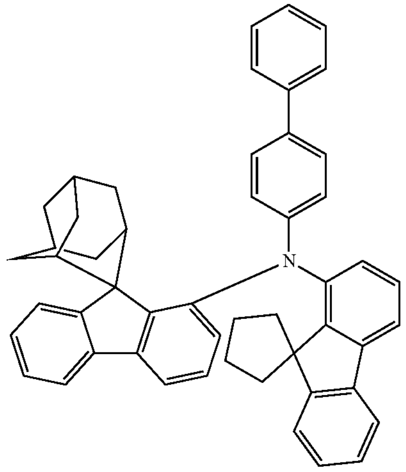
265
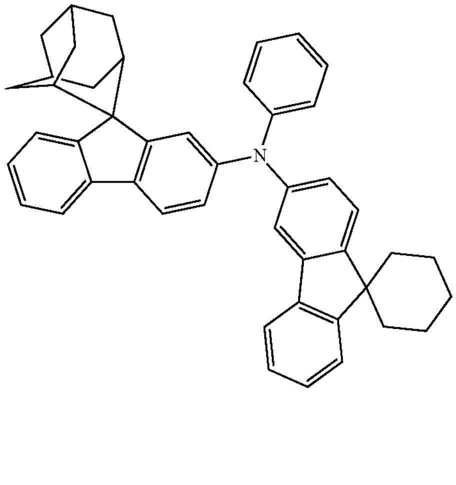

-continued
266
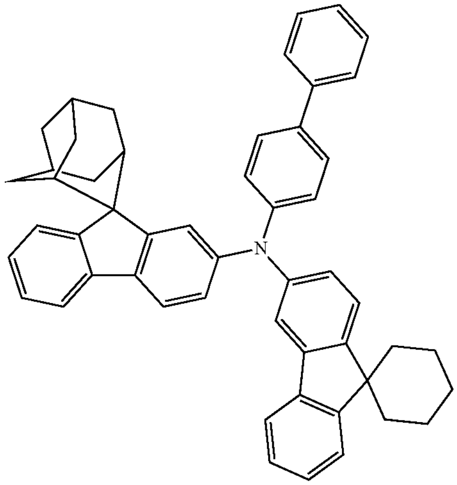
267
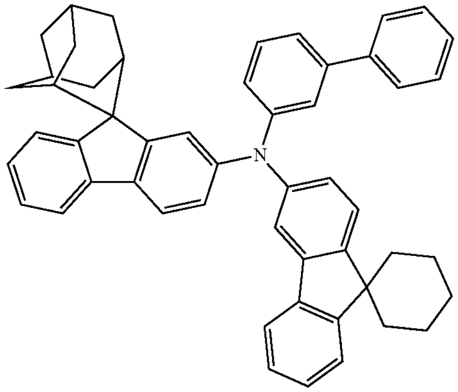
268
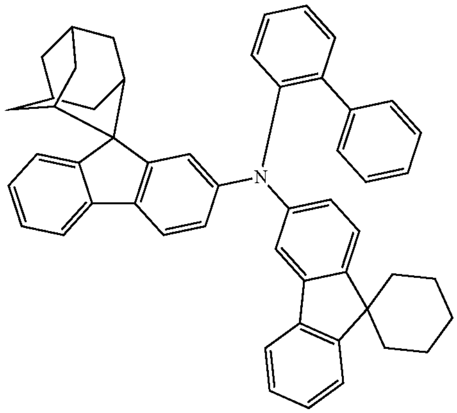
-continued
269
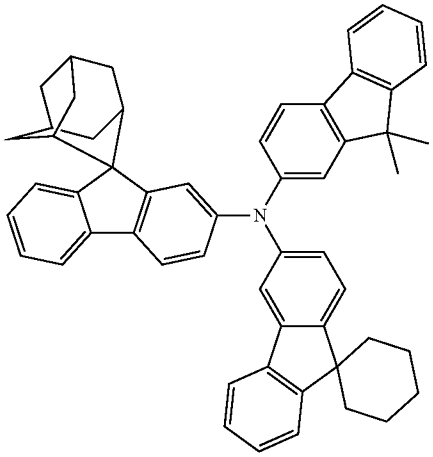
270
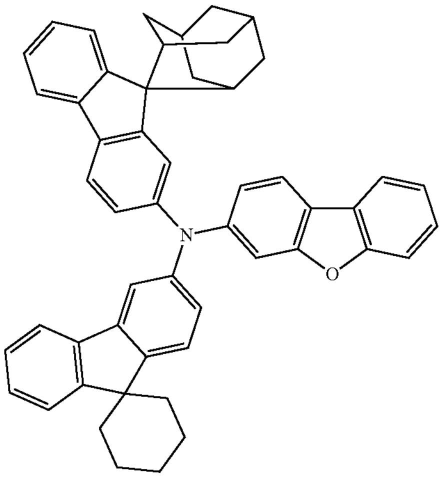
271
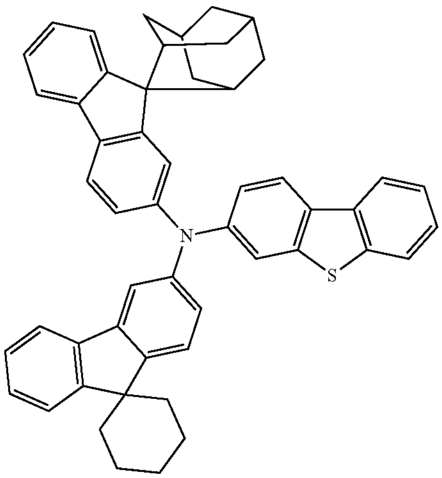

-continued
272
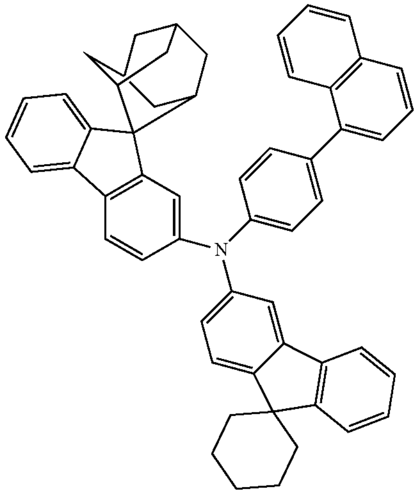
273
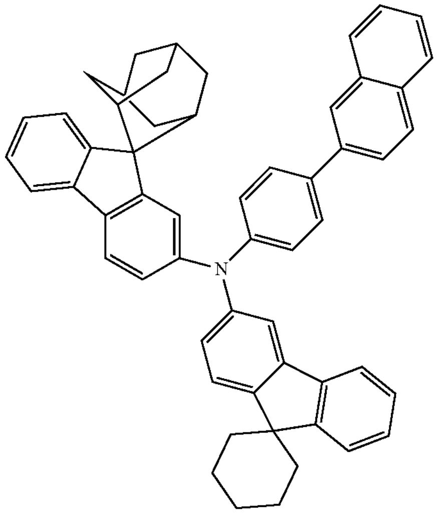
274
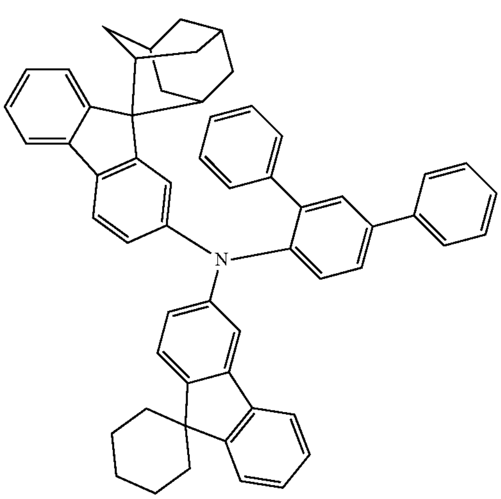
-continued
275
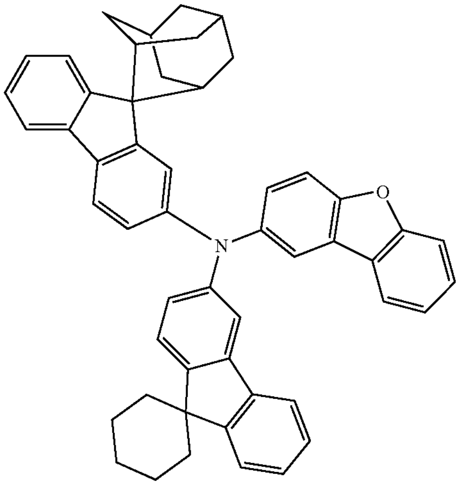
276
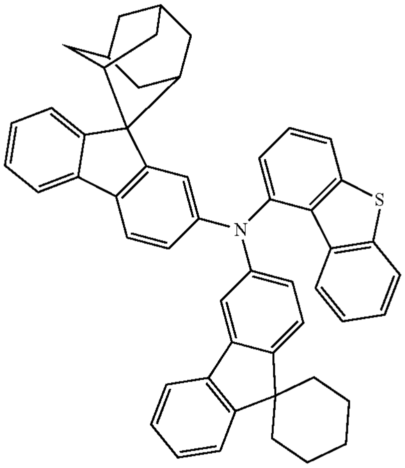
277
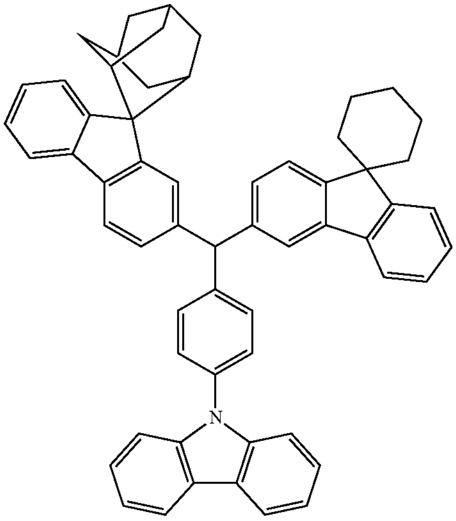

-continued
278
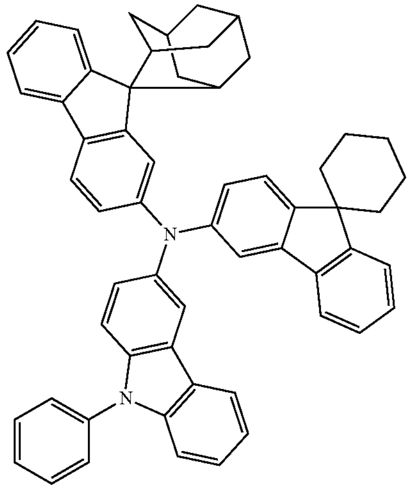
279
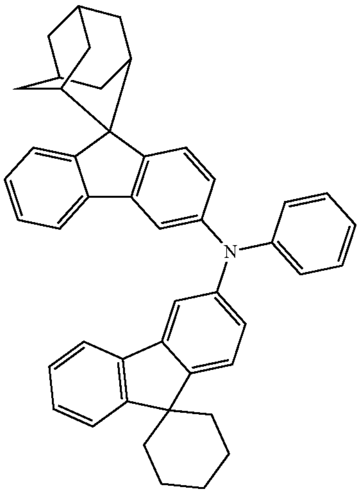
280
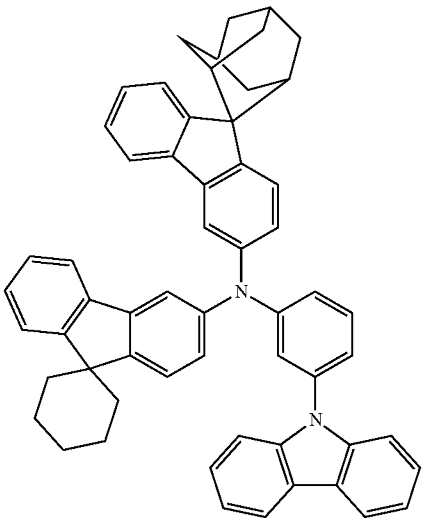
-continued
281
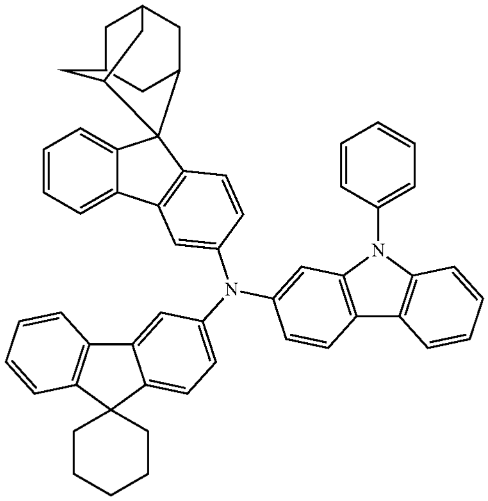
282
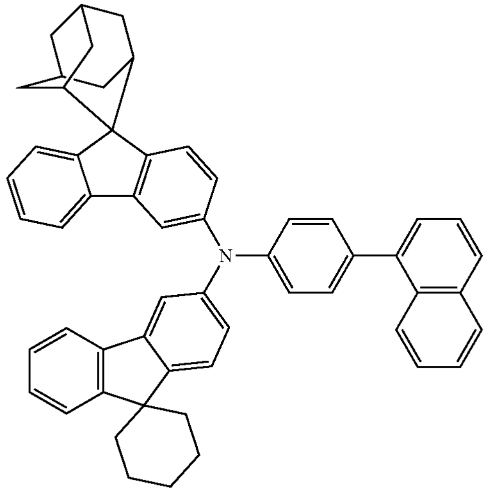
283
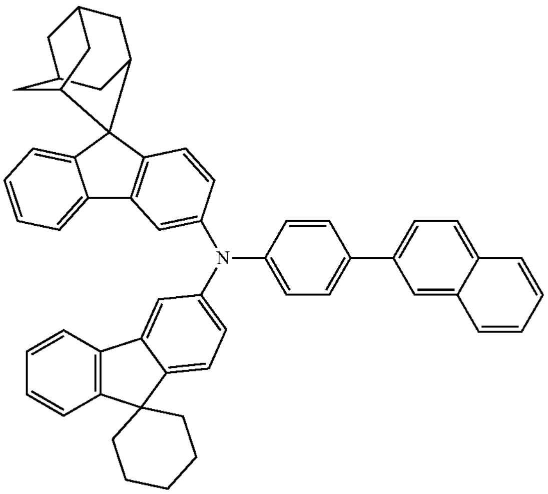

-continued
284
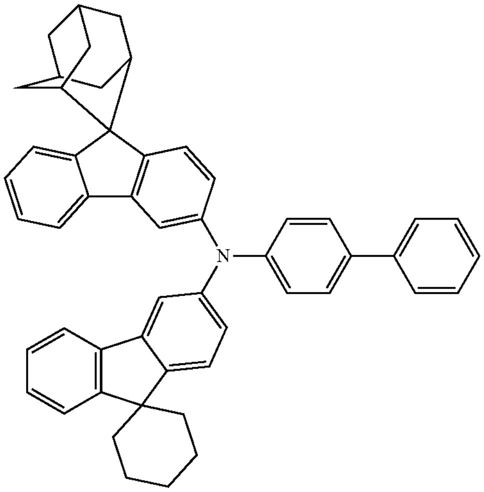
285
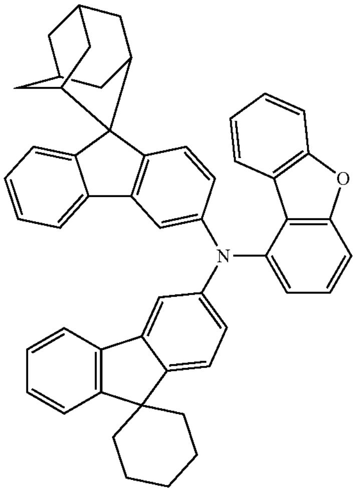
286
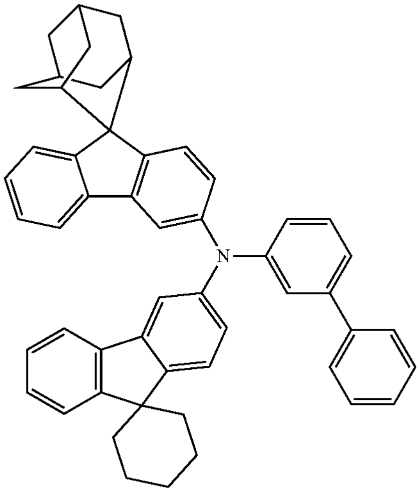
-continued
287
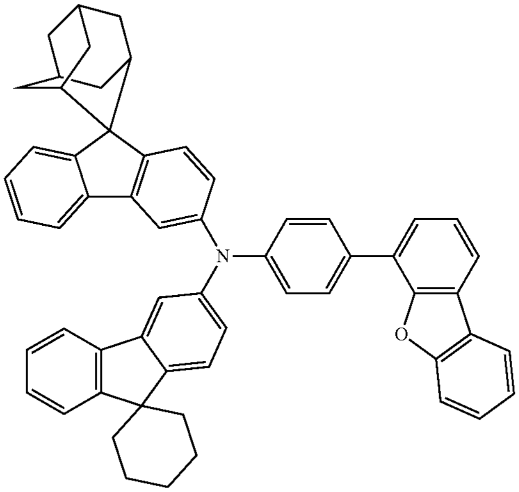
288
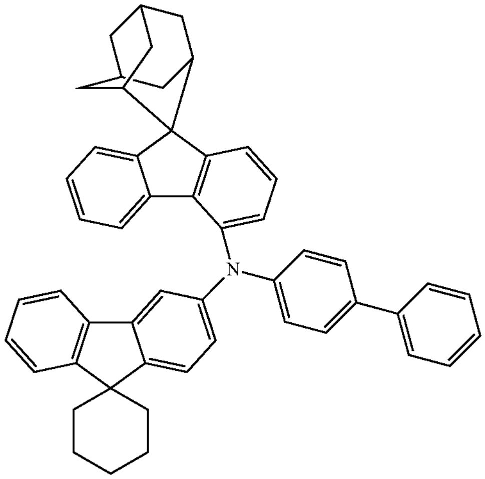
289
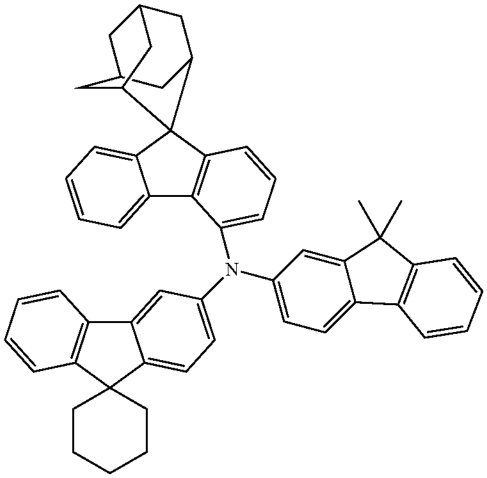

-continued
290
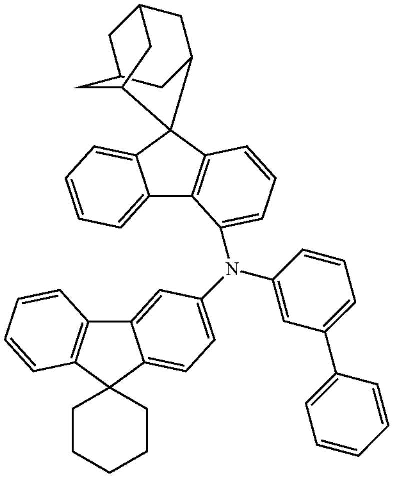
291
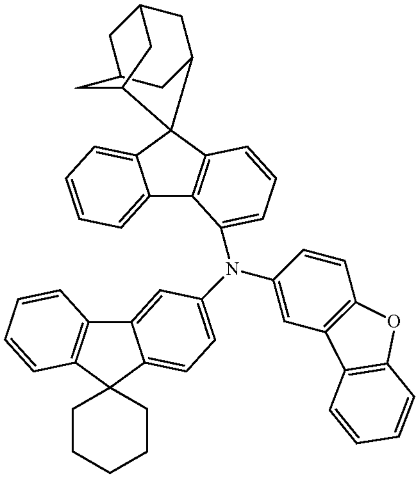
292
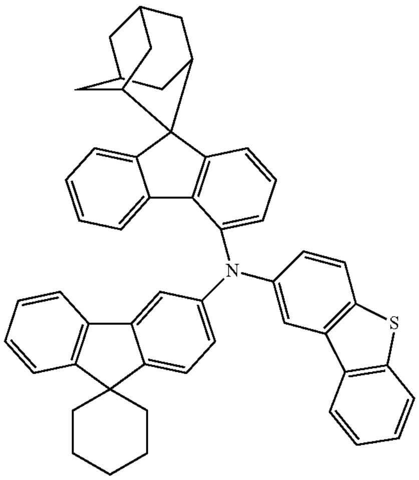
-continued
293
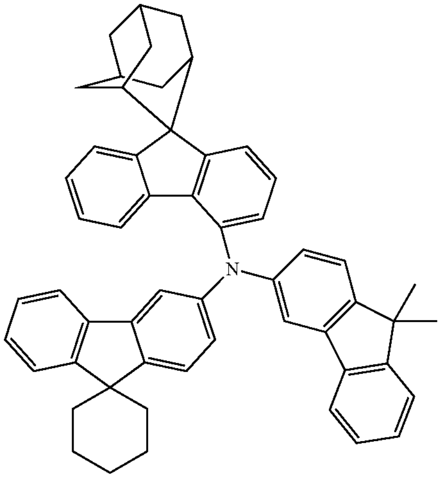
294
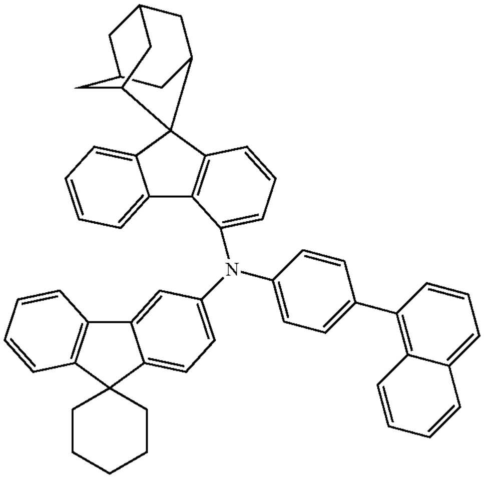
295
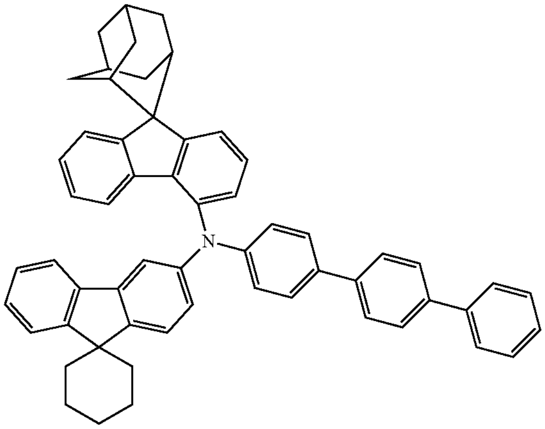

296
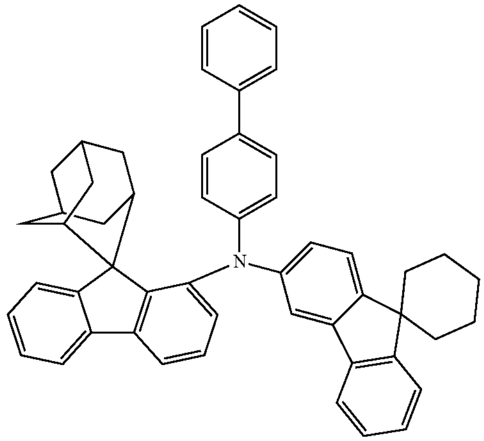
297
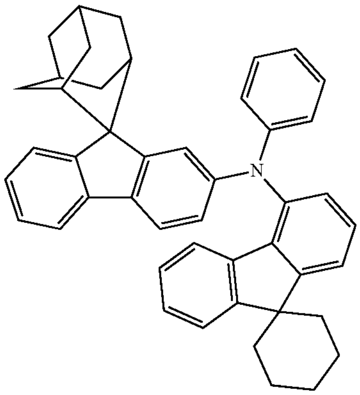
298
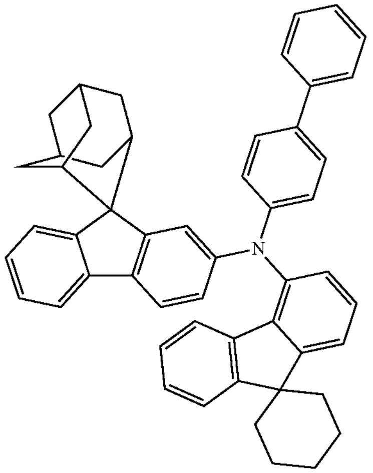
299
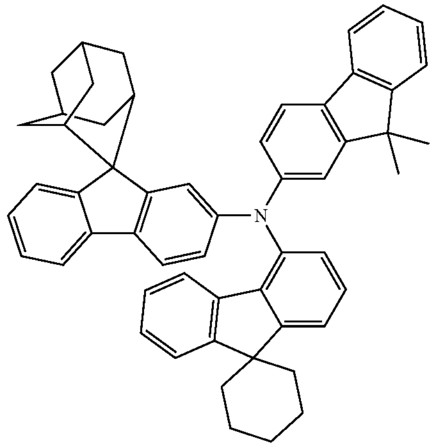
300
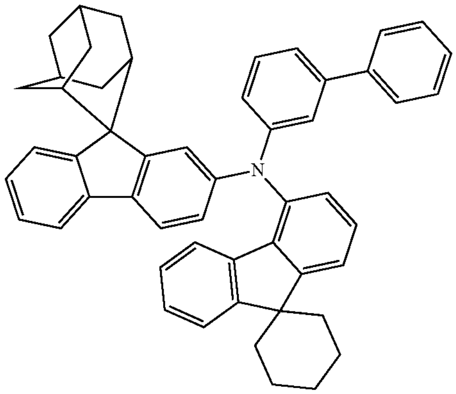
301
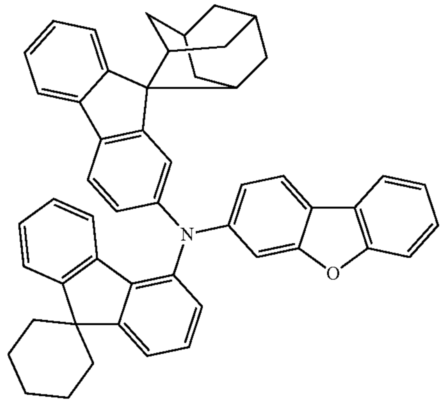
302
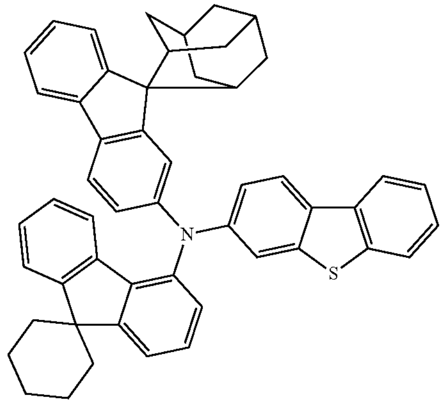

-continued
303
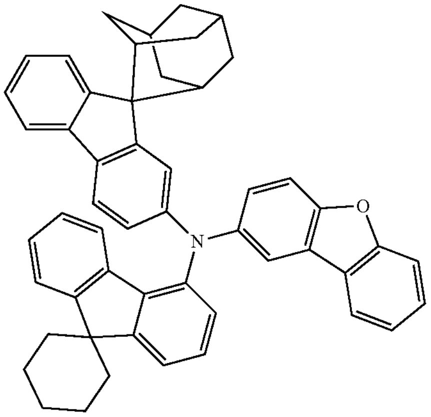
304
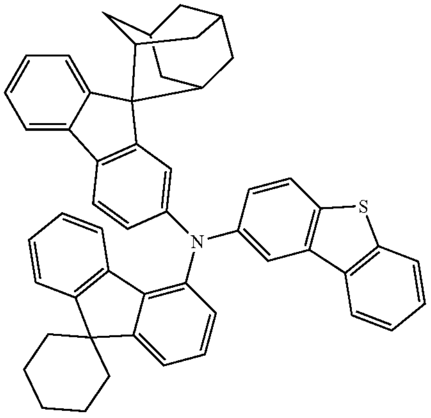
305
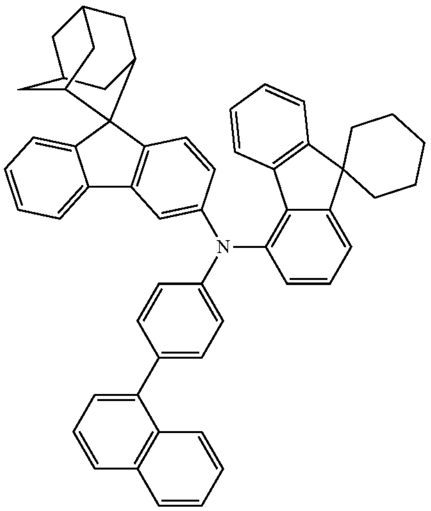
-continued
306
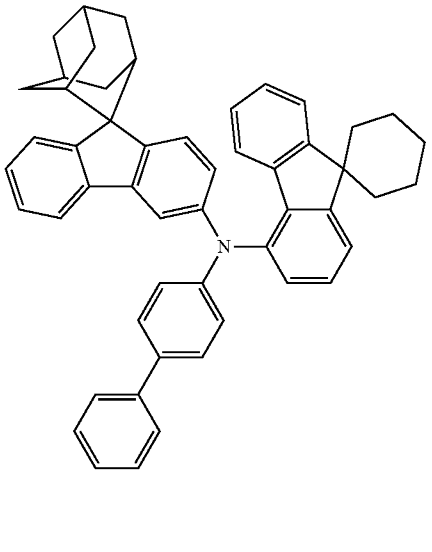
307
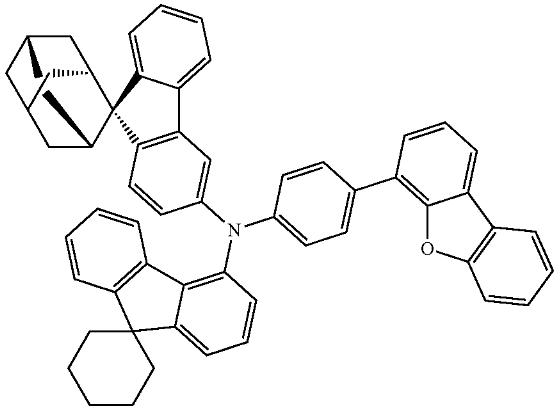
308
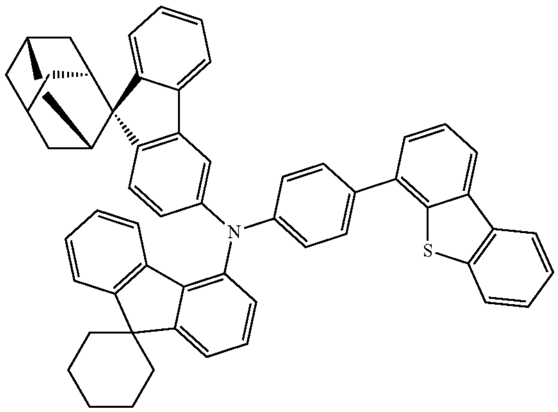

-continued
309
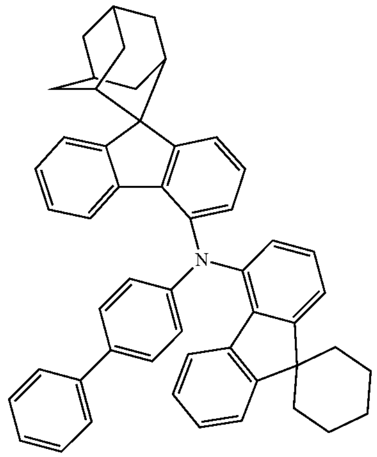
310
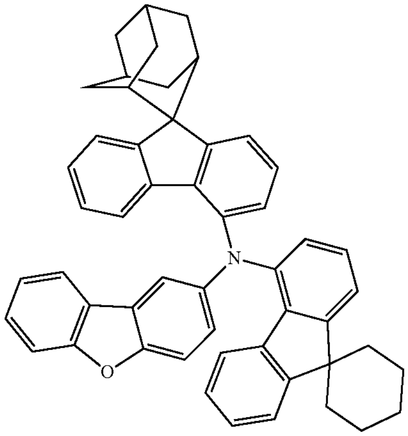
311
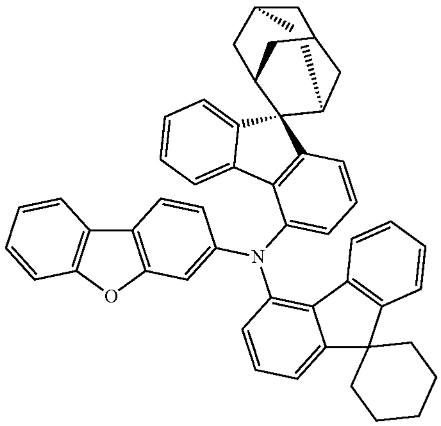
-continued
312
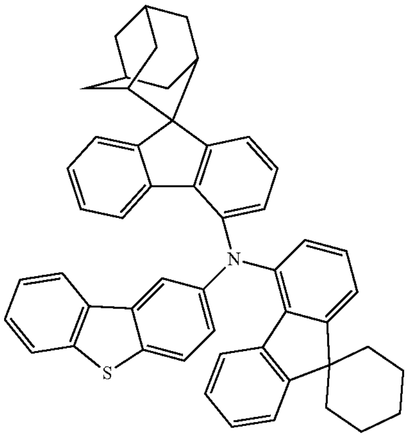
313
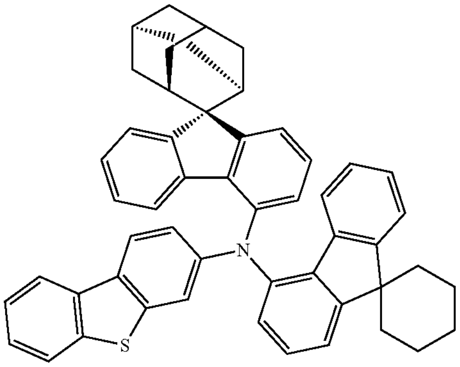
314
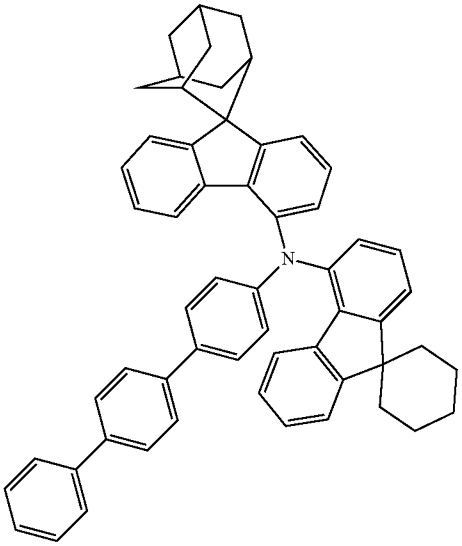

-continued
315
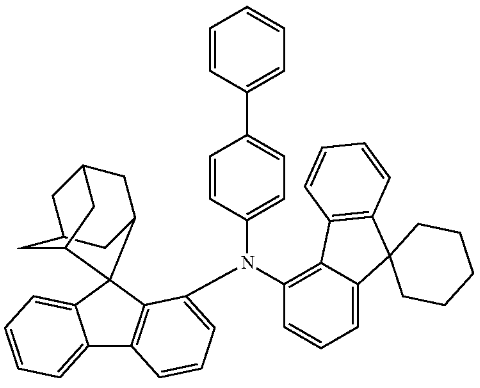
316
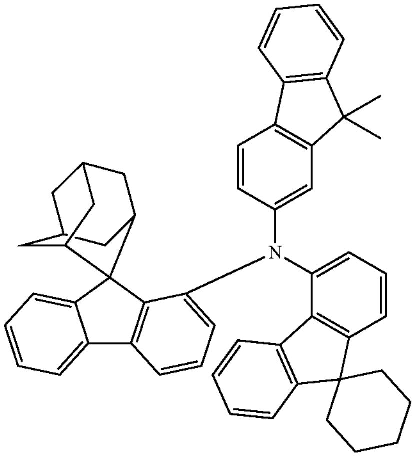
317
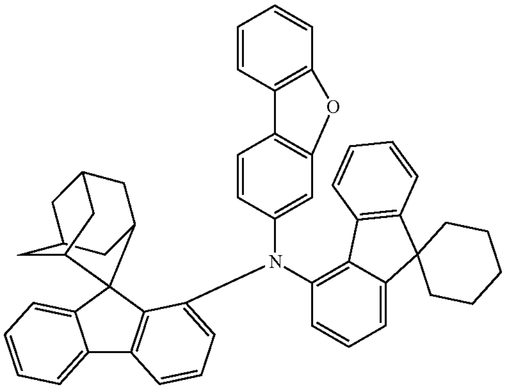
-continued
318
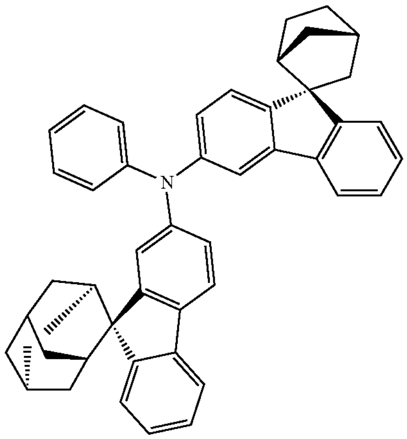
319
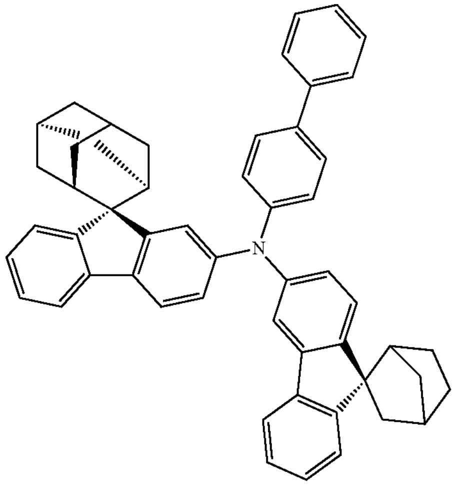
320
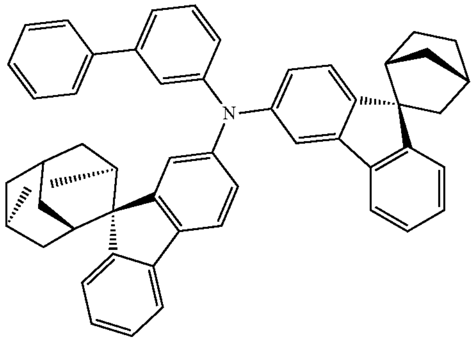

-continued
321
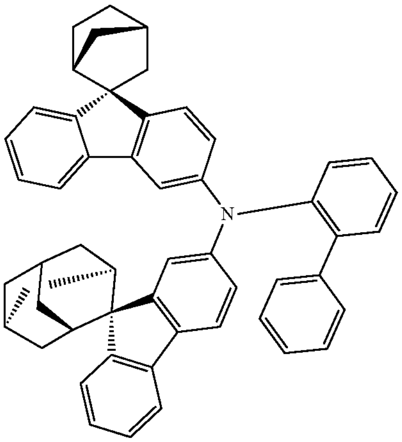
322
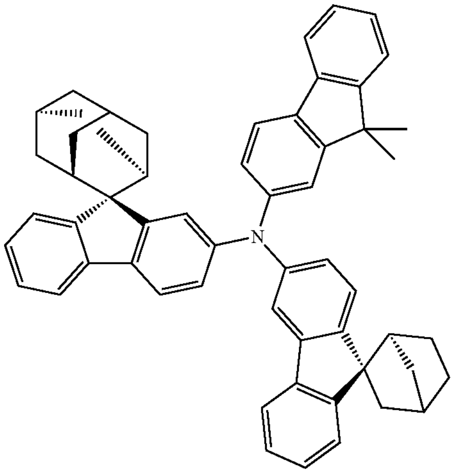
323
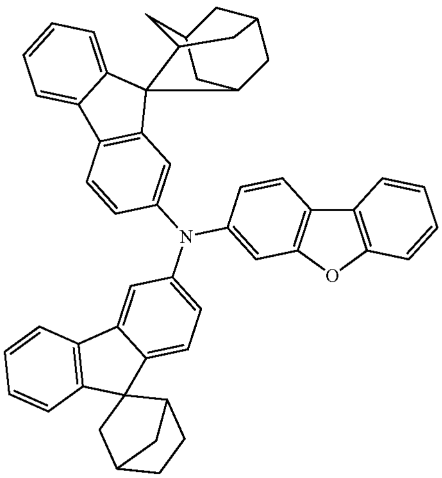
-continued
324
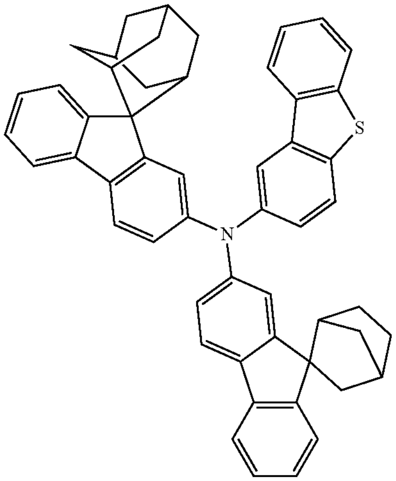
325
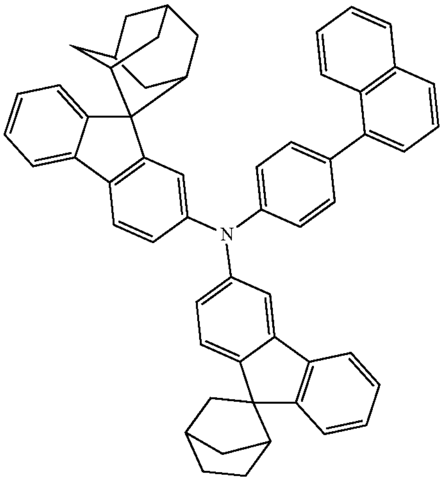
326
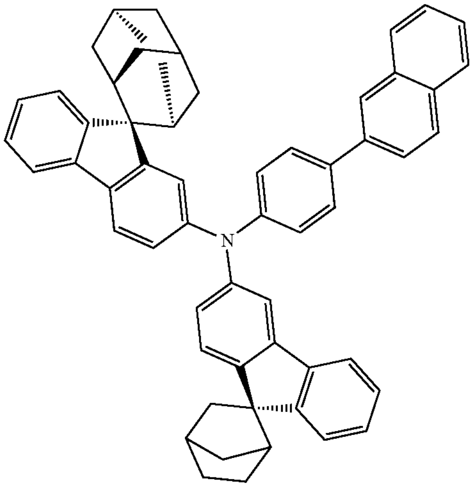

327
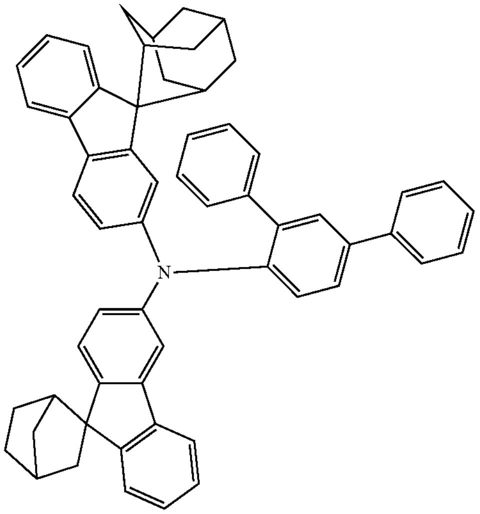
328
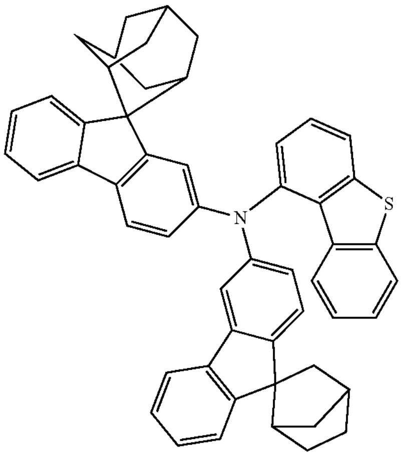
329
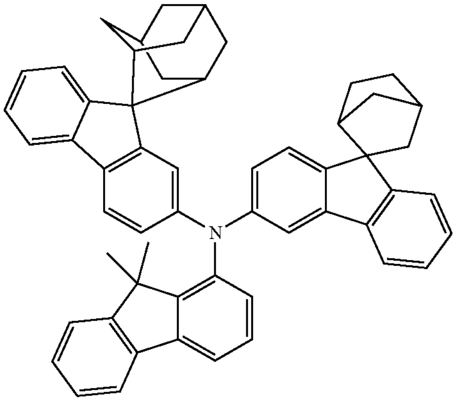
330
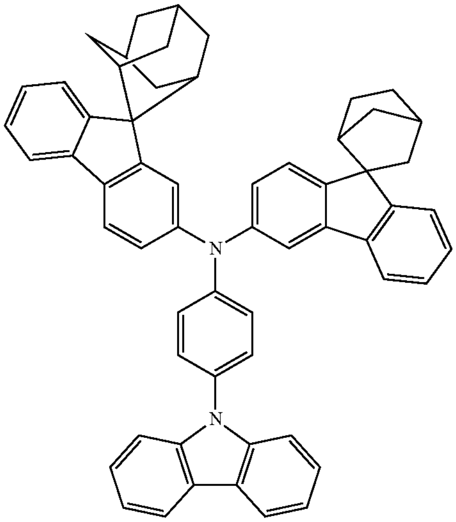
331
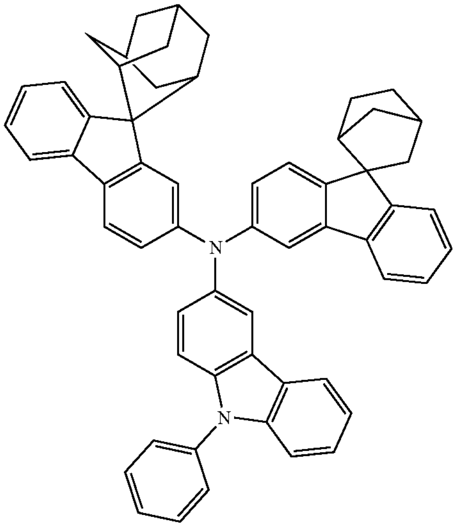
332
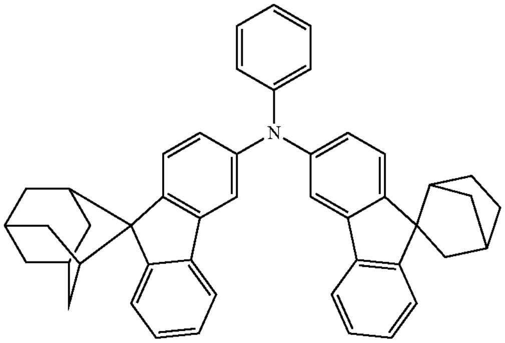

-continued
333
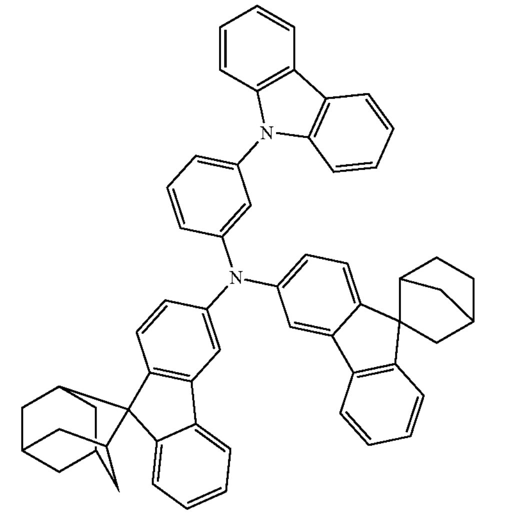
334
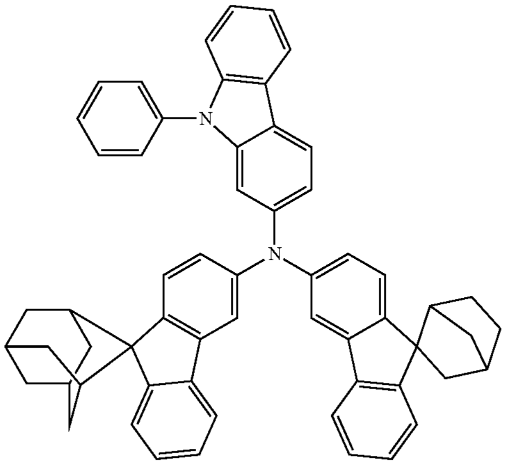
335
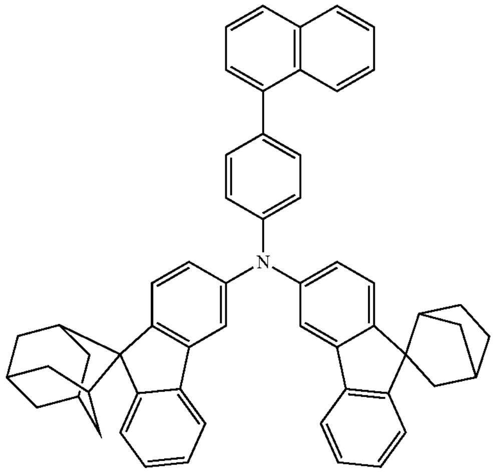
-continued
336
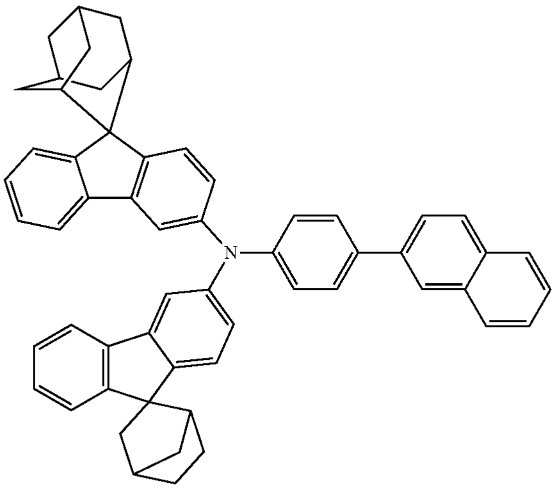
337
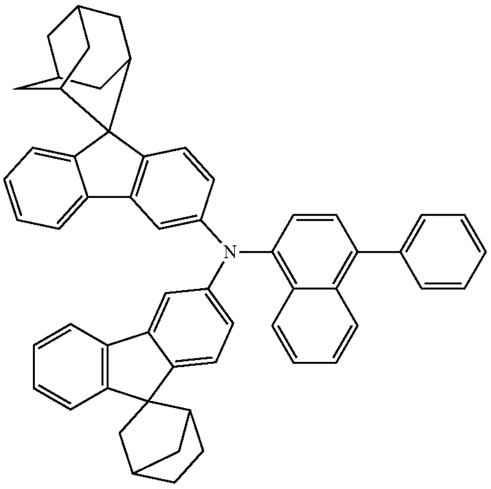
338
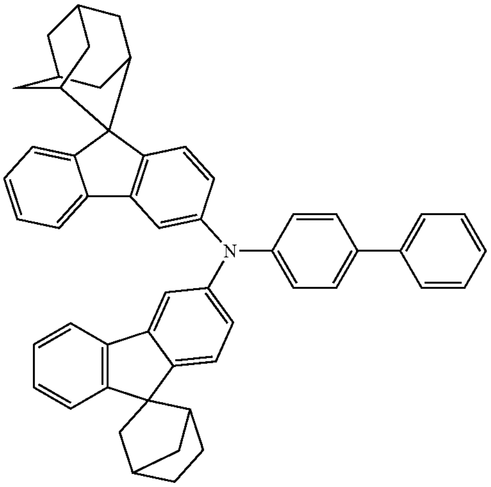

-continued
339
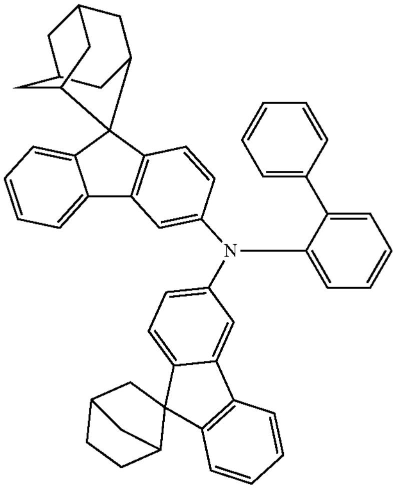
340
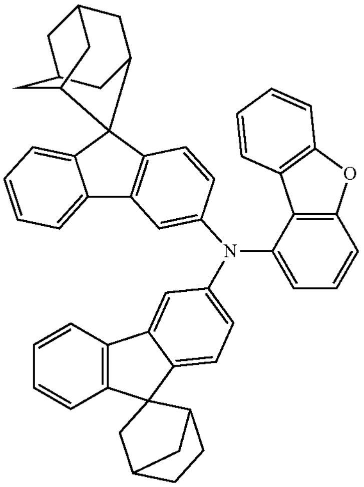
341
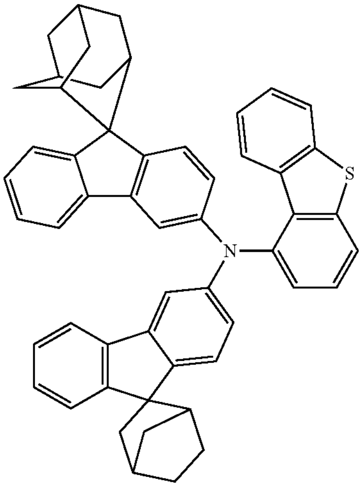
-continued
342
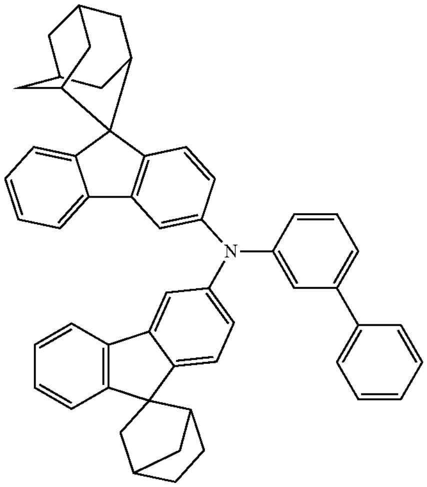
343
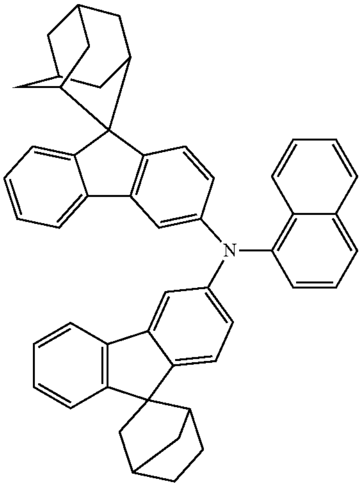
344
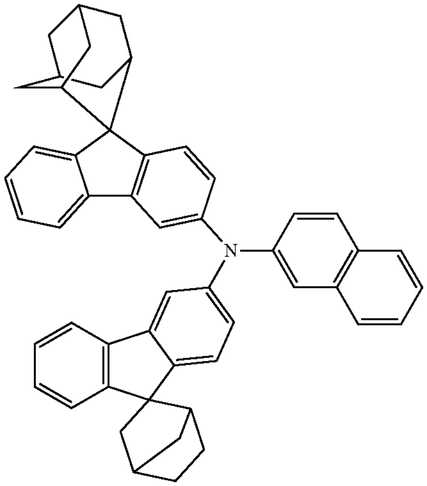

-continued
345
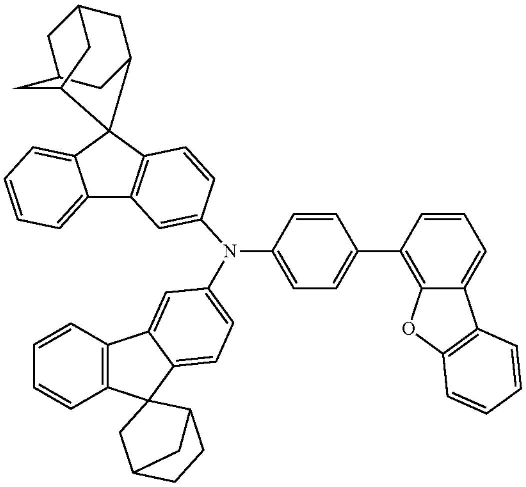
346
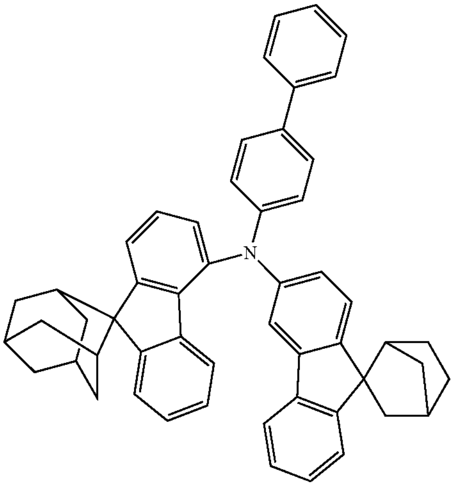
347
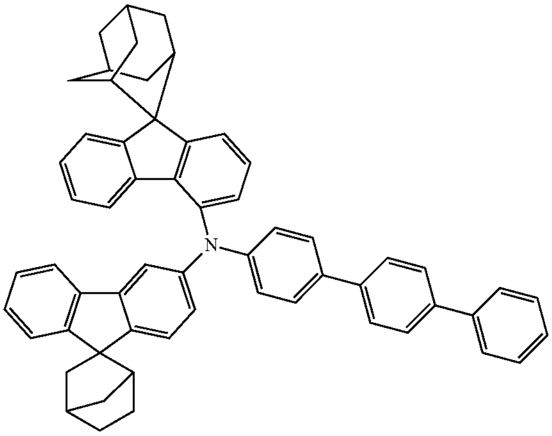
-continued
348
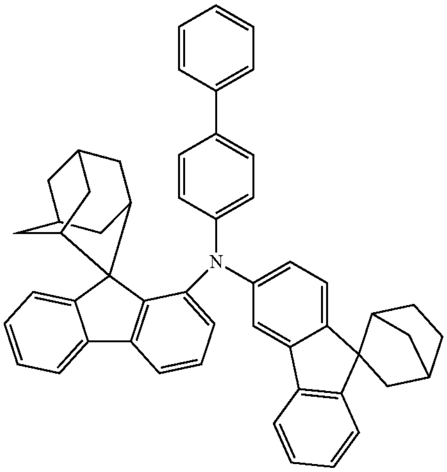
349
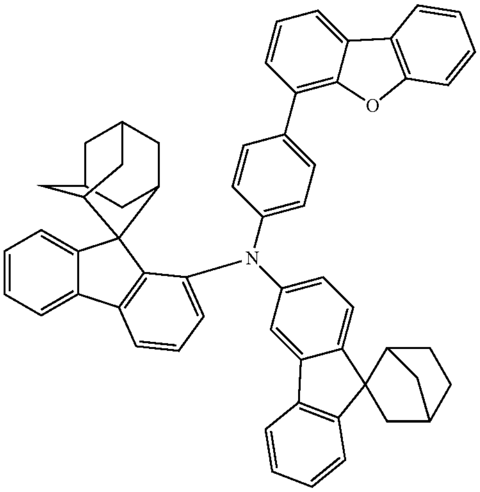
350
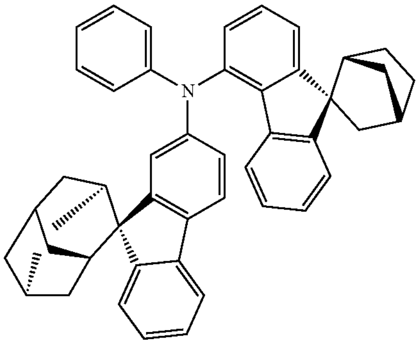

-continued
351
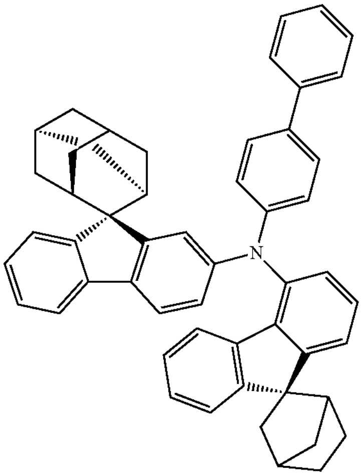
352
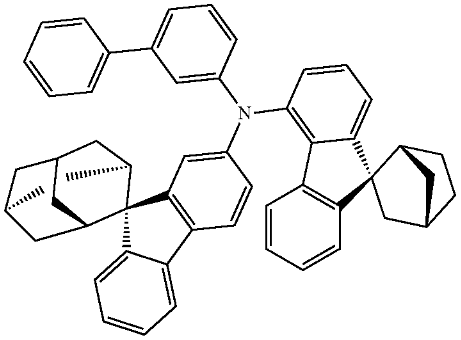
353
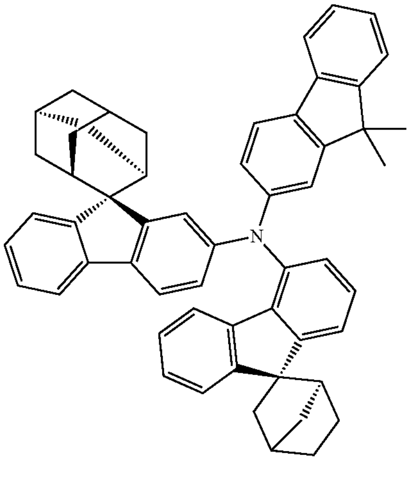
-continued
354
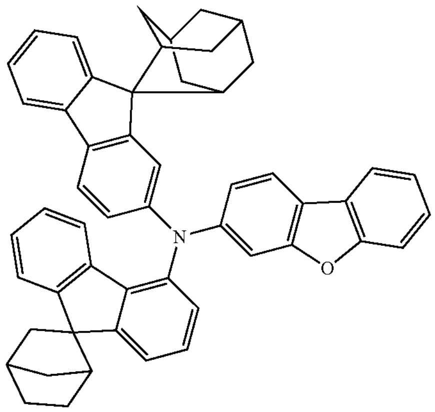
355
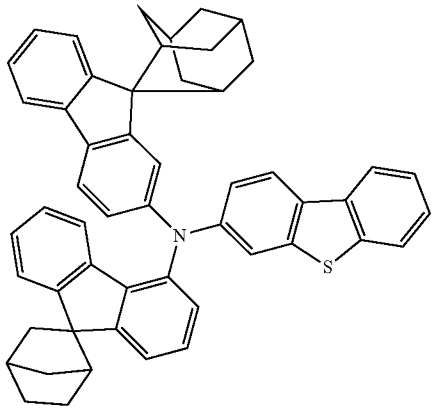
356
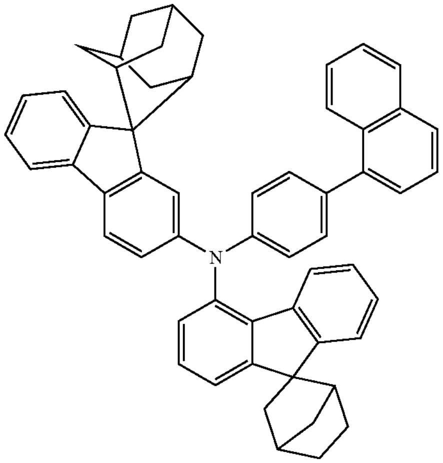

-continued
357
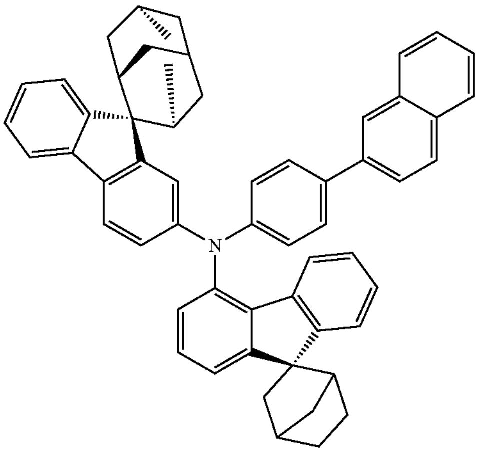
358
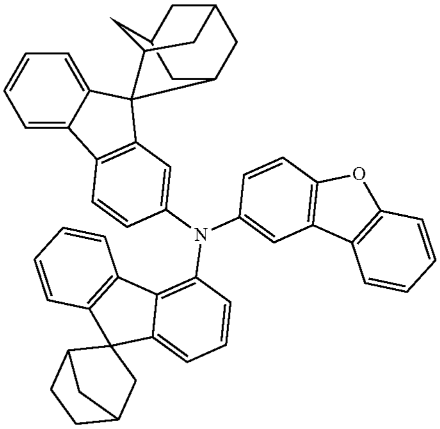
359
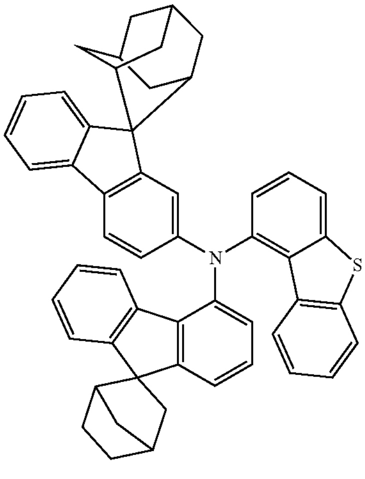
-continued
360
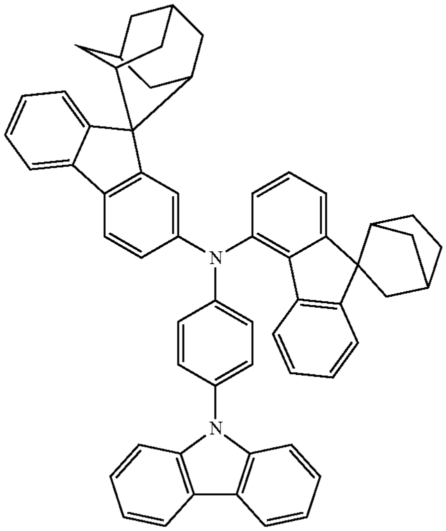
361
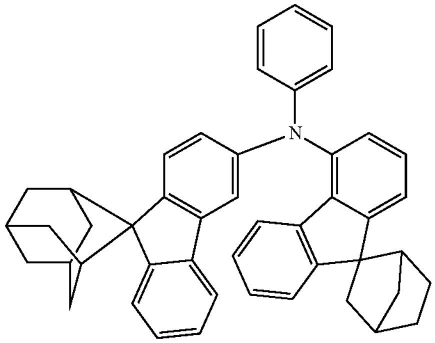
362
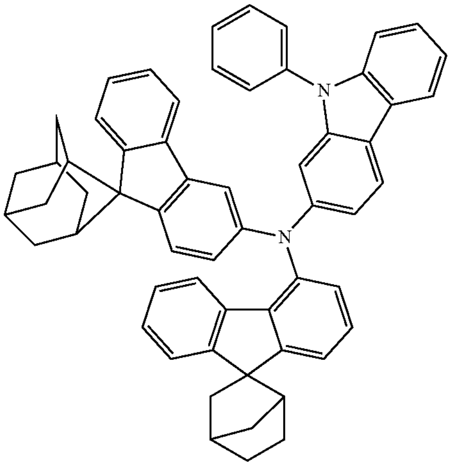

-continued
363
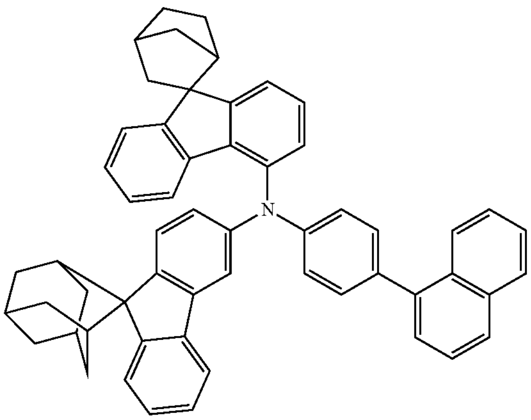
364
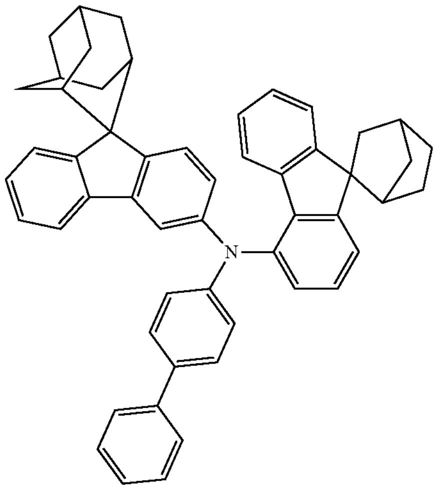
365
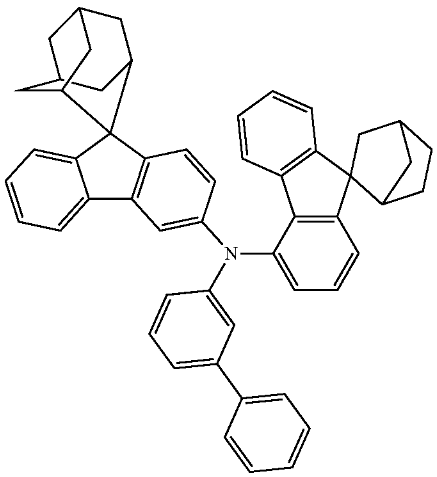
-continued
366
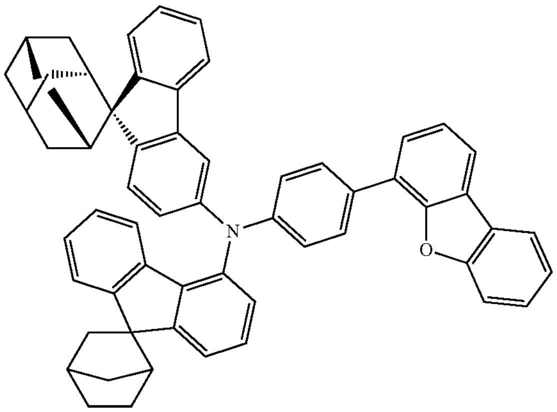
367
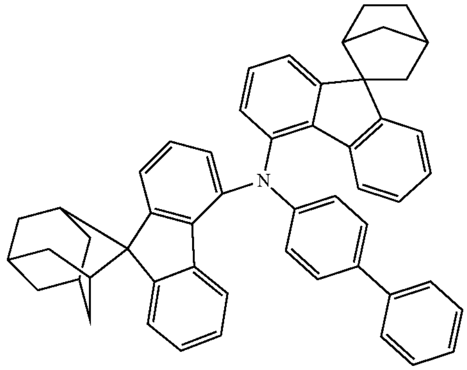
368
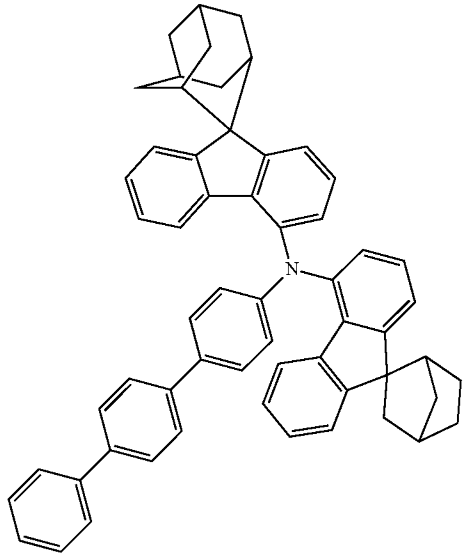

369
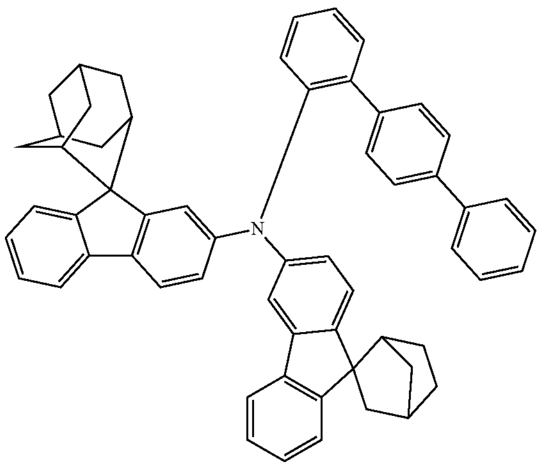
370
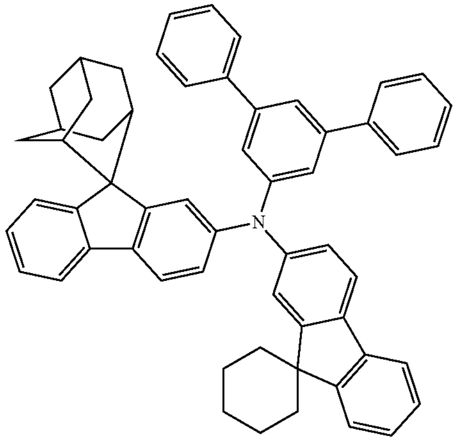
371
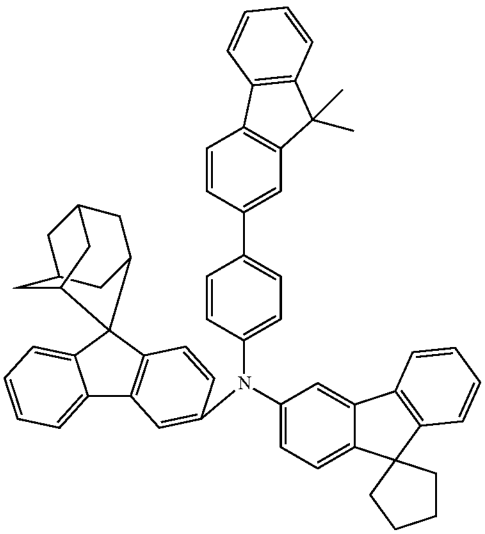
372
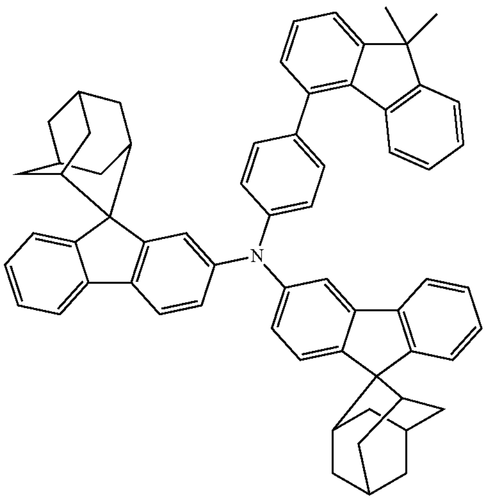
373
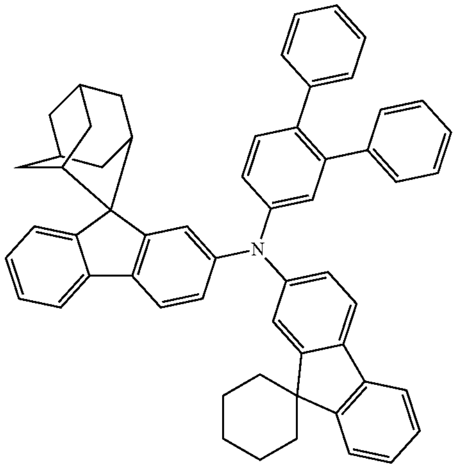
374
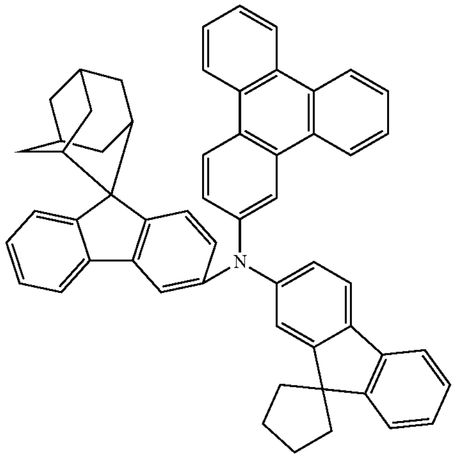

375
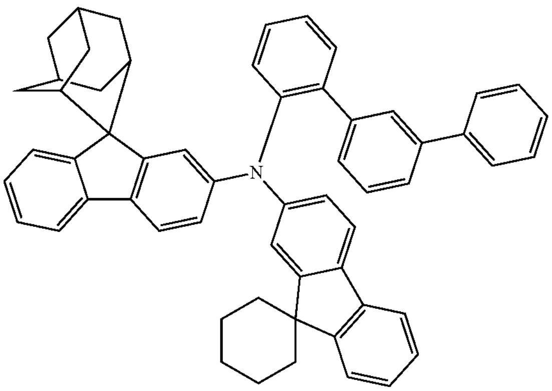
376
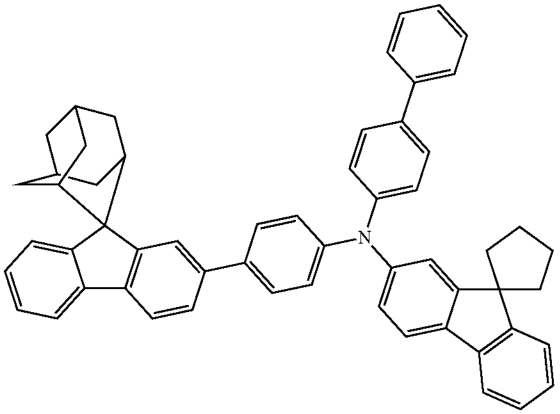
377
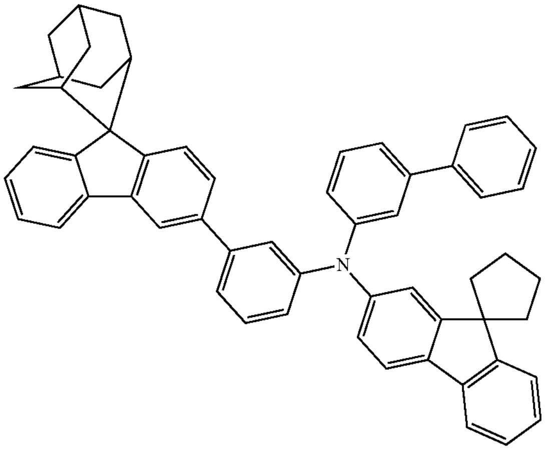
378
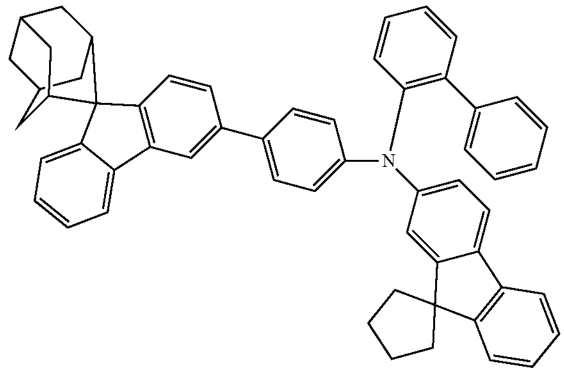
379
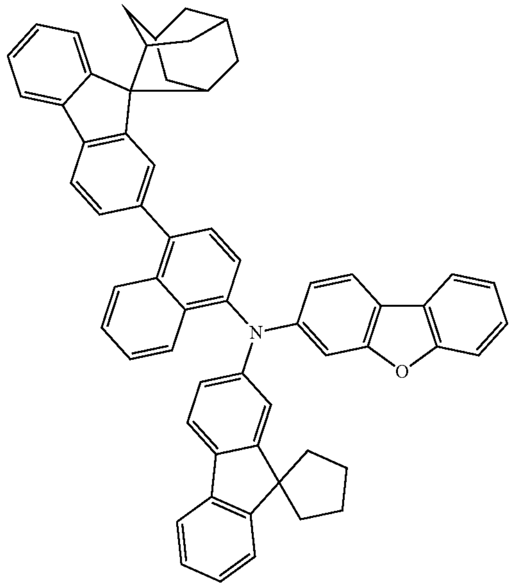
380
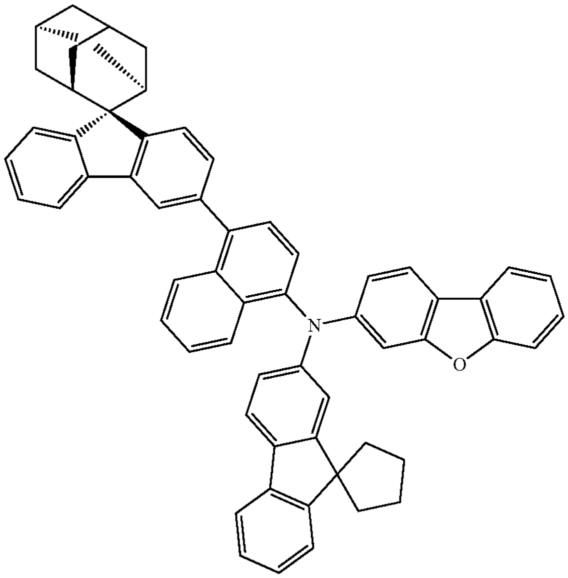

-continued
381
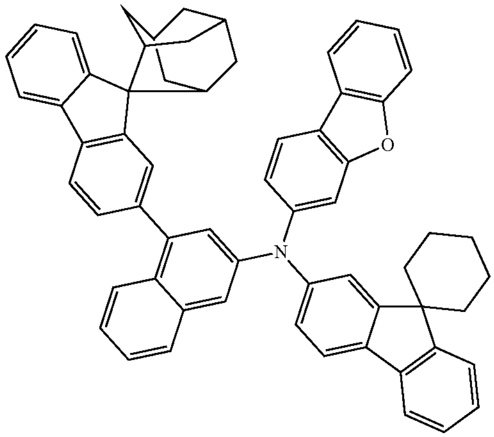
382
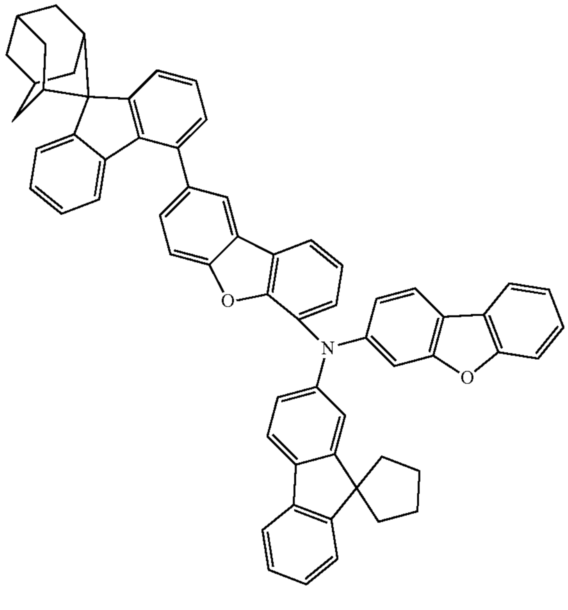
-continued
383
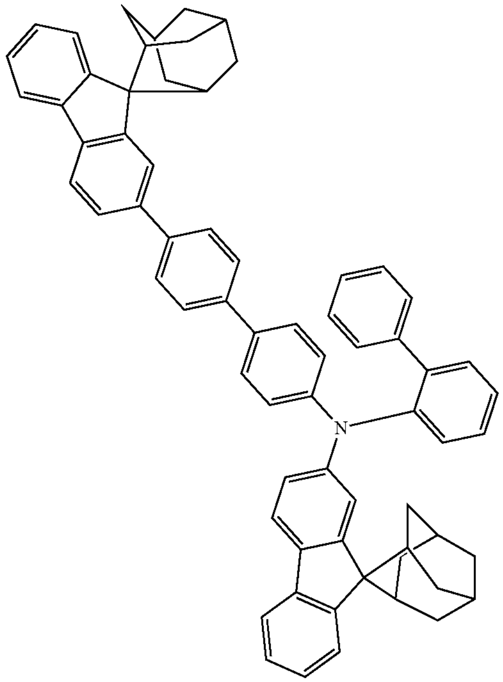
384
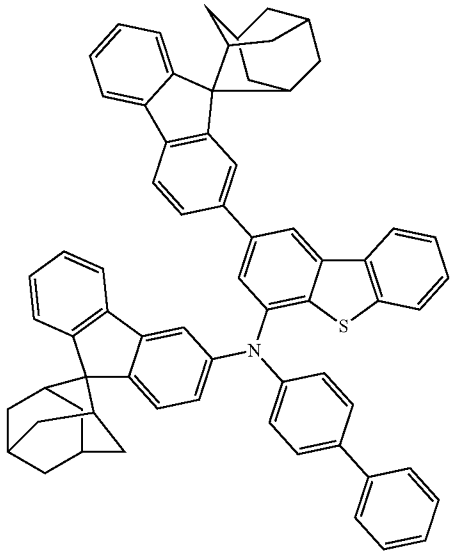
385
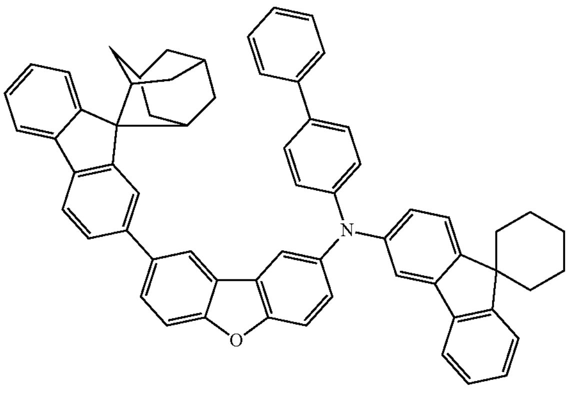

-continued
386
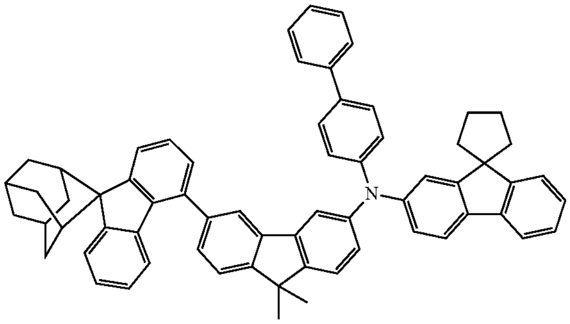
387
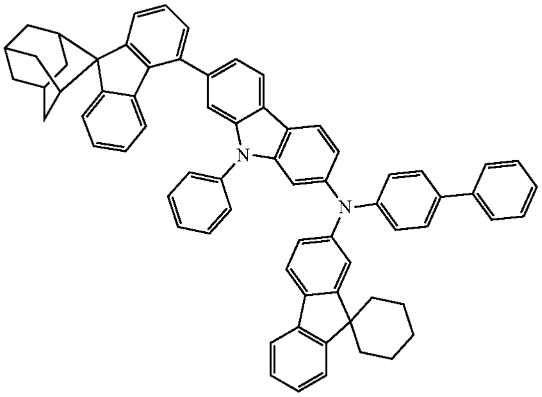
388
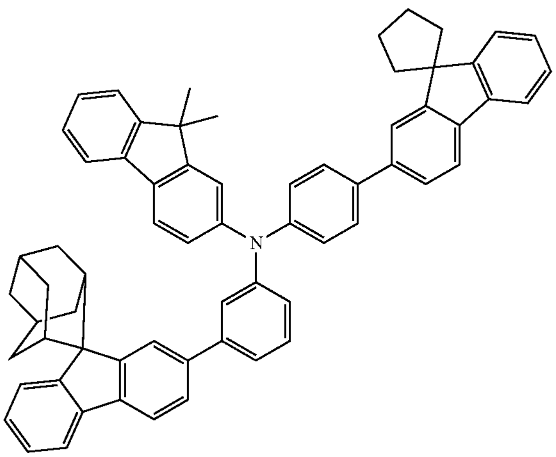
-continued
389
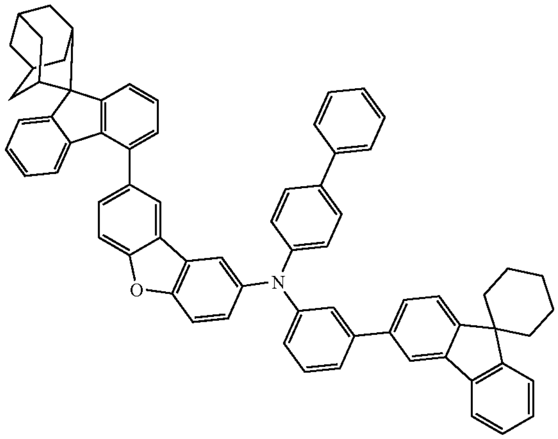
390
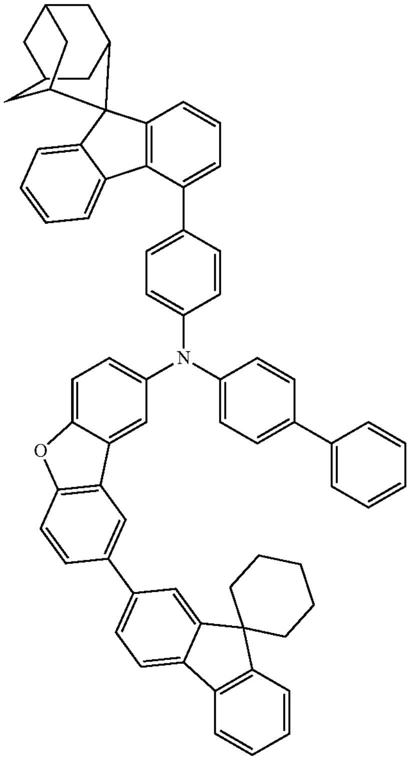
391
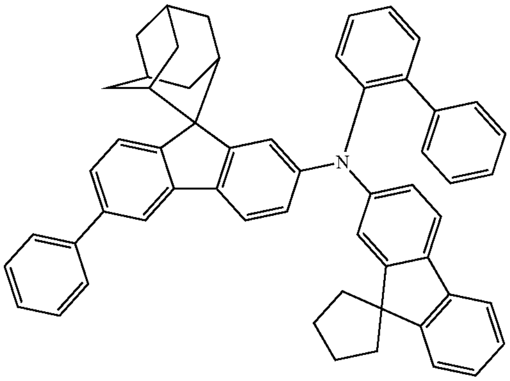

-continued
392
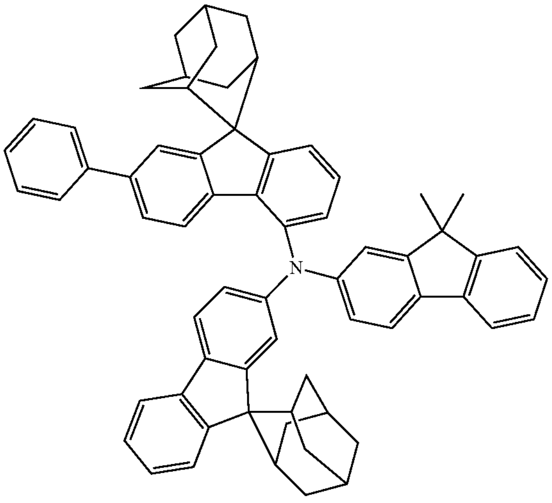
393
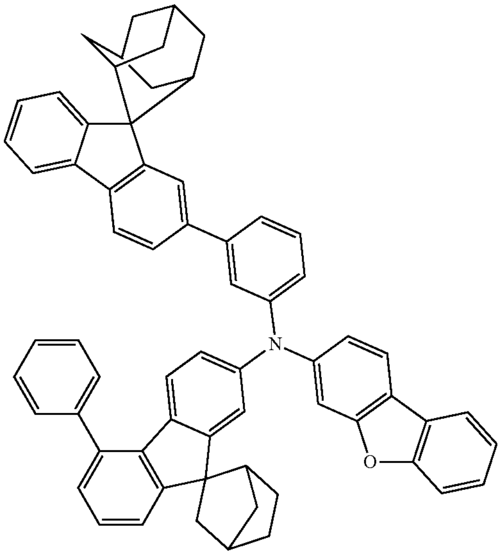
394
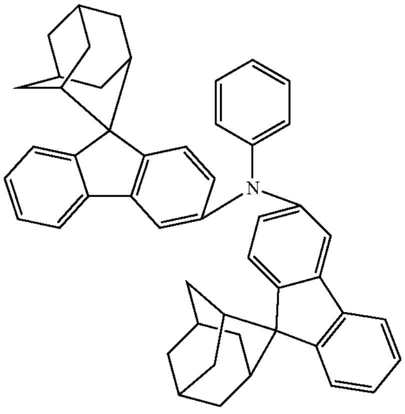
-continued
395
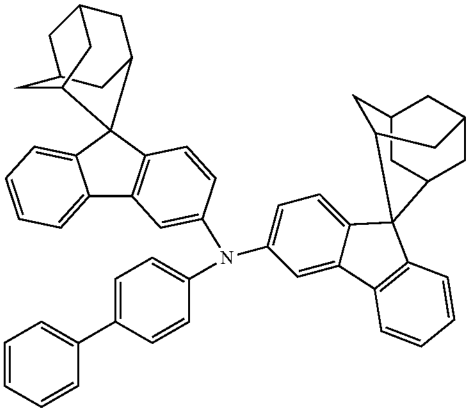
396
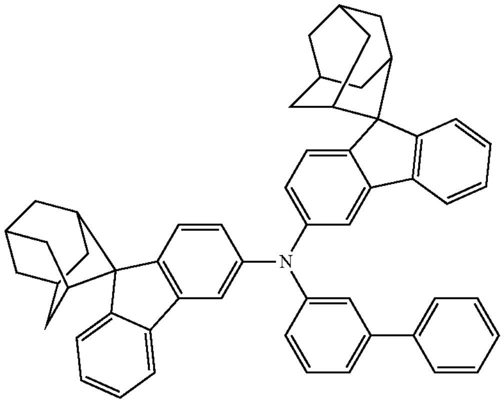
397
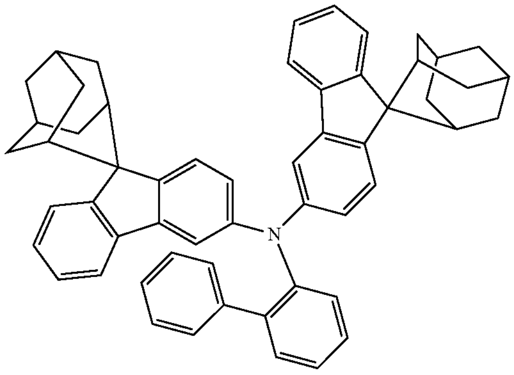

-continued
399
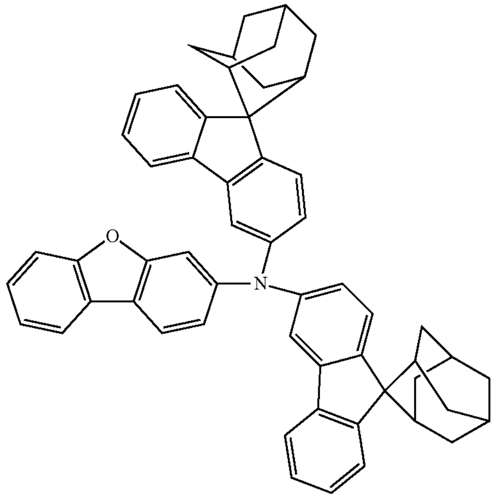
400
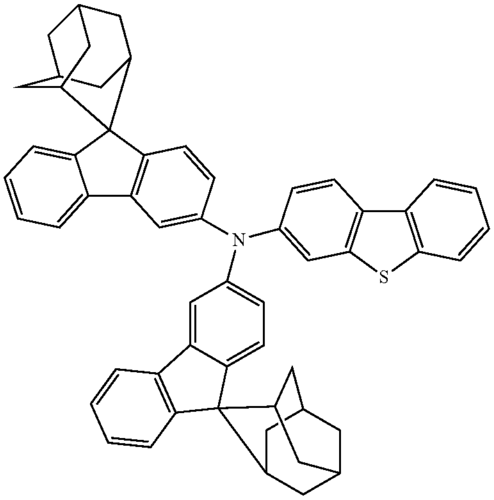
401
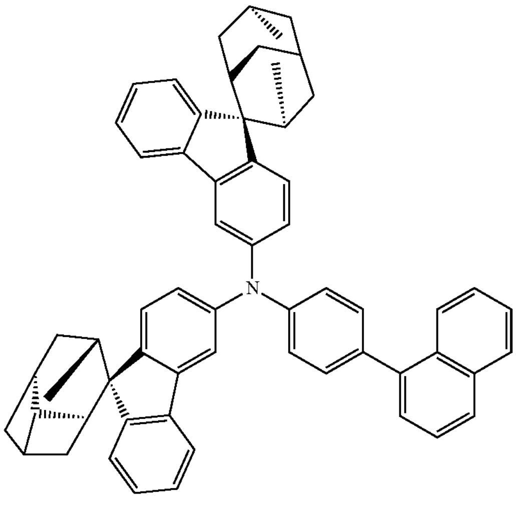
-continued
402
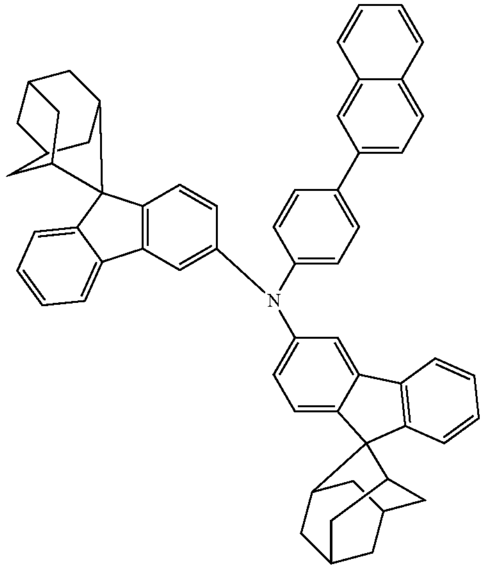
403
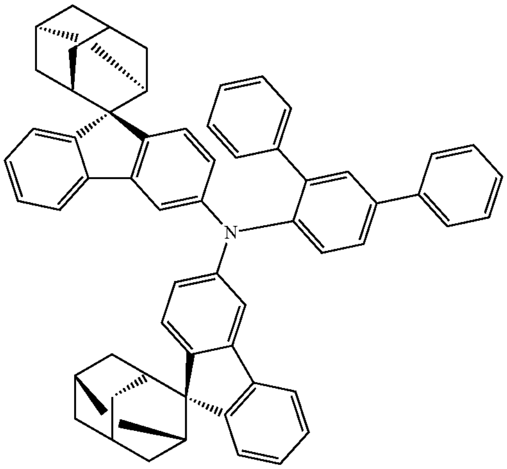
404
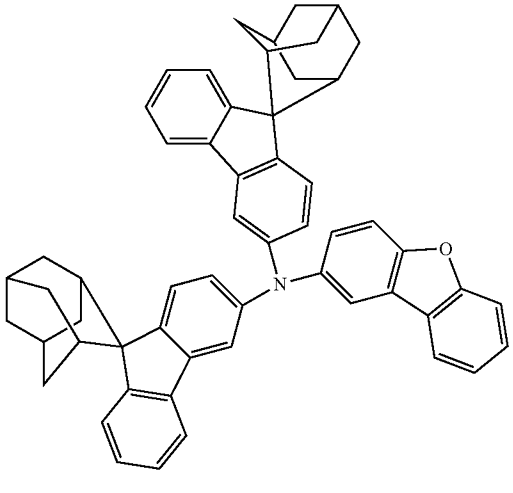

405
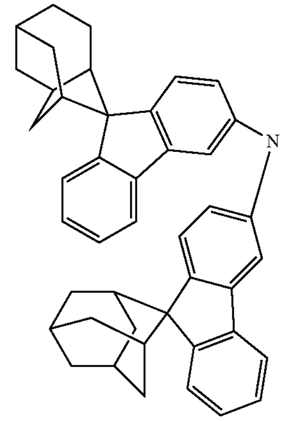
406
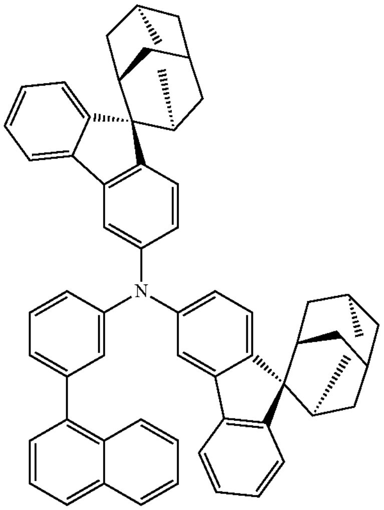
407
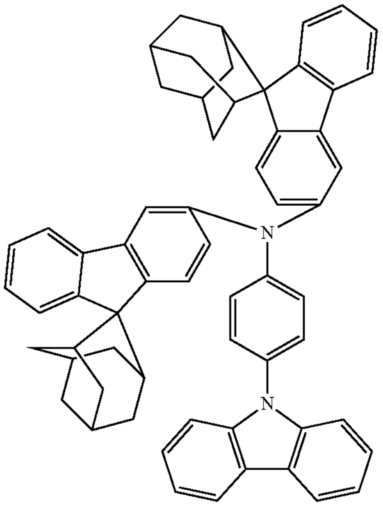
408
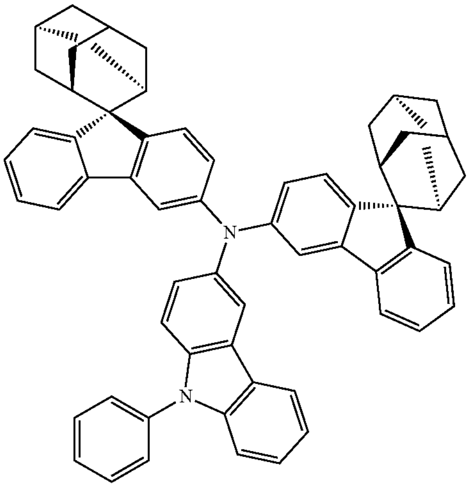
409
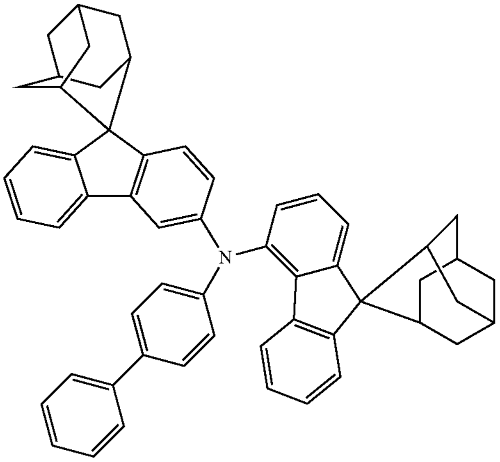
410
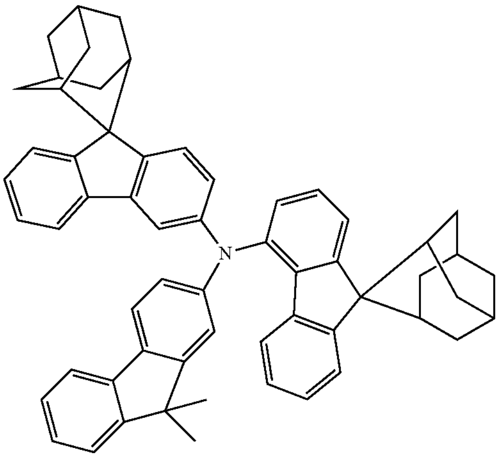

-continued
411
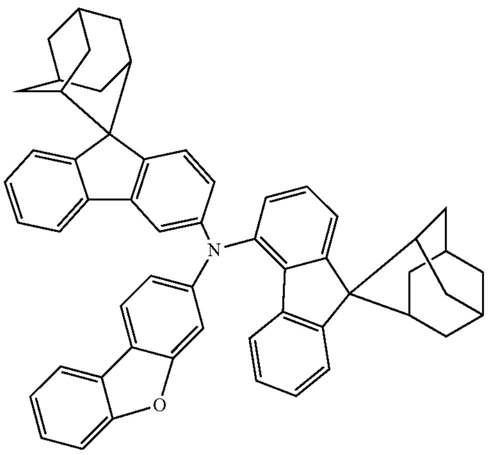
412
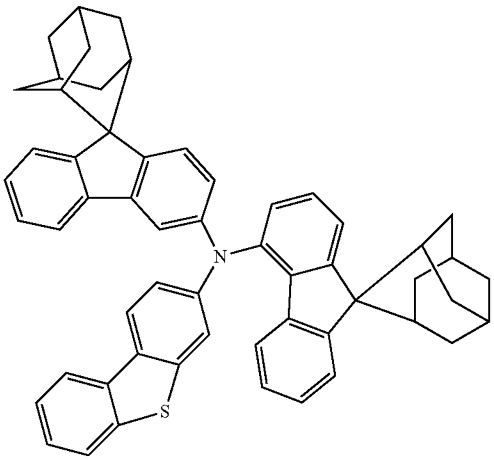
413
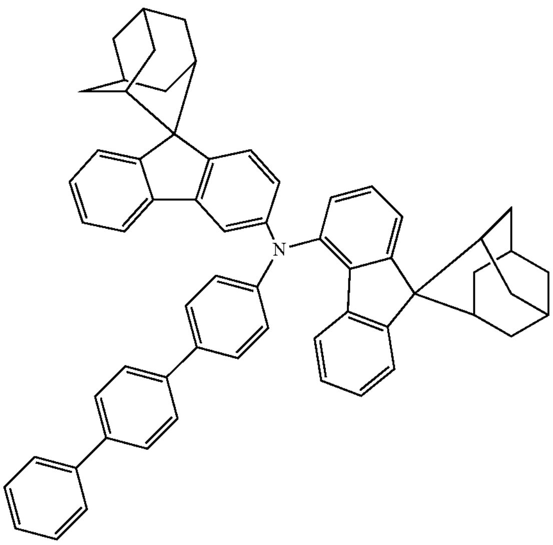
-continued
414
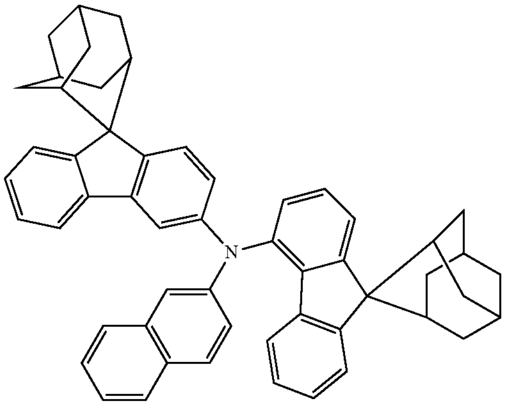
415
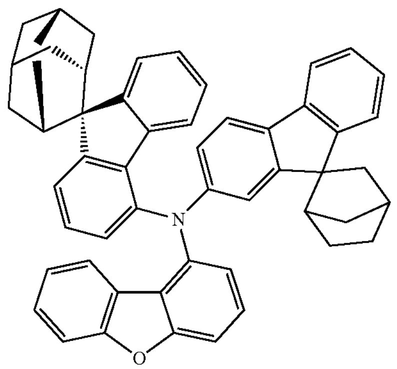
416
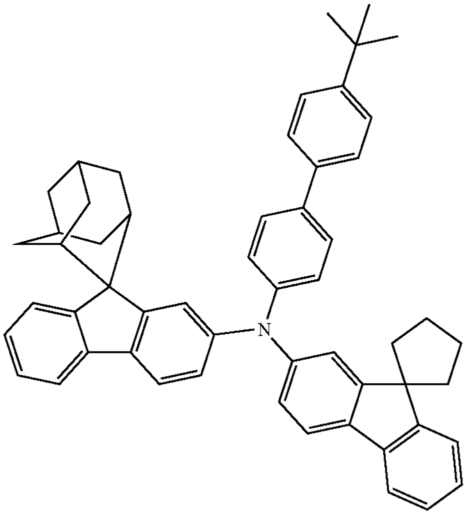

-continued
417
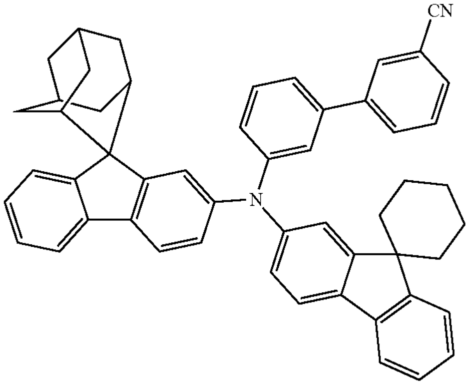
418
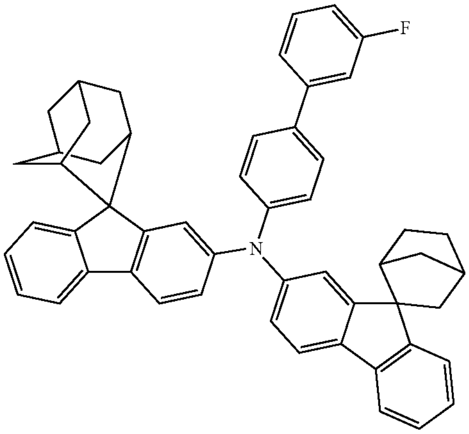
419
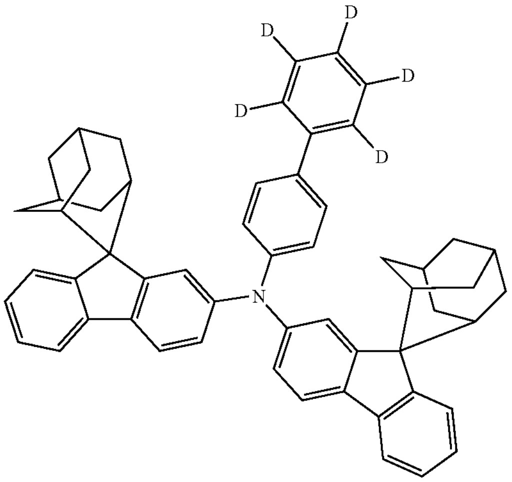
420
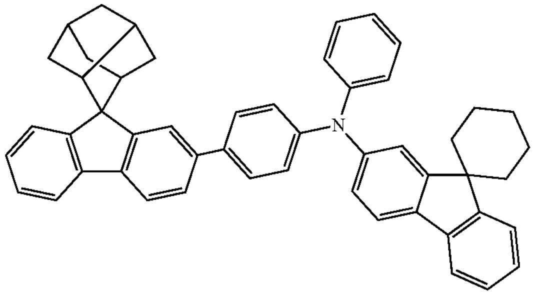
-continued
421
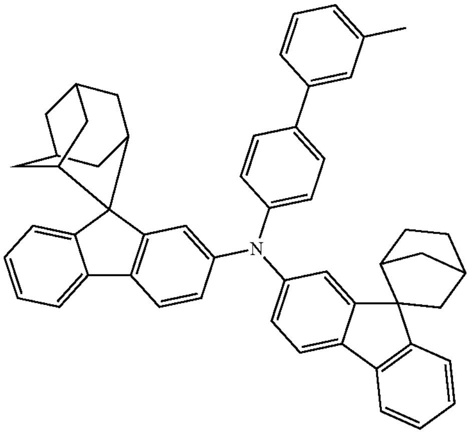
422
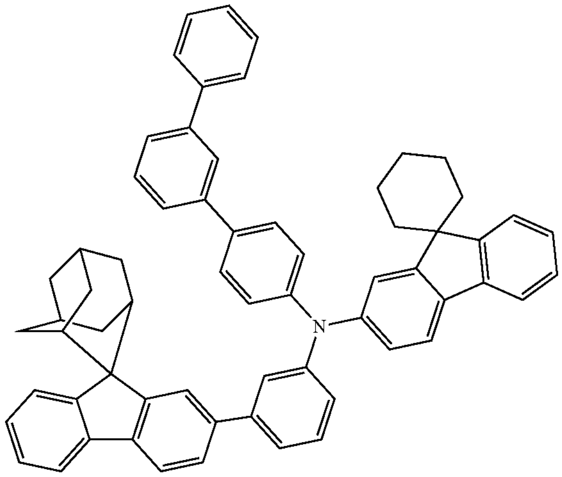
423
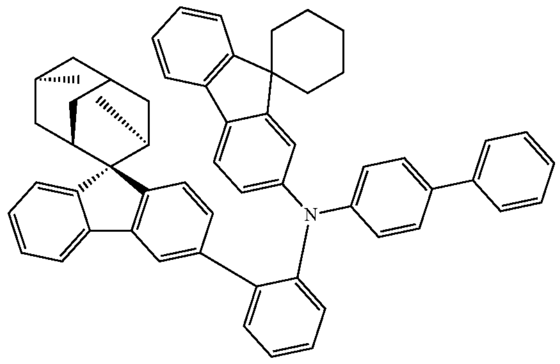

-continued
424
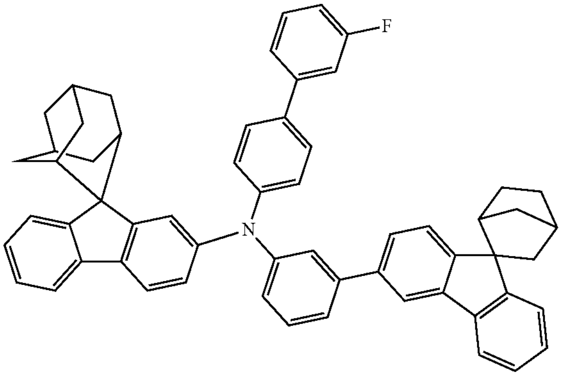
425
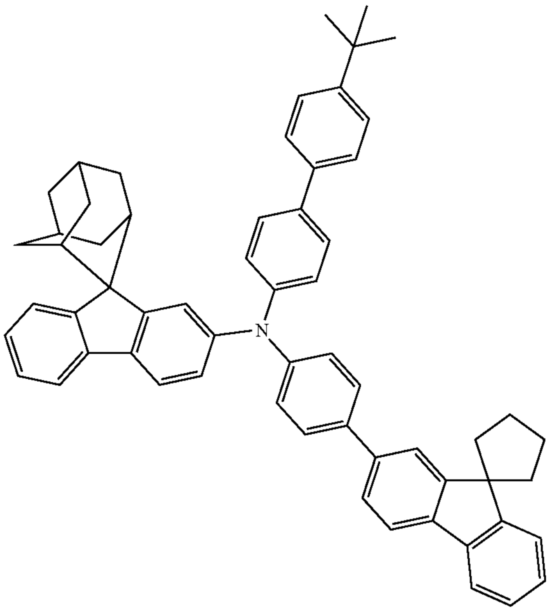
426
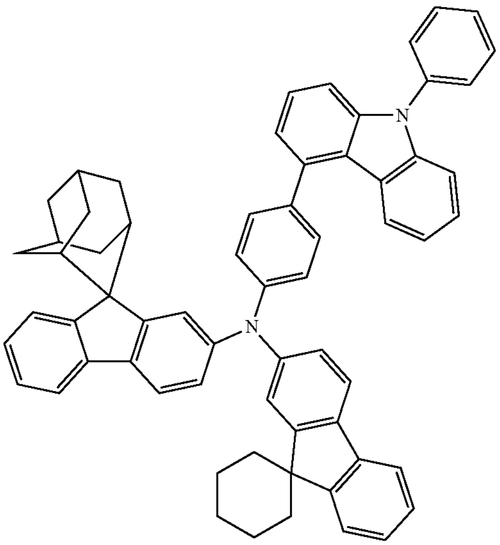
-continued
455
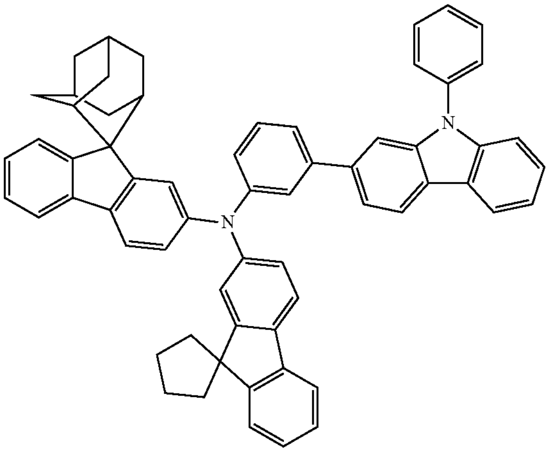
427
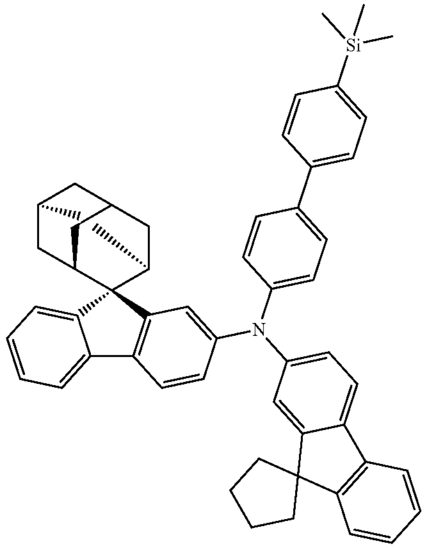
428
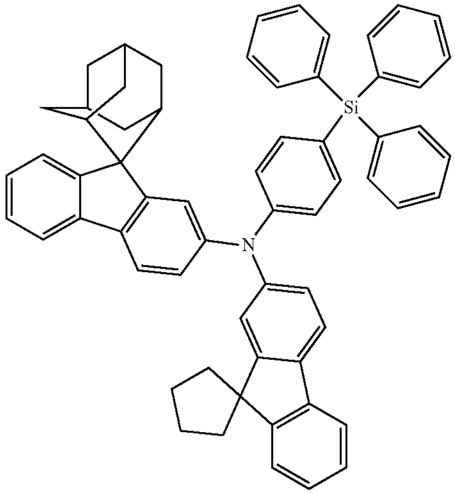

429
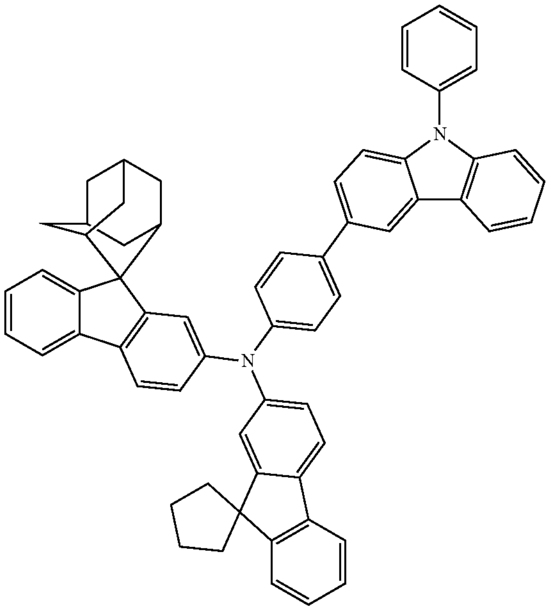
430
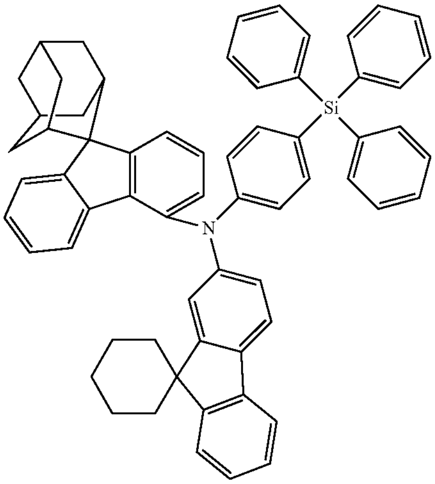
431
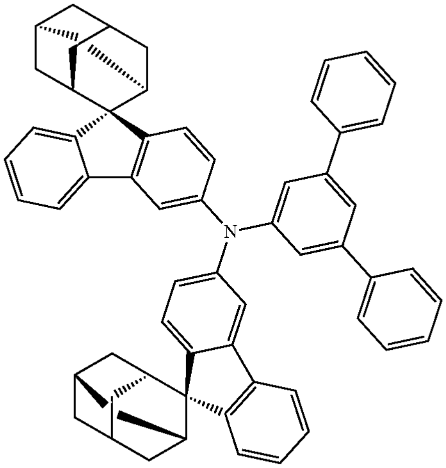
432
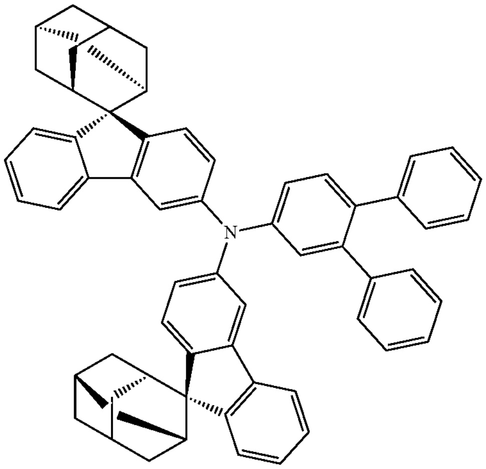
433
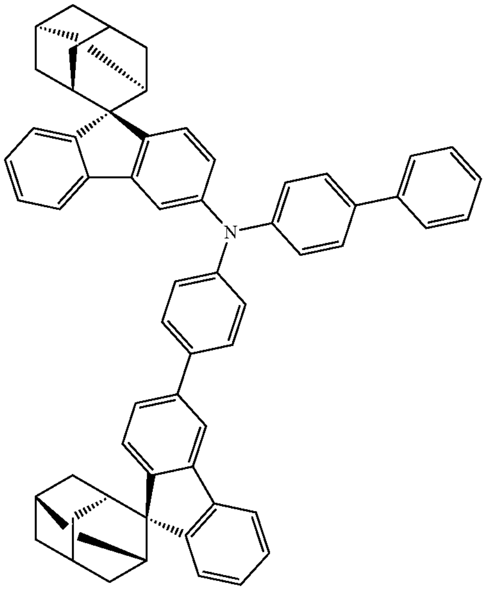
434
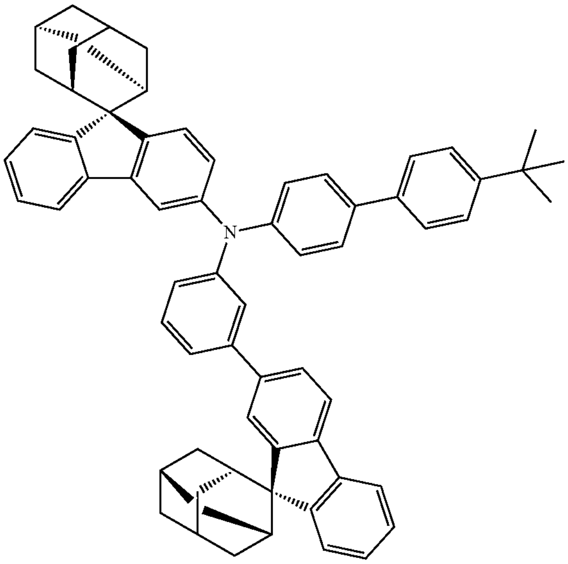

-continued
435
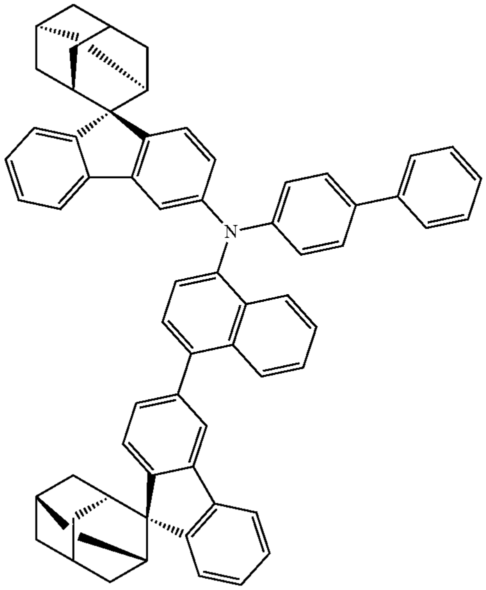
437
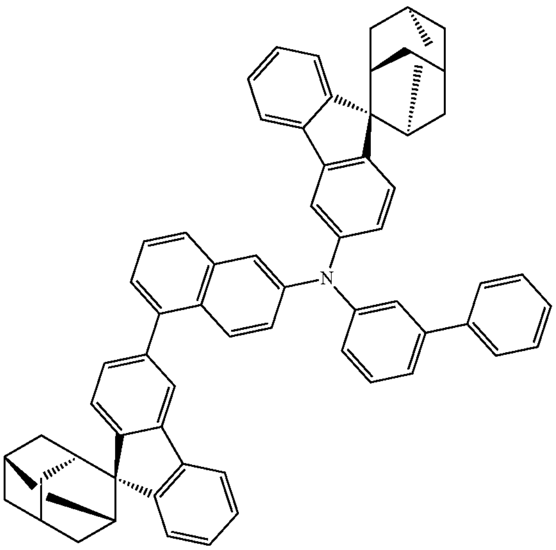
436
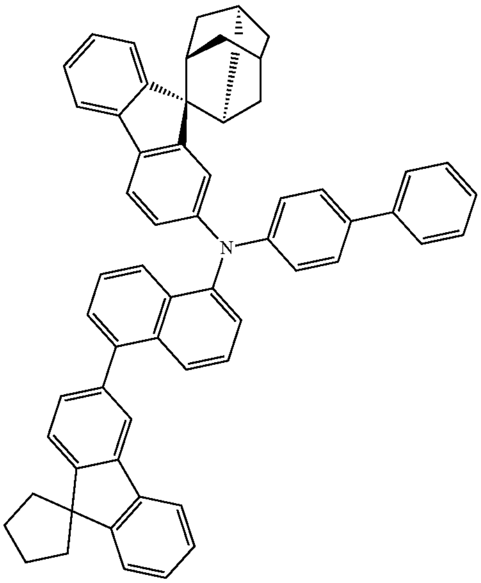
438
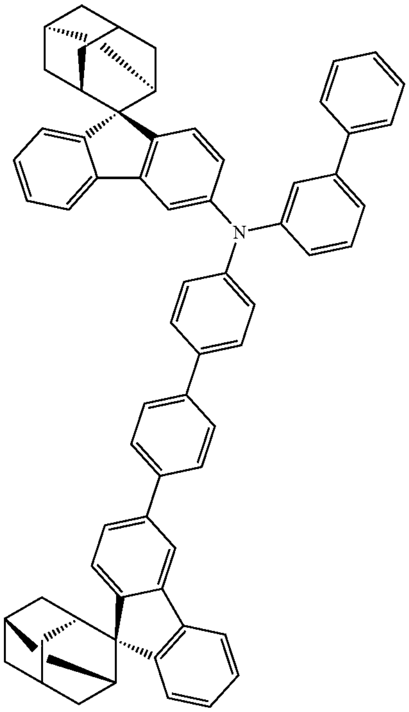

439
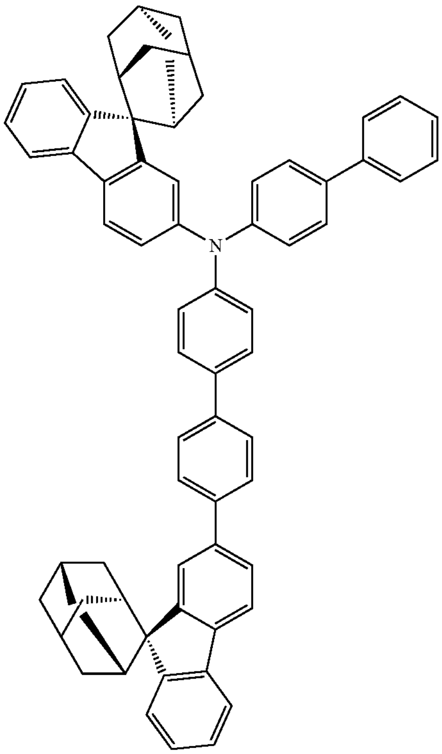
440
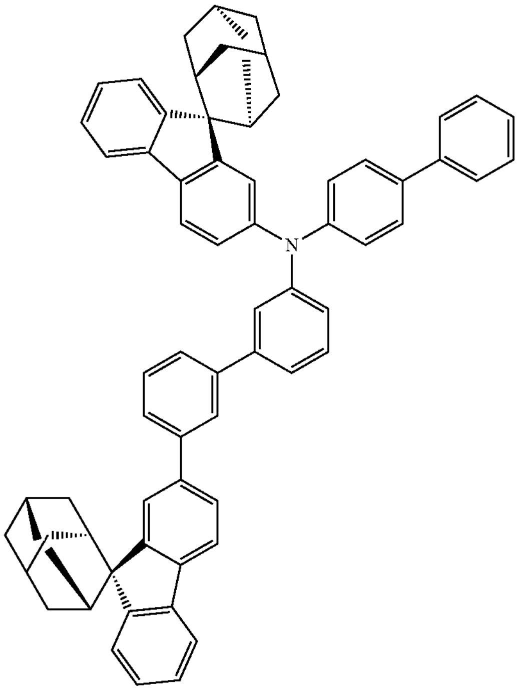
441
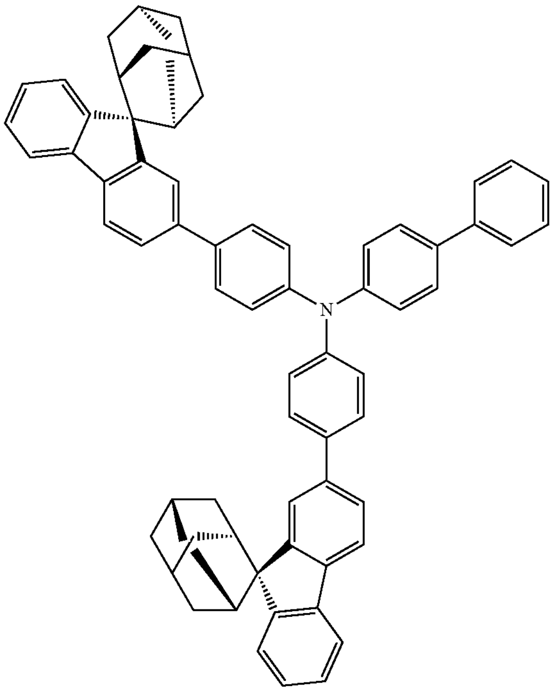
442
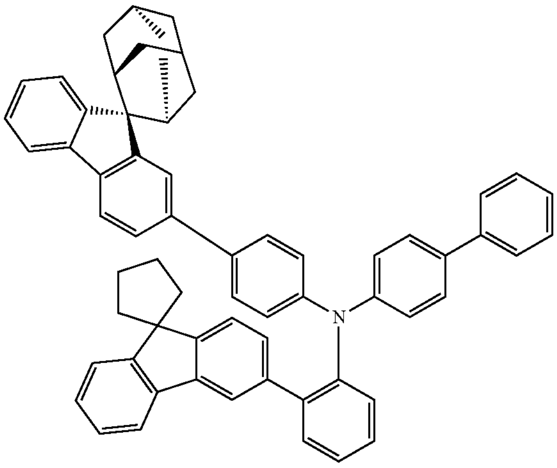

-continued
443
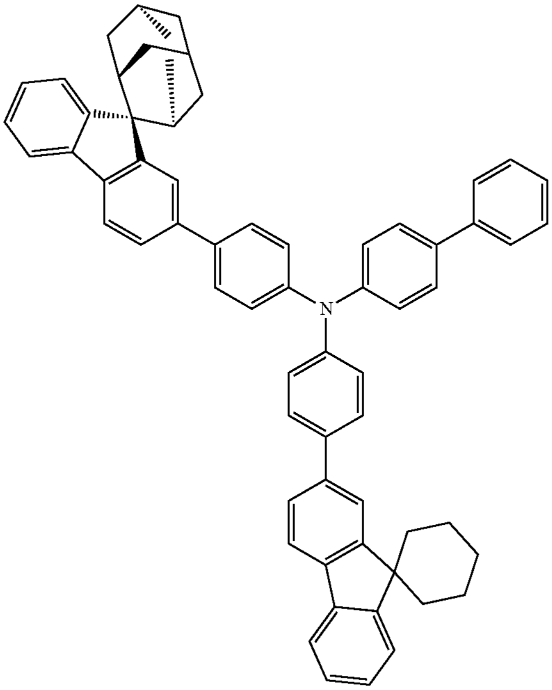
444
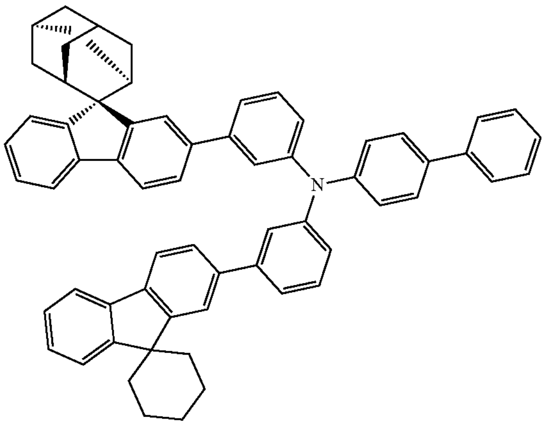
445
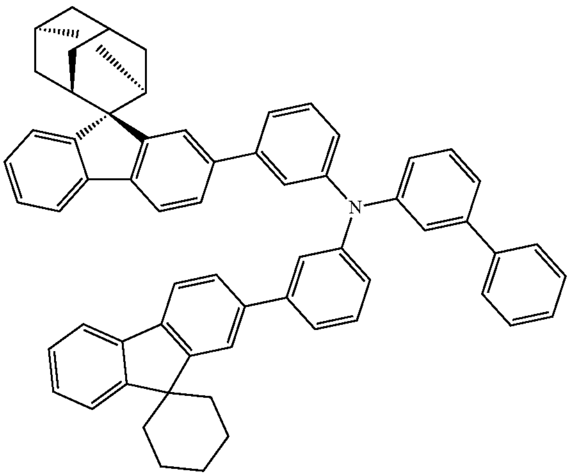
-continued
446
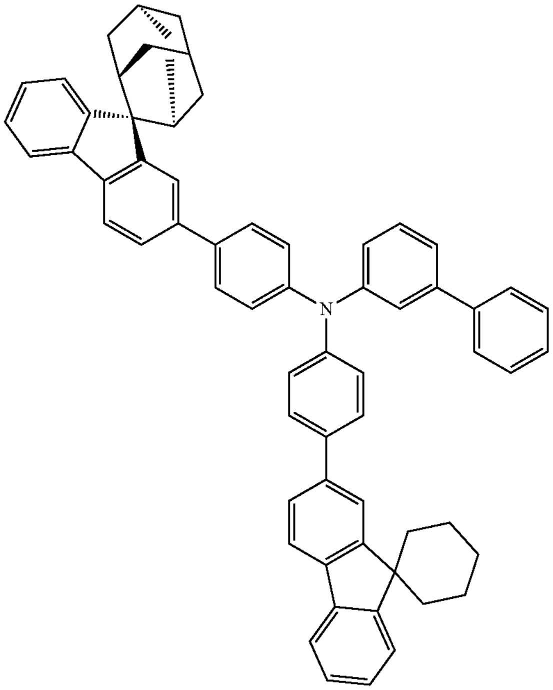
447
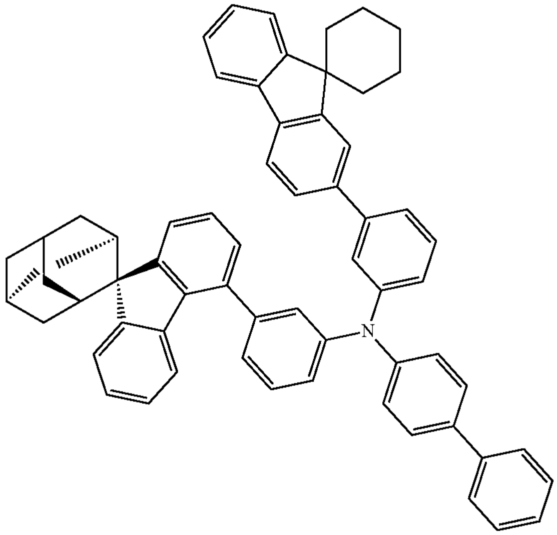

-continued
448
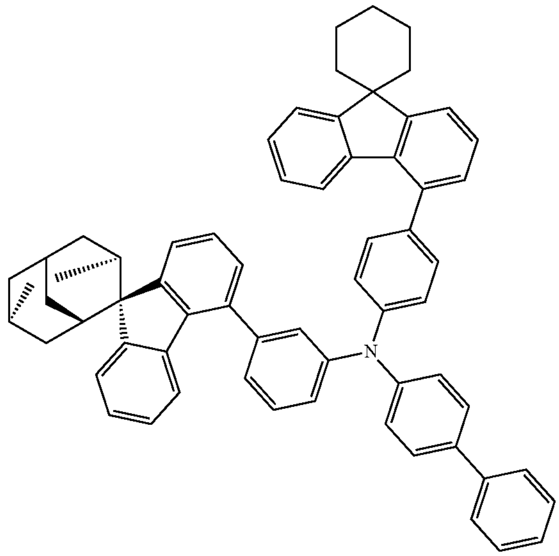
449
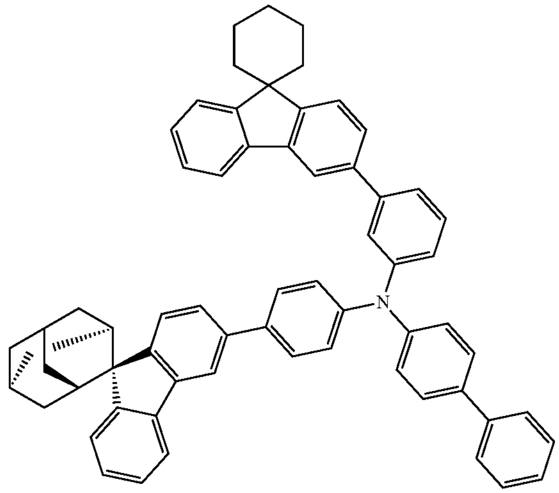
450
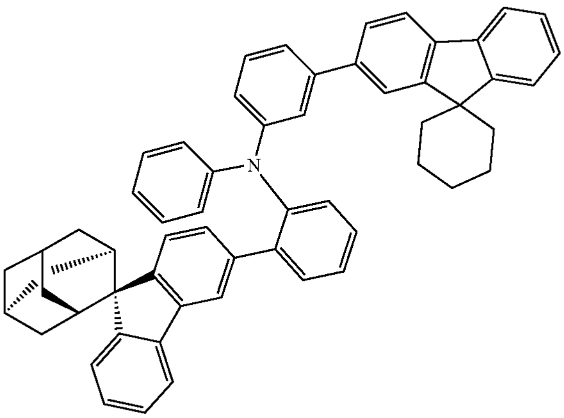
-continued
451
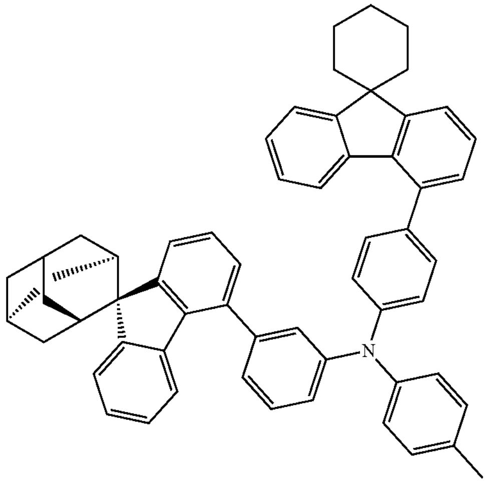
452
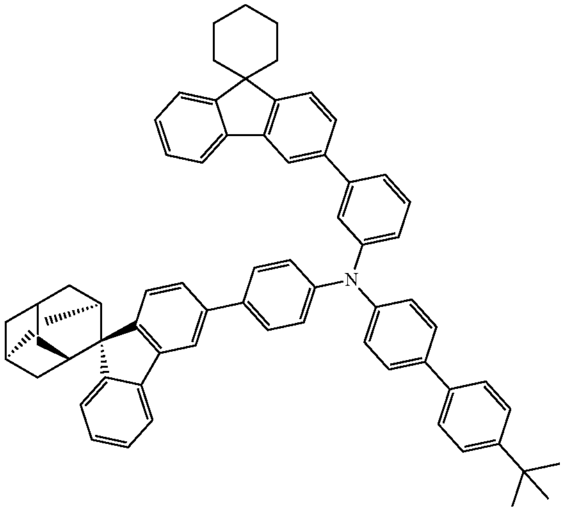
453
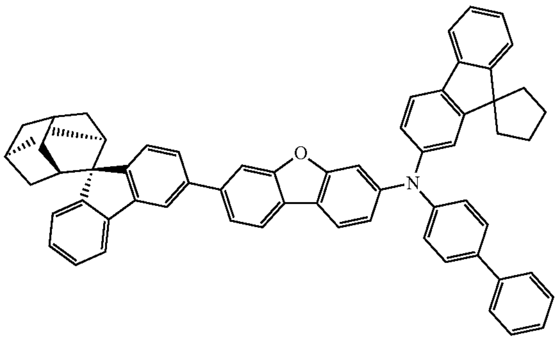

-continued
454
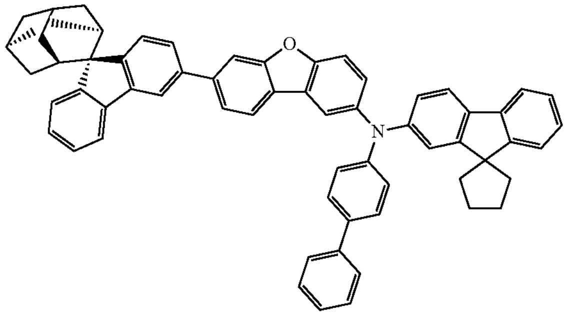
456
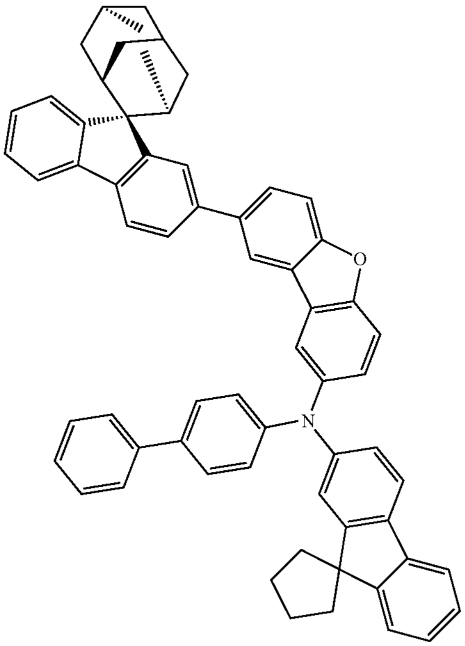
457
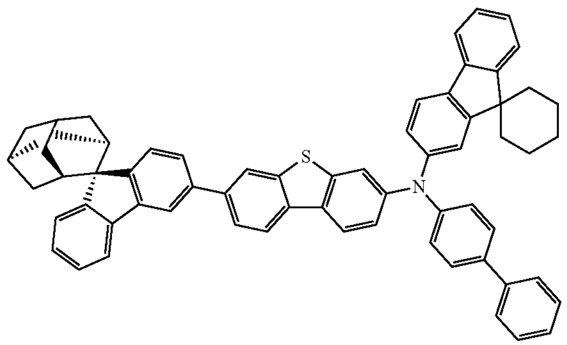
-continued
458
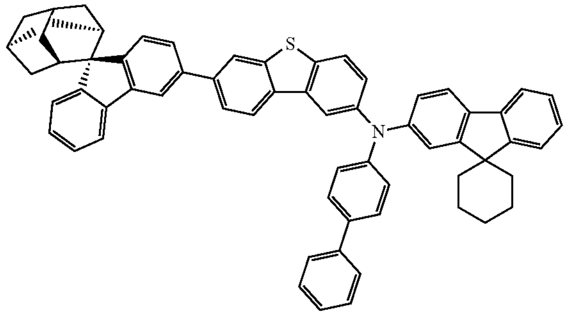
459
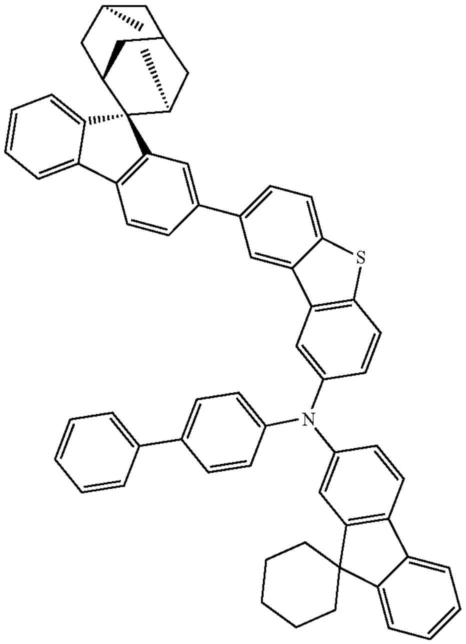

-continued
460
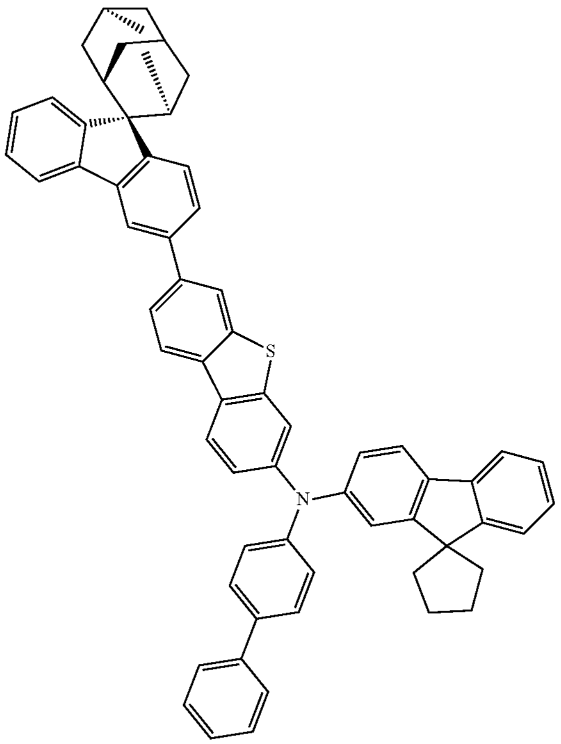
461
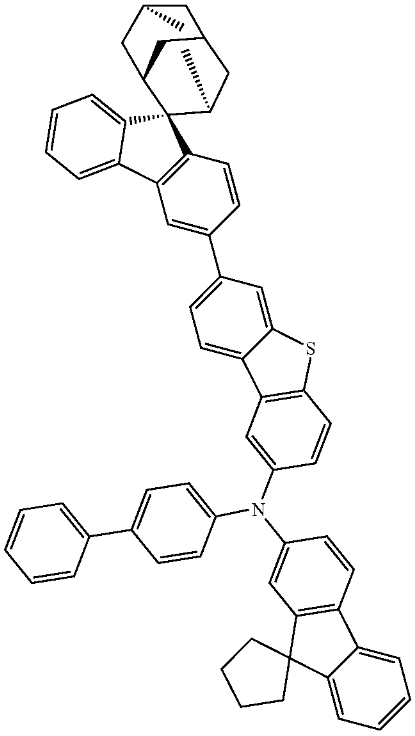
-continued
462
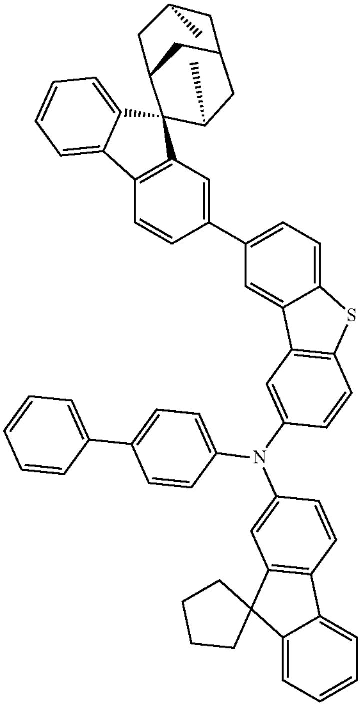
463
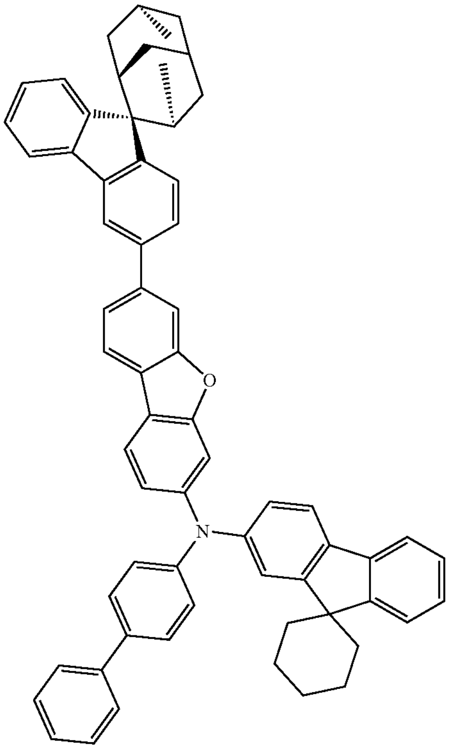

-continued
464
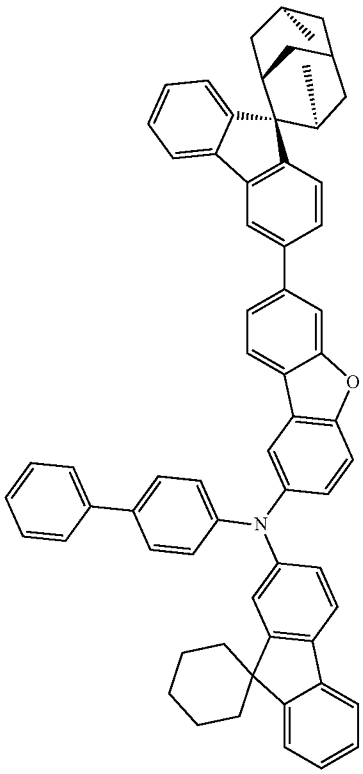
465
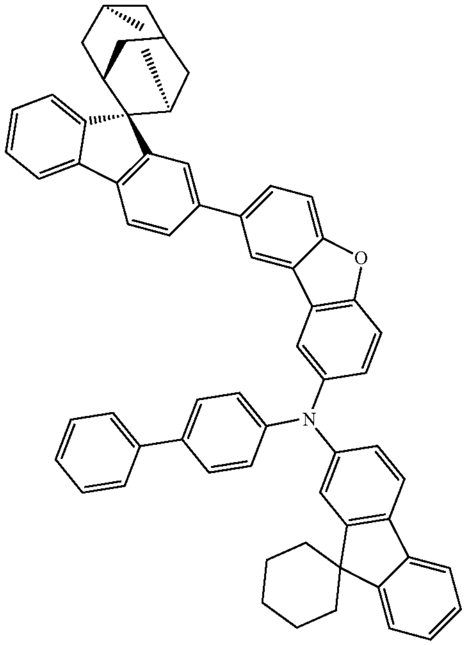
-continued
466
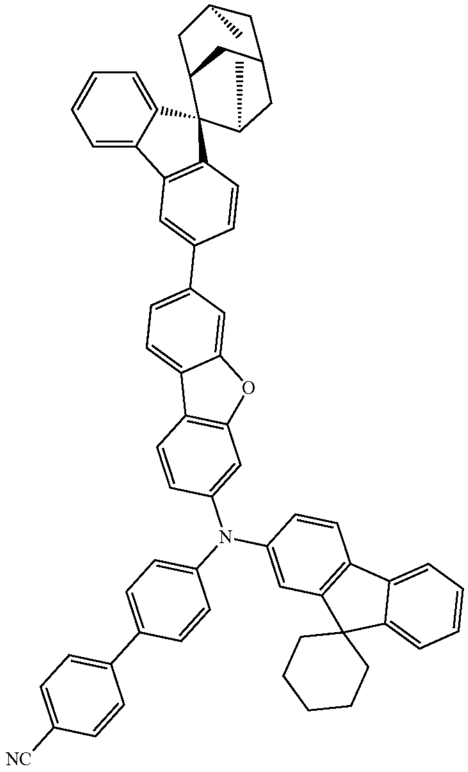
467
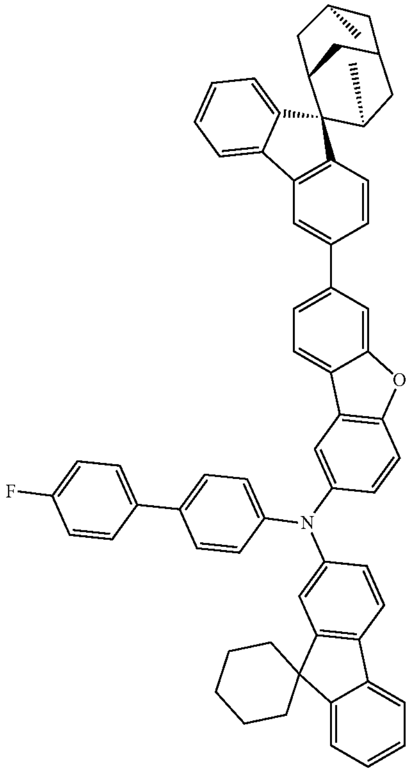

468
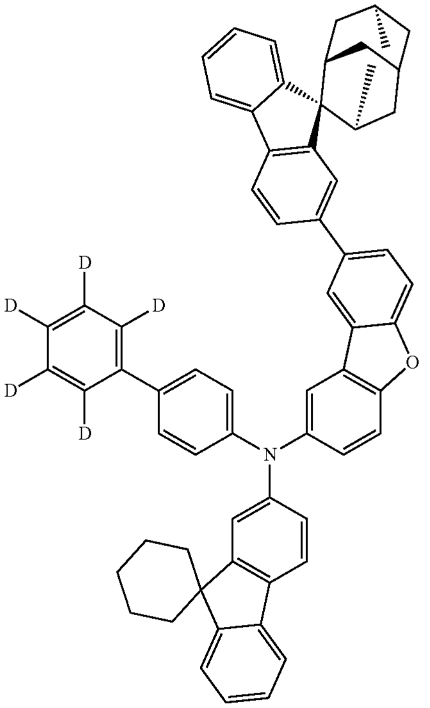
469
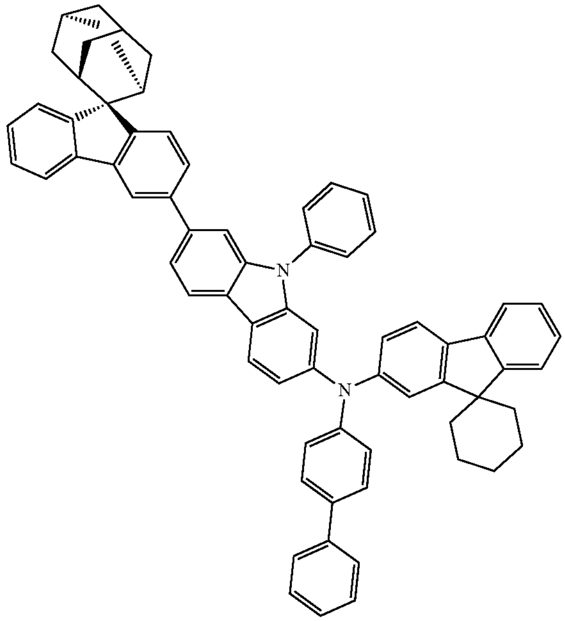
470
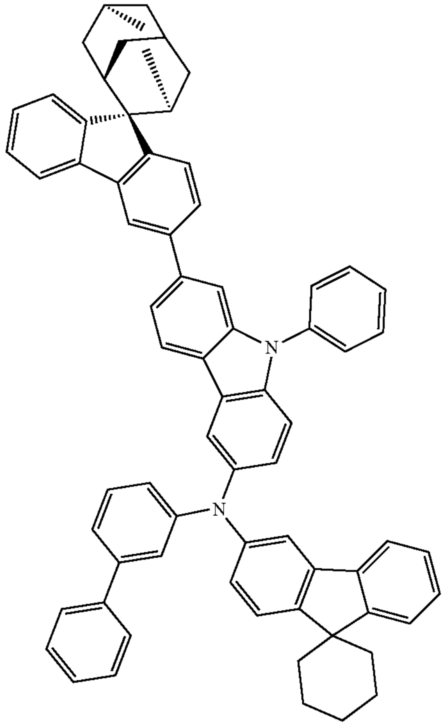
471
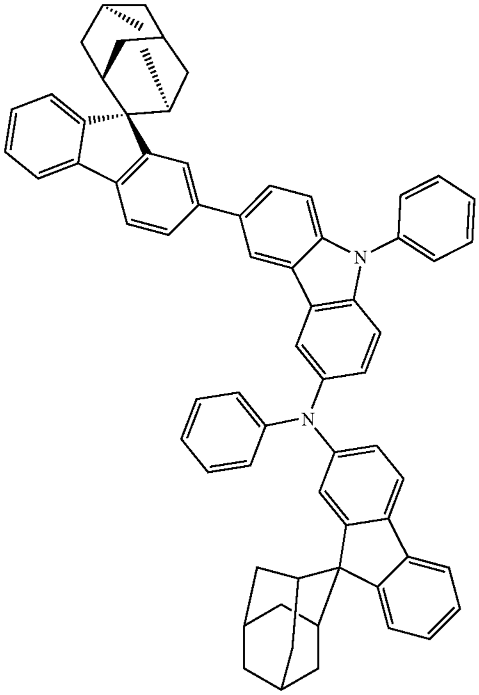

-continued

472

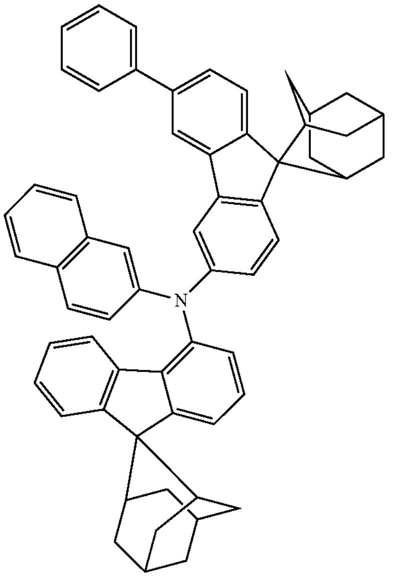

473

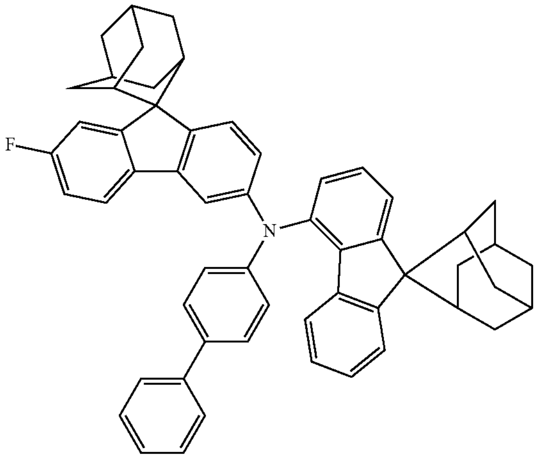

-continued

474

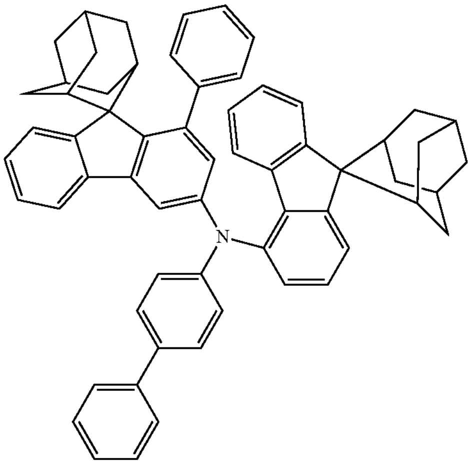

.

13. An electronic component, comprising an anode, a cathode which is disposed oppositely to the anode, and a functional layer disposed between the anode and the cathode; wherein the functional layer contains the arylamine compound according to claim 1.

14. The electronic component according to claim 13, wherein the functional layer of the electronic component comprises a hole transport layer, and the hole transport layer contains the arylamine compound.

15. The electronic component according to claim 13, wherein the electronic component is an organic electroluminescent device or a photoelectric conversion device.

16. The electronic component according to claim 13, wherein the electronic component is an organic electroluminescent device, the hole transport layer comprises a first hole transport layer and a second hole transport layer;

the first hole transport layer is adjacent to the second hole transport layer and is closer to anode than the second hole transport layer;

the first hole transport layer and/or the second hole transport layer contain(s) the arylamine compound.

17. An electronic device, comprising the electronic component according to claim 13.

18. The arylamine compound according to claim 1, wherein the substituents in $L_1$, $L_2$ and $L_3$ are the same or different, and are each independently selected from deuterium, fluorine, cyano, methyl, ethyl, n-propyl, isopropyl, tert-butyl, phenyl, naphthyl and biphenyl.

* * * * *